US012338437B2

(12) United States Patent
Aznarez et al.

(10) Patent No.: US 12,338,437 B2
(45) Date of Patent: Jun. 24, 2025

(54) OPA1 ANTISENSE OLIGOMERS FOR TREATMENT OF CONDITIONS AND DISEASES

(71) Applicant: Stoke Therapeutics, Inc., Bedford, MA (US)

(72) Inventors: Isabel Aznarez, Boston, MA (US); Aditya Venkatesh, Natick, MA (US); Gene Liau, Wayland, MA (US)

(73) Assignee: STOKE THERAPEUTICS, INC., Bedford, MA (US)

( * ) Notice: Subject to any disclaimer, the term of this patent is extended or adjusted under 35 U.S.C. 154(b) by 68 days.

(21) Appl. No.: 17/924,966

(22) PCT Filed: Apr. 30, 2021

(86) PCT No.: PCT/US2021/030254

§ 371 (c)(1),
(2) Date: Nov. 11, 2022

(87) PCT Pub. No.: WO2021/231107

PCT Pub. Date: Nov. 18, 2021

(65) Prior Publication Data

US 2023/0287410 A1 Sep. 14, 2023

Related U.S. Application Data

(60) Provisional application No. 63/023,013, filed on May 11, 2020, provisional application No. 63/112,458, filed on Nov. 11, 2020.

(51) Int. Cl.

| | |
|---|---|
| ***C12N 15/113*** | (2010.01) |
| ***A61K 9/00*** | (2006.01) |
| ***A61P 27/02*** | (2006.01) |
| ***C12N 15/86*** | (2006.01) |

(52) U.S. Cl.

CPC .......... *C12N 15/113* (2013.01); *A61K 9/0048* (2013.01); *A61P 27/02* (2018.01); *C12N 15/86* (2013.01); *C12N 2310/11* (2013.01); *C12N 2310/20* (2017.05); *C12N 2310/314* (2013.01); *C12N 2310/315* (2013.01); *C12N 2310/321* (2013.01); *C12N 2750/14143* (2013.01)

(58) Field of Classification Search

None

See application file for complete search history.

(56) References Cited

U.S. PATENT DOCUMENTS

| | | | |
|---|---|---|---|
| 4,476,116 | A | 10/1984 | Anik |
| 4,522,811 | A | 6/1985 | Eppstein et al. |
| 4,866,042 | A | 9/1989 | Neuwelt |
| 5,034,506 | A | 7/1991 | Summerton et al. |
| 5,142,047 | A | 8/1992 | Summerton et al. |
| 5,151,510 | A | 9/1992 | Stec et al. |
| 5,166,315 | A | 11/1992 | Summerton et al. |
| 5,185,444 | A | 2/1993 | Summerton et al. |
| 5,217,866 | A | 6/1993 | Summerton et al. |
| 5,506,337 | A | 4/1996 | Summerton et al. |
| 5,521,063 | A | 5/1996 | Summerton et al. |
| 5,656,612 | A | 8/1997 | Monia |
| 5,665,593 | A | 9/1997 | Kole et al. |
| 5,698,685 | A | 12/1997 | Summerton et al. |
| 5,914,396 | A | 6/1999 | Cook et al. |
| 5,916,808 | A | 6/1999 | Kole et al. |
| 5,976,879 | A | 11/1999 | Kole et al. |
| 6,083,482 | A | 7/2000 | Wang |
| 6,147,200 | A | 11/2000 | Manoharan et al. |
| 6,166,197 | A | 12/2000 | Cook et al. |
| 6,210,892 | B1 | 4/2001 | Bennett et al. |
| 6,294,520 | B1 | 9/2001 | Naito |
| 6,383,752 | B1 | 5/2002 | Agrawal et al. |
| 6,391,452 | B1 | 5/2002 | Antonsen et al. |
| 6,436,657 | B1 | 8/2002 | Famodu et al. |
| 6,451,991 | B1 | 9/2002 | Martin et al. |
| 6,485,960 | B1 | 11/2002 | Harris et al. |
| 6,531,591 | B1 | 3/2003 | Fensholdt |
| 6,573,073 | B2 | 6/2003 | Harris |
| 6,605,611 | B2 | 8/2003 | Simmonds et al. |
| 6,632,427 | B1 | 10/2003 | Finiels et al. |
| 6,639,059 | B1 | 10/2003 | Kochkine et al. |
| 6,670,461 | B1 | 12/2003 | Wengel et al. |
| 6,677,445 | B1 | 1/2004 | Innis et al. |

(Continued)

FOREIGN PATENT DOCUMENTS

| | | | |
|---|---|---|---|
| AU | 2018322319 | B2 | 8/2021 |
| AU | 2016334804 | B2 | 3/2022 |

(Continued)

OTHER PUBLICATIONS

Braunschweig, Intron Retention, Supplemental Figure Legends.
Du, et al., "Downregulation of neuronal sodium channel subunits Nav. 1. and Nav1.6 in the sinoatrial node from vol. overloaded heart failure rat", Pflugers Arch—Eur J Physiol (2007) 454:451-459.
Escayg et al., Sodium channel SCN1A and epilepsy: mutations and mechanisms, Epilepsia, Sep. 2010, vol. 51, No. 9, pp. 1-16.

(Continued)

*Primary Examiner* — Brian Whiteman

(74) *Attorney, Agent, or Firm* — Wilson Sonsini Goodrich & Rosati

(57) ABSTRACT

Alternative splicing events in genes can lead to non-productive mRNA transcripts which in turn can lead to aberrant protein expression, and therapeutic agents which can target the alternative splicing events in genes can modulate the expression level of functional proteins in patients and/or inhibit aberrant protein expression. Such therapeutic agents can be used to treat a condition or disease caused by protein deficiency and/or mitochondrial function deficit.

20 Claims, 67 Drawing Sheets

Specification includes a Sequence Listing.

(56) References Cited

U.S. PATENT DOCUMENTS

| | | | |
|---|---|---|---|
| 6,734,291 B2 | 5/2004 | Kochkine et al. | |
| 6,756,523 B1 | 6/2004 | Kahn et al. | |
| 6,770,748 B2 | 8/2004 | Imanishi et al. | |
| 6,794,499 B2 | 9/2004 | Wengel et al. | |
| 6,846,921 B2 | 1/2005 | Innis et al. | |
| 6,936,589 B2 | 8/2005 | Naito | |
| 6,963,589 B1 | 11/2005 | Sugata et al. | |
| 6,998,484 B2 | 2/2006 | Koch et al. | |
| 7,015,315 B1 | 3/2006 | Cook et al. | |
| 7,034,133 B2 | 4/2006 | Wengel et al. | |
| 7,053,199 B2 | 5/2006 | Imanishi et al. | |
| 7,053,207 B2 | 5/2006 | Wengel | |
| 7,060,809 B2 | 6/2006 | Wengel et al. | |
| 7,071,324 B2 | 7/2006 | Preparata et al. | |
| 7,084,125 B2 | 8/2006 | Wengel | |
| 7,101,993 B1 | 9/2006 | Cook et al. | |
| 7,169,594 B2 | 1/2007 | Guan | |
| 7,214,783 B2 | 5/2007 | Jeon et al. | |
| 7,217,805 B2 | 5/2007 | Imanishi et al. | |
| 7,314,923 B2 | 1/2008 | Kaneko et al. | |
| 7,335,765 B2 | 2/2008 | Kaneko et al. | |
| 7,368,549 B2 | 5/2008 | Dempcy et al. | |
| 7,399,845 B2 | 7/2008 | Seth et al. | |
| 7,432,249 B2 | 10/2008 | Crooke | |
| 7,432,250 B2 | 10/2008 | Crooke | |
| 7,547,684 B2 | 6/2009 | Seth et al. | |
| 7,553,644 B2 | 6/2009 | Germino et al. | |
| 7,569,575 B2 | 8/2009 | Soerensen et al. | |
| 7,569,686 B1 | 8/2009 | Bhat et al. | |
| 7,572,582 B2 | 8/2009 | Wengel et al. | |
| 7,595,304 B2 | 9/2009 | Zhao et al. | |
| 7,615,619 B2 | 11/2009 | Imanishi et al. | |
| 7,662,946 B2 | 2/2010 | Ginsburg et al. | |
| 7,662,948 B2 | 2/2010 | Kurreck et al. | |
| 7,666,854 B2 | 2/2010 | Seth et al. | |
| 7,687,617 B2 | 3/2010 | Thrue et al. | |
| 7,696,345 B2 | 4/2010 | Allerson et al. | |
| 7,741,457 B2 | 6/2010 | Seth et al. | |
| 7,750,131 B2 | 7/2010 | Seth et al. | |
| 7,816,333 B2 | 10/2010 | Kaneko et al. | |
| 7,846,686 B2 | 12/2010 | Kramer | |
| 7,951,934 B2 | 5/2011 | Freier | |
| 7,994,145 B2 | 8/2011 | Imanishi et al. | |
| 8,022,193 B2 | 9/2011 | Seth et al. | |
| 8,030,467 B2 | 10/2011 | Seth et al. | |
| 8,048,998 B2 | 11/2011 | Rasmussen et al. | |
| 8,067,569 B2 | 11/2011 | Iversen et al. | |
| 8,084,458 B2 | 12/2011 | Soerensen et al. | |
| 8,088,746 B2 | 1/2012 | Seth et al. | |
| 8,090,542 B2 | 1/2012 | Khvorova et al. | |
| 8,110,674 B2 | 2/2012 | Manoharan et al. | |
| 8,124,745 B2 | 2/2012 | Allerson et al. | |
| 8,129,515 B2 | 3/2012 | Esau et al. | |
| 8,168,605 B2 | 5/2012 | Zhao et al. | |
| 8,258,109 B2 | 9/2012 | Bennett et al. | |
| 8,268,980 B2 | 9/2012 | Seth et al. | |
| 8,278,036 B2 | 10/2012 | Kariko et al. | |
| 8,278,283 B2 | 10/2012 | Seth et al. | |
| 8,278,425 B2 | 10/2012 | Prakash et al. | |
| 8,278,426 B2 | 10/2012 | Seth et al. | |
| 8,293,684 B2 | 10/2012 | Mouritzen et al. | |
| 8,361,979 B2 | 1/2013 | Aartsma-Rus et al. | |
| 8,383,792 B2 | 2/2013 | Okamoto et al. | |
| 8,394,947 B2 | 3/2013 | Bhat et al. | |
| 8,415,465 B2 | 4/2013 | Freier | |
| 8,436,163 B2 | 5/2013 | Iversen et al. | |
| 8,450,467 B2 | 5/2013 | Manoharan et al. | |
| 8,461,124 B2 | 6/2013 | Chattopadhyaya | |
| 8,492,390 B2 | 7/2013 | Detlef et al. | |
| 8,501,703 B2 | 8/2013 | Bennett et al. | |
| 8,501,805 B2 | 8/2013 | Seth et al. | |
| 8,518,908 B2 | 8/2013 | Hrdlicka et al. | |
| 8,530,640 B2 | 9/2013 | Seth et al. | |
| 8,541,562 B2 | 9/2013 | Obika et al. | |
| 8,546,556 B2 | 10/2013 | Seth et al. | |
| 8,592,156 B2 | 11/2013 | Liu et al. | |
| 8,637,478 B2 | 1/2014 | Bennett | |
| RE44,779 E | 2/2014 | Imanishi et al. | |
| 8,653,252 B2 | 2/2014 | Elmen et al. | |
| 8,673,560 B2 | 3/2014 | Leamon et al. | |
| 8,680,254 B2 | 3/2014 | Lutz et al. | |
| 8,691,783 B2 | 4/2014 | Thum et al. | |
| 8,703,728 B2 | 4/2014 | Swayze et al. | |
| 8,710,021 B2 | 4/2014 | Anro et al. | |
| 8,735,366 B2 | 5/2014 | Bauer et al. | |
| 8,748,089 B2 | 6/2014 | Kariko et al. | |
| 8,779,118 B2 | 7/2014 | Allerson et al. | |
| 8,796,437 B2 | 8/2014 | Swayze et al. | |
| 8,809,516 B2 | 8/2014 | Manoharan et al. | |
| 8,846,386 B2 | 9/2014 | Ambati et al. | |
| 8,846,637 B2 | 9/2014 | Seth et al. | |
| 8,846,639 B2 | 9/2014 | Swayze et al. | |
| 8,846,885 B2 | 9/2014 | Hirai et al. | |
| 8,895,722 B2 | 11/2014 | Iversen et al. | |
| 8,957,040 B2 | 2/2015 | Bennett et al. | |
| 8,957,200 B2 | 2/2015 | Seth et al. | |
| 8,957,201 B2 | 2/2015 | Kaneko et al. | |
| 9,005,906 B2 | 4/2015 | Swayze et al. | |
| 9,006,194 B2 | 4/2015 | Katsikis et al. | |
| 9,006,415 B2 | 4/2015 | Ren et al. | |
| 9,012,139 B2 | 4/2015 | Collard et al. | |
| 9,029,335 B2 | 5/2015 | Prakash et al. | |
| 9,045,518 B2 | 6/2015 | Christensen et al. | |
| 9,045,754 B2 | 6/2015 | Bhanot et al. | |
| 9,057,066 B2 | 6/2015 | Hung et al. | |
| 9,109,001 B2 | 8/2015 | Parsy et al. | |
| 9,127,272 B2 | 9/2015 | Esau et al. | |
| 9,127,276 B2 | 9/2015 | Prakash et al. | |
| 9,156,873 B2 | 10/2015 | Prakash et al. | |
| 9,157,081 B2 | 10/2015 | Bennett et al. | |
| 9,181,549 B2 | 11/2015 | Prakash et al. | |
| 9,187,515 B2 | 11/2015 | Mayes et al. | |
| 9,192,621 B2 | 11/2015 | Mayes et al. | |
| 9,193,752 B2 | 11/2015 | Migawa et al. | |
| 9,193,969 B2 | 11/2015 | Montefeltro et al. | |
| 9,211,300 B2 | 12/2015 | Mayes et al. | |
| 9,217,147 B2 | 12/2015 | Singh et al. | |
| 9,221,864 B2 | 12/2015 | Seth et al. | |
| 9,243,245 B2 | 1/2016 | De Kimpe et al. | |
| 9,290,534 B2 | 3/2016 | Seth et al. | |
| 9,296,778 B2 | 3/2016 | Parsy et al. | |
| 9,309,275 B2 | 4/2016 | Stewart et al. | |
| 9,315,535 B2 | 4/2016 | Mitsuoka et al. | |
| 9,334,495 B2 | 5/2016 | Khvorova et al. | |
| 9,339,541 B2 | 5/2016 | Dousson et al. | |
| 9,347,068 B2 | 5/2016 | Dhugga et al. | |
| 9,359,445 B2 | 6/2016 | Finkbeiner et al. | |
| 9,359,603 B2 | 6/2016 | Lutz et al. | |
| 9,359,609 B2 | 6/2016 | Duffield et al. | |
| 9,410,155 B2 | 8/2016 | Collard et al. | |
| 9,428,534 B2 | 8/2016 | Christensen et al. | |
| 9,447,166 B2 | 9/2016 | Ambati et al. | |
| 9,453,261 B2 | 9/2016 | Lee et al. | |
| 9,464,292 B2 | 10/2016 | Okumura et al. | |
| 9,499,818 B2 | 11/2016 | Van Deutekom | |
| 9,518,259 B2 | 12/2016 | Rigo et al. | |
| 9,534,222 B2 | 1/2017 | Ambati et al. | |
| 9,550,988 B2 | 1/2017 | Swayze | |
| 9,714,422 B2 | 7/2017 | Vorechovsky et al. | |
| 9,745,577 B2 | 8/2017 | Vorechovsky et al. | |
| 9,771,579 B2 | 9/2017 | Collard et al. | |
| 9,914,922 B2 | 3/2018 | Freier et al. | |
| 9,976,143 B2 | 5/2018 | Krainer et al. | |
| 10,119,168 B2 | 11/2018 | Vaidya et al. | |
| 10,196,639 B2 | 2/2019 | Vorechovsky et al. | |
| 10,517,853 B2 | 12/2019 | Welch et al. | |
| 10,583,128 B2 | 3/2020 | Collard et al. | |
| 10,683,503 B2 | 6/2020 | Aznarez et al. | |
| 10,696,969 B2 | 6/2020 | Krainer et al. | |
| 10,906,931 B2 * | 2/2021 | Moghadam | C07H 21/04 |
| 10,913,947 B2 | 2/2021 | Aznarez et al. | |
| 10,941,405 B2 | 3/2021 | Vorechovsky et al. | |
| 11,083,745 B2 | 8/2021 | Aznarez et al. | |
| 11,096,956 B2 | 8/2021 | Aznarez et al. | |

(56) References Cited

U.S. PATENT DOCUMENTS

| | | | |
|---|---|---|---|
| 11,390,869 B2 | 7/2022 | Vorechovsky et al. | |
| 11,702,660 B2 | 7/2023 | Vorechovsky et al. | |
| 11,814,622 B2 | 11/2023 | Aznarez et al. | |
| 11,873,490 B2 | 1/2024 | Aznarez et al. | |
| 11,891,605 B2 | 2/2024 | Vorechovsky et al. | |
| 2003/0087861 A1 | 5/2003 | Iversen | |
| 2003/0148974 A1 | 8/2003 | Monia et al. | |
| 2004/0063129 A1 | 4/2004 | Gaarde et al. | |
| 2004/0102401 A1 | 5/2004 | Dean et al. | |
| 2004/0219515 A1 | 11/2004 | Bentwich | |
| 2005/0221354 A1 | 10/2005 | Mounts | |
| 2005/0233327 A1 | 10/2005 | Welch et al. | |
| 2005/0244851 A1* | 11/2005 | Blume | C12Q 1/6876 435/287.2 |
| 2006/0062790 A1 | 3/2006 | Reinhard et al. | |
| 2006/0134670 A1 | 6/2006 | Piu | |
| 2006/0166922 A1 | 7/2006 | Eichler et al. | |
| 2007/0009899 A1 | 1/2007 | Mounts | |
| 2007/0087376 A1 | 4/2007 | Potashkin | |
| 2007/0249538 A1 | 10/2007 | Sazani et al. | |
| 2008/0269123 A1 | 10/2008 | Li et al. | |
| 2009/0186846 A1 | 7/2009 | Chabot et al. | |
| 2009/0186946 A1 | 7/2009 | Taketomi et al. | |
| 2009/0264353 A1 | 10/2009 | Orum et al. | |
| 2009/0270332 A1 | 10/2009 | Bare et al. | |
| 2010/0016215 A1 | 1/2010 | Moulton et al. | |
| 2010/0088778 A1 | 4/2010 | Mulley et al. | |
| 2010/0111935 A1 | 5/2010 | Bhagat et al. | |
| 2010/0150839 A1 | 6/2010 | Kelleher | |
| 2010/0166784 A1 | 7/2010 | Murphy et al. | |
| 2011/0124591 A1 | 5/2011 | Bennett | |
| 2011/0229891 A1 | 9/2011 | Michaud et al. | |
| 2012/0157512 A1 | 6/2012 | Ben-Chanoch et al. | |
| 2012/0190728 A1 | 7/2012 | Bennett et al. | |
| 2012/0252877 A1 | 10/2012 | Lo | |
| 2013/0072671 A1 | 3/2013 | Van Deutekom | |
| 2013/0096183 A1 | 4/2013 | Collard et al. | |
| 2013/0109850 A1 | 5/2013 | Prakash et al. | |
| 2013/0136732 A1 | 5/2013 | Wagner et al. | |
| 2013/0184223 A1 | 7/2013 | Land et al. | |
| 2013/0253036 A1 | 9/2013 | Collard et al. | |
| 2013/0266560 A1 | 10/2013 | Demopulos et al. | |
| 2013/0289092 A1 | 10/2013 | Rigo et al. | |
| 2014/0011761 A1 | 1/2014 | Hotamisligil et al. | |
| 2014/0128449 A1 | 5/2014 | Liu et al. | |
| 2014/0154783 A1 | 6/2014 | Rossomando et al. | |
| 2014/0186839 A1 | 7/2014 | Margulies et al. | |
| 2014/0194610 A1 | 7/2014 | Verdine et al. | |
| 2014/0235605 A1 | 8/2014 | Shiffman et al. | |
| 2014/0309181 A1 | 10/2014 | Collard et al. | |
| 2014/0336238 A1 | 11/2014 | Collin et al. | |
| 2014/0343127 A1 | 11/2014 | Kammler | |
| 2014/0349290 A1 | 11/2014 | Watnick et al. | |
| 2014/0378526 A1 | 12/2014 | Rossi et al. | |
| 2014/0378527 A1 | 12/2014 | Van Deutekom | |
| 2014/0378533 A1 | 12/2014 | Freier | |
| 2015/0004217 A1 | 1/2015 | Guild et al. | |
| 2015/0018540 A1 | 1/2015 | Prakash et al. | |
| 2015/0184153 A1 | 7/2015 | Freier et al. | |
| 2015/0211006 A1 | 7/2015 | Butler et al. | |
| 2015/0211010 A1 | 7/2015 | Kerem et al. | |
| 2015/0232845 A1 | 8/2015 | Ozsolak | |
| 2015/0232858 A1 | 8/2015 | Ozsolak | |
| 2015/0238516 A1 | 8/2015 | Dowdy et al. | |
| 2015/0267192 A1 | 9/2015 | Heartlein et al. | |
| 2015/0291957 A1 | 10/2015 | Smith | |
| 2015/0329918 A1 | 11/2015 | Kang et al. | |
| 2015/0337310 A1 | 11/2015 | Walker et al. | |
| 2015/0361497 A1 | 12/2015 | Rose | |
| 2016/0017322 A1 | 1/2016 | Vorechovsky et al. | |
| 2016/0024500 A1 | 1/2016 | Popplewell et al. | |
| 2016/0046935 A1 | 2/2016 | Bentwich et al. | |
| 2016/0122767 A1 | 5/2016 | Gouya et al. | |
| 2016/0201063 A1 | 7/2016 | Ozsolak | |
| 2016/0201064 A1 | 7/2016 | Ozsolak | |
| 2016/0208264 A1 | 7/2016 | Wilton et al. | |
| 2016/0215291 A1 | 7/2016 | Garcia et al. | |
| 2016/0244762 A1 | 8/2016 | Vorechovsky et al. | |
| 2016/0244767 A1 | 8/2016 | Hastings | |
| 2016/0298121 A1 | 10/2016 | Krainer et al. | |
| 2017/0044540 A1 | 2/2017 | Sætrom et al. | |
| 2017/0159049 A9 | 6/2017 | Krainer et al. | |
| 2017/0240904 A1 | 8/2017 | Tallent et al. | |
| 2018/0002694 A1 | 1/2018 | Vorechovsky et al. | |
| 2018/0201937 A1 | 7/2018 | Gomez et al. | |
| 2018/0296501 A1 | 10/2018 | During | |
| 2018/0346907 A1 | 12/2018 | Crooke et al. | |
| 2018/0362987 A1 | 12/2018 | Krainer et al. | |
| 2018/0369275 A1 | 12/2018 | Arnarez et al. | |
| 2019/0024118 A1 | 1/2019 | Tagliatela et al. | |
| 2019/0024119 A1 | 1/2019 | Tagliatela et al. | |
| 2019/0024120 A1 | 1/2019 | Tagliatela et al. | |
| 2019/0024121 A1 | 1/2019 | Tagliatela et al. | |
| 2019/0070213 A1 | 3/2019 | Aznarez et al. | |
| 2019/0192691 A1 | 6/2019 | Barrett et al. | |
| 2019/0218255 A1 | 7/2019 | Chung et al. | |
| 2019/0225939 A1 | 7/2019 | Chambers et al. | |
| 2019/0264211 A1 | 8/2019 | Vorechovsky et al. | |
| 2020/0085838 A1 | 3/2020 | Martinez Botella et al. | |
| 2020/0101174 A1 | 4/2020 | Coller et al. | |
| 2020/0399640 A1 | 12/2020 | Gottesman et al. | |
| 2021/0087238 A1 | 3/2021 | Hoffmann et al. | |
| 2021/0108208 A1 | 4/2021 | Krainer et al. | |
| 2021/0155936 A1 | 5/2021 | Vorechovsky | |
| 2021/0261963 A1 | 8/2021 | Uno et al. | |
| 2021/0268667 A1* | 9/2021 | Aznarez | A61K 48/005 |
| 2021/0309996 A1 | 10/2021 | Aznarez et al. | |
| 2021/0317462 A1 | 10/2021 | Petrou | |
| 2022/0162605 A1 | 5/2022 | Aznarez | |
| 2023/0116704 A1 | 4/2023 | Aznarez et al. | |
| 2023/0183693 A1 | 6/2023 | Vorechovsky et al. | |
| 2023/0250429 A1 | 8/2023 | Aznarez et al. | |
| 2023/0287410 A1 | 9/2023 | Aznarez et al. | |
| 2023/0416756 A1 | 12/2023 | Vorechovsky et al. | |
| 2024/0033378 A1 | 2/2024 | Aznarez et al. | |
| 2024/0102011 A1 | 3/2024 | Aznarez et al. | |
| 2024/0150760 A1 | 5/2024 | Aznarez et al. | |
| 2024/0254488 A1 | 8/2024 | Aznarez et al. | |
| 2024/0309377 A1 | 9/2024 | Vorechovsky et al. | |
| 2025/0059535 A1 | 2/2025 | Aznarez et al. | |

FOREIGN PATENT DOCUMENTS

| | | | |
|---|---|---|---|
| AU | 2022204606 | A1 | 7/2022 |
| CN | 102171342 | A | 8/2011 |
| CN | 103667438 | A | 3/2014 |
| CN | 109312343 | A | 2/2019 |
| CN | 111278991 | A | 6/2020 |
| CN | 111518898 | A | 8/2020 |
| EP | 0549615 | A1 | 7/1993 |
| EP | 1281758 | A2 | 2/2003 |
| EP | 1201678 | B1 | 9/2004 |
| EP | 1409497 | B1 | 1/2005 |
| EP | 1579015 | A2 | 9/2005 |
| EP | 1007714 | B1 | 12/2005 |
| EP | 1334109 | B1 | 5/2006 |
| EP | 1178999 | B1 | 3/2007 |
| EP | 1203827 | B1 | 5/2007 |
| EP | 1501848 | B1 | 8/2007 |
| EP | 1569661 | B1 | 9/2009 |
| EP | 1161439 | B1 | 4/2010 |
| EP | 1984381 | B1 | 9/2010 |
| EP | 2284269 | A2 | 2/2011 |
| EP | 1013661 | B1 | 1/2012 |
| EP | 2092065 | B1 | 1/2012 |
| EP | 2099461 | B1 | 3/2012 |
| EP | 2170917 | B1 | 6/2012 |
| EP | 2066684 | B1 | 7/2012 |
| EP | 2356129 | B1 | 4/2013 |
| EP | 2376516 | B1 | 4/2013 |
| EP | 2114981 | B1 | 5/2013 |
| EP | 2149605 | B1 | 7/2013 |
| EP | 2285819 | B1 | 10/2013 |
| EP | 2161038 | B1 | 12/2013 |

(56) References Cited

FOREIGN PATENT DOCUMENTS

| | | | |
|---|---|---|---|
| EP | 1562971 | B1 | 2/2014 |
| EP | 2295441 | B1 | 5/2014 |
| EP | 2314594 | B1 | 7/2014 |
| EP | 2410053 | B1 | 10/2014 |
| EP | 2176280 | B2 | 6/2015 |
| EP | 2361921 | B1 | 6/2015 |
| EP | 2462153 | B1 | 7/2015 |
| EP | 1015469 | B2 | 11/2015 |
| EP | 2173760 | B2 | 11/2015 |
| EP | 1937312 | B1 | 6/2016 |
| EP | 2141233 | B1 | 10/2016 |
| EP | 2410054 | B1 | 1/2017 |
| EP | 3329909 | A1 | 6/2018 |
| EP | 3359685 | A1 | 8/2018 |
| EP | 2753317 | B1 | 2/2020 |
| EP | 3673080 | A1 | 7/2020 |
| EP | 3700570 | A1 | 9/2020 |
| EP | 3155124 | B1 | 11/2021 |
| EP | 4015648 | A1 | 6/2022 |
| EP | 4069256 | A1 | 10/2022 |
| GB | 1517937 | A | 7/1978 |
| GB | 2546719 | A | 8/2017 |
| JP | 2007534772 | A | 11/2007 |
| JP | 6923517 | B2 | 8/2021 |
| JP | 2021180669 | A | 11/2021 |
| KR | 20130026484 | A | 3/2013 |
| WO | WO-9402501 | A1 | 2/1994 |
| WO | WO-9426887 | A1 | 11/1994 |
| WO | WO-9747772 | A2 | 12/1997 |
| WO | WO-0010608 | A1 | 3/2000 |
| WO | WO-0107660 | A1 | 2/2001 |
| WO | WO-2005049651 | A2 | 6/2005 |
| WO | WO-2006107846 | A2 | 10/2006 |
| WO | WO-2007002390 | A2 | 1/2007 |
| WO | WO-2007048628 | A2 | 5/2007 |
| WO | WO-2007048629 | A2 | 5/2007 |
| WO | WO-2007056113 | A2 | 5/2007 |
| WO | WO-2008036127 | A2 | 3/2008 |
| WO | WO-2009003694 | A2 | 1/2009 |
| WO | WO-2009084472 | A1 | 7/2009 |
| WO | WO-2009099942 | A2 | 8/2009 |
| WO | WO-2010148249 | A1 | 12/2010 |
| WO | WO-2011057350 | A1 | 5/2011 |
| WO | WO-2011163499 | A2 | 12/2011 |
| WO | WO-2012168435 | A1 | 12/2012 |
| WO | WO-2012178146 | A1 | 12/2012 |
| WO | WO-2013036105 | A1 | 3/2013 |
| WO | WO-2013081755 | A1 | 6/2013 |
| WO | WO-2013106770 | A1 | 7/2013 |
| WO | WO-2013119916 | A2 | 8/2013 |
| WO | WO-2014012081 | A2 | 1/2014 |
| WO | WO-201428459 | A1 | 2/2014 |
| WO | WO-2014028459 | A1 | 2/2014 |
| WO | WO-2014031575 | A1 | 2/2014 |
| WO | WO-2014049536 | A2 | 4/2014 |
| WO | WO-2014121287 | A2 | 8/2014 |
| WO | WO-2014172698 | A1 | 10/2014 |
| WO | WO-2014201413 | A1 | 12/2014 |
| WO | WO-2014209841 | A2 | 12/2014 |
| WO | WO-2015024876 | A2 | 2/2015 |
| WO | WO-2015035091 | A1 | 3/2015 |
| WO | WO-2015190922 | A1 | 12/2015 |
| WO | WO-2015193651 | A1 | 12/2015 |
| WO | WO-2015198054 | A1 | 12/2015 |
| WO | WO-2016022914 | A1 | 2/2016 |
| WO | WO-2016027168 | A2 | 2/2016 |
| WO | WO-2016054615 | A2 | 4/2016 |
| WO | WO-2016061509 | A1 | 4/2016 |
| WO | WO-2016077837 | A1 | 5/2016 |
| WO | WO-2016081885 | A2 | 5/2016 |
| WO | WO-2016087842 | A1 | 6/2016 |
| WO | WO-2016118697 | A1 | 7/2016 |
| WO | WO-2016128343 | A1 | 8/2016 |
| WO | WO-2016138534 | A2 | 9/2016 |
| WO | WO-2016161429 | A1 | 10/2016 |
| WO | WO-2016196386 | A1 | 12/2016 |
| WO | WO-2017053982 | A1 | 3/2017 |
| WO | WO-2017060731 | A1 | 4/2017 |
| WO | WO-2017106210 | A1 | 6/2017 |
| WO | WO-2017106211 | A1 | 6/2017 |
| WO | WO-2017106283 | A1 | 6/2017 |
| WO | WO-2017106292 | A1 | 6/2017 |
| WO | WO-2017106364 | | 6/2017 |
| WO | WO-2017106364 | A2 | 6/2017 |
| WO | WO-2017106370 | A1 | 6/2017 |
| WO | WO-2017106375 | A1 | 6/2017 |
| WO | WO-2017106377 | A1 | 6/2017 |
| WO | WO-2017106382 | A1 | 6/2017 |
| WO | WO-2018007980 | A1 | 1/2018 |
| WO | WO-2018187363 | A1 | 10/2018 |
| WO | WO-2018191482 | A2 | 10/2018 |
| WO | WO-2018206924 | A1 | 11/2018 |
| WO | WO-2019040923 | A1 | 2/2019 |
| WO | WO-2019084050 | A1 | 5/2019 |
| WO | WO-2019109051 | A1 | 6/2019 |
| WO | WO-2019191341 | A1 | 10/2019 |
| WO | WO-2019199867 | A1 | 10/2019 |
| WO | WO-2019224864 | A1 | 11/2019 |
| WO | WO-2019227096 | A1 | 11/2019 |
| WO | WO-2019236750 | A2 | 12/2019 |
| WO | WO-2019243430 | A1 | 12/2019 |
| WO | WO-2020041348 | A1 | 2/2020 |
| WO | WO-2020176776 | A1 | 9/2020 |
| WO | WO-2020237294 | A1 | 12/2020 |
| WO | WO-2021113541 | A1 | 6/2021 |
| WO | WO-2021119756 | A1 | 6/2021 |
| WO | WO-2021231107 | A1 | 11/2021 |
| WO | WO-2022067398 | A1 | 4/2022 |
| WO | WO-2023028575 | A2 | 3/2023 |
| WO | WO-2023086342 | | 5/2023 |
| WO | WO-2023141681 | A1 | 8/2023 |
| WO | WO-2023178386 | A1 | 9/2023 |
| WO | WO-2024026122 | A2 | 2/2024 |
| WO | WO-2024173582 | A2 | 8/2024 |
| WO | WO-2024249949 | | 12/2024 |

OTHER PUBLICATIONS

Han Zhou et al: "Antisense-Mediated Increase of SCN1A Expression Using TANGO Technology for the Treatment of Dravet Syndrome", Molecular Therapy, vol. 27, No. 4, Suppl. 1, Apr. 22, 2019 (Apr. 22, 2019), pp. 304-305.

Hug, et al., "Mechanism and regulation of the nonsense-mediated decay pathway", Nucleic Acids Research, 2016, vol. 44, No. 4 1483-1495.

International search report and written opinion dated Jun. 26, 2020 for PCT Application No. PCT/US20/20175.

International Search Report and Written Opinion for corresponding PCT application PCT/GB2016/053136 issued Jan. 19, 2017.

Kwong et al. Identification of SCN1A and PCDH19 Mutations in Chinese Children with Dravet Syndrome. PloS one, vol. 7, Issue, 7, Jul. 2012: e41802.

Le Gal, et al., "A case of SUDEP in a patient with Dravet syndrome with SCNIA mutation" (2010) Epilepsia, 5199): 1915-1918.

Mantegazza et al., Identification of a Nav1.1 sodium channel (SCN1A) loss-of-function mutation associated with familial simple febrile seizures, PNAS, Dec. 13, 2005, vol. 102, No. 50, p. 18177-18182.

Martinez-Losa, et al." Nav1.1-Overexpressing Interneuron Transplants Restore Brain Tyhthms and Cognition in a Mouse Model of Alzheimer's Disease", Neuron. Apr. 4, 2018; 98(1): 75-89..

Menzi, et al., "Towards Improved Oligonucleotide Therapeutics Through Faster Target Binding Kinetics", (2017) ChemPubSoc Europe, 23, p. 14221-14230.

Office Action issued in European Patent Application No. 18871437.2 dated Sep. 12, 2023.

Ogiwara et al. Nav1.1 Localizes to Axons of Parvalbumin-Positive Inhibitory Interneurons: A Circuit Basis for Epileptic Seizures in Mice Carrying an Scn1a Gene Mutation. The Journal of Neuroscience 27(22):5903-5914 (May 30, 2007).

(56) References Cited

OTHER PUBLICATIONS

Parihar, et al., "The SCN1A gene variants and epileptic encephalophathies", Journal of Human Genetics (2013) 58, 573-580.
Raghavan, et al., "The spliceosomal U1 snRNP component Mud1 is autoregulated by promoting premature cleavage and polyadenylation of its own transcript", The Nineteenth Annual Meeting of the RNA Society.
Scheffer, et al., "SCN1A-related pehnotypes: Epilepsy and beyond" Epilepsia (2019);60(s3):S17-S24.
Vacher, et al., "ATM has a major role in the double-strand break repair pathway dysregulation in sporadic breast carcinomas and is an independent prognostic marker at both mRNA and protein levels", (2015), Br J Cancer 112: 1059-1066.
Van Wart, et al., "Imparied Firing an dCell-Specific compensation in Neurons Lacking Navv1.6 sodium Channels" The Journal of Neuroscience, (2006), 26(27):7172-7180.
Vickers, et al., "Fully modified 2' MOE oligonucleotides redirect polyadenylation", Isis Pharmaceuticals, Department of Molecular and Structural Biology, Nucleic Acids Research, 2001, vol. 29, No. 6 p. 1293-1299.
Vorechovsky, "Modulating Splicing-Mediated gene expression using antisense technology", Southhampton.sc.uk/business.
Weiss, et al., "Sodium channels SCN1A, SCN2A, SCN3A in familial autism", (2003) 8, p. 186-194.
Aartsma-Rus et al.: Antisense-mediated exon skipping: a versatile tool with therapeutic and research applications. RNA 13(10):1609-24 (2007). Epub Aug. 7, 2007.
Aceti et al.: Syngap1 haploinsufficiency damages a postnatal critical period of pyramidal cell structural maturation linked to cortical circuit assembly, Biol Psychiatry 77(9):805-815 (2015).
Aizer et al.: Lack of reduction in racial disparities in cancer-specific mortality over a 20-year period. Cancer 120:1532-9 (2014).
Altschul et al.: Basic local alignment search tool. J. Mol. Biol. 215(3)403-410 (1990).
Altschul et al.: Iterated profile searches with PSI-BLAST-a tool for discovery in protein databases. J. Mol. Biol. 215:403-410 (1990).
Aly et al.: Extreme genetic risk for type 1A diabetes. Proc Natl Acad Sci U.S.A. 103(38): 14074-9 (2006). Epub Sep. 11, 2006.
Amarnath et al.: The PDL1-PD1 Axis Converts Human TH1 Cells into Regulatory T Cells. Science Translational Medicine 3(111):1-13 (2011).
Anders et al.: Detecting differential usage of exons from RNA-seq data. Genome Res. 22(10):2008-17 (2012). Epub Jun. 23, 2012. doi: gr.133744.111 [pii] 10.1101/gr.133744.111. PubMed PMID: 22722343.
Au et al.: Molecular Genetic Basis of Tuberous Sclerosis Complex: From Bench to Bedside. Journal of Child Neurology 19:9 (2004).
Audentes Therapeutics Announces Expansion of AAV Technology Platform and Pipeline with New Development Programs for Duchenne Muscular Dystrophy and Myotonic Dystrophy. PRNewswire Apr. 8, 2019 (7 pgs).
Aznarez et al.: TANGO—Targeted augmentation of nuclear gene output—for the treatment of genetic diseases [abstract]. In: 2018 Annual Meeting Abstract of the American Society of Gene and Cell Therapy, May 16-19, 2018, Chicago, IL (2018), Abstract No. 304.
Bakkenist et al.: DNA damage activates ATM through intermolecular autophosphorylation and dimer dissociation. Nature 421(6922):499-506 (2003). doi: 10.1038/nature01368. PubMed PMID: 12556884.
Balagurumoorthy et al.: Hairpin and parallel quartet structures for telomeric sequences. Nucleic Acids Res. 20(15):4061-7 (1992).
Balkwill et al.: Repression of translation of human estrogen receptor alpha by G-quadruplex formation. Biochemistry 48(48):11487-95 (2009). doi: 10.1021/bi901420k.
Barratt et al.: Remapping the insulin gene/IDDM2 locus in type 1 diabetes. Diabetes 53(7):1884-9 (2004).
Bassi et al.: A novel mutation in the ATP1A2 gene causes alternating hemiplegia of childhood. J. Med. Genet. 41:621-628 (2004).
Battistini et al.: A new CACNA1A gene mutation in acetazolamide-responsive familial hemiplegic migraine and ataxia. Neurology 53(1):38-43 (1999).

Baughan et al.: Delivery of bifunctional RNAs that target an intronic repressor and increase SMN levels in an animal model of spinal muscular atrophy. Hum Mol Genet. 18(9):1600-11 (2009). doi: 10.1093/hmg/ddp076. Epub Feb. 19, 2009.
Bauman et al.: Therapeutic potential of splice-switching oligonucleotides. Oligonucleotides 19.1:1-13 (2009).
Beaudoin et al.: 5'-UTR G-quadruplex structures acting as translational repressors. Nucleic Acids Res. 38(20):7022-36 (2010). doi: 10.1093/nar/gkq557. Epub Jun. 22, 2010.
Beli et al.: Proteomic investigations reveal a role for RNA processing factor THRAP3 in the DNA damage response. Mol Cell. 46(2):212-25 (2012). doi: 10.1016/j.molcel.2012.01.026. PubMed PMID: 22424773; PubMed Central PMCID: PMC3565437.
Berge et al.: Pharmaceutical Salts. J. Pharmaceutical Sciences 66(1):1-19 (1977).
Berger et al.: The molecular basis of human retinal and vitreoretinal diseases. Progress in Retinal and Eye Research 29:335-375 (2010).
Bethke et al.: Comprehensive analysis of the role of DNA repair gene polymorphisms on risk of glioma. Hum Mol Genet. 17(6):800-5 (2008). Epub Dec. 1, 2007.doi: ddm351 [pii] 10.1093/hmg/ddm351. PubMed PMID: 18048407.
Bicknell et al.: Introns in UTRs: why we should stop ignoring them. Bioessays 34(12):1025-34 (2012). doi: 10.1002/bies.201200073. Epub Oct. 26, 2012.
Blencowe, Benjamin: Reflections for the 20th anniversary issue of RNA journal. RNA Journal 21(4):573-575 (2015).
Blencowe BJ: Splicing regulation: the cell cycle connection. Curr. Biol. 13(4):R149-51 (2003). PubMed PMID: 12593819.
Bolognini et al.: Characterization of two novel intronic OPA1 mutations resulting in aberrant pre-mRNA splicing. BMC Medical Genetics 18:22 (2017).
Bonifert et al.: Antisense Oligonucleotide Mediated Splice Correction of a Deep Intronic Mutation in OPA1. Molecular Therapy-Nucleic Acids, vol. 5 (2016).
Bonifert et al.: Pure and syndromic optic atrophy explained by deep intronic OPA1 mutations and an intralocus modifier. Brain 137(8):2164-2177 (2014).
Bonnen et al.: Haplotypes at ATM identify coding-sequence variation and indicate a region of extensive linkage disequilibrium. Am J Hum Genet. 67(6):1437-51 (2000). Epub Nov. 15, 2000.doi: S0002-9297(07)63213-3 [pii] 10.1086/316908. PubMed PMID: 11078475.
Boothby et al.: Removal of Retained Introns Regulates Translation in the Rapidly Developing Gametophyte of Marsilea vestita. Developmental Cell 24:517-529 (2013).
Booy et al.: The RNA helicase Rhau (DHX36) unwinds a G4-quadruplex in human telomerase RNA and promotes the formation of the P1 helix template boundary. Nucleic Acids Res. (9):4110-24 (2012). doi: 10.1093/nar/gkr1306. Epub Jan. 11, 2012.
Boutz et al.: Detained introns are a novel, widespread class of post-transcriptionally spliced introns. Genes Dev. 29(1):63-80 (2015). doi: 10.1101/gad.247361.114.
Braunschweig et al.: Widespread intron retention in mammals functionally tunes transcriptomes. Widespread intron retention in mammals functionally tunes transcriptomes. Genome Res. 24(11):1774-86 (2014). doi: 10.1101/gr.177790.114. Epub Sep. 25, 2014.
Bravo-Gil et al.: Improving the management of Inherited Retinal Dystrophies by targeted sequencing of a population-specific gene panel. Scientific Reports 6:23910, 10 pages (2015).
Brooks et al.: A pan-cancer analysis of transcriptome changes associated with somatic mutations in U2AF1 reveals commonly altered splicing events. PLoS One. 9(1): e87361 (2014). Epub Feb. 6, 2014.doi: 10.1371/journal.pone.0087361 PONE-D-13-26905 [pii]. PubMed PMID: 24498085.
Buchman et al.: Comparison of intron-dependent and intron-independent gene expression. Mol Cell Biol. 8(10):4395-405 (1988).
Buckley et al.: Cytoplasmic intron retention, function, splicing, and the sentinel RNA hypothesis. WIREs RNA 5:223-2330 (2014).
Bugaut et al.: 5'-UTR Rna G-quadruplexes: translation regulation and targeting. Nucleic Acids Res. 40(11):4727-41 (2012). doi: 10.1093/nar/gks068. Epub Feb. 20, 2012.

(56) References Cited

OTHER PUBLICATIONS

Bugaut et al.: An RNA hairpin to G-quadruplex conformational transition. J Am Chem Soc. 134(49):19953-6 (2012). doi: 10.1021/ja308665g. Epub Nov. 29, 2012.
Buratti et al.: DBASS3 and DBASS5: databases of aberrant 3'- and 5'-splice sites. Nucleic Acids Res. 39(Database issue):D86-91 (2011). doi: 10.1093/nar/gkq887. Epub Oct. 6, 2010.
Buratti et al.: RNA folding affects the recruitment of SR proteins by mouse and human polypurinic enhancer elements in the fibronectin EDA exon. Mol Cell Biol. 24(3):1387-400 (2004).
Burnette et al.: Subdivision of large introns in *Drosophila* by recursive splicing at non-exonic elements. Genetics (2005).
Burns et al.: Connections between pre-mRNA processing and regulation of the eukaryotic cell cycle. Front Horm Res. 25:59-82 (1999).
Buschmann et al.: Chitosans for delivery of nucleic acids. Advanced drug delivery reviews 65.9:1234-1270 (2013).
Busslinger et al.: β+ Thalassemia: Aberrant splicing results from a single point mutation in an intron. Cell 27.2:289-298 (1981).
Callis et al. Introns increase gene expression in cultured maize cells. Genes Dev. 1(10):1183-200 (1987).
Catterall et al.: Nav1.1 channels and epilepsy. J Physiol. 1;588(Pt 11):1849-59 (2010).
Cavaloc et al.: The splicing factors 9G8 and SRp20 transactivate splicing through different and specific enhancers. RNA 5(3):468-83 (1999).
Cazzola et al.: Translational pathophysiology: a novel molecular mechanism of human disease. Blood 95(11):3280-8 (2000).
Chambers et al.: The INO80 chromatin remodeling complex prevents polyploidy and maintains normal chromatin structure at centromeres. Genes Dev. 26(23):2590-603 (2012). Epub Dec. 5, 2012.doi: 26/23/2590 [pii] 10.1101/gad.199976.112. PubMed PMID: 23207916.
Chen et al.: A functional single nucleotide polymorphism in promoter of ATM is associated with longevity. Mech Ageing Dev. 131:636-40 (2010).
Chen et al.: Chk1 kinase negatively regulates mitotic function of Cdc25A phosphatase through 14-3-3 binding. Mol Cell Biol. 23(21):7488-97 (2003). PubMed PMID: 14559997; PubMed Central Pmcid: PMC207598.
"Schimpf, S. et al., "Activation of cryptic splice sites is a frequent splicing defect mechanism caused by mutations in exon and intron sequences of the OPA1 gene," Human Genetics, 2006, vol. 118, No. 6, pp. 767-771".
Choi et al.: CHK2 kinase promotes pre-mRNA splicing via phosphorylating CDK11p110. Oncogene 33:108-15 (2014).
Colla et al.: Telomere dysfunction drives aberrant hematopoietic differentiation and myelodysplastic syndrome. Cancer Cell. 27(5):644-57 (2015). doi: 10.1016/j.ccell.2015.04.007. PubMed PMID: 25965571.
Collie et al.: The application of DNA and RNA G-quadruplexes to therapeutic medicines. Chem Soc Rev. 40(12):5867-92 (2011). doi: 10.1039/c1cs15067g. Epub Jul. 25, 2011.
Collin et al.: Antisense Oligonucleotide (AON)-based Therapy for Leber Congenital Amaurosis caused by a Frequent Mutation in CEP290. Molecular Therapy-Nucleic Acids, pp. 1-7 (2012).
Consortium. TGP. An integrated map of genetic variation from 1,092 human genomes. Nature (London). 491:56-65 (2012).
Corallini et al.: Transcriptional and Posttranscriptional Regulation of the CTNS Gene. Pediatric Research 70(2):130-135 (2011).
Corey et al.: A non-classical translocation involving 17q12 (retinoic acid receptor alpha) in acute promyelocytic leukemia (APML) with atypical features. Leukemia 8(8):1350-3 (1994). PubMed PMID: 8057672.
Cornille et al.: Reversible optic neuropathy with OPA1 exon 5b mutation. Annals of Neurology 63(5):667-671 (2008).
Corvelo et al.: Genome-wide association between branch point properties and alternative splicing. PLoS Comput Biol. 6(11):e1001016 (2010). Epub Dec. 3, 2010.doi: 10.1371/journal.pcbi.1001016. PubMed PMID: 21124863.
Coulombe-Huntington et al.: Fine-Scale Variation and Genetic Determinants of Alternative Splicing across Individuals. PLoS Genet. 5(12):e1000766 (2009). Epub 2009/12/17.doi: 10.1371/journal.pgen. 1000766. PubMed PMID: 20011102.
Coutinho et al.: Functional significance of a deep intronic mutation in the ATM gene and evidence for an alternative exon 28a. Hum Mutat. 25(2):118-24 (2005). Epub Jan. 12, 2005.doi: 10.1002/humu.20170. PubMed PMID: 15643608.
Creacy, et al. G4 resolvase 1 binds both DNA and RNA tetramolecular quadruplex with high affinity and is the major source of tetramolecular quadruplex G4-DNA and G4-RNA resolving activity in HeLa cell lysates. J Biol Chem. 283(50):34626-34 (2008). doi: 10.1074/jbc.M806277200. Epub Oct. 7, 2008.
Creson et al.: Re-expression of SynGAP Protein in Adulthood Improves Translatable Measures of Brain Function and Behavior in a Model of Neurodevelopmental Disorders. Departments of Neuroscience and Molecular medicine, The Scripps Research Institute (2018).
Culler et al.: Functional selection and systematic analysis of intronic splicing elements identify active sequence motifs and associated splicing factors. Nucleic Acids Res. 38(15):5152-65 (2010). doi: 10.1093/nar/gkq248. Epub Apr. 12, 2010.
Database Geneseq [Online], Nov. 13, 2008 (Nov. 13, 2008), Dual label detection probe, QF probe 1, 5. 3.11, XP055572852, retrieved from EBI Accession No. GSN:ARK21623.
Davies et al.: A genome-wide search for human type 1 diabetes susceptibility genes. Nature 8;371(6493):130-6 (1994).
Decorsiere et al.: Essential role for the interaction between hnRNP H/F and a G quadruplex in maintaining p53 pre-mRNA 3'-end processing and function during DNA damage. Genes Dev. 25(3):220-5 (2011). doi: 10.1101/gad.607011.
Dedic et al.: Alagille Syndrome Mimicking Biliary Atresia in Early Infancy, Plos Oone, 10(11):e0143939: pp. 1-7 (2015).
Deere et al.: Antisense Phosphorodiamidate Morpholino Oligomer Length and Target Position Effects on Gene-Specific Inhibition in *Escherichia coli*. Antimicrobial Agents Andchemotherapy 49(1):249-255 (2005).
Del Dotto et al.: OPA1 Isoforms in the Hierarchical Organization of Mitochondrial Functions. Cell Reports 19(12):2557-2571 (2017).
Derecka et al.: Occurrence of a quadruplex motif in a unique insert within exon C of the bovine estrogen receptor alpha gene (ESR1). Biochemistry 49(35):7625-33 (2010). doi: 10.1021/bi100804f.
Dias et al.: Antisense oligonucleotides: basic concepts and mechanisms Mol. Cancer Ther. 1:347-355 ( 2002).
Didiot et al.: The G-quartet containing FMRP binding site in FMR1 mRNA is a potent exonic splicing enhancer. Nucleic Acids Res. Sep. 2008;36(15):4902-12. doi: 10.1093/nar/gkn472. Epub Jul. 24, 2008.
Ding, H. et al. DeliveringPD-1 inhibitory signal concomitant with blocking ICOS co-stimulation suppresses lupus-like syndrome in autoimmune BXSB mice. Clinical Immunology, vol. 118, pp. 258-267, (2006).
Divina, P. et al. Ab initio prediction of cryptic splice-site activation and exon skipping. Eur J Hum Genet. 2009; 17:759-65.
Dominski, et al. Restoration of correct splicing in thalassemic pre-mRNA by antisense oligonucleotides. Proc Natl Acad Sci U S A. Sep. 15, 1993;90(18):8673-7.
Dredge, et al. NeuN/Rbfox3 Nuclear and Cytoplasmic Isoforms Differentially Regulate Alternative Splicing and Nonsense-Mediated Decay of Rbfox2. PLoS One. 2011; 6(6): e21585.
Du, et al. "Correction of prototypic ATM splicing mutations and aberrant ATM function with antisense morpholino oligonucleotides" (2007) PNAS, vol. 104, No. 14, pp. 6007-6012.
Ducros et al. Recurrence of the T666M calcium channel CACNA1A gene mutation in familial hemiplegic migraine with progressive cerebellar ataxia. Am J Hum Genet. vol. 64, No. 1, pp. 89-98 (Jan. 1999).
Duikers, et al. " Antisense Oligonucleotide-Based Splicing Correction in Individuals with Leber Congenital Amaurosis due to Compound Heterozygosity for the c.2991+1655AG Mutation in CEP290" (2018) International Journal of Molecular Sciences, 19, 753, pp. 1-12.

(56) References Cited

OTHER PUBLICATIONS

Dulla, et al., "Splice-Modulating Oligonucleotide QR-110 Restores CEP290 mRNA and Function in Human c.2991+1655AG LCA10 Models" (2018) Molecular Therapy: Nucleic Acids, vol. pp. 730-740.
Duryagina R, et al. Overexpression of Jagged-1 and its intracellular domain in human mesenchymal stromal cells differentially affect the interaction with hematopoietic stem and progenitor cells.Stem Cells Dev. vol. 22, No. 20, pp. 2736-2750 (2013).
Dutertre, M., et al. et al. DNA damage: RNA-binding proteins protect from near and far. Trends Biochem Sci. 2014; 39(3):141-9. Epub Feb. 19, 2014.doi: S0968-0004(14)00015-2 [pii] 10.1016/j.tibs.2014.01.003. PubMed PMID: 24534650.
Eddy, et al. G4 motifs correlate with promoter-proximal transcriptional pausing in human genes. Nucleic Acids Res. Jul. 2011;39(12):4975-83. doi: 10.1093/nar/gkr079. Epub Mar. 3, 2011.
El Bougrini et al.: PML positively regulates interferon gamma signaling. Biochimie. 2011; 93(3):389-98. doi: 10.1016/j.biochi.2010.11.005. PubMed PMID: 21115099.
Emerick, et al. Multivariate analysis and visualization of splicing correlations in single-gene transcriptomes. BMC Bioinformatics. Jan. 18, 2007;8:16.
EP 15846242.4 Partial Supplementary Search Report and Search Opinion dated May 2, 2018.
EP 16876621.0 Extended European Search Report and Search Opinion dated Mar. 7, 2019.
EP15729929.8 Office Action dated Dec. 22, 2017.
EP15729929.8 Office Action dated Oct. 30, 2018.
EP15846242.4 Extended European Search Report dated Aug. 21, 2018.
EP16781187.6 Office Action dated May 20, 2019.
EP16876499.1 Extended Search Report dated Jun. 14, 2019.
EP168766061.1 Extended Search Report dated May 24, 2019.
Fairbrother, W.G., et al. Predictive identification of exonic splicing enhancers in human genes. Science. 2002; 297(5583):1007-13. PubMed PMID: 12114529.
Fededa, et al. A polar mechanism coordinates different regions of alternative splicing within a single gene. Mol Cell. Aug. 5, 2005;19(3):393-404.
Ferreira, P.G., et al.: Transcriptome characterization by RNA sequencing identifies a major molecular and clinical subdivision in chronic lymphocytic leukemia. Genome Res. 2014; 24:212-26.
Fletcher, Sue et al. Antisense suppression of donor splice site mutations in the dystrophin gene transcript. Molecular Genetics & Genomic Medicine, vol. 1, No. 3, pp. 162-173, Jun. 13, 2013.
Fred et al.: The human insulin mRNA is partly translated via a cap- and elF4A-independent mechanism. Biochem Biophys Res Commun. Sep. 9, 2011;412(4):693-8. doi: 10.1016/j.bbrc.2011.08.030. Epub Aug. 16, 2011.
Friedman, et al., "Correction of Aberrant Splicing of the Cystic Fibrosis Transmembrane conductance Regulator (CFTR) Gene by Antisense Oligonucleotides" (1999) The Journal of Biological Chemistry, vol. 274, No. 51, pp. 36193-36199.
Friend, KL et al. Detection of a novel missense mutation and second recurrent mutation in the CACNA1A gene in individuals with EA-2 and FHM. Hum Genet. vol. 105(3):261-5 (Sep. 1999).
Furukawa & Kish 2008, GeneReviews Pagon Ra et al. eds. Univ. of WA Seattle, NCBI Bookshelf ID NBK1437.
Galante, et al.: Detection and evaluation of intron retention events in the human transcriptome. RNA. May 2004;10(5):757-65.
"Gallus, G. N. et al., "Alu-element insertion in an OPA1 intron sequence associated with autosomal dominant optic atrophy," Molecular vision, 2010, vol. 16, pp. 178-183".
Garanto, et al., "In vitro and in vivo rescue of aberrant splicing in CEP290-associted LCA by antisense oligonucleotide delivery" (2016) Human Molecular Genetics, vol. 25, No. 12, pp. 2552-2563.
Garner, et al. Selectivity of small molecule ligands for parallel and anti-parallel DNA G-quadruplex structures. Org Biomol Chem. Oct. 21, 2009;7(20):4194-200. doi: 10.1039/b910505k. Epub Aug. 14, 2009.
Geary et al.: Absolute Bioavailability of 29-O-(2-Methoxyethyl)-Modified Antisense Oligonucleotides following Intraduodenal Instillation in Rats. J Pharmacal Exp Ther. vol. 296, No. 3, pp. 898-904 (Mar. 2001).
Geary, et al., "Pharmacokinetics, biodistribution and cell uptake of antisense oligonucleotides", (2015) Advance Drug Delivery Reviews.
Geary, RS, et al., Pharmacokinetic properties of 2'-O-(2-methoxyethyl)-modified oligonucleotide analogs in ratsJ Pharmacal Exp Ther. vol. 296, No. 3, pp. 890-897 (Mar. 2001).
Gerard, et al., "AON-mediated Exon Skipping Restores ciliation in Fibroblasts Harboring the Common Leber Congenital Amaurosis CEP290 Mutation" (2012) Molecular Therapy-Nucleic Acids, pp. 1-9.
Gianchecchi et al. Recent insights into the role of the PD-1/PD-L1 pathway in immunological tolerance and autoimmunity. Autoimmunity Reviews 12:1091-1100 (2013).
Gibson, G.: Hints of hidden heritability in GWAS. Nat Genet. 2010; 42(7):558-60. Epub Jun. 29, 2010.doi: ng0710-558 [pii] 10.1038/ng0710-558. PubMed PMID: 20581876.
Gohring, J. et al. Imaging of Endogenous MessengerRNA Splice Variants in Living Cells Reveals Nuclear Retention of Transcripts Inaccessible to Nonsense-Mediated Decay in *Arabidopsis*. The Plant Cell. vol. 26, pp. 754-764.(Feb. 2014).
Gomes et al. Translating chitosan to clinical delivery of nucleic acid-based drugs. MRS bulletin 39.1 (2014): 60-70.
Gomez, et al. Telomerase downregulation induced by the G-quadruplex ligand 12459 in A549 cells is mediated by hTERT RNA alternative splicing. Nucleic Acids Res. Jan. 16, 2004;32(1):371-9. Print 2004.
Goncharova et al. Tuberin regulates p70 S6 kinase activation and ribosomal protein S6 phosphorylation. A role for the TSC2 tumor suppressor gene in pulmonary lymphangioleiomyomatosis (LAM). J. Biol. Chem. (Aug. 23, 2002) 277(34);30958-67. EPub Jun. 3, 2002.
Gonzalez-Santos, et al., Mutation in the splicing factor Hprp3p linked to retinitis pigmentosa impairs interactions within the U4/U6 snRNP pigmentosa impairs interactions within the U4/U6 snRNP complex, PubMed Central Canada , Author Manuscript, 29 pages.
Goto, et al., "Targeted skipping of a Single Exon Harboring a Premature termination Codon Mutation: Implications and Potential for Gene Correction Therapy for Selective Dystrophic Epiderolysis Bullosa Patients" (2006) Journal of Investigative Dermatology, vol. 126, pp. 2614-262.
Goyenvalie et al.: Therapeutic approaches to muscular dystrophy. Hum Mol Genet. Apr. 15, 2011;20(R1):R69-78. doi: 10.1093/hmg/ddr105. Epub Mar. 24, 2011.
Gozani, O., et al.: A potential role for U2AF-SAP 155 interactions in recruiting U2 snRNP to the branch site. Mol Cell Biol. 1998; 18(8):4752-60. PubMed PMID: 9671485.
Graveley, B.R. The haplo-spliceo-transcriptome: common variations in alternative splicing in the human population. Trends Genet. 2008; 24(1):5-7. Epub Dec. 7, 2007.doi: S0168-9525(07)00349-6 [pii] 10.1016/j.tig.2007.10.004. PubMed PMID: 18054116.
Gutell, R.R., et al. A story: unpaired adenosine bases in ribosomal RNAs. J Mol Biol. 2000; 304(3):335-54. Epub Nov. 25, 2000.doi: 10.1006/jmbi.2000.4172 S0022-2836(00)94172-X [pii]. PubMed PMID: 11090278.
Guth, S., et al. Dual function for U2AF(35) in AG-dependent pre-mRNA splicing. Mol Cell Biol. 2001;21(22):7673-81. PubMed PMID: 11604503.
Guy et al. A mouse Mecp2-null mutation causes neurological symptoms that mimic Rett syndrome. Nat Genet 27:322-326 (2001).
Hai, et al.: A G-tract element in apoptotic agents-induced alternative splicing. Nucleic Acids Res. Jun. 2008;36(10):3320-31. doi: 10.1093/nar/gkn207. Epub Apr. 24, 2008.
"Hamdan, et al., "Mutations in SYNGAP1 in autosomal nonsyndromic mental retardation," New England Journal of Medicine, 2009, vol. 360, No. 6, pp. 599-605".
Hamdan, F. F. et al. De Novo SYNGAP1 Mutations in Nonsyndromic Intellectual Disability and Autism, Biol. Psychiatry, 69:898-901 (2011).
Hammond, et al"Genetic therapies for RNA mis-splicing diseases" (2011) Cell Press 10 pages.

(56) References Cited

OTHER PUBLICATIONS

Han, et al., "Antisense oligonucleotides increase Scn1a expression and reduce seizures and SUDEP incidence in a mouse model of Dravet syndrome" (2020) Science Translational Medicine, 12, pp. 1-14.
Han, et al. TANGO-Targeted augmentation of nuclear gene output for the treatment of genetic diseases. Poster session presented at the American Society of Gene and Cell Therapy, Chicago, IL. (May 2018).
Hargous, et al. Molecular basis of RNA recognition and TAP binding by the SR proteins SRp20 and 9G8. EMBO J. Nov. 1, 2006;25(21):5126-37. Epub Oct. 12, 2006.
Harkin, et al. The spectrum of SCN1A-related infantile epileptic encephalopathies. Brain. Mar. 2007;130(Pt 3):843-52.
Hastings, M.L., et al. Control of pre-mRNA splicing by the general splicing factors PUF60 and U2AF. PLoS One. 2007;2:e538. PubMed PMID: 17579712.
Havens, et al., "Targeting RNA Splicing fo rDisease Therapy" (2013) Wiley Interdiscip Rev RNA , 4(3): 247-266.
He, Y.H., et al. Association of the insulin-like growth factor binding protein 3 (IGFBP-3) polymorphism with longevity in Chinese nonagenarians and centenarians. Aging (Milano). 2014;6:944-56.
Hegele et al.: Dynamic protein-protein interaction wiring of the human spliceosome. Mol Cell. Feb. 24, 2012;45(4):567-80. doi: 10.1016/j.molcel.2011.12.034.
Hernan, I. et al. :Cellular Expression and siRNA-Mediated Interference of Rhodopsin cis-Acting Splicing Mutants Associated with Autosomal Dominant Retinitis Pigmentosa, Invest Ophthalmol. Vis. Sci. (2011) 52:3723-3729.
Heyn, P. et al.: Introns and gene expression: Cellular constraints, transcriptional regulation, and evolutionary consequences. Bioessays vol. 37, pp. 148-154 (2014).
Hiller et al. Pre-mRNA secondary structures influence exon recognition. PLoS genetics 3.11 (2007): e204.
Hirata et al.Prevention of Experimental Autoimmune Encephalomyelitis by Transfer of Embryonic Stem Cell-Derived Dendritic Cells Expressing Myelin Oligodendrocyte Glycoprotein Peptide along with TRAIL or Programmed Death-1 Ligand.J. Immunology vol. 174 pp. 1888-1897 (2005).
Hishida, A. et al.: Polymorphisms in PPAR Genes (PPARD, PPARG, and PPARGC1A) and the Risk of Chronic Kidney Disease in Japanese: Cross-Sectional Data from the J-MICC Study. PPAR 2013; 980471 pp. 1-8.
*Homo sapiens* pre-mRNA processing factor 3 (PRPF3), mRNA, NCBI Reference Sequence: NM_004698.2 Accessed Apr. 6, 2017.
Hua, et al.: Antisense correction of SMN2 splicing in the CNS rescues necrosis in a type III SMA mouse model. Genes Dev. Aug. 1, 2010;24(15): 1634-44. doi: 10.1101/gad.1941310. Epub Jul. 12, 2010.
Hua et al.: Antisense masking of an hnRNP A1/A2 intronic splicing silencer corrects SMN2 splicing in transgenic mice. Am. J. Hum. Genet. 82:834-848 (Mar. 27, 2008).
Hua, Y., et al. Enhancement of SMN2 exon 7 inclusion by antisense oligonucleotides targeting the exon. PLoS Biol. 2007;5(4):e73. Epub Mar. 16, 2007.doi: 06-PLBI-RA-1492R3 [pii] 10.1371/journal.pbio.0050073. PubMed PMID: 17355180.
Hunt, et al. Negligible impact of rare autoimmune-locus coding-region variants on missing heritability. Nature. Jun. 13, 2013;498(7453):232-5. doi: 10.1038/nature12170. Epub May 22, 2013.
Huynh, K.D., et al. BCoR, a novel corepressor involved in BCL-6 repression. Genes Dev. 2000;14(14):1810-23. PubMed PMID: 10898795; PubMed Central PMCID: PMC316791.
International Application No. PCT/GB2015/051756 International Preliminary Report on Patentability, Dec. 26, 2016.
International Application No. PCT/GB2015/051756 International Search Report and Written Opinion Mailed Nov. 30, 2015.
International Application No. PCT/GB2016/053136 International Search Report and Written Opinion Mailed Mar. 6, 2017.
International Application No. PCT/GB2016/053136 Partial International Search Report Mailed Jan. 19, 2017.
International Application No. PCT/US16/66576 International Search Report and Written Opinion Mailed May 4, 2017.
International Application No. PCT/US16/66691 International Search Report and Written Opinion Mailed May 10, 2017.
International Application No. PCT/US16/66708 International Search Report and Written Opinion Mailed May 8, 2017.
International Application No. PCT/US16/66721 International Search Report and Written Opinion mailed May 1, 2017.
International Application No. PCT/US2015/053896 International Preliminary Report on Patentability Mailed Apr. 4, 2017.
International Application No. PCT/US2015/53896 International Search Report and Written Opinion dated Mar. 3, 2016.
International Application No. PCT/US2016/066414 International Search Report and Written Opinion Mailed Apr. 19, 2017.
International Application No. PCT/US2016/066417 International Search Report and Written Opinion Mailed Apr. 19, 2017.
International Application No. PCT/US2016/066564 International Search Report and Written Opinion Mailed May 4, 2017.
International Application No. PCT/US2016/066705 International Search Report and Written Opinion Mailed Apr. 24, 2017.
International Application No. PCT/US2018/048031 International Search Report and Written Opinion Mailed Jan. 22, 2019.
International Preliminary Report on Patentability issued in PCT/US2021/030254, dated Nov. 15, 2022.
International search report and written opinion dated Jun. 5, 2017 for PCT Application No. PCT/US2016/066684.
International Search Report and Written Opinion issued in PCT/US2021/030254, mailed Jul. 28, 2021.
International Search Report and Written Opinion dated Mar. 28, 2019 for PCT/US2018/057165.
Itoh et al.: Methyl CpG-binding Protein Isoform MeCP2_e2 Is Dispensable for Rett Syndrome Phenotypes but Essential for Embryo Viability and Placenta Development. J Biol Chem 287:13859-13867 (2012).
Iwamoto, et al.: Transcription-dependent nucleolar cap localization and possible nuclear function of DExH RNA helicase RHAU. Exp Cell Res. Apr. 1, 2008;314(6):1378-91. doi: 10.1016/j.yexcr.2008.01.006. Epub Jan. 16, 2008.
Jacob et al.: Intron retention as a component of regulated gene expression programs. Hum Genet 136:1043-1057 (2017).
Jarver, P. et al., "A Chemical View of Oligonucleotides for Exon Skipping and Related Drug Applications," Nucleic Acid Therapeutics, 2014, vol. 24, No. 1, pp. 37-47.
Jearawiriyapaisarn et al. Sustained Dystrophin Expression Induced by Peptide-conjugated Morpholino Oligomers in the Muscles of mdx Mice. Mol Ther. 16(9): 1624-1629 (2008).
Jurka et al. Identification of new medium reiteration frequency repeats in the genomes of Primates, Rodentia and Lagomorpha. Genetica98.3 (1996): 235-247.
Jurkiewicz, D. et al.: Spectrum of JAG1 gene mutations in Polish patients with Alagille syndrome J. Appl. Genetics vol. 55, pp. 329-336, (2014).
Kach et al. A novel antisense oligonucleotide approach to treat eye diseases by increasing target gene expression. No. 3423-A0194 ARVO Poster Apr. 19, 2019 (1 pg.).
"Kamakari, S. et al., "First report of OPA1 screening in Greek patients with autosomal dominant optic atrophy and identification of a previously undescribed OPA1 mutation," Molecular Vision, 2014, vol. 20, pp. 691-703".
Kaminker, P.G., et al. A novel form of the telomere-associated protein TIN2 localizes to the nuclear matrix. Cell Cycle. 2009;8(6):931-9. PubMed PMID: 19229133; PubMed Central PMCID: PMC2751576.
Kang et al. Up-regulation of luciferase gene expression with antisense oligonucleotides: implications and applications in functional assay development. Biochemistry 37.18 (1998): 6235-6239.
Kaplan et al. Medium reiteration frequency repetitive sequences in the human genome. Nucleic acids research 19.17 (1991): 4731-4738.
Katsani, K.R. et al.: Functional Genomics Evidence Unearths New Moonlighting Roles of Outer Ring Coat Nucleoporins Scientific Reports vol. 4, No. 4655 (Apr. 11, 2014).

(56) References Cited

OTHER PUBLICATIONS

Kawamata, N., et al. Genetic differences between Asian and Caucasian chronic lymphocytic leukemia. Int J Oncol. 2013;43(2):561-5. doi: 10.3892/ijo.2013.1966. PubMed PMID: 23708256; PubMed Central PMCID: PMC3775563.
Ke, et al.: Quantitative evaluation of all hexamers as exonic splicing elements. Genome Res. Aug. 2011;21(8):1360-74. doi: 10.1101/gr.119628.110. Epub Jun. 9, 2011.
Keir, M.E. et al.: PD-1 and Its Ligands in Tolerance and Immunity. Annu. Rev. Immunol. vol. 26, pp. 677-704 (2008).
Kervestin et al. NMD: a multifaceted response to premature translational termination. Nature reviews Molecular cell biology13.11 (2012): 700.
Kikin, et al.: QGRS Mapper: a web-based server for predicting G-quadruplexes in nucleotide sequences. Nucleic Acids Res. Jul. 1, 2006;34(Web Server issue):W676-82.
Kim, E., et al. SRSF2 Mutations Contribute to Myelodysplasia by Mutant-Specific Effects on Exon Recognition. Cancer Cell. 2015;27(5):617-30. doi: 10.1016/j.ccell.2015.04.006. PubMed PMID: 25965569; PubMed Central PMCID: PMC4429920.
Kim et al.: ChimerDB 2.0—a knowledgebase for fusion genes updated. Nucleic Acids Res. 2009;38(Database issue): D81-5. Epub Nov. 13, 2009.doi: gkp982 [pii] 10.1093/nar/gkp982. PubMed PMID: 19906715.
Kim et al. The role of synaptic GTPase-activating protein in neuronal development and synaptic plasticity. J. Neurosci. 23(4):1119-1124 (Feb. 15, 2003).
Kim et al.: The splicing factor U2AF65 stabilizes TRF1 protein by inhibiting its ubiquitin-dependent proteolysis. Biochem Biophys Res Commun. 2014;443(3):1124-30. doi: 10.1016/j.bbrc.2013.12.118. PubMed PMID: 24389012.
Knudsen et al. Increased skewing of X chromosome inactivation in Rett syndrome patients and their mothers. Eur J Hum Genet 14:1189-1194 (2006).
Kole, et al. RNA therapeutics: beyond RNA interference and antisense oligonucleotides. Nat Rev Drug Discov. Jan. 20, 2012;11(2):125-40. doi: 10.1038/nrd3625.
Kralovicova, et al.: Allele-specific recognition of the 3' splice site of INS intron 1. Hum Genet. Oct. 2010;128(4):383-400. doi: 10.1007/s00439-010-0860-1. Epub Jul. 14, 2010.
Kralovicova, et al.: Compensatory signals associated with the activation of human GC 5' splice sites. Nucleic Acids Res. Sep. 1, 2011;39(16):7077-91. doi: 10.1093/nar/gkr306. Epub May 23, 2011.
Kralovicova et al.: Exon-centric regulation of ATM expression is population-dependent and amenable to antisense modification by pseudoexon targeting, Scientific Reports, 6:18741, doi:10.1038/srep18741, Jan. 6, 2016, 13 pages.
Kralovicova, et al. Global control of aberrant splice-site activation by auxiliary splicing sequences: evidence for a gradient in exon and intron definition. Nucleic Acids Res. Oct. 2007; 35(19): 6399-6413.
Kralovicova, et al. Identification of U2AF(35)-dependent exons by RNA-Seq reveals a link between 3' splice-site organization and activity of U2AF-related proteins. Nucleic Acids Res. Apr. 20, 2015;43(7):3747-63. doi: 10.1093/nar/gkv194. Epub Mar. 16, 2015.
Kralovicova, et al. Optimal antisense target reducing INS intron 1 retention is adjacent to a parallel G quadruplex. Nucleic Acids Res. Jul. 2014;42(12):8161-73. doi: 10.1093/nar/gku507. Epub Jun. 17, 2014.
Kralovicova, et al. Phenotypic consequences of branch point substitutions. Hum Mutat. Aug. 2006;27(8):803-13.
Kralovicova, et al. Position-dependent repression and promotion of DQB1 intron 3 splicing by GGGG motifs. J Immunol. Feb. 15, 2006;176(4):2381-8.
Kralovicova, et al.: Variants in the human insulin gene that affect pre-mRNA splicing: is—23Hphl a functional single nucleotide polymorphism at IDDM2? Diabetes. Jan. 2006;55(1):260-4.
Kralovicova, et al.Antisense Oligonucleotides Modulating Activation of a Nonsense-Mediated RNA Decay Switch Exon in theATMGene. Nucleic Acid Ther. Dec. 1, 2016; 26(6): 392-400.
Kralovicova, J. et al. Branch sites haplotypes that control alternative splicing. Hum Mol Genet. 2004;13:3189-202.
Kralovicova, J. et al. The role of short RNA loops in recognition of a single-hairpin exon derived from a mammalian-wide interspersed repeat. RNA Biol. 2015;12(1):54-69. doi: 10.1080/15476286.2015.1017207. PubMed PMID: 25826413.
Kriaucionis et al.: The major form of MeCP2 has a novel N-terminus generated by alternative splicing. Nucleic Acids Res 32:1818-1823 (2004).
Krishnaraj et al. RettBASE: Rett syndrome database update. Hum Mutat 38:922-931 (2017).
Laceerra, et al., "Restoration of hemoglobin A synthesis in erythroid cells from peripheral blood of thalassemic patients" (2000) PNAS, vol. 97, No. 17, pp. 9591-9596.
Lander, et al. Initial sequencing and analysis of the human genome. Nature 409:860-921 (Feb. 15, 2001).
Laplanche, L.A et al., "Phosphorothioate-modified oligodeoxyribonucleotides. III. NMR and UV spectroscoptc studies of the Rp-Rp, Sp-Sp, and Rp-Sp duplexes, [d(GGSAATTCC)]2, derived from diastereomeric O-ethyl phosphorothioates," Nucleic Acids Res., 1986, vol. 14, No. 22, pp. 9081-9083.
Le Hir, et al. How introns influence and enhance eukaryotic gene expression. Trends Biochem Sci. Apr. 2003;28(4):215-20.
Lee et al.: The Consensus 5' Splice Site Motif Inhibits mRNA Nuclear Export.PLoS One vol. 10, No. 3, p. e0122743 (Mar. 31, 2015).
Lee, J., et al.: Metastasis of neuroendocrine tumors are characterized by increased cell proliferation and reduced expression of the ATM gene. PLoS One. 2012;7:e34456.
LeFave, et al., "Splicing factor hnRNPH drives an oncogenic splicing switch in gliomas",(2011) The EMBO Journal, vol. 30, No. 19, pp. 4084-4097.
Lehir, H. et al.: 5'-End RET Splicing: Absence of Variants in Normal Tissues and Intron Retention in Pheochromocytomas, Oncology 63:84-91 (2002).
Lei et al. Exonization of Alu Ya5 in the human ACE gene requires mutations in both 3' and 5' splice sites and is facilitated by a conserved splicing enhancer. Nucleic acids research 33.12 (2005): 3897-3906.
Lei, et al.: Identification of splicing silencers and enhancers in sense Alus: a role for pseudoacceptors in splice site repression. Mol Cell Biol. Aug. 2005;25(16):6912-20.
Lemaire, M., et al. CDC25B phosphorylation by p38 and MK-2. Cell Cycle. 2006;5(15):1649-53. PubMed PMID: 16861915.
Lenaers, G. et al., "Dominant optic atrophy," Orphanet J Rare Diseases, 2012, vol. 7, No. 46, pp. 1-12.
Levin, et al., "Treating Disease at the RNA Level with Oligonucleotides" (2019) The New England Journal of Medicine 380:57-70.
Lev-Maor et al. Intronic Alus influence alternative splicing. PLoS genetics 4.9 (2008): e1000204.
Lev-Maor et al. The birth of an alternatively spliced exon: 3'splice-site selection in Alu exons. Science 300.5623 (2003): 1288-1291.
Levy et al. TranspoGene and micro TranspoGene: transposed elements influence on the transcriptome of seven vertebrates and invertebrates. Nucleic acids research 36.suppl_1 (2007): D47-D52.
Li et al. JAG1 Mutation Spectrum and Origin in Chinese Children with Clinical Features of Alagille Syndrome. PLoS One 10(6):e0130355 (2015).
Li et al. PD-L1-Driven Tolerance Protects Neurogenin3-Induced Islet Neogenesis to Reverse Established Type 1 Diabetes in NOD Mice.Diabetes vol. 64, pp. 529-540 (Feb. 2015; epub Oct. 20, 2014).
Liang et al. Short intronic repeat sequences facilitate circular RNA production. Genes & development (2014): gad-251926.
Liang, Xue-Hai et al., Translation efficiency of mRNAs is increased by antisense oligonucleotides targeting upstream open reading frames, Nature Biotechnology, 34(8):875-882 (Aug. 2016).
Lianoglou, S., et al. Ubiquitously transcribed genes use alternative polyadenylation to achieve tissue-specific expression. Genes Dev. 2013;27(21):2380-96. Epub Oct. 23, 2013.doi: gad.229328.113 [pii] 10.1101/gad.229328.113. PubMed PMID: 24145798.
Lim et al. A computational analysis of sequence features involved in recognition of short introns. Proceedings of the National Academy of Sciences98.20 (2001): 11193-11198.

(56) References Cited

OTHER PUBLICATIONS

Lim, et al., "Antisense oligonucleotide modulation of non-productive alternative splicing upregulates gene expression" (2020) Nature Communication.
Litchfield, D.W., et al. Pin1: Intimate involvement with the regulatory protein kinase networks in the global phosphorylation landscape. Biochem Biophys Acta. 2015. doi: 10.1016/j.bbagen.2015.02.018. PubMed PMID: 25766872.
Liu et al. Alternative splicing and retinal degeneration. Clinical Genetics 84(2):142-149 (2013).
Llorian et al. Position-dependent alternative splicing activity revealed by global profiling of alternative splicing events regulated by PTB. Nature structural & molecular biology 17.9 (2010): 1114.
Lo, YL et al. ATM Polymorphisms and risk of lung cancer among never smokers, Lung Cancer 69(2):148-154 (2010).
Long et al.: Correction of diverse muscular dystrophy mutations in human engineered heart muscle by single-site genome editing. Sci Adv 4:eaap9004 (2018).
Lorenz, et al. 2D meets 4G: G-Quadruplexes in RNA Secondary Structure Prediction. IEEE/ACM Trans Comput Biol Bioinform. Jul.-Aug. 2013;10(4):832-44. doi: 10.1109/TCBB.2013.7.
Lu, F.: Conditional JAG1 MutationShows the Developing Heart Is More Sensitive Than Developing Liver to JAG1 Dosage.Am. J. Hum. Genet. Vol. 72, pp. 1065-1070 (2003).
Ludecke et al.Recessively inherited L-DOPA-responsive parkinsonism in infancy caused by a point mutation (L205P) in the tyrosine hydroxylase gene Hum. Mol. Genet. vol. 5, pp. 1023-1028, (1996).
Luo et al.: Palmitic Acid Suppresses Apolipoprotein M Gene Expression via the Pathway of PPARb/d in HepG2 Cells. Biochemical and Biophysical Research Communications, 445(1):203-207 (Feb. 2014).
Magi-Galuzzi, C. et al. TMPRSS2-ERG gene fusion prevalence and class are significantly difference in prostate cancer of Caucasian, African-American and Japanese patients. The Prostate. 2011;71:489-97.
Makishima, et al. Mutations in the spliceosome machinery, a novel and ubiquitous pathway in leukemogenesis. Blood. Apr. 5, 2012;119(14):3203-10. doi: 10.1182/blood-2011-12-399774. Epub Feb. 9, 2012.
Maniatis et al. An extensive network of coupling among gene expression machines. Nature 416.6880 (2002): 499.
Mansouri, S. et al.: Epstein-Barr Virus EBNA1 Protein Regulates Viral Latency through Effects on let-7 MicroRNA and Dicer. Journal of Virology, vol. 88, No. 19, pp. 11166-11177, (Oct. 2014).
Marcel, et al. G-quadruplex structures in TP53 intron 3: role in alternative splicing and in production of p53 mRNA isoforms. Carcinogenesis. Mar. 2011;32(3):271-8. doi: 10.1093/carcin/bgq253. Epub Nov. 26, 2010.
Marquez, Y. et al. Unmasking alternative splicing inside protein-coding exons defines exitrons and their role inproteome plasticity. Genome vol. 25, pp. 995-1007 (2015).
Matsuoka et al. ATM and ATR substrate analysis reveals extensive protein networks responsive to DNA damage. Science 316(5828):1160-1166 (2007).
Matsuoka, S., et al. Ataxia telangiectasia-mutated phosphorylates Chk2 in vivo and in vitro. Proc Natl Acad Sci USA. 2000;97:10389-94.
Mayeda, et al. Surveying cis-acting sequences of pre-mRNA by adding antisense 2'-O-methyl oligoribonucleotides to a splicing reaction. J Biochem. Sep. 1990;108(3):399-405.
McKie et al. Mutations in the pre-mRNA splicing factor gene PRPC8 in autosomal dominant retinitis pigmentosa (RP13). Human Molecular Genetics 10(15):1555-1562 (2001).
Melhuish, et al. The Tgif2 gene contains a retained intron within the coding sequence, BMC Molecular Biology 7(2);1-10 (2006).
Melko, et al. Functional characterization of the AFF (AF4/FMR2) family of RNA-binding proteins: insights into the molecular pathology of FRAXE intellectual disability. Hum Mol Genet. May 15, 2011;20(10):1873-85. doi: 10.1093/hmg/ddr069. Epub Feb. 17, 2011.
Mendell, J.T., ap Rhys CM, Dietz HC. Separable roles for rent1/hUpf1 in altered splicing and decay of nonsense transcripts. Science. 2002;298(5592):419-22. Epub 2002/09/14.doi: 10.1126/science.1074428 1074428 [pii]. PubMed PMID: 12228722.
Merendino, L., et al. Inhibition of msl-2 splicing by Sex-lethal reveals interaction between U2AF35 and the 3' splice site AG. Nature. 1999;402(6763):838-41. PubMed PMID: 10617208.
Michael, et al. Mfold web server for nucleic acid folding and hybridization prediction. Nucleic Acids Research. 31 (2003): 3406-3415.
Miller at al. 1993-2015 GeneReviews Eds. Pagon RA et al. Seattle (WA); University of WA, Seattle Bookshelf ID NBK1318.
Millevoi, et al. G-quadruplexes in RNA biology. Wiley Interdiscip Rev RNA. Jul.-Aug. 2012;3(4):495-507. doi: 10.1002/wrna.1113. Epub Apr. 4, 2012.
Min et al. Optimization of a novel series of ataxia-telangiectasia mutated kinase inhibitors as potential radiosensitizing agents. Journal of medicinal chemistry 59.2 (2016): 559-577.
Mirey, G., et al. CDC25B phosphorylated by pEg3 localizes to the centrosome and the spindle poles at mitosis. Cell Cycle. 2005;4(6):806-11. PubMed PMID: 15908796.
Mitelman, F., et al. The impact of translocations and gene fusions on cancer causation. Nat Rev Cancer. 2007;7(4):233-45. Epub Mar. 16, 2007.
Mnatzakanian et al. A previously unidentified MECP2 open reading frame defines a new protein isoform relevant to Rett syndrome. Nat Genet 36:339-341 (2004).
Mochizuki, T. et al. PKD2, a gene for polycystic kidney disease that encodes an integral membrane protein.Science vol. 272, pp. 1339-1342 (1996).
Montecucco, A., et al. Pre-mRNA processing factors meet the DNA damage response. Front Genet. 2013;4:102. doi: 10.3389/fgene.2013.00102. PubMed PMID: 23761808; PubMed Central PMCID: PMC3674313.
Moreno et al. Delivery of splice switching oligonucleotides by amphiphilic chitosan-based nanoparticles. Molecular pharmaceutics 13.2 (2016): 344-356.
Morris, et al. An RNA G-quadruplex is essential for cap-independent translation initiation in human VEGF IRES. J Am Chem Soc. Dec. 22, 2010;132(50):17831-9. doi: 10.1021/ja106287x. Epub Nov. 24, 2010.
Morrison, A.J., et al. Mec1/Tel1 phosphorylation of the INO80 chromatin remodeling complex influences DNA damage checkpoint responses. Cell. 2007;130(3):499-511. doi: 10.1016/j.cell.2007.06.010. PubMed PMID: 17693258.
Moskowitz, et al., Mutation in Scheie syndrome (MPS IS): a G-->A transition creates new splice site in intron 5 of one IDUA allele, Hum. Mutat. 2(2):141-144 (1993).
Mulley et al. A new molecular mechanism for severe myoclonic epilepsy of infancy: Exonic deletions in SCN1A.Neurol. vol. 67, pp. 1094-1095 (2006).
Mulley et al. SCN1A mutations and epilepsy.Hum. Muta. vol. 25, pp. 535-542 (2005).
Murray, S.F. et al. Allele-Specific Inhibition of Rhodopsin with an Antisense Oligonucleotide Slows Photoreceptor Cell Degeneration, Invest Ophthalmol. Vis. Sci. 56:6362-6375 (Oct. 2015).
Neidle, S. and Balasubramanian, S. (2006) Quadruplex Nucleic Acids. RSC Biomolecular Sciences, Cambridge, UK.
Nemeroff et al. Identification of cis-acting intron and exon regions in influenza virus NS1 mRNA that inhibit splicing and cause the formation of aberrantly sedimenting presplicing complexes. Molecular and cellular biology 12.3 (1992): 962-970.
Nguyen, L.A., et al. Physical and functional link of the leukemia-associated factors AML1 and PML. Blood. 2005;105(1):292-300. doi: 10.1182/blood-2004-03-1185. PubMed PMID: 15331439.
Nishi, M. et al. Insulin gene mutations and diabetes. Journal of Diabetes Investigation vol. 2 Issue 2 (Apr. 2011).
Nishida, A. et al. Tissue- and Case-specific retention of intron 40 in mature dystrophin mRNA, Journal of Human Genetic 60;327-333 (2015).
Nisole, S., et al. Differential Roles of PML Isoforms. Front Oncol. 2013;3:125. doi: 10.3389/fonc.2013.00125. PubMed PMID: 23734343; PubMed Central PMCID: PMC3660695.

(56) References Cited

OTHER PUBLICATIONS

Nomakuchi et al. Antisense-oligonucleotide-directed inhibition of nonsense-mediated mRNA decay. Nat. Biotechnol. 34(2):164-166 (Feb. 2016).
Nozu et al. Alport syndrome caused by a COL4A5 deletion and exonization of an adjacent AluY. Molecular genetics & genomic medicine 2.5 (2014): 451-453.
Nussinov. Conserved quartets near 5' intron junctions in primate nuclear pre-mRNA. J Theor Biol. Jul. 8, 1988;133(1):73-84.
Oda, T. et al. Identification and cloning of the human homolog (JAG) of the rat Jagged1 gene from the Alagille syndrome critical region at 20p12.Genomics vol. 43, No. 3, pp. 376-379 (1997).
Okazaki, T. et al. PD-1 and PD-1 ligands: from discovery to clinical application. International Immunology(The Japanese Society for Immunology), vol. 19, No. 7, pp. 813-824, (2007).
Oustric, V. et al. Antisense oligonucleotide-based therapy in human erythropoietic protoporphyria. Am J Hum Genet. 2014;94(4):611-7. doi: 10.1016/j.ajhg.2014.02.010. PubMed PMID: 24680888; PubMed Central PMCID: PMC3980518.
Pacheco, et al. Diversity of vertebrate splicing factor U2AF35: identification of alternatively spliced U2AF1 mRNAS. J Biol Chem. Jun. 25, 2004;279(26):27039-49. Epub Apr. 19, 2004.
Pacheco, et al. RNA interference knockdown of hU2AF35 impairs cell cycle progression and modulates alternative splicing of Cdc25 transcripts. Mol Biol Cell. Oct. 2006; 17(10):4187-99. Epub Jul. 19, 2006.
Page-McCaw, P.S., et al. PUF60: a novel U2AF65-related splicing activity. RNA. 1999;5(12):1548-60. PubMed PMID: 10606266.
Palazzo et al. Non-coding RNA: what is functional and what is junk?. Frontiers in genetics 6 (2015): 2.
Pandit et al. Genome-wide analysis reveals SR protein cooperation and competition in regulated splicing. Molecular cell 50.2 (2013): 223-235.
Papaemmanuil, et al. Clinical and biological implications of driver mutations in myelodysplastic syndromes. Blood. Nov. 21, 2013;122(22):3616-27; quiz 3699. doi: 10.1182/blood-2013-08-518886. Epub Sep. 12, 2013.
Passamonti, C. et al. A novel inherited SCN1A mutation associated with different neuropsychological phenotypes: Is there a common core deficit? Epilepsy & Behavior 43:89-92 (2015).
Pastor, et al. Interaction of hnRNPA1/A2 and DAZAP1 with an Alu-derived intronic splicing enhancer regulates ATM aberrant splicing. PLoS One. 2011;6(8):e23349. doi: 10.1371/journal.pone.0023349. Epub Aug. 8, 2011.
Pastor, F., et al. Induction of tumour immunity by targeted inhibition of nonsense-mediated mRNA decay. Nature. 2010;465(7295):227-30. doi: 10.1038/nature08999. PubMed PMID: 20463739; PubMed Central PMCID: PMC3107067.
Paz, A., et al. SPIKE: a database of highly curated human signaling pathways. Nucleic Acids Res. 2011;39(Database issue):D793-9. doi: 10.1093/nar/gkq1167. PubMed PMID: 21097778; PubMed Central PMCID: PMC3014840.
PCT/US2021/030254 International Search Report and Written Opinion dated Jul. 28, 2023.
Pear, Warren S.: New roles for Notch in tuberous sclerosis, Journal of Clinical Investigation, 120(1):84-87 (Jan. 4, 2010).
Pecarelli et al. Regulation of natural mRNAs by the nonsense-mediated mRNA decay pathway. Eukaryotic cell(2014): EC-00090.
Pellagatti, A., et al. Deregulated gene expression pathways in myelodysplastic syndrome hematopoietic stem cells. Leukemia. 2010;24(4):756-64. doi: 10.1038/leu.2010.31. PubMed PMID: 20220779.
Peng, et al. Functional importance of different patterns of correlation between adjacent cassette exons in human and mouse. BMC Genomics. Apr. 26, 2008;9:191. doi: 10.1186/1471-2164-9-191.
Penton, A.L.Notch signaling in humandevelopment and disease. Seminars in Cell & Developmental Biology. vol. 23, pp. 450-457 (2012).
Perdiguero, E., et al. Regulation of Cdc25C activity during the meiotic G2/M transition. Cell Cycle. 2004;3(6):733-7. PubMed PMID: 15136768.
Piaceri, I., et al. Ataxia-telangiectasia mutated (ATM) genetic variant in Italian centenarians. Neurophysiology. 2013;34:573-5.
Pilia et al. Jagged-1 mutation analysis in Italian Alagille syndrome patients. Hum Mut 14(5):394-400 (1999).
Pomentel et al. A dynamic intron retention program enriched in RNA processing genes regulates gene expression during terminal erythropoiesis. Nucleic acids research 44.2 (2015):838-851.
Precursor mRNA-Processing Factor 3, S. Cerevisiae, Homolog OF; PRPF3m, 3 pages.
Przychodzen, B., et al. Patterns of missplicing due to somatic U2AF1 mutations in myeloid neoplasms. Blood. 2013; 122:999-1006. Epub Jun. 19, 2013.doi: blood-2013-01-480970 [pii] 10.1182/blood-2013-01-480970. PubMed PMID: 23775717.
Pugliese, et al. The insulin gene is transcribed in the human thymus and transcription levels correlated with allelic variation at the INS VNTR-IDDM2 susceptibility locus for type 1 diabetes. Nat Genet. Mar. 1997;15(3):293-7.
Rainey et al. Transient inhibition of ATM kinase is sufficient to enhance cellular sensitivity to ionizing radiation. Cancer research68.18 (2008): 7466-7474.
Ramocki et al. The MECP2 duplication syndrome. Am J Med Genet A 152A:1079-1088 (2010).
Rangasamy et al.: Reduced neuronal size and mTOR pathway activity in the Mecp2 A140V Rett syndrome mouse model. F1000research 5:2269 (2016).
Ray, D. et al. A compendium of RNA-binding motifs for decoding gene regulation. Nature. vol. 499, No. 7457, pp. 172-177 (Jul. 11, 2013).
Reineke, E.L., et al. Degradation of the tumor suppressor PML by Pin1 contributes to the cancer phenotype of breast cancer MDA-MB-231 cells. Mol Cell Biol. 2008;28(3):997-1006. doi: 10.1128/MCB.01848-07. PubMed PMID: 18039859; PubMed Central PMCID: PMC2223389.
Rendu, J. et al. Hum Gene Ther. Exon skipping as a therapeutic strategy applied to an RYR1 mutation with pseudo-exon inclusion causing a severe core myopathy. Jul. 2013;24(7):702-13. doi: 10.1089/hum.2013.052.
Reynolds, DM et al.Aberrant Splicing in the PKD2 Gene as a Cause of Polycystic Kidney Disease.Am. Soc. Nephrol. vol. 10, pp. 2342-2351 (1999).
Ritprajak et al. Keratinocyte-Associated B7-H1 Directly Regulates Cutaneous Effector CD8+ T Cell Responses.J Immunology vol. 184, pp. 4918-4925 (2010).
RNA 2-14 The Nineteenth Annual Meeting of the RNA Society. Quebec City, Canada. (Jun. 3-8, 2014).
Roberts, Jennifer et al. Efficient and Persistent Splice Switching by Systemically Delivered LNA Oligonucleotides in Mice. Molecular Therapy, Nature Publishing, vol. 14, No. 4, pp. 471-475, Oct. 1, 2006.
Romero, P.R., et al. Alternative splicing in concert with protein intrinsic disorder enables increased functional diversity in multicellular organisms. Proc Natl Acad Sci USA. 2006;103(22):8390-5. Epub May 24, 2006.doi: 0507916103 [pii] 10.1073/pnas.0507916103. PubMed PMID: 16717195.
Rosenbloom et al. The UCSC Genome Browser database: 2015 Update. Nucleic Acids Research 43, Database Issue doi: 101093/nar/gku1177.
Ruchlemer, R. et al.: Geography, ethnicity and “roots” in chronic lymphocytic leukemia. Leuk Lymphoma. 2013;54(6):1142-50. doi: 10.3109/10428194.2012.740670. PubMed PMID: 23121522.
Rudd, M.F., et al. Variants in the ATM-BRCA2-CHEK2 axis predispose to chronic lymphocytic leukemia. Blood. 2006;108(2):638-44. Epub Apr. 1, 2006.doi: 2005-12-5022 [pii] 10.1182/blood-2005-12-5022. PubMed PMID: 16574953.
Ruskin, et al. A factor, U2AF, is required for U2 snRNP binding and splicing complex assembly. Cell. Jan. 29, 1988;52(2):207-19.
Sadleir, et al. Not all SCN1A epileptic encephalopathies are Dravet syndrome. Neurology. Sep. 5, 2017; 89(10): 1-8.
Sahashi et al. Pathological impact of SMN2 mis-splicing in adult SMA mice. EMBO Mol. Med. 5(10):1586-601 (Oct. 2013).

(56) References Cited

OTHER PUBLICATIONS

Sahashi et al. TSUNAMI: an antisense method to phenocopy splicing-associated diseases in animals. Genes Dev. 26(16):1874-1884 (Aug. 15, 2012).
Sakabe, et al. Sequence features responsible for intron retention in human. BMC Genomics. Feb. 26, 2007;8:59.
Samatanga, et al. The high kinetic stability of a G-quadruplex limits hnRNP F qRRM3 binding to G-tract RNA. Nucleic Acids Res. Feb. 1, 2013;41(4):2505-16. doi: 10.1093/nar/gks1289. Epub Dec. 28, 2012.
Sazani, et al., "Therapeutic potential of antisense oligonucleotides as modulators of alternative splicing" (2003) The Journal of clinical Investigation, 112(4):481-486.
Schanen et al.: A Severely Affected Male Born into a Rett Syndrome Kindred Supports X-Linked Inheritance and Allows Extension of the Exclusion Map. Am J Hum Genetics 63:267-269 (1998).
Schwarze, et al. Redefinition of exon 7 in the COL1A1 gene of type I collagen by an intron 8 splice-donor-site mutation in a form of osteogenesis imperfecta: influence of intron splice order on outcome of splice-site mutation. Am J Hum Genet. Aug. 1999;65(2):336-44.
Scott, S.P., et al. Missense mutations but not allelic variants alter the function of ATM by dominant interference in patients with breast cancer. Proc Natl Acad Sci USA. 2002;99:925-30.
SG 11201702682P Search Report and Written Opinion dated Apr. 9, 2018.
Shao, C., et al. Mechanisms for U2AF to define 3' splice sites and regulate alternative splicing in the human genome. Nat Struct Mol Biol. 2014;doi: 10.1038/nsmb.2906.
Shcherbakova, I., et al. Alternative spliceosome assembly pathways revealed by single-molecule fluorescence microscopy. Cell Rep. 2013;5(1):151-65. Epub Oct. 1, 2013.doi: S2211-1247(13)00467-1 [pii] 10.1016/j.celrep.2013.08.026. PubMed PMID: 24075986.
Shen, M., et al. Characterization and cell cycle regulation of the related human telomeric proteins Pin2 and TRF1 suggest a role in mitosis. Proc Natl Acad Sci USA. 1997;94(25):13618-23. PubMed PMID: 9391075; PubMed Central PMCID: PMC28355.
Shiloh, Y., et al.The ATM protein kinase: regulating the cellular response to genotoxic stress, and more. Nat Rev Mol Cell Biol. 2013; 14(4):197-210. doi: 10.1038/nrm3546. PubMed PMID: 23486281.
Shiria, C.L. et al. Mutant U2AF1 Expression Alters Hematopoiesis and Pre-mRNA Splicing In Vivo. Cancer Cell. 2015;27(5):631-43. doi: 10.1016/j.ccell.2015.04.008. PubMed PMID: 25965570; PubMed Central PMCID: PMC4430854.
Shirley, M.H., et al.Incidence of haematological malignancies by ethnic group in England, Jul. 2001. Br J Haematol. 2013;163(4):465-77. doi: 10.1111/bjh.12562. PubMed PMID: 24033296.
Sierakowska, H et al. Repair of thalassemic human beta-globin mRNA in mammalian cells by antisense oligonucleotides. Proc Natl Acad Sci U S A. Nov. 12, 1996;93(23):12840-4.
Singh, et al. An antisense microwalk reveals critical role of an intronic position linked to a unique long-distance interaction in pre-mRNA splicing. RNA. Jun. 2010;16(6):1167-81. doi: 10.1261/rna.2154310. Epub Apr. 22, 2010.
Sirand-Pugnet, et al.: An intronic (A/U)GGG repeat enhances the splicing of an alternative intron of the chicken beta-tropomyosin pre-mRNA. Nucleic Acids Res. Sep. 11, 1995;23(17):3501-7.
Skjevik et al. The N-Terminal Sequence of Tyrosine Hydroxylase Is a Conformationally Versatile Motif That Binds 14-3-3 Proteins and Membranes.J. Mol. Bio. vol. 426, pp. 150-168 (2014).
Smith, C.W., et al. Scanning and competition between AGs are involved in 3' splice site selection in mammalian introns. Mol Cell Biol. 1993;13(8):4939-52. PubMed PMID: 8336728.
Smith, et al.: Alternative pre-mRNA splicing: the logic of combinatorial control. Trends Biochem Sci. 25(8):381-8 (2000).
Smith, et al.,: Nonsense-mediated RNA decay—a switch and dial for regulating gene expression. Bioessays 37(6): 612-623 (2015).
Smith, P.J., et al. An increased specificity score matrix for the prediction of SF2/ASF-specific exonic splicing enhancers. Hum Mol Genet. 2006; 15(16):2490-508. PubMed PMID: 16825284.
Soo, R.A., et al.: Ethnic differences in survival outcome in patients with advanced stage non-small cell lung cancer. J Thorac Oncol. 2011;6:1030-8.
Sorek et al. Minimal conditions for exonization of intronic sequences: 5' splice site formation in alu exons. Molecular cell 14.2 (2004): 221-231.
Soutar et al. Mechanisms of disease: genetic causes of familial hpercholesterolemia. Nat. Clin. Pract. Cardiovasc. Med. 4:214-255 (Apr. 1, 2007).
Spellman et al. Regulation of alternative splicing by PTB and associated factors. (2005): 457-460.
Spinner et al. Jagged1 mutations in alagille syndrome. Hum Mutat 17(1):18-33 (2001).
Stamm, S.: Regulation of alternative splicing by reversible protein phosphorylation. J Biol Chem. 2008;283(3):1223-7. PubMed PMID: 18024427.
Stankovic, T., et al.: Inactivation of ataxia telangiectasia mutated gene in B-cell chronic lymphocytic leukaemia. Lancet. 1999;353(9146):26-9. doi: 10.1016/S0140-6736(98)10117-4. PubMed PMID: 10023947.
Staropoli et al. Rescue of gene-expression changes in an induced mouse model of spinal muscular atrophy by an antisense oligonucleotide that promotes inclusion of SMN2 exon 7. Genomics 105:220-228 (2015).
Stead, et al. Global haplotype diversity in the human insulin gene region. Genome Res. Sep. 2003;13(9):2101-11.
Stec, W.J. et al., "Automated solid-phase synthesis, separation, and stereochemistry of phosphorothioate analogs of oligodeoxyribonucleotides," J. Am. Chem. Soc., 1984, vol. 106, No. 20, pp. 6077-6079.
Stein, C.A. et al., "Physicochemical properties of phosphorothioate oligodeoxynucleotides," Nucleic Acids Res., 1988, vol. 16, No. 8, pp. 3209-3221.
Stein et al.: FDA-Approved Oligonucleotide Therapies in 2017. Mol Ther 25:1069-1075 (2017).
Story, M.D. et al. ATM has a major role in the double-stand break repair pathway dysregulation in sporadic breast carcinomas and is an independent prognostic marker at both mRNA and protein levels, Breast Diseases: A Yearbook Quarterly, 26(4);297-299 (Mar. 17, 2015).
Strausfeld, U., et al. Activation of p34cdc2 protein kinase by microinjection of human cdc25C into mammalian cells. Requirement for prior phosphorylation of cdc25C by p34cdc2 on sites phosphorylated at mitosis. J Biol Chem. 1994;269(8):5989-6000. PubMed PMID: 8119945.
Suarez, F. et al. Incidence, presentation, and prognosis of malignancies in ataxia-telangiectasia: a report from the French national registry of primary immune deficiencies. J Clin Oncol. 2015;33(2):202-8. doi: 10.1200/JCO.2014.56.5101. PubMed PMID: 25488969.
Summerton, James. Morpholino Antisense Oligos: Applications in Biopharmaceutical ResearchMorpholinos constitute a radical re-design of DNA, providing decisive advantages over the moreconventional oligo types used for modulating gene expression. Innovations in Pharmaceutical Technology Issue No. 17 (2005).
Sun, H., et al.: Multiple splicing defects in an intronic false exon. Mol Cell Biol. 2000;20(17):6414-25. PubMed PMID: 10938119.
Supplementary European Search Report dated Apr. 18, 2019 for EP16876615.2.
Svasti, et al. RNA repair restores hemoglobin expression in IVS2-654 thalassemic mice. Proc Natl Acad Sci U S A. Jan. 27, 2009; 106(4): 1205-1210.
Swaans, RJM et al. Four novel mutations in the Tyrosine Hydroxylase gene in patients with infantile parkinsonism Annals of Human Genetic, vol. 64, No. 1, pp. 25-31, (Jan. 2000).
Tabrez, S. et al.: A Synopsis of the Role of Tyrosine Hydroxylase in Parkinson's Disease.CNS & Neurological Disorders—Drug Targets vol. 11, No. 4 (2012).
Takahashi et al. Skewed X chromosome inactivation failed to explain the normal phenotype of a carrier female with MECP2 mutation resulting in Rett syndrome. Clin Genet 73:257-261 (2008).

(56) References Cited

OTHER PUBLICATIONS

Tavanez, J.P., et al. hnRNP A1 proofreads 3' splice site recognition by U2AF. Mol Cell. 2012;45(3):314-29. Epub Feb. 14, 2012. doi: S1097-2765(12)00032-9 [pii] 10.1016/j.molcel.2011.11.033. PubMed PMID: 22325350.
Taylor, A.M., et al. Ataxia telangiectasia: more variation at clinical and cellular levels. Clin Genet. 2015;87(3):199-208. doi: 10.1111/cge.12453. PubMed PMID: 25040471.
Taylor, A.M., et al.: Leukemia and lymphoma in ataxia telangiectasia. Blood. 1996;87(2):423-38. PubMed PMID: 8555463.
Thisted, et al. Optimized RNA targets of two closely related triple KH domain proteins, heterogeneous nuclear ribonucleoprotein K and alphaCP-2KL, suggest Distinct modes of RNA recognition. J Biol Chem. May 18, 2001;276(20): 17484-96. Epub Feb. 2, 2001.
Tilgner, H. et al., "Deep sequencing of subcellular RNA fractions shows splicing to be predominantly co-transcriptional in the human genome but inefficient for IncRNAs," Genome Research, 2012, vol. 22, No. 9, pp. 1616-1625.
Tillotson et al. Radically truncated MeCP2 rescues Rett syndrome-like neurological defects. Nature 550:398 (2017).
Torres, V.E. et al. Autosomal dominant polycystic kidney disease: the last 3 years.Kidney International vol. 76, pp. 149-168 (May 20, 2009).
Trabattoni et al.: Costimulatory Pathways in Multiple Disease Sclerosis: Distinctive Expression of PD-1 and PD-L1 in Patients with Different Patterns of Disease.J. Immunol. vol. 183, pp. 4984-4993 (2009).
Trapnell, C. et al. Differential gene and transcript expression analysis of RNA-seq experiments with Top Hat and Cufflinks. Nat Protoc. 2012;7(3):562-78. Epub Mar. 3, 2012.doi: nprot.2012.016 [pii] 10.1038/nprot.2012.016. PubMed PMID: 22383036.
Turnpenny, P.D. et al. Alagille syndrome: pathogenesis, diagnosis and management. European Journal of Human Genetics vol. 20, pp. 251-257 (2012.
Uhlmann, E. et al., "Antisense oligonucleotides: a new therapeutic principle, " Chemical Reviews, 1990, vol. 90, No. 4, pp. 543-584.
U.S. Appl. No. 14/741,071 Non-Final Office Action mailed Dec. 1, 2016.
U.S. Appl. No. 14/874,420 Non-Final Office Action Mailed Mar. 21, 2017.
U.S. Appl. No. 14/874,420 Office Action dated Oct. 24, 2017 .
U.S. Appl. No. 15/619,984 Office Action dated Dec. 17, 2018.
U.S. Appl. No. 15/949,902 Office Action dated Mar. 1, 2019.
U.S. Appl. No. 15/288,415 Office Action dated Jun. 26, 2018.
Vafiadis, et al. Insulin expression in human thymus is modulated by INS VNTR alleles at the IDDM2 locus. Nat Genet. Mar. 1997;15(3):289-92.
Van Nostrand et al. Robust transcriptome-wide discovery of RNA-binding protein binding sites with enhanced CLIP (eCLIP). Nature methods 13.6 (2016): 508.
Venkatesh, A. et al., "Antisense oligonucleotide mediated increase of OPA1 expression using TANGO technology for the treatment of autosomal dominant optic atrophy," Molecular Therapy, 2020, vol. 28, No. 4S1.
Venkatesh, A. et al., "Antisense oligonucleotide mediated increase of OPA1 expression using TANGO technology for the treatment of autosomal dominant optic atrophy," ARVO Annual Meeting (Abrstract), 2020, vol. 61, No. 2755.
Verhaart, I.E.C. AON-Mediated Exon Skipping for Duchenne Muscular Dystrophy. Chapter 3. pp. 1-26 (Aug. 1, 2012).
Verret et al., Inhibitory Interneuron Deficit Links Altered Network Activity and Cognitive Dysfunction in Alzheimer Model, Cell, 149(3): 708-721 (2012).
Vieira, N. et al.: Jagged 1Rescues the Duchenne Muscular Dystrophy Phenotype. Cell vol. 163, pp. 1204-1213 (Nov. 19, 2015).
Voelker, et al. A comprehensive computational characterization of conserved mammalian intronic sequences reveals conserved motifs associated with constitutive and alternative splicing. Genome Res. Jul. 2007;17(7):1023-33. Epub May 24, 2007.
Vorechovsky Correspondence Pediatric Research 2010.
Vorechovsky, I. Letter to the Editor: MER91B-assisted cryptic exon activation in Gitelman syndrome. Pediatric research 67.4 (2010): 444-445.
Vorechovsky Transposable elements in disease-associated cryptic exons. Human genetics 127.2 (2010): 135-154.
Wahl, et al. The spliceosome: design principles of a dynamic RNP machine. Cell. Feb. 20, 2009;136(4):701-18. doi: 10.1016/j.cell.2009.02.009.
Wan, W.B. et al., "Synthesis, biophysical properties and biological activity of second generation antisense oligonucleotides containing chiral phosphorothioate linkages," Nucleic Acids Research, 2014, vol. 42, No. 22, p. 13456-13468.
Wang, et al. A complex network of factors with overlapping affinities represses splicing through intronic elements. Nat Struct Mol Biol. Jan. 2013;20(1):36-45. doi: 10.1038/nsmb.2459. Epub Dec. 16, 2012.
Wang et al. Alternative isoform regulation in human tissue transcriptomes. Nature. 2008;456(November):470-476.
Wang et al. Human Adenovirus Type 36 Enhances Glucose Uptake in Diabetic and Nondiabetic Human Skeletal Muscle Cells Independent of Insulin Signaling. Diabetes vol. 57, pp. 1861-1869 (2008).
Wang, et al.: Intronic splicing enhancers, cognate splicing factors and context-dependent regulation rules. Nat Struct Mol Biol. Oct. 2012;19(10):1044-52. doi: 10.1038/nsmb.2377. Epub Sep. 16, 2012.
Wang, et al.: Regulation of insulin preRNA splicing by glucose. Proc Natl Acad Sci U S A. Apr. 29, 1997;94(9):4360-5.
Wang, Z. et al.: Systematic identification and analysis of exonic splicing silencers. Cell. 2004;119(6):831-45. PubMed PMID: 15607979.
Warf, M.B., et al.: Role of RNA structure in regulating pre-mRNA splicing. Trends Biochem Sci. 2010;35(3):169-78. Epub 2009/12/05.doi: S0968-0004(09)00196-0 [pii].
Wieland, et al.: RNA quadruplex-based modulation of gene expression. Chem Biol. Jul. 2007;14(7):757-63.
Wilton, et al. Splice modification to restore functional dystrophin synthesis in Duchenne muscular dystrophy. Current pharmaceutical design 16.8 (2010): 988-1001.
Wong et al. Orchestrated intron retention regulates normal granulocyte differentiation. Cell 154.3 (2013): 583-595.
Wu et al. AT-AC Pre-mRNA Splicing Mechanisms and Conservation of Minor Introns in Voltage-Gated Ion Channel Genes. Molecular and Cellular Biology 19(5): 3225-3236 (May 1999).
Wu et al.: Functional recognition of the 3' splice site AG by the splicing factor U2AF35.Nature. 1999;402(6763):832-5. PubMed PMID: 10617206.
Wu et al.: MRE11-RAD50-NBS1 and ATM function as co-mediators of TRF1 in telomere length control. Nat Struct Mol Biol. 2007;14(9):832-40. doi: 10.1038/nsmb1286. PubMed PMID: 17694070.
Wu, J.Y., et al.: Specific interactions between proteins implicated in splice site selection and regulated alternative splicing. Cell. 1993;75(6):1061-70. Epub Dec. 17, 1993.doi: 0092-8674(93)90316-I [pii]. PubMed PMID: 8261509.
Xia, Y. et al.: Frequencies of SF3B1, NOTCH1, MYD88, BIRC3 and IGHV mutations and TP53 disruptions in Chinese with chronic lymphocytic leukemia: disparities with Europeans. Oncotarget. 2015;6(7):5426-34. PubMed PMID: 25605254.
Xing, et al.: The multiassembly problem: reconstructing multiple transcript isoforms from EST fragment mixtures. Genome Res. Mar. 2004;14(3):426-41. Epub Feb. 12, 2004.
Yamamoto et al. Mib-Jag1-Notch signalling regulates patterning and structural roles of the notochord by controlling cell-fate decisions. Development 137(15):2527-2537 (2010).
Yamamoto, Y., et al. BCOR as a novel fusion partner of retinoic acid receptor alpha in a t(X;17)(p11;q12) variant of acute promyelocytic leukemia. Blood. 2010;116(20):4274-83. doi: 10.1182/blood-2010-01-264432. PubMed PMID: 20807888.
Yan, et al. Systematic discovery of regulated and conserved alternative exons in the mammalian brain reveals NMD modulating chromatin regulators. Proc Natl Acad Sci U S A. Mar. 17, 2015; 112(11): 3445-3450.
Yang et al.: Biophysical analysis and small-angle X-ray scattering-derived structures of MeCP2-nucleosome complexes. Nucleic Acids Res 39:4122-4135 (2011).

(56) References Cited

OTHER PUBLICATIONS

Yang, S. et al. PML-dependent apoptosis after DNA damage is regulated by the checkpoint kinase hCds1/Chk2. Nat Cell Biol. 2002;4(11):865-70. doi: 10.1038/ncb869. PubMed PMID: 12402044.
Yang, S., et al. Promyelocytic leukemia activates Chk2 by mediating Chk2 autophosphorylation. J Biol Chem. 2006;281(36):26645-54. doi: 10.1074/jbc.M604391200. PubMed PMID: 16835227.
Yang, Y. et al. Oligomerization of the polycystin-2 C-terminal tail and effects on its Ca2+binding properties.J. Bio. Chem. vol. 290, No. 16, pp. 10544-10554 (2015).
Yeo, et al.: Discovery and analysis of evolutionarily conserved intronic splicing regulatory elements. PLoS Genet. May 25, 2007;3(5):e85. Epub Apr. 13, 2007.
Yoshida, et al. Frequent pathway mutations of splicing machinery in myelodysplasia. Nature. Sep. 11, 2011;478(7367):64-9. doi: 10.1038/nature10496.
Yoshida, K., et al. Splicing factor mutations and cancer. Wiley Interdiscip Rev RNA. 2014;5(4):445-59. doi: 10.1002/wrna.1222. PubMed PMID: 24523246.
Young et al. 915—a GABA-Selective AAV Vector-Based Approach to Up-Regulate Endogenous Scn1a Expression reverses key Phenotypes in a Mouse Model of Dravet Syndrome. 22nd Annual Meeting American Society of Gene & Cell Therapy. Washington, D.C. Apr. 29-May 2, 2019 (Abstract).
Yu, E.Y., et al. Regulation of telomere structure and functions by subunits of the INO80 chromatin remodeling complex. Mol Cell Biol. 2007;27(16):5639-49. doi: 10.1128/MCB.00418-07. PubMed PMID: 17562861; PubMed Central PMCID: PMC1952117.
Yuan et al. Brain localization and neurotoxicity evaluation of polysorbate 80-modified chitosan nanoparticles in rats. PloS one 10.8 (2015): e0134722.
Yuan X., et al. Nuclear protein profiling of Jurkat cells during heat stress-induced apoptosis by 2-DE and MS/MS. Electrophoresis. 2007;28(12):2018-26. doi: 10.1002/elps.200600821. PubMed PMID: 17523140.
Zammarchi, et al. "Antitumorigenic potential of STAT3 alternative splicing modulation", (2011) PNAS, vol. 108, No. 43, pp. 17779-17784.
Zamore, P.D., et al. Identification, purification, and biochemical characterization of U2 small nuclear ribonucleoprotein auxiliary factor. Proc Natl Acad Sci USA. 1989;86(23):9243-7. PubMed PMID: 2531895.
Zarnack K., et al. Direct competition between hnRNP C and U2AF65 protects the transcriptome from the exonization of Alu elements. Cell. 2013;152(3):453-66. Epub 2013/02/05.doi: S0092-8674(12)01545-0 [pii] 10.1016/j.cell.2012.12.023. PubMed PMID: 23374342.
Zhang C., et al. RNA landscape of evolution for optimal exon and intron discrimination. Proc Natl Acad Sci USA. 2008; 105(15):5797-802. Epub 2008/04/09.doi: 0801692105 [pii] 10.1073/pnas.0801692105. PubMed PMID: 18391195.
Zhang et al.: Computational definition of sequence motifs governing constitutive exon splicing. Genes Dev. 2004;18:1241-50. PubMed PMID: 15145827.
Zhang, et al. Insulin as an autoantigen in NOD/human diabetes. Curr Opin Immunol. Feb. 2008;20(1):111-8. doi: 10.1016/j.coi.2007.11.005.
Zhang, et al.: The kinetics and folding pathways of intramolecular G-quadruplex nucleic acids. J Am Chem Soc. Nov. 21, 2012;134(46):19297-308. doi: 10.1021/ja309851t. Epub Nov. 12, 2012.
Zhang, J. et al., "PowerBlast: A network application for automated analysis of large genomic sequences," Genome Methods, 1997, vol. 7, pp. 649-656.
Zimrin et al. An Antisense Oligonucleotide to the Notch Ligand Jagged Enhances Firbroblast Growth Factor-induced Angiogenesis in Vitro. J. Biol. Chem. 271(51):32499-502 (Dec. 20, 1996).
Zon et al. Phosphorothioate oligonucleotides: chemistry, purification, analysis, scale-up and future directions. Anti Cancer Drug Design vol. 6, No. 6, pp. 539-568 (1991).
Zon G. and Stec, W.J. (1991) In Eckstein,F. (ed.), Oligonucleotides and Analogues: A Practical Approach. Oxford University Press, Oxford, UK, pp. 87-108.
Zorio, D.A., et al. Both subunits of U2AF recognize the 3' splice site in Caenorhabditis elegans. Nature. 1999;402(6763):835-8. PubMed PMID: 10617207.
Zuker, M. Mfold web server for nucleic acid folding and hybridization prediction. Nucleic Acids Res. 31, 3406-3415 (2003).
Arzimanoglou, A. et al.: A Review of the New Antiepileptic Drugs for Focal-Onset Seizures in Pediatrics: Role of Extrapolation, Pediatr. Drugs 20(3):249-64 (2018).
AU 2018322319 Examination Report No. 1 dated Oct. 16, 2020.
Berecki, G. et al.: SCN1A Gain of Function in Early Infantile Encephalopathy. Ann Neurol. 85:514-25 (2019).
Boutz, et al.: Detained intron are a novel, widespread class of post-transcriptionally spliced introns. Genes & Development 29: 63-80.
Braunschweig et al., "Widespread intron retention in mammal functionally tunes transcriptomes", Chold Spring Harbor Laboratory Press, 2014 p. 1-14.
Carvill, et al., "Aberrant Inclusion of a Poison Exon Causes Dravet Syndrome and Related SCN1A-Associated Genetic Epilepsies", The American Journal of Human Genetics, Vo. 103, No. 6, pp. 1022-1029 (2018).
"Cestele, S. et al., "Nonfunctional NaV1.1 familial hemiplegic migraine mutant transformed into gain of function by partial rescue of folding defects," Proc. Natl. Acad. Sci., 2013, vol. 110, No. 43, pp. 17546-17551".
"Cheah, C. S. et al., "Correlations in timing of sodium channel expression, epilepsy, and sudden death in Dravet syndrome," Channels, 2013, vol. 7, No. 6, pp. 468-472".
"Cheah, C. S. et al., "Specific deletion of NaV1.1 sodium channels in inhibitory interneurons causes seizures and premature death in a mouse model of Dravet syndrome," PNAS, 2012, vol. 109, No. 36, pp. 14646-14651".
Creson, et al., "Re-expression of SynGAP Protein in Adulthood Improves Translatable Measure of Brain Function and Behavior in a Model of Neurodevelopmental Disorders" BioRxiv (2018) pp. 1-27.
De-Lange et al.: Influence of contraindicated medication use on cognitive outcome in Dravet syndrome and age at first afebrile seizure as a clinical predictor in SCN1A-related seizure phenotypes, Epilepsia 59:1154-65 (2018).
"Depienne, C. et al., "Spectrum of SCN1A gene mutations associated with Dravet syndrome: analysis of 333 patients," J. Med Genet., 2009, vol. 46, pp. 183-191".
"Dhifallah, S. et al., "Gain of Function for the SCN1A/hNav1.1-L1670W Mutation Responsible for Familial Hemiplegic Migraine," Front Mol. Neurosci., 2018, vol. 11, No. 232, pp. 1-14".
"Djemie, T. et al., "Pitfalls in genetic testing: the story of missed SCN1A mutations," Mol Genet Genomic Med., 2016, vol. 4, No. 4, pp. 457-464".
European Patent Application No. 21209655.6 Search Report dated May 23, 2022.
"Fan, C. et al., "Early-onset familial hemiplegic migraine due to a novel SCN1A mutation," Cephalalgia, 2016, vol. 36, No. 13, pp. 1238-1247".
"Gataullina, S. et al., "From genotype to phenotype in Dravet disease," Seizure, 2017, vol. 44, pp. 58-64".
"Genton, P. et al., "Dravet syndrome: the long-term outcome," Epilepsia, 2011, vol. 52, Suppl 2, pp. 44-49".
Han, et al., "TANGO—Targeted Augmentation of Nuclear Gene Output for the Treatment of Genetic Diseases" Poster.
Hsiao, J. et al., "Upregulation of Haploinsufficient Gene Expression in the Brain by Targeting a Long Non-coding RNA Improves Seizure Phenotype in a Model of Dravet Syndrome," EBioMedicine, 2016, vol. 9, pp. 257-277.
Khorkova et al., Oligonucleotide therapies for disorders of the nervous system. Nat Biotechnol. Mar. 2017;35(3):249-263. doi: 10.1038/nbt.3784. Epub Feb. 27, 2017. PMID: 28244991; PMCID: PMC6043900.
Kim, et al. "Reduced Sodium Channel nav1.1 Levels in BACE1-NULL Mice", JBC (2010) 1-21.

(56) References Cited

OTHER PUBLICATIONS

Kralovicova, et al., "Optimal antisense target reducing INS intron 1 retention is adjacent to a parallel G quadruplex" (2014) Nucleic Acids Research, v. 42, n.12, p. 8161-8173.
Kralovicova, et al., "Exon-Centric Regulation of ATM expression is population-dependent and amenable to antisense modification by pseudoexon targeting", Scientific Reports (2016) p. 1-13.
"Lagae, L. et al., "Quality of life and comorbidities associated with Dravet syndrome severity: a multinational cohort survey," Dev. Med. Child Neurol., 2018, vol. 60, No. 1, pp. 63-72".
Liang, et al., "Translation efficiency of mRNAs is increased by antisnse oligonucleotides targeting upstream open reading frames" (2016) Nature Biotechnology, V. 34, N. 8, p. 875-882.
"Liu, Y. et al., "Dravet syndrome patient-derived neurons suggest a novel epilepsy mechanism," Ann Neurol., 2013, vol. 74, No. 1, pp. 128-139".
Lo, et al., "ATM polymorphisms and risk of lung cancer among never smokers", (2010) Lund Cancer 69, p. 148-154.
Maljevic, et al., "Models for discovery of targeted therapy in genetic epileptic encephalopathies", Journal of Neurochemistry (2017) Vo. 143, No. 1, pp. 30-48.
"Meng, H. et al., "The SCN1A Mutation Database: Updating Information and Analysis of the Relationships among Genotype, Functional Alteration, and Phenotype," Hum Mutation, 2015, vol. 36, No. 6, pp. 573-580".
Minn; Alexandra H. et al.: Insulinomas and expression of an insulin splice variant. Lancet 363(9406):363-367 (2004). doi: 10.1016/S0140-6736(04)15438-X. Abstract.
Palhais, Bruno et al.: Splice-shifting oligonucleotide (SSO) mediated blocking of an exonic splicing enhancer (ESE) created by the prevalent c.903+469TC MTRR mutation corrects splicing and restores enzyme activity in patient cells. Nucleic Acids Research 43(9):4627. 4639 (2015). https://doi.org/10.1093/nar/gkv275.
"Ragona, F. et al., "Cognitive development in Dravet syndrome: A retrospective, multicenter study of 26 patients," Epilepsia, 2011, vol. 52, No. 2, pp. 386-392,".
Sazani, et al., "Splice Switching Oligonucleotides as Potential Therapeutics", Antisense Drug Technology, Second Edition, p. 90-114.
Sierakowska, et al., Repair of thalassemic human B-globin mRNA in mammalian cells by antisense oligonucleotides. PNAS 93: 12840-4 (1996).
Supplemental European Search Report issued in corresponding EP application No. 18848036 issued Apr. 15, 2021.
Takeshima Y. et al.: Modulation of in vitro splicing of the upstream intron by modifying an intra-exon sequence which is deleted from the dystrophin gene in dystrophin Kobe. The Journal of Clinical Investigation 95(2):515-20 (1995). doi: 10.1172/JCI117693.
Tsuchiya, Teizo et al.: Evidence for the Essential Role of Myosin Subfragment-2 in the ATP-Dependent Actin-Myosin Sliding in Muscle Contraction. The Japanese Journal of Physiology 48(5):383-387 (1998). https://doi.org/10.2170/jjphysiol.48.383.
Abramova, Tatyana V. et al. Novel Oligonucleotide Analogues Based on Morpholino Nucleoside Subunits Antisense Technologies: New Chemical Possibilities. Indian Journal of Chemistry 48B:1721-1726 (2009).
Alanis, Eugenio F., et al., An exon-specific U1 small nuclear RNA (snRNA) strategy to correct splicing defects. Human Molecular Genetics 21(11):2389-2398 (2012). https://doi.org/10.1093/hmg/dds045.
Araujo et al.: Before It Gets Started: Regulating Translation at the 5' UTR. Comp Funct Genomics. 2012:475731 (2012) doi: 10.1155/2012/475731.
Boisguerin, P. et al. Delivery of therapeutic oligonucleotides with cell penetrating peptides. Advanced Drug Delivery Reviews 87:56-27 (2015).
Co-pending U.S. Appl. No. 18/658,390, inventors Aznarez; Isabel et al., filed May 8, 2024.
Co-pending U.S. Appl. No. 18/672,649, filed May 23, 2024.
EP16781187.6 European Second Office Action dated Feb. 24, 2023.
EP20763143.3 Extended European Search Report dated Nov. 13, 2023.
European Supplementary Search Report dated Sep. 20, 2023 issued in European Patent Application No. 20897381.
Gadgil, Ankur, et al., U7 snRNA: A tool for gene therapy. The Journal of Gene Medicine 23(4):e3321 (2021). https://doi.org/10.1002/jgm.3321.
Gong, Q. et al. Inhibition of nonsense-mediated mRNA decay by antisense morpholino oligonucleotides restores functional expression of hERG nonsense and frameshift mutations in long-QT syndrome. J Mol Cell Cardiol. 50(1):223-9 (2011).
Han et al.: Antisense-Mediated Increase of SCN1A Expression Using TANGO Technology for the Treatment of Dravet Syndrome. Molecular Therapy 22nd Annual Meeting of the American Society of Gene and Cell Therapy (ASGCT) 27(4):304-305 (2019).
Harris, et al. Single-molecule DNA sequencing of a viral genome. Science 320(5872):106-9 (2008).
Huppert et al.: Prevalence of quadruplexes in the human genome. Nucleic Acids Res. 33(9):2908-16 (2005).
Koizumi, Makoto. ENA Oligonucleotides as Therapeutics. Current Opinion in Molecular Therapeutics 8(2):144-149 (2006).
Kralovicova, et al., "Global control of aberrant splice-site activation by auxiliary splicing sequences: evidence for a gradient in exon and intron definition", (2007) Nucleic Acids Research, v. 35, n. 19, p. 6399-6413.
Kuzmiak, HA et al. Applying nonsense-mediated mRNA decay research to the clinic: progress and challenges. Trends Mol Med. 12(7):306-16 (2006).
Lochmann, D. et al. Drug delivery of oligonucleotides by peptides. European Journal of Pharmaceutics and Biopharmaceutics 58: 237-251 (2004).
Margulies et al.: Genome sequencing in microfabricated high-density picolitre reactors. Nature. 437(7057):376-380 (2005).
Martin, L. et al. Identification and characterization of small molecules that inhibit nonsense- mediated RNA decay and suppress nonsense p53 mutations. Cancer Res. 74(11):3104-13 (2014).
Meyer et al.: Antisense Derivatives of U7 Small Nuclear RNA as Modulators of Pre-mRNA Splicing. Alternative pre-mRNA Splicing: Theory and Protocols (2012). https://doi.org/10.1002/9783527636778.ch45.
Michaels, W. et al. Antisense oligonucleotide-mediated correction of CFTR splicing improves chloride secretion in cystic fibrosis patient-derived bronchial epithelial cells. Nucleic Acids Research 48(13): 7454-7467 (2020).
Mishra et al.: G4IPDB: A database for G-quadruplex structure forming nucleic acid interacting proteins. Sci Rep. 6:38144 pp. 1-9 (2016).
Obika, et al. "Synthesis of 2'-0,4'-C-methyleneuridine and -cytidine. Novel bicyclic nucleosides having a fixed C3, -endo sugar puckering". Tetrahedron Letters 38 (50): 8735 (1997).
PCT/US2016/066708 International Preliminary Report on Patentability dated Jun. 28, 2018.
PCT/US2020/063157 International Search Report and Written Opinion dated Mar. 10, 2021.
PCT/US2022/049318 International Search Report and Written Opinion dated Mar. 4, 2024 (Pub. No. WO2023086342).
PCT/US2023/029040 International Search Report and Written Opinion dated Feb. 16, 2024.
PCT/US2024/015838 International Search Report and Written Opinion dated Sep. 3, 2024.
Popp, MW et al. Attenuation of nonsense-mediated mRNA decay facilitates the response to chemotherapeutics. Nat Commun. 6(6632): 1-32 (2015).
Scheffer, Ingrid E. Diagnosis and Long-term Course of Dravet Syndrome. European Journal of Paediatric Neurology 16(Suppl 1):S5-S8 (2012).
Singh et al. Encyclopedia of Pharmaceutical Technology 2nd Ed. pp. 751-753 (2002).
Stefanovic et al.: Assemble, nuclear import and function of U7 snRNPs studied by microinjection of synthetic U7 RNA into Xenopus oocytes. Nucleic Acids Research 23(16):3141-3151 (1995). https://doi.org/10.1093/nar/23.16.3141.

(56) References Cited

OTHER PUBLICATIONS

Stoke Therapeutics Presents Data from the Phase 1/2a MONARCH Study of STK-001 in Children and Adolescents with Dravet Syndrome at the American Epilepsy Society (AES) 2021 Annual Meeting. Stoke Therapeutics. American Epilepsy Society (AES) 2021 Annual Meeting: 1-3 (2021).
The AON based uORF blockage in the expression of OPA1—a pre-clinical development of therepy for OPA1-linked optic atrophy, Wissinger Lab, Molecular Genetics Laboratory, Web page http://www.eye-tuebingen.de/wissinger/lab/members/ting-xiao/, 3 pages, Oct. 22, 20109, retrieved from Internet Archive Wayback Machine https://web.archive.org/web/20191022233241/ http://www.eye-tuebingen.de/wissinger/lab/members/ting-xiao/ on Jun. 7, 2022.
Todd et al.: Highly prevalent putative quadruplex sequence motifs in human DNA. Nucleic Acids Res. 33(9):2901-7 (2005).
U.S. Appl. No. 16/561,960 Pre-Interview First Office Action Mailed Dec. 19, 2019.
Venkatesh, Aditya: Antisense oligonucleotide mediated increase of OPA1 expression using TANGO technology for the treatment of autosomal dominant optic atrophy. Stoke Therapeutics. Association for Research in Vision & Ophthalmology Meeting 2020.
Wagnon, J. Tango With SCNIA: Can This Molecular Dance Defeat Dravet Syndrome? Epilpesy Currents 21(1):60-61 (2021).
Wang, AG et al., OPA1 expression in the human retina and optic nerve,. Exp Eye Res 83(5):1171-1178 (2006).
Wang, W. et al. The developmental changes of Na(v)1.1 and Na(v)1.2 expression in the human hippocampus and temporal lobe, Brain Res 1389:61-70 (2011).
Wu, Y. et al. Incidence of Dravet Syndrome in a US Population. Pediatrics 136(5): e1310-e1315 (2015).
Hinnebusch, Alan G., et al. Translational control by 5'-untranslated regions of eukaryotic mRNAs. Science 352.6292: 1413-1416. (2016).
Lebedeva, I.V. et al., Chapter 6:Phosphorothioate Oligodeoxynucleotides as Inhibitors of Gene Expression: Antisense and Non-Antisense Effects, Applications of Antisense Therapies to Restenosis, p. 101 (1999).
Leppek, Kathrin, et al. Functional 5' UTR mRNA structures in eukaryotic translation regulation and how to find them. Nature Reviews, Molecular Cell Biology: pp. 1-17. (2017).
Liang, Xue-hai, et al. Antisense oligonucleotides targeting translation inhibitory elements in 5' UTRs can selectively increase protein levels. Nucleic acids research 45.16: 9528-9546. (2017).
PCT/US2023/029040 International Preliminary Report on Patentability dated Feb. 13, 2025.
PCT/US2024/026656 Invitation to Pay Additional Fees mailed Oct. 31, 2024.
PCT/US2024/032131 International Search Report mailed Jan. 10, 2025.
PCT/US2024/039369 International Search Report and Written Opinion dated Dec. 26, 2024.
Romagnoli, M. et al. Idebenone increases chance of stabilization/recovery of visual acuity in OPA1-dominant optic atrophy. Annals of Clinical and Translational Neurology 7(4): 590-594 (2020).
U.S. Appl. No. 16/696,635 Final Office Action mailed Sep. 17, 2021.
U.S. Appl. No. 16/696,635 Non-Final Office Action mailed Feb. 23, 2021.
U.S. Appl. No. 17/412,664 Office Action dated Nov. 1, 2024.
Zhang Y. et al., Pharmacological characterization of an antisense knockdown zebrafish model of Dravet syndrome: inhibition of epileptic seizures by the serotonin agonist fenfluramine. PLoS One, 10(5): 1-19, Article e0125898: I2015).
Kosei, T. et al. Physiological Function Analysis by Antisense Oligonucleotides. Molecular Biology for Physiologists, 60: 383-400 (1998). Machine translation pp. 1-23.

* cited by examiner

| Group | N | Treatment | Dose (ug/eye) | Final conc. expected in vitreous* (uM) | Dose volume (uL/eye) | Dose and regimen | Matrices collected (OU) |
|---|---|---|---|---|---|---|---|
| 1 | 3 | Vehicle (PBS) | NA | N/A | | | Retinae split along the nasal-temporal axes, temporal half used for RNA, nasal for protein |
| 2 | 3 | NT ASO | 110 | 12 | | | |
| 3 | 3 | Test ASO – Low Dose | 39 | 4 | 30 | IVT OU on Day 1 | |
| 4 | 3 | Test ASO – High Dose | 116 | 12 | | | |

| | | Chemistry | |
|---|---|---|---|
| Compound ID No.: | Sequence (5'-3') | (All MOE unless otherwise noted; G-LNA, C-5MeC-MOE) | |
| 1 | AGGCCATTCTGAAATTCT | AGGCCATTCTGAAATTCT | |
| 2 | CATTGAGGCCATTCTGAA | CATTGAGGCCATTCTGAA | |
| 3 | TAAGGCATTGAGGCCATT | TAAGGCATTGAGGCCATT | |
| 4 | CCTATTAAGGCATTGAGG | CCTATTAAGGCATTGAGG | |
| 5 | TTCTTCCTATTAAGGCAT | TTCTTCCTATTAAGGCAT | |
| 6 | AGTATTTCTTCCTATTAA | AGTATTTCTTCCTATTAA | |
| 7 | TTTCAAGTATTTCTTCCT | TTTCAAGTATTTCTTCCT | |
| 8 | AAAAATTTCAAGTATTTC | AAAAATTTCAAGTATTTC | |
| 9 | AATTTAAAAATTTCAAGT | AATTTAAAAATTTCAAGT | |
| 10 | GCCCTAATTTAAAAATTT | GCCCTAATTTAAAAATTT | |
| 11 | ACCAAGCCCTAATTTAAA | ACCAAGCCCTAATTTAAA | |
| 12 | ACAAAACCAAGCCCTAAT | ACAAAACCAAGCCCTAAT | |
| 13 | TCCTCACAAAACCAAGCC | TCCTCACAAAACCAAGCC | |
| 14 | CTAGCTCCTCACAAAACC | CTAGCTCCTCACAAAACC | |
| 15 | CTTTACTAGCTCCTCACA | CTTTACTAGCTCCTCACA | |
| 16 | AAAACCTTTACTAGCTCC | AAAACCTTTACTAGCTCC | |
| 17 | AGAGAAAAACCTTTACTA | AGAGAAAAACCTTTACTA | |
| 18 | CTGAAAGAGAAAAACCTT | CTGAAAGAGAAAAACCTT | |
| 19 | AAGCTGAAAGAGAAAAAC | AAGCTGAAAGAGAAAAAC | |
| 20 | CTAAAGCTGAAAGAGAAA | CTAAAGCTGAAAGAGAAA | |

FIG. 15

| | | Chemistry | |
|---|---|---|---|
| Compound ID No.: | Sequence (5'-3') | (All MOE unless otherwise noted; G-LNA, C-5MeC-MOE) | |
| 21 | AAGCTAAAGCTGAAAGAG | AAGCTAAAGCTGAAAGAG | |
| 22 | AACAAGCTAAAGCTGAAA | AACAAGCTAAAGCTGAAA | |
| 23 | AGAAACAAGCTAAAGCTG | AGAAACAAGCTAAAGCTG | |
| 24 | CGCAGAAACAAGCTAAAG | CGCAGAAACAAGCTAAAG | |
| 25 | TCCTCCGCAGAAACAAGC | TCCTCCGCAGAAACAAGC | |
| 26 | CGGAATCCTCCGCAGAAA | CGGAATCCTCCGCAGAAA | |
| 27 | AAGAGCGGAATCCTCCGC | AAGAGCGGAATCCTCCGC | |
| 28 | GGAGAAAGAGCGGAATCC | GGAGAAAGAGCGGAATCC | |
| 29 | CTGATGGAGAAAGAGCGG | CTGATGGAGAAAGAGCGG | |
| 30 | TGAAACTGATGGAGAAAG | TGAAACTGATGGAGAAAG | |
| 31 | GGCTATGAAACTGATGGA | GGCTATGAAACTGATGGA | |
| 32 | TCCAGGGCTATGAAACTG | TCCAGGGCTATGAAACTG | |
| 33 | ACAATTCCAGGGCTATGA | ACAATTCCAGGGCTATGA | |
| 34 | TTTCTACAATTCCAGGGC | TTTCTACAATTCCAGGGC | |
| 35 | GAGCTTTTCTACAATTCC | GAGCTTTTCTACAATTCC | |
| 36 | AACCAGAGCTTTTCTACA | AACCAGAGCTTTTCTACA | |
| 37 | CTTGAAACCAGAGCTTTT | CTTGAAACCAGAGCTTTT | |
| 38 | ATGGTCTTGAAACCAGAG | ATGGTCTTGAAACCAGAG | |
| 39 | TATCAATGGTCTTGAAAC | TATCAATGGTCTTGAAAC | |
| 40 | ATGGATATCAATGGTCTT | ATGGATATCAATGGTCTT | |

FIG. 15 cont.

| | | Chemistry | |
|---|---|---|---|
| Compound ID No.: | Sequence (5'-3') | (All MOE unless otherwise noted; G-LNA, C-5MeC-MOE) | |
| 41 | CAGAAATGGATATCAATG | CAGAAATGGATATCAATG | |
| 42 | CCTGACAGAAATGGATAT | CCTGACAGAAATGGATAT | |
| 43 | CACCCTGACAGAAATGGA | CACCCTGACAGAAATGGA | |
| 44 | ACTCACCCTGACAGAAAT | ACTCACCCTGACAGAAAT | |
| 45 | AAAACTCACCCTGACAGA | AAAACTCACCCTGACAGA | |
| 46 | TTTAAAACTCACCCTGAC | TTTAAAACTCACCCTGAC | |
| 47 | AAATTTAAAACTCACCCT | AAATTTAAAACTCACCCT | |
| 48 | AATAAATTTAAAACTCAC | AATAAATTTAAAACTCAC | |
| 49 | CATGAAATAAATTTAAAA | CATGAAATAAATTTAAAA | |
| 50 | TGCATCATGAAATAAATT | TGCATCATGAAATAAATT | |
| 51 | TTGTTTGCATCATGAAAT | TTGTTTGCATCATGAAAT | |
| 52 | ATATATTGTTTGCATCAT | ATATATTGTTTGCATCAT | |
| 53 | GTTCAATATATTGTTTGC | GTTCAATATATTGTTTGC | |
| 54 | CTGTTGTTCAATATATTG | CTGTTGTTCAATATATTG | |
| 55 | ATGTCCTGTTGTTCAATA | ATGTCCTGTTGTTCAATA | |
| 56 | AGTTCATGTCCTGTTGTT | AGTTCATGTCCTGTTGTT | |
| 57 | GAACAAGTTCATGTCCTG | GAACAAGTTCATGTCCTG | |
| 58 | AACAAGAACAAGTTCATG | AACAAGAACAAGTTCATG | |
| 59 | CTTACAACAAGAACAAGT | CTTACAACAAGAACAAGT | |
| 60 | AGCCACTTACAACAAGAA | AGCCACTTACAACAAGAA | |

FIG. 15 cont.

| | | Chemistry | |
|---|---|---|---|
| Compound ID No.: | Sequence (5'-3') | (All MOE unless otherwise noted; G-LNA, C-5MeC-MOE) | |
| 61 | AATTCAGCCACTTACAAC | AATTCAGCCACTTACAAC | |
| 62 | GATAAAATTCAGCCACTT | GATAAAATTCAGCCACTT | |
| 63 | TTACTGATAAAATTCAGC | TTACTGATAAAATTCAGC | |
| 64 | GTGCTTTACTGATAAAAT | GTGCTTTACTGATAAAAT | |
| 65 | TTGATGTGCTTTACTGAT | TTGATGTGCTTTACTGAT | |
| 66 | TGGAGAAAGAGCGGAATC | TGGAGAAAGAGCGGAATC | |
| 67 | ATGGAGAAAGAGCGGAAT | ATGGAGAAAGAGCGGAAT | |
| 68 | GATGGAGAAAGAGCGGAA | GATGGAGAAAGAGCGGAA | |
| 69 | TGATGGAGAAAGAGCGGA | TGATGGAGAAAGAGCGGA | |
| 70 | ACTGATGGAGAAAGAGCG | ACTGATGGAGAAAGAGCG | |
| 71 | AACTGATGGAGAAAGAGC | AACTGATGGAGAAAGAGC | |
| 72 | AAACTGATGGAGAAAGAG | AAACTGATGGAGAAAGAG | |
| 73 | GAAACTGATGGAGAAAGA | GAAACTGATGGAGAAAGA | |
| 74 | ATGAAACTGATGGAGAAA | ATGAAACTGATGGAGAAA | |
| 75 | TATGAAACTGATGGAGAA | TATGAAACTGATGGAGAA | |
| 76 | CTATGAAACTGATGGAGA | CTATGAAACTGATGGAGA | |
| 77 | GCTATGAAACTGATGGAG | GCTATGAAACTGATGGAG | |
| 78 | GGGCTATGAAACTGATGG | GGGCTATGAAACTGATGG | |
| 79 | AGGGCTATGAAACTGATG | AGGGCTATGAAACTGATG | |
| 80 | CAGGGCTATGAAACTGAT | CAGGGCTATGAAACTGAT | |

FIG. 15 cont.

| | | Chemistry | |
|---|---|---|---|
| Compound ID No.: | Sequence (5'-3') | (All MOE unless otherwise noted; G-LNA, C-5MeC-MOE) | |
| 81 | CCAGGGCTATGAAACTGA | CCAGGGCTATGAAACTGA | |
| 82 | CTGATGGAGAAAGAGCGGAATC | CTGATGGAGAAAGAGCGGAATC | |
| 83 | CTGATGGAGAAAGAGCGGAA | CTGATGGAGAAAGAGCGGAA | |
| 84 | AACTGATGGAGAAAGAGCGGAA | AACTGATGGAGAAAGAGCGGAA | |
| 85 | AACTGATGGAGAAAGAGCGG | AACTGATGGAGAAAGAGCGG | |
| 86 | GAAACTGATGGAGAAAGAGCGG | GAAACTGATGGAGAAAGAGCGG | |
| 87 | GGCTATGAAACTGATGGAGAAA | GGCTATGAAACTGATGGAGAAA | |
| 88 | GGCTATGAAACTGATGGAGA | GGCTATGAAACTGATGGAGA | |
| 89 | AGGGCTATGAAACTGATGGAGA | AGGGCTATGAAACTGATGGAGA | |
| 90 | AGGGCTATGAAACTGATGGA | AGGGCTATGAAACTGATGGA | |
| 91 | CCAGGGCTATGAAACTGATGGA | CCAGGGCTATGAAACTGATGGA | |
| 92 | TTCTTACCCATTTAATTA | TTCTTACCCATTTAATTA | |
| 93 | TGCTTCTTACCCATTTAA | TGCTTCTTACCCATTTAA | |
| 94 | TAATGCTTCTTACCCATT | TAATGCTTCTTACCCATT | |
| 95 | AGATAATGCTTCTTACCC | AGATAATGCTTCTTACCC | |
| 96 | CAGATAATGCTTCTTACC | CAGATAATGCTTCTTACC | |
| 97 | CCCTTCAGATAATGCTTC | CCCTTCAGATAATGCTTC | |
| 98 | CTACTCCCTTCAGATAAT | CTACTCCCTTCAGATAAT | |
| 99 | AGCTCCTACTCCCTTCAG | AGCTCCTACTCCCTTCAG | |
| 100 | TTCACAGCTCCTACTCCC | TTCACAGCTCCTACTCCC | |

FIG. 15 cont.

| | | Chemistry | |
|---|---|---|---|
| Compound ID No.: | Sequence (5'-3') | (All MOE unless otherwise noted; G-LNA, C-5MeC-MOE) | |
| 101 | TAAAATTCACAGCTCCTA | TAAAATTCACAGCTCCTA | |
| 102 | AAATCTAAAATTCACAGC | AAATCTAAAATTCACAGC | |
| 103 | GAATAAAATCTAAAATTC | GAATAAAATCTAAAATTC | |
| 104 | GATGGGAATAAAATCTAA | GATGGGAATAAAATCTAA | |
| 105 | GCTGTGATGGGAATAAAA | GCTGTGATGGGAATAAAA | |
| 106 | TAGAGGCTGTGATGGGAA | TAGAGGCTGTGATGGGAA | |
| 107 | AAAGATAGAGGCTGTGAT | AAAGATAGAGGCTGTGAT | |
| 108 | AAAAGAAAGATAGAGGCT | AAAAGAAAGATAGAGGCT | |
| 109 | GACCTAAAAGAAAGATAG | GACCTAAAAGAAAGATAG | |
| 110 | ATAAAGACCTAAAAGAAA | ATAAAGACCTAAAAGAAA | |
| 111 | GAGATATAAAGACCTAAA | GAGATATAAAGACCTAAA | |
| 112 | GGCTGTGATGGGAATAAA | GGCTGTGATGGGAATAAA | |
| 113 | AGGCTGTGATGGGAATAA | AGGCTGTGATGGGAATAA | |
| 114 | GAGGCTGTGATGGGAATA | GAGGCTGTGATGGGAATA | |
| 115 | AGAGGCTGTGATGGGAAT | AGAGGCTGTGATGGGAAT | |
| 116 | ATAGAGGCTGTGATGGGA | ATAGAGGCTGTGATGGGA | |
| 117 | GATAGAGGCTGTGATGGG | GATAGAGGCTGTGATGGG | |
| 118 | AGATAGAGGCTGTGATGG | AGATAGAGGCTGTGATGG | |
| 119 | AAGATAGAGGCTGTGATG | AAGATAGAGGCTGTGATG | |
| 120 | TAGAGGCTGTGATGGGAATAAA | TAGAGGCTGTGATGGGAATAAA | |

FIG. 15 cont.

| | | Chemistry | |
|---|---|---|---|
| Compound ID No.: | Sequence (5'-3') | (All MOE unless otherwise noted; G-LNA, C-5MeC-MOE) | |
| 121 | ATAGAGGCTGTGATGGGAATAA | ATAGAGGCTGTGATGGGAATAA | |
| 122 | GATAGAGGCTGTGATGGGAATA | GATAGAGGCTGTGATGGGAATA | |
| 123 | AGATAGAGGCTGTGATGGGAAT | AGATAGAGGCTGTGATGGGAAT | |
| 124 | AAGATAGAGGCTGTGATGGGAA | AAGATAGAGGCTGTGATGGGAA | |
| 125 | GAGGCTGTGATGGGAATAAA | GAGGCTGTGATGGGAATAAA | |
| 126 | AGAGGCTGTGATGGGAATAA | AGAGGCTGTGATGGGAATAA | |
| 127 | TAGAGGCTGTGATGGGAATA | TAGAGGCTGTGATGGGAATA | |
| 128 | ATAGAGGCTGTGATGGGAAT | ATAGAGGCTGTGATGGGAAT | |
| 129 | GATAGAGGCTGTGATGGGAA | GATAGAGGCTGTGATGGGAA | |
| 130 | AGATAGAGGCTGTGATGGGA | AGATAGAGGCTGTGATGGGA | |
| 131 | AAGATAGAGGCTGTGATGGG | AAGATAGAGGCTGTGATGGG | |
| 132 | CTGTGATGGGAATAAA | CTGTGATGGGAATAAA | |
| 133 | GCTGTGATGGGAATAA | GCTGTGATGGGAATAA | |
| 134 | GGCTGTGATGGGAATA | GGCTGTGATGGGAATA | |
| 135 | AGGCTGTGATGGGAAT | AGGCTGTGATGGGAAT | |
| 136 | GAGGCTGTGATGGGAA | GAGGCTGTGATGGGAA | |
| 137 | AGAGGCTGTGATGGGA | AGAGGCTGTGATGGGA | |
| 138 | TAGAGGCTGTGATGGG | TAGAGGCTGTGATGGG | |
| 139 | ATAGAGGCTGTGATGG | ATAGAGGCTGTGATGG | |
| 140 | GATAGAGGCTGTGATG | GATAGAGGCTGTGATG | |

FIG. 15 cont.

| | | Chemistry | |
|---|---|---|---|
| Compound ID No.: | Sequence (5'-3') | (All MOE unless otherwise noted; G-LNA, C-5MeC-MOE) | |
| 141 | AGATAGAGGCTGTGAT | AGATAGAGGCTGTGAT | |
| 142 | AAGATAGAGGCTGTGA | AAGATAGAGGCTGTGA | |
| 143 | AGGCTGTGATGTGAATAA | AGGCTGTGATGTGAATAA | |
| 144 | AGGCTGTGATGTGAATAA | AGGCTGTGATGTGAATAA | |
| 145 | AGGCTGTGATGTGAATAA | AGGCTGTGATGTGAATAA | |
| 146 | AGAGGCTGTGATGTGAAT | AGAGGCTGTGATGTGAAT | |
| 147 | AGAGGCTGTGATGTGAAT | AGAGGCTGTGATGTGAAT | |
| 148 | AGAGGCTGTGATGTGAAT | AGAGGCTGTGATGTGAAT | |
| 149 | TAGAGGCTGTGATGTGAA | TAGAGGCTGTGATGTGAA | |
| 150 | TAGAGGCTGTGATGTGAA | TAGAGGCTGTGATGTGAA | |
| 151 | TAGAGGCTGTGATGTGAA | TAGAGGCTGTGATGTGAA | |
| 152 | GATAGAGGCTGTGATTGG | GATAGAGGCTGTGATTGG | |
| 153 | GATAGAGGCTGTGATTGG | GATAGAGGCTGTGATTGG | |
| 154 | GATAGAGGCTGTGATTGG | GATAGAGGCTGTGATTGG | |
| 155 | AGATAGAGGCTGTGATGG | AGATAGAGGCTGTGATGG | |
| 156 | GGCTGTGATGTGAATA | GGCTGTGATGTGAATA | |
| 157 | GGCTGTGATGTGAATA | GGCTGTGATGTGAATA | |
| 158 | GGCTGTGATGTGAATA | GGCTGTGATGTGAATA | |
| 159 | GAGGCTGTGATGTGAA | GAGGCTGTGATGTGAA | |
| 160 | GAGGCTGTGATGTGAA | GAGGCTGTGATGTGAA | |

FIG. 15 cont.

| | | Chemistry | |
|---|---|---|---|
| Compound ID No.: | Sequence (5'-3') | (All MOE unless otherwise noted; G-LNA, C-5MeC-MOE) | |
| 161 | GAGGCTGTGATGTGAA | GAGGCTGTGATGTGAA | |
| 162 | TAGAGGCTGTGATTGG | TAGAGGCTGTGATTGG | |
| 163 | TAGAGGCTGTGATTGG | TAGAGGCTGTGATTGG | |
| 164 | TAGAGGCTGTGATTGG | TAGAGGCTGTGATTGG | |
| 165 | ATAGAGGCTGTGATGG | ATAGAGGCTGTGATGG | |
| 166 | GATAGAGGCTGTGATG | GATAGAGGCTGTGATG | |
| 167 | AGATAGAGGCTGTGAT | AGATAGAGGCTGTGAT | |
| 168 | GGCTATGAAACTGATGGAGA | GGCTATGAAACTGATGGAGA | |
| 169 | CTATGAAACTGATGGAGA | CTATGAAACTGATGGAGA | |
| 170 | GCTATGAAACTGATGGAG | GCTATGAAACTGATGGAG | |
| 171 | GGCTATGAAACTGATGGA | GGCTATGAAACTGATGGA | |
| 172 | ATGAAACTGATGGAGA | ATGAAACTGATGGAGA | |
| 173 | ATGAAACTGATGGAGA | ATGAAACTGATGGAGA | |
| 174 | CTATGAAACTGATGGA | CTATGAAACTGATGGA | |
| 175 | CTATGAAACTGATGGA | CTATGAAACTGATGGA | |
| 176 | GGCTATGAAACTGATG | GGCTATGAAACTGATG | |
| 177 | GGCTATGAAACTGATG | GGCTATGAAACTGATG | |
| 178 | GAAACTGATGGAGA | GAAACTGATGGAGA | |
| 179 | ATGAAACTGATGGA | ATGAAACTGATGGA | |
| 180 | CTATGAAACTGATG | CTATGAAACTGATG | |

FIG. 15 cont.

| | | Chemistry | |
|---|---|---|---|
| Compound ID No.: | Sequence (5'-3') | (All MOE unless otherwise noted; G-LNA, C-5MeC-MOE) | |
| 181 | GGCTATGAAACTGA | GGCTATGAAACTGA | |
| 182 | TAGAGGCTGTGATGGGAATAAA | TAGAGGCTGTGATGGGAATAAA | PMO |
| 183 | TAGAGGCTGTGATGGGAATAAAAT | TAGAGGCTGTGATGGGAATAAAAT | PMO |
| 184 | ATAGAGGCTGTGATGGGAATAA | ATAGAGGCTGTGATGGGAATAA | PMO |
| 185 | ATAGAGGCTGTGATGGGAATAAAA | ATAGAGGCTGTGATGGGAATAAAA | PMO |
| 186 | ATAGAGGCTGTGATGGGAATAAAAT | ATAGAGGCTGTGATGGGAATAAAAT | PMO |
| 187 | AAAGATAGAGGCTGTGATGGGAATA | AAAGATAGAGGCTGTGATGGGAATA | PMO |
| 188 | GGCTATGAAACTGATGGAGAA | GGCTATGAAACTGATGGAGAA | PMO |
| 189 | GGCTATGAAACTGATGGAGAAA | GGCTATGAAACTGATGGAGAAA | PMO |
| 190 | GGCTATGAAACTGATGGAGAAAGA | GGCTATGAAACTGATGGAGAAAGA | PMO |
| 191 | AGGGCTATGAAACTGATGGAGAAAG | AGGGCTATGAAACTGATGGAGAAAG | PMO |
| 192 | CATTTAATTAAATTATAT | CATTTAATTAAATTATAT | |
| 193 | CCATTTAATTAAATTATA | CCATTTAATTAAATTATA | |
| 194 | CCCATTTAATTAAATTAT | CCCATTTAATTAAATTAT | |
| 195 | ACCCATTTAATTAAATTA | ACCCATTTAATTAAATTA | |
| 196 | TACCCATTTAATTAAATT | TACCCATTTAATTAAATT | |
| 197 | TTACCCATTTAATTAAAT | TTACCCATTTAATTAAAT | |
| 198 | CTTACCCATTTAATTAAA | CTTACCCATTTAATTAAA | |
| 199 | TCTTACCCATTTAATTAA | TCTTACCCATTTAATTAA | |
| 200 | GATAGAGGCTGTGATGG | GATAGAGGCTGTGATGG | |

FIG. 15 cont.

| | | Chemistry | |
|---|---|---|---|
| Compound ID No.: | Sequence (5'-3') | (All MOE unless otherwise noted; G-LNA, C-5MeC-MOE) | |
| 201 | GGCTGTGAAACTGATGGA | GGCTGTGAAACTGATGGA | |
| 202 | GGCTGTGAAACTGATGGAGA | GGCTGTGAAACTGATGGAGA | |
| 203 | CTATGAAACTGATGGA | CTATGAAACTGATGGA | |
| 204 | GCTATGAAACTGATGG | GCTATGAAACTGATGG | |
| 205 | GGCTATGAAACTGATG | GGCTATGAAACTGATG | |
| 206 | ATGAAACTGATGGA | ATGAAACTGATGGA | |
| 207 | TATGAAACTGATGG | TATGAAACTGATGG | |
| 208 | CTATGAAACTGATG | CTATGAAACTGATG | |
| 209 | GCTATGAAACTGAT | GCTATGAAACTGAT | |
| 210 | GGCTATGAAACTGA | GGCTATGAAACTGA | |
| 211 | GCTGTGAAACTGATGGAGAA | GCTGTGAAACTGATGGAGAA | |
| 212 | GGGCTGTGAAACTGATGGAG | GGGCTGTGAAACTGATGGAG | |
| 213 | TGTGAAACTGATGGAGAA | TGTGAAACTGATGGAGAA | |
| 214 | CTGTGAAACTGATGGAGA | CTGTGAAACTGATGGAGA | |
| 215 | GCTGTGAAACTGATGGAG | GCTGTGAAACTGATGGAG | |
| 216 | GGGCTGTGAAACTGATGG | GGGCTGTGAAACTGATGG | |
| 217 | TGAAACTGATGGAGAA | TGAAACTGATGGAGAA | |
| 218 | GTGAAACTGATGGAGA | GTGAAACTGATGGAGA | |
| 219 | TGTGAAACTGATGGAG | TGTGAAACTGATGGAG | |
| 220 | CTGTGAAACTGATGGA | CTGTGAAACTGATGGA | |

FIG. 15 cont.

| | | Chemistry | |
|---|---|---|---|
| Compound ID No.: | Sequence (5'-3') | (All MOE unless otherwise noted; G-LNA, C-5MeC-MOE) | |
| 221 | GCTGTGAAACTGATGG | GCTGTGAAACTGATGG | |
| 222 | GGCTGTGAAACTGATG | GGCTGTGAAACTGATG | |
| 223 | GGGCTGTGAAACTGAT | GGGCTGTGAAACTGAT | |
| 224 | CGGTCCAGGAATGAC | CGGTCCAGGAATGAC | |
| 225 | CCGGTCCAGGAATGA | CCGGTCCAGGAATGA | |
| 226 | CCCGGTCCAGGAATG | CCCGGTCCAGGAATG | |
| 227 | TCCCGGTCCAGGAAT | TCCCGGTCCAGGAAT | |
| 228 | CTCCCGGTCCAGGAA | CTCCCGGTCCAGGAA | |
| 229 | GCTCCCGGTCCAGGA | GCTCCCGGTCCAGGA | |
| 230 | GGCTCCCGGTCCAGG | GGCTCCCGGTCCAGG | |
| 231 | CGGGAGCCCCCGTGT | CGGGAGCCCCCGTGT | |
| 232 | GCGGGAGCCCCCGTG | GCGGGAGCCCCCGTG | |
| 233 | CGCGGGAGCCCCCGT | CGCGGGAGCCCCCGT | |
| 234 | ACGCGGGAGCCCCCG | ACGCGGGAGCCCCCG | |
| 235 | CACGCGGGAGCCCCC | CACGCGGGAGCCCCC | |
| 236 | CCACGCGGGAGCCCC | CCACGCGGGAGCCCC | |
| 237 | GCCACGCGGGAGCCC | GCCACGCGGGAGCCC | |
| 238 | GGCCACGCGGGAGCC | GGCCACGCGGGAGCC | |
| 239 | CGGCCACGCGGGAGC | CGGCCACGCGGGAGC | |
| 240 | ACGGCCACGCGGGAG | ACGGCCACGCGGGAG | |

FIG. 15 cont.

| | | Chemistry | |
|---|---|---|---|
| Compound ID No.: | Sequence (5'-3') | (All MOE unless otherwise noted; G-LNA, C-5MeC-MOE) | |
| 241 | GACGGCCACGCGGGA | GACGGCCACGCGGGA | |
| 242 | AGACGGCCACGCGGG | AGACGGCCACGCGGG | |
| 243 | GCTAGGGAGGGATGGTTA | GCTAGGGAGGGATGGTTA | |
| 244 | TGTAAGCTAGGGAGGGAT | TGTAAGCTAGGGAGGGAT | |
| 245 | ACAGATGTAAGCTAGGGA | ACAGATGTAAGCTAGGGA | |
| 246 | AAGGAACAGATGTAAGCT | AAGGAACAGATGTAAGCT | |
| 247 | CAACAAAGGAACAGATGT | CAACAAAGGAACAGATGT | |
| 248 | GGGTGCAACAAAGGAACA | GGGTGCAACAAAGGAACA | |
| 249 | ACCAAGGGTGCAACAAAG | ACCAAGGGTGCAACAAAG | |
| 250 | GTTAAACCAAGGGTGCAA | GTTAAACCAAGGGTGCAA | |
| 251 | ATAATGTTAAACCAAGGG | ATAATGTTAAACCAAGGG | |
| 252 | GGAGAATAATGTTAAACC | GGAGAATAATGTTAAACC | |
| 253 | GGGGAGGAGAATAATGTT | GGGGAGGAGAATAATGTT | |
| 254 | AAATTGGGGAGGAGAATA | AAATTGGGGAGGAGAATA | |
| 255 | AGAGGAAATTGGGGAGGA | AGAGGAAATTGGGGAGGA | |
| 256 | GGAGAAGAGGAAATTGGG | GGAGAAGAGGAAATTGGG | |
| 257 | AATGAGGAGAAGAGGAAA | AATGAGGAGAAGAGGAAA | |
| 258 | TTCACAATGAGGAGAAGA | TTCACAATGAGGAGAAGA | |
| 259 | ACGAGTTCACAATGAGGA | ACGAGTTCACAATGAGGA | |
| 260 | CTGCCACGAGTTCACAAT | CTGCCACGAGTTCACAAT | |

FIG. 15 cont.

| | | Chemistry | |
|---|---|---|---|
| Compound ID No.: | Sequence (5'-3') | (All MOE unless otherwise noted; G-LNA, C-5MeC-MOE) | |
| 261 | AGACCCTGCCACGAGTTC | AGACCCTGCCACGAGTTC | |
| 262 | CAAGCAGACCCTGCCACG | CAAGCAGACCCTGCCACG | |
| 263 | CTCACCAAGCAGACCCTG | CTCACCAAGCAGACCCTG | |
| 264 | GAGCTCACCAAGCAGACC | GAGCTCACCAAGCAGACC | |
| 265 | AGAATGAGCTCACCAAGC | AGAATGAGCTCACCAAGC | |
| 266 | GTAAGAGAATGAGCTCAC | GTAAGAGAATGAGCTCAC | |
| 267 | TTGTTGTAAGAGAATGAG | TTGTTGTAAGAGAATGAG | |
| 268 | ATTTGTTGTTGTAAGAGA | ATTTGTTGTTGTAAGAGA | |
| 269 | CTTGAATTTGTTGTTGTA | CTTGAATTTGTTGTTGTA | |
| 270 | ATGCTCTTGAATTTGTTG | ATGCTCTTGAATTTGTTG | |
| 271 | TCTTCATGCTCTTGAATT | TCTTCATGCTCTTGAATT | |
| 272 | CTTCCTCTTCATGCTCTT | CTTCCTCTTCATGCTCTT | |
| 273 | GCGCGCTTCCTCTTCATG | GCGCGCTTCCTCTTCATG | |
| 274 | GCTCTGCGCGCTTCCTCT | GCTCTGCGCGCTTCCTCT | |
| 275 | GGCCAGCGGCTCTGCGCG | GGCCAGCGGCTCTGCGCG | |
| 276 | ATATTGGCCAGCGGCTCT | ATATTGGCCAGCGGCTCT | |
| 277 | GTGCTATATTGGCCAGCG | GTGCTATATTGGCCAGCG | |
| 278 | AGCTCGTGCTATATTGGC | AGCTCGTGCTATATTGGC | |
| 279 | GGCATAGCTCGTGCTATA | GGCATAGCTCGTGCTATA | |
| 280 | TGTTGGGCATAGCTCGTG | TGTTGGGCATAGCTCGTG | |

FIG. 15 cont.

| | | Chemistry | |
|---|---|---|---|
| Compound ID No.: | Sequence (5'-3') | (All MOE unless otherwise noted; G-LNA, C-5MeC-MOE) | |
| 281 | GCTTCTGTTGGGCATAGC | GCTTCTGTTGGGCATAGC | |
| 282 | CTTGCGCTTCTGTTGGGC | CTTGCGCTTCTGTTGGGC | |
| 283 | CACCTTGCGCTTCTGTTG | CACCTTGCGCTTCTGTTG | |
| 284 | TCCATCACCTTGCGCTTC | TCCATCACCTTGCGCTTC | |
| 285 | AACCATCCATCACCTTGC | AACCATCCATCACCTTGC | |
| 286 | CCTTAAACCATCCATCAC | CCTTAAACCATCCATCAC | |
| 287 | AGCCCCCTTAAACCATCC | AGCCCCCTTAAACCATCC | |
| 288 | TCGGTAGCCCCCTTAAAC | TCGGTAGCCCCCTTAAAC | |
| 289 | ATGTATCGGTAGCCCCCT | ATGTATCGGTAGCCCCCT | |
| 290 | TGTGAATGTATCGGTAGC | TGTGAATGTATCGGTAGC | |
| 291 | ATTAGTGTGAATGTATCG | ATTAGTGTGAATGTATCG | |
| 292 | GGCTGATTAGTGTGAATG | GGCTGATTAGTGTGAATG | |
| 293 | GAAATGGCTGATTAGTGT | GAAATGGCTGATTAGTGT | |
| 294 | TGGCAGAAATGGCTGATT | TGGCAGAAATGGCTGATT | |
| 295 | GATCTTGGCAGAAATGGC | GATCTTGGCAGAAATGGC | |
| 296 | GACATGATCTTGGCAGAA | GACATGATCTTGGCAGAA | |
| 297 | GAGGTGACATGATCTTGG | GAGGTGACATGATCTTGG | |
| 298 | AGATTGAGGTGACATGAT | AGATTGAGGTGACATGAT | |
| 299 | TGAACAGATTGAGGTGAC | TGAACAGATTGAGGTGAC | |
| 300 | GTCCATGAACAGATTGAG | GTCCATGAACAGATTGAG | |

FIG. 15 cont.

| | | Chemistry | |
|---|---|---|---|
| Compound ID No.: | Sequence (5'-3') | (All MOE unless otherwise noted; G-LNA, C-5MeC-MOE) | |
| 301 | TTGGAGTCCATGAACAGA | TTGGAGTCCATGAACAGA | |
| 302 | TGTATTTGGAGTCCATGA | TGTATTTGGAGTCCATGA | |
| 303 | TTTCTTGTATTTGGAGTC | TTTCTTGTATTTGGAGTC | |

FIG. 15 cont.

MinION Sequencing Data in HEK293 cells transfected with ASO-14

| Isoform | Exons | Mock | ASO-14 |
|---|---|---|---|
| 1 | 6-7-8 | 60.1% | 49.0% |
| 2 | 6-8 | 35.8% | 47.3% |
| 3* | 6a-8 | 1.2% | 1.3% |
| 4* | 6-7x-8 | n.d. | n.d. |
| 5* | 6-7-7x-8 | 0.6% | 0.0% |

OPA1 ANTISENSE OLIGOMERS FOR TREATMENT OF CONDITIONS AND DISEASES

CROSS-REFERENCE

This application is the national phase application of PCT Application No. PCT/US2021/030254, filed Apr. 30, 2021, which claims the benefit of U.S. Provisional Application No. 63/023,013, filed May 11, 2020, and U.S. Provisional Application No. 63/112,458, filed Nov. 11, 2020, each of which is incorporated herein by reference in its entirety.

SEQUENCE LISTING

The instant application contains a Sequence Listing which has been submitted electronically in ASCII format and is hereby incorporated by reference in its entirety. Said ASCII copy, created on Jun. 7, 2021, is named 47991-731_601_SL.txt and is 379,760 bytes in size.

BACKGROUND

Alternative splicing events in genes can lead to non-productive mRNA transcripts which in turn can lead to aberrant or reduced protein expression, and therapeutic agents which can target the alternative splicing events in genes can modulate the expression level of functional proteins in patients and/or inhibit aberrant protein expression. Such therapeutic agents can be used to treat a condition or disease caused by the protein deficiency.

Autosomal dominant optic atrophy (ADOA) is one of the most commonly diagnosed optic neuropathies. This optic nerve disease is associated with structural and functional mitochondrial deficits that lead to degeneration of the retinal ganglion cells and progressive, irreversible loss of vision. A majority of ADOA patients carry mutations in OPA1 and most mutations lead to haploinsufficiency (Lenaers G. et al. Orphanet J Rare Dis 2012). OPA1 encodes a mitochondrial GTPase with a critical role in mitochondrial fusion, ATP synthesis and apoptosis. Currently, there is no approved disease-modifying treatment for ADOA patients and there is a need for such treatments.

SUMMARY

Described herein, in some aspects, is a method of modulating expression of an OPA1 protein in a cell having a pre-mRNA that is transcribed from an OPA1 gene and that comprises a non-sense mediated RNA decay-inducing exon (NMD exon), the method comprising contacting an agent or a vector encoding the agent to the cell, whereby the agent modulates splicing of the NMD exon from the pre-mRNA, thereby modulating a level of processed mRNA that is processed from the pre-mRNA, and modulating the expression of the OPA1 protein in the cell, wherein the agent comprises an antisense oligomer with at least 80% sequence identity to a sequence selected from the group consisting of SEQ ID NOs: 6-275 and 280-299.

In some embodiments, the agent: (a) binds to a targeted portion of the pre-mRNA; (b) modulates binding of a factor involved in splicing of the NMD exon; or (c) a combination of (a) and (b). In some embodiments, the agent interferes with binding of the factor involved in splicing of the NMD exon to a region of the targeted portion. In some embodiments, the targeted portion of the pre-mRNA is proximal to the NMD exon. In some embodiments, the targeted portion of the pre-mRNA is at most about 1500 nucleotides, about 1000 nucleotides, about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides upstream of 5' end of the NMD exon. In some embodiments, the targeted portion of the pre-mRNA is at least about 1500 nucleotides, about 1000 nucleotides, about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides, about 40 nucleotides, about 30 nucleotides, about 20 nucleotides, about 10 nucleotides, about 5 nucleotides, about 4 nucleotides, about 2 nucleotides, about 1 nucleotides upstream of 5' end of the NMD exon. In some embodiments, the targeted portion of the pre-mRNA is at most about 1500 nucleotides, about 1000 nucleotides, about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides downstream of 3' end of the NMD exon. In some embodiments, the targeted portion of the pre-mRNA is at least about 1500 nucleotides, about 1000 nucleotides, about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides, about 40 nucleotides, about 30 nucleotides, about 20 nucleotides, about 10 nucleotides, about 5 nucleotides, about 4 nucleotides, about 2 nucleotides, about 1 nucleotides downstream of 3' end of the NMD exon. In some embodiments, the targeted portion of the pre-mRNA is at most about 1500 nucleotides, about 1000 nucleotides, about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides upstream of genomic site GRCh38/hg38: chr3 193628509. In some embodiments, the targeted portion of the pre-mRNA is about 1500 nucleotides, about 1000 nucleotides, about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides upstream of genomic site GRCh38/hg38: chr3 193628509. In some embodiments, the targeted portion of the pre-mRNA is at most about 1500 nucleotides, about 1000 nucleotides, about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides downstream of genomic site GRCh38/hg38: chr3 193628616. In some embodiments, the targeted portion of the pre-mRNA is about 1500 nucleotides, about 1000 nucleotides, about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides downstream of genomic site GRCh38/hg38: chr3 193628616. In some embodiments, the targeted portion of the pre-mRNA is located in an intronic region between two canonical exonic regions of the pre-mRNA, and wherein the intronic region contains the NMD exon. In some embodiments, the targeted portion of the pre-mRNA at least partially overlaps with the NMD exon. In some embodiments, the targeted portion of the pre-mRNA at least partially overlaps with an intron upstream or downstream of the NMD exon. In some embodiments, the targeted portion of the pre-mRNA comprises 5' NMD exon-intron junction or 3' NMD exon-intron junction. In some embodiments, the targeted portion of the pre-mRNA is within the NMD exon. In some embodiments, the targeted portion of the pre-mRNA comprises about 5, 6, 7, 8, 9, 10, 11, 12, 13, 14, 15, 16, 17, 18, 19, 20, 21, 22, 23, 24, 25, 26, 27, 28, 29, 30, or more consecutive nucleotides of the NMD exon.

In some embodiments, the NMD exon comprises a sequence with at least 80%, at least 90%, or 100% sequence identity to SEQ ID NO: 279. In some embodiments, the NMD exon comprises a sequence of SEQ ID NO: 279. In some embodiments, the targeted portion of the pre-mRNA is within the non-sense mediated RNA decay-inducing exon GRCh38/hg38: chr3 193628509 to 193628616. In some embodiments, the targeted portion of the pre-mRNA is upstream or downstream of the non-sense mediated RNA decay-inducing exon GRCh38/hg38: chr3 193628509 to 193628616. In some embodiments, the targeted portion of the pre-mRNA comprises an exon-intron junction of exon GRCh38/hg38: chr3 193628509 to 193628616. In some embodiments, the OPA1 protein expressed from the processed mRNA is a full-length OPA1 protein or a wild-type OPA1 protein. In some embodiments, the OPA1 protein expressed from the processed mRNA is a functional OPA1 protein. In some embodiments, the OPA1 protein expressed from the processed mRNA is at least partially functional as compared to a wild-type OPA1 protein. In some embodiments, the OPA1 protein expressed from the processed mRNA is at least partially functional as compared to a full-length wild-type OPA1 protein. In some embodiments, the OPA1 protein expressed from the processed mRNA is an OPA1 protein that lacks an amino acid sequence encoded by a nucleic acid sequence with at least 80% sequence identity to SEQ ID NO: 277.

In some embodiments, the method promotes exclusion of the NMD exon from the pre-mRNA. In some embodiments, the exclusion of the NMD exon from the pre-mRNA in the cell contacted with the agent is increased by about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to in the absence of the agent. In some embodiments, the method results in an increase in the level of the processed mRNA in the cell. In some embodiments, the level of the processed mRNA in the cell contacted with the agent is increased by about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to in the absence of the agent. In some embodiments, the method results in an increase in the expression of the OPA1 protein in the cell. In some embodiments, a level of the OPA1 protein expressed from the processed mRNA in the cell contacted with the agent is increased by about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to in the absence of the agent.

In some embodiments, the agent comprises an antisense oligomer with at least 80%, at least 90%, or 100% sequence identity to a sequence selected from the group consisting of SEQ ID NOs: 36, 236, 242, 250, 280-283, 288, and 290-292. In some embodiments, the agent further comprises a gene editing molecule. In some embodiments, the gene editing molecule comprises CRISPR-Cas9.

Described herein, in some aspects, is a method of modulating expression of an OPA1 protein in a cell having a pre-mRNA that is transcribed from an OPA1 gene, wherein the pre-mRNA comprises a coding exon, the method comprising contacting an agent or a vector encoding the agent to the cell, whereby the agent promotes exclusion of the coding exon from the pre-mRNA, thereby increasing a level of a processed mRNA that is processed from the pre-mRNA and that lacks the coding exon in the cell. In some embodiments, the agent: (a) binds to a targeted portion of the pre-mRNA; (b) modulates binding of a factor involved in splicing of the coding exon; or (c) a combination of (a) and (b). In some embodiments, the agent interferes with binding of the factor involved in splicing of the coding exon to a region of the targeted portion. In some embodiments, the targeted portion of the pre-mRNA is proximal to the coding exon. In some embodiments, the targeted portion of the pre-mRNA is located in an intronic region immediately upstream of the coding exon. In some embodiments, the targeted portion of the pre-mRNA is within a region spanning from 100 to 50, from 90 to 50, from 80 to 50, from 70 to 50, from 60 to 50, from 60 to 40, from 60 to 30, from 60 to 20, from 60 to 10, from 49 to 1, from 39 to 1, from 29 to 1, or from 19 to 1 nucleotides upstream of 5' end of the coding exon. In some embodiments, the targeted portion of the pre-mRNA is within a region spanning from 49 to 1, from 39 to 1, from 29 to 1, or from 19 to 1 nucleotides upstream of 5' end of the coding exon. In some embodiments, the targeted portion of the pre-mRNA is located in an intronic region immediately downstream of the coding exon. In some embodiments, the targeted portion of the pre-mRNA is within a region spanning from 1 to 49, from 1 to 39, from 1 to 29, from 1 to 19, from 10 to 60, from 20 to 60, from 30 to 60, from 40 to 60, from 50 to 60, from 50 to 70, from 50 to 80, from 50 to 90, or from 50 to 100 nucleotides downstream of 3' end of the coding exon. In some embodiments, the targeted portion of the pre-mRNA is within a region spanning from 1 to 49, from 1 to 39, from 1 to 29, or from 1 to 19 nucleotides downstream of 3' end of the coding exon. In some embodiments, the targeted portion of the pre-mRNA at least partially overlaps with the coding exon. In some embodiments, the targeted portion of the pre-mRNA at least partially overlaps with an intron immediately upstream or immediately downstream of the coding exon. In some embodiments, the targeted portion of the pre-mRNA comprises 5' coding exon-intron junction or 3' coding exon-intron junction. In some embodiments, the targeted portion is within the coding exon of the pre-mRNA. In some embodiments, the coding exon is an alternatively spliced exon.

In some embodiments, the coding exon comprises a sequence with at least 80%, at least 90%, or 100% sequence identity to SEQ ID NO: 277. In some embodiments, the coding exon comprises SEQ ID NO: 277. In some embodiments, the targeted portion of the pre-mRNA is immediately upstream of the coding exon GRCh38/hg38: chr3 193626092 to 193626202. In some embodiments, the targeted portion of the pre-mRNA is within a region spanning from 49 to 1, from 39 to 1, from 29 to 1, or from 19 to 1 nucleotides upstream of genomic site GRCh38/hg38: chr3 193626092. In some embodiments, the targeted portion of the pre-mRNA is immediately downstream of the coding exon GRCh38/hg38: chr3 193626092 to 193626202. In some embodiments, the targeted portion of the pre-mRNA is within a region spanning from 1 to 49, from 1 to 39, from 1 to 29, or from 1 to 19 nucleotides downstream of genomic site GRCh38/hg38: chr3 193626202. In some embodiments, the targeted portion of the pre-mRNA is within the coding exon GRCh38/hg38: chr3 193626092 to 193626202. In some embodiments, the targeted portion of the pre-mRNA comprises an exon-intron junction of exon GRCh38/hg38: chr3 193626092 to 193626202. In some embodiments, the targeted portion comprises about 5, 6, 7, 8, 9, 10, 11, 12, 13, 14, 15, 16, 17, 18, 19, 20, 21, 22, 23, 24, 25, 26, 27, 28, 29, 30, or more consecutive nucleotides of the coding exon. In some embodiments, the targeted portion of the pre-mRNA comprises a sequence with at least 80%, 85%, 90%, 95%, 97%, or 100% sequence identity to a region comprising at least 8 contiguous nucleic acids of SEQ ID NO: 277.

In some embodiments, the exclusion of the coding exon from the pre-mRNA in the cell contacted with the agent is increased by about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to in the absence of the agent. In some embodiments, the method results in an increase in expression of the OPA1 protein in the cell. In some embodiments, a level of the OPA1 protein expressed from the processed mRNA in the cell contacted with the agent is increased by about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to in the absence of the agent. In some embodiments, a level of the OPA1 protein expressed from the processed mRNA in the cell contacted with the agent is increased by at least about 1.5-fold compared to in the absence of the agent.

In some embodiments, the OPA1 protein expressed from the processed mRNA is a functional OPA1 protein. In some embodiments, the OPA1 protein expressed from the processed mRNA is at least partially functional as compared to a wild-type OPA1 protein. In some embodiments, the OPA1 protein expressed from the processed mRNA is at least partially functional as compared to a full-length wild-type OPA1 protein. In some embodiments, the agent promotes exclusion of a non-sense mediated RNA decay-inducing exon (NMD exon) from the pre-mRNA. In some embodiments, the NMD exon comprises a sequence with at least 80%, at least 90%, or 100% sequence identity to SEQ ID NO: 279. In some embodiments, the NMD exon comprises a sequence of SEQ ID NO: 279. In some embodiments, the OPA1 protein expressed from the processed mRNA comprises fewer proteolytic cleavage sites than an OPA1 protein encoded by a corresponding mRNA containing the coding exon.

In some embodiments, the agent comprises an antisense oligomer with at least 80%, at least 90%, or 100% sequence identity to a sequence selected from the group consisting of SEQ ID NOs: 227-242, 250, 280-283, 288, and 290-292. In some embodiments, the agent comprises a gene editing molecule. In some embodiments, the gene editing molecule comprises CRISPR-Cas9.

Described herein, in some aspects, is a method of modulating expression of an OPA1 protein in a cell having a pre-mRNA that is transcribed from an OPA1 gene, wherein the pre-mRNA comprises a coding exon, the method comprising contacting an agent or a vector encoding the agent to the cell, wherein the agent comprises an antisense oligomer that binds to: (a) a targeted portion of the pre-mRNA within an intronic region immediately upstream of a 5' end of the coding exon of the pre-mRNA; or (b) a targeted portion of the pre-mRNA within an intronic region immediately downstream of a 3' end of the coding exon of the pre-mRNA; whereby the agent increases a level of a processed mRNA that is processed from the pre-mRNA and that contains the coding exon in the cell.

In some embodiments, the coding exon is an alternatively spliced exon. In some embodiments, the method promotes inclusion of the coding exon in the processed mRNA during splicing of the pre-mRNA in the cell. In some embodiments, the target portion of the pre-mRNA is within a region spanning from 100 to 50, from 100 to 60, from 100 to 70, from 100 to 80, or from 100 to 90 nucleotides upstream of a 5' end of the coding exon. In some embodiments, the target portion of the pre-mRNA is within a region spanning from 40 to 100, from 50 to 100, from 60 to 100, from 70 to 100, from 80 to 100, or from 90 to 100 nucleotides downstream of a 3' end of the coding exon. In some embodiments, the coding exon comprises a sequence with at least 80%, at least 90%, or 100% sequence identity to SEQ ID NO: 277. In some embodiments, the coding exon comprises SEQ ID NO: 277. In some embodiments, the targeted portion of the pre-mRNA is within a region spanning from 100 to 50, from 100 to 60, from 100 to 70, from 100 to 80, or from 100 to 90 nucleotides upstream of genomic site GRCh38/hg38: chr3 193626092. In some embodiments, the targeted portion of the pre-mRNA is within a region spanning from 40 to 100, from 50 to 100, from 60 to 100, from 70 to 100, from 80 to 100, or from 90 to 100 nucleotides downstream of genomic site GRCh38/hg38: chr3 193626202. In some embodiments, the inclusion of the coding exon in the processed mRNA in the cell contacted with the agent is increased by about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to in the absence of the agent. In some embodiments, the agent comprises an antisense oligomer with at least 80%, at least 90%, or 100% sequence identity to SEQ ID NO: 267.

Described herein, in some aspects, is a method of modulating expression of a target protein in a cell having a pre-mRNA transcribed from a gene that encodes the target protein, wherein the pre-mRNA comprises a coding exon and a non-sense mediated RNA decay-inducing exon (NMD exon), the method comprising contacting an agent or a vector encoding the agent to the cell, wherein the agent promotes exclusion of both the coding exon and the NMD exon from the pre-mRNA, thereby increasing a level of a processed mRNA that is processed from the pre-mRNA and that lacks both the NMD exon and the coding exon in the cell.

In some embodiments, the agent: (a) binds to a targeted portion of the pre-mRNA; (b) modulates binding of a factor involved in splicing of the coding exon, the NMD exon, or both; or (c) a combination of (a) and (b). In some embodiments, the agent interferes with binding of the factor involved in splicing of the coding exon, the NMD exon, or both, to a region of the targeted portion. In some embodiments, the NMD exon is within an intronic region adjacent to the coding exon. In some embodiments, the NMD exon is within an intronic region immediately upstream of the coding exon. In some embodiments, the NMD exon is within an intronic region immediately downstream of the coding exon. In some embodiments, the targeted portion of the pre-mRNA is proximal to the coding exon. In some embodiments, the targeted portion of the pre-mRNA is located in an intronic region immediately upstream of the coding exon. In some embodiments, the targeted portion of the pre-mRNA is located in an intronic region immediately downstream of the coding exon. In some embodiments, the targeted portion of the pre-mRNA is located within the coding exon. In some embodiments, the targeted portion of the pre-mRNA is within a region spanning from 49 to 1, from 39 to 1, from 29 to 1, or from 19 to 1 nucleotides upstream of 5' end of the coding exon. In some embodiments, the targeted portion of the pre-mRNA is within a region spanning from 100 nucleotides upstream of the coding exon to 100 nucleotides downstream of the coding exon. In some embodiments, the coding exon is an alternatively spliced exon. In some embodiments, the coding exon comprises a sequence with at least 80%, at least 90%, or 100% sequence identity to SEQ ID NO: 277.

In some embodiments, the coding exon comprises SEQ ID NO: 277. In some embodiments, the targeted portion of the pre-mRNA is immediately upstream of the coding exon GRCh38/hg38: chr3 193626092 to 193626202. In some embodiments, the targeted portion of the pre-mRNA is immediately downstream of the coding exon GRCh38/hg38: chr3 193626092 to 193626202. In some embodiments, the targeted portion of the pre-mRNA is within a region spanning from 49 to 1, from 39 to 1, from 29 to 1, or from 19 to 1 nucleotides upstream of GRCh38/hg38: chr3 193626092. In some embodiments, the targeted portion of the pre-mRNA is within a region spanning from 100 nucleotides upstream of genomic site GRCh38/hg38: chr3 193626092. to 100 nucleotides downstream of genomic site GRCh38/hg38: chr3 193626202. In some embodiments, the targeted portion of the pre-mRNA is within the coding exon GRCh38/hg38: chr3 193626092 to 193626202. In some embodiments, the targeted portion of the pre-mRNA comprises an exon-intron junction of the coding exon GRCh38/hg38: chr3 193626092 to 193626202. In some embodiments, the targeted portion comprises about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more consecutive nucleotides of the coding exon. In some embodiments, the targeted portion of the pre-mRNA is proximal to the NMD exon. In some embodiments, the targeted portion of the pre-mRNA is located in an intronic region immediately upstream of the NMD exon. In some embodiments, the targeted portion of the pre-mRNA is located in an intronic region immediately downstream of the NMD exon. In some embodiments, the targeted portion of the pre-mRNA is located within the NMD exon. In some embodiments, the targeted portion of the pre-mRNA is within a region spanning from 100 nucleotides upstream of the NMD exon to 100 nucleotides downstream of the NMD exon. In some embodiments, the NMD exon comprises a sequence with at least 80%, at least 90%, or 100% sequence identity to SEQ ID NO: 279. In some embodiments, the NMD exon comprises SEQ ID NO: 279. In some embodiments, the targeted portion of the pre-mRNA is immediately upstream of the NMD exon GRCh38/hg38: chr3 193628509 to 193628616. In some embodiments, the targeted portion of the pre-mRNA is immediately downstream of the NMD exon GRCh38/hg38: chr3 193628509 to 193628616. In some embodiments, the targeted portion of the pre-mRNA is within a region spanning from 100 nucleotides upstream of genomic site GRCh38/hg38: chr3 193628509 to 100 nucleotides downstream of genomic site GRCh38/hg38: chr3 193628616. In some embodiments, the targeted portion of the pre-mRNA is within the NMD exon GRCh38/hg38: chr3 193628509 to 193628616. In some embodiments, the targeted portion of the pre-mRNA comprises an exon-intron junction of the NMD exon GRCh38/hg38: chr3 193628509 to 193628616. In some embodiments, the targeted portion comprises about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more consecutive nucleotides of the NMD exon.

In some embodiments, the exclusion of the coding exon from the pre-mRNA in the cell contacted with the agent is increased by about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to in the absence of the agent. In some embodiments, the exclusion of the NMD exon from the pre-mRNA in the cell contacted with the agent is increased by about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to in the absence of the agent. In some embodiments, the agent results in an increase in the level of the processed mRNA in the cell. In some embodiments, the level of the processed mRNA in the cell contacted with the agent is increased by about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to in the absence of the agent. In some embodiments, the method results in an increase in expression of the target protein in the cell. In some embodiments, a level of the target protein expressed from the processed mRNA in the cell contacted with the agent is increased by about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to in the absence of the agent. In some embodiments, the target protein is an OPA1 protein. In some embodiments, a level of the OPA1 protein expressed from the processed mRNA in the cell contacted with the agent is increased by at least about 1.5-fold compared to in the absence of the agent. In some embodiments, the OPA1 protein expressed from the processed mRNA is a functional OPA1 protein.

In some embodiments, the OPA1 protein expressed from the processed mRNA is at least partially functional as compared to a wild-type OPA1 protein. In some embodiments, the OPA1 protein expressed from the processed mRNA is at least partially functional as compared to a full-length wild-type OPA1 protein.

In some embodiments, the agent comprises an antisense oligomer with at least 80%, at least 90%, or 100% sequence identity to a sequence selected from the group consisting of SEQ ID NOs: 236, 242, 250, 280-283, 288, and 290-292. In some embodiments, the agent comprises a gene editing molecule. In some embodiments, the gene editing molecule comprises CRISPR-Cas9.

In some embodiments, the agent is an antisense oligomer (ASO) and wherein the antisense oligomer comprises a backbone modification comprising a phosphorothioate linkage or a phosphorodiamidate linkage. In some embodiments, the agent is an antisense oligomer (ASO) and wherein the antisense oligomer comprises a phosphorodiamidate morpholino, a locked nucleic acid, a peptide nucleic acid, a 2'-O-methyl moiety, a 2'-Fluoro moiety, or a 2'-O-methoxyethyl moiety. In some embodiments, the therapeutic agent is an antisense oligomer (ASO) and wherein the antisense oligomer comprises at least one modified sugar moiety. In some embodiments, each sugar moiety is a modified sugar moiety. In some embodiments, the agent is an antisense oligomer (ASO) and wherein the antisense oligomer consists of from 8 to 50 nucleobases, 8 to 40 nucleobases, 8 to 35 nucleobases, 8 to 30 nucleobases, 8 to 25 nucleobases, 8 to 20 nucleobases, 8 to 15 nucleobases, 9 to 50 nucleobases, 9 to 40 nucleobases, 9 to 35 nucleobases, 9 to 30 nucleobases, 9 to 25 nucleobases, 9 to 20 nucleobases, 9 to 15 nucleobases, 10 to 50 nucleobases, 10 to 40 nucleobases, 10 to 35 nucleobases, 10 to 30 nucleobases, 10 to 25 nucleobases, 10 to 20 nucleobases, 10 to 15 nucleobases, 11 to 50 nucleobases, 11 to 40 nucleobases, 11 to 35 nucleobases, 11 to 30 nucleobases, 11 to 25 nucleobases, 11 to 20 nucleobases, 11 to 15 nucleobases, 12 to 50 nucleobases, 12 to 40 nucleobases, 12 to 35 nucleobases, 12 to 30 nucleobases, 12 to 25 nucleobases, 12 to 20 nucleobases, or 12 to 15 nucleobases. In some embodiments, the vector comprises a viral vector encoding the agent. In some embodiments, the viral vector comprises an adenoviral vector, adeno-associated viral (AAV) vector, lentiviral vector, Herpes Simplex Virus (HSV) viral vector, or retroviral vector.

In some embodiments, the method further comprises assessing mRNA level or expression level of the OPA1 protein. In some embodiments, the agent is a therapeutic agent.

Described herein, in some aspects, is a pharmaceutical composition comprising the therapeutic agent as disclosed herein or a vector encoding the therapeutic agent as disclosed herein, and a pharmaceutically acceptable excipient.

Described herein, in some aspects, is a pharmaceutical composition, comprising a therapeutic agent or a vector encoding a therapeutic agent, and a pharmaceutically acceptable excipient, wherein the therapeutic agent comprises an antisense oligomer with at least 80% sequence identity to a sequence selected from the group consisting of SEQ ID NOs: 6-275 and 280-299. In some embodiments, the therapeutic agent comprises an antisense oligomer with at least 80%, at least 90%, or 100% sequence identity to a sequence selected from the group consisting of SEQ ID NOs: 36, 236, 242, 250, 280-283, 288, and 290-292. In some embodiments, the therapeutic agent comprises an antisense oligomer with at least 80%, at least 90%, or 100% sequence identity to a sequence selected from the group consisting of SEQ ID NOs: 227-242, 250, 280-283, 288, and 290-292. In some embodiments, the therapeutic agent comprises an antisense oligomer with at least 80%, at least 90%, or 100% sequence identity to SEQ ID NO: 267. In some embodiments, the therapeutic agent comprises an antisense oligomer with at least 80%, at least 90%, or 100% sequence identity to a sequence selected from the group consisting of SEQ ID NOs: 236, 242, 250, 280-283, 288, and 290-292.

Described herein, in some aspects, is a composition, comprising an antisense oligomer with at least 80% sequence identity to a sequence selected from the group consisting of SEQ ID NOs: 6-275 and 280-299, wherein the antisense oligomer comprises a backbone modification, a sugar moiety modification, or a combination thereof. In some embodiments, the antisense oligomer has at least 80%, at least 90%, or 100% sequence identity to a sequence selected from the group consisting of SEQ ID NOs: 36, 236, 242, 250, 280-283, 288, and 290-292. In some embodiments, the antisense oligomer has at least 80%, at least 90%, or 100% sequence identity to a sequence selected from the group consisting of SEQ ID NOs: 227-242, 250, 280-283, 288, and 290-292. In some embodiments, the antisense oligomer has at least 80%, at least 90%, or 100% sequence identity to SEQ ID NO: 267. In some embodiments, the antisense oligomer has at least 80%, at least 90%, or 100% sequence identity to a sequence selected from the group consisting of SEQ ID NOs: 236, 242, 250, 280-283, 288, and 290-292.

Described herein, in some aspects, is a pharmaceutical composition, comprising a therapeutic agent or a vector encoding the therapeutic agent, and a pharmaceutically acceptable excipient, wherein the therapeutic agent promotes exclusion of a coding exon from a pre-mRNA, thereby increasing a level of a processed mRNA that is processed from the pre-mRNA and that lacks the coding exon in a cell, wherein the pre-mRNA is transcribed from an OPA1 gene and that comprises the coding exon.

Described herein, in some aspects, is a pharmaceutical composition, comprising a therapeutic agent or a vector encoding the therapeutic agent, and a pharmaceutically acceptable excipient, wherein the therapeutic agent comprises an antisense oligomer that binds to a pre-mRNA that is transcribed from an OPA1 gene in a cell, wherein the antisense oligomer binds to: (a) a targeted portion of the pre-mRNA within an intronic region immediately upstream of a 5' end of the coding exon of the pre-mRNA; or (b) a targeted portion of the pre-mRNA within an intronic region immediately downstream of a 3' end of the coding exon of the pre-mRNA; whereby the therapeutic agent increases a level of a processed mRNA that is processed from the pre-mRNA and that contains the coding exon in the cell.

Described herein, in some aspects, is a pharmaceutical composition, comprising a therapeutic agent or a vector encoding the therapeutic agent, and a pharmaceutically acceptable excipient, wherein the therapeutic agent promotes exclusion of both a coding exon and a non-sense mediated RNA decay-inducing exon (NMD exon) from a pre-mRNA, thereby increasing a level of a processed mRNA that is processed from the pre-mRNA and that lacks the coding exon and the NMD exon in a cell, wherein the pre-mRNA is transcribed from an OPA1 gene in the cell and comprises the coding exon and the NMD exon.

In some embodiments, the pharmaceutical composition is formulated for intracerebroventricular injection, intraperitoneal injection, intramuscular injection, intrathecal injection, subcutaneous injection, oral administration, synovial injection, intravitreal administration, subretinal injection, topical application, implantation, or intravenous injection. In some embodiments, the pharmaceutical composition is formulated for intravitreal injection. In some embodiments, the pharmaceutical composition further comprises a second therapeutic agent. In some embodiments, the second therapeutic agent comprises a small molecule. In some embodiments, the second therapeutic agent comprises an antisense oligomer. In some embodiments, the second therapeutic agent corrects intron retention. In some embodiments, the antisense oligomer is selected from the group consisting of Compound ID NOs: 1-303.

Described herein, in some aspects, is a method of treating or reducing the likelihood of developing a disease or condition in a subject in need thereof by modulating expression of an OPA1 protein in a cell of the subject, comprising contacting to cells of the subject the therapeutic agent as disclosed herein. In some embodiments, the disease or condition is associated with a loss-of-function mutation in an OPA1 gene. In some embodiments, the disease or condition is associated with haploinsufficiency of the OPA1 gene, and wherein the subject has a first allele encoding a functional OPA1 protein, and a second allele from which the OPA1 protein is not produced or produced at a reduced level, or a second allele encoding a nonfunctional OPA1 protein or a partially functional OPA1 protein. In some embodiments, the disease or condition comprises an eye disease or condition. In some embodiments, the disease or condition comprises ADOA-plus syndrome; a mitochondrial disorder; glaucoma; normal tension glaucoma; Charcot-Marie-Tooth disease; mitochondria dysfunction; diabetic retinopathy; age-related macular degeneration; retinal ganglion cell death; mitochondrial fission-mediated mitochondrial dysfunction; progressive external ophthalmoplegia; deafness; ataxia; motor neuropathy; sensory neuropathy; myopathy; Behr syndrome; brain dysfunction; encephalopathy; peripheral neuropathy; fatal infantile mitochondrial encephalomyopathy; hypertrophic cardiomyopathy; spastic ataxic syndrome; sensory motor peripheral neuropathy; hypotonia; gastrointestinal dysmotility and dysphagia; optic atrophy; optic atrophy plus syndrome; Mitochondrial DNA depletion syndrome 14; late-onset cardiomyopathy; diabetic cardiomyopathy; Alzheimer's Disease; focal segmental glomerulosclerosis; kidney disease; Huntington's Disease; cognitive function decline in healthy aging; Prion diseases; late onset dementia and parkinsonism; mitochondrial myopathy; Leigh syndrome; Friedreich's ataxia; Parkinson's disease; MELAS (Mitochondrial encephalomyopathy, lactic acidosis, and stroke-like episodes); pyruvate dehydrogenase complex deficiency; chronic kidney disease; Leber's hereditary optic neuropathy; obesity; age-related systemic neurodegeneration; skeletal muscle atrophy; heart and brain ischemic damage; or massive liver apoptosis. In some embodiments, the disease or condition comprises Optic atrophy type 1. In some embodiments, the disease or condition comprises autosomal dominant optic atrophy (ADOA). In some embodiments, the disease or condition is associated with an autosomal recessive mutation of OPA1 gene, wherein the subject has a first allele encoding from which: (i) OPA1 protein is not produced or produced at a reduced level compared to a wild-type allele; or (ii) the OPA1 protein produced is nonfunctional or partially functional compared to a wild-type allele, and a second allele from which: (iii) the OPA1 protein is produced at a reduced level compared to a wild-type allele and the OPA1 protein produced is at least partially functional compared to a wild-type allele; or (iv) the OPA1 protein produced is partially functional compared to a wild-type allele.

In some embodiments, the subject is a human. In some embodiments, the subject is a non-human animal. In some embodiments, the subject is a fetus, an embryo, or a child. In some embodiments, the cells that the methods and compositions described herein are applicable to are ex vivo. In some embodiments, the therapeutic agent is administered by intracerebroventricular injection, intraperitoneal injection, intramuscular injection, intrathecal injection, subcutaneous injection, oral administration, synovial injection, intravitreal administration, subretinal injection, topical application, implantation, or intravenous injection. In some embodiments, the therapeutic agent is administered by intravitreal injection. In some embodiments, the method disclosed herein treats the disease or condition.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIG. 1A shows a cell divided into nuclear and cytoplasmic compartments. In the nucleus, a pre-mRNA transcript of a target gene undergoes splicing to generate mRNA, and this mRNA is exported to the cytoplasm and translated into target protein. For this target gene, some fraction of the mRNA contains a nonsense-mediated mRNA decay-inducing exon (NMD exon mRNA) that is degraded in the cytoplasm, thus leading to no target protein production. FIG. 1B shows an example of the same cell divided into nuclear and cytoplasmic compartments. Treatment with a therapeutic agent, such as an antisense oligomer (ASO), promotes the exclusion of the nonsense-mediated mRNA decay-inducing exon and results in an increase in mRNA, which is in turn translated into higher levels of target protein. FIG. 1C shows an example schematic of a Novel NMD exon inclusion event (Exon X) identified in the OPA1 gene which leads to the introduction of a premature termination codon (PTC) resulting in a non-productive mRNA transcript degraded by non-sense mediated decay (NMD).

FIG. 2 discloses SEQ ID NO: 300.

FIG. 3 discloses SEQ ID NO: 301.

FIG. 5 discloses SEQ ID NOS 302-304, respectively, in order of appearance.

FIG. 9A confirms expression of OPA1 transcripts containing the NMD exon in these cells.

FIG. 15 illustrates exemplary OPA1 ASOs of this disclosure. The right two columns in the chart illustrate the chemical modifications of the exemplary ASOs. Each nucleotide of all the ASOs has 2'-O-methoxyethyl (2'MOE) modification ("MOE") unless otherwise noted, for instance, letters of larger font size (e.g., G) are locked nucleic acids ("LNA"), underlined letters (e.g., C) are 5' methyl-cytosines that have 2'-MOE moiety ("5MeC-MOE"), and some ASOs are noted as phosphorodiamidate morpholino oligomers ("PMO"). FIG. 15 discloses SEQ ID NOS 6-148, 148, 148, 149, 149, 149, 150, 150, 150-151, 151, 151, 123, 152, 152, 152-153, 153, 153-154, 154, 154, 144-146, 93, 81-82, 36, 155, 155-156, 156-157, 157-161, 125, 162, 126, 163-166, 92, 167-179, 156, 180, 157, 159, 181, 160, 182, 161, 183-275, and 305-607 respectively, in order of column.

FIG. 18D summarizes the Ct values for the qPCR reactions, and FIG. 18E summarizes the relative amounts.

FIG. 24B shows the immunoblot gel images of OPA1 and β-actin proteins, and FIG. 24C is a histogram that summarizes quantification of the immunoblot results.

FIG. 27A shows representative time courses of the oxygen consumption rate of WT cells, F35 cells, and F36 cells at baseline level and when challenged sequentially with oligomycin, FCCP, rotenone and antimycin A. FIGS. 27B-27E show histograms demonstrating that patient fibroblast cells, F35 and F36 cells had reduced basal oxygen consumption rate (FIG. 27B), ATP linked respiration (FIG. 27C), maximal respiration (FIG. 27D), and spare respiratory capacity (FIG. 27E), as compared to WT fibroblast cells.

DETAILED DESCRIPTION

Figure 1A:
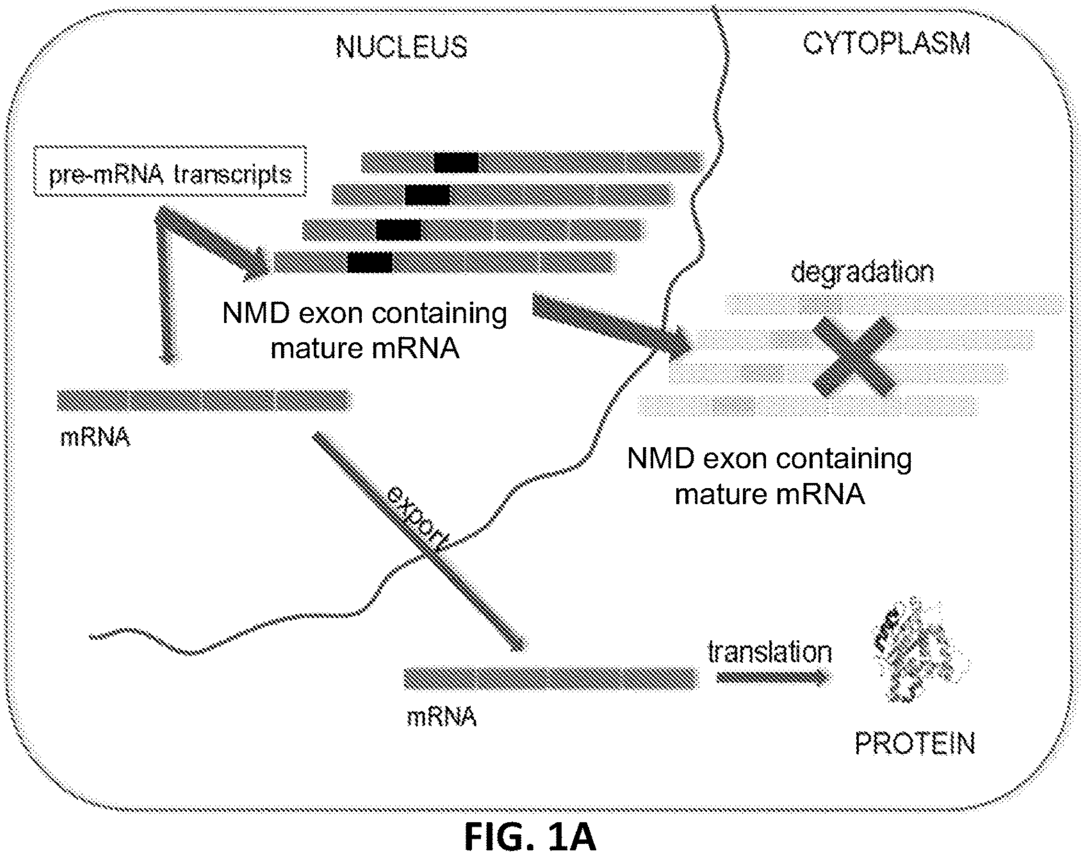
FIGS. 1A-1C depict a schematic representation of a target mRNA that contains a non-sense mediated mRNA decay-inducing exon (NMD exon mRNA) and therapeutic agent-mediated exclusion of the nonsense-mediated mRNA decay-inducing exon to increase expression of the full-length target protein or functional RNA.
Figure 1B:
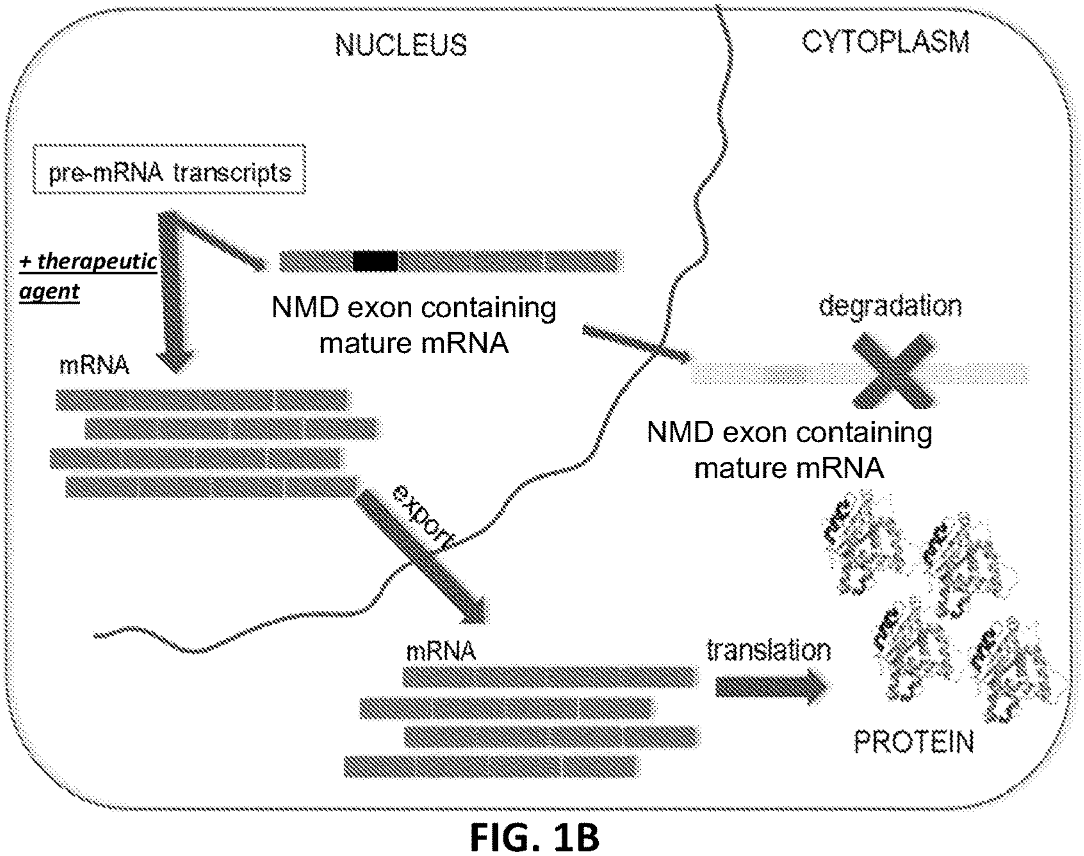
Figure 1C:
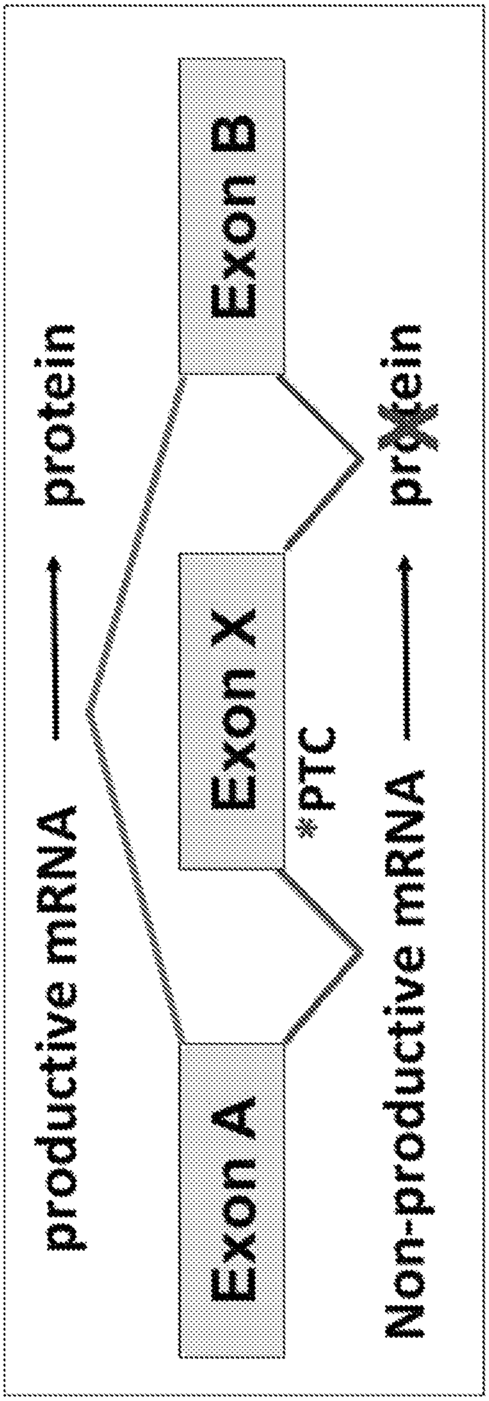

Alternative splicing events in the OPA1 gene can lead to non-productive mRNA transcripts which in turn can lead to aberrant protein expression, and therapeutic agents which can target the alternative splicing events in the OPA1 gene can modulate the expression level of functional proteins in DS patients and/or inhibit aberrant protein expression. Such therapeutic agents can be used to treat a condition caused by OPA1 protein deficiency.

One of the alternative splicing events that can lead to non-productive mRNA transcripts is the inclusion of an extra exon in the mRNA transcript that can induce non-sense mediated mRNA decay. The present disclosure provides compositions and methods for modulating alternative splicing of OPA1 to increase the production of protein-coding mature mRNA, and thus, translated functional OPA1 protein. These compositions and methods include antisense oligomers (ASOs) that can cause exon skipping, e.g., pseudoexon skipping, and promote constitutive splicing of OPA1 pre-mRNA. In various embodiments, functional OPA1 protein can be increased using the methods of the disclosure to treat a condition caused by OPA1 protein deficiency.

mRNA Splicing

Intervening sequences in RNA sequences or introns are removed by a large and highly dynamic RNA-protein complex termed the spliceosome, which orchestrates complex interactions between primary transcripts, small nuclear RNAs (snRNAs) and a large number of proteins. Spliceosomes assemble ad hoc on each intron in an ordered manner, starting with recognition of the 5' splice site (5'ss) by U1 snRNA or the 3'splice site (3'ss) by the U2 pathway, which involves binding of the U2 auxiliary factor (U2AF) to the 3'ss region to facilitate U2 binding to the branch point sequence (BPS). U2AF is a stable heterodimer composed of a U2AF2-encoded 65-kD subunit (U2AF65), which binds the polypyrimidine tract (PPT), and a U2AF1-encoded 35-kD subunit (U2AF35), which interacts with highly conserved AG dinucleotides at 3'ss and stabilizes U2AF65 binding. In addition to the BPS/PPT unit and 3'ss/5'ss, accurate splicing requires auxiliary sequences or structures that activate or repress splice site recognition, known as intronic or exonic splicing enhancers or silencers. These elements allow genuine splice sites to be recognized among a vast excess of cryptic or pseudo-sites in the genome of higher eukaryotes, which have the same sequences but outnumber authentic sites by an order of magnitude. Although they often have a regulatory function, the exact mechanisms of their activation or repression are poorly understood.

The decision of whether to splice or not to splice can be typically modeled as a stochastic rather than deterministic process, such that even the most defined splicing signals can sometimes splice incorrectly. However, under normal conditions, pre-mRNA splicing proceeds at surprisingly high fidelity. This is attributed in part to the activity of adjacent cis-acting auxiliary exonic and intronic splicing regulatory elements (ESRs or ISRs). Typically, these functional elements are classified as either exonic or intronic splicing enhancers (ESEs or ISEs) or silencers (ESSs or ISSs) based on their ability to stimulate or inhibit splicing, respectively. Although there is now evidence that some auxiliary cis-acting elements may act by influencing the kinetics of spliceosome assembly, such as the arrangement of the complex between U1 snRNP and the 5'ss, it seems very likely that many elements function in concert with trans-acting RNA-binding proteins (RBPs). For example, the serine- and arginine-rich family of RBPs (SR proteins) is a conserved family of proteins that have a key role in defining exons. SR proteins promote exon recognition by recruiting components of the pre-spliceosome to adjacent splice sites or by antagonizing the effects of ESSs in the vicinity. The repressive effects of ESSs can be mediated by members of the heterogeneous nuclear ribonucleoprotein (hnRNP) family and can alter recruitment of core splicing factors to adjacent splice sites. In addition to their roles in splicing regulation, silencer elements are suggested to have a role in repression of pseudo-exons, sets of decoy intronic splice sites with the typical spacing of an exon but without a functional open reading frame. ESEs and ESSs, in cooperation with their cognate trans-acting RBPs, represent important components in a set of splicing controls that specify how, where and when mRNAs are assembled from their precursors.

Alternative splicing is a regulated process during gene expression that can result in multiple isoforms of mature mRNA transcripts that are processed from a single primary mRNA transcript that is transcribed from a single gene, and the resultant multiple proteins that are translated from at least some of the multiple mature mRNA isoforms. In this process, particular exons of a gene may be included within or excluded from the final, processed mRNA produced from that gene. Consequently, the proteins translated from alternatively splices mRNAs will contain differences in their amino acid sequence and, in some cases, in their biological functions.

As described herein, an "alternatively spliced exon" can refer to an exon of a gene that can be either included or excluded naturally from a mature mRNA transcript, thus resulting in different protein products that are translated from the different mature mRNA transcripts. The inclusion or skipping of an alternatively spliced exon can take place naturally in a cell, either randomly, or in a regulated manner, e.g., subject to regulation by external physiological or pathological stimuli, or intracellular signaling. In some cases, the production of alternatively spliced mRNAs, e.g., the splicing of the alternatively spliced exon, is regulated by a system of trans-acting proteins that bind to cis-acting sites on the primary transcript itself. In some cases, an alternatively spliced exon is a coding exon, e.g., an exon that, when included in the mature mRNA transcript, is translated into an amino acid sequence as part of the protein product translated from the mature mRNA transcript. In some cases, the inclusion of an alternatively spliced exon in the mature mRNA transcript would maintain the canonical open reading frame as compared to a mature mRNA transcript without the alternatively spliced exon, e.g., the number of nucleotides in the alternatively spliced exon is divisible by 3.

The sequences marking the exon-intron boundaries are degenerate signals of varying strengths that can occur at high frequency within human genes. In multi-exon genes, different pairs of splice sites can be linked together in many different combinations, creating a diverse array of transcripts from a single gene. This is commonly referred to as alternative pre-mRNA splicing. Although most mRNA isoforms produced by alternative splicing can be exported from the nucleus and translated into functional polypeptides, different mRNA isoforms from a single gene can vary greatly in their translation efficiency. Those mRNA isoforms with premature termination codons (PTCs) at least 50 bp upstream of an exon junction complex are likely to be targeted for degradation by the nonsense-mediated mRNA decay (NMD) pathway. Mutations in traditional (BPS/PPT/3'ss/5'ss) and auxiliary splicing motifs can cause aberrant splicing, such as exon skipping or cryptic (or pseudo-) exon inclusion or splice-site activation, and contribute significantly to human morbidity and mortality. Both aberrant and alternative splicing patterns can be influenced by natural DNA variants in exons and introns.

Given that exon-intron boundaries can occur at any of the three positions of a codon, it is clear that only a subset of alternative splicing events can maintain the canonical open reading frame. For example, only exons that are evenly divisible by 3 can be skipped or included in the mRNA without any alteration of reading frame. Splicing events that do not have compatible phases will induce a frame-shift. Unless reversed by downstream events, frame-shifts can certainly lead to one or more PTCs, probably resulting in subsequent degradation by NMD. NMD is a translation-coupled mechanism that eliminates mRNAs containing PTCs. NMD can function as a surveillance pathway that exists in all eukaryotes. NMD can reduce errors in gene expression by eliminating mRNA transcripts that contain premature stop codons. Translation of these aberrant mRNAs could, in some cases, lead to deleterious gain-of-function or dominant-negative activity of the resulting proteins. NMD targets not only transcripts with PTCs but also a broad array of mRNA isoforms expressed from many endogenous genes, suggesting that NMD is a master regulator that drives both fine and coarse adjustments in steady-state RNA levels in the cell.

A NMD-inducing exon ("NIE" or "NMD exon") is an exon or a pseudo-exon that is a region within an intron and can activate the NMD pathway if included in a mature RNA transcript. In constitutive splicing events, the intron containing an NMD exon is usually spliced out, but the intron or a portion thereof (e.g. NMD exon) may be retained during alternative or aberrant splicing events. Mature mRNA transcripts containing such an NMD exon may be non-productive due to frame shifts which induce the NMD pathway. Inclusion of a NMD exon in mature RNA transcripts may downregulate gene expression. mRNA transcripts containing an NMD exon may be referred to as "NIE-containing mRNA" or "NMD exon mRNA" in the current disclosure.

Cryptic (or pseudo-splice sites) have the same splicing recognition sequences as genuine splice sites but are not used in splicing reactions. They outnumber genuine splice sites in the human genome by an order of a magnitude and are normally repressed by thus far poorly understood molecular mechanisms. Cryptic 5' splice sites have the consensus NNN/GUNNNN or NNN/GCNNNN where N is any nucleotide and/is the exon-intron boundary. Cryptic 3' splice sites have the consensus NAG/N. Their activation is positively influenced by surrounding nucleotides that make them more similar to the optimal consensus of authentic splice sites, namely MAG/GURAGU and YAG/G, respectively, where M is C or A, R is G or A, and Y is C or U.

Splice sites and their regulatory sequences can be readily identified by a skilled person using suitable algorithms publicly available, listed for example in Kralovicova, J. and Vorechovsky, I. (2007) Global control of aberrant splice site activation by auxiliary splicing sequences: evidence for a gradient in exon and intron definition. Nucleic Acids Res., 35, 6399-6413 (www.ncbi.nlm.nih.gov/pmc/articles/PMC2095810/pdf/gkm680.pdf).

The cryptic splice sites or splicing regulatory sequences may compete for RNA-binding proteins, such as U2AF, with a splice site of the NMD exon. In some embodiments, an agent may bind to a cryptic splice site or splicing regulatory sequence to prevent binding of RNA-binding proteins and thereby favor binding of RNA-binding proteins to the NMD exon splice sites.

In some embodiments, the cryptic splice site may not comprise the 5' or 3' splice site of the NMD exon. In some embodiments, the cryptic splice site may be at least 10 nucleotides, at least 20 nucleotides, at least 50 nucleotides, at least 100 nucleotides or at least 200 nucleotides upstream of the NMD exon 5' splice site. In some embodiments, the cryptic splice site may be at least 10 nucleotides, at least 20 nucleotides, at least 50 nucleotides, at least 100 nucleotides, at least 200 nucleotides downstream of the NMD exon 3' splice site.

Target Transcripts

In some embodiments, the methods and compositions of the present disclosure exploit the presence of NMD exon in the pre-mRNA transcribed from the OPA1 gene. Splicing of the identified OPA1 NMD exon pre-mRNA species to produce functional mature OPA1 mRNA may be induced using an agent such as an ASO that stimulates exon skipping of an NMD exon. Induction of exon skipping may result in inhibition of an NMD pathway. The resulting mature OPA1 mRNA can be translated normally without activating NMD pathway, thereby increasing the amount of OPA1 protein in the patient's cells and alleviating symptoms of a condition or disease associated with OPA1 deficiency, such as an eye disease or condition, Optic atrophy type 1, autosomal dominant optic atrophy (ADOA), ADOA-plus syndrome; a mitochondrial disorder; glaucoma; normal tension glaucoma; Charcot-Marie-Tooth disease; mitochondria dysfunction; diabetic retinopathy; age-related macular degeneration; retinal ganglion cell death; mitochondrial fission-mediated mitochondrial dysfunction; progressive external ophthalmoplegia; deafness; ataxia; motor neuropathy; sensory neuropathy; myopathy; Behr syndrome; brain dysfunction; encephalopathy; peripheral neuropathy; fatal infantile mitochondrial encephalomyopathy; hypertrophic cardiomyopathy; spastic ataxic syndrome; sensory motor peripheral neuropathy; hypotonia; gastrointestinal dysmotility and dysphagia; optic atrophy; optic atrophy plus syndrome; Mitochondrial DNA depletion syndrome 14; late-onset cardiomyopathy; diabetic cardiomyopathy; Alzheimer's Disease; focal segmental glomerulosclerosis; kidney disease; Huntington's Disease; cognitive function decline in healthy aging; Prion diseases; late onset dementia and parkinsonism; mitochondrial myopathy; Leigh syndrome; Friedreich's ataxia; Parkinson's disease; MELAS (Mitochondrial encephalomyopathy, lactic acidosis, and stroke-like episodes); pyruvate dehydrogenase complex deficiency; chronic kidney disease; Leber's hereditary optic neuropathy; obesity; age-related systemic neurodegeneration; skeletal muscle atrophy; heart and brain ischemic damage; or massive liver apoptosis.

In some embodiments, the methods and compositions of the present disclosure exploit the alternative splicing of the pre-mRNA transcribed from the OPA1 gene. In some cases, splicing of a coding exon, e.g., an alternatively spliced exon, e.g., OPA1 exon 7 (or an exon encoded by genomic region spanning from GRCh38/hg38: chr3 193626092 to 193626202), can modulate the level of OPA1 protein expressed from the OPA1 gene. As described herein, the term "OPA1 exon 7" or grammatically equivalents thereof, is used interchangeably with the term "exon (GRCh38/hg38: chr3 193626092 to 193626202)" or "an exon encoded by genomic region spanning from GRCh38/hg38: chr3 193626092 to 193626202." Without wishing to be bound by a certain theory, the presence or absence of an amino acid sequence encoded by exon 7 or exon (GRCh38/hg38: chr3 193626092 to 193626202) can modulate the stability of the OPA1 protein. For instance, in some cases, the OPA1 protein encoded by a mature mRNA transcript that lacks exon 7 can have fewer proteolytic cleavage sites as compared to an OPA1 protein encoded by a corresponding mature mRNA transcript that has contains exon 7. In some cases, the OPA1 protein an OPA1 protein encoded by a corresponding mature mRNA transcript that has contains encoded by a mature mRNA transcript that lacks exon 7 is a functional protein. The OPA1 protein encoded by a mature mRNA transcript that lacks exon 7 can be at least partially functional as compared to an OPA1 protein encoded by a corresponding mature mRNA transcript that has contains exon 7. In some cases, the OPA1 protein encoded by a mature mRNA transcript that lacks exon 7 is at least partially functional as compared to a full-length wild-type OPA1 protein. In some cases, increase of OPA1 protein encoded by a mature mRNA transcript that lacks exon 7 in a cell can result in more functional OPA1 protein in the cell, due to the higher stability of the OPA1 protein lacking exon 7 and its at least partial functional equivalence.

In other embodiments, a coding exon of OPA1 pre-mRNA other than exon 7 is targeted by an agent disclosed herein, which promotes exclusion of the coding exon other than exon 7. In these other embodiments, the agent that promotes exclusion of the coding exon other than exon 7 increases expression of OPA1 protein encoded by a mature mRNA transcript that lacks the excluded exon.

Alternative splicing of the OPA1 pre-mRNA species, e.g., skipping of a coding exon, e.g., an alternatively spliced exon, e.g., exon 7, to produce functional mature OPA1 protein may be induced using an agent such as an ASO that stimulates the exon skipping. Induction of exon skipping may result in modulation of levels of different alternatively spliced mRNA transcripts. The resulting mature OPA1 mRNA can be translated into different OPA1 proteins, thereby modulating the amount of OPA1 protein in the patient's cells and alleviating symptoms of a condition or disease associated with OPA1 deficiency, such as an eye disease or condition, Optic atrophy type 1, autosomal dominant optic atrophy (ADOA), ADOA-plus syndrome; a mitochondrial disorder; glaucoma; normal tension glaucoma; charcot-Marie-tooth disease; mitochondria dysfunction; diabetic retinopathy; age-related macular degeneration; retinal ganglion cell death; mitochondrial fission-mediated mitochondrial dysfunction; progressive external ophthalmoplegia; deafness; ataxia; motor neuropathy; sensory neuropathy; myopathy; Behr syndrome; brain dysfunction; encephalopathy; peripheral neuropathy; fatal infantile mitochondrial encephalomyopathy; hypertrophic cardiomyopathy; spastic ataxic syndrome; sensory motor peripheral neuropathy; hypotonia; gastrointestinal dysmotility and dysphagia; optic atrophy; optic atrophy plus syndrome; Mitochondrial DNA depletion syndrome 14; late-onset cardiomyopathy; diabetic cardiomyopathy; Alzheimer's Disease; focal segmental glomerulosclerosis; kidney disease; Huntington's Disease; cognitive function decline in healthy aging; Prion diseases; late onset dementia and parkinsonism; mitochondrial myopathy; Leigh syndrome; Friedreich's ataxia; Parkinson's disease; MELAS (Mitochondrial encephalomyopathy, lactic acidosis, and stroke-like episodes); pyruvate dehydrogenase complex deficiency; chronic kidney disease; Leber's hereditary optic neuropathy; obesity; age-related systemic neurodegeneration; skeletal muscle atrophy; heart and brain ischemic damage; or massive liver apoptosis.

In some embodiments, the diseases or conditions that can be treated or ameliorated using the method or composition disclosed herein are not directly associated with the target protein (gene) that the therapeutic agent targets. In some embodiments, a therapeutic agent provided herein can target a protein (gene) that is not directly associated with a disease or condition, but the modulation of expression of the target protein (gene) can treat or ameliorate the disease or condition.

In various embodiments, the present disclosure provides a therapeutic agent which can target OPA1 mRNA transcripts to modulate splicing or protein expression level. The therapeutic agent can be a small molecule, polynucleotide, or polypeptide. In some embodiments, the therapeutic agent is an ASO. Various regions or sequences on the OPA1 pre-mRNA can be targeted by a therapeutic agent, such as an ASO. In some embodiments, the ASO targets an OPA1 pre-mRNA transcript containing an NMD exon. In some embodiments, the ASO targets a sequence within an NMD exon of an OPA1 pre-mRNA transcript. In some embodiments, the ASO targets a sequence upstream (or 5') from the 5' end of an NMD exon (3'ss) of an OPA1 pre-mRNA transcript. In some embodiments, the ASO targets a sequence downstream (or 3') from the 3' end of an NMD exon (5'ss) of an OPA1 pre-mRNA transcript. In some embodiments, the ASO targets a sequence that is within an intron flanking on the 5' end of the NMD exon of an OPA1 pre-mRNA transcript. In some embodiments, the ASO targets a sequence that is within an intron flanking the 3' end of the NMD exon of an OPA1 pre-mRNA transcript. In some embodiments, the ASO targets a sequence comprising an NMD exon-intron boundary of an OPA1 pre-mRNA transcript. An NMD exon-intron boundary can refer to the junction of an intron sequence and an NMD exon region. The intron sequence can flank the 5' end of the NMD exon, or the 3' end of the NMD exon. In some embodiments, the ASO targets a sequence within an exon of an OPA1 pre-mRNA transcript. In some embodiments, the ASO targets a sequence within an intron of an OPA1 pre-mRNA transcript. In some embodiments, the ASO targets a sequence comprising both a portion of an intron and a portion of an exon of an OPA1 pre-mRNA transcript.

In some embodiments, the ASO targets a sequence about 4 to about 300 nucleotides upstream (or 5') from the 5' end of the NMD exon. In some embodiments, the ASO targets a sequence about 1 to about 20 nucleotides, about 20 to about 50 nucleotides, about 50 to about 100 nucleotides, about 100 to about 150 nucleotides, about 150 to about 200 nucleotides, about 200 to about 250 nucleotides, or about 250 to about 300 nucleotides upstream (or 5') from the 5' end of the NMD exon region. In some embodiments, the ASO may target a sequence more than 300 nucleotides upstream from the 5' end of the NMD exon. In some embodiments, the ASO targets a sequence about 4 to about 300 nucleotides downstream (or 3') from the 3' end of the NMD exon. In some embodiments, the ASO targets a sequence about 1 to about 20 nucleotides, about 20 to about 50 nucleotides, about 50 to about 100 nucleotides, about 100 to about 150 nucleotides, about 150 to about 200 nucleotides, about 200 to about 250 nucleotides, or about 250 to about 300 nucleotides downstream from the 3' end of the NMD exon. In some embodiments, the ASO targets a sequence more than 300 nucleotides downstream from the 3' end of the NMD exon.

In some embodiments, the OPA1 NMD exon-containing pre-mRNA transcript is encoded by a genetic sequence with at least about 80%, 85%, 90%, 95%, 96%, 97%, 98%, 99% or 100% sequence identity to SEQ ID NO. 1. In some embodiments, the OPA1 NMD exon pre-mRNA transcript comprises a sequence with at least about 80%, 85%, 90%, 95%, 96%, 97%, 98%, 99% or 100% sequence identity to any one of SEQ ID NOs: 2-5.

In some embodiments, the OPA1 NMD exon-containing pre-mRNA transcript (or NMD exon mRNA) comprises a sequence with at least about 80%, 85%, 90%, 95%, 97%, or 100% sequence identity to any one of SEQ ID NOs: 2-5. In some embodiments, OPA1 NMD exon-containing pre-mRNA transcript (or NMD exon mRNA) is encoded by a sequence with at least about 80%, 85%, 90%, 95%, 97%, or 100% sequence identity to any one of SEQ ID NOs: 2-5. In some embodiments, the targeted portion of the NMD exon mRNA comprises a sequence with at least 80%, 85%, 90%, 95%, 97%, or 100% sequence identity to a region comprising at least 8 contiguous nucleic acids of any one of SEQ ID NOs: 2-5.

In some embodiments, the ASO targets exon 6x of an OPA1 NMD exon-containing pre-mRNA comprising NIE exon 6, exon 7x of an OPA1 NMD exon-containing pre-mRNA comprising NIE exon 7, or exon 28x of an OPA1 NMD exon-containing pre-mRNA comprising NIE exon 28. In some embodiments, the ASO targets exon (GRCh38/hg38: chr3 193628509 193628616) of OPA1 pre-mRNA; or exon (GRCh38/hg38: chr3 193603500 193603557) of OPA1. In some embodiments, the ASO targets an NMD exon of OPA1 pre-mRNA other than NMD exon (GRCh38/hg38: chr3 193628509 193628616).

In some embodiments, the ASO targets a sequence about 1500 nucleotides, about 1000 nucleotides, about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides upstream (or 5') from the 5' end of exon 6x of OPA1, exon 7x of OPA1, or exon 28x of OPA1. In some embodiments, the ASO targets a sequence about 1500 nucleotides, about 1000 nucleotides, about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides upstream (or 5') from GRCh38/hg38: chr3 193628509 of OPA1; or GRCh38/hg38: chr3 193603500 of OPA1.

In some embodiments, the ASO targets a sequence at most about 1500 nucleotides, about 1000 nucleotides, about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides upstream (or 5') from the 5' end of exon 6x of OPA1, exon 7x of OPA1, or exon 28x of OPA1. In some embodiments, the ASO targets a sequence at most about 1500 nucleotides, about 1000 nucleotides, about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides upstream (or 5') from GRCh38/hg38: chr3 193628509 of OPA1; or GRCh38/hg38: chr3 193603500 of OPA1.

In some embodiments, the ASO targets a sequence about 1500 nucleotides, about 1000 nucleotides, about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides downstream (or 3') from the 3' end of exon 6x of OPA1, exon 7x of OPA1, or exon 28x of OPA1. In some embodiments, the ASO targets a sequence about 1500 nucleotides, about 1000 nucleotides, about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides downstream (or 3') from GRCh38/hg38: chr3 193628616 of OPA1; or GRCh38/hg38: chr3 193603557 of OPA1.

In some embodiments, the ASO targets a sequence at most about 1500 nucleotides, about 1000 nucleotides, about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides downstream (or 3') from the 3' end of exon 6x of OPA1, exon 7x of OPA1, or exon 28x of OPA1. In some embodiments, the ASO targets a sequence at most about 1500 nucleotides, about 1000 nucleotides, about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides downstream (or 3') from GRCh38/hg38: chr3 193628616 of OPA1; or GRCh38/hg38: chr3 193603557 of OPA1.

In some embodiments, the ASO has a sequence complementary to the targeted portion of the NMD exon mRNA according to any one of SEQ ID NOs: 2-5, or 279.

In some embodiments, the ASO targets a sequence upstream from the 5' end of an NMD exon. For example, ASOs targeting a sequence upstream from the 5' end of an NMD exon (exon 6x of OPA1, exon 7x of OPA1, or exon 28x of OPA1) comprises a sequence that is at least about 80%, 85%, 90%, 95%, 97%, or 100% complimentary to at least 8 contiguous nucleic acids of SEQ ID NO: 2 or 3. For example, ASOs targeting a sequence upstream from the 5' end of an NMD exon (e.g., exon (GRCh38/hg38: chr3 193628509 to 193628616) of OPA1; or exon (GRCh38/ hg38: chr3 193603500 193603557) of OPA1) can comprise a sequence with at least 80%, 85%, 90%, 95%, 97%, or 100% sequence identity to SEQ ID NO: 4 or 5.

In some embodiments, the ASOs target a sequence containing an exon-intron boundary (or junction). For example, ASOs targeting a sequence containing an exon-intron boundary can comprise a sequence that is at least about 80%, 85%, 90%, 95%, 97%, or 100% complimentary to at least 8 contiguous nucleic acids of any one of SEQ ID NOs: 2-5. In some embodiments, the ASOs target a sequence downstream from the 3' end of an NMD exon. For example, ASOs targeting a sequence downstream from the 3' end of an NMD exon (e.g., exon 6x of OPA1, exon 7x of OPA1, or exon 28x of OPA1) can comprise a sequence with at least 80%, 85%, 90%, 95%, 97%, or 100% sequence identity to SEQ ID NO: 2 or 3, or at least 8 contiguous nucleic acids of SEQ ID NO: 2 or 3. For example, ASOs targeting a sequence downstream from the 3' end of an NMD exon (e.g., exon (GRCh38/hg38: chr3 193628509 to 193628616) of OPA1; or exon (GRCh38/hg38: chr3 193603500 to 193603557) of OPA1) can comprise a sequence with at least 80%, 85%, 90%, 95%, 97%, or 100% sequence identity to SEQ ID NO: 4 or 5, or at least 8 contiguous nucleic acids of SEQ ID NO: 4 or 5. In some embodiments, ASOs target a sequence within an NMD exon.

In some embodiments, the ASO targets exon 6x of an OPA1 NMD exon-containing pre-mRNA comprising NIE exon 6, exon 7x of an OPA1 NMD exon-containing pre-mRNA comprising NIE exon 7, or exon 28x of an OPA1 NMD exon-containing pre-mRNA comprising NIE exon 28. In some embodiments, the ASO targets a sequence downstream (or 3') from the 5' end of exon 6x, exon 7x, or exon 28x of an OPA1 pre-mRNA. In some embodiments, the ASO targets a sequence upstream (or 5') from the 3' end of exon 6x, exon 7x, or exon 28x of an OPA1 pre-mRNA.

In some embodiments, the targeted portion of the OPA1 NMD exon-containing pre-mRNA is in intron 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50. In some embodiments, hybridization of an ASO to the targeted portion of the NMD exon pre-mRNA results in exon skipping of at least one of NMD exon within intron 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50, and subsequently increases OPA1 protein production. In some embodiments, the targeted portion of the OPA1 NMD exon-containing pre-mRNA is in intron 6 of OPA1, or intron 28 of OPA1. In some embodiments, the targeted portion of the OPA1 NMD exon-containing pre-mRNA is intron (GRCh38/hg38: chr3 193626203 to 193631611) of OPA1; or intron (GRCh38/hg38: chr3 193593374 to 193614710) of OPA1.

In some embodiments, the methods and compositions of the present disclosure are used to increase the expression of OPA1 by inducing exon skipping of a pseudo-exon of an OPA1 NMD exon-containing pre-mRNA. In some embodiments, the pseudo-exon is a sequence within any of introns 1-50. In some embodiments, the pseudo-exon is a sequence within any of introns 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50. In some embodiments, the pseudo-exon can be an OPA1 intron or a portion thereof. In some embodiments, the pseudo-exon is within intron 6 of OPA1, or intron 28 of OPA1. In some embodiments, the pseudo-exon is within intron (GRCh38/hg38: chr3 193626203 to 193631611) of OPA1; or intron (GRCh38/hg38: chr3 193593374 to 193614710) of OPA1.

In some embodiments, the ASO targets an OPA1 pre-mRNA transcript to induce exon skipping of a coding exon, e.g., an alternatively spliced exon. In some embodiments, the ASO targets a sequence within a coding exon, e.g., an alternatively spliced exon, of an OPA1 pre-mRNA transcript. In some embodiments, the ASO targets a sequence upstream (or 5') from the 5' end of a coding exon (3'ss) of an OPA1 pre-mRNA transcript. In some embodiments, the ASO targets a sequence downstream (or 3') from the 3' end of a coding exon (5'ss) of an OPA1 pre-mRNA transcript. In some embodiments, the ASO targets a sequence that is within an intron flanking on the 5' end of the coding exon of an OPA1 pre-mRNA transcript. In some embodiments, the ASO targets a sequence that is within an intron flanking the 3' end of the coding exon of an OPA1 pre-mRNA transcript. In some embodiments, the ASO targets a sequence comprising an exon-intron boundary of an OPA1 pre-mRNA transcript. An exon-intron boundary can refer to the junction of an intron sequence and an exon sequence. The intron sequence can flank the 5' end of the coding exon, or the 3' end of the coding exon. In some embodiments, the ASO targets a sequence within an exon of an OPA1 pre-mRNA transcript. In some embodiments, the ASO targets a sequence within an intron of an OPA1 pre-mRNA transcript. In some embodiments, the ASO targets a sequence comprising both a portion of an intron and a portion of an exon of an OPA1 pre-mRNA transcript.

In some embodiments, the ASO targets a sequence about 4 to about 300 nucleotides upstream (or 5') from the 5' end of the coding exon, e.g., alternatively spliced exon. In some embodiments, the ASO targets a sequence about 1 to about 20 nucleotides, about 20 to about 50 nucleotides, about 50 to about 100 nucleotides, about 100 to about 150 nucleotides, about 150 to about 200 nucleotides, about 200 to about 250 nucleotides, or about 250 to about 300 nucleotides upstream (or 5') from the 5' end of the coding exon region. In some embodiments, the ASO may target a sequence more than 300 nucleotides upstream from the 5' end of the coding exon. In some embodiments, the ASO targets a sequence about 4 to about 300 nucleotides downstream (or 3') from the 3' end of the coding exon. In some embodiments, the ASO targets a sequence about 1 to about 20 nucleotides, about 20 to about 50 nucleotides, about 50 to about 100 nucleotides, about 100 to about 150 nucleotides, about 150 to about 200 nucleotides, about 200 to about 250 nucleotides, or about 250 to about 300 nucleotides downstream from the 3' end of the coding exon. In some embodiments, the ASO targets a sequence more than 300 nucleotides downstream from the 3' end of the coding exon.

In some embodiments, the OPA1 pre-mRNA transcript is encoded by a genetic sequence with at least about 80%, 85%, 90%, 95%, 96%, 97%, 98%, 99% or 100% sequence identity to SEQ ID NO. 1. In some embodiments, the OPA1 pre-mRNA transcript comprises a sequence with at least about 80%, 85%, 90%, 95%, 96%, 97%, 98%, 99% or 100% sequence identity to any one of SEQ ID NOs: 2-5.

In some embodiments, the OPA1 pre-mRNA transcript (or NMD exon mRNA) comprises a sequence with at least about 80%, 85%, 90%, 95%, 97%, or 100% sequence identity to any one of SEQ ID NOs: 2-5. In some embodiments, OPA1 pre-mRNA transcript (or NMD exon mRNA) is encoded by a sequence with at least about 80%, 85%, 90%, 95%, 97%, or 100% sequence identity to any one of SEQ ID NOs: 2-5. In some embodiments, the targeted portion of the OPA1 pre-mRNA comprises a sequence with at least 80%, 85%, 90%, 95%, 97%, or 100% sequence identity to a region comprising at least 8 contiguous nucleic acids of any one of SEQ ID NOs: 2-5.

In some embodiments, the ASO targets exon 7 of an OPA1 pre-mRNA, i.e., the ASO targets exon (GRCh38/hg38: chr3 193626092 to 193626202) of OPA1 pre-mRNA.

In some embodiments, the ASO targets a coding exon of an OPA1 pre-mRNA other than exon 7, i.e., the ASO targets an exon of OPA1 pre-mRNA other than exon defined by (GRCh38/hg38: chr3 193626092 to 193626202).

In some embodiments, the ASO targets a sequence about 1500 nucleotides, about 1000 nucleotides, about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides upstream (or 5') from the 5' end of exon 7 of OPA1. In some embodiments, the ASO targets a sequence about 1500 nucleotides, about 1000 nucleotides, about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides upstream (or 5') from GRCh38/hg38: chr3 193626092 of OPA1.

In some embodiments, the ASO targets a sequence at most about 1500 nucleotides, about 1000 nucleotides, about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides upstream (or 5') from the 5' end of exon 7 of OPA1. In some embodiments, the ASO targets a sequence at most about 1500 nucleotides, about 1000 nucleotides, about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides upstream (or 5') from GRCh38/hg38: 193626092 of OPA1.

In some embodiments, the ASO targets a sequence about 1500 nucleotides, about 1000 nucleotides, about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides downstream (or 3') from the 3' end of exon 7 of OPA1. In some embodiments, the ASO targets a sequence about 1500 nucleotides, about 1000 nucleotides, about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides downstream (or 3') from GRCh38/hg38: chr3 193626202 of OPA1.

In some embodiments, the ASO targets a sequence at most about 1500 nucleotides, about 1000 nucleotides, about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides downstream (or 3') from the 3' end of exon 7 of OPA1. In some embodiments, the ASO targets a sequence at most about 1500 nucleotides, about 1000 nucleotides, about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides downstream (or 3') from GRCh38/hg38: chr3 193626202 of OPA1.

In some embodiments, the ASO has a sequence complementary to the targeted portion of the NMD exon mRNA according to any one of SEQ ID NOs: 2-5, or 277.

In some embodiments, the ASO targets a sequence upstream from the 5' end of a coding exon, e.g., an alternatively spliced exon. For example, ASOs targeting a sequence upstream from the 5' end of a coding exon (e.g., exon 7 of OPA1) comprises a sequence that is at least about 80%, 85%, 90%, 95%, 97%, or 100% complimentary to at least 8 contiguous nucleic acids of SEQ ID NO: 2 or 3. For example, ASOs targeting a sequence upstream from the 5' end of a coding exon (e.g., exon (GRCh38/hg38: 193626092 to 193626202) of OPA1) can comprise a sequence with at least 80%, 85%, 90%, 95%, 97%, or 100% sequence identity to SEQ ID NO: 4 or 5.

In some embodiments, the ASOs target a sequence containing an exon-intron boundary (or junction). For example, ASOs targeting a sequence containing an exon-intron boundary can comprise a sequence that is at least about 80%, 85%, 90%, 95%, 97%, or 100% complimentary to at least 8 contiguous nucleic acids of any one of SEQ ID NOs: 2-5. In some embodiments, the ASOs target a sequence downstream from the 3' end of a coding exon, e.g., an alternatively spliced exon. For example, ASOs targeting a sequence downstream from the 3' end of a coding exon (e.g., exon 7 of OPA1) can comprise a sequence with at least 80%, 85%, 90%, 95%, 97%, or 100% sequence identity to SEQ ID NO: 2 or 3, or at least 8 contiguous nucleic acids of SEQ ID NO: 2 or 3. For example, ASOs targeting a sequence downstream from the 3' end of a coding exon (e.g., exon 7 of OPA1) can comprise a sequence with at least 80%, 85%, 90%, 95%, 97%, or 100% sequence identity to SEQ ID NO: 4 or 5, or at least 8 contiguous nucleic acids of SEQ ID NO: 4 or 5. In some embodiments, ASOs target a sequence within a coding exon, e.g., an alternatively spliced exon.

Protein Expression

In some embodiments, the methods described herein are used to increase the production of a functional OPA1 protein or RNA. As used herein, the term "functional" refers to the amount of activity or function of an OPA1 protein or RNA that is necessary to eliminate any one or more symptoms of a treated condition or disease, e.g., Optic atrophy type 1. In some embodiments, the methods are used to increase the production of a partially functional OPA1 protein or RNA. As used herein, the term "partially functional" refers to any amount of activity or function of the OPA1 protein or RNA that is less than the amount of activity or function that is necessary to eliminate or prevent any one or more symptoms of a disease or condition. In some embodiments, a partially functional protein or RNA will have at least 10%, at least 20%, at least 30%, at least 40%, at least 50%, at least 60%, at least 70%, at least 75%, at least 80%, at least 85%, at least 90%, or at least 95% less activity relative to the fully functional protein or RNA.

In some embodiments, the method is a method of increasing the expression of the OPA1, protein by cells of a subject having an OPA1 pre-mRNA, wherein the subject has a disease or condition, e.g., Optic atrophy type 1, caused by a deficient amount of activity of OPA1 protein, and wherein the deficient amount of the OPA1 protein is caused by haploinsufficiency of the OPA1 protein. In such an embodiment, the subject has a first allele encoding a functional OPA1 protein, and a second allele from which the OPA1 protein is not produced. In another such embodiment, the subject has a first allele encoding a functional OPA1 protein, and a second allele encoding a nonfunctional OPA1 protein. In another such embodiment, the subject has a first allele encoding a functional OPA1 protein, and a second allele encoding a partially functional OPA1 protein. In any of these embodiments, the antisense oligomer binds to a targeted portion of the OPA1 pre-mRNA transcribed from the second allele, thereby inducing exon skipping of the pseudo-exon from the pre-mRNA, and causing an increase in the level of mature mRNA encoding functional OPA1 protein, and an increase in the expression of the OPA1 protein in the cells of the subject.

In some embodiments, the method is a method of increasing the expression of the OPA1 protein by cells of a subject having an OPA1 pre-mRNA, wherein the subject has a disease or condition caused by a deficient amount of activity of OPA1 protein, and wherein the deficient amount of the OPA1 protein is caused by autosomal recessive inheritance.

In some embodiments, the method is a method of increasing the expression of the OPA1 protein by cells of a subject having an OPA1 pre-mRNA, wherein the subject has a disease or condition, e.g., Optic atrophy type 1, caused by a deficient amount of activity of OPA1, protein, and wherein the deficient amount of the OPA1 protein is caused by autosomal dominant inheritance.

In related embodiments, the method is a method of using an ASO to increase the expression of a protein or functional RNA. In some embodiments, an ASO may be used to increase the expression of OPA1 protein in cells of a subject having an OPA1 pre-mRNA, wherein the subject has a deficiency, e.g., Optic atrophy type 1; in the amount or function of an OPA1 protein.

In some embodiments, the pre-mRNA transcript that encodes the protein that is causative of the disease or condition is targeted by the agent, e.g., the oligonucleotides, described herein. In some cases, it is the NMD exon-containing pre-mRNA transcript targeted by the agent, e.g., the oligonucleotides, described herein. In some cases, the agent, e.g., the oligonucleotides, described herein, are designed to target a coding exon of the pre-mRNA. In some cases, the agent, e.g., the oligonucleotides, described herein can induce skipping of the NMD exon, a coding exon, or both. In some embodiments, a NMD exon-containing pre-mRNA transcript that encodes a protein that is not causative of the disease is targeted by the ASOs. For example, a disease that is the result of a mutation or deficiency of a first protein in a particular pathway may be ameliorated by targeting a pre-mRNA that encodes a second protein, thereby increasing production of the second protein. In some embodiments, the function of the second protein is able to compensate for the mutation or deficiency of the first protein (which is causative of the disease or condition).

In some embodiments, the subject has:

(a) a first mutant allele from which
  - (i) the OPA1 protein is produced at a reduced level compared to production from a wild-type allele,
  - (ii) the OPA1 protein is produced in a form having reduced function compared to an equivalent wild-type protein, or
  - (iii) the OPA1 protein or functional RNA is not produced; and (b) a second mutant allele from which
  - (i) the OPA1 protein is produced at a reduced level compared to production from a wild-type allele,
  - (ii) the OPA1 protein is produced in a form having reduced function compared to an equivalent wild-type protein, or
  - (iii) the OPA1 protein is not produced, and wherein the NMD exon-containing pre-mRNA is transcribed from the first allele and/or the second allele. In these embodiments, the ASO binds to a targeted portion of the NMD exon-containing pre-mRNA transcribed from the first allele or the second allele, thereby inducing exon skipping of the pseudo-exon from the NMD exon-containing pre-mRNA, and causing an increase in the level of mRNA encoding OPA1 protein and an increase in the expression of the target protein or functional RNA in the cells of the subject. In these embodiments, the target protein or functional RNA having an increase in expression level resulting from the exon skipping of the pseudo-exon from the NMD exon-containing pre-mRNA may be either in a form having reduced function compared to the equivalent wild-type protein (partially-functional), or having full function compared to the equivalent wild-type protein (fully-functional).

In some embodiments, the subject has:

(a) a first mutant allele from which
  - (i) the OPA1 protein is produced at a reduced level compared to production from a wild-type allele,
  - (ii) the OPA1 protein is produced in a form having reduced function compared to an equivalent wild-type protein, or
  - (iii) the OPA1 protein or functional RNA is not produced; and (b) a second mutant allele from which
  - (i) the OPA1 protein is produced at a reduced level compared to production from a wild-type allele,
  - (ii) the OPA1 protein is produced in a form having reduced function compared to an equivalent wild-type protein, or
  - (iii) the OPA1 protein is not produced, and wherein the OPA1 pre-mRNA is transcribed from the first allele and/or the second allele. In these embodiments, the ASO binds to a targeted portion of the OPA1 pre-mRNA transcribed from the first allele or the second allele, thereby inducing exon skipping of a coding exon from the OPA1 pre-mRNA, and causing an increase in the expression of the target OPA1 protein in the cells of the subject. In these embodiments, the target OPA1 protein having an increase in expression level resulting from the exon skipping of the coding exon from the OPA1 pre-mRNA may be either in a form having reduced function compared to the equivalent full-length wild-type protein (partially-functional), or having full function compared to the equivalent full-length wild-type protein (fully-functional).

In some embodiments, the level of mRNA encoding OPA1 protein is increased 1.1 to 10-fold, when compared to the amount of mRNA encoding OPA1 protein that is produced in a control cell, e.g., one that is not treated with the antisense oligomer or one that is treated with an antisense oligomer that does not bind to the targeted portion of the OPA1 pre-mRNA.

In some embodiments, a subject treated using the methods of the present disclosure expresses a partially functional OPA1 protein from one allele, wherein the partially functional OPA1 protein may be caused by a frameshift mutation, a nonsense mutation, a missense mutation, or a partial gene deletion. In some embodiments, a subject treated using the methods of the disclosure expresses a nonfunctional OPA1 protein from one allele, wherein the nonfunctional OPA1 protein may be caused by a frameshift mutation, a nonsense mutation, a missense mutation, a partial gene deletion, in one allele. In some embodiments, a subject treated using the methods of the disclosure has an OPA1 whole gene deletion, in one allele.

Exon Inclusion

As used herein, a "NMD exon-containing pre-mRNA" is a pre-mRNA transcript that contains at least one pseudo-exon. Alternative or aberrant splicing can result in inclusion of the at least one pseudo-exon in the mature mRNA transcripts. The terms "mature mRNA," and "fully-spliced mRNA," are used interchangeably herein to describe a fully processed mRNA. Inclusion of the at least one pseudo-exon can be non-productive mRNA and lead to NMD of the mature mRNA. NMD exon-containing mature mRNA may sometimes lead to aberrant protein expression.

In some embodiments, the included pseudo-exon is the most abundant pseudo-exon in a population of NMD exon-containing pre-mRNAs transcribed from the gene encoding the target protein in a cell. In some embodiments, the included pseudo-exon is the most abundant pseudo-exon in a population of NMD exon-containing pre-mRNAs transcribed from the gene encoding the target protein in a cell, wherein the population of NMD exon-containing pre-mRNAs comprises two or more included pseudo-exons. In some embodiments, an antisense oligomer targeted to the most abundant pseudo-exon in the population of NMD exon-containing pre-mRNAs encoding the target protein induces exon skipping of one or two or more pseudo-exons in the population, including the pseudo-exon to which the antisense oligomer is targeted or binds. In some embodiments, the targeted region is in a pseudo-exon that is the most abundant pseudo-exon in a NMD exon-containing pre-mRNA encoding the OPA1 protein.

The degree of exon inclusion can be expressed as percent exon inclusion, e.g., the percentage of transcripts in which a given pseudo-exon is included. In brief, percent exon inclusion can be calculated as the percentage of the amount of RNA transcripts with the exon inclusion, over the sum of the average of the amount of RNA transcripts with exon inclusion plus the average of the amount of RNA transcripts with exon exclusion.

In some embodiments, an included pseudo-exon is an exon that is identified as an included pseudo-exon based on a determination of at least about 5%, at least about 10%, at least about 15%, at least about 20%, at least about 25%, at least about 30%, at least about 35%, at least about 40%, at least about 45%, or at least about 50%, inclusion. In embodiments, a included pseudo-exon is an exon that is identified as a included pseudo-exon based on a determination of about 5% to about 100%, about 5% to about 95%, about 5% to about 90%, about 5% to about 85%, about 5% to about 80%, about 5% to about 75%, about 5% to about 70%, about 5% to about 65%, about 5% to about 60%, about 5% to about 55%, about 5% to about 50%, about 5% to about 45%, about 5% to about 40%, about 5% to about 35%, about 5% to about 30%, about 5% to about 25%, about 5% to about 20%, about 5% to about 15%, about 10% to about 100%, about 10% to about 95%, about 10% to about 90%, about 10% to about 85%, about 10% to about 80%, about 10% to about 75%, about 10% to about 70%, about 10% to about 65%, about 10% to about 60%, about 10% to about 55%, about 10% to about 50%, about 10% to about 45%, about 10% to about 40%, about 10% to about 35%, about 10% to about 30%, about 10% to about 25%, about 10% to about 20%, about 15% to about 100%, about 15% to about 95%, about 15% to about 90%, about 15% to about 85%, about 15% to about 80%, about 15% to about 75%, about 15% to about 70%, about 15% to about 65%, about 15% to about 60%, about 15% to about 55%, about 15% to about 50%, about 15% to about 45%, about 15% to about 40%, about 15% to about 35%, about 15% to about 30%, about 15% to about 25%, about 20% to about 100%, about 20% to about 95%, about 20% to about 90%, about 20% to about 85%, about 20% to about 80%, about 20% to about 75%, about 20% to about 70%, about 20% to about 65%, about 20% to about 60%, about 20% to about 55%, about 20% to about 50%, about 20% to about 45%, about 20% to about 40%, about 20% to about 35%, about 20% to about 30%, about 25% to about 100%, about 25% to about 95%, about 25% to about 90%, about 25% to about 85%, about 25% to about 80%, about 25% to about 75%, about 25% to about 70%, about 25% to about 65%, about 25% to about 60%, about 25% to about 55%, about 25% to about 50%, about 25% to about 45%, about 25% to about 40%, or about 25% to about 35%, inclusion. ENCODE data (described by, e.g., Tilgner, et al., 2012, "Deep sequencing of subcellular RNA fractions shows splicing to be predominantly co-transcriptional in the human genome but inefficient for lncRNAs," Genome Research 22 (9): 1616-25) can be used to aid in identifying exon inclusion.

In some embodiments, contacting cells with an ASO that is complementary to a targeted portion of an OPA1 pre-mRNA transcript results in an increase in the amount of OPA1 protein produced by at least 10, 20, 30, 40, 50, 60, 80, 100, 150, 200, 250, 300, 350, 400, 450, 500, or 1000%, compared to the amount of the protein produced by a cell in the absence of the ASO/absence of treatment. In some embodiments, the total amount of OPA1 protein produced by the cell to which the antisense oligomer is contacted is increased about 20% to about 300%, about 50% to about 300%, about 100% to about 300%, about 150% to about 300%, about 20% to about 50%, about 20% to about 100%, about 20% to about 150%, about 20% to about 200%, about 20% to about 250%, about 50% to about 100%, about 50% to about 150%, about 50% to about 200%, about 50% to about 250%, about 100% to about 150%, about 100% to about 200%, about 100% to about 250%, about 150% to about 200%, about 150% to about 250%, about 200% to about 250%, at least about 10%, at least about 20%, at least about 50%, at least about 100%, at least about 150%, at least about 200%, at least about 250%, or at least about 300%, compared to the amount of target protein produced by a control compound. In some embodiments, the total amount of OPA1 protein produced by the cell to which the antisense oligomer is contacted is increased about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to the amount of target protein produced by a control compound. A control compound can be, for example, an oligonucleotide that is not complementary to a targeted portion of the pre-mRNA.

In some embodiments, contacting cells with an ASO that is complementary to a targeted portion of an OPA1 pre-mRNA transcript results in an increase in the amount of mRNA encoding OPA1, including the mature mRNA encoding the target protein. In some embodiments, the amount of mRNA encoding OPA1 protein, or the mature mRNA encoding the OPA1 protein, is increased by at least 10, 20, 30, 40, 50, 60, 80, 100, 150, 200, 250, 300, 350, 400, 450, 500, or 1000%, compared to the amount of the protein produced by a cell in the absence of the ASO/absence of treatment. In some embodiments, the total amount of the mRNA encoding OPA1 protein, or the mature mRNA encoding OPA1 protein produced in the cell to which the antisense oligomer is contacted is increased about 20% to about 300%, about 50% to about 300%, about 100% to about 300%, about 150% to about 300%, about 20% to about 50%, about 20% to about 100%, about 20% to about 150%, about 20% to about 200%, about 20% to about 250%, about 50% to about 100%, about 50% to about 150%, about 50% to about 200%, about 50% to about 250%, about 100% to about 150%, about 100% to about 200%, about 100% to about 250%, about 150% to about 200%, about 150% to about 250%, about 200% to about 250%, at least about 10%, at least about 20%, at least about 50%, at least about 100%, at least about 150%, at least about 200%, at least about 250%, or at least about 300%, compared to the amount of mature RNA produced in an untreated cell, e.g., an untreated cell or a cell treated with a control compound. In some embodiments, the total amount of the mRNA encoding OPA1 protein, or the mature mRNA encoding OPA1 protein produced in the cell to which the antisense oligomer is contacted is increased about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold compared to the amount of mature RNA produced in an untreated cell, e.g., an untreated cell or a cell treated with a control compound. A control compound can be, for example, an oligonucleotide that is not complementary to a targeted portion of the OPA1 NMD exon-containing pre-mRNA.

The NMD exon can be in any length. In some embodiments, the NMD exon comprises a full sequence of an intron, in which case, it can be referred to as intron retention. In some embodiments, the NMD exon can be a portion of the intron. In some embodiments, the NMD exon can be a 5' end portion of an intron including a 5'ss sequence. In some embodiments, the NMD exon can be a 3' end portion of an intron including a 3'ss sequence. In some embodiments, the NMD exon can be a portion within an intron without inclusion of a 5'ss sequence. In some embodiments, the NMD exon can be a portion within an intron without inclusion of a 3'ss sequence. In some embodiments, the NMD exon can be a portion within an intron without inclusion of either a 5'ss or a 3'ss sequence. In some embodiments, the NMD exon can be from 5 nucleotides to 10 nucleotides in length, from 10 nucleotides to 15 nucleotides in length, from 15 nucleotides to 20 nucleotides in length, from 20 nucleotides to 25 nucleotides in length, from 25 nucleotides to 30 nucleotides in length, from 30 nucleotides to 35 nucleotides in length, from 35 nucleotides to 40 nucleotides in length, from 40 nucleotides to 45 nucleotides in length, from 45 nucleotides to 50 nucleotides in length, from 50 nucleotides to 55 nucleotides in length, from 55 nucleotides to 60 nucleotides in length, from 60 nucleotides to 65 nucleotides in length, from 65 nucleotides to 70 nucleotides in length, from 70 nucleotides to 75 nucleotides in length, from 75 nucleotides to 80 nucleotides in length, from 80 nucleotides to 85 nucleotides in length, from 85 nucleotides to 90 nucleotides in length, from 90 nucleotides to 95 nucleotides in length, or from 95 nucleotides to 100 nucleotides in length. In some embodiments, the NMD exon can be at least 10 nucleotides, at least 20 nucleotides, at least 30 nucleotides, at least 40 nucleotides, at least 50 nucleotides, at least 60 nucleoids, at least 70 nucleotides, at least 80 nucleotides in length, at least 90 nucleotides, or at least 100 nucleotides in length. In some embodiments, the NMD exon can be from 100 to 200 nucleotides in length, from 200 to 300 nucleotides in length, from 300 to 400 nucleotides in length, from 400 to 500 nucleotides in length, from 500 to 600 nucleotides in length, from 600 to 700 nucleotides in length, from 700 to 800 nucleotides in length, from 800 to 900 nucleotides in length, from 900 to 1,000 nucleotides in length. In some embodiments, the NMD exon may be longer than 1,000 nucleotides in length.

Inclusion of a pseudo-exon can lead to a frameshift and the introduction of a premature termination codon (PIC) in the mature mRNA transcript rendering the transcript a target of NMD. Mature mRNA transcript containing NMD exon can be non-productive mRNA transcript which does not lead to protein expression. The PIC can be present in any position downstream of an NMD exon. In some embodiments, the PIC can be present in any exon downstream of an NMD exon. In some embodiments, the PIC can be present within the NMD exon. For example, inclusion of exon 6x of OPA1, exon 7x of OPA1, or exon 28x of OPA1, in an mRNA transcript encoded by the OPA1 gene can induce a PIC in the mRNA transcript. For example, inclusion of exon (GRCh38/hg38: chr3 193628509 193628616) of OPA1; or exon (GRCh38/hg38: chr3 193603500 193603557) of OPA1 in an mRNA transcript encoded by the OPA1.

In some aspects, provided herein is a method of modulating expression of an OPA1 protein by promoting inclusion of a coding exon. The method can comprise contacting an agent to a cell having an OPA1 pre-mRNA, wherein the agent comprises an oligonucleotide that binds to: (a) a targeted portion of the pre-mRNA within an intronic region immediately upstream of a 5' end of the coding exon of the pre-mRNA; or (b) a targeted portion of the pre-mRNA within an intronic region immediately downstream of a 3' end of the coding exon of the pre-mRNA; whereby the agent increases a level of a processed mRNA that is processed from the pre-mRNA and that contains the coding exon in the cell. In some cases, the coding exon to be included is an alternatively spliced exon. In some cases, the method promotes inclusion of the coding exon in the processed mRNA during splicing of the pre-mRNA in the cell.

In some of these embodiments for inclusion of coding exon, the target portion of the pre-mRNA is within a region spanning from 100 to 50, from 100 to 60, from 100 to 70, from 100 to 80, or from 100 to 90 nucleotides upstream of a 5' end of the coding exon. In some cases, the target portion of the pre-mRNA is within a region spanning from 40 to 100, from 50 to 100, from 60 to 100, from 70 to 100, from 80 to 100, or from 90 to 100 nucleotides downstream of a 3' end of the coding exon. In some cases, the coding exon is exon 7 of OPA1. In some cases, the coding exon comprises a sequence with at least 80%, at least 90%, or 100% sequence identity to SEQ ID NO: 277. In some cases, the coding exon comprises SEQ ID NO: 277. The targeted portion of the pre-mRNA can be within a region spanning from 100 to 50, from 100 to 60, from 100 to 70, from 100 to 80, or from 100 to 90 nucleotides upstream of genomic site GRCh38/hg38: chr3 193626092. In some cases, the targeted portion of the pre-mRNA is within a region spanning from 40 to 100, from 50 to 100, from 60 to 100, from 70 to 100, from 80 to 100, or from 90 to 100 nucleotides downstream of genomic site GRCh38/hg38: chr3 193626202.

In some cases, the inclusion of the coding exon in the processed mRNA in the cell contacted with the agent is increased by about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to in the absence of the agent.

Exclusion of Both NMD Exon and Coding Exon

In some embodiments, provided herein is a method of modulating expression of a target protein by targeting a pre-mRNA and modulating exclusion of both a coding exon and a non-sense mediated RNA decay-inducing exon (NMD exon) from the pre-mRNA. In some cases, the method comprises contacting an agent to the cell, and the agent promotes exclusion of both the coding exon and the NMD exon from the pre-mRNA, thereby increasing level of a processed mRNA that is processed from the pre-mRNA and lacks both the coding exon and the NMD exon. In some cases, the agent binds to a targeted portion of the pre-mRNA, or modulates binding of a factor involved in splicing of the coding exon, the NMD exon, or both. In some cases, the agent interferes with binding of the factor involved in splicing of the coding exon, the NMD exon, or both, to a region of the targeted portion. In some cases, the NMD exon is within an intronic region adjacent to the coding exon. In some cases, the NMD exon is within an intronic region immediately upstream of the coding exon. In some cases, the NMD exon is within an intronic region immediately downstream of the coding exon. In some cases, the coding exon is an alternatively spliced exon.

In some cases, the targeted portion of the pre-mRNA is proximal to the coding exon. The targeted portion of the pre-mRNA can be located in an intronic region immediately upstream of the coding exon. The targeted portion of the pre-mRNA can be located in an intronic region immediately downstream of the coding exon. In some cases, the targeted portion of the pre-mRNA can be located within the coding exon. In some cases, the targeted portion of the pre-mRNA is within a region spanning from 49 to 1, from 39 to 1, from 29 to 1, or from 19 to 1 nucleotides upstream of 5' end of the coding exon. In some cases, the targeted portion of the pre-mRNA is within a region spanning from 100 nucleotides upstream of the coding exon to 100 nucleotides downstream of the coding exon. In some cases, the targeted portion comprises about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more consecutive nucleotides of the coding exon.

In some cases, the targeted portion of the pre-mRNA is proximal to the NMD exon. In some cases, the targeted portion of the pre-mRNA is located in an intronic region immediately upstream of the NMD exon. In some cases, the targeted portion of the pre-mRNA is located in an intronic region immediately downstream of the NMD exon. In some cases, the targeted portion of the pre-mRNA is located within the NMD exon. In some cases, the targeted portion of the pre-mRNA is within a region spanning from 100 nucleotides upstream of the NMD exon to 100 nucleotides downstream of the NMD exon.

In some embodiments, the method described herein is applicable to modulation of expression of OPA1 protein by modulating exclusion of both exon 7 and an NMD exon (e.g., exon 7x) of OPA1 pre-mRNA that contains both exon 7 and exon 7x. In some cases, the coding exon comprises a sequence with at least 80%, at least 90%, or 100% sequence identity to SEQ ID NO: 277. In some cases, the coding exon comprises SEQ ID NO: 277. In some cases, the targeted portion of the pre-mRNA is immediately upstream of the coding exon GRCh38/hg38: chr3 193626092 to 193626202. In some cases, the targeted portion of the pre-mRNA is immediately downstream of the coding exon GRCh38/hg38: chr3 193626092 to 193626202. In some cases, the targeted portion of the pre-mRNA is within a region spanning from 49 to 1, from 39 to 1, from 29 to 1, or from 19 to 1 nucleotides upstream of GRCh38/hg38: chr3 193626092. In some cases, the targeted portion of the pre-mRNA is within a region spanning from 100 nucleotides upstream of genomic site GRCh38/hg38: chr3 193626092 to 100 nucleotides downstream of genomic site GRCh38/hg38: chr3 193626202. In some cases, the targeted portion of the pre-mRNA is within the coding exon GRCh38/hg38: chr3 193626092 to 193626202. In some cases, the targeted portion of the pre-mRNA comprises an exon-intron junction of the coding exon GRCh38/hg38: chr3 193626092 to 193626202. In some cases, the NMD exon comprises a sequence with at least 80%, at least 90%, or 100% sequence identity to SEQ ID NO: 279. In some cases, the NMD exon comprises SEQ ID NO: 279. In some cases, the targeted portion of the pre-mRNA is immediately upstream of the NMD exon GRCh38/hg38: chr3 193628509 to 193628616. In some cases, the targeted portion of the pre-mRNA is immediately downstream of the NMD exon GRCh38/hg38: chr3 193628509 to 193628616. In some cases, the targeted portion of the pre-mRNA is within a region spanning from 100 nucleotides upstream of genomic site GRCh38/hg38: chr3 193628509 to 100 nucleotides downstream of genomic site GRCh38/hg38: chr3 193628616.

In some cases, the targeted portion of the pre-mRNA is within the NMD exon GRCh38/hg38: chr3 193628509 to 193628616. In some cases, the targeted portion of the pre-mRNA comprises an exon-intron junction of the NMD exon GRCh38/hg38: chr3 193628509 to 193628616. In some cases, the targeted portion comprises about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more consecutive nucleotides of the NMD exon.

In some cases, the exclusion of the coding exon from the pre-mRNA in the cell contacted with the agent is increased by about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to in the absence of contacting with the agent. In some cases, the exclusion of the NMD exon from the pre-mRNA in the cell contacted with the agent is increased by about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to in the absence of contacting with the agent. In some cases, the method results in an increase in the level of the processed mRNA in the cell. The level of the processed mRNA in the cell contacted with the agent can be increased by about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to in the absence of contacting with the agent.

In some cases, the method results in an increase in expression of the OPA1 protein in the cell. A level of the OPA1 protein expressed from the processed mRNA in the cell contacted with the agent can be increased by about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to in the absence of contacting with the agent.

In some cases, a level of the OPA1 protein expressed from the processed mRNA in the cell contacted with the agent is increased by at least about 1.5-fold compared to in the absence of contacting with the agent.

In some cases, the OPA1 protein expressed from the processed mRNA that lacks exon 7 and exon 7x is a functional OPA1 protein. The OPA1 protein expressed from the processed mRNA that lacks exon 7 and exon 7x can be at least partially functional as compared to a wild-type OPA1 protein. The OPA1 protein expressed from the processed mRNA that lacks exon 7 and exon 7x can be at least partially functional as compared to a full-length wild-type OPA1 protein.

Therapeutic Agents

In various embodiments of the present disclosure, compositions and methods comprising a therapeutic agent are provided to modulate protein expression level of OPA1. In some embodiments, provided herein are compositions and methods to modulate alternative splicing of OPA1 pre-mRNA. In some embodiments, provided herein are compositions and methods to induce exon skipping in the splicing of OPA1 pre-mRNA, e.g., to induce skipping of a pseudo-exon during splicing of OPA1 pre-mRNA. In other embodiments, therapeutic agents may be used to induce the inclusion of an exon in order to decrease the protein expression level.

A therapeutic agent disclosed herein can be a NIE repressor agent. A therapeutic agent may comprise a polynucleic acid polymer.

According to one aspect of the present disclosure, provided herein is a method of treatment or prevention of a condition or disease associated with a functional OPA1 protein deficiency, comprising administering a NIE repressor agent to a subject to increase levels of functional OPA1 protein, wherein the agent binds to a region of the pre-mRNA transcript to decrease inclusion of the NMD exon in the mature transcript. For example, provided herein is a method of treatment or prevention of a condition associated with a functional OPA1 protein deficiency, comprising administering a NIE repressor agent to a subject to increase levels of functional OPA1 protein, wherein the agent binds to a region of an intron containing an NMD exon (e.g., exon 6x of OPA1, exon 7x of OPA1, or exon 28x of OPA1) of the pre-mRNA transcript or to a NMD exon-activating regulatory sequence in the same intron. For example, provided herein is a method of treatment or prevention of a condition associated with a functional OPA1 protein deficiency, comprising administering a NIE repressor agent to a subject to increase levels of functional OPA1 protein, wherein the agent binds to a region of an intron containing an NMD exon (e.g., exon (GRCh38/hg38: chr3 193628509 193628616) of OPA1; or exon (GRCh38/hg38: chr3 193603500 193603557) of OPA1) of the pre-mRNA transcript or to a NMD exon-activating regulatory sequence in the same intron. In some embodiments, the method comprises administering a NIE repressor agent to a subject to increase levels of functional OPA1 protein, wherein the agent binds to a region of an intron containing an NMD exon (e.g., exon of OPA1 other than exon 7x defined by (GRCh38/hg38: chr3 193628509 193628616) or exon defined by (GRCh38/hg38: chr3 193603500 193603557)) of the pre-mRNA transcript or to a NMD exon-activating regulatory sequence in the same intron. In some embodiments, the therapeutic agent promotes exclusion of an NMD exon of OPA1 pre-mRNA other than exon 7x defined by (GRCh38/hg38: chr3 193628509 193628616) or exon defined by (GRCh38/hg38: chr3 193603500 193603557). In some embodiments, the composition disclosed herein includes an agent that promotes exclusion of an NMD exon of OPA1 pre-mRNA other than exon 7x defined by (GRCh38/hg38: chr3 193628509 193628616) or exon defined by (GRCh38/hg38: chr3 193603500 193603557).

Where reference is made to reducing NMD exon inclusion in the mature mRNA, the reduction may be complete, e.g., 100%, or may be partial. The reduction may be clinically significant. The reduction/correction may be relative to the level of NMD exon inclusion in the subject without treatment, or relative to the amount of NMD exon inclusion in a population of similar subjects. The reduction/correction may be at least 10% less NMD exon inclusion relative to the average subject, or the subject prior to treatment. The reduction may be at least 20% less NMD exon inclusion relative to an average subject, or the subject prior to treatment. The reduction may be at least 40% less NMD exon inclusion relative to an average subject, or the subject prior to treatment. The reduction may be at least 50% less NMD exon inclusion relative to an average subject, or the subject prior to treatment. The reduction may be at least 60% less NMD exon inclusion relative to an average subject, or the subject prior to treatment. The reduction may be at least 80% less NMD exon inclusion relative to an average subject, or the subject prior to treatment. The reduction may be at least 90% less NMD exon inclusion relative to an average subject, or the subject prior to treatment.

According to one aspect of the present disclosure, provided herein is a method of treatment or prevention of a condition or disease associated with a functional OPA1 protein deficiency, comprising administering an agent to a subject to increase levels of functional OPA1 protein, wherein the agent binds to a region of the pre-mRNA transcript to decrease inclusion of a coding exon (e.g., exon 7) in the mature transcript. For example, provided herein is a method of treatment or prevention of a condition associated with a functional OPA1 protein deficiency, comprising administering an agent to a subject to increase levels of functional OPA1 protein, wherein the agent binds to a region containing a coding exon (e.g., exon 7 of OPA1) of the pre-mRNA transcript. For example, provided herein is a method of treatment or prevention of a condition associated with a functional OPA1 protein deficiency, comprising administering an agent to a subject to increase levels of functional OPA1 protein, wherein the agent binds to a region containing a coding exon (e.g., exon (GRCh38/hg38: chr3 193626092 to 193626202) of OPA1) of the pre-mRNA transcript. In some embodiments, the method comprises administering an agent to a subject to increase levels of functional OPA1 protein, wherein the agent binds to a region containing a coding exon (e.g., exon of OPA1 other than exon 7 defined by (GRCh38/hg38: chr3 193626092 to 193626202)) of the pre-mRNA transcript. In some embodiments, the therapeutic agent promotes exclusion of a coding exon of OPA1 pre-mRNA other than exon 7 defined by (GRCh38/hg38: chr3 193626092 to 193626202). In some embodiments, the composition disclosed herein includes an agent that promotes exclusion of a coding exon of OPA1 pre-mRNA other than exon 7 defined by (GRCh38/hg38: chr3 193626092 to 193626202).

Where reference is made to increasing active OPA1 protein levels, the increase may be clinically significant. The increase may be relative to the level of active OPA1 protein in the subject without treatment, or relative to the amount of active OPA1 protein in a population of similar subjects. The increase may be at least 10% more active OPA1 protein relative to the average subject, or the subject prior to treatment. The increase may be at least 20% more active OPA1 protein relative to the average subject, or the subject prior to treatment. The increase may be at least 40% more active OPA1 protein relative to the average subject, or the subject prior to treatment. The increase may be at least 50% more active OPA1 protein relative to the average subject, or the subject prior to treatment. The increase may be at least 80% more active OPA1 protein relative to the average subject, or the subject prior to treatment. The increase may be at least 100% more active OPA1 protein relative to the average subject, or the subject prior to treatment. The increase may be at least 200% more active OPA1 protein relative to the average subject, or the subject prior to treatment. The increase may be at least 500% more active OPA1 protein relative to the average subject, or the subject prior to treatment.

In embodiments wherein the NIE repressor agent comprises a polynucleic acid polymer, the polynucleic acid polymer may be about 50 nucleotides in length. The polynucleic acid polymer may be about 45 nucleotides in length. The polynucleic acid polymer may be about 40 nucleotides in length. The polynucleic acid polymer may be about 35 nucleotides in length. The polynucleic acid polymer may be about 30 nucleotides in length. The polynucleic acid polymer may be about 24 nucleotides in length. The polynucleic acid polymer may be about 25 nucleotides in length. The polynucleic acid polymer may be about 20 nucleotides in length. The polynucleic acid polymer may be about 19 nucleotides in length. The polynucleic acid polymer may be about 18 nucleotides in length. The polynucleic acid polymer may be about 17 nucleotides in length. The polynucleic acid polymer may be about 16 nucleotides in length. The polynucleic acid polymer may be about 15 nucleotides in length. The polynucleic acid polymer may be about 14 nucleotides in length. The polynucleic acid polymer may be about 13 nucleotides in length. The polynucleic acid polymer may be about 12 nucleotides in length. The polynucleic acid polymer may be about 11 nucleotides in length. The polynucleic acid polymer may be about 10 nucleotides in length. The polynucleic acid polymer may be between about 10 and about 50 nucleotides in length. The polynucleic acid polymer may be between about 10 and about 45 nucleotides in length. The polynucleic acid polymer may be between about 10 and about 40 nucleotides in length. The polynucleic acid polymer may be between about 10 and about 35 nucleotides in length. The polynucleic acid polymer may be between about 10 and about 30 nucleotides in length. The polynucleic acid polymer may be between about 10 and about 25 nucleotides in length. The polynucleic acid polymer may be between about 10 and about 20 nucleotides in length. The polynucleic acid polymer may be between about 15 and about 25 nucleotides in length. The polynucleic acid polymer may be between about 15 and about 30 nucleotides in length. The polynucleic acid polymer may be between about 12 and about 30 nucleotides in length.

The sequence of the polynucleic acid polymer may be at least 50%, 55%, 60%, 65%, 70%, 75%, 80%, 85%, 90%, 91%, 92%, 93%, 94%, 95%, 96%, 97%, 98%, 99%, or 99.5% complementary to a target sequence of an mRNA transcript, e.g., a partially processed mRNA transcript. The sequence of the polynucleic acid polymer may be 100% complementary to a target sequence of a pre-mRNA transcript.

The sequence of the polynucleic acid polymer may have 4 or fewer mismatches to a target sequence of the pre-mRNA transcript. The sequence of the polynucleic acid polymer may have 3 or fewer mismatches to a target sequence of the pre-mRNA transcript. The sequence of the polynucleic acid polymer may have 2 or fewer mismatches to a target sequence of the pre-mRNA transcript. The sequence of the polynucleic acid polymer may have 1 or fewer mismatches to a target sequence of the pre-mRNA transcript. The sequence of the polynucleic acid polymer may have no mismatches to a target sequence of the pre-mRNA transcript.

The polynucleic acid polymer may specifically hybridize to a target sequence of the pre-mRNA transcript. For example, the polynucleic acid polymer may have 91%, 92%, 93%, 94%, 95%, 96%, 97%, 98%, 99%, 99.5% or 100% sequence complementarity to a target sequence of the premRNA transcript. The hybridization may be under high stringent hybridization conditions.

The polynucleic acid polymer comprising a sequence with at least 50%, 55%, 60%, 65%, 70%, 75%, 80%, 85%, 90%, 91%, 92%, 93%, 94%, 95%, 96%, 97%, 98%, 99%, or 99.5% sequence identity to a sequence selected from the group consisting of SEQ ID NOs: 2-5. The polynucleic acid polymer may comprise a sequence with 100% sequence identity to a sequence selected from the group consisting of SEQ ID NOs: 2-5.

Where reference is made to a polynucleic acid polymer sequence, the skilled person will understand that one or more substitutions may be tolerated, optionally two substitutions may be tolerated in the sequence, such that it maintains the ability to hybridize to the target sequence; or where the substitution is in a target sequence, the ability to be recognized as the target sequence. References to sequence identity may be determined by BLAST sequence alignment using standard/default parameters. For example, the sequence may have 99% identity and still function according to the present disclosure. In other embodiments, the sequence may have 98% identity and still function according to the present disclosure. In another embodiment, the sequence may have 95% identity and still function according to the present disclosure. In another embodiment, the sequence may have 90% identity and still function according to the present disclosure.

Antisense Oligomers

Provided herein is a composition comprising an antisense oligomer that induces exon skipping by binding to a targeted portion of an OPA1 pre-mRNA, e.g., an OPA1 NMD exon-containing pre-mRNA. As used herein, the terms “ASO” and “antisense oligomer” are used interchangeably and refer to an oligomer such as a polynucleotide, comprising nucleobases that hybridizes to a target nucleic acid (e.g., an OPA1 pre-mRNA, e.g., an OPA1 NMD exon-containing pre-mRNA) sequence by Watson-Crick base pairing or wobble base pairing (G-U). The ASO may have exact sequence complementary to the target sequence or near complementarity (e.g., sufficient complementarity to bind the target sequence and enhancing splicing at a splice site). ASOs are designed so that they bind (hybridize) to a target nucleic acid (e.g., a targeted portion of a pre-mRNA transcript) and remain hybridized under physiological conditions. Typically, if they hybridize to a site other than the intended (targeted) nucleic acid sequence, they hybridize to a limited number of sequences that are not a target nucleic acid (to a few sites other than a target nucleic acid). Design of an ASO can take into consideration the occurrence of the nucleic acid sequence of the targeted portion of the pre-mRNA transcript or a sufficiently similar nucleic acid sequence in other locations in the genome or cellular pre-mRNA or transcriptome, such that the likelihood the ASO will bind other sites and cause “off-target” effects is limited. Any antisense oligomers known in the art (for example, in PCT Application No. PCT/US2014/054151, published as WO 2015/035091, titled “Reducing Nonsense-Mediated mRNA Decay,” incorporated by reference herein), can be used to practice the methods described herein.

In some embodiments, ASOs “specifically hybridize” to or are “specific” to a target nucleic acid or a targeted portion of an OPA1 pre-mRNA, e.g., a NMD exon-containing pre-mRNA. Typically such hybridization occurs with a $T_m$ substantially greater than 37° C., preferably at least 50° C., and typically between 60° C. to approximately 90° C. Such hybridization preferably corresponds to stringent hybridization conditions. At a given ionic strength and pH, the $T_m$ is the temperature at which 50% of a target sequence hybridizes to a complementary oligonucleotide.

Oligomers, such as oligonucleotides, are “complementary” to one another when hybridization occurs in an antiparallel configuration between two single-stranded polynucleotides. A double-stranded polynucleotide can be “complementary” to another polynucleotide, if hybridization can occur between one of the strands of the first polynucleotide and the second. Complementarity (the degree to which one polynucleotide is complementary with another) is quantifiable in terms of the proportion (e.g., the percentage) of bases in opposing strands that are expected to form hydrogen bonds with each other, according to generally accepted base-pairing rules. The sequence of an antisense oligomer (ASO) need not be 100% complementary to that of its target nucleic acid to hybridize. In certain embodiments, ASOs can comprise at least 70%, at least 75%, at least 80%, at least 85%, at least 90%, at least 95%, at least 96%, at least 97%, at least 98%, or at least 99% sequence complementarity to a target region within the target nucleic acid sequence to which they are targeted. For example, an ASO in which 18 of 20 nucleobases of the oligomeric compound are complementary to a target region, and would therefore specifically hybridize, would represent 90 percent complementarity. In this example, the remaining noncomplementary nucleobases may be clustered together or interspersed with complementary nucleobases and need not be contiguous to each other or to complementary nucleobases. Percent complementarity of an ASO with a region of a target nucleic acid can be determined routinely using BLAST programs (basic local alignment search tools) and PowerBLAST programs known in the art (Altschul, et al., J. Mol. Biol., 1990, 215, 403-410; Zhang and Madden, Genome Res., 1997, 7, 649-656).

An ASO need not hybridize to all nucleobases in a target sequence and the nucleobases to which it does hybridize may be contiguous or noncontiguous. ASOs may hybridize over one or more segments of a pre-mRNA transcript, such that intervening or adjacent segments are not involved in the hybridization event (e.g., a loop structure or hairpin structure may be formed). In certain embodiments, an ASO hybridizes to noncontiguous nucleobases in a target pre-mRNA transcript. For example, an ASO can hybridize to nucleobases in a pre-mRNA transcript that are separated by one or more nucleobase(s) to which the ASO does not hybridize.

The ASOs described herein comprise nucleobases that are complementary to nucleobases present in a target portion of an OPA1 pre-mRNA, e.g., a NMD exon-containing pre-mRNA. The term ASO embodies oligonucleotides and any other oligomeric molecule that comprises nucleobases capable of hybridizing to a complementary nucleobase on a target mRNA but does not comprise a sugar moiety, such as a peptide nucleic acid (PNA). The ASOs may comprise naturally-occurring nucleotides, nucleotide analogs, modified nucleotides, or any combination of two or three of the preceding. The term “naturally occurring nucleotides” includes deoxyribonucleotides and ribonucleotides. The term “modified nucleotides” includes nucleotides with modified or substituted sugar groups and/or having a modified backbone. In some embodiments, all of the nucleotides of the ASO are modified nucleotides. Chemical modifications of ASOs or components of ASOs that are compatible with the methods and compositions described herein will be evident to one of skill in the art and can be found, for example, in U.S. Pat. No. 8,258,109 B2, U.S. Pat. No. 5,656,612, U.S. Patent Publication No. 2012/0190728, and Dias and Stein, Mol. Cancer Ther. 2002, 347-355, herein incorporated by reference in their entirety.

One or more nucleobases of an ASO may be any naturally occurring, unmodified nucleobase such as adenine, guanine, cytosine, thymine and uracil, or any synthetic or modified nucleobase that is sufficiently similar to an unmodified nucleobase such that it is capable of hydrogen bonding with a nucleobase present on a target pre-mRNA. Examples of modified nucleobases include, without limitation, hypoxanthine, xanthine, 7-methylguanine, 5,6-dihydrouracil, 5-methylcytosine, and 5-hydroxymethoylcytosine.

The ASOs described herein also comprise a backbone structure that connects the components of an oligomer. The term "backbone structure" and "oligomer linkages" may be used interchangeably and refer to the connection between monomers of the ASO. In naturally occurring oligonucleotides, the backbone comprises a 3'-5' phosphodiester linkage connecting sugar moieties of the oligomer. The backbone structure or oligomer linkages of the ASOs described herein may include (but are not limited to) phosphorothioate, phosphorodithioate, phosphoroselenoate, phosphorodiselenoate, phosphoroanilothioate, phosphoraniladate, phosphoramidate, and the like. See, e.g., LaPlanche, et al., Nucleic Acids Res. 14:9081 (1986); Stec, et al., J. Am. Chem. Soc. 106:6077 (1984), Stein, et al., Nucleic Acids Res. 16:3209 (1988), Zon, et al., Anti-Cancer Drug Design 6:539 (1991); Zon, et al., Oligonucleotides and Analogues: A Practical Approach, pp. 87-108 (F. Eckstein, Ed., Oxford University Press, Oxford England (1991)); Stec, et al., U.S. Pat. No. 5,151,510; Uhlmann and Peyman, Chemical Reviews 90:543 (1990). In some embodiments, the backbone structure of the ASO does not contain phosphorous but rather contains peptide bonds, for example in a peptide nucleic acid (PNA), or linking groups including carbamate, amides, and linear and cyclic hydrocarbon groups. In some embodiments, the backbone modification is a phosphorothioate linkage. In some embodiments, the backbone modification is a phosphoramidate linkage.

In some embodiments, the stereochemistry at each of the phosphorus internucleotide linkages of the ASO backbone is random. In some embodiments, the stereochemistry at each of the phosphorus internucleotide linkages of the ASO backbone is controlled and is not random. For example, U.S. Pat. App. Pub. No. 2014/0194610, "Methods for the Synthesis of Functionalized Nucleic Acids," incorporated herein by reference, describes methods for independently selecting the handedness of chirality at each phosphorous atom in a nucleic acid oligomer. In some embodiments, an ASO used in the methods of the disclosure, including, but not limited to, any of the ASOs set forth herein in Tables 5 and 6, comprises an ASO having phosphorus internucleotide linkages that are not random. In some embodiments, a composition used in the methods of the disclosure comprises a pure diastereomeric ASO. In some embodiments, a composition used in the methods of the disclosure comprises an ASO that has diastereomeric purity of at least about 90%, at least about 91%, at least about 92%, at least about 93%, at least about 94%, at least about 95%, at least about 96%, at least about 97%, at least about 98%, at least about 99%, about 100%, about 90% to about 100%, about 91% to about 100%, about 92% to about 100%, about 93% to about 100%, about 94% to about 100%, about 95% to about 100%, about 96% to about 100%, about 97% to about 100%, about 98% to about 100%, or about 99% to about 100%.

In some embodiments, the ASO has a nonrandom mixture of Rp and Sp configurations at its phosphorus internucleotide linkages. For example, it has been suggested that a mix of Rp and Sp is required in antisense oligonucleotides to achieve a balance between good activity and nuclease stability (Wan, et al., 2014, "Synthesis, biophysical properties and biological activity of second generation antisense oligonucleotides containing chiral phosphorothioate linkages," Nucleic Acids Research 42 (22): 13456-13468, incorporated herein by reference). In some embodiments, an ASO used in the methods of the disclosure, including, but not limited to, any of the ASOs set forth herein in SEQ ID NOs: 2-5, comprises about 5-100% Rp, at least about 5% Rp, at least about 10% Rp, at least about 15% Rp, at least about 20% Rp, at least about 25% Rp, at least about 30% Rp, at least about 35% Rp, at least about 40% Rp, at least about 45% Rp, at least about 50% Rp, at least about 55% Rp, at least about 60% Rp, at least about 65% Rp, at least about 70% Rp, at least about 75% Rp, at least about 80% Rp, at least about 85% Rp, at least about 90% Rp, or at least about 95% Rp, with the remainder Sp, or about 100% Rp. In some embodiments, an ASO used in the methods of the disclosure, including, but not limited to, any of the ASOs set forth herein comprise a sequence with at least about 80%, 85%, 90%, 95%, 97%, or 100% sequence identity to a region comprising at least 8 contiguous nucleic acids of any one of SEQ ID NOs: 2-5, comprises about 10% to about 100% Rp, about 15% to about 100% Rp, about 20% to about 100% Rp, about 25% to about 100% Rp, about 30% to about 100% Rp, about 35% to about 100% Rp, about 40% to about 100% Rp, about 45% to about 100% Rp, about 50% to about 100% Rp, about 55% to about 100% Rp, about 60% to about 100% Rp, about 65% to about 100% Rp, about 70% to about 100% Rp, about 75% to about 100% Rp, about 80% to about 100% Rp, about 85% to about 100% Rp, about 90% to about 100% Rp, or about 95% to about 100% Rp, about 20% to about 80% Rp, about 25% to about 75% Rp, about 30% to about 70% Rp, about 40% to about 60% Rp, or about 45% to about 55% Rp, with the remainder Sp.

In some embodiments, an ASO used in the methods of the disclosure, including, but not limited to, any of the ASOs set forth herein comprise a sequence with at least about 80%, 85%, 90%, 95%, 97%, or 100% sequence identity to a region comprising at least 8 contiguous nucleic acids of any one of SEQ ID NOs: 2-5, comprises about 5-100% Sp, at least about 5% Sp, at least about 10% Sp, at least about 15% Sp, at least about 20% Sp, at least about 25% Sp, at least about 30% Sp, at least about 35% Sp, at least about 40% Sp, at least about 45% Sp, at least about 50% Sp, at least about 55% Sp, at least about 60% Sp, at least about 65% Sp, at least about 70% Sp, at least about 75% Sp, at least about 80% Sp, at least about 85% Sp, at least about 90% Sp, or at least about 95% Sp, with the remainder Rp, or about 100% Sp. In embodiments, an ASO used in the methods of the disclosure, including, but not limited to, any of the ASOs set forth herein comprise a sequence with at least about 80%, 85%, 90%, 95%, 97%, or 100% sequence identity to a region comprising at least 8 contiguous nucleic acids of any one of SEQ ID NOs: 2-5, comprises about 10% to about 100% Sp, about 15% to about 100% Sp, about 20% to about 100% Sp, about 25% to about 100% Sp, about 30% to about 100% Sp, about 35% to about 100% Sp, about 40% to about 100% Sp, about 45% to about 100% Sp, about 50% to about 100% Sp, about 55% to about 100% Sp, about 60% to about 100% Sp, about 65% to about 100% Sp, about 70% to about 100% Sp, about 75% to about 100% Sp, about 80% to about 100% Sp, about 85% to about 100% Sp, about 90% to about 100% Sp, or about 95% to about 100% Sp, about 20% to about 80%

Sp, about 25% to about 75% Sp, about 30% to about 70% Sp, about 40% to about 60% Sp, or about 45% to about 55% Sp, with the remainder Rp.

Any of the ASOs described herein may contain a sugar moiety that comprises ribose or deoxyribose, as present in naturally occurring nucleotides, or a modified sugar moiety or sugar analog, including a morpholine ring. Non-limiting examples of modified sugar moieties include 2' substitutions such as 2'-O-methyl (2'-O-Me), 2'-O-methoxyethyl (2'MOE), 2'-O-aminoethyl, 2'F; N3'→P5' phosphoramidate, 2'dimethylaminooxyethoxy, 2'dimethylaminoethoxyethoxy, 2'-guanidinidium, 2'-O-guanidinium ethyl, carbamate modified sugars, and bicyclic modified sugars. In some embodiments, the sugar moiety modification is selected from 2'-O-Me, 2'F, and 2'MOE. In some embodiments, the sugar moiety modification is an extra bridge bond, such as in a locked nucleic acid (LNA). In some embodiments the sugar analog contains a morpholine ring, such as phosphorodiamidate morpholino (PMO). In some embodiments, the sugar moiety comprises a ribofuransyl or 2'deoxyribofuransyl modification. In some embodiments, the sugar moiety comprises 2'4'-constrained 2'O-methyloxyethyl (cMOE) modifications. In some embodiments, the sugar moiety comprises cEt 2', 4' constrained 2'-O ethyl BNA modifications. In some embodiments, the sugar moiety comprises tricycloDNA (tcDNA) modifications. In some embodiments, the sugar moiety comprises ethylene nucleic acid (ENA) modifications. In some embodiments, the sugar moiety comprises MCE modifications. Modifications are known in the art and described in the literature, e.g., by Jarver, et al., 2014, "A Chemical View of Oligonucleotides for Exon Skipping and Related Drug Applications," Nucleic Acid Therapeutics 24 (1): 37-47, incorporated by reference for this purpose herein.

In some embodiments, each monomer of the ASO is modified in the same way, for example each linkage of the backbone of the ASO comprises a phosphorothioate linkage or each ribose sugar moiety comprises a 2'O-methyl modification. Such modifications that are present on each of the monomer components of an ASO are referred to as "uniform modifications." In some examples, a combination of different modifications may be desired, for example, an ASO may comprise a combination of phosphorodiamidate linkages and sugar moieties comprising morpholine rings (morpholinos). Combinations of different modifications to an ASO are referred to as "mixed modifications" or "mixed chemistries."

In some embodiments, the ASO comprises one or more backbone modifications. In some embodiments, the ASO comprises one or more sugar moiety modification. In some embodiments, the ASO comprises one or more backbone modifications and one or more sugar moiety modifications. In some embodiments, the ASO comprises a 2'MOE modification and a phosphorothioate backbone. In some embodiments, the ASO comprises a phosphorodiamidate morpholino (PMO). In some embodiments, the ASO comprises a peptide nucleic acid (PNA). Any of the ASOs or any component of an ASO (e.g., a nucleobase, sugar moiety, backbone) described herein may be modified in order to achieve desired properties or activities of the ASO or reduce undesired properties or activities of the ASO. For example, an ASO or one or more components of any ASO may be modified to enhance binding affinity to a target sequence on a pre-mRNA transcript; reduce binding to any non-target sequence; reduce degradation by cellular nucleases (i.e., RNase H); improve uptake of the ASO into a cell and/or into the nucleus of a cell; alter the pharmacokinetics or pharmacodynamics of the ASO; and/or modulate the half-life of the ASO.

In some embodiments, the ASOs are comprised of 2'-O-(2-methoxyethyl) (MOE) phosphorothioate-modified nucleotides. ASOs comprised of such nucleotides are especially well-suited to the methods disclosed herein; oligomers having such modifications have been shown to have significantly enhanced resistance to nuclease degradation and increased bioavailability, making them suitable, for example, for oral delivery in some embodiments described herein. See e.g., Geary, et al., J Pharmacol Exp Ther. 2001; 296 (3): 890-7; Geary, et al., J Pharmacol Exp Ther. 2001; 296 (3): 898-904.

Methods of synthesizing ASOs will be known to one of skill in the art. Alternatively or in addition, ASOs may be obtained from a commercial source.

Unless specified otherwise, the left-hand end of single-stranded nucleic acid (e.g., pre-mRNA transcript, oligonucleotide, ASO, etc.) sequences is the 5' end and the left-hand direction of single or double-stranded nucleic acid sequences is referred to as the 5' direction. Similarly, the right-hand end or direction of a nucleic acid sequence (single or double stranded) is the 3' end or direction. Generally, a region or sequence that is 5' to a reference point in a nucleic acid is referred to as "upstream," and a region or sequence that is 3' to a reference point in a nucleic acid is referred to as "downstream." Generally, the 5' direction or end of an mRNA is where the initiation or start codon is located, while the 3' end or direction is where the termination codon is located. In some aspects, nucleotides that are upstream of a reference point in a nucleic acid may be designated by a negative number, while nucleotides that are downstream of a reference point may be designated by a positive number. For example, a reference point (e.g., an exon-exon junction in mRNA) may be designated as the "zero" site, and a nucleotide that is directly adjacent and upstream of the reference point is designated "minus one," e.g., "−1," while a nucleotide that is directly adjacent and downstream of the reference point is designated "plus one," e.g., "+1."

In some embodiments, the ASOs are complementary to (and bind to) a targeted portion of an OPA1 pre-mRNA, e.g., an OPA1 NMD exon-containing pre-mRNA, that is downstream (in the 3' direction) of the 5' splice site (or 3' end of the NMD exon) of the included exon in an OPA1 pre-mRNA (e.g., the direction designated by positive numbers relative to the 5' splice site). In some embodiments, the ASOs are complementary to a targeted portion of the OPA1 pre-mRNA, e.g., the OPA1 NMD exon-containing pre-mRNA that is within the region about +1 to about +500 relative to the 5' splice site (or 3' end) of the included exon. In some embodiments, the ASOs may be complementary to a targeted portion of an OPA1 pre-mRNA, e.g., an OPA1 NMD exon-containing pre-mRNA, that is within the region between nucleotides +6 and +40,000 relative to the 5' splice site (or 3' end) of the included exon. In some aspects, the ASOs are complementary to a targeted portion that is within the region about +1 to about +40,000, about +1 to about +30,000, about +1 to about +20,000, about +1 to about +15,000, about +1 to about +10,000, about +1 to about +5,000, about +1 to about +4,000, about +1 to about +3,000, about +1 to about +2,000, about +1 to about +1,000, about +1 to about +500, about +1 to about +490, about +1 to about +480, about +1 to about +470, about +1 to about +460, about +1 to about +450, about +1 to about +440, about +1 to about +430, about +1 to about +420, about +1 to about +410, about +1 to about +400, about +1 to about +390, about +1 to about +380, about +1 to about +370, about +1 to about +360, about +1 to about +350, about +1 to about +340, about +1 to about +330, about +1 to about +320, about +1 to about +310, about +1 to about +300, about +1 to about +290, about +1 to about +280, about +1 to about +270, about +1 to about +260, about +1 to about +250, about +1 to about +240, about +1 to about +230, about +1 to about +220, about +1 to about +210, about +1 to about +200, about +1 to about +190, about +1 to about +180, about +1 to about +170, about +1 to about +160, about +1 to about +150, about +1 to about +140, about +1 to about +130, about +1 to about +120, about +1 to about +110, about +1 to about +100, about +1 to about +90, about +1 to about +80, about +1 to about +70, about +1 to about +60, about +1 to about +50, about +1 to about +40, about +1 to about +30, or about +1 to about +20 relative to 5' splice site (or 3' end) of the included exon. In some aspects, the ASOs are complementary to a targeted portion that is within the region from about +1 to about +100, from about +100 to about +200, from about +200 to about +300, from about +300 to about +400, or from about +400 to about +500 relative to 5' splice site (or 3' end) of the included exon.

In some embodiments, the ASOs are complementary to (and bind to) a targeted portion of an OPA1 pre-mRNA, e.g., an OPA1 NMD exon-containing pre-mRNA, that is upstream (in the 5' direction) of the 5' splice site (or 3' end) of the included exon in an OPA1 pre-mRNA, e.g., an OPA1 NMD exon-containing pre-mRNA (e.g., the direction designated by negative numbers relative to the 5' splice site). In some embodiments, the ASOs are complementary to a targeted portion of the OPA1 pre-mRNA, e.g., the OPA1 NMD exon-containing pre-mRNA, that is within the region about −4 to about −270 relative to the 5' splice site (or 3'end) of the included exon. In some embodiments, the ASOs may be complementary to a targeted portion of an OPA1 pre-mRNA, e.g., an OPA1 NMD exon-containing pre-mRNA, that is within the region between nucleotides −1 and −40,000 relative to the 5' splice site (or 3' end) of the included exon. In some aspects, the ASOs are complementary to a targeted portion that is within the region about −1 to about −40,000, about −1 to about −30,000, about −1 to about −20,000, about −1 to about −15,000, about −1 to about −10,000, about −1 to about −5,000, about −1 to about −4,000, about −1 to about −3,000, about −1 to about −2,000, about −1 to about −1,000, about −1 to about −500, about −1 to about −490, about −1 to about −480, about −1 to about −470, about −1 to about −460, about −1 to about −450, about −1 to about −440, about −1 to about −430, about −1 to about −420, about −1 to about −410, about −1 to about −400, about −1 to about −390, about −1 to about −380, about −1 to about −370, about −1 to about −360, about −1 to about −350, about −1 to about −340, about −1 to about −330, about −1 to about −320, about −1 to about −310, about −1 to about −300, about −1 to about −290, about −1 to about −280, about −1 to about −270, about −1 to about −260, about −1 to about −250, about −1 to about −240, about −1 to about −230, about −1 to about −220, about −1 to about −210, about −1 to about −200, about −1 to about −190, about −1 to about −180, about −1 to about −170, about −1 to about −160, about −1 to about −150, about −1 to about −140, about −1 to about −130, about −1 to about −120, about −1 to about −110, about −1 to about −100, about −1 to about −90, about −1 to about −80, about −1 to about −70, about −1 to about −60, about −1 to about −50, about −1 to about −40, about −1 to about −30, or about −1 to about −20 relative to 5' splice site (or 3' end) of the included exon.

In some embodiments, the ASOs are complementary to a targeted region of an OPA1 pre-mRNA, e.g., an OPA1 NMD exon-containing pre-mRNA, that is upstream (in the 5' direction) of the 3' splice site (or 5' end) of the included exon in an OPA1 pre-mRNA (e.g., in the direction designated by negative numbers). In some embodiments, the ASOs are complementary to a targeted portion of the OPA1 pre-mRNA, e.g., the OPA1 NMD exon-containing pre-mRNA, that is within the region about −1 to about −500 relative to the 3' splice site (or 5' end) of the included exon. In some embodiments, the ASOs are complementary to a targeted portion of the OPA1 pre-mRNA that is within the region −1 to −40,000 relative to the 3' splice site of the included exon. In some aspects, the ASOs are complementary to a targeted portion that is within the region about −1 to about −40,000, about −1 to about −30,000, −1 to about −20,000, about −1 to about −15,000, about −1 to about −10,000, about −1 to about −5,000, about −1 to about −4,000, about −1 to about −3,000, about −1 to about −2,000, about −1 to about −1,000, about −1 to about −500, about −1 to about −490, about −1 to about −480, about −1 to about −470, about −1 to about −460, about −1 to about −450, about −1 to about −440, about −1 to about −430, about −1 to about −420, about −1 to about −410, about −1 to about −400, about −1 to about −390, about −1 to about −380, about −1 to about −370, about −1 to about −360, about −1 to about −350, about −1 to about −340, about −1 to about −330, about −1 to about −320, about −1 to about −310, about −1 to about −300, about −1 to about −290, about −1 to about −280, about −1 to about −270, about −1 to about −260, about −1 to about −250, about −1 to about −240, about −1 to about −230, about −1 to about −220, about −1 to about −210, about −1 to about −200, about −1 to about −190, about −1 to about −180, about −1 to about −170, about −1 to about −160, about −1 to about −150, about −1 to about −140, about −1 to about −130, about −1 to about −120, about −1 to about −110, about −1 to about −100, about −1 to about −90, about −1 to about −80, about −1 to about −70, about −1 to about −60, about −1 to about −50, about −1 to about −40, about −1 to about −30, or about −1 to about −20 relative to 3' splice site of the included exon. In some aspects, the ASOs are complementary to a targeted portion that is within the region from about −1 to about −100, from about −100 to about −200, from about −200 to about −300, from about −300 to about −400, or from about −400 to about −500 relative to 3' splice site of the included exon.

In some embodiments, the ASOs are complementary to a targeted region of an OPA1 pre-mRNA, e.g., an OPA1 NMD exon-containing pre-mRNA, that is downstream (in the 3' direction) of the 3' splice site (5' end) of the included exon in an OPA1 pre-mRNA, e.g., an OPA1 NMD exon-containing pre-mRNA (e.g., in the direction designated by positive numbers). In some embodiments, the ASOs are complementary to a targeted portion of the OPA1 pre-mRNA that is within the region of about +1 to about +40,000 relative to the 3' splice site of the included exon. In some aspects, the ASOs are complementary to a targeted portion that is within the region about +1 to about +40,000, about +1 to about +30,000, about +1 to about +20,000, about +1 to about +15,000, about +1 to about +10,000, about +1 to about +5,000, about +1 to about +4,000, about +1 to about +3,000, about +1 to about +2,000, about +1 to about +1,000, about +1 to about +500, about +1 to about +490, about +1 to about +480, about +1 to about +470, about +1 to about +460, about +1 to about +450, about +1 to about +440, about +1 to about +430, about +1 to about +420, about +1 to about +410, about +1 to about +400, about +1 to about +390, about +1 to about +380, about +1 to about +370, about +1 to about +360, about +1 to about +350, about +1 to about +340, about +1 to about +330, about +1 to about +320, about +1 to about +310, about +1 to about +300, about +1 to about +290, about +1 to about +280, about +1 to about +270, about +1 to about +260, about +1 to about +250, about +1 to about +240, about +1 to about +230, about +1 to about +220, about +1 to about +210, about +1 to about +200, about +1 to about +190, about +1 to about +180, about +1 to about +170, about +1 to about +160, about +1 to about +150, about +1 to about +140, about +1 to about +130, about +1 to about +120, about +1 to about +110, about +1 to about +100, about +1 to about +90, about +1 to about +80, about +1 to about +70, about +1 to about +60, about +1 to about +50, about +1 to about +40, about +1 to about +30, or about +1 to about +20, or about +1 to about +10 relative to 3' splice site of the included exon.

In some embodiments, the targeted portion of the OPA1 pre-mRNA, e.g., the OPA1 NMD exon-containing pre-mRNA, is within the region +100 relative to the 5' splice site (3' end) of the included exon to −100 relative to the 3' splice site (5' end) of the included exon. In some embodiments, the targeted portion of the OPA1 NMD exon-containing pre-mRNA is within the NMD exon. In some embodiments, the target portion of the OPA1 NMD exon-containing pre-mRNA comprises a pseudo-exon and intron boundary.

The ASOs may be of any length suitable for specific binding and effective enhancement of splicing. In some embodiments, the ASOs consist of 8 to 50 nucleobases. For example, the ASO may be 8, 9, 10, 11, 12, 13, 14, 15, 16, 17, 18, 19, 20, 21, 22, 23, 24, 25, 26, 27, 28, 29, 30, 31, 32, 33, 34, 35, 40, 45, or 50 nucleobases in length. In some embodiments, the ASOs consist of more than 50 nucleobases. In some embodiments, the ASO is from 8 to 50 nucleobases, 8 to 40 nucleobases, 8 to 35 nucleobases, 8 to 30 nucleobases, 8 to 25 nucleobases, 8 to 20 nucleobases, 8 to 15 nucleobases, 9 to 50 nucleobases, 9 to 40 nucleobases, 9 to 35 nucleobases, 9 to 30 nucleobases, 9 to 25 nucleobases, 9 to 20 nucleobases, 9 to 15 nucleobases, 10 to 50 nucleobases, 10 to 40 nucleobases, 10 to 35 nucleobases, 10 to 30 nucleobases, 10 to 25 nucleobases, 10 to 20 nucleobases, 10 to 15 nucleobases, 11 to 50 nucleobases, 11 to 40 nucleobases, 11 to 35 nucleobases, 11 to 30 nucleobases, 11 to 25 nucleobases, 11 to 20 nucleobases, 11 to 15 nucleobases, 12 to 50 nucleobases, 12 to 40 nucleobases, 12 to 35 nucleobases, 12 to 30 nucleobases, 12 to 25 nucleobases, 12 to 20 nucleobases, 12 to 15 nucleobases, 13 to 50 nucleobases, 13 to 40 nucleobases, 13 to 35 nucleobases, 13 to 30 nucleobases, 13 to 25 nucleobases, 13 to 20 nucleobases, 14 to 50 nucleobases, 14 to 40 nucleobases, 14 to 35 nucleobases, 14 to 30 nucleobases, 14 to 25 nucleobases, 14 to 20 nucleobases, 15 to 50 nucleobases, 15 to 40 nucleobases, 15 to 35 nucleobases, 15 to 30 nucleobases, 15 to 25 nucleobases, 15 to 20 nucleobases, 20 to 50 nucleobases, 20 to 40 nucleobases, 20 to 35 nucleobases, 20 to 30 nucleobases, 20 to 25 nucleobases, 25 to 50 nucleobases, 25 to 40 nucleobases, 25 to 35 nucleobases, or 25 to 30 nucleobases in length. In some embodiments, the ASOs are 18 nucleotides in length. In some embodiments, the ASOs are 15 nucleotides in length. In some embodiments, the ASOs are 25 nucleotides in length.

In some embodiments, two or more ASOs with different chemistries but complementary to the same targeted portion of the pre-mRNA, e.g., NMD exon-containing pre-mRNA, are used. In some embodiments, two or more ASOs that are complementary to different targeted portions of the pre-mRNA, e.g., the NMD exon-containing pre-mRNA, are used.

In some embodiments, the antisense oligonucleotides of the disclosure are chemically linked to one or more moieties or conjugates, e.g., a targeting moiety or other conjugate that enhances the activity or cellular uptake of the oligonucleotide. Such moieties include, but are not limited to, a lipid moiety, e.g., as a cholesterol moiety, a cholesteryl moiety, an aliphatic chain, e.g., dodecandiol or undecyl residues, a polyamine or a polyethylene glycol chain, or adamantane acetic acid. Oligonucleotides comprising lipophilic moieties and preparation methods have been described in the published literature. In embodiments, the antisense oligonucleotide is conjugated with a moiety including, but not limited to, an abasic nucleotide, a polyether, a polyamine, a polyamide, a peptides, a carbohydrate, e.g., N-acetylgalactosamine (GalNAc), N-Ac-Glucosamine (GluNAc), or mannose (e.g., mannose-6-phosphate), a lipid, or a polyhydrocarbon compound. Conjugates can be linked to one or more of any nucleotides comprising the antisense oligonucleotide at any of several positions on the sugar, base or phosphate group, as understood in the art and described in the literature, e.g., using a linker. Linkers can include a bivalent or trivalent branched linker. In embodiments, the conjugate is attached to the 3' end of the antisense oligonucleotide. Methods of preparing oligonucleotide conjugates are described, e.g., in U.S. Pat. No. 8,450,467, "Carbohydrate conjugates as delivery agents for oligonucleotides," incorporated by reference herein.

In some embodiments, the nucleic acid to be targeted by an ASO is an OPA1 pre-mRNA, e.g., NMD exon-containing pre-mRNA expressed in a cell, such as a eukaryotic cell. In some embodiments, the term "cell" may refer to a population of cells. In some embodiments, the cell is in a subject. In some embodiments, the cell is isolated from a subject. In some embodiments, the cell is ex vivo. In some embodiments, the cell is a condition or disease-relevant cell or a cell line. In some embodiments, the cell is in vitro (e.g., in cell culture).

Pharmaceutical Compositions

Pharmaceutical compositions or formulations comprising the agent, e.g., antisense oligonucleotide, of the described compositions and for use in any of the described methods can be prepared according to conventional techniques well known in the pharmaceutical industry and described in the published literature. In embodiments, a pharmaceutical composition or formulation for treating a subject comprises an effective amount of any antisense oligomer as described herein, or a pharmaceutically acceptable salt, solvate, hydrate or ester thereof. The pharmaceutical formulation comprising an antisense oligomer may further comprise a pharmaceutically acceptable excipient, diluent or carrier.

Pharmaceutically acceptable salts are suitable for use in contact with the tissues of humans and lower animals without undue toxicity, irritation, allergic response, etc., and are commensurate with a reasonable benefit/risk ratio. (See, e.g., S. M. Berge, et al., J. Pharmaceutical Sciences, 66:1-19 (1977), incorporated herein by reference for this purpose. The salts can be prepared in situ during the final isolation and purification of the compounds, or separately by reacting the free base form with a suitable organic acid. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other documented methodologies such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

In some embodiments, the compositions are formulated into any of many possible dosage forms such as, but not limited to, tablets, capsules, gel capsules, liquid syrups, soft gels, suppositories, and enemas. In embodiments, the compositions are formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers. In embodiments, a pharmaceutical formulation or composition of the present disclosure includes, but is not limited to, a solution, emulsion, microemulsion, foam or liposome-containing formulation (e.g., cationic or noncationic liposomes).

The pharmaceutical composition or formulation described herein may comprise one or more penetration enhancers, carriers, excipients or other active or inactive ingredients as appropriate and well known to those of skill in the art or described in the published literature. In embodiments, liposomes also include sterically stabilized liposomes, e.g., liposomes comprising one or more specialized lipids. These specialized lipids result in liposomes with enhanced circulation lifetimes. In embodiments, a sterically stabilized liposome comprises one or more glycolipids or is derivatized with one or more hydrophilic polymers, such as a polyethylene glycol (PEG) moiety. In some embodiments, a surfactant is included in the pharmaceutical formulation or compositions. The use of surfactants in drug products, formulations and emulsions is well known in the art. In embodiments, the present disclosure employs a penetration enhancer to effect the efficient delivery of the antisense oligonucleotide, e.g., to aid diffusion across cell membranes and/or enhance the permeability of a lipophilic drug. In some embodiments, the penetration enhancers are a surfactant, fatty acid, bile salt, chelating agent, or non-chelating nonsurfactant.

In some embodiments, the pharmaceutical formulation comprises multiple antisense oligonucleotides. In embodiments, the antisense oligonucleotide is administered in combination with another drug or therapeutic agent.

Combination Therapies

In some embodiments, the ASOs disclosed in the present disclosure can be used in combination with one or more additional therapeutic agents. In some embodiments, the one or more additional therapeutic agents can comprise a small molecule. For example, the one or more additional therapeutic agents can comprise a small molecule described in WO2016128343A1, WO2017053982A1, WO2016196386A1, WO201428459A1, WO201524876A2, WO2013119916A2, and WO2014209841A2, which are incorporated by reference herein in their entirety. In some embodiments, the one or more additional therapeutic agents comprise an ASO that can be used to correct intron retention.

Treatment of Subjects

Any of the compositions provided herein may be administered to an individual. "Individual" may be used interchangeably with "subject" or "patient." An individual may be a mammal, for example a human or animal such as a non-human primate, a rodent, a rabbit, a rat, a mouse, a horse, a donkey, a goat, a cat, a dog, a cow, a pig, or a sheep. In embodiments, the individual is a human. In embodiments, the individual is a fetus, an embryo, or a child. In other embodiments, the individual may be another eukaryotic organism, such as a plant. In some embodiments, the compositions provided herein are administered to a cell ex vivo.

In some embodiments, the compositions provided herein are administered to an individual as a method of treating a disease or disorder. In some embodiments, the individual has a genetic disease, such as any of the diseases described herein. In some embodiments, the individual is at risk of having a disease, such as any of the diseases described herein. In some embodiments, the individual is at increased risk of having a disease or disorder caused by insufficient amount of a protein or insufficient activity of a protein. If an individual is "at an increased risk" of having a disease or disorder caused insufficient amount of a protein or insufficient activity of a protein, the method involves preventative or prophylactic treatment. For example, an individual may be at an increased risk of having such a disease or disorder because of family history of the disease. Typically, individuals at an increased risk of having such a disease or disorder benefit from prophylactic treatment (e.g., by preventing or delaying the onset or progression of the disease or disorder). In embodiments, a fetus is treated in utero, e.g., by administering the ASO composition to the fetus directly or indirectly (e.g., via the mother).

In some cases, the subject pharmaceutical composition and method are applicable for treatment of a condition or disease associated with OPA1 deficiency. In some cases, the subject pharmaceutical composition and method are applicable for treatment of an eye disease or condition. In some cases, the subject pharmaceutical composition and method are applicable for treatment of Optic atrophy type 1, autosomal dominant optic atrophy (ADOA), ADOA-plus syndrome; a mitochondrial disorder; glaucoma; normal tension glaucoma; Charcot-Marie-Tooth disease; mitochondria dysfunction; diabetic retinopathy; age-related macular degeneration; retinal ganglion cell death; mitochondrial fission-mediated mitochondrial dysfunction; progressive external ophthalmoplegia; deafness; ataxia; motor neuropathy; sensory neuropathy; myopathy; Behr syndrome; brain dysfunction; encephalopathy; peripheral neuropathy; fatal infantile mitochondrial encephalomyopathy; hypertrophic cardiomyopathy; spastic ataxic syndrome; sensory motor peripheral neuropathy; hypotonia; gastrointestinal dysmotility and dysphagia; optic atrophy; optic atrophy plus syndrome; Mitochondrial DNA depletion syndrome 14; late-onset cardiomyopathy; diabetic cardiomyopathy; Alzheimer's Disease; focal segmental glomerulosclerosis; kidney disease; Huntington's Disease; cognitive function decline in healthy aging; Prion diseases; late onset dementia and parkinsonism; mitochondrial myopathy; Leigh syndrome; Friedreich's ataxia; Parkinson's disease; MELAS (Mitochondrial encephalomyopathy, lactic acidosis, and stroke-like episodes); pyruvate dehydrogenase complex deficiency; chronic kidney disease; Leber's hereditary optic neuropathy;

obesity; age-related systemic neurodegeneration; skeletal muscle atrophy; heart and brain ischemic damage; or massive liver apoptosis.

Autosomal dominant optic atrophy (ADOA) is the most common inherited optic nerve disorder and is characterized by retinal ganglion cell loss. In some cases, 65-90% of ADOA cases are caused by mutations in one allele of the OPA1 gene. OPA1 gene encodes an OPA1 protein that is a mitochondrial GTPase, which can have a critical maintenance role in mitochondria structure and function. Most OPA1 mutations can lead to a haploinsufficiency, resulting in about a 50% decrease of normal OPA1 protein levels. Approximately 1 out of 30,000 people are affected globally with a higher incidence of ~1 out of 10,000 in Denmark due to a founder effect. ADOA can present within the first decade of life. 80% of ADOA patients are symptomatic before 10 years of age. The disease can cause progressive and irreversible vision loss and up to 46% of patients are registered as legally blind.

In some cases, a therapeutic agent comprises an oligonucleotide. In some cases, a therapeutic agent comprises a vector, e.g., a viral vector, expressing a oligonucleotide that binds to the targeted region of a pre-mRNA the encodes the target peptide sequence. The methods provided herein can be adapted to contacting a vector that encodes an agent, e.g., an oligonucleotide, to a cell, so that the agent binds to a pre-mRNA in the cell and modulates the processing of the pre-mRNA. In some cases, the viral vector comprises an adenoviral vector, adeno-associated viral (AAV) vector, lentiviral vector, Herpes Simplex Virus (HSV) viral vector, retroviral vector, or any applicable viral vector. In some cases, a therapeutic agent comprises a gene editing tool that is configured to modify a gene encoding the target peptide sequence such that a gene region that encodes the inefficient translation region is deleted. In some cases, a gene editing tool comprises vector, e.g., viral vector, for gene editing based on CRISPR-Cas9, TALEN, Zinc Finger, or other applicable technologies.

Suitable routes for administration of ASOs of the present disclosure may vary depending on cell type to which delivery of the ASOs is desired. Multiple tissues and organs are affected by ADOA, with the eye being the most significantly affected tissue. The ASOs of the present disclosure may be administered to patients parenterally, for example, by intravitreal injection, intrathecal injection, intracerebroventricular injection, intraperitoneal injection, intramuscular injection, subcutaneous injection, or intravenous injection.

In embodiments, the antisense oligonucleotide is administered with one or more agents capable of promoting penetration of the subject antisense oligonucleotide across the blood-brain barrier by any method known in the art. For example, delivery of agents by administration of an adenovirus vector to motor neurons in muscle tissue is described in U.S. Pat. No. 6,632,427, "Adenoviral-vector-mediated gene transfer into medullary motor neurons," incorporated herein by reference. Delivery of vectors directly to the brain, e.g., the striatum, the thalamus, the hippocampus, or the substantia nigra, is described, e.g., in U.S. Pat. No. 6,756,523, "Adenovirus vectors for the transfer of foreign genes into cells of the central nervous system particularly in brain," incorporated herein by reference.

In some embodiments, the antisense oligonucleotides are linked or conjugated with agents that provide desirable pharmaceutical or pharmacodynamic properties. In embodiments, the antisense oligonucleotide is coupled to a substance, known in the art to promote penetration or transport across the blood-brain barrier, e.g., an antibody to the transferrin receptor. In embodiments, the antisense oligonucleotide is linked with a viral vector, e.g., to render the antisense compound more effective or increase transport across the blood-brain barrier. In embodiments, osmotic blood brain barrier disruption is assisted by infusion of sugars, e.g., meso erythritol, xylitol, D(+) galactose, D(+) lactose, D(+) xylose, dulcitol, myo-inositol, L(−) fructose, D(−) mannitol, D(+) glucose, D(+) arabinose, D(−) arabinose, cellobiose, D(+) maltose, D(+) raffinose, L(+) rhamnose, D(+) melibiose, D(−) ribose, adonitol, D(+) arabitol, L(−) arabitol, D(+) fucose, L(−) fucose, D(−) lyxose, L(+) lyxose, and L(−) lyxose, or amino acids, e.g., glutamine, lysine, arginine, asparagine, aspartic acid, cysteine, glutamic acid, glycine, histidine, leucine, methionine, phenylalanine, proline, serine, threonine, tyrosine, valine, and taurine. Methods and materials for enhancing blood brain barrier penetration are described, e.g., in U.S. Pat. No. 9,193,969, "Compositions and methods for selective delivery of oligonucleotide molecules to specific neuron types," U.S. Pat. No. 4,866,042, "Method for the delivery of genetic material across the blood brain barrier," U.S. Pat. No. 6,294,520, "Material for passage through the blood-brain barrier," and U.S. Pat. No. 6,936,589, "Parenteral delivery systems," each incorporated herein by reference.

In some embodiments, subjects treated using the methods and compositions are evaluated for improvement in condition using any methods known and described in the art.

Methods of Identifying Additional ASOs that Induce Exon Skipping

Also within the scope of the present disclosure are methods for identifying or determining ASOs that induce exon skipping of an OPA1 NMD exon-containing pre-mRNA. For example, a method can comprise identifying or determining ASOs that induce pseudo-exon skipping of an OPA1 NMD exon-containing pre-mRNA. ASOs that specifically hybridize to different nucleotides within the target region of the pre-mRNA may be screened to identify or determine ASOs that improve the rate and/or extent of splicing of the target intron. In some embodiments, the ASO may block or interfere with the binding site(s) of a splicing repressor(s)/silencer. Any method known in the art may be used to identify (determine) an ASO that when hybridized to the target region of the exon results in the desired effect (e.g., pseudo-exon skipping, protein or functional RNA production). These methods also can be used for identifying ASOs that induce exon skipping of the included exon by binding to a targeted region in an intron flanking the included exon, or in a non-included exon. An example of a method that may be used is provided below.

A round of screening, referred to as an ASO "walk" may be performed using ASOs that have been designed to hybridize to a target region of a pre-mRNA. For example, the ASOs used in the ASO walk can be tiled every 5 nucleotides from approximately 100 nucleotides upstream of the 3' splice site of the included exon (e.g., a portion of sequence of the exon located upstream of the target/included exon) to approximately 100 nucleotides downstream of the 3' splice site of the target/included exon and/or from approximately 100 nucleotides upstream of the 5' splice site of the included exon to approximately 100 nucleotides downstream of the 5' splice site of the target/included exon (e.g., a portion of sequence of the exon located downstream of the target/included exon). For example, a first ASO of 15 nucleotides in length may be designed to specifically hybridize to nucleotides +6 to +20 relative to the 3' splice site of the target/included exon. A second ASO may be designed to specifically hybridize to nucleotides +11 to +25 relative to the 3' splice site of the target/included exon. ASOs are designed as such spanning the target region of the pre-mRNA. In embodiments, the ASOs can be tiled more closely, e.g., every 1, 2, 3, or 4 nucleotides. Further, the ASOs can be tiled from 100 nucleotides downstream of the 5' splice site, to 100 nucleotides upstream of the 3' splice site. In some embodiments, the ASOs can be tiled from about 1,160 nucleotides upstream of the 3' splice site, to about 500 nucleotides downstream of the 5' splice site. In some embodiments, the ASOs can be tiled from about 500 nucleotides upstream of the 3' splice site, to about 1,920 nucleotides downstream of the 3' splice site.

One or more ASOs, or a control ASO (an ASO with a scrambled sequence, sequence that is not expected to hybridize to the target region) are delivered, for example by transfection, into a disease-relevant cell line that expresses the target pre-mRNA (e.g., a NMD exon-containing pre-mRNA described herein). The exon skipping effects of each of the ASOs may be assessed by any method known in the art, for example by reverse transcriptase (RT)-PCR using primers that span the splice junction, as described in Example 4. A reduction or absence of a longer RT-PCR product produced using the primers spanning the region containing the included exon (e.g. including the flanking exons of the NMD exon) in ASO-treated cells as compared to in control ASO-treated cells indicates that splicing of the target NMD exon has been enhanced. In some embodiments, the exon skipping efficiency (or the splicing efficiency to splice the intron containing the NMD exon), the ratio of spliced to unspliced pre-mRNA, the rate of splicing, or the extent of splicing may be improved using the ASOs described herein. The amount of protein or functional RNA that is encoded by the target pre-mRNA can also be assessed to determine whether each ASO achieved the desired effect (e.g., enhanced functional protein production). Any method known in the art for assessing and/or quantifying protein production, such as Western blotting, flow cytometry, immunofluorescence microscopy, and ELISA, can be used.

A second round of screening, referred to as an ASO "micro-walk" may be performed using ASOs that have been designed to hybridize to a target region of a pre-mRNA. The ASOs used in the ASO micro-walk are tiled every 1 nucleotide to further refine the nucleotide acid sequence of the pre-mRNA that when hybridized with an ASO results in exon skipping (or enhanced splicing of NMD exon).

Regions defined by ASOs that promote splicing of the target intron are explored in greater detail by means of an ASO "micro-walk", involving ASOs spaced in 1-nt steps, as well as longer ASOs, typically 18-25 nt.

As described for the ASO walk above, the ASO micro-walk is performed by delivering one or more ASOs, or a control ASO (an ASO with a scrambled sequence, sequence that is not expected to hybridize to the target region), for example by transfection, into a disease-relevant cell line that expresses the target pre-mRNA. The splicing-inducing effects of each of the ASOs may be assessed by any method known in the art, for example by reverse transcriptase (RT)-PCR using primers that span the NMD exon, as described herein (see, e.g., Example 4). A reduction or absence of a longer RT-PCR product produced using the primers spanning the NMD exon in ASO-treated cells as compared to in control ASO-treated cells indicates that exon skipping (or splicing of the target intron containing an NMD exon) has been enhanced. In some embodiments, the exon skipping efficiency (or the splicing efficiency to splice the intron containing the NMD exon), the ratio of spliced to unspliced pre-mRNA, the rate of splicing, or the extent of splicing may be improved using the ASOs described herein. The amount of protein or functional RNA that is encoded by the target pre-mRNA can also be assessed to determine whether each ASO achieved the desired effect (e.g., enhanced functional protein production). Any method known in the art for assessing and/or quantifying protein production, such as Western blotting, flow cytometry, immunofluorescence microscopy, and ELISA, can be used.

ASOs that when hybridized to a region of a pre-mRNA result in exon skipping (or enhanced splicing of the intron containing a NMD exon) and increased protein production may be tested in vivo using animal models, for example transgenic mouse models in which the full-length human gene has been knocked-in or in humanized mouse models of disease. Suitable routes for administration of ASOs may vary depending on the disease and/or the cell types to which delivery of the ASOs is desired. ASOs may be administered, for example, by intravitreal injection, intrathecal injection, intracerebroventricular injection, intraperitoneal injection, intramuscular injection, subcutaneous injection, or intravenous injection. Following administration, the cells, tissues, and/or organs of the model animals may be assessed to determine the effect of the ASO treatment by for example evaluating splicing (e.g., efficiency, rate, extent) and protein production by methods known in the art and described herein. The animal models may also be any phenotypic or behavioral indication of the disease or disease severity.

Also within the scope of the present disclosure is a method to identify or validate an NMD-inducing exon in the presence of an NMD inhibitor, for example, cycloheximide. An exemplary method is provided in Example 2.

Specific Embodiments (A)

Embodiment A1. A method of treating Optic atrophy type 1 in a subject in need thereof, by increasing the expression of a target protein or functional RNA by a cell of the subject, wherein the cell has an mRNA that contains a non-sense mediated RNA decay-inducing exon (NMD exon mRNA), and wherein the NMD exon mRNA encodes the target protein or functional RNA, the method comprising contacting the cell of the subject with a therapeutic agent that binds to a targeted portion of the NMD exon mRNA encoding the target protein or functional RNA, whereby the non-sense mediated RNA decay-inducing exon is excluded from the NMD exon mRNA encoding the target protein or functional RNA, thereby increasing the level of mRNA encoding the target protein or functional RNA, and increasing the expression of the target protein or functional RNA in the cell of the subject.

Embodiment A2. The method of embodiment A1, wherein the target protein is OPA1.

Embodiment A3. A method of increasing expression of OPA1 protein by a cell having an mRNA that contains a non-sense mediated RNA decay-inducing exon (NMD exon mRNA) and encodes OPA1 protein, the method comprising contacting the cell with an agent that binds to a targeted portion of the NMD exon mRNA encoding OPA1 protein, whereby the non-sense mediated RNA decay-inducing exon is excluded from the NMD exon mRNA encoding OPA1 protein, thereby increasing the level of mRNA encoding OPA1 protein, and increasing the expression of OPA1 protein in the cell.

Embodiment A4. The method of any one of embodiments A1 to A3, wherein the non-sense mediated RNA decay-inducing exon is spliced out from the NMD exon mRNA encoding the target protein or functional RNA.

Embodiment A5. The method of any one of embodiments A1 to A4, wherein the target protein does not comprise an amino acid sequence encoded by the non-sense mediated RNA decay-inducing exon.

Embodiment A6. The method of any one of embodiments A1 to A5, wherein the target protein is a full-length target protein.

Embodiment A7. The method of any one of embodiments A1 to A6, wherein the agent is an antisense oligomer (ASO) complementary to the targeted portion of the NMD exon mRNA.

Embodiment A8. The method of any one of embodiments A1 to A7, wherein the mRNA is pre-mRNA.

Embodiment A9. The method of any one of embodiments A1 to A8, wherein the contacting comprises contacting the therapeutic agent to the mRNA, wherein the mRNA is in a nucleus of the cell.

Embodiment A10. The method of any one of embodiments A1 to A9, wherein the target protein or the functional RNA corrects a deficiency in the target protein or functional RNA in the subject.

Embodiment A11. The method of any one of embodiments A1 to A10, wherein the cells are in or from a subject with a condition caused by a deficient amount or activity of an OPA1 protein.

Embodiment A12. The method of any one of embodiments A1 to A11, wherein the deficient amount of the target protein is caused by haploinsufficiency of the target protein, wherein the subject has a first allele encoding a functional target protein, and a second allele from which the target protein is not produced, or a second allele encoding a nonfunctional target protein, and wherein the antisense oligomer binds to a targeted portion of a NMD exon mRNA transcribed from the first allele.

Embodiment A13. The method of any one of embodiments A1 to A11, wherein the subject has a condition caused by a disorder resulting from a deficiency in the amount or function of the target protein, wherein the subject has (a) a first mutant allele from which
  (i) the target protein is produced at a reduced level compared to production from a wild-type allele,
  (ii) the target protein is produced in a form having reduced function compared to an equivalent wild-type protein, or
  (iii) the target protein is not produced, and
(b) a second mutant allele from which
  (i) the target protein is produced at a reduced level compared to production from a wild-type allele,
  (ii) the target protein is produced in a form having reduced function compared to an equivalent wild-type protein, or
  (iii) the target protein is not produced, and wherein when the subject has a first mutant allele (a) (iii), the second mutant allele is (b) (i) or (b) (ii) and wherein when the subject has a second mutant allele (b) (iii), the first mutant allele is (a) (i) or (a) (ii), and wherein the NMD exon mRNA is transcribed from either the first mutant allele that is (a) (i) or (a) (ii), and/or the second allele that is (b) (i) or (b) (ii).

Embodiment A14. The method of embodiment A13, wherein the target protein is produced in a form having reduced function compared to the equivalent wild-type protein.

Embodiment A15. The method of embodiment A13, wherein the target protein is produced in a form that is fully-functional compared to the equivalent wild-type protein.

Embodiment A16. The method of any one of embodiments A1 to A15, wherein the targeted portion of the NMD exon mRNA is within the non-sense mediated RNA decay-inducing exon.

Embodiment A17. The method of any one of embodiments A1 to A15, wherein the targeted portion of the NMD exon mRNA is either upstream or downstream of the non-sense mediated RNA decay-inducing exon.

Embodiment A18. The method of any one of embodiments A1 to A17, wherein the NMD exon mRNA comprises a sequence with at least about 80%, 85%, 90%, 95%, 97%, or 100% sequence identity to SEQ ID NO: 2 or 3.

Embodiment A19. The method of any one of embodiments A1 to A17, wherein the NMD exon mRNA is encoded by a genetic sequence with at least about 80%, 85%, 90%, 95%, 97%, or 100% sequence identity to SEQ ID NO: 1.

Embodiment A20. The method of any one of embodiments A1 to A17, wherein the targeted portion of the NMD exon mRNA comprises a sequence with at least 80%, 85%, 90%, 95%, 97%, or 100% sequence identity to a region comprising at least 8 contiguous nucleic acids of SEQ ID NO: 2 or 3.

Embodiment A21. The method of any one of embodiments A1 to A20, wherein the agent is an antisense oligomer (ASO) and wherein the ASO comprises a sequence that is at least about 80%, 85%, 90%, 95%, 97%, or 100% complementary to at least 8 contiguous nucleic acids of SEQ ID NO: 2 or 3.

Embodiment A22. The method of any one of embodiments A1 to A15, wherein the targeted portion of the NMD exon mRNA is within the non-sense mediated RNA decay-inducing exon 6x of OPA1, exon 7x of OPA1, or exon 28x of OPA1.

Embodiment A23. The method of any one of embodiments A1 to A15, wherein the targeted portion of the NMD exon mRNA is upstream or downstream of the non-sense mediated RNA decay-inducing exon 6x of OPA1, exon 7x of OPA1, or exon 28x of OPA1.

Embodiment A24. The method of any one of embodiments A1 to A15, wherein the targeted portion of the NMD exon mRNA comprises an exon-intron junction exon 6x of OPA1, exon 7x of OPA1, or exon 28x of OPA1.

Embodiment A25. The method of any one of embodiments A1 to A24, wherein the target protein produced is full-length protein, or wild-type protein.

Embodiment A26. The method of any one of embodiments A1 to A25, wherein the total amount of the mRNA encoding the target protein or functional RNA produced in the cell contacted with the antisense oligomer is increased about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to the total amount of the mRNA encoding the target protein or functional RNA produced in a control cell.

Embodiment A27. The method of any one of embodiments A1 to A25, wherein the total amount of the mRNA encoding the target protein or functional RNA produced in the cell contacted with the antisense oligomer is increased about 20% to about 300%, about 50% to about 300%, about 100% to about 300%, about 150% to about 300%, about 20% to about 50%, about 20% to about 100%, about 20% to about 150%, about 20% to about 200%, about 20% to about 250%, about 50% to about 100%, about 50% to about 150%, about 50% to about 200%, about 50% to about 250%, about 100% to about 150%, about 100% to about 200%, about 100% to about 250%, about 150% to about 200%, about 150% to about 250%, about 200% to about 250%, at least about 10%, at least about 20%, at least about 50%, at least about 100%, at least about 150%, at least about 200%, at least about 250%, or at least about 300%, compared to the total amount of the mRNA encoding the target protein or functional RNA produced in a control cell.

Embodiment A28. The method of one any of embodiments A1 to A25, wherein the total amount of target protein produced by the cell contacted with the antisense oligomer is increased about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to the total amount of target protein produced by a control cell.

Embodiment A29. The method of one any of embodiments A1 to A25, wherein the total amount of target protein produced by the cell contacted with the antisense oligomer is increased about 20% to about 300%, about 50% to about 300%, about 100% to about 300%, about 150% to about 300%, about 20% to about 50%, about 20% to about 100%, about 20% to about 150%, about 20% to about 200%, about 20% to about 250%, about 50% to about 100%, about 50% to about 150%, about 50% to about 200%, about 50% to about 250%, about 100% to about 150%, about 100% to about 200%, about 100% to about 250%, about 150% to about 200%, about 150% to about 250%, about 200% to about 250%, at least about 10%, at least about 20%, at least about 50%, at least about 100%, at least about 150%, at least about 200%, at least about 250%, or at least about 300%, compared to the total amount of target protein produced by a control cell.

Embodiment A30. The method of any one of embodiments A1 to 29, wherein the agent is an antisense oligomer (ASO) and wherein the antisense oligomer comprises a backbone modification comprising a phosphorothioate linkage or a phosphorodiamidate linkage.

Embodiment A31. The method of any one of embodiments A1 to A30, wherein the agent is an antisense oligomer (ASO) and wherein the antisense oligomer comprises a phosphorodiamidate morpholino, a locked nucleic acid, a peptide nucleic acid, a 2'-O-methyl, a 2'-Fluoro, or a 2'-O-methoxyethyl moiety.

Embodiment A32. The method of any one of embodiments A1 to A31, wherein the agent is an antisense oligomer (ASO) and wherein the antisense oligomer comprises at least one modified sugar moiety.

Embodiment A33. The method of embodiment A32, wherein each sugar moiety is a modified sugar moiety.

Embodiment A34. The method of any one of embodiments A1 to A33, wherein the agent is an antisense oligomer (ASO) and wherein the antisense oligomer consists of from 8 to 50 nucleobases, 8 to 40 nucleobases, 8 to 35 nucleobases, 8 to 30 nucleobases, 8 to 25 nucleobases, 8 to 20 nucleobases, 8 to 15 nucleobases, 9 to 50 nucleobases, 9 to 40 nucleobases, 9 to 35 nucleobases, 9 to 30 nucleobases, 9 to 25 nucleobases, 9 to 20 nucleobases, 9 to 15 nucleobases, 10 to 50 nucleobases, 10 to 40 nucleobases, 10 to 35 nucleobases, 10 to 30 nucleobases, 10 to 25 nucleobases, 10 to 20 nucleobases, 10 to 15 nucleobases, 11 to 50 nucleobases, 11 to 40 nucleobases, 11 to 35 nucleobases, 11 to 30 nucleobases, 11 to 25 nucleobases, 11 to 20 nucleobases, 11 to 15 nucleobases, 12 to 50 nucleobases, 12 to 40 nucleobases, 12 to 35 nucleobases, 12 to 30 nucleobases, 12 to 25 nucleobases, 12 to 20 nucleobases, or 12 to 15 nucleobases.

Embodiment A35. The method of any one of embodiments A1 to A34, wherein the agent is an antisense oligomer (ASO) and wherein the antisense oligomer is at least 80%, at least 85%, at least 90%, at least 95%, at least 98%, at least 99%, or 100%, complementary to the targeted portion of the NMD exon mRNA encoding the protein.

Embodiment A36. The method of any one of embodiments A1 to A35, wherein the method further comprises assessing OPA1 mRNA or protein expression.

Embodiment A37. The method of any one of embodiments A1 to A36, wherein Optic atrophy type 1 is treated and wherein the antisense oligomer binds to a targeted portion of an OPA1 NMD exon mRNA, wherein the targeted portion is within SEQ ID NO: 2 or 3.

Embodiment A38. The method of any one of embodiments A1 to A37, wherein the subject is a human.

Embodiment A39. The method of any one of embodiments A1 to A38, wherein the subject is a non-human animal.

Embodiment A40. The method of any one of embodiments A1 to A39, wherein the subject is a fetus, an embryo, or a child.

Embodiment A41. The method of any one of embodiments A1 to A40, wherein the cells are ex vivo.

Embodiment A42. The method of any one of embodiments A1 to A41, wherein the therapeutic agent is administered by intrathecal injection, intracerebroventricular injection, intraperitoneal injection, intramuscular injection, subcutaneous injection, or intravenous injection of the subject.

Embodiment A43. The method of any of embodiments A1 to A42, wherein the method further comprises administering a second therapeutic agent to the subject.

Embodiment A44. The method of embodiment A43, wherein the second therapeutic agent is a small molecule.

Embodiment A45. The method of embodiment A43, wherein the second therapeutic agent is an ASO.

Embodiment A46. The method of any one of embodiments A43 to A45, wherein the second therapeutic agent corrects intron retention.

Embodiment A47. An antisense oligomer as used in a method of any of embodiments A1 to A46.

Embodiment A48. An antisense oligomer comprising a sequence with at least about 80%, 85%, 90%, 95%, 97%, or 100% sequence identity to a region comprising at least 8 contiguous nucleic acids of SEQ ID NO: 2 or 3.

Embodiment A49. A pharmaceutical composition comprising the antisense oligomer of embodiment A47 or A48 and an excipient.

Embodiment A50. A method of treating a subject in need thereof, comprising administering the pharmaceutical composition of embodiment A49 to the subject, wherein the administering is by intravitreal injection, intrathecal injection, intracerebroventricular injection, intraperitoneal injection, intramuscular injection, subcutaneous injection, or intravenous injection.

Embodiment A51. A composition comprising a therapeutic agent for use in a method of increasing expression of a target protein or a functional RNA by cells to treat Optic atrophy type 1 in a subject in need thereof, associated with a deficient protein or deficient functional RNA, wherein the deficient protein or deficient functional RNA is deficient in amount or activity in the subject, wherein the target protein is:

(a) the deficient protein; or (b) a compensating protein which functionally augments or replaces the deficient protein or in the subject;

and wherein the functional RNA is:

(c) the deficient RNA; or (d) a compensating functional RNA which functionally augments or replaces the deficient functional RNA in the subject;

wherein the therapeutic agent enhances exclusion of the non-sense mediated RNA decay-inducing exon from the NMD exon mRNA encoding the target protein or functional RNA, thereby increasing production or activity of the target protein or the functional RNA in the subject.

Embodiment A52. A composition comprising a therapeutic agent for use in a method of treating a condition associated with OPA1 protein in a subject in need thereof, the method comprising the step of increasing expression of OPA1 protein by cells of the subject, wherein the cells have an mRNA that contains a non-sense mediated RNA decay-inducing exon (NMD exon mRNA) and encodes OPA1 protein, the method comprising contacting the cells with the therapeutic agent, whereby the non-sense mediated RNA decay-inducing exon is excluded from the NMD exon mRNA that encodes OPA1 protein, thereby increasing the level of mRNA encoding OPA1 protein, and increasing the expression of OPA1 protein in the cells of the subject.

Embodiment A53. The composition of embodiment A52, wherein the condition is a disease or disorder.

Embodiment A54. The composition of embodiment A53, wherein the disease or disorder is Optic atrophy type 1.

Embodiment A55. The composition of any one of embodiments A52 to 54, wherein the OPA1 protein and NMD exon mRNA are encoded by the OPA1 gene.

Embodiment A56. The composition of any one of embodiments A51 to A55, wherein the non-sense mediated RNA decay-inducing exon is spliced out from the NMD exon mRNA encoding the OPA1 protein.

Embodiment A57. The composition of any one of embodiments A51 to A56, wherein the OPA1 protein does not comprise an amino acid sequence encoded by the non-sense mediated RNA decay-inducing exon.

Embodiment A58. The composition of any one of embodiments A51 to A57, wherein the OPA1 protein is a full-length OPA1 protein.

Embodiment A59. The composition of any one of embodiments A51 to A58, wherein the therapeutic agent is an antisense oligomer (ASO) complementary to the targeted portion of the NMD exon mRNA.

Embodiment A60. The composition of any of embodiments A51 to A59, wherein the therapeutic agent is an antisense oligomer (ASO) and wherein the antisense oligomer targets a portion of the NMD exon mRNA that is within the non-sense mediated RNA decay-inducing exon.

Embodiment A61. The composition of any of embodiments A51 to A59, wherein the therapeutic agent is an antisense oligomer (ASO) and wherein the antisense oligomer targets a portion of the NMD exon mRNA that is upstream or downstream of the non-sense mediated RNA decay-inducing exon.

Embodiment A62. The composition of any one of embodiments A51 to A61, wherein the target protein is OPA1.

Embodiment A63. The composition of embodiment A62, wherein the NMD exon mRNA comprises a sequence with at least about 80%, 85%, 90%, 95%, 97%, or 100% sequence identity to SEQ ID NO: 2 or 3.

Embodiment A64. The composition of embodiment A62, wherein the NMD exon mRNA is encoded by a genetic sequence with at least about 80%, 85%, 90%, 95%, 97%, or 100% sequence identity to SEQ ID NO: 1.

Embodiment A65. The composition of embodiment A62, wherein the targeted portion of the NMD exon mRNA comprises a sequence with at least 80%, 85%, 90%, 95%, 97%, or 100% sequence identity to a region comprising at least 8 contiguous nucleic acids of SEQ ID NO: 2 or 3.

Embodiment A66. The composition of any one of embodiments A62 to A65, wherein the targeted portion of the NMD exon mRNA is within the non-sense mediated RNA decay-inducing exon 6x of OPA1, exon 7x of OPA1, or exon 28x of OPA1.

Embodiment A67. The composition of any one of embodiments A62 to A65, wherein the targeted portion of the NMD exon mRNA is upstream or downstream of the non-sense mediated RNA decay-inducing exon 6x of OPA1, exon 7x of OPA1, or exon 28x of OPA1.

Embodiment A68. The composition of any one of embodiments A62 to A65, wherein the targeted portion of the NMD exon mRNA comprises an exon-intron junction of exon 6x of OPA1, exon 7x of OPA1, or exon 28x of OPA1.

Embodiment A69. The composition of any one of embodiments A62 to A68, wherein the therapeutic agent is an antisense oligomer (ASO) and wherein the ASO comprises a sequence that is at least about 80%, 85%, 90%, 95%, 97%, or 100% complementary to a region comprising at least 8 contiguous nucleic acids of SEQ ID NO: 2 or 3.

Embodiment A70. The composition of any one of embodiments A51 to A69, wherein the mRNA encoding the target protein or functional RNA is a full-length mature mRNA, or a wild-type mature mRNA.

Embodiment A71. The composition of any one of embodiments A51 to A70, wherein the target protein produced is full-length protein, or wild-type protein.

Embodiment A72. The composition of any one of embodiments A51 to A71, wherein the therapeutic agent is an antisense oligomer (ASO) and wherein the antisense oligomer comprises a backbone modification comprising a phosphorothioate linkage or a phosphorodiamidate linkage.

Embodiment A73. The composition of any of embodiments A51 to A72, wherein the therapeutic agent is an antisense oligomer (ASO) and wherein said antisense oligomer is an antisense oligonucleotide.

Embodiment A74. The composition of any of embodiments A51 to A73, wherein the therapeutic agent is an antisense oligomer (ASO) and wherein the antisense oligomer comprises a phosphorodiamidate morpholino, a locked nucleic acid, a peptide nucleic acid, a 2'-O-methyl, a 2'-Fluoro, or a 2'-O-methoxyethyl moiety.

Embodiment A75. The composition of any of embodiments A51 to A74, wherein the therapeutic agent is an antisense oligomer (ASO) and wherein the antisense oligomer comprises at least one modified sugar moiety.

Embodiment A76. The composition of embodiment A75, wherein each sugar moiety is a modified sugar moiety.

Embodiment A77. The composition of any of embodiments A51 to A76, wherein the therapeutic agent is an antisense oligomer (ASO) and wherein the antisense oligomer consists of from 8 to 50 nucleobases, 8 to 40 nucleobases, 8 to 35 nucleobases, 8 to 30 nucleobases, 8 to 25 nucleobases, 8 to 20 nucleobases, 8 to 15 nucleobases, 9 to 50 nucleobases, 9 to 40 nucleobases, 9 to 35 nucleobases, 9 to 30 nucleobases, 9 to 25 nucleobases, 9 to 20 nucleobases, 9 to 15 nucleobases, 10 to 50 nucleobases, 10 to 40 nucleobases, 10 to 35 nucleobases, 10 to 30 nucleobases, 10 to 25 nucleobases, 10 to 20 nucleobases, 10 to 15 nucleobases, 11 to 50 nucleobases, 11 to 40 nucleobases, 11 to 35 nucleobases, 11 to 30 nucleobases, 11 to 25 nucleobases, 11 to 20 nucleobases, 11 to 15 nucleobases, 12 to 50 nucleobases, 12 to 40 nucleobases, 12 to 35 nucleobases, 12 to 30 nucleobases, 12 to 25 nucleobases, 12 to 20 nucleobases, or 12 to 15 nucleobases.

Embodiment A78. A pharmaceutical composition comprising the therapeutic agent of any of the compositions of embodiments A51 to A77, and an excipient.

Embodiment A79. A method of treating a subject in need thereof, comprising administering the pharmaceutical composition of embodiment A78 to the subject, wherein the administering is by intravitreal injection, intrathecal injection, intracerebroventricular injection, intraperitoneal injection, intramuscular injection, subcutaneous injection, or intravenous injection.

Embodiment A80. The method of any of embodiments A51 to A79, wherein the method further comprises administering a second therapeutic agent to the subject.

Embodiment A81. The method of embodiment A80, wherein the second therapeutic agent is a small molecule.

Embodiment A82. The method of embodiment A80, wherein the second therapeutic agent is an ASO.

Embodiment A83. The method of any one of embodiments A80 to A82, wherein the second therapeutic agent corrects intron retention.

Embodiment A84. A pharmaceutical composition comprising: an antisense oligomer that hybridizes to a target sequence of an OPA1 mRNA transcript, wherein the OPA1 mRNA transcript comprises a non-sense mediated RNA decay-inducing exon, wherein the antisense oligomer induces exclusion of the non-sense mediated RNA decay-inducing exon from the OPA1 mRNA transcript; and a pharmaceutical acceptable excipient.

Embodiment A85. The pharmaceutical composition of embodiment A84, wherein the OPA1 mRNA transcript is an OPA1 NMD exon mRNA transcript.

Embodiment A86. The pharmaceutical composition of embodiment A84 or A85, wherein the targeted portion of the NMD exon mRNA is within the non-sense mediated RNA decay-inducing exon 6x of OPA1, exon 7x of OPA1, or exon 28x of OPA1.

Embodiment A87. The pharmaceutical composition of embodiment A84 or A85, wherein the targeted portion of the NMD exon mRNA is upstream or downstream of the non-sense mediated RNA decay-inducing exon 6x of OPA1, exon 7x of OPA1, or exon 28x of OPA1.

Embodiment A88. The pharmaceutical composition of embodiment A84 or A85, wherein the targeted portion of the NMD exon mRNA comprises an exon-intron junction exon 6x of OPA1, exon 7x of OPA1, or exon 28x of OPA1.

Embodiment A89. The pharmaceutical composition of any one of embodiments A84 to A88, wherein the OPA1 NMD exon mRNA transcript is encoded by a genetic sequence with at least about 80%, 85%, 90%, 95%, 96%, 97%, 98%, 99% or 100% sequence identity to SEQ ID NO: 1.

Embodiment A90. The pharmaceutical composition of embodiment A84 or A88, wherein the OPA1 NMD exon mRNA transcript comprises a sequence with at least about 80%, 85%, 90%, 95%, 96%, 97%, 98%, 99% or 100% sequence identity to SEQ ID NO: 2 or 3.

Embodiment A91. The pharmaceutical composition of embodiment A84, wherein the antisense oligomer comprises a backbone modification comprising a phosphorothioate linkage or a phosphorodiamidate linkage.

Embodiment A92. The pharmaceutical composition of embodiment A84, wherein the antisense oligomer is an antisense oligonucleotide.

Embodiment A93. The pharmaceutical composition of embodiment A84, wherein the antisense oligomer comprises a phosphorodiamidate morpholino, a locked nucleic acid, a peptide nucleic acid, a 2'-O-methyl, a 2'-Fluoro, or a 2'-O-methoxyethyl moiety.

Embodiment A94. The pharmaceutical composition of embodiment A84, wherein the antisense oligomer comprises at least one modified sugar moiety.

Embodiment A95. The pharmaceutical composition of embodiment A84, wherein the antisense oligomer comprises from 8 to 50 nucleobases, 8 to 40 nucleobases, 8 to 35 nucleobases, 8 to 30 nucleobases, 8 to 25 nucleobases, 8 to 20 nucleobases, 8 to 15 nucleobases, 9 to 50 nucleobases, 9 to 40 nucleobases, 9 to 35 nucleobases, 9 to 30 nucleobases, 9 to 25 nucleobases, 9 to 20 nucleobases, 9 to 15 nucleobases, 10 to 50 nucleobases, 10 to 40 nucleobases, 10 to 35 nucleobases, 10 to 30 nucleobases, 10 to 25 nucleobases, 10 to 20 nucleobases, 10 to 15 nucleobases, 11 to 50 nucleobases, 11 to 40 nucleobases, 11 to 35 nucleobases, 11 to 30 nucleobases, 11 to 25 nucleobases, 11 to 20 nucleobases, 11 to 15 nucleobases, 12 to 50 nucleobases, 12 to 40 nucleobases, 12 to 35 nucleobases, 12 to 30 nucleobases, 12 to 25 nucleobases, 12 to 20 nucleobases, or 12 to 15 nucleobases.

Embodiment A96. The pharmaceutical composition of embodiment A84 or A85, wherein the antisense oligomer is at least 80%, at least 85%, at least 90%, at least 95%, at least 98%, at least 99%, or is 100% complementary to a targeted portion of the OPA1 NMD exon mRNA transcript.

Embodiment A97. The pharmaceutical composition of embodiment A84 or A85, wherein the targeted portion of the OPA1 NMD exon mRNA transcript is within SEQ ID NO: 2 or 3.

Embodiment A98. The pharmaceutical composition of embodiment A84, wherein the antisense oligomer comprises a nucleotide sequence that is at least about 80%, 85%, 90%, 91%, 92%, 93%, 94%, 95%, 96%, 97%, 98%, or 99% sequence identity to a region comprising at least 8 contiguous nucleic acids of SEQ ID NO: 2 or 3.

Embodiment A99. The pharmaceutical composition of embodiment A84, wherein the antisense oligomer comprises a nucleotide sequence that is identical a region comprising at least 8 contiguous nucleic acids SEQ ID NO: 2 or 3.

Embodiment A100. The pharmaceutical composition of any one of the embodiments A84 to A99, wherein the pharmaceutical composition is formulated for intravitreal injection, intrathecal injection, intracerebroventricular injection, intraperitoneal injection, intramuscular injection, subcutaneous injection, or intravenous injection.

Embodiment A101. The method of any of embodiments A84 to A100, wherein the method further comprises administering a second therapeutic agent to the subject.

Embodiment A102. The method of embodiment A101, wherein the second therapeutic agent is a small molecule.

Embodiment A103. The method of embodiment A101, wherein the second therapeutic agent is an ASO.

Embodiment A104. The method of any one of embodiments A101 to A103, wherein the second therapeutic agent corrects intron retention.

Embodiment A105. A method of inducing processing of a deficient OPA1 mRNA transcript to facilitate removal of a non-sense mediated RNA decay-inducing exon to produce a fully processed OPA1 mRNA transcript that encodes a functional form of an OPA1 protein, the method comprising:

(a) contacting an antisense oligomer to a target cell of a subject;
(b) hybridizing the antisense oligomer to the deficient OPA1 mRNA transcript, wherein the deficient OPA1 mRNA transcript is capable of encoding the functional form of an OPA1 protein and comprises at least one non-sense mediated RNA decay-inducing exon;
(c) removing the at least one non-sense mediated RNA decay-inducing exon from the deficient OPA1 mRNA transcript to produce the fully processed OPA1 mRNA transcript that encodes the functional form of OPA1 protein; and
(d) translating the functional form of OPA1 protein from the fully processed OPA1 mRNA transcript.

Embodiment A106. A method of treating a subject having a condition caused by a deficient amount or activity of OPA1 protein comprising administering to the subject an antisense oligomer comprising a nucleotide sequence with at least about 80%, 85%, 90%, 91%, 92%, 93%, 94%, 95%, 96%, 97%, 98%, or 99% sequence identity to a region comprising at least 8 contiguous nucleic acids of SEQ ID NO: 2 or 3.

Embodiment A107. A method of treating Optic atrophy type 1 in a subject in need thereof, by increasing the expression of a target protein or functional RNA by a cell of the subject, wherein the cell has an mRNA that contains a non-sense mediated RNA decay-inducing exon (NMD exon mRNA), and wherein the NMD exon mRNA encodes the target protein or functional RNA, the method comprising contacting the cell of the subject with a therapeutic agent that modulates splicing of the NMD exon mRNA encoding the target protein or functional RNA, whereby the non-sense mediated RNA decay-inducing exon is excluded from the NMD exon mRNA encoding the target protein or functional RNA, thereby increasing the level of mRNA encoding the target protein or functional RNA, and increasing the expression of the target protein or functional RNA in the cell of the subject.

Embodiment A108. A method of increasing expression of OPA1 protein by a cell having an mRNA that contains a non-sense mediated RNA decay-inducing exon (NMD exon mRNA) and encodes OPA1 protein, the method comprising contacting the cell with an agent that modulates splicing of the NMD exon mRNA encoding OPA1 protein, whereby the non-sense mediated RNA decay-inducing exon is excluded from the NMD exon mRNA encoding OPA1 protein, thereby increasing the level of mRNA encoding OPA1 protein, and increasing the expression of OPA1 protein in the cell.

Embodiment A109. The method of embodiment A107 or A108, wherein the agent (a) binds to a targeted portion of the NMD exon mRNA encoding the target protein or functional RNA;
(b) binds to one or more components of a spliceosome; or
(c) a combination of (a) and (b).

Embodiment B1. A method of modulating expression of a target protein, by a cell having an mRNA that comprises a non-sense mediated RNA decay-inducing exon (NMD exon) and encodes the target protein, the method comprising contacting a therapeutic agent to the cell, whereby the therapeutic agent modulates splicing of the NMD exon from the mRNA, thereby modulating level of processed mRNA encoding the target protein, and modulating the expression of the target protein in the cell, wherein the target protein is selected from the group consisting of: OPA1 proteins.

Embodiment B2. A method of treating a disease or condition in a subject in need thereof by modulating expression of a target protein in a cell of the subject, comprising: contacting the cell of the subject with a therapeutic agent that modulates splicing of a non-sense mediated mRNA decay-inducing exon (NMD exon) from an mRNA in the cell, wherein the mRNA comprises the NMD exon and encodes the target protein, thereby modulating level of processed mRNA encoding the target protein, and modulating expression of the target protein in the cell of the subject, wherein the target protein is selected from the group consisting of: OPA1 proteins.

Embodiment B3. The method of embodiment B1 or B2, wherein the therapeutic agent (a) binds to a targeted portion of the mRNA encoding the target protein;
(b) modulates binding of a factor involved in splicing of the NMD exon; or
(c) a combination of (a) and (b).

Embodiment B4. The method of embodiment B3, wherein the therapeutic agent interferes with binding of the factor involved in splicing of the NMD exon to a region of the targeted portion.

Embodiment B5. The method of embodiment B3 or B4, wherein the targeted portion is proximal to the NMD exon.

Embodiment B6. The method of any one of embodiments B3 to B5, wherein the targeted portion is at most about 1500 nucleotides, about 1000 nucleotides, about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides upstream of 5' end of the NMD exon.

Embodiment B7. The method of any one of embodiments B3 to B6, wherein the targeted portion is at least about 1500 nucleotides, about 1000 nucleotides, about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides, about 40 nucleotides, about 30 nucleotides, about 20 nucleotides, about 10 nucleotides, about 5 nucleotides, about 4 nucleotides, about 2 nucleotides, about 1 nucleotides upstream of 5' end of the NMD exon.

Embodiment B8. The method of any one of embodiments B3 to B5, wherein the targeted portion is at most about 1500 nucleotides, about 1000 nucleotides, about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides downstream of 3' end of the NMD exon.

Embodiment B9. The method of any one of embodiments B3 to B5 or B8, wherein the targeted portion is at least about 1500 nucleotides, about 1000 nucleotides, about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides, about 40 nucleotides, about 30 nucleotides, about 20 nucleotides, about 10 nucleotides, about 5 nucleotides, about 4 nucleotides, about 2 nucleotides, about 1 nucleotides downstream of 3' end of the NMD exon.

Embodiment B10. The method of any one of embodiments B3 to B5, wherein the targeted portion is at most about 1500 nucleotides, about 1000 nucleotides, about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides upstream of genomic site selected from the group consisting of: GRCh38/hg38: chr3 193628509; and GRCh38/hg38: chr3 193603500.

Embodiment B11. The method of any one of embodiments B3 to B5 or B10, wherein the targeted portion is about 1500 nucleotides, about 1000 nucleotides, about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides upstream of genomic site selected from the group consisting of: GRCh38/hg38: chr3 193628509; and GRCh38/hg38: chr3 193603500.

Embodiment B12. The method of any one of embodiments B3 to B5, wherein the targeted portion is at most about 1500 nucleotides, about 1000 nucleotides, about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides downstream of genomic site selected from the group consisting of: GRCh38/hg38: chr3 193628616; and GRCh38/hg38: chr3 193603557.

Embodiment B13. The method of any one of embodiments B3 to B5 or B12, wherein the targeted portion is about 1500 nucleotides, about 1000 nucleotides, about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides downstream of genomic site selected from the group consisting of: GRCh38/hg38: chr3 193628616; and GRCh38/hg38: chr3 193603557.

Embodiment B14. The method of any one of embodiments B3 to B13, wherein the targeted portion is located in an intronic region between two canonical exonic regions of the mRNA encoding the target protein, and wherein the intronic region contains the NMD exon.

Embodiment B15. The method of any one of embodiments B3 to B14, wherein the targeted portion at least partially overlaps with the NMD exon.

Embodiment B16. The method of any one of embodiments B3 to B15, wherein the targeted portion at least partially overlaps with an intron upstream or downstream of the NMD exon.

Embodiment B17. The method of any one of embodiments B3 to B16, wherein the targeted portion comprises 5' NMD exon-intron junction or 3' NMD exon-intron junction.

Embodiment B18. The method of any one of embodiments B3 to B16, wherein the targeted portion is within the NMD exon.

Embodiment B19. The method of any one of embodiments B1 to B18, wherein the targeted portion comprises about 5, 6, 7, 8, 9, 10, 11, 12, 13, 14, 15, 16, 17, 18, 19, 20, 21, 22, 23, 24, 25, 26, 27, 28, 29, 30, or more consecutive nucleotides of the NMD exon.

Embodiment B20. The method of any one of embodiments B1 to B19, wherein the mRNA encoding the target protein comprises a sequence with at least about 80%, 85%, 90%, 95%, 97%, or 100% sequence identity to SEQ ID NO: 4 or 5.

Embodiment B21. The method of any one of embodiments B1 to B20, wherein the mRNA encoding the target protein is encoded by a genetic sequence with at least about 80%, 85%, 90%, 95%, 97%, or 100% sequence identity to SEQ ID NO: 1.

Embodiment B22. The method of any one of embodiments B3 to B21, wherein the targeted portion of the mRNA comprises a sequence with at least 80%, 85%, 90%, 95%, 97%, or 100% sequence identity to a region comprising at least 8 contiguous nucleic acids of SEQ ID NO: 4 or 5.

Embodiment B23. The method of any one of embodiments B1 to B22, wherein the agent is an antisense oligomer (ASO) and wherein the ASO comprises a sequence that is at least about 80%, 85%, 90%, 95%, 97%, or 100% complementary to at least 8 contiguous nucleic acids of SEQ ID Ns: 4 or 5.

Embodiment B24. The method of any one of embodiments B3 to B23, wherein the targeted portion of the mRNA is within the non-sense mediated RNA decay-inducing exon selected from the group consisting of: GRCh38/hg38: chr3 193628509 193628616; and GRCh38/hg38: chr3 193603500 193603557.

Embodiment B25. The method of any one of embodiments B3 to B23, wherein the targeted portion of the mRNA is upstream or downstream of the non-sense mediated RNA decay-inducing exon selected from the group consisting of: GRCh38/hg38: chr3 193628509 193628616; and GRCh38/hg38: chr3 193603500 193603557.

Embodiment B26. The method of any one of embodiments B3 to B23, wherein the targeted portion of the mRNA comprises an exon-intron junction of exon selected from the group consisting of: GRCh38/hg38: chr3 193628509 193628616; and GRCh38/hg38: chr3 193603500 193603557.

Embodiment B27. The method of any one of embodiments B1 to B26, wherein the target protein produced is a full-length protein or a wild-type protein.

Embodiment B28. The method of any one of embodiments B1 to B27, wherein the therapeutic agent promotes exclusion of the NMD exon from the pre-mRNA encoding the target protein.

Embodiment B29. The method of embodiment B28, wherein exclusion of the NMD exon from the pre-mRNA encoding the target protein in the cell contacted with the therapeutic agent is increased by about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to exclusion of the NMD exon from the pre-mRNA encoding the target protein in a control cell.

Embodiment B30. The method of embodiment B28 or B29, wherein the therapeutic agent increases the level of the processed mRNA encoding the target protein in the cell.

Embodiment B31. The method of any one of embodiments B28 to B30, wherein the level of the processed mRNA encoding the target protein produced in the cell contacted with the therapeutic agent is increased by about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to a level of the processed mRNA encoding the target protein in a control cell.

Embodiment B32. The method of any one of embodiments B28 to B31, wherein the therapeutic agent increases the expression of the target protein in the cell.

Embodiment B33. The method of any one of embodiments B28 to B32, wherein a level of the target protein produced in the cell contacted with the therapeutic agent is increased by about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to a level of the target protein produced in a control cell.

Embodiment B34. The method of any one of embodiments B2 to B33, wherein the disease or condition is induced by a loss-of-function mutation in the target protein.

Embodiment B35. The method of embodiment B34, wherein the disease or condition is associated with haploinsufficiency of a gene encoding the target protein, and wherein the subject has a first allele encoding a functional target protein, and a second allele from which the target protein is not produced or produced at a reduced level, or a second allele encoding a nonfunctional target protein or a partially functional target protein.

Embodiment B36. The method of any one of embodiments B2 to B35, wherein the disease or condition is selected from the group consisting of: Optic atrophy type 1.

Embodiment B37. The method of any one of embodiments B34 to B36, wherein the therapeutic agent promotes exclusion of the NMD exon from the pre-mRNA encoding the target protein and increases the expression of the target protein in the cell.

Embodiment B38. The method of any one of embodiments B1 to B27, wherein the therapeutic agent inhibits exclusion of the NMD exon from the pre-mRNA encoding the target protein.

Embodiment B39. The method of embodiment B38, wherein exclusion of the NMD exon from the pre-mRNA encoding the target protein in the cell contacted with the therapeutic agent is decreased by about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to exclusion of the NMD exon from the pre-mRNA encoding the target protein in a control cell.

Embodiment B40. The method of embodiment B38 or B39, wherein the therapeutic agent decreases the level of the processed mRNA encoding the target protein in the cell.

Embodiment B41. The method of any one of embodiments B38 to B40, wherein the level of the processed mRNA encoding the target protein in the cell contacted with the therapeutic agent is decreased by about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to a level of the processed mRNA encoding the target protein in a control cell.

Embodiment B42. The method of any one of embodiments B38 to B41, wherein the therapeutic agent decreases the expression of the target protein in the cell.

Embodiment B43. The method of any one of embodiments B38 to B42, wherein a level of the target protein produced in the cell contacted with the therapeutic agent is decreased by about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to a level of the target protein produced in a control cell.

Embodiment B44. The method of any one of embodiments B2 to B27 or B38 to B43, wherein the disease or condition is induced by a gain-of-function mutation in the target protein Embodiment B45. The method of embodiment B44, wherein the subject has an allele from which the target protein is produced at an increased level, or an allele encoding a mutant target protein that exhibits increased activity in the cell.

Embodiment B46. The method of embodiment B44 or B45, wherein the therapeutic agent inhibits exclusion of the NMD exon from the pre-mRNA encoding the target protein and decreases the expression of the target protein in the cell.

Embodiment B47. The method of any one of embodiments B1 to B46, wherein the therapeutic agent is an antisense oligomer (ASO) and wherein the antisense oligomer comprises a backbone modification comprising a phosphorothioate linkage or a phosphorodiamidate linkage.

Embodiment B48. The method of any one of embodiments B1 to B47, wherein the therapeutic agent is an antisense oligomer (ASO) and wherein the antisense oligomer comprises a phosphorodiamidate morpholino, a locked nucleic acid, a peptide nucleic acid, a 2'-O-methyl, a 2'-Fluoro, or a 2'-O-methoxyethyl moiety.

Embodiment B49. The method of any one of embodiments B1 to B48, wherein the therapeutic agent is an antisense oligomer (ASO) and wherein the antisense oligomer comprises at least one modified sugar moiety.

Embodiment B50. The method of embodiment B49, wherein each sugar moiety is a modified sugar moiety.

Embodiment B51. The method of any one of embodiments B1 to B50, wherein the therapeutic agent is an antisense oligomer (ASO) and wherein the antisense oligomer consists of from 8 to 50 nucleobases, 8 to 40 nucleobases, 8 to 35 nucleobases, 8 to 30 nucleobases, 8 to 25 nucleobases, 8 to 20 nucleobases, 8 to 15 nucleobases, 9 to 50 nucleobases, 9 to 40 nucleobases, 9 to 35 nucleobases, 9 to 30 nucleobases, 9 to 25 nucleobases, 9 to 20 nucleobases, 9 to 15 nucleobases, 10 to 50 nucleobases, 10 to 40 nucleobases, 10 to 35 nucleobases, 10 to 30 nucleobases, 10 to 25 nucleobases, 10 to 20 nucleobases, 10 to 15 nucleobases, 11 to 50 nucleobases, 11 to 40 nucleobases, 11 to 35 nucleobases, 11 to 30 nucleobases, 11 to 25 nucleobases, 11 to 20 nucleobases, 11 to 15 nucleobases, 12 to 50 nucleobases, 12 to 40 nucleobases, 12 to 35 nucleobases, 12 to 30 nucleobases, 12 to 25 nucleobases, 12 to 20 nucleobases, or 12 to 15 nucleobases.

Embodiment B52. The method of any one of embodiments B3 to B51, wherein the therapeutic agent is an antisense oligomer (ASO) and wherein the antisense oligomer is at least 80%, at least 85%, at least 90%, at least 95%, at least 98%, at least 99%, or 100%, complementary to the targeted portion of the mRNA.

Embodiment B53. The method of any one of embodiments B1 to B52, wherein the method further comprises assessing mRNA level or expression level of the target protein.

Embodiment B54. The method of any one of embodiments B1 to B53, wherein the subject is a human.

Embodiment B55. The method of any one of embodiments B1 to B53, wherein the subject is a non-human animal.

Embodiment B56. The method of any one of embodiments B2 to B54, wherein the subject is a fetus, an embryo, or a child.

Embodiment B57. The method of any one of embodiments B1 to B56, wherein the cells are ex vivo.

Embodiment B58. The method of any one of embodiments B2 to B56, wherein the therapeutic agent is administered by intravitreal injection, intrathecal injection, intracerebroventricular injection, intraperitoneal injection, intramuscular injection, subcutaneous injection, intravitreal, or intravenous injection of the subject.

Embodiment B59. The method of any one of embodiments B2 to B56 or B58, wherein the method further comprises administering a second therapeutic agent to the subject.

Embodiment B60. The method of any one of embodiments B1 to B59, wherein the second therapeutic agent is a small molecule.

Embodiment B61. The method of any one of embodiments B1 to B59, wherein the second therapeutic agent is an antisense oligomer.

Embodiment B62. The method of any one of embodiments B1 to B61, wherein the second therapeutic agent corrects intron retention.

Embodiment B63. The method of any one of embodiments B2 to B62, wherein the disease or condition is Optic atrophy type 1.

Further Specific Embodiments

Embodiment 1. A method of modulating expression of an OPA1 protein in a cell having a pre-mRNA that is transcribed from an OPA1 gene and that comprises a non-sense mediated RNA decay-inducing exon (NMD exon), the method comprising contacting an agent or a vector encoding the agent to the cell, whereby the agent modulates splicing of the NMD exon from the pre-mRNA, thereby modulating a level of processed mRNA that is processed from the pre-mRNA, and modulating the expression of the OPA1 protein in the cell, wherein the agent comprises an antisense oligomer with at least 80% sequence identity to a sequence selected from the group consisting of SEQ ID NOs: 6-275 and 280-299.

Embodiment 2. The method of embodiment 1, wherein the agent:

(a) binds to a targeted portion of the pre-mRNA;

(b) modulates binding of a factor involved in splicing of the NMD exon; or (c) a combination of (a) and (b).

Embodiment 3. The method of embodiment 2, wherein the agent interferes with binding of the factor involved in splicing of the NMD exon to a region of the targeted portion Embodiment 4. The method of embodiment 2, wherein the targeted portion of the pre-mRNA is proximal to the NMD exon.

Embodiment 5. The method of embodiment 2, wherein the targeted portion of the pre-mRNA is at most about 1500 nucleotides, about 1000 nucleotides, about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides upstream of 5' end of the NMD exon.

Embodiment 6. The method of embodiment 2, wherein the targeted portion of the pre-mRNA is at least about 1500 nucleotides, about 1000 nucleotides, about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides, about 40 nucleotides, about 30 nucleotides, about 20 nucleotides, about 10 nucleotides, about 5 nucleotides, about 4 nucleotides, about 2 nucleotides, about 1 nucleotides upstream of 5' end of the NMD exon.

Embodiment 7. The method of embodiment 2, wherein the targeted portion of the pre-mRNA is at most about 1500 nucleotides, about 1000 nucleotides, about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides downstream of 3' end of the NMD exon.

Embodiment 8. The method of embodiment 2, wherein the targeted portion of the pre-mRNA is at least about 1500 nucleotides, about 1000 nucleotides, about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides, about 40 nucleotides, about 30 nucleotides, about 20 nucleotides, about 10 nucleotides, about 5 nucleotides, about 4 nucleotides, about 2 nucleotides, about 1 nucleotides downstream of 3' end of the NMD exon.

Embodiment 9. The method of embodiment 2, wherein the targeted portion of the pre-mRNA is at most about 1500 nucleotides, about 1000 nucleotides, about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides upstream of genomic site GRCh38/hg38: chr3 193628509.

Embodiment 10. The method of embodiment 2, wherein the targeted portion of the pre-mRNA is about 1500 nucleotides, about 1000 nucleotides, about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides upstream of genomic site GRCh38/hg38: chr3 193628509.

Embodiment 11. The method of embodiment 2, wherein the targeted portion of the pre-mRNA is at most about 1500 nucleotides, about 1000 nucleotides, about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides downstream of genomic site GRCh38/hg38: chr3 193628616.

Embodiment 12. The method of embodiment 2, wherein the targeted portion of the pre-mRNA is about 1500 nucleotides, about 1000 nucleotides, about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides downstream of genomic site GRCh38/hg38: chr3 193628616.

Embodiment 13. The method of embodiment 2, wherein the targeted portion of the pre-mRNA is located in an intronic region between two canonical exonic regions of the pre-mRNA, and wherein the intronic region contains the NMD exon.

Embodiment 14. The method of embodiment 2, wherein the targeted portion of the pre-mRNA at least partially overlaps with the NMD exon.

Embodiment 15. The method of embodiment 2, wherein the targeted portion of the pre-mRNA at least partially overlaps with an intron upstream or downstream of the NMD exon.

Embodiment 16. The method of embodiment 2, wherein the targeted portion of the pre-mRNA comprises 5' NMD exon-intron junction or 3' NMD exon-intron junction.

Embodiment 17. The method of embodiment 2, wherein the targeted portion of the pre-mRNA is within the NMD exon.

Embodiment 18. The method of embodiment 2, wherein the targeted portion of the pre-mRNA comprises about 5, 6, 7, 8, 9, 10, 11, 12, 13, 14, 15, 16, 17, 18, 19, 20, 21, 22, 23, 24, 25, 26, 27, 28, 29, 30, or more consecutive nucleotides of the NMD exon.

Embodiment 19. The method of any one of embodiments 1 to 18, wherein the NMD exon comprises a sequence with at least 80%, at least 90%, or 100% sequence identity to SEQ ID NO: 279.

Embodiment 20. The method of any one of embodiments 1 to 18, wherein the NMD exon comprises a sequence of SEQ ID NO: 279.

Embodiment 21. The method of embodiment 2, wherein the targeted portion of the pre-mRNA is within the non-sense mediated RNA decay-inducing exon GRCh38/hg38: chr3 193628509 to 193628616.

Embodiment 22. The method of embodiment 2, wherein the targeted portion of the pre-mRNA is upstream or downstream of the non-sense mediated RNA decay-inducing exon GRCh38/hg38: chr3 193628509 to 193628616.

Embodiment 23. The method of embodiment 2, wherein the targeted portion of the pre-mRNA comprises an exon-intron junction of exon GRCh38/hg38: chr3 193628509 to 193628616.

Embodiment 24. The method of any one of embodiments 1 to 23, wherein the OPA1 protein expressed from the processed mRNA is a full-length OPA1 protein or a wild-type OPA1 protein.

Embodiment 25. The method of any one of embodiments 1 to 23, wherein the OPA1 protein expressed from the processed mRNA is a functional OPA1 protein.

Embodiment 26. The method of any one of embodiments 1 to 23, wherein the OPA1 protein expressed from the processed mRNA is at least partially functional as compared to a wild-type OPA1 protein.

Embodiment 27. The method of any one of embodiments 1 to 23, wherein the OPA1 protein expressed from the processed mRNA is at least partially functional as compared to a full-length wild-type OPA1 protein.

Embodiment 28. The method of any one of embodiments 1 to 23, or 25 to 27, wherein the OPA1 protein expressed from the processed mRNA is an OPA1 protein that lacks an amino acid sequence encoded by a nucleic acid sequence with at least 80% sequence identity to SEQ ID NO: 277.

Embodiment 29. The method of any one of embodiments 1 to 28, wherein the method promotes exclusion of the NMD exon from the pre-mRNA.

Embodiment 30. The method of embodiment 29, wherein the exclusion of the NMD exon from the pre-mRNA in the cell contacted with the agent is increased by about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to in the absence of the agent.

Embodiment 31. The method of any one of embodiments 1 to 30, wherein the method results in an increase in the level of the processed mRNA in the cell.

Embodiment 32. The method of embodiment 31, wherein the level of the processed mRNA in the cell contacted with the agent is increased by about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to in the absence of the agent.

Embodiment 33. The method of any one of embodiments 1 to 32, wherein the method results in an increase in the expression of the OPA1 protein in the cell.

Embodiment 34. The method of embodiment 33, wherein a level of the OPA1 protein expressed from the processed mRNA in the cell contacted with the agent is increased by about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to in the absence of the agent.

Embodiment 35. The method of any one of embodiments 1 to 34, wherein the agent comprises an antisense oligomer with at least 80%, at least 90%, or 100% sequence identity to a sequence selected from the group consisting of SEQ ID NOs: 36, 236, 242, 250, 280-283, 288, and 290-292.

Embodiment 36. The method of any one of embodiments 1 to 34, wherein the agent further comprises a gene editing molecule.

Embodiment 37. The method of embodiment 36, wherein the gene editing molecule comprises CRISPR-Cas9.

Embodiment 38. A method of modulating expression of an OPA1 protein in a cell having a pre-mRNA that is transcribed from an OPA1 gene, wherein the pre-mRNA comprises a coding exon, the method comprising contacting an agent or a vector encoding the agent to the cell, whereby the agent promotes exclusion of the coding exon from the pre-mRNA, thereby increasing a level of a processed mRNA that is processed from the pre-mRNA and that lacks the coding exon in the cell.

Embodiment 39. The method of embodiment 38, wherein the agent:

(a) binds to a targeted portion of the pre-mRNA;

(b) modulates binding of a factor involved in splicing of the coding exon; or (c) a combination of (a) and (b).

Embodiment 40. The method of embodiment 39, wherein the agent interferes with binding of the factor involved in splicing of the coding exon to a region of the targeted portion.

Embodiment 41. The method of embodiment 39, wherein the targeted portion of the pre-mRNA is proximal to the coding exon.

Embodiment 42. The method of embodiment 39, wherein the targeted portion of the pre-mRNA is located in an intronic region immediately upstream of the coding exon.

Embodiment 43. The method of embodiment 39, wherein the targeted portion of the pre-mRNA is within a region spanning from 100 to 50, from 90 to 50, from 80 to 50, from 70 to 50, from 60 to 50, from 60 to 40, from 60 to 30, from 60 to 20, from 60 to 10, from 49 to 1, from 39 to 1, from 29 to 1, or from 19 to 1 nucleotides upstream of 5' end of the coding exon.

Embodiment 44. The method of embodiment 39, wherein the targeted portion of the pre-mRNA is within a region spanning from 49 to 1, from 39 to 1, from 29 to 1, or from 19 to 1 nucleotides upstream of 5' end of the coding exon.

Embodiment 45. The method of embodiment 39, wherein the targeted portion of the pre-mRNA is located in an intronic region immediately downstream of the coding exon.

Embodiment 46. The method of embodiment 39, wherein the targeted portion of the pre-mRNA is within a region spanning from 1 to 49, from 1 to 39, from 1 to 29, from 1 to 19, from 10 to 60, from 20 to 60, from 30 to 60, from 40 to 60, from 50 to 60, from 50 to 70, from 50 to 80, from 50 to 90, or from 50 to 100 nucleotides downstream of 3' end of the coding exon.

Embodiment 47. The method of embodiment 39, wherein the targeted portion of the pre-mRNA is within a region spanning from 1 to 49, from 1 to 39, from 1 to 29, or from 1 to 19 nucleotides downstream of 3' end of the coding exon.

Embodiment 48. The method of embodiment 39, wherein the targeted portion of the pre-mRNA at least partially overlaps with the coding exon.

Embodiment 49. The method of embodiment 39, wherein the targeted portion of the pre-mRNA at least partially overlaps with an intron immediately upstream or immediately downstream of the coding exon.

Embodiment 50. The method of embodiment 39, wherein the targeted portion of the pre-mRNA comprises 5' coding exon-intron junction or 3' coding exon-intron junction.

Embodiment 51. The method of embodiment 39, wherein the targeted portion is within the coding exon of the pre-mRNA.

Embodiment 52. The method of any one of embodiments 39 to 51, wherein the coding exon is an alternatively spliced exon.

Embodiment 53. The method of any one of embodiments 39 to 52, wherein the coding exon comprises a sequence with at least 80%, at least 90%, or 100% sequence identity to SEQ ID NO: 277.

Embodiment 54. The method of any one of embodiments 39 to 52, wherein the coding exon comprises SEQ ID NO: 277.

Embodiment 55. The method of embodiment 39, wherein the targeted portion of the pre-mRNA is immediately upstream of the coding exon GRCh38/hg38: chr3 193626092 to 193626202.

Embodiment 56. The method of embodiment 39, wherein the targeted portion of the pre-mRNA is within a region spanning from 49 to 1, from 39 to 1, from 29 to 1, or from 19 to 1 nucleotides upstream of genomic site GRCh38/hg38: chr3 193626092.

Embodiment 57. The method of embodiment 39, wherein the targeted portion of the pre-mRNA is immediately downstream of the coding exon GRCh38/hg38: chr3 193626092 to 193626202.

Embodiment 58. The method of embodiment 39, wherein the targeted portion of the pre-mRNA is within a region spanning from 1 to 49, from 1 to 39, from 1 to 29, or from 1 to 19 nucleotides downstream of genomic site GRCh38/hg38: chr3 193626202.

Embodiment 59. The method of embodiment 39, wherein the targeted portion of the pre-mRNA is within the coding exon GRCh38/hg38: chr3 193626092 to 193626202.

Embodiment 60. The method of embodiment 39, wherein the targeted portion of the pre-mRNA comprises an exon-intron junction of exon GRCh38/hg38: chr3 193626092 to 193626202.

Embodiment 61. The method of embodiment 39, wherein the targeted portion comprises about 5, 6, 7, 8, 9, 10, 11, 12, 13, 14, 15, 16, 17, 18, 19, 20, 21, 22, 23, 24, 25, 26, 27, 28, 29, 30, or more consecutive nucleotides of the coding exon.

Embodiment 62. The method of embodiment 39, wherein the targeted portion of the pre-mRNA comprises a sequence with at least 80%, 85%, 90%, 95%, 97%, or 100% sequence identity to a region comprising at least 8 contiguous nucleic acids of SEQ ID NO: 277.

Embodiment 63. The method of any one of embodiments 38 to 62, wherein the exclusion of the coding exon from the pre-mRNA in the cell contacted with the agent is increased by about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to in the absence of the agent.

Embodiment 64. The method of any one of embodiments 38 to 63, wherein the method results in an increase in expression of the OPA1 protein in the cell.

Embodiment 65. The method of embodiment 64, wherein a level of the OPA1 protein expressed from the processed mRNA in the cell contacted with the agent is increased by about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to in the absence of the agent.

Embodiment 66. The method of embodiment 64, wherein a level of the OPA1 protein expressed from the processed mRNA in the cell contacted with the agent is increased by at least about 1.5-fold compared to in the absence of the agent.

Embodiment 67. The method of any one of embodiments 64 to 66, wherein the OPA1 protein expressed from the processed mRNA is a functional OPA1 protein.

Embodiment 68. The method of any one of embodiments 64 to 66, wherein the OPA1 protein expressed from the processed mRNA is at least partially functional as compared to a wild-type OPA1 protein.

Embodiment 69. The method of any one of embodiments 64 to 66, wherein the OPA1 protein expressed from the processed mRNA is at least partially functional as compared to a full-length wild-type OPA1 protein.

Embodiment 70. The method of any one of embodiments 64 to 69, wherein the OPA1 protein expressed from the processed mRNA comprises fewer proteolytic cleavage sites than an OPA1 protein encoded by a corresponding mRNA containing the coding exon.

Embodiment 71. The method of any one of embodiments 38 to 70, wherein the agent promotes exclusion of a nonsense mediated RNA decay-inducing exon (NMD exon) from the pre-mRNA.

Embodiment 72. The method of embodiment 71, wherein the NMD exon comprises a sequence with at least 80%, at least 90%, or 100% sequence identity to SEQ ID NO: 279.

Embodiment 73. The method of embodiment 71, wherein the NMD exon comprises a sequence of SEQ ID NO: 279.

Embodiment 74. The method of any one of embodiments 64 to 73, wherein the OPA1 protein expressed from the processed mRNA comprises fewer proteolytic cleavage sites than an OPA1 protein encoded by a corresponding mRNA containing the coding exon.

Embodiment 75. The method of any one of embodiments 38 to 74, wherein the agent comprises an antisense oligomer with at least 80%, at least 90%, or 100% sequence identity to a sequence selected from the group consisting of SEQ ID NOs: 227-242, 250, 280-283, 288, and 290-292.

Embodiment 76. The method of any one of embodiments 38 to 74, wherein the agent comprises a gene editing molecule.

Embodiment 77. The method of embodiment 76, wherein the gene editing molecule comprises CRISPR-Cas9.

Embodiment 78. A method of modulating expression of an OPA1 protein in a cell having a pre-mRNA that is transcribed from an OPA1 gene, wherein the pre-mRNA comprises a coding exon, the method comprising contacting an agent or a vector encoding the agent to the cell, wherein the agent comprises an antisense oligomer that binds to:

(a) a targeted portion of the pre-mRNA within an intronic region immediately upstream of a 5' end of the coding exon of the pre-mRNA; or (b) a targeted portion of the pre-mRNA within an intronic region immediately downstream of a 3' end of the coding exon of the pre-mRNA;

whereby the agent increases a level of a processed mRNA that is processed from the pre-mRNA and that contains the coding exon in the cell.

Embodiment 79. The method of embodiments 78, wherein the coding exon is an alternatively spliced exon.

Embodiment 80. The method of embodiments 78 or 79, wherein the method promotes inclusion of the coding exon in the processed mRNA during splicing of the pre-mRNA in the cell.

Embodiment 81. The method of any one of embodiments 78 to 80, wherein the target portion of the pre-mRNA is within a region spanning from 100 to 50, from 100 to 60, from 100 to 70, from 100 to 80, or from 100 to 90 nucleotides upstream of a 5' end of the coding exon.

Embodiment 82. The method of any one of embodiments 78 to 80, wherein the target portion of the pre-mRNA is within a region spanning from 40 to 100, from 50 to 100, from 60 to 100, from 70 to 100, from 80 to 100, or from 90 to 100 nucleotides downstream of a 3' end of the coding exon.

Embodiment 83. The method of any one of embodiments 78 to 80, wherein the coding exon comprises a sequence with at least 80%, at least 90%, or 100% sequence identity to SEQ ID NO: 277.

Embodiment 84. The method of any one of embodiments 78 to 80, wherein the coding exon comprises SEQ ID NO: 277.

Embodiment 85. The method of any one of embodiments 78 to 80, wherein the targeted portion of the pre-mRNA is within a region spanning from 100 to 50, from 100 to 60, from 100 to 70, from 100 to 80, or from 100 to 90 nucleotides upstream of genomic site GRCh38/hg38: chr3 193626092.

Embodiment 86. The method of any one of embodiments 78 to 80, wherein the targeted portion of the pre-mRNA is within a region spanning from 40 to 100, from 50 to 100, from 60 to 100, from 70 to 100, from 80 to 100, or from 90 to 100 nucleotides downstream of genomic site GRCh38/hg38: chr3 193626202.

Embodiment 87. The method of any one of embodiments 78 to 86, wherein the inclusion of the coding exon in the processed mRNA in the cell contacted with the agent is increased by about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to in the absence of the agent.

Embodiment 88. The method of any one of embodiments 78 to 87, wherein the agent comprises an antisense oligomer with at least 80%, at least 90%, or 100% sequence identity to SEQ ID NO: 267.

Embodiment 89. A method of modulating expression of a target protein in a cell having a pre-mRNA transcribed from a gene that encodes the target protein, wherein the pre-mRNA comprises a coding exon and a non-sense mediated RNA decay-inducing exon (NMD exon), the method comprising contacting an agent or a vector encoding the agent to the cell, wherein the agent promotes exclusion of both the coding exon and the NMD exon from the pre-mRNA, thereby increasing a level of a processed mRNA that is processed from the pre-mRNA and that lacks both the NMD exon and the coding exon in the cell.

Embodiment 90. The method of embodiment 89, wherein the agent:

(a) binds to a targeted portion of the pre-mRNA;

(b) modulates binding of a factor involved in splicing of the coding exon, the NMD exon, or both; or (c) a combination of (a) and (b).

Embodiment 91. The method of embodiment 90, wherein the agent interferes with binding of the factor involved in splicing of the coding exon, the NMD exon, or both, to a region of the targeted portion.

Embodiment 92. The method of any one of embodiments 89 to 91, wherein the NMD exon is within an intronic region adjacent to the coding exon.

Embodiment 93. The method of embodiment 92, wherein the NMD exon is within an intronic region immediately upstream of the coding exon.

Embodiment 94. The method of embodiment 92, wherein the NMD exon is within an intronic region immediately downstream of the coding exon.

Embodiment 95. The method of any one of embodiments 90 to 94, wherein the targeted portion of the pre-mRNA is proximal to the coding exon.

Embodiment 96. The method of any one of embodiments 90 to 94, wherein the targeted portion of the pre-mRNA is located in an intronic region immediately upstream of the coding exon.

Embodiment 97. The method of any one of embodiments 90 to 94, wherein the targeted portion of the pre-mRNA is located in an intronic region immediately downstream of the coding exon.

Embodiment 98. The method of any one of embodiments 90 to 94, wherein the targeted portion of the pre-mRNA is located within the coding exon.

Embodiment 99. The method of any one of embodiments 90 to 94, wherein the targeted portion of the pre-mRNA is within a region spanning from 49 to 1, from 39 to 1, from 29 to 1, or from 19 to 1 nucleotides upstream of 5' end of the coding exon.

Embodiment 100. The method of any one of embodiments 90 to 94, wherein the targeted portion of the pre-mRNA is within a region spanning from 100 nucleotides upstream of the coding exon to 100 nucleotides downstream of the coding exon.

Embodiment 101. The method of any one of embodiments 89 to 100, wherein the coding exon is an alternatively spliced exon.

Embodiment 102. The method of any one of embodiments 89 to 101, wherein the coding exon comprises a sequence with at least 80%, at least 90%, or 100% sequence identity to SEQ ID NO: 277.

Embodiment 103. The method of any one of embodiments 89 to 101, wherein the coding exon comprises SEQ ID NO: 277.

Embodiment 104. The method of embodiment 90, wherein the targeted portion of the pre-mRNA is immediately upstream of the coding exon GRCh38/hg38: chr3 193626092 to 193626202.

Embodiment 105. The method of embodiment 90, wherein the targeted portion of the pre-mRNA is immediately downstream of the coding exon GRCh38/hg38: chr3 193626092 to 193626202.

Embodiment 106. The method of any one of embodiments 90 to 94, wherein the targeted portion of the pre-mRNA is within a region spanning from 49 to 1, from 39 to 1, from 29 to 1, or from 19 to 1 nucleotides upstream of GRCh38/hg38: chr3 193626092.

Embodiment 107. The method of embodiment 90, wherein the targeted portion of the pre-mRNA is within a region spanning from 100 nucleotides upstream of genomic site GRCh38/hg38: chr3 193626092. to 100 nucleotides downstream of genomic site GRCh38/hg38: chr3 193626202.

Embodiment 108. The method of embodiment 90, wherein the targeted portion of the pre-mRNA is within the coding exon GRCh38/hg38: chr3 193626092 to 193626202.

Embodiment 109. The method of embodiment 90, wherein the targeted portion of the pre-mRNA comprises an exon-intron junction of the coding exon GRCh38/hg38: chr3 193626092 to 193626202.

Embodiment 110. The method of embodiment 90, wherein the targeted portion comprises about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more consecutive nucleotides of the coding exon.

Embodiment 111. The method of embodiment 90, wherein the targeted portion of the pre-mRNA is proximal to the NMD exon.

Embodiment 112. The method of embodiment 90, wherein the targeted portion of the pre-mRNA is located in an intronic region immediately upstream of the NMD exon.

Embodiment 113. The method of embodiment 90, wherein the targeted portion of the pre-mRNA is located in an intronic region immediately downstream of the NMD exon.

Embodiment 114. The method of embodiment 90, wherein the targeted portion of the pre-mRNA is located within the NMD exon.

Embodiment 115. The method of embodiment 90, wherein the targeted portion of the pre-mRNA is within a region spanning from 100 nucleotides upstream of the NMD exon to 100 nucleotides downstream of the NMD exon.

Embodiment 116. The method of any one of embodiments 89 to 115, wherein the NMD exon comprises a sequence with at least 80%, at least 90%, or 100% sequence identity to SEQ ID NO: 279.

Embodiment 117. The method of embodiment 89, wherein the NMD exon comprises SEQ ID NO: 279.

Embodiment 118. The method of embodiment 90, wherein the targeted portion of the pre-mRNA is immediately upstream of the NMD exon GRCh38/hg38: chr3 193628509 to 193628616.

Embodiment 119. The method of embodiment 90, wherein the targeted portion of the pre-mRNA is immediately downstream of the NMD exon GRCh38/hg38: chr3 193628509 to 193628616.

Embodiment 120. The method of embodiment 90, wherein the targeted portion of the pre-mRNA is within a region spanning from 100 nucleotides upstream of genomic site GRCh38/hg38: chr3 193628509 to 100 nucleotides downstream of genomic site GRCh38/hg38: chr3 193628616.

Embodiment 121. The method of embodiment 90, wherein the targeted portion of the pre-mRNA is within the NMD exon GRCh38/hg38: chr3 193628509 to 193628616.

Embodiment 122. The method of embodiment 90, wherein the targeted portion of the pre-mRNA comprises an exon-intron junction of the NMD exon GRCh38/hg38: chr3 193628509 to 193628616.

Embodiment 123. The method of embodiment 90, wherein the targeted portion comprises about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more consecutive nucleotides of the NMD exon.

Embodiment 124. The method of any one of embodiments 89 to 123, wherein the exclusion of the coding exon from the pre-mRNA in the cell contacted with the agent is increased by about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to in the absence of the agent.

Embodiment 125. The method of any one of embodiments 89 to 124, wherein the exclusion of the NMD exon from the pre-mRNA in the cell contacted with the agent is increased by about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to in the absence of the agent.

Embodiment 126. The method of any one of embodiments 89 to 125, wherein the agent results in an increase in the level of the processed mRNA in the cell.

Embodiment 127. The method of embodiment 126, wherein the level of the processed mRNA in the cell contacted with the agent is increased by about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to in the absence of the agent.

Embodiment 128. The method of any one of embodiments 89 to 127, wherein the method results in an increase in expression of the target protein in the cell.

Embodiment 129. The method of embodiment 128, wherein a level of the target protein expressed from the processed mRNA in the cell contacted with the agent is increased by about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to in the absence of the agent.

Embodiment 130. The method of any one of embodiments 89 to 128, wherein the target protein is an OPA1 protein.

Embodiment 131. The method of embodiment 130, wherein a level of the OPA1 protein expressed from the processed mRNA in the cell contacted with the agent is increased by at least about 1.5-fold compared to in the absence of the agent.

Embodiment 132. The method of embodiment 130, wherein the OPA1 protein expressed from the processed mRNA is a functional OPA1 protein.

Embodiment 133. The method of embodiment 130, wherein the OPA1 protein expressed from the processed mRNA is at least partially functional as compared to a wild-type OPA1 protein.

Embodiment 134. The method of embodiment 130, wherein the OPA1 protein expressed from the processed mRNA is at least partially functional as compared to a full-length wild-type OPA1 protein.

Embodiment 135. The method of any one of embodiments 89 to 127, wherein the agent comprises an antisense oligomer with at least 80%, at least 90%, or 100% sequence identity to a sequence selected from the group consisting of SEQ ID NOs: 236, 242, 250, 280-283, 288, and 290-292.

Embodiment 136. The method of any one of embodiments 78 to 135, wherein the agent comprises a gene editing molecule.

Embodiment 137. The method of embodiment 136, wherein the gene editing molecule comprises CRISPR-Cas9.

Embodiment 138. The method of any one of embodiments 1 to 75 or 78 to 135, wherein the agent is an antisense oligomer (ASO) and wherein the antisense oligomer comprises a backbone modification comprising a phosphorothioate linkage or a phosphorodiamidate linkage.

Embodiment 139. The method of any one of embodiments 1 to 75 or 78 to 138, wherein the agent is an antisense oligomer (ASO) and wherein the antisense oligomer comprises a phosphorodiamidate morpholino, a locked nucleic acid, a peptide nucleic acid, a 2'-O-methyl moiety, a 2'-Fluoro moiety, or a 2'-O-methoxyethyl moiety.

Embodiment 140. The method of any one of embodiments 1 to 75 or 78 to 139, wherein the therapeutic agent is an antisense oligomer (ASO) and wherein the antisense oligomer comprises at least one modified sugar moiety.

Embodiment 141. The method of embodiment 140, wherein each sugar moiety is a modified sugar moiety.

Embodiment 142. The method of any one of embodiments 1 to 75 or 78 to 141, wherein the agent is an antisense oligomer (ASO) and wherein the antisense oligomer consists of from 8 to 50 nucleobases, 8 to 40 nucleobases, 8 to 35 nucleobases, 8 to 30 nucleobases, 8 to 25 nucleobases, 8 to 20 nucleobases, 8 to 15 nucleobases, 9 to 50 nucleobases, 9 to 40 nucleobases, 9 to 35 nucleobases, 9 to 30 nucleobases, 9 to 25 nucleobases, 9 to 20 nucleobases, 9 to 15 nucleobases, 10 to 50 nucleobases, 10 to 40 nucleobases, 10 to 35 nucleobases, 10 to 30 nucleobases, 10 to 25 nucleobases, 10 to 20 nucleobases, 10 to 15 nucleobases, 11 to 50 nucleobases, 11 to 40 nucleobases, 11 to 35 nucleobases, 11 to 30 nucleobases, 11 to 25 nucleobases, 11 to 20 nucleobases, 11 to 15 nucleobases, 12 to 50 nucleobases, 12 to 40 nucleobases, 12 to 35 nucleobases, 12 to 30 nucleobases, 12 to 25 nucleobases, 12 to 20 nucleobases, or 12 to 15 nucleobases.

Embodiment 143. The method of any one of embodiments 1 to 142, wherein the vector comprises a viral vector encoding the agent.

Embodiment 144. The method of embodiment 143, wherein the viral vector comprises an adenoviral vector, adeno-associated viral (AAV) vector, lentiviral vector, Herpes Simplex Virus (HSV) viral vector, or retroviral vector.

Embodiment 145. The method of any one of embodiments 1 to 144, wherein the method further comprises assessing mRNA level or expression level of the OPA1 protein.

Embodiment 146. The method of any one of embodiments 1 to 145, wherein the agent is a therapeutic agent.

Embodiment 147. A pharmaceutical composition comprising the therapeutic agent of embodiment 146 or a vector encoding the therapeutic agent of embodiment 146, and a pharmaceutically acceptable excipient.

Embodiment 148. A pharmaceutical composition, comprising a therapeutic agent or a vector encoding a therapeutic agent, and a pharmaceutically acceptable excipient, wherein the therapeutic agent comprises an antisense oligomer with at least 80% sequence identity to a sequence selected from the group consisting of SEQ ID NOs: 6-275 and 280-299.

Embodiment 149. The pharmaceutical composition of embodiment 148, wherein the therapeutic agent comprises an antisense oligomer with at least 80%, at least 90%, or 100% sequence identity to a sequence selected from the group consisting of SEQ ID NOs: 227-242 and 250.

Embodiment 150. The pharmaceutical composition of embodiment 148, wherein the therapeutic agent comprises an antisense oligomer with at least 80%, at least 90%, or 100% sequence identity to SEQ ID NO: 267.

Embodiment 151. The pharmaceutical composition of embodiment 148, wherein the therapeutic agent comprises an antisense oligomer with at least 80%, at least 90%, or 100% sequence identity to a sequence selected from the group consisting of SEQ ID NOs: 36, 236, 242, 250, and 280-299.

Embodiment 152. A composition, comprising an antisense oligomer with at least 80% sequence identity to a sequence selected from the group consisting of SEQ ID NOs: 6-275 and 280-299, wherein the antisense oligomer comprises a backbone modification, a sugar moiety modification, or a combination thereof.

Embodiment 153. The composition of embodiment 152, wherein the antisense oligomer has at least 80%, at least 90%, or 100% sequence identity to a sequence selected from the group consisting of SEQ ID NOs: 227-242 and 250.

Embodiment 154. The composition of embodiment 152, wherein the antisense oligomer has at least 80%, at least 90%, or 100% sequence identity to SEQ ID NO: 267.

Embodiment 155. The composition of embodiment 152, wherein the antisense oligomer has at least 80%, at least 90%, or 100% sequence identity to a sequence selected from the group consisting of SEQ ID NOs: 36, 236, 242, 250, and 280-299.

Embodiment 156. A pharmaceutical composition, comprising a therapeutic agent or a vector encoding the therapeutic agent, and a pharmaceutically acceptable excipient, wherein the therapeutic agent promotes exclusion of a coding exon from a pre-mRNA, thereby increasing a level of a processed mRNA that is processed from the pre-mRNA and that lacks the coding exon in a cell, wherein the pre-mRNA is transcribed from an OPA1 gene and that comprises the coding exon.

Embodiment 157. A pharmaceutical composition, comprising a therapeutic agent or a vector encoding the therapeutic agent, and a pharmaceutically acceptable excipient, wherein the therapeutic agent comprises an antisense oligomer that binds to a pre-mRNA that is transcribed from an OPA1 gene in a cell, wherein the antisense oligomer binds to:

(a) a targeted portion of the pre-mRNA within an intronic region immediately upstream of a 5' end of the coding exon of the pre-mRNA; or (b) a targeted portion of the pre-mRNA within an intronic region immediately downstream of a 3' end of the coding exon of the pre-mRNA;

whereby the therapeutic agent increases a level of a processed mRNA that is processed from the pre-mRNA and that contains the coding exon in the cell.

Embodiment 158. A pharmaceutical composition, comprising a therapeutic agent or a vector encoding the therapeutic agent, and a pharmaceutically acceptable excipient, wherein the therapeutic agent promotes exclusion of both a coding exon and a non-sense mediated RNA decay-inducing exon (NMD exon) from a pre-mRNA, thereby increasing a level of a processed mRNA that is processed from the pre-mRNA and that lacks the coding exon and the NMD exon in a cell, wherein the pre-mRNA is transcribed from an OPA1 gene in the cell and comprises the coding exon and the NMD exon.

Embodiment 159. The pharmaceutical composition of any one of embodiments 147 to 158, wherein the pharmaceutical composition is formulated for intracerebroventricular injection, intraperitoneal injection, intramuscular injection, intrathecal injection, subcutaneous injection, oral administration, synovial injection, intravitreal administration, subretinal injection, topical application, implantation, or intravenous injection.

Embodiment 160. The pharmaceutical composition of any one of embodiments 147 to 158, wherein the pharmaceutical composition is formulated for intravitreal injection.

Embodiment 161. The pharmaceutical composition of any one of embodiments 147 to 160, wherein the pharmaceutical composition further comprises a second therapeutic agent.

Embodiment 162. The pharmaceutical composition of embodiment 161, wherein the second therapeutic agent comprises a small molecule.

Embodiment 163. The pharmaceutical composition of embodiment 161, wherein the second therapeutic agent comprises an antisense oligomer.

Embodiment 164. The pharmaceutical composition of embodiment 161, wherein the second therapeutic agent corrects intron retention.

Embodiment 165. The pharmaceutical composition or composition of any one of embodiments 147 to 160, wherein the antisense oligomer is selected from the group consisting of Compound ID NOs: 1-303.

Embodiment 166. A method of treating or reducing the likelihood of developing a disease or condition in a subject in need thereof by modulating expression of an OPA1 protein in a cell of the subject, comprising contacting to cells of the subject the therapeutic agent of any one of embodiments 147 to 165.

Embodiment 167. The method of embodiment 166, wherein the disease or condition is associated with a loss-of-function mutation in an OPA1 gene.

Embodiment 168. The method of embodiment 166 or 167, wherein the disease or condition is associated with haploinsufficiency of the OPA1 gene, and wherein the subject has a first allele encoding a functional OPA1 protein, and a second allele from which the OPA1 protein is not produced or produced at a reduced level, or a second allele encoding a nonfunctional OPA1 protein or a partially functional OPA1 protein.

Embodiment 169. The method of any one of embodiments 166 to 168, wherein the disease or condition comprises an eye disease or condition.

Embodiment 170. The method of any one of embodiments 166 to 168, wherein the disease or condition comprises ADOA-plus syndrome; a mitochondrial disorder; glaucoma; normal tension glaucoma; Charcot-Marie-Tooth disease; mitochondria dysfunction; diabetic retinopathy; age-related macular degeneration; retinal ganglion cell death; mitochondrial fission-mediated mitochondrial dysfunction; progressive external ophthalmoplegia; deafness; ataxia; motor neuropathy; sensory neuropathy; myopathy; Behr syndrome; brain dysfunction; encephalopathy; peripheral neuropathy; fatal infantile mitochondrial encephalomyopathy; hypertrophic cardiomyopathy; spastic ataxic syndrome; sensory motor peripheral neuropathy; hypotonia; gastrointestinal dysmotility and dysphagia; optic atrophy; optic atrophy plus syndrome; Mitochondrial DNA depletion syndrome 14; late-onset cardiomyopathy; diabetic cardiomyopathy; Alzheimer's Disease; focal segmental glomerulosclerosis; kidney disease; Huntington's Disease; cognitive function decline in healthy aging; Prion diseases; late onset dementia and parkinsonism; mitochondrial myopathy; Leigh syndrome; Friedreich's ataxia; Parkinson's disease; MELAS (Mitochondrial encephalomyopathy, lactic acidosis, and stroke-like episodes); pyruvate dehydrogenase complex deficiency; chronic kidney disease; Leber's hereditary optic neuropathy; obesity; age-related systemic neurodegeneration; skeletal muscle atrophy; heart and brain ischemic damage; or massive liver apoptosis.

Embodiment 171. The method of any one of embodiments 166 to 168, wherein the disease or condition comprises Optic atrophy type 1.

Embodiment 172. The method of any one of embodiments 166 to 168, wherein the disease or condition comprises autosomal dominant optic atrophy (ADOA).

Embodiment 173. The method of embodiment 166 or 167, wherein the disease or condition is associated with an autosomal recessive mutation of OPA1 gene, wherein the subject has a first allele encoding from which:

(i) OPA1 protein is not produced or produced at a reduced level compared to a wild-type allele; or (ii) the OPA1 protein produced is nonfunctional or partially functional compared to a wild-type allele, and a second allele from which:

(iii) the OPA1 protein is produced at a reduced level compared to a wild-type allele and the OPA1 protein produced is at least partially functional compared to a wild-type allele; or (iv) the OPA1 protein produced is partially functional compared to a wild-type allele.

Embodiment 174. The method of any one of embodiments 166 to 173, wherein the subject is a human.

Embodiment 175. The method of any one of embodiments 166 to 173, wherein the subject is a non-human animal.

Embodiment 176. The method of any one of embodiments 166 to 173, wherein the subject is a fetus, an embryo, or a child.

Embodiment 177. The method of any one of embodiments 166 to 173, wherein the cells are ex vivo.

Embodiment 178. The method of any one of embodiments 166 to 173, wherein the therapeutic agent is administered by intracerebroventricular injection, intraperitoneal injection, intramuscular injection, intrathecal injection, subcutaneous injection, oral administration, synovial injection, intravitreal administration, subretinal injection, topical application, implantation, or intravenous injection.

Embodiment 179. The method of any one of embodiments 166 to 173, wherein the therapeutic agent is administered by intravitreal injection.

Embodiment 180. The method of any one of embodiments 166 to 179, wherein the method treats the disease or condition.

EXAMPLES

The present disclosure will be more specifically illustrated by the following Examples. However, it should be understood that the present disclosure is not limited by these examples in any manner.

Figure 2:
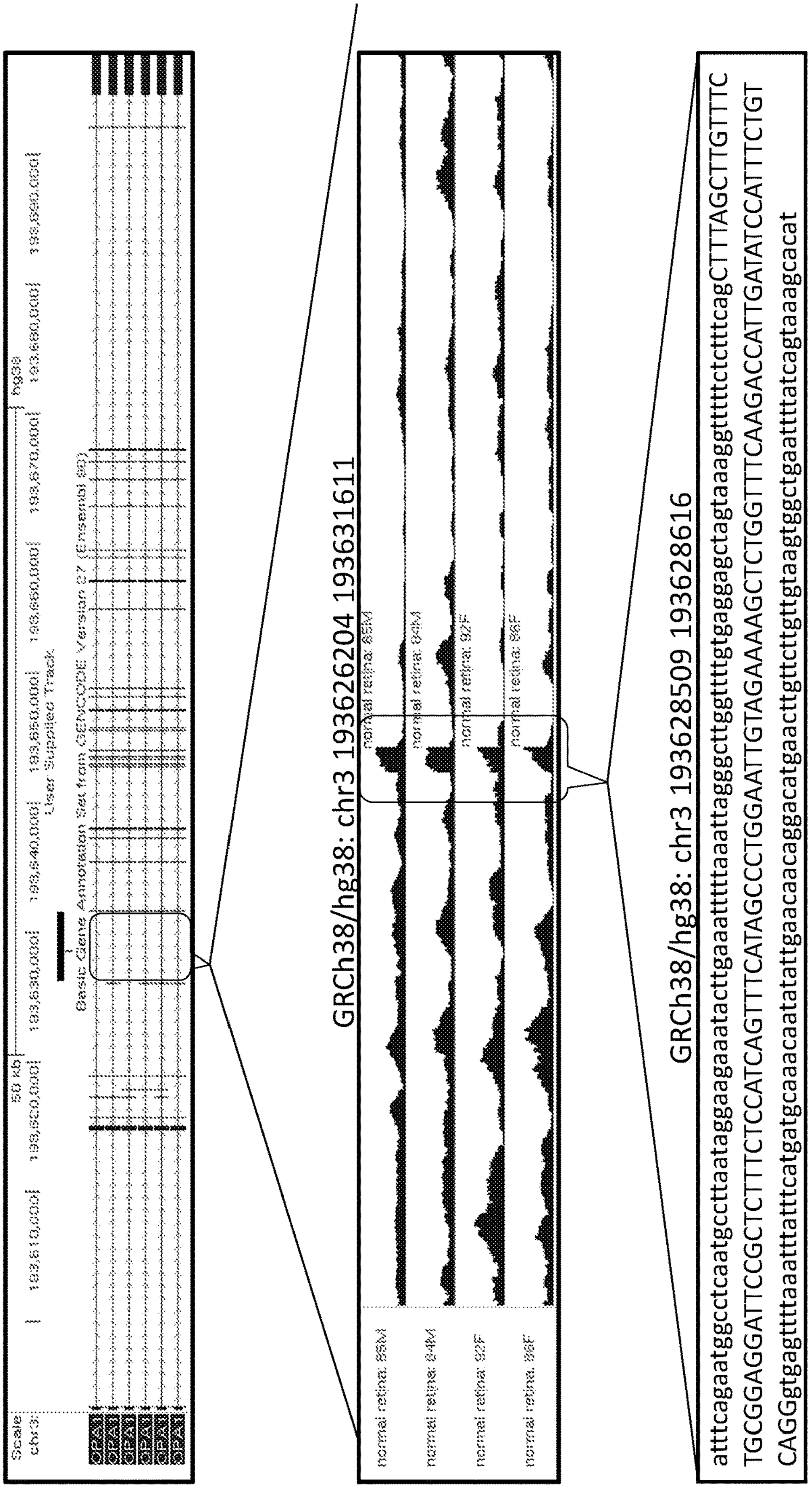
FIG. 2 depicts identification of an exemplary nonsense-mediated mRNA decay (NMD)-inducing exon in the OPA1 gene. The identification of the NMD-inducing exon in the OPA1 gene using RNA sequencing is shown, visualized in the UCSC genome browser. The upper panel shows a graphic representation of the OPA1 gene to scale. Peaks corresponding to RNA sequencing reads were identified in intron GRCh38/hg38: chr3 193626204 to 193631611, shown in the middle panel. Bioinformatic analysis identified an exon-like sequence (bottom panel, sequence highlighted in uppercase; GRCh38/hg38: chr3 193628509 to 193628616) flanked by 3' and 5' splice sites. Inclusion of this exon leads to the introduction of a premature termination codon rendering the transcript a target of NMD.
Figure 3:
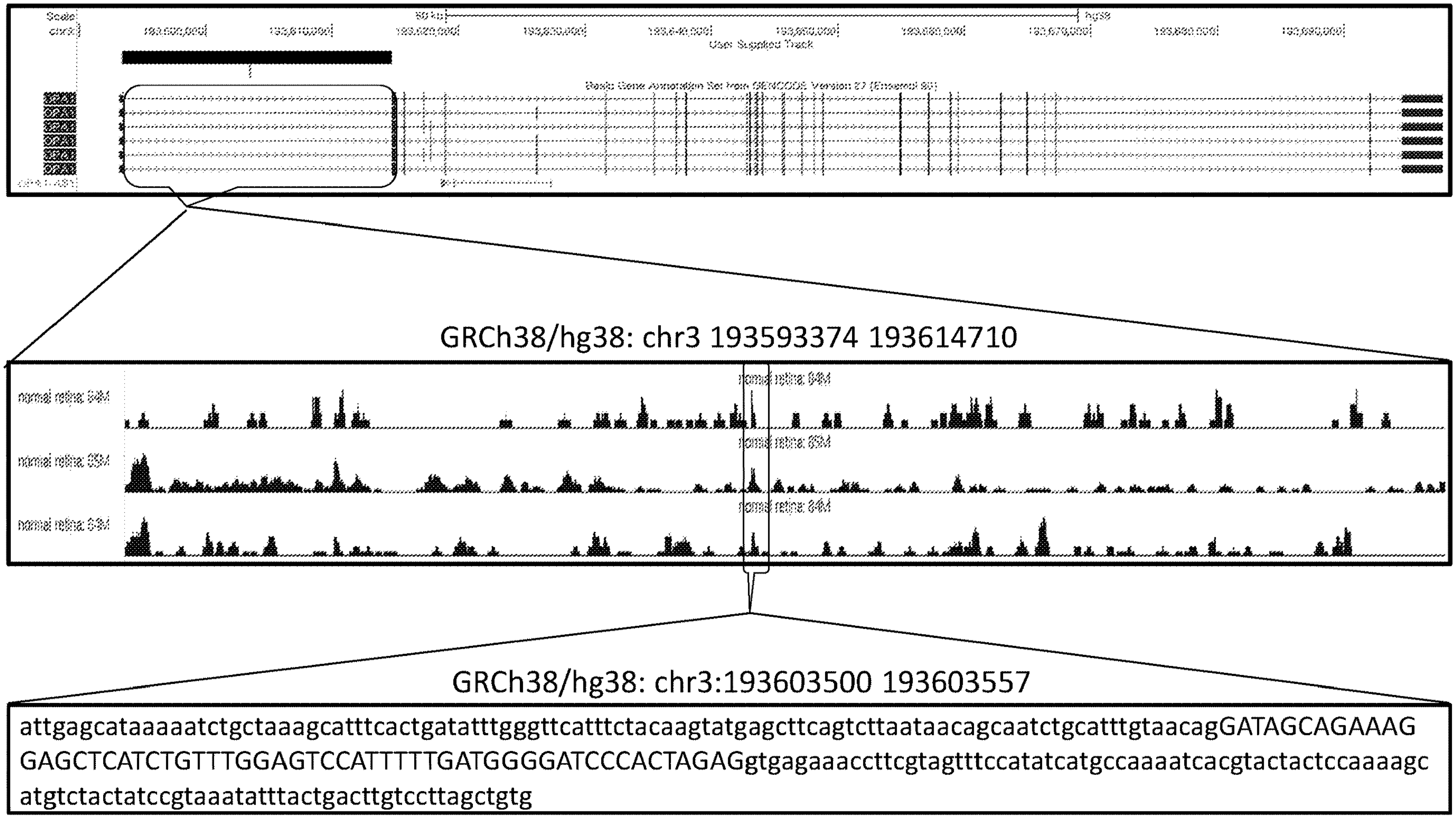
FIG. 3 depicts identification of an exemplary nonsense-mediated mRNA decay (NMD)-inducing exon in the OPA1 gene. The identification of the NMD-inducing exon in the OPA1 gene using RNA sequencing is shown, visualized in the UCSC genome browser. The upper panel shows a graphic representation of the OPA1 gene to scale. Peaks corresponding to RNA sequencing reads were identified in intron GRCh38/hg38: chr3 193593374 to 193614710, shown in the middle panel. Bioinformatic analysis identified an exon-like sequence (bottom panel, sequence highlighted in uppercase; GRCh38/hg38: chr3 193603500 to 193603557) flanked by 3' and 5' splice sites. Inclusion of this exon leads to the introduction of a premature termination codon rendering the transcript a target of NMD.

Example 1: Identification of NMD-Inducing Exon Inclusion Events in Transcripts by RNAseq Using Next Generation Sequencing Whole transcriptome shotgun sequencing is carried out using next generation sequencing to reveal a snapshot of transcripts produced by the genes described herein to identify NMD exon inclusion events. For this purpose, poly A+ RNA from nuclear and cytoplasmic fractions of human cells is isolated and cDNA libraries are constructed using Illumina's TruSeq Stranded mRNA library Prep Kit. The libraries are pair-end sequenced resulting in 100-nucleotide reads that are mapped to the human genome (February 2009, GRCh37/hg19 assembly). FIGS. 2 and 3 depict identification of different exemplary nonsense-mediated mRNA decay (NMD)-inducing exons in various genes.

Exemplary genes and intron sequences are summarized in Table 1 and Table 2 (SEQ ID NOs indicate the corresponding nucleotide sequences represented by the Gene ID Nos). The sequence for each intron is summarized in Table 3 and Table 4. Table 5 lists sequences of OPA1 antisense oligomers of this disclosure.

TABLE 1

List of exemplary target gene sequences.

| Gene Symbol | Gene ID No. | SEQ ID No. | Disease | OMIM | Genetics | Introns |
|---|---|---|---|---|---|---|
| OPA1 | 4976 | 1 | Optic atrophy type 1; Autosomal dominant optic atrophy (ADOA) | 165500 | Haploinsufficient | ENST00000361908.7: 6<br>ENST00000361908.7: 28 |

TABLE 2

List of exemplary target gene sequences.

| Gene Symbol | Gene ID No. | SEQ ID No. | Disease | OMIM | Genetics | Introns |
|---|---|---|---|---|---|---|
| OPA1 | 4976 | 1 | Optic atrophy type 1; Autosomal dominant optic atrophy (ADOA) | 165500 | Haploinsufficient | GRCh38/hg38: chr3193626203193631611<br>GRCh38/hg38: chr3193593374193614710 |

TABLE 3

Sequences of exemplary target introns in pre-mRNA transcripts.

| Gene | SEQ ID NO. | Intron |
|---|---|---|
| OPA1 | 2 | Intron 6:<br>gtgatggatggtttaaggggctaccgatacattcacactaatcagccatttctgccaagatcatgtcacctcaatctgt<br>tcatggactccaaatacaagaaattaatttgacaaagtgaaaatataaaagatgcatcatataaatatgtaacttttctgg<br>agtgggtagtataggtaaagccaaaagaaacaaattcaagcagaggaattttggtttctgaaaattaggttgtctgtag<br>ggtccctgtatttatacttagaacaaaattaggaatttctgtttatgtggtccagttattgagtcaccctaagtttgtaggca<br>tcttacctacctacttgctccccaagtttttatttctaaaatgaaaagcattgctgtagatgaccagtttacactaaagaata<br>acatttatttatttgttttagctaaagtatatggacagggaacattcatattcttgtagaagaaaattattttgacttttgggca<br>aaagcatgtagttcttatacactttgacaaactcattgcgtacatttttcacattaatcaaagtcagcacaaataaattttca<br>ccttggaccacggagggtttgaacactggaaatttgatataattctggttgctaaagaacaagttctaataaaagcttaa<br>gtgtataccaatatgtggctgttggtgcaatcagcaggtccgtaaaaatatgattttaatggttaggtaatcccacaacg<br>gagatcccaaagttcatgtttggaagagacttttgggtcaaagtgaaatcagtgtaatgaatttaaaattatactctgaga<br>tcttgaaatcagctaattatgttacatcttattagctcagaaaagttttgaagttatatacaaatgctagtcaggaaaaaag<br>attcagtcatgtaattcttgtacattctactatttaaatcaaccaatattatagattatgatttagtgcagtaattctgctggct |

TABLE 3-continued

Sequences of exemplary target introns in pre-mRNA transcripts.

| Gene | SEQ ID NO. | Intron |
|---|---|---|
| | | aaccttatctcatttggtggtggttagtacttcagagtactcaccatagtttcatttatgttttcagcatcacttcctggtttttc |
| | | tcaattccatggctgtggaatcaattcatatgtatatttagcttcggtgagcaaaaacatagctagaaaaagaaaagaa |
| | | gtgagtttcctacctggttaaattaaagtcgatgtgttaagccaaggaggacttcttttgaatggtactttaacaatccctg |
| | | ttctgtatactgtgaatatatcatttaaatagcctaataaattggatgcttaggctgagccacctatactttagttttgttatg |
| | | gaaagaagggagaggagcaagtatgttcttatatgttacttagaaataagaatgtagctgtagttacacattgttcttaa |
| | | gtttttttcgtaagacaacttgaaatgagtcccataggcctgctatttaacattctaagatatgacttaaggttaatgatga |
| | | gcttttgaatctgacaattcaagagatatccataatgaatactgattcatttctacattgctgaaagctaatgttcattttaa |
| | | gcctactttagtagcctttatttgggcttagagatgttattcctctttctgatatttattgggttatctgtttaacccttttatatct |
| | | ccctttcccgatttgtaaattagagactggcaagactttttaccctgagtagagcaccaaacatggcttgtttctgcccac |
| | | actgtagttaccttgaggggaagtaaatgggactttaaaagcaatttatgctcttttatagtgaaattatccctcttactatc |
| | | ccgaaagactgttaccttacaatatcctccactcctttcccccctgtagttactatagagatgacttttcggttcttcactgcc |
| | | ataatgatcaaaatcctaattcatgagatttttatcattccaggcatgtgaggtttacttgatgcataaaaccgcaagtact |
| | | ttttgttgtttttaattgtttttctctcttatcttcttgaaagtctaagtagatcatcattttgatgtcttattagtagcaactaat |
| | | aaattttccctgtatcttctcagcaaaagaactcaagcagagacagaagattagaactaccattggtagttttgcttccta |
| | | tggatatgttcacatacatagaaattttacaatgaccttttatatatgtatttcagaatttcagaatggcctcaatgcctta |
| | | ataggaagaaatacttgaaattttaaattagggcttggttttgtgaggagctagtaaaggtttttctctttcagctttagctt |
| | | gtttctgcggaggattccgctctttctccatcagtttcatagccctggaattgtagaaaagctctggtttcaagaccattg |
| | | atatccatttctgtcagggtgagttttaaatttatttcatgatgcaaacaatatattgaacaacaggacatgaacttgttctt |
| | | gttgtaagtggctgaattttatcagtaaagcacatcaaaataaaatataccccaattgctagttaagacctagagtgaca |
| | | gattgaaaatagcttgtgttattctcttaagaaaatatataaaaattatcatctcatcaatctttaatgtttgttttataaatcta |
| | | aatgtttttatattgtttcctaggaaatattaggtctaatttttactttaccaccagctgtcttttatttactcttttttgagacg |
| | | gagtttcgctcttgttgcttaggctagagtgcagtggcactatctcagctcactgcgacctctgcctcccgggttcaag |
| | | cgattctcctgcctcagtctcccgagtagctgggattacaggcacatgccactacaccaggctaattttgtatttttagta |
| | | gagacggggtttcttcatgttggtcaggctggtctcgaactcccgacctcaggtgatccgcctgcctcggcctcccag |
| | | agtgctgggattacaggcatgagccaccgcacctggccagctgtcttttaatataacattatgattaattgtgatgttcca |
| | | ttaaactaagcggagaggaaacatgctggtaaaccatgtgtgagttattcattgtaccagaaaggcaaatgatacattt |
| | | tatcctaaaattcaaatttataaacatcttaacacttgtgatcattaaatactactaatctagcatataaattatatttgtaggc |
| | | gggcacggtggctcacgcctgtaatcccagcactttgggaggctgaggtgggcagatcacgaggtcaggagatc |
| | | gagaccatcctggctaacatggtgaaaccccatctctactaaaaatacaaaaaaaattagctgggtgtgctggggg |
| | | cacctgtagtcccagctacttgggaggctgaggcaggagaatggcgtgaccccaggaggcagagcttccagcctg |
| | | ggcgactccgtctcaaaaaaaaagaaaaaagaaattatatttgtaatattctactaaccttatatcattttaacttttatata |
| | | actttttattttaccaaattaagttaaccttttatagcccttggcttatactaaacatcctaactttttgtttaattgtattagttt |
| | | ttaagttattgccccagatgtcaagtaatgttggattttctataataatttaggatatattgcatgaagtcagttagtatttac |
| | | atttaaaactaaaacaatttatactaatacagtttatacatttcatactaatttagctacagttggataaatatttaatggaac |
| | | aaagtaaatcaaagtaccttttcaaatgaattggaaattaaatccacataacaatttttatgaccacactattacagtgtg |
| | | atggcatgccaaatgatcataatgtggaattatgtatttcttcattggctttcaagattctgttctttagtttgtgggctcctct |
| | | ccaacttgcttgtctcctcacagtttaggcgactgtttataattcttgtccatcctgcataaacacacacagtcaaaatga |
| | | aaaaaagcttctatcagcagatctgtgcttgctgtacagaaatgggaaaacaattgaagtttgcattatctttttctaatta |
| | | ccagatc gtttttggagctatttaggcatacgcttttaaggaaaaaagaaaaaaagagtgtaccttttgtttctaacaaag |
| | | gttgttatctatattattgaaataaaaaattggggatagttatgacaaagtatttagaaataggaattaaaatcttaaaataa |
| | | cttttcatagcatggacaagacttattaatgtctacctcaataagcaaatcatttaaaaatttttcatgtatatttgctgccat |
| | | gatgtgttgtgattgcttaaataaccaatgaatgaagatcaacaaggatttaaatgaagaagaatatggatttaactatttt |
| | | ctcctgtgaaataagttcatatttacaagttttgattttcagaaattagacaattatttttaaaggctgggatgacaacttctg |
| | | cctcttaccaagaagtcaaagcacagttatgtgaattcatcataaatcacatcattttattatatttgtatttataattgtatt |
| | | gtgactactttaaaacctgttataaaataaaattgtttttaatatttatttagaattattagcattaataacaatttgaagtag |
| | | tttacacaatacctgtgagttttattttgttttatattgaaattaatttagttgctttacttggcttcattgctatggatgcattct |
| | | ctgtgttacgagttagcagatctttccttggaactgaatttaaaagcaagcatttggctccacttaaatctctgaaaatgc |
| | | aacttgttctttgcatttattacataattcgctacttatggtacagaaatggatacaatacaaaaatatttccttataagatac |
| | | actgtgaccaatgagctttttaaatagctgtaatcagtaacatgtatttgacttttcaaaacacatttctggagggatatca |
| | | gtgctttatttccccaaatatctgaatccctatgctttagtacaaaacaacttctgaagaatttagtaaccatatgtgttgat |
| | | ctcttgtttttctaactagtctttcataagaaatgactagaatagcaacagggaaatgattgccttttaaggtttttgtttctc |
| | | aatataaaattttggtgaaccattttattgataaatacaggtatttttactttcttaaatcacttgatttaaaattactttgatta |
| | | aatatgcatataaagtcagttgtttttaactctcaatacttatcaaaaaaatttaacttgctgtacattctgtataaacctaatt |
| | | ctattcaactaaaattattttaaacatttag |
| | 3 | Intron 28: |
| | | gtgagtagttcttactgccctctaccttactacctttccacctttcccatttccatttgtttgttgatccatttaatctcaaactt |
| | | acagaaaagttacaaggaactgggctgagcacggtggctcacgcttgtaatcccagcactttgggaggccaagatg |
| | | ggtggaaaacaaggtcagaagatcaagaccatcctggctaacacagtgaaaccccgtctctactaaaaatacaaaa |
| | | aacttagccaggtgtggtggtgggtgcctatagtcccagctacttgggaggctgaggcaggagaatggtgtgaacc |
| | | cgggaggcggagcttgcggtgagccaagatcctgccactgcactccagcctgagcgacagggcgagattctgtct |
| | | caaaaaaaaaaaaaaaaaaaagttacaaggaatttttttcttctctgaagtatttgagagtaagttgctgaccttaagtc |
| | | ctatcacttccaagtaggttcatgtatagttcttagaaacagattttctcatagcaaccgaacattgataaattacaatatct |
| | | aattctcagacccctttcaagtttcacccgttgtcccagtattatccctccatataacaagatgttccaggctcaatacctg |
| | | acccagcttcctttttttgaagaatggtgtttagaaatggagacctagaaattatatatgctgttattggaatatcactgttc |
| | | cctggtttctcagtggaaagagctaggaactaagtgttgtgaatgtttgtgtgtgtgcaggtgaatatacacacactgac |
| | | atctgtattcctaaatcatgtgtatatttatttattaaaaactgtgagttgatgctgatacttcccattttaatccagcattaca |
| | | aggtttgttctagtgttctccctttcgatatttgtcacttgctttcctgatagaaaacgggcttctagtatccttaatatatttc |
| | | atatttggtcagtcctcctatacgtaacccaacttgaatgaagatatgtccttttccattgcagaaatgttctttttccccag |
| | | ctcggactcaacactacacaccaggccaccacatggcgccgcacccagcattgacacttcttttaccttgtctgggct |
| | | ctgacatccgtgccaggttgctcttcgtcatggagtcccttttactgagctctgctctgacgctttgtgccaggtgcctct |
| | | ccatctcatccttcccacccgctagcctctgcccgaccccagacagattccttcctcacctgaagccagaccatgcctt |
| | | tgtggagataccctctttaccctgcctgtgcttcgccagcctgcaccaggccaccctcctgcacagatactctcctcag |
| | | tactggaccaggctaccaacagccccatgtgaacccattgtaacccaggtcaggcattaacacctgcagtaggctac |

TABLE 3-continued

Sequences of exemplary target introns in pre-mRNA transcripts.

| Gene | SEQ ID NO. | Intron |
|---|---|---|
| | | catggcttccccttcccaccccccctagcttggccctactaataatcactttgtcactgtttggggttgatatttggttgtttct |
| | | tgtaggttcctagctttaagataggattgcatactaaaatttacttagatctttgagaactcaaggaaatcagtgaaacatt |
| | | attgttattaaataaaaataaaatacctgtagttggtacctctgtttgagcctgccttgttacaagtttcactgacttcagctt |
| | | cgtgtaacaaagtatctttttctttcaacgtgtacttaaatttcctgtcttattagttttctgatatctaaaaggaaaaaaagc |
| | | agatatcgttaataaattagaaagaagttctgcaaatttaaaagtgccttctaagctgagttgtaggattacagtacaatc |
| | | catagggttatcctgaagaagccaggcagggctcttctgtgttacaccctgtgcctgcgcagcatgctcaccccttgc |
| | | catcagcgcttgcggccccattctctccctctagtaataatctaagttctgcattgctttctcctttcctttctttcttccttta |
| | | aatattcttctttcgagacatatctcatttaacttttattttcatttctgtcacttttggtttttctcatgccaccttggcaatgta |
| | | gttaagtttgtgctaacgtagaagattagtgctcaaatctgaattgccatttactactagctgtgtcatcttcggcaggga |
| | | atctcccagagccttagcttctttatttgtaaaatgactattatagtggttatttctcaggattgttagaattacttccgcaaa |
| | | catttgcaagtccctggttcataatttcatgctaaattagtaccgttacaggaagtggtatatcattgtcacagtgtataca |
| | | aatatatttcttttatatccctcgtgatataattatcaagacagtgaaacaattcaatgaattttaccagcataacacattttta |
| | | agtgattggaaaatcataagtatcttttcttatgtttttagtagaggctttgcaaccccattactctccgctcccaatttgatt |
| | | atttaaaggaagtggattactaactcagatatgtacactgtcaagccaagttctatgttctactgctggttttcctgagaaa |
| | | gcagtcatataactcccttgaaatgatttactacttttgtacatataaaattataatggtgttaatgtaccaaataatgtcctt |
| | | ggaagcaagggttttgccagtaactcagctgcatcagtcaccctcaaggagatgagccatgactttgttcattagttgg |
| | | aaaagagtctggagagtgccttttcgttactgtttatctttggtctgacacttgggaatagggtcatggatacttcagcca |
| | | gaaaactttccaaatttaagttattaatgtattataaggatcaaagtttctagtatagcctgttcaattagaacatagtgtgtt |
| | | ggttgattggatttggagaaagggaggcaatcaaatttttactacagtttcagcctgttacagaatattgtatagagtgtt |
| | | aaaatgttgatgcattcatattttttgccagttttaagcttgtacgattttaaatcatttccttaccttggagacttccccccca |
| | | cctttttttttttttttgagatggagtctcgctgtgtcgcccaggctagagtgcagtggcacgatctcggctcactgcaag |
| | | gtggttctcccacctctgcctcccgagtagctggggctacaggcgcccgccaccatgcctggcttatttttttgtattttta |
| | | gtagagacggggtttccccatgttagccaggatggtctcgatctcctgacctcatgatccgcccgcctcggcctccca |
| | | aagtgctggaattataggcatgagccaccatgcccagccctgactgccctttaagatgagtacataagtagtagtagt |
| | | acattttttttcacatcctggagaagatatactgtgttcactattgaaatgaaaccataaagctagagttaggaagattg |
| | | aagaaatgaaaaaggagctcacatgattttgtctcaggagaggctcttccaggattctttggagatatggtagattccat |
| | | agctggagcagggaaaggacaggatgagcctgtgggtgtagaaaggaagggagtgcttgaaagatgatgagga |
| | | gatgtcagcaggtcacagaaaccctctgaaggaggctccaactggccaggctggggacaatttgggccccaaaat |
| | | aatgacagtaacaaattgtaactcattgaatgaaataggaatccatacattggtaattatataaataagggaataaaacc |
| | | atgatgcaaaaagggatgtttatgtcatcacgcaaaatatgttcacagaaaatatgtactaattaaaagagggaaaaga |
| | | gtaactttacagtggatgaagcctggcaatcatcactttaagcaagtggtcagagttaatattatcagtaatggtcaaat |
| | | caaaaccatatgcaagaagactctaaaatgcaagaagactcctgaagtacttcttaccaaagatgtagaacttaaattc |
| | | agtcataacaatacatgagacaaacccaagttagagcacagtctgcaaaataactggcctgtaatcttcaaatgcatc |
| | | aagatcatgaaagacaaggaaagagtgaagagctgctccagttggaagagacttaaaactaaatgcaatgtatgatc |
| | | ctagattggatctttttgctctaaggacattaatgggccagttagtgatatttgaaggggatccgagggttccattgtagt |
| | | aatatatcagtgttaatttttaaatttttattaggttgggattattttggaaaataccattattcatagcgaatacaaagtagaa |
| | | tatttggggatgataatgcatgattacaacaaatgtttcaggagaaatatgatctttgtagtggtcttgcaacttttctgtaa |
| | | gtctgaaattgtttatgcataaaaggttaaaaaaaggttaaattttgtttttataactaataatggattagggtcatgtgaaa |
| | | gtactttagaggaaatgagacttttgagaacatcatccctgaagacgttgaaacactgagttacctcatggataatttaa |
| | | taggatatgcagctgatttttctaccttaatttcttgtttgcagtatctacccatacttagaattgtctggtgttaaaatatgcc |
| | | cactgggactttcatgaaattcttttgattttctagaaaattcagtttcaaaggatttttttaaatagatattttaagtttggtgtc |
| | | aacttagataaaatctgtttggagtcccagtgtaagttttagtaatgtgtccaatctgtttattgaaatagtataactttagaa |
| | | tactttctttggagagatgaagattggtatgttatagttcaattcaaagttgttctttctattatgatctattttataattcataaa |
| | | atctatcttatgattgtcatcataagtgcaatttgtttttttgccccattctacctcagaaactaagtatctgggcatcaataac |
| | | aattggtagtagtgtttgctgctaagccaagtttcaccagtacagtgtggaattattttattgtttttttctgtgaacattgtatc |
| | | tgctgttactaggttattgtgaggtattgggccttcatagaaattgcctggaacccttgttcactaaagcctgttacactttt |
| | | tattctctgtgcgtgtaatcagagacttattgatactgacacattcaaggggcattattgatcatttagattgctctaagac |
| | | ctaaggagtcttggccggatgcggtgcctcacgcctgtaatcccagcactatgggaggccgaggcgggtggatca |
| | | cctgaggtcaggagttcgagatcagcctggccaacatggtgaaaccccgtctctactaaaaatgcgaaaattagctg |
| | | ggcatggtggcaggcgcctgtaattccagctactcgggaggctgagacaggagaatcgcctgaacccgggaggc |
| | | agaggttgcagtgagccaagactgtgccattgcattccagcctgggtaacagagcgagactccatctcaaaaaaaa |
| | | aaaaaaaacgaaaaacaaaaacctaaggagtcttttctccttattttacaataaattccttttgattttgtgtaaaaacttga |
| | | aactgtttatgaatgtaaaataacatttgaatacttttcttgtgccagatattaggttaaatgctttatgtgaattttcatttgat |
| | | tctcacaacttttgagttaggtagttatttttctcattttacagatgaaatggagggttaggaactcgtaggtagtagatgct |
| | | gaagctgagatttgggcctgggtcttttcactactgtgccagaatcatttgggagggagtaaaaactcaagcctttgga |
| | | aaatatgatgacataaaattgtcctttatattgagaagcttccatagttaccagtgtccttcacagggttgatcggaaaga |
| | | catacatgttagtgatgatgataatgatgaagataatcattattaccacaggtacttcctataatataagcatctttcaaatt |
| | | gtatgagaactttcatagaacatctgagtaaatgaacagtacagtgtgcatgaaaccactaagcaaaccaagggaag |
| | | ttaattttctttatatgaattgtaaacatgtctctagatatcctttatcagattccaccatgcgtaagtagtgtctaagttgccc |
| | | catatttagagtttttcaatgaggttgtgttcctacttagaatcctaaagttcagctataacagatatattaataaaatctgtg |
| | | gaatctttaattgagcataatggtggctgttattttaacttgaggcttttttgttgagctggattggaagtgcaacttattaga |
| | | aattacagtgtatttattcctatttcttgttctttatgtgagagaagatatactttagtagactgaatacttcagagctgtatct |
| | | catttaccaataaaatgtgaaaacagtggtaaattccttcacttgggctaccattgtacaggcctattttaatggtatagttt |
| | | gatatccttaatgttaaaagcaatatagcttaaagaggctggtaaattagaattttccaatatcctcagcttttttttcctctca |
| | | cagttaatttgctctgctgactccctacgcgaggtggcaacagctggcccttttactggagcttgtggggattagagag |
| | | tcgggctcgcagcagcgtgctcggcctcttgcctctgttgactgttctttattgtttgatgcctgagcatctcccagacag |
| | | cgagcaattgtttctggaaacttaaagtttgtttctcttgggagtagacaatgcttttggggcttgtctttgtgtttcttcactt |
| | | tcccagtctcctcttatccttcatcctgtgctttctcttgataattagaaaggagcaaagataccaccttttttatttaggtctg |
| | | catgagattctaaaacttagaagtataggctatagatgaaagtttcttttttcagtaagccacctcagtaacaaatcatgtt |
| | | ttaaatgaaaactttgttcttcataatatcatttagtgagagaaaacaaatgcatgagtgcatttttgaaattatggtactaa |
| | | aagggagcagcagcaaggtgacctaatactgccattttaaaagctaggattagaaatgtatcataactgcttaaatcta |
| | | aaaagattctttcactgaatccaaaatatagttctaatttataggatagttataagaaatctctatgccatgtggaaacatg |
| | | aataaaaagtagtcagaacatagctaaatagaaccctgaggtaggcagaatgattttattcttcacatttagaaaagaa |
| | | aacatcaaggtaccctggaacttaatttctacagtgacttcacattccgacacttctcccatacctgccataccccttgagt |

TABLE 3-continued

Sequences of exemplary target introns in pre-mRNA transcripts.

| Gene | SEQ ID NO. | Intron |
|---|---|---|
| | | gttgttac ggatgagaatatcgtctgtgaagtagtatgagatggaaattttcctagaaagattattgtactcggaatttgg |
| | | aactgaaaagtgtagaaaggggaagtgatgtgtttaaaactgtttgcggaggtggggctctgccatgtgtattttgaca |
| | | aagctacacaggtgattcttgccatccccgattaccgtgtacccgcctgcccctgagctggcactccaaagagttcttt |
| | | cagtgcatagcaagacaattttcatgctattaattgggataaaattgacatacattcatttgtagagtctgagacacaac |
| | | gtcactttggaaaatttggtgagcaatttgaactgcatctgcactggtgtgttctttttgtttctgtagacttaaccaaagaa |
| | | aatgaactttaaagggactttaaaggcatctgcactggtgtgttctttttgtttctgtagacttaaccaaagaaaatgaattt |
| | | taaaggaagagagggtgataccaagttgtagaattctaggtatgtaggttcagaggagattttttttttttaagaaaaaaa |
| | | aaaaaaaaaaaaaaacacccaatcaagaagaatagagcagggtgtcccgaagagaacgtgtgagctcgaagca |
| | | tcccggcagcatctttcatatctcagtactgttgctctgtttcttgggctcacaacaccatttcctctctcctggcttttaaca |
| | | catctcgaggcaaccttttccctttttttatgcacttctctcactgcgtctcttctatatcatcatcacttcaacctaaccca |
| | | gtatttttatcccacctgcttatttaccttccttcagtgactaaaaaccttactcagatactgccagtgttgtttaattgagca |
| | | gaatagaggcttctcactataggcaactgtaaatcaatgaaaataaccatttaaagaagaaaaacattttcatgtctatc |
| | | acggtc gatcccttctgccaaagtgatttggttcattcataaattccccatacctcgtgtgttacatattgtactgtacacat |
| | | ttactgaatgttcgattgtgatcttgtaatacagactgttcattagccccccttctcttgacttaaaaagttgggggggaacta |
| | | actcttttcatcccaaggaaactttcttctactctgtcttgccagaaagttactgctcatttctcttgtagagcagcttgcct |
| | | gtgtggcattcactcctgttctgcccactcccttcctaatatcgtgcagtctggctttcatctatatcaaaaccacttattga |
| | | tagatcaccaatgatttcctaatgccagtctacccagttcaccaggaaactttaataactttttatgtttattaggaattttta |
| | | agttcattggaatacattcaagtacttttttggaatgattatatgatgtagaaatgtgtatgtttgagagacagaaaaaattga |
| | | ttttttttcctcttcactacagaataaataatgtatttgttttatggtagcaatacttgaactctttaaggcatcttttcatggta |
| | | aatctggcaattttaaaaatctgggctttgtaaaataattttttttatagtaaggcagttaacacattaaagcaactaggaa |
| | | agatagtgaagaattattttttaccttgagtctgtatagatgaagtaggctctgctttgtgttggaacagaacaaacaaaca |
| | | aaaaaacctgagttgatacaaagataaagtaatcctcaaggaaagtcctctctgttagagaagtggttatttacacaca |
| | | gaattccacatgacaacgcctgagtggtgtggtttccaggttattgatgagaaaatcgagactcaaaatgggtcttttta |
| | | gaatgaagtacattttttcatggcctaagtctgtctttaaaagtcaccgttgtggccgggtgtggtggctcacgcctgtaa |
| | | tcccagcactttaggaggccaaggtgggcggatcacaaggtcaggagatccagaccatcctggctaacacagtga |
| | | aaccccgtctctactaaaaatacaaaaaatttagccaggcgtggtggggggcgcctgtagtcccagctgctgggga |
| | | ggctgaggcaggagaatggcgtgaacctgggaggcggagcttgcggtgagccgagatcgcgccactgcactcc |
| | | agcctgggtgacagagcaagactcgtctcaaaaaaaaaaaaaaaaaaaaaaaaaaaagtcactgttgaagaatatcaat |
| | | aaattagtacaagcgtaaaagaacatttcttttctataatattatacatgctgctggtaatcaacactttactagcaagtat |
| | | attcttttgctttaaactcaagttttaactgattaagaataaagacaagaatgttctctacaataatgtatggattgaatttgc |
| | | catttatcattttaatgtaggttttacttatatactattgtgaaaatactcttaatgtattcaaaaggccagtgcacaattttttttt |
| | | tcttttacttcttttttttttttttttttctttagaaagagtgtcacttgctgcccaggctagagtgcagtggtgtgatcatggctc |
| | | actgcagccttgaactcctgggctcaagtgatctaatacctttaaagttgggaataaactttatcttaagcgtttttattttta |
| | | aattatgtttttgcatatttgatagaaaaagtagaatgtagtaattgaaaacctaatcacaaaacaattcattggactctgc |
| | | aacagtatataaaaaataaaattaaacgagataggaaatcttaagggattggtggattgatgcacatgaaactggtaa |
| | | cctctgttaagtacagttctccaggtagttggagaaattagttaaatgtgaagagaattttaattttgcactattttgtacatt |
| | | tctaaactgtgtctcccacagcccttctcccccagtgagcacgattcagaattactttgaaatgttgtagtcttaattatcc |
| | | tattcatggaaatgacgaagctaatacacgatgtgctctatcttaaaagtaacagatattttcccaagtaacctactgctg |
| | | gttgtgatgctgagggacatttcatgggactgcatggtcgttgctcatcgtgataccatcctcagtggttgggggattca |
| | | cagtgaattctcatatcctgtaactatgcatcatggatctatcatctgaaaataaatcaaaatctttgttgaactcacagttt |
| | | ccacacttgtatcacccatttaagattgtttcattgttacctcctgtgtacagaatatttcatttcaatttctcttagaacagct |
| | | cattcatctattctctagtttcaatattctgagcagtagaagtttgctgttttgattaacttcagttagatctcttttctgggcca |
| | | agaattaaagccatttatctttagtctctcctttttgttggcactgcttcatagactgtgtcatatatacagatctgtctttaga |
| | | ctgatctttaccaaagtacactactggaatttgagggtttttttttttaacatccttttcattatgagagagctagtgtatatgc |
| | | attgtgggaaattagaaactatagatggcaaaattttaaaaaataattgccaccacccagagattgcactgtagtttaag |
| | | acacttttgaatgtggtcctagggacataatttctggaacacatttttcgtgaagaggtctcaggttggcttcttataccca |
| | | cagctcgttgtcattgcccctagttttaatttcccatcgctcagtgggctagatttttttttcattttcttcatataaacttatttca |
| | | gaaatgttcattaagaggaataagcagcattagtaaaaatgaaacctatggtacccattactttatatagttcaagtattct |
| | | ggaagccatattgtagcatagcatgtactgaaaatcactctcctttgaacagtaatcccatacctgtatttgggacctgg |
| | | ccttcctttgtgtgcttgtgtattcattatatcccctttctctcttcaaagatgctcaagtcattctcatcttaaaactaatgggt |
| | | tgaaccttccatgcagtctagtagctactgtgaactctaatctctattacaaaggttagctctttgagtctcacttctactga |
| | | agttgtttttttttcccaagattactgaaaatttaagagaaaataatggcccaggcatgcattcaggactagaaaatactt |
| | | ccatgtacagaaaaccaaacaccacatgttctcactcataagtgggaattgaacattgagaacacatggacacaggg |
| | | aggggaacagcatacgccagggcctgttggggcgtggggggcgaggggagggaacttagaggacttaagtgca |
| | | gcagaccaccatggcacacgtatacctgtgtagcctgcacattctgcacatagagcccgcttttgtttttgtttttgtttttta |
| | | agaagaaataacggggaaaaaaaaaggtttcaaaactcataaagaaagagaaagagagggagggagggagggaa |
| | | gaaaatgcttccatgtaactgcatcatttggtactttggagtccatatcctacttgaaactctaggatctggccctcacatt |
| | | tatgtagtgctttattttacagtttacaaaacttctgcttgtccatgtgtgtctgtaaagtcatatgaggcattatgcccattgt |
| | | tcagatagagaaattaacgttcattgacataaatggttaagcccattatgtaaatatttatggcaaagctggggctaatc |
| | | atatgtgttacagataggactttttttaaagaattgtttaggtattctgttcatcattagtctctgggtttgtgtttgtggtaacc |
| | | atagacaaccaagttcatataatttggcttctttttttatgtgattttgatacgtgttaaggatctataacaatgaatttgcctc |
| | | ctaaagaggtacataatgttttcattcctccaaaaagataattctaggtttataaatctatgtatgctcagtgccagttgaat |
| | | tttgtgattgttcaatagaaaagaaattgtgacttaaaggtgattttccagtttaatggaataaatgaaattagtttagaagt |
| | | tatttttattttttctgagcctgattctcactcagttgtgataaacagcacctctgtaagataaactcggtgataaaccgaga |
| | | acttctgaaatcagcctaacatgaatacctgttcttcttgtgctaagtttcataatgctttatcctaatacaccattttttttaag |
| | | aaatggaacttgtatttcattttgctttcatctcacctaattcataatttattaaaacctacgattttaatttcttttttttatgaat |
| | | ttttagtttggtgtataaatcagaattacattctctgatcttttacttttaaaattacagtgatgaactgactgtttaagaatcat |
| | | tctcatgattcattcgtctgttatgcctcctttttaaagcttcagcactgaaggtcttttgacaaaccaatatttataacagttt |
| | | gacagcaggatgaggaacagcgtttgtctttgtaacagcttgaagaaagaccctttccaggacccagtcatgcagtta |
| | | caatcttgacctctttcttatgctgggaacatgcatacagcagcacctcccatgtgttttcttgtcccattgactgtccattc |
| | | acttcccatctgttttgcagtcttaaaggaacagaaggggccttcttataaatctgtctttgcaggtgataaatgatgcct |
| | | acctctttaagagctgcctgggtggtttcctttttcttagaacatttctgctttcctcctaactaaatcagggaaaaatacaa |
| | | ttttaggaataagagaaaaagaagaaaagatgaattttttaaagcatttaattgactaagaatattttactgatctttttttaatc |
| | | ttcccaattaattgcctaaatcatatttttttaaaatgtattatcgatatttagattttttgtcagggagtaaaatgaatgtattcat |

TABLE 3-continued

Sequences of exemplary target introns in pre-mRNA transcripts.

| Gene | SEQ ID NO. | Intron |
|---|---|---|
| | | tttgaaataatgtaactctttttgagaaaacaaagccatgtatcattaatgagttaacatataaaataacttttaagtttttt<br>gtgataatttaagtgtggagcatcttatgtattggatacaaaagtaaaatatttcagagtaaatcattgtaatcttatggtaa<br>aatctattcatttttacatttaaaaagatgatcataaatcccataaacatttatgcttttacttctgttgctgaaaataagtatt<br>gtaggaatagatattgatatcattgggttttctaagaattcagcagaaataaaaataatttactttttctcccatgcagaaat<br>tatttatgcaaggttttatgtaacaaatattgtccctctatggccctgcagaatattcttaaattactgatttaaaaactattac<br>cagtataaaatgaccacttttagaatattgtggtgtattatgtgaatcagctggctaataatatatcttctgtggactagctt<br>gttagtttgtttattaattccctggcatattccaaaaggaatttgaggcagcttacatatatcctacgcaaaagataaaact<br>acttaagtgaaaaatttgggttgaaagaaaaggaaaatccaggcaagtgaaataaagtaaactttcagataaaattgg<br>tgcccctcaaagtgcatgctcaagggttctacgtacaggcagacctcattgtattgcatgtcactttattgcacttcaca<br>gttattgcattttaacaatagaagttttgtggcaaccctgcattgaacaagcctgttggcactattttcccaacagccatg<br>tgctcacctcatgtcactgtcacattttggtaattcttgcaatatttcaaatttttccattattattctgtctgtcatggtgatctt<br>tgatgtttgtattgtagctattttgggtaccactaactgtgcccatattagtcagtgaccttaatcagtaaacgtgtgtattct<br>ggctgttccaccaactagacattccctgtctctctcctcctcttcaggcctccctattccataggacacaacaatattgaa<br>atttggccagctaataaccctacaatggcctctacatgttcaagtgaaagaaagagtgccatatttcactttaaatcaac<br>aactagaaatgattaagcttagtaaaggaggtttgttgaaagccaaaatgggctattagccaaattgtgaatgcaaaag<br>aaaagttcttgaaggaaattaaaagtgttattccagtgaacacacgaatgataaagcagaacagccttattgcctgaga<br>cgcaggaagtttcactggtctggatagaagatcaaaccagccataacattcccttaagctaaaacctaatccagagca<br>agttcctaactctattcaattctccgaaagctgagaggtgaggaagctgcagaataaaatttgaagctagcaaagtttg<br>gttcataaggtttaagaggaaaaaagccattctgcaacatgaaagtgcaaggtgctgatgtagcagctgcagcaagtt<br>atcaagaatatctaactaagataattgatgaaggtgattatactaaacaacagattcttgatgcagatgaagtagctgtct<br>attggaagacgatgccatctagtaatttaatagctagagagaagtcaatgcccagcttcgaggcttcgaaagagagg<br>ctatcccctcatttgggtgccaatgcagcaggtgcctttaagttgaagccaacctaaagaatttaccattctgaaaatc<br>ctagggcccttaaggattatgctaagtctatcctgcttgttttctaaaagtggaacaaaaagcctggatgacagcacatc<br>tgtttacagcatggtttactgaatattataactctcgagacctgctcagaaaagtttctttcaaaatattactgctcattgac<br>aatgcatctggtcaagcaagagttctgagggagatgtacaaggagatttatgttgtttttgtgcctgctagcacaacatc<br>cattctgcagcccatggatcaaggaatactttcaaccttgaagtcttattattttaaaaatacgtgtcttaaggccctagct<br>gccatagatagtgattcctctgatggatttaggagaaaaaaaaaggaaaagcttctggaaaggactcaccattttagat<br>gctgttaagaccattcaggattcatgggaggaggtcagaatgtcaccattaacagtttggaagaagttgattccaacc<br>ctcatggatgactttgaagagtttgggacttaagaggaggaagtaactgcagatatggtagagacagcaatagaact<br>agaattagttctgttgtaatatgataaaacttgaacagatgaaacattgcttttttatggacaagcaaagaaagtggtttctt<br>ttttctttttttttttttggcagtctcagtttgaagaaagtggtttcttgagatggaatctgttcctggtgaagatgctgtgaa<br>cattgttgaaatggcagtaaaggatttagaatattacataaacttagtagataaagcagctgcagggtttgagaagata<br>gtgtcccaattttaaagaagaaaaatttgagtaaatttgggtaaaatttacccaaaattacctattgtgggtaaaatgcta<br>tcagacagcatcacatcctactgtgaaatctttcatgaaaggaagaatcaatcagtgcagcaaactacaattgttgtctt<br>attttaagaaattgccatagccaccgtaacctgcaacagccaccaccctgatcagtcagcagccatcaacgtcaggg<br>ccagaccctccaccagcaaaaagattatgacttgctgaaggctcaggtgatccttagcatttgttagcaataaagtact<br>tttaaataagttatgtacattgtctttttagacataatgctattacacacttaatatattacagtatactgtaaacgtaacttaa<br>acgcaccggaaaaccaaaaaaccttatgtgactcactttattgtgatatacgctttattgtggcagtctagaaccaaact<br>tgcatatctcccaagtatgctgggactttgctagaggtaagctgcaaatttagccctcagtttcctggtggctggcagtt<br>acaaaatggaaagcagaggtcattccatcattcatggtggccatcagacaacaacacagcagttgcttaggagaag<br>catgggtcttcttcgtacgcacaactgagagaaatttcccttaaagtggacactgagttagatgatacaatgaatctaat<br>ggctacacataatcatgaaaatcatggggccctttattgtaatgtttctcatgcgggctaacatgcgtagttctagggaa<br>aatatgatgctgtccaaacatacagctatttggtttggcttatctaaagataaaatacatagtatccagagaaatagatga<br>actgtatgtcctccatacagtctcccataaatattatttctttttgcagctgatccttttagtaaatatcaggtagccagaagt<br>tcaagattttacactcattgacattgacaagcacctggaatggtactaccttttttttttttttttttttgagacagagtcttg<br>ctctgtcacccaggctggagtgcagtggcatgatcttggctcactacaacctccgcctcctggattcaagtgattctcc<br>tgcctcagcctcccaggtagctgggattacaggcgcccgccactacgcccggctaatttttgtatttttagtagagatg<br>ggttttcgccatgttggccagggtgatcttgaactcctgacctcatgtgatccacccgcctcggcctcccaaagtgctg<br>ggattacaggcgtgagccactgcgcccagccaagtactatttttattagttaagtcagagccataatcattataactgag<br>ctgaaattagaattgccatccacttaagaaagttgagtggtctaacaagtataaaagcctaaatataaggctaattcatg<br>ttcatactgaagccttttggggaataggccttaaaatatgtagaaagtatttgaagcggttttaattgtactagccaaaag<br>gagcctagtagaaatgcttgtgttataagagtttatttttaaaaagctgaatttatctgaccaggcgcggtggttcacgc<br>ctgtaatcccagcactttgggaggccaaggcaggtggatcacgaggtcaggagtttgagaccagcctagccaatat<br>ggtgaaaccccatcactactaaaaatacaaaaaaattggccaggcatggtgatgcctgcctgtagtcccagctactcc<br>ggaggctgaggcagaagaatcatttgaaaccgggaggcggaggttgcagtgagccgagattgcgccactgcact<br>ccagcctggacgacagagcgagactccatctcaaaaaaaaaaaaaagctgaatttatcaacaaattgctgtggagtttt<br>ttatatattcagcaggcatcagttgtaatttacctcacagactttcttaaggttgctttctttctaaattatactttatggggt<br>cacaaaatagcaattttaaataatcacctttaatgattaagtattgtttaagtcagatcactcaactatgaatgcatgaata<br>ttcatggacatctattacatagcaagcagtgctatgctgggccgagtgattttaaatgacagacttttggtaagtagag<br>aatttacccaagcagtccttgctgttctccacattaatgctcagaaaaaatacattataaaaatgatctttccaaaatgaat<br>tatgaagccccatgagaatgatatggcaatttgtggttacatattttactagaggattaatatccaataaataaaaagata<br>ctaaggaataaacaaaaaaaatttaaaagatgaagtatataatgaattagaacaatacattttaatcataagttttaaatta<br>gtgtggactttgaattctcctggacagattccttcattttatagataaagctaggactgtgacttatccagttatgaggtta<br>acggcgaatacaacattgtcatatatttaaatgacacacattacaacatgttctctgctttataaaaatcatatcaaataat<br>tgccccatagattattaaaggtgttagactagggattcttaaaaaaaatttcatcaaatgtttctttcattattaatcccatg<br>aagtccatgttacagaagattttgtctacaacagtgcagttacattcttctcgttagaaatacaaccaccagttagagttc<br>ctaatcagtataaggaagtagttgttaggagaggggatgggtttcttgtccaaatgaagttttccatttgagtttttgaagt<br>agtgaaactaacccagcgtttacaggccccagaaatctgggaacctcagctttcaaagtactgtaccagtctttaaca<br>gttttcctggacgtgtgaattgatgcctccttctgtaacatgcaggagtgttctgtctgtcttcattgagtgttaaaaaataa<br>tcatgcctatttcaaggaaaaaatctacagaactaagatgcagaagataagtgctagatttaatcatattccttcatctat<br>ctgtttggttcaacctttcatcaactaaaagatgcacctttttttcttgtgctaactctaagattttagctacagttttgagaatc<br>ttgagtgtagtctcttgtttaccttttttcctttttttgtttcccccacaccctagattcatttaaatactgaacttctaaagggc<br>aagtatatagtgtagtttaataaaaagcaaaccttttcatgaacaatatatattacataataagaagcgttcctttacttttca<br>gtactctagtgaatagctttctacagtagaatctcacttagagggtgtcttaaagcttaacaccaagtgctcaggcagca |

TABLE 3-continued

Sequences of exemplary target introns in pre-mRNA transcripts.

| Gene | SEQ ID NO. | Intron |
|---|---|---|
| | | tgttatacaacagttccattaaggtacatttggatctttggatgtgtggtttgcttaaagtacactgcattagtaagttggca<br>gcttgctttctttaaaaacatcaaaagttttaaaaggtttatttcagggcatgtgttagtgttttgtgtgtggttctttgttcctg<br>ttctaaactgttattaaccactgaagtgaaccttctcccgggtttggcctttggtattcacagtgtattcaaaacctaatta<br>cagattagtctatatttgagacttttagagcaagtatcagaagacccaaaaagaaaatgagagtagcagtatcatttcat<br>gtagagataaagagacccaaaacatgaatgggtgtcaagtcagctgaagaaaagaaaaaagagaaggaacttcatt<br>cactgagacggtttatgagttggggattatgggaatattcatgactcaatcaagaagcacagtgaattgatgtttgaaat<br>agctcatcttttaagtaaacattggataaatggaaagtagactcagtattcactacacgtagaaatagctatttctgtata<br>gcagaaatagcagtttgttaatcccttcctgagtttggtttaatttaccaagtaaatcacaaattttattctttatttgtgaatat<br>ttaattcaaatatttaatggaaatatgagtttgctttataattagtcatgctgatccatacacgtatttctgagagaaagcaa<br>tttctaatggtgaaatagttacaataatattttgaaatttgaaagcaccgtgatactgaagcattaatctgaaggatcgga<br>aagtagggagtttttgttgccaacatttaacttcattgtttatggataacttggttttctgggcagccagatggcacagtta<br>gtatacagacattcttggaaacttgtatcaaaatttaaaatgaatgaatttatgagaaataattctgcttattatttgtaatgt<br>agctttcttgaaaagcaagaaatcggaatgtagtttctaaagctgcaagtgaatatgtatacatagccagctctttcagc<br>cttgataataaggtgcaaccattaagatgaagggatttttttttcccacttgtgtttttgggcccgagtatcctgatctgtgt<br>tgcttgtctggttcaggtgtgagccaccagctttctttgactttcattatctatgtgtatcttgcctcctgttcccaggcttgc<br>tctagctcttctgatcctgtcttcctccctcttgatcactagtgtagtattcatgaagccagctaagttagtttttccctttgaa<br>aaccacagcccttatcttctgtgccatatttgggcaacttcgtttatcattgattgaccgtacgcagtgatcaggccttgt<br>tctagacactgaagactctgagcattttgggcccattttgtactcctgtattgttctccaggggcttctccaagtgtgcgt<br>caatttagtcttctcaagagggcatcattttcatcagaatatgatagcatattatggagtgtccggtcatccttaggcata<br>gactacttaggaggtgtaactgttttgttccctgatttttactgaaatgggtcttttcttttttttttttttttttttttttttttttttt<br>tttttttttgagacagagtctcgctatgtcaccaggctggagtgcagtggcatgatctcagctcactgcaacctccgcc<br>tcccgattctccctgaaatgcgtcttatttaagtcaaaggtaatacttaaaaaagaccaaagagacttaaaataacagc<br>atttgcttcgtcactatgagctttgttattatgagttaacatacagtagcagactgggtgtagtagctcacgccctgtaatt<br>ccagcagtttgtgaagccgagtggggaggattgcttgaggccaagacttcgagaccagcctgggcaacatagtga<br>gacccccatcttgacaaaaaaaattgttttaaattagccaggtgtggtgctgcatgcctgtggtcccagctacttggaa<br>ggctaaggtaggagaatcgcttgagcctgggaggtcgaggctgtagtgagccgtgtttgcatcactgcactcctggg<br>tgacagtgcaagactctgcgtcagacaaacaaacatcgtagcagatgtgtttcttaatcagagaagtgtagacaagg<br>ctaactccaggctttaatgtcctcatatttagcaatgatacctgcaaggttgtatgagaaccaaatgaaacgccaaattt<br>ggaaatacatagtagatacatcatagcagagtaagccaggaatgcttctcaaaggtaggatatcatctgtgtcctcata<br>tcactttatgaagtacattgtgaaagtgaaagaacaaagaaataaatgtttttagttaatgtttaaaggatacatttatcat<br>aattgctcttttaacactcacctccagtctcccctccgttcacacctcctacccccattacttcctggtaacttagttaagtg<br>tcctttgtcattcctgaggtttcaaggcatggtagtactgtgtcctgatattctaatcgtaaatatttaagggaaattcggc<br>attttttcattttgtggttttcatattaaagtacattaaatagtctttttgcttttatttaggaaaaaaactgcttacctgttaatttt<br>agaaaaatctgattttcatttagaccttacagggtgagacacctgcatcagggtggctcttggtatctttcaattcaattg<br>gatcttctctgaatagtctcttgtagggagtgaggctgctgtaccacctccctgcagtagtccatccagcttaagatgg<br>gggtcaccagtaggccaaaagaatgggtagacctggccatgcactgccctattgtactcaaatcgtgtatcaaatgg<br>agttggatttcttctcttcatacagtacagcatttccaagtagaaatatttctcaatgaaatgtggagagaagcacccgttt<br>gagattcccgtgtgttgtgtgatttaagttagatggtttttaagaccacattcatttccagcattctaggtaacaatttaga<br>aaatgtctttctcctaacctccccactttttaaaaatcctccaactgatgaactgatgtgaaactttcttacattcactgaaa<br>aaaaaaaaaaataggttaagctgtttctaagcaactagatgaattaattttaaactaagaatgtggccttattttgggaa<br>aacaagaatatttacttgtttgtctgctgtttaaaaaatggaagtcagcctaccaaaaaattgagactcaacttctaggag<br>atgggttaggattttttttttaagtttctctagtttaattttatatataaggggttaatgctaccttcataataactattatcatat<br>tttctcaatacatagcttgattaaaacaactggactcccccccacccccaccccacacacacacagatttatatcagtc<br>tgaatctaatgcctagaataagaagtgcttcagccaggcatagtggcactcacctgtagtctcagctactcaggaggc<br>tgaggcagcaggatcaattgagcccaggagtctgagtctagcctgggcaacatagtgagacctagaagttttaaatt<br>actggaaaaataatatgaaaagaataaattactggaaaaagaatatgaaaatgttacgttctttatatccaaccgtggta<br>ggctttttttgagttcctgcaatgctaataagaattcataaaaaggacaattcttcattttcttgggtactcatcactaatagc<br>tgcctcgctggtaaaaaggaatacatgtatcttcaattgcagattatttacttttaaatataaaagatataaatgtcaaatat<br>taaatgcatcttacatggttttcctacatagtgaaagtagaatgcttgccagttttgcctctaggtcactcactttgaacca<br>gccaacccaccttaattgatcatttccactaatatgttaaattaccttaaaagaacaaaaatatttatcatgcttactataac<br>ctgtgttttaaaataggaggccaggcacagtggctcacacctgtaatcccaggactttgggaggccaaggcaggag<br>gatcacttgagcccaggtgttcaggaccagcctgggcaacaaagtgagatcctatctccacaaaaaaattaaaaata<br>aaaacttagccaggcgtggtggcacgtgcctgtggtcttagctacgtgggaggccaaggcgggaggatcacctga<br>gctcaggaggttgaggctgcagtaagccctgccaacaccactgcacgccaacctgggcgacagagtaggacccc<br>catctcagaatataaaataaagtaggaggtgcatgtgaagtagtatagatcatgacttttccaattttaagaggggattg<br>gcatgtactatgagcagttcacatttgtggaggaaatctacatttcagagagtatatatttcatttggaagtctataaacat<br>gaaaacctaaaataaataatgtaaatctacctctagtggctctggtatttttaaacttatttatagctggcaaagtactttttt<br>gtatgtattttttatagcaccattgcacttctcatgtttgttgcaagcatctcccacagcttcctttgtcttttaattttatgacat<br>ataaataaaagtatacatttcaatatggccatattgattgatcttttcctttgtaactcttactactttatatttaaaaagtcattt<br>cccagtctaaggccacctctatttcttttagtttttttaaaatggtttcattgttttatatttgcctatgatccagacattagtaa<br>ctgtgggttcttaattgggcttcagagaatctgagaattccttaaaattctctacataattgtacatgtacttaatacatgctt<br>ttttccatgttaagagtccagagtttttgttagatcctcaaaggggtcagtcagtctctcctcccacttccaaaaaatgtct<br>gagacctactactataatccatctggactttatttgggtaaaaggtggtatggtgagactcatatttttctttttcccgcaaa<br>tagttaagtataccaaccatttagtaaataattacctcctgatttgtgatacctttgaaaaataaatgtttttctttatttttatct<br>ccacag |

TABLE 4

| Exemplary target gene intron sequences |
|---|

SEQ ID NO: 4
Gene: OPA1
Intron: GRCh38/hg38: chr3 193626203 to 193631611
Intron Sequence:
gtgatggatggtttaaggggctaccgatacattcacactaatcagccatttctgccaagatcatgtcacctcaatctgttcatggactcca
aatacaagaaattaatttgacaaagtgaaaatataaaagatgcatcatataaatatgtaacttttctggagtgggtagtataggtaaagcca
aaagaaacaaattcaagcagaggaattttggtttctgaaaattaggttgtctgtagggtccctgtatttatacttagaacaaaattaggaattt
ctgtttatgtggtccagttattgagtcaccctaagtttgtaggcatcttacctacctacttgctccccaagtttttatttctaaaatgaaaagcat
tgctgtagatgaccagtttacactaaagaataacatttatttatttgttttagctaaagtatatggacagggaacattcatattcttgtagaaga
aaattattttgacttttgggcaaaagcatgtagttcttatacactttgacaaactcattgcgtacatttttcacattaatcaaagtcagcacaaat
aaattttcaccttggaccacggagggtttgaacactggaaatttgatataattctggttgctaaagaacaagttctaataaaagcttaagtgt
ataccaatatgtggctgttggtgcaatcagcaggtccgtaaaaatatgattttaatggttaggtaatcccacaacggagatcccaaagttc
atgtttggaagagacttttgggtcaaagtgaaatcagtgtaatgaatttaaaattatactctgagatcttgaaatcagctaattatgttacatct
tattagctcagaaaagttttgaagttatatacaaatgctagtcaggaaaaaagattcagtcatgtaattcttgtacattctactatttaaatcaa
ccaatattatagattatgatttagtgcagtaattctgctggctaaccttatctcatttggtggtggttagtacttcagagtactcaccatagtttc
atttatgttttcagcatcacttcctggtttttctcaattccatggctgtggaatcaattcatatgtatatttagcttcggtgagcaaaaacatagct
agaaaaagaaaagaagtgagtttcctacctggttaaattaaagtcgatgtgttaagccaaggaggacttcttttgaatggtactttaacaat
ccctgttctgtatactgtgaatatatcatttaaatagcctaataaattggatgcttaggctgagccacctatactttagttttgttatggaaaga
agggagaggagcaagtatgttcttatatgttacttagaaataagaatgtagctgtagttacacattgttcttaagtttttttcgtaagacaactt
gaaatgagtcccataggcctgctatttaacattctaagatatgacttaaggttaatgatgagcttttgaatctgacaattcaagagatatccat
aatgaatactgattcattttctacattgctgaaagctaatgttcattttaagcctactttagtagcctttatttgggcttagagatgttattcctcttt
ctgatatttattgggttatctgtttaacccttttatatctccctttcccgatttgtaaattagagactggcaagactttttaccctgagtagagcac
caaacatggcttgtttctgcccacactgtagttaccttgaggggaagtaaatgggactttaaaagcaatttatgctcttttatagtgaaattat
ccctcttactatcccgaaagactgttaccttacaatatcctccactcctttccccctgtagttactatagagatgacttttcggttcttcactgc
cataatgatcaaaatcctaattcatgagatttttatcattccaggcatgtgaggtttacttgatgcataaaaccgcaagtacttttttgttgtttttt
aattgtttttctctcttatcttcttgaaagtctaagtagatcatcattttttgatgtcttattagtagcaactaataaatttccctgtatcttctcagc
aaaagaactcaagcagagacagaagattagaactaccattggtagttttgcttcctatggatatgttcacatacatagaaatttttacaatga
cctttttatatatgtatttcagaatttcagaatggcctcaatgccttaataggaagaaatacttgaaatttttaaattagggcttggttttgtgag
gagctagtaaaggtttttctctttcagctttagcttgtttctgcggaggattccgctctttctccatcagtttcatagccctggaattgtagaaa
agctctggtttcaagaccattgatatccatttctgtcagggtgagttttaaatttatttcatgatgcaaacaatatattgaacaacaggacatg
aacttgttcttgttgtaagtggctgaattttatcagtaaagcacatcaaaataaaatataccccaattgctagttaagacctagagtgacaga
ttgaaaatagcttgtgttattctcttaagaaaatatataaaaattatcatctcatcaatctttaatgtttgttttataaatctaaatgtttttatattgttt
cctaggaaatattaggtctaatttttttactttaccaccagctgtcttttattttactcttttttttgagacggagtttcgctcttgttgcttaggctaga
gtgcagtggcactatctcagctcactgcgacctctgcctcccgggttcaagcgattctcctgcctcagtctcccgagtagctgggattac
aggcacatgccactacaccaggctaatttgtatttttagtagagacggggtttcttcatgttggtcaggctggtctcgaactcccgacctc
aggtgatccgcctgcctcggcctcccagagtgctgggattacaggcatgagccaccgcacctggccagctgtcttttaatataacattat
gattaattgtgatgttccattaaactaagcggagaggaaacatgctggtaaaccatgtgtgagttattcattgtaccagaaaggcaaatga
tacattttatcctaaaattcaaatttataaacatcttaacacttgtgatcattaaatactactaatctagcatataaattatatttgtaggcggggc
acggtggctcacgcctgtaatcccagcactttgggaggctgaggtgggcagatcacgaggtcaggagatcgagaccatcctggctaa
catggtgaaaccccatctctactaaaaatacaaaaaaaattagctgggtgtgctggcgggcacctgtagtcccagctacttgggaggct
gaggcaggagaatggcgtgaccccaggaggcagagcttccagcctgggcgactccgtctcaaaaaaaaagaaaaaagaaattatat
ttgtaatattctactaaccttatatcattttaacttttttatataactttttttattttaccaaattaagttaaccttttatagcccttggcttatactaaaca
tcctaactttttttgtttaattgtattagtttttaagttattgccccagatgtcaagtaatgttggattttctataataatttaggatatattgcatgaag
tcagttagtatttacatttaaaactaaaacaatttatactaatacagtttatacatttcatactaatttagctacagttggataaatatttaatggaa
caaagtaaatcaaagtaccttttcaaatgaattggaaattaaatccacataacaatttttttatgaccacactattacagtgtgatggcatgcc
aaatgatcataatgtggaattatgtatttcttcattggctttcaagattctgttctttagtttgtgggctcctctccaacttgcttgtctcctcacag
tttaggcgactgtttataattcttgtccatcctgcataaacacacacagtcaaaatgaaaaaaagcttctatcagcagatctgtgcttgctgt
acagaaatgggaaaacaattgaagtttgcattatctttttttctaattaccagatcgtttttggagctatttaggcatacgcttttaaggaaaaaa
gaaaaaaagagtgtaccttttgtttctaacaaaggttgttatctatattattgaaataaaaaattggggatagttatgacaaagtatttagaaat
aggaattaaaatcttaaaataacttttcatagcatggacaagacttattaatgtctacctcaataagcaaatcatttaaaaatttttcatgtatat
ttgctgccatgatgtgttgtgattgcttaaataaccaatgaatgaagatcaacaaggatttaaatgaagaagaatatggatttaactattttct
cctgtgaaataagttcatatttacaagttttgattttcagaaattagacaattatttttaaaggctgggatgacaacttctgcctcttaccaaga
agtcaaagcacagttatgtgaattcatcataaatcacatcatttttattatatttttgtatttataattgtattgtgactactttaaaacctgttataaa
ataaaattgtttttttaatattttattttagaattattagcattaataacaatttgaagtagtttacacaatacctgtgagttttattttttgttttatattga
aattaatttagttgctttacttggcttcattgctatggatgcattctctgtgttacgagttagcagatctttccttggaactgaatttaaaagcaa
gcatttggctccacttaaatctctgaaaatgcaacttgttctttgcatttattacataattcgctacttatggtacagaaatggatacaatacaa
aaatatttccttataagatacactgtgaccaatgagctttttaaatagctgtaatcagtaacatgtatttgacttttcaaaacacatttctggag
ggatatcagtgctttatttccccaaatatctgaatccctatgctttagtacaaaacaacttctgaagaatttagtaaccatatgtgttgatctctt
gtttttctaactagtctttcataagaaatgactagaatagcaacagggaaatgattgccttttaaggtttttgtttctcaatataaaattttggtga
accattttttattgataaatacaggtattttttactttcttaaatcacttgatttaaaattactttgattaaatatgcatataaagtcagttgtttttaactc
tcaatacttatcaaaaaaaatttaacttgctgtacattctgtataaacctaattctattcaactaaaattattttaaacatttag SEQ ID NO: 5
Gene: OPA1
Intron: GRCh38/hg38: chr3 193593374 to 193614710
Intron Sequence:
gtaagtgcaggctctaatctggccccgttaattctggggcctcttgagagtggggctgtcttatctctatctccaaaaatgtgcaggtgact
ctcaggccaggccgacggcagttggagaattcccagatgttcttgaggacccagaatgacaggagccctggctgggcttacgttcgg
agccggcttcaatactggcccttttctctggccctacccaacccgaaaattctggacgcctctcaatcttggcccgtctctattgtccttttgt
ctctgccctttacacccttgtgtcttcagtgttctgtctgtctctggttgcctcttttgcctttttttctgtcctctccctgccaggtttggctctgtcc
atgagtcacctctctccacatttctcctaactctcggtgtcttcttttttcttccatttccacgccatgtgtacattgcatcttcaggtacctgggct
cttctatcggggaaaggggcgtccgtctctttccctagcccgctgatagaagtcagaactagagcaatgacgcacacggtgtcagaga
cggtgattcgagatgccctttcaatagcagctttttttctgtgtttcgggagggagacttacttttttgatgcaaggtcgtgaacgtggcacca
cctttctaatctcaatcattgttgccctggggggtttaattctaaatagaaaatcatagaaatcttttcatttctgtgcgttactatatgcattgta
atgagattaaattggattttataggaaatttgttctagtatcattagataccttcaagcttagctcattgttgcaggcatttgataggaagtaa
gatgcatcaagcaaaattggaaaaacgtggttttcctgaattaacttctaagcagttgttttgaatttttttccagaccttttttaagtggtatagat
aatttatcgtgtttataaggaatggaatgcattcgttagtttgtttttgttttgttttgagacggagtcttgctctgtcgtccaggctggagtgca
gtagcgctatctcggctcactgcaacctccgcctcccaggttcaagcaattctcctgtctccgcctccggagtagctggaattacaggca TABLE 4-continued

| Exemplary target gene intron sequences |
| --- |
| cgcgccagcacgcctagctaatttttgtatttttagtagagagggggtttcaccattttggccaggctggtctcgaactcctgacctcatgt |
| gatccaccctcctcgacttcccaaagtgctgggattacaaccgtgagccaccgcgcccggcccaatttgttttatataggttaactggagt |
| ccaaaatacagaactagatgagataacaatagttaacagtgttagtcagttagaattattgcataggtatttttaatctcatggaattttagtct |
| ttgagtaagttcacagcccttggtattaaagtaagttatttacaacccttgcatttctacttctcaatatttagtgaggaaacatatctgattttct |
| ttaaataaaaagagaaaagactgcagaagatagcattctctgttggagcaattaagatgtataagaagaactacaaagacggagttttaa |
| aacaaactgatttataagtggtatttatttaattggctgtcattgggctaaattatttctaaagttaccatggatgccattgagtcatggcttaaa |
| aatgtctcctggtgatggcacagtttagctacctaaagaagtagagatgtgggaagccagaagccccaagctctgcagttttcttttgct |
| atagttcctttgcatgttgtgaaagaatacagttaaattcctgctccctaacagatgagagcataagcatttctttgggcatacatatgtaaat |
| acatgctcatggacatgtgaaaagatcaatactaacatttgggtgcaataaataattgtgtaaaattatttttaaaagaattacatattaggaa |
| atgatatattgattaaaagtgatagtcaatgaacaagagagtagatttctgggggaaacctattttgcatcatacttgattttttagttttgactg |
| aatattgaagtctatattcaaaattcttttcctttagaactgtaaaggcattgctgcattttcttctaatgtaattgtttattgctgctgagaattctt |
| atgacaatctgatttttttcatcttcatgattatcttgtttttcccttcatggaatctgttagggtcttgactttatcctttatcctaaatttctcaaggc |
| ttggaccaggtgtgggtttggttttgttttcttttgctactcatttgacttggcacactcagtgggcctttccctttatctttcttcatttctgagac |
| gtttttctctcttatttttattatcttcctttcattttcctgtccttttttctttctagacatctcttaggaggatagtggtcctcttagattgatatgttat |
| gtccgtgatttccaaagtaagatttgtactcgtcgtctgttaaaaggaaaagcatacatataccctatgtatatatgcacactttttttatttttaa |
| attatatatgtatctgtactaattatttacattgtaagtcaaccctaacataatcttaaaggataagatacaaaacatactgcatctagaagctt |
| cagtactttcttcctgaatcccagtagatccttttgttcatcccacgggatgcattccgcccccatcctcccactccctttggataccacatta |
| ccacagctctgcatcacttaactttcctcttatgttttcaccttttttttttttttttttgcattttatgtcctggggaatttccttaattcatttcatgg |
| ttttactgttgatttttttaatattggccatcgcaactttcttttcttttcctttcctttcctttcctttcctttcctttcttttcttttttttcttttctt |
| aattttcttttcttttcttttcttttctgttcttttcttttcttttcttttcttttctttcacacaggatcttggcgtgttgtccaggctggcctcgaactcct |
| gggctcaggtaatcctctcaccttggcctcccaaaatgccaggattacaggcgtgcgccactgcatttggcggcaacttaatttttttattttttatttt |
| tccttttagaggacacctagcactgagcattgcaacttttcatttccatgaacttttaagaaaactcttaaagacatgtttaattctgtacacttt |
| ctattgttctttgattgctgtttttgaataacaacaaggagtacgccttagcattttgatggtatcctcttaatagtcgcaataatagtccccttg |
| gcgctctgtatactctcaagtcttaaatgttttgtatgcagctgtacgttgacagttgaatggtctcgctccaagtggatcagcaagaacata |
| aagaatcatttaactggtacaggctgcggcttgtgaattccctattaacaccaaagaagacgtgtgagactccgtactgaaactaaagac |
| gacttgtgagttccacactgagatcaaataagtctttatgatggtgacagagagtggtgtcaacgcctaaagttttggttaatctctctaaat |
| tgaggggctgaccaaaaggggggaacttaactgtattagacataattttgagaaacatgggtatgtggatggtaatggaggaaatgggtg |
| tagatgagattgcctagggagagtgagaagtaggttaggtctaagccttgatgagttcccaacatttccaagggtagttgaggatactga |
| aaatgagtggccagtgagatagaggtaaagctagagactgcccaggggagaggaattttcaacaatgaggaggtgtcaacattgtca |
| ggtattgctgagaggtcagataaaaccagaattgagcaaaatggccattggaagcctatggtgccctccgtaagagctgtttcgctgaa |
| gtgatagaaacggaaatcaggctgggcacagtggctcactcctgtaatcccagcactttgggaggccgaggtgggcggatcacctga |
| ggttaggagttcgagaccagcctggccaacatggtgaaaccctgtctctactaaaaatacaaaaagtagccaggtgtggtggcaggtc |
| cctgtaatcccagctactcaggaggctgaggcaggagaatcgcttgagcccagaggcggaggttgcagtgagcagagatcgagcc |
| actgcactccaacctgggtgacagagcaagactccgtttcaaaaaaaaaaaaaaaaaaaaagaaatggaaatcaggatggtttggcttttta |
| ttttaataaaatagctagagcagggaaatggggtactttttttcccccttttaagatgagacatagccaggtgcagtggcttacacctgtaat |
| cccaacactttgaaagggagggtcgcttgagctcaggagtttgagaccagcctaggcaacatagcaagaccttgtctctactaaaattc |
| aaaaaaaattaactgggcatgctggcacacacctctagtcccagctatttatgaagctgaggcaggaggatcacacttgagcccagata |
| cgtggggctgcagtgagccctgataatgccattgcactccacgttgggcaacagagcaagacttcgtctcaaaaataaataaataccct |
| gtctcaaaaaaaaaaataaatatgggaggagagatttgacttagattcctcaaagggcaggaggaaagagaattccaaacagtgattc |
| acctttaatgggagaaagatcgcttaattttacatgaggaagaagaggattggtggagatacagtaggtgaacagtttttgtatgaggaa |
| gttgaacatgtgtcattctaatagcttccattctctgtgaagtagagggcaaggtcatctactgagagttggggaggtcaagagagataa |
| ggggagattagaagagctcttctagcagagagtggaagaatgaattgctaagagagatgaagtaggattgttaagtagttttgagggcc |
| ctgttgagatgtgcttccagttgggtgtgattttctccagtagtgctttatttccctgggtacaggcagagagaaaaacaataaggctcatgt |
| agggtttgtattttgttggacaagtcaaacagaaaagtcagaggacgagggagtttagaatgtttgcaaaagagttattgaaacgatgaa |
| ccgcataatctaaggtggtaagtgggtgaatagataaggaggatgtgaataggtaaggagaagaaagaaatatcagattattgattattg |
| atggcgactctctaatacagctattatgccattttaaccgattaagaaactaaggctttagaaaattcataatttgccctaactgcacagcta |
| gtaagcagtggaaatgtgattggaaccagagttcttctgactcaatagactaaatggatgtaaggatgtagttgaaagaagggtgagcta |
| aacgttgtggaaccatgagctctttctctggttgatatccctctctgtaagtgataacatgggtcacgctggataaaaccttgtggtgattgg |
| tgactttcctttgtccttcctcctgtgcctagtctggcgagtatctgcctttccctttcctttctcattgctgccacctaactttaggctcttcccct |
| tacatctgggtaactgaaataagatcaccttttttgttccccttctgatttactttgacctaacattatctttactattttctttaaattaatgtttcatta |
| gtcttattctactcaggaactctgtagttccccattgcctacgaaaaaaagttaagcctcagccttatattcagtgactcttcaattggatattc |
| agtccagttttactcctcctatgagccttctatgccagctccttgggtctcttgccctttcattgtctcagctctgcacccttctttctctttttttatt |
| ctttttttttttttgtactttttttggtttctttttggtttcttttttttgttttatttattaaacctccatcacacttcatcctatggagttttgaaccacagcaa |
| ggtgcagtatcatcctggggctctggaggaagtggcagggagtccaaaatgtcaccttagcttcttatctggggccacatgtatttctgc |
| atctgctgcttcccacactcttgcccacaagtgtcgcttgtggaaataatttgagatttactgtctggctgaccctagtttcaatctcttttcca |
| ccatttgctaatcattctaccttgggcaaaacatagaattaaaagaaaacttcagacaagttaaatttgatggagtttaattgagcaaagaa |
| aaaaaatgatccacaaattgggcagtctccagaatcaccgcagattcagagagactccaggggtgcctcgtggtcagaacaaatttata |
| gacagaaaaggtaaagtgacctacaggaatcagaattgagacatagaaacagtgagattggttacagctcggcgtttgccttatttgaa |
| cgcagtttgaacactcagcagtctatgagtggttgaagtatggccgctgggattggccaacactcagctgttattacagatgcatactact |
| aagttaggttttcgattttgtctgcctatttgagctaggttacagttcgtccacaaggactcaaatataaaagtacggagtcctcttcgggcc |
| atatttagttcgctttaacaattcccccttttggtcagcccctcaatttagagagattgaccaaaactttaggcgttgacaccactctctgtca |
| ccatcataaagacttatttggtctcagtgtggaactcacaagtcgtctttagtttcagtatggagtctcacacatcttctttggtgttaataggg |
| aattcacaagttgcaactttgtaccagctaaatgattctttatgttcttgctgatccagttggagtaagaccattcaactgtcaatgtacagct |
| gcatacaaaacatttaagacttgagagtatacagtgcaccaaggggactattattatgactgttaagaggacaccgtcaaaatgctaagg |
| tgtactccttaataaaagttcttatgaaatgaactgaaccaaatcagccaagttaaggttcagacaatataagcagttcagcagtattgggg |
| tctgattggtcagagtcttcagttggagtatgatagtgattaaggatcatagttcgctgtaaagtagcttgacttaaagaggtgctcgttttca |
| ttgttaccttgttaatacaagtcataataacttgaaaacctgctagaagagatataaagattagaaacccttggaaaacccaagcttgccat |
| tcaccacttaggatgcctgcaaaccaactgttagttgctcctataaacatatcgtgggttcctttctcttgagagatttctttattgtacttggtg |
| gcagtgtctaaggaaacagcagtatcagccaccttttaaattaagctttttgtagtaacagaatcaggggagggattagtacaaaattcag |
| ttttgtttaacaccaaacataggcctccagcttgagcaaaaagaagatctaagactgcatgatcttccattaagtgttttcgttgaatatgtat |
| gttgtcatgtgcctttctgagagtagcttctacccatctgaaaccctgggaggtctgattggctaccaaatccaagaattttcccaatataca |
| aattagttttaaattccgtacaaatggtacttcactaccaccaagagtgagcccccaggaaccccagtggaatctttccccggtagaaact |
| agcttatcctcgtctatttcgaggctagtgctaatttcagttattgatcattttggcctccaagtataagggctatcatgagaattttcaggga |
| agcaattcgaaaggcaggagcaggccaggccagataacaagaaccaaaccaaccaaggaggcagaacagaatatgcagattctcc |
| acagacccaatagagaccctcaggggttggaaaaggggggccacctagttgtatttgagcagggatcattcaggtttgttcgaccatgaa |
| tctgtagctcctgaataacatccagtgggaaatttacttttctatggcccctttgtagtgtgttgtaagggtgtataaccacatctagtaaaaa |
| gagaccctactggatatacaagcaatcacttgtactaacataagtaattcccaaatcttgagtatgtgatgcctgcaagcacaatatacgtt |
| ttgtaggcatcatttggatttgtttttatatttggtgtgatcgactttatcagttgaaaaagagtgttgtttttagtgagtgtaggaaagcaagta |

TABLE 4-continued

| Exemplary target gene intron sequences |
|---|
| ctagtgatgtttagagtatcaagaatagctttccattcttcccttggggtttcagggtgactcattgggaaacgtggaggggcactggcac |
| ccttggaatcatttcctgatttttggcattagcccacaaacccaacagttaccctggttttgtgctagagcataagcttgagctgaagccat |
| ccactgattatggtcccatggattttcatgtaaggaaaaggaaaggattagggaaaaaaataaggaaaacagaaaaacacataaggctt |
| tcatggtggtagagaagtcttgatctgtgatctagggaaagctgtctgtaaccaggatgctgtctgcttctgggaagagatttccctggtc |
| agctttaccttaaagtctccaacgggtatatagtaccaggagtctgaggggccctttgaattgtgagatgtggacccatggttcaaagc |
| cctgaagcttctctgcactgtgggtggtaagaaggacttggtatggtcccatccaacgaggttcaagagtgatcttcttctgatgtcatttc |
| cggaaggcccagtctccaaattccagaccatggagggtttgattgtcctcagttggtggatcttgaaatgcttcctttacctggtggaagt |
| atactttggcgtaatacattaaagccttgcagtatttagtcatatcagagtttaagagagcaggagaagcatgagatgctattattagggac |
| atgggcctcccagtgactatttcataaggggtcaatttatgttttccaacaggattgaatctgattgccattaaaaccaaaaggtagtacctt |
| tggccaaggcaactcaattgattcagttaacttggacagtttcagttttcaaatgccatttgttctttcaagctttcctgaagactgagggtaa |
| taaggacaatggtaatgcaactgtgtcagtaacaccttatttaactgctttataacttgctcagtaaaatgagttcctctatcactggagactt |
| ttagagggatcccccataaaggaaaaacattttctaataatttcttagctatggtcacagcatcagctttcctacatgggaaggcctttatcc |
| aaccagaaaacatgcaaactattacaagaacatactgataccccattgagggtggtaactgaatgaagtccatctgtaaatgttcaaatg |
| gtccatcaggtggtggaaatatactgcctctagtttttctgggattatgagtttgacaagtcaaacattgattataagccatttagtaatgtca |
| gaatagtcaccccaccagtatttttcataatttggatcactttgtctgttccatgatgagctgtggagagctttcaataatggaagcttcaaa |
| gattcaggaaggaccaggcggccgtccgggccctttgtgagtctttgcttcacgttaaatttacatccttttagataccagttttgtttttgca |
| aatcagatgcgttgcactgtttattaaataggtcatcgtaaggaaattggcttggattaatcttatggagttcattcagattgcgtatcttgatg |
| gttccagcactagctgattgagcataaaaatctgctaaagcatttcactgatatttgggttcatttctacaagtatgagcttcagtcttaataa |
| cagcaatctgcatttgtaacaggatagcagaaaggagctcatctgtttggagtccattttgatggggatcccactagaggtgagaaacc |
| ttcgtagtttccatatcatgccaaaatcacgtactactccaaaagcatgtctactatccgtaaatatttactgacttgtccttagctgtgtgaca |
| tgttcaggtaagggcagaaagttctgcaggttgggctgacttgacttgaagagttcgcttctctattaactcattttgggtggtaacagcat |
| atcctgactgatatttttttttctgagtttttggcataggacccatcaacaaaaagtgttaattcaggattatccagtggagtatcttgtatagca |
| acacgaggggccactatttctgatactacactcacaccgttgtggtcttcaccatcatcaggcagagatacagagtagcagcattaagt |
| agattacagcctttagatgaagataagaaggagatggagaagtaattcataagatgttagtctactcactgaaaaatgctgggtttgatt |
| ggaatttaatagactttccacagcgtgtgggacttgcaaattaagttcatttcctaaaaccagatctgatgaagcttctaccagcttggctgc |
| tgctactgcttttaaacaattaggatatgccttagagactgggcctaattgcaggctatagtatgcagtggtcctatgtttagcaccgtgttc |
| ctgattattacattcatgaacaaacaaagtgaaaggtttagtgtaatttggaagtcctaaagctgggggctgttgtaaggccaacttcatttg |
| gctaaaagcctgctcatgactgtcttcccaaggtaaaggctctggtacagcattttagtgagctcatacagtggtgaagctattaaggaa |
| aaatttggaacccaggatctgcaatatcctgcaagcctaagaaagccttttgtcttttggttgcaggtcgaggaaaactttaaataggtttta |
| tcctctcaggtaagagggaaatcccttcagcagccaagtcatgtcccaaatagtggactttttttttgaaaattgaagttttggccaggca |
| tggtggctaacgcctgtaatcccagcactttgggaggctgaggcaggcggatcacctgaggtcgggagttcaaggacagcctgacca |
| acatggagaaaccctgtctctactaaaaatacaaaattagccaggcgtggtggtgcatgcctgtaatcccagctactcgggaggctgag |
| gcaggagaatcgcttgaacccaggaggcagaggttgtggtgagccagtatcacaccattgcactccagcctgggcaacaagagtga |
| aactccatctcaaaaaaaaaaaaaaaagaaaaaagaaaagaaaaaattgaagtttttccattgaagccctgtgacctttatatgcaagttgc |
| tgtaaaaggtaaactgagtcaatttccgggcactccttaataggagagcataacaataagttatctacatactgaatgagagtagaattttg |
| aggaaactgtagtgtcattaactcctgatgcagtgcctggggaaaatatgaaggggcttcagtaaacccttgtggcattacactccaggt |
| gtattgctgatttttccaagtaaaggcaaacaagtattgactttctttatggaatgctagagaaggctgagccaagatctattactgtggaca |
| acttggaatcagtgggtacattaggttataaagtattaggatttgggactacaggaaatcttggtattacaattttattaattgcctgtaaatct |
| ggaacaaatctccagtctcatccatttgtttttaactggtaggattggagtgttacaggggctggtgcatggaattatgagtccttgtttaat |
| taaatcttctacaattggtgagagcccttaaattgcttcaggttttagtggatattgtggtaattaggcaaaggtttagaatgatctgttagtac |
| ttttataggttctacacttttaattcttcctatatcagttgggaagaggcccataaacattaggtgttttcgaaagatcaggggtattacaggct |
| tgagtttcgatcttatcaatttctgcctgtagacagcataacaattctagttcaggagaatcaggaaaactcttaagattatttctgtttctgag |
| gaaaatttaggtgcccttttagctttgaaagtaaatcttgccctaccaagtttactggaacagtatcacgtagtaaaaaactgtgtttttctga |
| aagggggctcagagttaattggatgggttcagatatgggaacctctggaacttgatttgaaacccctgtcacagaaatgaccttttactct |
| aagggatttgttggcttattaaggtggggtttatggtagatagagtagccctggtatccataaggactatacacaactccctatttattttaac |
| ctctgtttccccatgttcctttaaaggtattacggggagcaatccactggagaatcccttagagcctcctttaagttgaatattgtcaggagg |
| actaaggtctcttgggctccctctagtggtgaaacagtttggcctagagggaggtttatcagccgacaatcccttttccagtgccctggtt |
| gtttgcaatacaggcagacatcttggggtaaagaaattcttgttctgggacctcttgatttgatttttttaatatataattttaaaaatattttcca |
| aagtgtgacttaaaaaaattttttttattatactttaagttttagggtacatgtgcacaacgtgcaggtttgttacatatgtatacatgtgccatg |
| ttggtgtgctgcacccattaactcatcatttacattaggtatatctcctaatgctatccctccccctcccccaaccccacaacaggcccca |
| gtgtgtgatgttccccttcctgtgtccaagtgttctcactgttcagttcccacctacgagtgagaacatgcggtgtttggtttttgtccttgtg |
| atagtttgctgagaatgatggtttccagcttcatccatgtccctacaaaggacattaactcatcatttttatggctccatagtattccatggtg |
| tatatatgccacattttcttaatccagtctatcattgttggacatttgtgttggttccaagtctttgctattgtgaatagtgctgcaataaacatac |
| gtgtgcatgtgtctttatagcagcatgatttataatcctttgggtatatacccagtaatgggatggctgggtcaaacggtatttctagttctag |
| atccctgaggaattgccacactgacttccacaatggttgaactagtttacagtcccaccaacagtgtaaaagtgttcctatttctccacatc |
| ctctccagcacctgttgtttcctgacttttaatgattgccattctaactggtgtgagttggtatctcattgtggttttgatttgcatttctctgatg |
| gccagtgatgatgagcatttttcatgtgtcttttggctgcataaatgtcttcttttgagaagtgtctgttcatatccttcacccacttgttgatgg |
| ggttgtttgtttttctcttgtaagtttgtttgagttctttgtagattctggatattagccctttgtcagatgagaagtttcagaaattttctcccattct |
| gtaggttgcctgttcactctgatggtagtttcttttgctgtgcagaagctctttactttaatgagatcccatttgtcaattttggcttttgttgccat |
| tgcttttggtgtttagacatgaagtccttggccatgcctatgtcctgaatggtattgcctaggttttcttctaggattttatggttttaggtctaa |
| attaagtctttaatctatcttgaattaattttgtataaggtgtaaggaagggatccagtttcagctttctacatatggctagccagttttcccag |
| caccatttattaaatagggaatcgtttccccgtttcttgttttgtcaggtttgtcaaagatcagatagttgtagatatgcggcgttatttctgag |
| ggctctgttctgttccattggcctatatctctgtttggtaccagtaccatgctgttttggtgactgtagccttgtatagtttgaagtcaggtagc |
| gtgatgcctccagctttgttctttggcttaggattgacttggcaatgcaggctctttttggttccatatgaactttaaagtagtttttccaattct |
| gtgaagaaagtctttggtagcttgatggggatggcattgaatctataaattaccctgggcagtatggccattttcacgatattgattcttccta |
| cccatgagcatggaatgttcttccatttgtttgtatcctcttttatttccttgagcagtggtttgtagttctccttgaagaggtctttcacatccctt |
| gtatgttggattcctaggtattttattctctttgaagcaattgtgaatgagagttcactcatgatttggctctctgtttgtctgttattggtatataa |
| gaatgctctcttttgttctttgttagtcttgctagcggtctatcaattttgttgatcttttcgaaaaaccagttactggattcattgatttttttgaagg |
| gtttttgtgtctctatctccttcagttctgctctggtcttatttatttcttgccttctgctggcttttgaatgtgtttgctcttgcttctctagttctttta |
| attgtgacgttagggtgtcaattttagatctttcctactttctcttgtgggcatttagtgctataaatttccctctacacactgctttgaatgtgtcc |
| cagagattctggtatgttgtgtctttgttctcattggtttcaaagaacatctttacttctgccttcatttcgttatgtacccagtagtcattcagga |
| gcaggttgttcagtttccatgtagttgagcagttttgagtgagtttcttaatcctgagttctagtttgattccactgtggtctgagagacagttt |
| gttataatttgtattcttttacatttctgaggagagctttatttccaactatgtggtcaattttggaataagtgcagtgtggtgctaagaagaac |
| gtatgttctgttgatttggggtggagagttctgtagatgtgtattaggtccgcttggtgcagagctgagttgaattcctggatatccttgttaa |
| ctttctgtctcgttggtctgtctaatgttgacagtggggtgttaaagtctcccattattgttgtgtgggagtctgagtctctttgtaggtcactca |
| gggcttgctttatgaatctgggtgctcctgtattggttgcatatatatttaggatagttagctcttcttgttgaattgatccctttaccattatgtaa |
| tggccttctttgtctcttttgatctttgttggtttaaagtctgttttaccagagactaggattgaaacccctgccttttttttgttttccatttgcttggt |
| agatcttcctccatccctttatttgagcctatgtgtgactctgcacgtgagatgggtttcctgaatacagcacactgatgggtcttgactcttt |

TABLE 4-continued

Exemplary target gene intron sequences atccaatttgccagtccgtgtcttttaattggagcatttagcccatttacatttaaggttaatattgttatgtgtgaatttgatcctgtcattctctc
aacatttgcttgtctgtaaaggattttatttctccttcacttatgaagcttagtttggctggatatgaaattctgggttgaaaattcttttctttaag
aatgttgaatattggcctccactctcttctggcgtgtagagtttctgccgagagatcagctgttggtctgatgggcttccctttgtgggtaac
ctgacctttctctctagctgccattaacatttttccttcatttcaactttggtgaatctgacaattatgtgtcttggagttgctcttttcgaggagt
atctttgtggcattctctgtgtttcctgaatttgaatgttggcctgccttgctagattggggaagttctcctggataatatcctgcagagtgtttt
ccaacttggttccattcttcccgtcactttcaggtacaccaatcagacgtagatttggtcttttcacatagtcccatatttcttggaggctttgtt
cgtttctttttattctttttctctaaacttctcttcccgcttcatttcattgatttgatcttccatcactgataccctttcttccagttgatcgaatcgg
ctactgaggcttgtgcatccgtcacgtagttctcgtgccttggttttcagctccatcaggtcctttaaggacttctctgcattagttattctagtt
agccgttcgtcgaatttttttcaaggttttaacttctttgccatgggttcgaacttcctcctttagcttggatagtttgattgtctgaagtcttcttc
tctcagctcgtcaaagtcattctctgtccagctttgttccgttgctggtgaggagctgcattcctttggaggaggagaggtgctctgattttta
gaattttcagtattttgctctgtttcttccccatctttgtggttttgtctacctttggtctttgatgatggtgatgtacagatgggtttttggtgtgg
atgtcctttctgtttgttagttttccttctaacagtcaggaccctcagctgcaggtctattggagtttgctggaggtccactccagaccatgttt
gcctgggtatcagcagcggaggctgcagaacaacgaatattggtgaacagcagatgttgctgcctgatcgttcctctggaagttttgtct
cagaggggtacccggccatgtgaggtgtcagtctgcccctactgggggtgcctcccagttaggctattcgggggtcagggacccac
ttgaggaggcagtctgtctgttctcagatctcaagctgtgtgctgggagaaccactgctctcttccaagctgtcagacagggacatttaag
tctgcagaggtttctgctgccttttgttcggctatgccctgcctgcagaggtggagtctacagaggaaggcaggcctccttgagctgcag
tgggctccacccagttcgagcttcccagctgctttttttacctgctcaagcctccgcaatgggggcacccctcccccagcctcgctgcc
accttgcagtttgatctcagactgctgtgctagcaatgagcgaggctccatgggcataggacccgctgagccaggcgcgggatatagt
ctcctggtgtgctgtttgctaagaccatcggaaaagcgcagtattagggggagtgacccaattttccaggtgctgtctgtcaccccttt
ccttggctaggaaagggaattccctgaccccttgtgcttcctgggtgaggcgatgcctcgccctgctttggctcatgctcggtgcgctgc
acccactgtcctgcacccactgtctgacaatccccagtgagatgaacccagtacctcagttggaaatgcagaaatcacccgttttctgcg
tcgctcaagctgggagctgtagactggagctgttcctatttggccatcttggaaccgcccgattgtgatttaaaatgagaacgagatggtc
cctttggttcctggtccctgtaactgttgcaattgaaggggcataagcttattagccttttgaggtttttttgctctagagtcttctcaaaatgc
ttagctaggttgggcacgatggctcacgcctgtaatcccagcactttggaaggccaaggggaggatcacgaggtcaggagatcaa
gaccatcctggctaagatggtgaaatcccatctctactaaaaatacacagattagctgggcatggtggcacacgcctgtagtcgcagct
actcgggaggctgaggcaagagaattgcttgaacctgggaggcagaggttgcagtgagccgagattgcgccactacactctagcctg
ggtgacagagcaagactccacctcaaaaaaaaaaaaaaaaaaaaaaaaagttcagctaaggccaccaattcagtcacatctctaactt
cccattgcaacttatgtttttagttaaactgctaagttcaggatggagtccatttataagtaaagcagttaatgctgtttcagcccctgcagg
gaatactccttgctgtactttgagcccaggatgtttcacaaatatttctaagcgacttctgtaatctgaaactggttcatcttttcttttcttttttttt
tgcttacaagattgtatgatggaccaatttttgtggaaaaatttaggaactgaatgttaaaaggttttcagcgatttttctagctatttttggtc
cttcttgtgaggagctcttagagggccctttaaaatgtcctcctcaggtttgtcccattctgctgctgccatccatttctgagcttcaccagcc
cccagtatcatatgaataaattggtaaattcatgaagtcctggatcgtaagctcctattaggattctaaattcctcagtaaattttgagactttt
cccttggaccagggaagtccttcacaatggggctaagctcagttttagaccatggagtgaaagtagttacagcaggcaggcctggctg
atataaggtctcactttgtaagacatctgtctaacttcctttttttttttttttttttttaaatcatcttcagggtgaaagtgtaatttaacaaaaagtt
tagtggactcagagtatgtaggtagagatggacaaagaaggaacagtccgagttagatcagtcaaagtacagtcctctttcttcatgtcct
tggtctgttgcttaagcttttcatttggttttgcaaagaatcttttaaggaggcacttttgattcacttagtcttttggaggcctttgcgtatcca
tgagacaatacatcccactgtatttgtggggctttgatccccttttctaatatgccttgcaaacaattttatccaaattaaaacttctccattg
tggccattttaattctaagttttctttagtgaggttaacccattttactgaaaatgcacatgttctgggcccataatttttatacgtaaaattagct
ggagtccctgaagatggagtcccagactccttggattgagatgatcccattattaaataaggtacttatcagaggtctgaggcctctaact
gaatccaatccagttaattatcaaatccaatttgatcttggatccagtccaggctaagtattgcttgagtaaactcggagagctcaaaacac
aagttagtggagctcggaatctgagagaaaactcacccatgacctccagttacaatcaagagaccagtgagagcaacggcctcagtg
ggtacctcaccaggtcacctggtgttccaggggggttgccagagtttttcttcaaatcccacttctgacaccagatctgttaaaagaaaactt
cagacaagttaaatttgatggagtttaattaagcaaggaaaataaacactttgcaaatcaggcagcctccagaattgaatgcagtttgaac
acttagcagtctattagtgcttgaagtatggccactgggattggccaacactcagctattattacagatgcatactactcaggttttccatttt
gtctgcctattgtgctaggttatggtttgtccacaagaacacaaatatagaagtatggagtccttctcaggccatatttagtttgctttaacaa
tacttaaaaaaaaaatttgtaaaataaggatacttaaccttactcggtgtttctgagagttaacatttatatagttatgtgtagtgaaaacagc
tagcgtaatgtctggtatgtataggaacacaagagataccgcttttcccatatccccataccattcttcacagcattgctcctgtcttccttga
ttcctcctcctccttctttgtttttttttttgtttgtttgtttgttttttttttggaggtggagtctcactctgttgcccaggctggagtgcagtggtgtga
tctcagcttactgcaacctctgcctcctgggttcaagtgattctcctgcctcagcctcctgaatagctgggattacaggcacacaccaaca
cactcagctaattttgtatttttagtagggatggggtttcaccatgttggccaggctggtcttgaactcctgacctcaggtgattcacccac
ctcagcctcccaaagtgctgggattacaggtgtgagccaccacaccctgcctccttcttaagaagtttccagtcccttgtaattaaaggaa
ttaatatttttttaactacttagaatcagactggccctgattattagtaagcaactaatagtaagcaagcaactatgtatgcaactatgagtgtat
gttaagatatggttgttggtaacctttcattctcttcaggaagaagaagagggtggagctctacagtcaatgtgtacatttaaattctgttccc
tttcgagctttttttgctactttcattcttctggggatccaggtgcttgagttgggattgattaacttccttaatttccacccctgtgctgtcaggat
cgggagacatagatgaaggtgttctaaactgctagaaatttgtttttgaaagcaaaagtttgcatgcatttttgttttcaactttacttacagt
gaatagtagttaataaaataagtccctgccttttctctctttggtttcaattcctgagaccaggatcatagcccacatattagagtggagtccc
actgctttggtttgaatcatgcctttgtttcttatgtcagtgtgactttgggcaagttatttaagtctttgcaccacattttcctcatctgtaaaatg
aggataatactagtactttctacatgggattgttagcaggattaaatgagatagcacatactgtaaccatgtctggcacatagtcaatggtt
agtaaatgtgaactattgtgtgacattgtggttagtcacgtatggggctgtgtttcctttagtatattgctcttttaatgtcatttcctttgtactgtt
accctctctgatctttcttccatattca SEQ ID NO: 276
Gene: OPA1
Intron: GRCh38/hg38: chr3 193618937 to 193626091
Intron Sequence:
gtaagtgtaaaagagaattgttcatgtaggtagtcttgaaagatttttttaaagtttttacttctttggaagattttaaaatgataacatctgagaa
gcaaatacaaaaacatccaagtagagatatcgttactaatcttagtgcaaagtacaaggtattacgtggcagttctggaaatataattgag
aagcccatttttttcacatatgtccagtgaagcattagtttcgagggttgtccccaagaaagagttgtgttgttaagtgtgtggggggagaa
aggctcgtttagacaaggcaagcggacttcttttctttccctaggacctctcatactgtaatatactcatgcgcattgtgaatttccaaggag
tcaaagcatacagtgttttcccaaattatttatcaacagaacccttttgctcatggaacgtcgtatagggactagatttcactttggggaaact
agaaagggaataggaattgggttattaggaaataaatcaattccctgatattgatagttaacaaagttatgtatggggttatttatggtatgtt
attttcaacacatattcattaacaaaatccatatgaaagttataggagaattgctgaggtagaataacatactttgtttgtatttataatactcat
atatttacctgacgttttctgagtcttcactttttttcattcttttggaattggtaaaataactgattccttgaaagttttttttctaaataatacctagat
aatagatttatagaaaaaatattgtatgaatgttttaacattcatgtaatatggaacatgtaatttttatactggaggttattatagttttaatacat
caaagaaataatgtttattttggaagcagaaagaagaaataatttctatgaataggttttcatctctttccttgttcttcaactttgaactttttata
ttccaaatttaattatatttcaaaagatttttttcttttgccttttaattttatcttttggagaaaaatgtatgtcaaaatgtatgtacgtgtatttgtct
tttgatttgatctttttttgaccctcttttgcattgacattattttaaccaaaggacactcttgattgttcatgctactgggggaaaaaaaaataagt
agaaattagcctaatagttgtggcttattttgagtgaaggccttagcccttaaggcaattaaatttactgtggagagaagagctaatctaatg TABLE 4-continued Exemplary target gene intron sequences gggagaaggagcctttgttacaggtgtggtagtgtggttctttgagtgacaagatttctgtttgccagattggttaggagaagtctgtgtgt
ctgctttctctcttatggcctaggatcactgtggtgaatgaaaaacctgtctcagggcctgactcagataattcccttaaaacccggctaag
gtcatagatgaataatcagtaattgaacagaagctctgcaatagaaaagaagccagataattattttggaaatttaattatatttacagatttt
attttatacagtagacatggaattaaatttattacattatgttctaatttactctttgcttgttttgatttgcttgtttgacaatacatgtccttgtaaa
ctatttccttttaacttttctcaatttatggtgcttattttccccattaaagacttaccaattttttttttaactatttgttacacatactgaatctagag
ttgtaattaagctactttcattactggttaagtcaaattatagcaaatgctactataaaaatttactatccaaaaatgtgtctcaagccccaact
gatggtttcaaattctgttattaataatatgcagcattgtgtttgcaaagcttggctgttacttgtgatgcttgagaatgatgagtcactcagct
aaactgagtgattttgagacttgtgtacaaattgatggttgaatgtaagcatgcaaagagagaccttagcttagcagtacccttttttgaaatc
actctgacatcaagtttgaaaatgtgggcaataatcagaggtggtaaggtggccaggctttagctgaatactttttttaactggttcagtctg
agggctgaaagccccagatttaaacagtatttagaatttgaagcagtcaagtattagtttaatggttgtcaggtttgtaacaaagtttctggc
tagacttctactagaaatgtaaaagtgcatgtgaatcagctttttaaaaaagtaataataattgaaaaacatttctacaactagaactaaaga
aaagatttgtcctttctaataggaaaacacatctggagaagtgctggcaactagcagaacagttaggaccattcagaatcaactgaagtg
aaagtgacggggagctgaggggaacacagatagtttgacttcagtcagacagaataaacatgatgaaccgataacctgtgattcccag
cctggggttactactggagttttaggtgtcctggaaagttataataccggtcttcaaaaagtctacagaaagcatagatttccacataatgc
tgcacaggctaacgaattaatcaagtttctttggtttggcctggatttatatccattcagtttgtggacactactgaattatttatgtcatgttgat
caaaagttctgatatgatttgattaatgaaacattgaaaaaaatagtaaaaccaaccattttttaaccttacactactatcttgaggtatgattga
catacattaaaaccacctcttaataaatgcttcttgttaatcaaaaatttgaaaacgtatgtccactggaggaaaaaagacatagccctgga
tgtgaactgaatattactgagactcggagaccttcagaactacctgaagatgaatcgaagtgctgcctactttagagaattggactaattta
atttgggagtcagcagattgctgtatatcagtcatcatatataccggtgacaagaccacttagttcattccctttttttagattctgtaagattatt
gtgttccagtgaaattgatttgcaaaatgagacattttatttctgtgcttttgttctatcatgtttctgattggtcataagcatctcacagaagta
agaaatatggcgattcagaaggcaacaagcacatttataatttatagaaaatatttgaaggactttttcatggcccaaatcatgaaaagtag
tagtattgttttaagtataattattaaattataatacattaatgttctttcttgcaacatattactctcattcttttttttttttttttttttttgagacggagtc
tcactctgtcacccggctggagtacagtggtacgatcttggcccactgcaacctctgcctcccgggttcaagcgattctcctgcctcagc
ctcccaagtagctgggattacaggctcctgccaccacgcctagctaatttttgtatttttagtagagacagggtttcaccaggttggccag
gatggtcttgatctcttgacctcatggtccgtccacctctgcctcccaaagtgttgggattacaggcgtgagccacccagcagtctgattc
ttaattttatagtttatgttgtacctccccagctgaagtatctcttttctttttttcccgcgtgtttagtgttcactcatctttatagcatagctcaattg
tcacttcatgaagccttccataacctttgtagctccattaattatattcttctgagtgtttaaaacacttgccatatgaaacactatttactttggc
ttacattcttactatctaatcggccatttctgttactaaatctttttctcagagcacctgggatagtcttgtgtcttagtaaaatcagttgattgatt
taactcggtagagtagaggctgattaaagtaaataaatctggttgatgccaacaaaatttttggtcccctcaatttttttgctctcattacctgca
aattctccctggccttcatatttggcaaccattgaggagaacaaggctgtaaaagtagttcatgtacttgatattctgaattggaattaagca
gagttgcttaagtaggacttgcttttctgggatttcttatgcaacaaataatgtagtaactggaaatccaagttcaagacactggcagattcg
atgtcttttgaggacccttggcttcatagatgatgccttctccctatatccttacatagcaaaaggggccaggcagctctggcctttttttgta
aggccaataactccagaaacctcatgacctcatcacctcccaaaggccccacctctcaatactatcacattgtgaggctaggtttcaaca
tatgaattgtgggagacaaaaattcagaccatagtataatatttcaagattacttaaactcttctctaccaaactcattaacttttaggttagca
cagtattttcattgatattttggtttctggagttattactaatttcttgatctgatgttataattaaaaaaaaaacaggactttgtacgtgaaatgag
actgagataaggaagctgattcagagatggagatttaaaaaaagagagatgagagattgagatctgcagtgtcaaactgacaatagcc
aggagtcaggagatattaagagactatatcatctgtgattgttaatgattatttattgttatttataaatactactgtattttatatattatatacatt
gttttaaaaattattttgtaccatttcttgaaagaaaaatgtctaagcttgggaaaatatttattgaaaaatgtggtttgtacatctgaggagtg
tatcttgcacagtaggtgcatagatttcttcctcttcctgttccacatggccttagcttagaggctgtgtggccatcacttggtatttagggta
agactggtgcacaaaatcaaagacaggtaaccttggtataagtgtagtatcatgtaaatagcttttctatgtctaattcttgttttcttcctactt
tttcaggaggtcaatttcagttcatttcaactatctttacataatagtgctttagtaacaggcatggaaggaaagagacatgtccctagagtg
ttttcttgaaatctaatagatgattggagtatttaccatgcagttgtgtatatacataagcagtgaattcgagaggaatttttaagctgtaaaaa
aaagcattgtgtgccttatagacgcgagtgagaaatgtggaatatggctgatccaaagggaatgagttatctcaattgattaatcacagtc
agttacagattgaactctttgttctactctttgccccttctcactattgctcttgactagtcttaagaaagaaatgtggaatattttctcacggc
tttgggattttataaattagaatactagtggtatgtaaatacagcaggtacactactgtataaaccaacataggaagccttctttaaagggaa
ttgtttgagaaatttgaacacttggataatttgaataaaggattgtgataaatgatcaaatgaaagaaaataaatcaggttactcttctttctgc
ttgataaagcaataattttttttaaaggtaaaaattatgagaatgatgaggatagtagttagcattgtctttctttgataggtttgttaatgatcat
aaaactgatttatttaaagacatgtctttttataactatttatactgttgtatctggaaacaaatattgaatttcatttgtcatgtggaagaaatca
actagttttaacctttgatttataataaatcaaccactttcatttattgtctaatactggcaatgaacacagcctaatgtatcaaaactaacaga
ataaaaattctccaagttatatccagactttaagacactttctaattatataaaataaaatatttgggcagtcatttttttaactctgaaactattta
aaactcctaatttagaatatcttaataaatacccatttcctctttttatttttataacttggtaaaaattgagtccattgttttcccagaacgctgtt
cttaaacaaatggttacctccttcattagaactttactttttttaggatttctaattaagaaaacattaggcttgtaacattgtcaaatcttggtgg
tctttcttccacgtttttttgaggtcgattatctaagaggccatcagttaataaagctatgcaggaaatgacatcatgccacatgtgaatatcct
gtattaaaaattgtatcaatatactattttataattatgaagtggaatgaattttagaaatagaaaaggtgatttttttgtgcataggtccaaactg
tgttttgttttcatttcagaatttcataataactatattgtctccatatcttaattgtgtttttttttatagcacttttgtttagtaatttgtatatgcttggct
gtattctcagaggctgtttctatttaatgttgtcaaaacagctcataaaaagtgaaaattcggtcagactagttatttgatattatatatgaaatc
aaaacaacctgaaacattatcttttaatttaaataaagaaccccaaattttaatcaaatgtatgcaaaggcacatagaatatatgacttaatgt
acaacctttattaacttgatgatggaaacctgttcctagggacctttacttgaataaatgaaatatcaagaaaaaatactaacttaagaataa
taatttaataagtaagtaagctattatgatcttcaatcagtcctgagagaatcatggttgagaattagaaaatttagaccagtaagatcaaca
ctgttaaaaaaaaaaaaaaaatcagtatttttttctccatatttttttatatatctggatcattttatttagcacttattattgcactttccttttcactttttta
aactatgctgttttattttttctgagacatctgatttactgaggaggaaaatggaaatgcggtacagagcccaagggtatgacggctttaaat
gagtttccatttctgttttaagttaaccatccctccctagcttacatctgttcctttgttgcacccttggtttaacattattctcctccccaatttcct
cttctcctcattgtgaactcgtggcag SEQ ID NO: 277
Gene: OPA1
Exon: GRCh38/hg38: chr3 193626092 to 193626202
Exon Sequence:
GGTCTGCTTGGTGAGCTCATTCTCTTACAACAACAAATTCAAGAGCATGAAGAGG
AAGCGCGCAGAGCCGCTGGCCAATATAGCACGAGCTATGCCCAACAGAAGCGCA
AG SEQ ID NO: 278
Gene: OPA1
Intron: GRCh38/hg38: chr3 193626203 to 193631611
Intron Sequence:
gtgatggatggtttaagggggctaccgatacattcacactaatcagccatttctgccaagatcatgtcacctcaatctgttcatggactcca
aatacaagaaattaatttgacaaagtgaaaatataaaagatgcatcatataaatatgtaacttttctggagtgggtagtataggtaaagcca TABLE 4-continued

| Exemplary target gene intron sequences |
|---|
| aaagaaacaaattcaagcagaggaattttggtttctgaaaattaggttgtctgtagggtccctgtatttatacttagaacaaaattaggaattt<br>ctgtttatgtggtccagttattgagtcaccctaagtttgtaggcatcttacctacctacttgctccccaagtttttatttctaaaatgaaaagcat<br>tgctgtagatgaccagtttacactaaagaataacatttatttatttgttttagctaaagtatatggacagggaacattcatattcttgtagaaga<br>aaattattttgacttttgggcaaaagcatgtagttcttatacactttgacaaactcattgcgtacatttttcacattaatcaaagtcagcacaaat<br>aaattttcaccttggaccacggagggtttgaacactggaaatttgatataattctggttgctaaagaacaagttctaataaaagcttaagtgt<br>ataccaatatgtggctgttggtgcaatcagcaggtccgtaaaaatatgattttaatggttaggtaatcccacaacggagatcccaaagttc<br>atgtttggaagagacttttgggtcaaagtgaaatcagtgtaatgaatttaaaattatactctgagatcttgaaatcagctaattatgttacatct<br>tattagctcagaaaagttttgaagttatatacaaatgctagtcaggaaaaaagattcagtcatgtaattcttgtacattctactatttaaatcaa<br>ccaatattatagattatgatttagtgcagtaattctgctggctaaccttatctcatttggtggtggttagtacttcagagtactcaccatagtttc<br>atttatgttttcagcatcacttcctggtttttctcaattccatggctgtggaatcaattcatatgtatatttagcttcggtgagcaaaaacatagct<br>agaaaaagaaaagaagtgagtttcctacctggttaaattaaagtcgatgtgttaagccaaggaggacttctttgaatggtactttaacaat<br>ccctgttctgtatactgtgaatatatcatttaaatagcctaataaattggatgcttaggctgagccacctatactttagttttgttatggaaaga<br>agggagaggagcaagtatgttcttatatgttacttagaaataagaatgtagctgtagttacacattgttcttaagtttttttcgtaagacaactt<br>gaaatgagtcccataggcctgctatttaacattctaagatatgacttaaggttaatgatgagcttttgaatctgacaattcaagagatatccat<br>aatgaatactgattcattttctacattgctgaaagctaatgttcattttaagcctactttagtagcctttatttgggcttagagatgttattcctcttt<br>ctgatatttattgggttatctgtttaacccttttatatctccctttcccgatttgtaaattagagactggcaagacttttaccctgagtagagcac<br>caaacatggcttgtttctgcccacactgtagttaccttgaggggaagtaaatgggactttaaaagcaatttatgctcttttatagtgaaattat<br>ccctcttactatcccgaaagactgttaccttacaatatcctccactcctttccccctgtagttactatagagatgacttttcggttcttcactgc<br>cataatgatcaaaatcctaattcatgagattttatcattccaggcatgtgaggtttacttgatgcataaaaccgcaagtacttttgttgtttttt<br>aattgtttttctctcttatcttcttgaaagtctaagtagatcatcattttgatgtcttattagtagcaactaataaatttccctgtatcttctcagc<br>aaaagaactcaagcagagacagaagattagaactaccattggtagttttgcttcctatggatatgttcacatacatagaaattttacaatga<br>cctttttatatatgtatttcagaatttcagaatggcctcaatgccttaataggaagaaatacttgaaatttttaaattagggcttggttttgtgag<br>gagctagtaaaggtttttctctttcagctttagcttgtttctgcggaggattccgctctttctccatcagtttcatagccctggaattgtagaaa<br>agctctggtttcaagaccattgatatccatttctgtcagggtgagttttaaatttatttcatgatgcaaacaatatattgaacaacaggacatg<br>aacttgttcttgttgtaagtggctgaattttatcagtaaagcacatcaaaataaaatataccccaattgctagttaagacctagagtgacaga<br>ttgaaaatagcttgtgttattctcttaagaaaatatataaaaattatcatctcatcaatctttaatgtttgttttataaatctaaatgtttttatattgttt<br>cctaggaaatattaggtctaatttttactttaccaccagctgtcttttatttactcttttttgagacggagtttcgctcttgttgcttaggctaga<br>gtgcagtggcactatctcagctcactgcgacctctgcctcccgggttcaagcgattctcctgcctcagtctcccgagtagctgggattac<br>aggcacatgccactacaccaggctaatttgtatttttagtagagacggggtttcttcatgttggtcaggctggtctcgaactcccgacctc<br>aggtgatccgcctgcctcggcctcccagagtgctgggattacaggcatgagccaccgcacctggccagctgtcttttaatataacattat<br>gattaattgtgatgttccattaaactaagcggagaggaaacatgctggtaaaccatgtgtgagttattcattgtaccagaaaggcaaatga<br>tacattttatcctaaaattcaaatttataaacatcttaacacttgtgatcattaaatactactaatctagcatataaattatatttgtaggcggggc<br>acggtggctcacgcctgtaatcccagcactttgggaggctgaggtgggcagatcacgaggtcaggagatcgagaccatcctggctaa<br>catggtgaaaccccatctctactaaaaatacaaaaaaaattagctgggtgtgctgggggcacctgtagtcccagctacttgggaggct<br>gaggcaggagaatggcgtgaccccaggaggcagagcttccagcctgggcgactccgtctcaaaaaaaaagaaaaaagaaattatat<br>ttgtaatattctactaaccttatatcattttaactttttatataactttttattttaccaaattaagttaaccttttatagcccttggcttatactaaaca<br>tcctaactttttgtttaattgtattagttttaagttattgccccagatgtcaagtaatgttggattttctataataatttaggatatattgcatgaag<br>tcagttagtatttacatttaaaactaaaacaatttatactaatacagtttatacatttcatactaatttagctacagttggataaatatttaatggaa<br>caaagtaaatcaaagtaccttttcaaatgaattggaaattaaatccacataacaatttttatgaccacactattacagtgtgatggcatgcc<br>aaatgatcataatgtggaattatgtatttcttcattggctttcaagattctgttctttagtttgtgggctcctctccaacttgcttgtctcctcacag<br>tttaggcgactgtttataattcttgtccatcctgcataaacacacacagtcaaaatgaaaaaaagcttctatcagcagatctgtgcttgctgt<br>acagaaatgggaaaacaattgaagtttgcattatctttttctaattaccagatcgtttttggagctatttaggcatacgctttaaggaaaaaa<br>gaaaaaaagagtgtacctttgtttctaacaaaggttgttatctatattattgaaataaaaaattggggatagttatgacaaagtatttagaaat<br>aggaattaaaatcttaaaataacttttcatagcatggacaagacttattaatgtctacctcaataagcaaatcatttaaaaattttcatgtatat<br>ttgctgccatgatgtgttgtgattgcttaaataaccaatgaatgaagatcaacaaggatttaaatgaagaagaatatggatttaactattttct<br>cctgtgaaataagttcatatttacaagttttgattttcagaaattagacaattatttttaaaggctgggatgacaacttctgcctcttaccaaga<br>agtcaaagcacagttatgtgaattcatcataaatcacatcattttattatatttgtatttataattgtattgtgactactttaaaacctgttataaa<br>ataaaattgtttttaatattttatttagaattattagcattaataacaatttgaagtagtttacacaatacctgtgagttttattttgttttatattga<br>aattaattttagttgctttacttggcttcattgctatggatgcattctctgtgttacgagttagcagatctttccttggaactgaatttaaaagcaa<br>gcatttggctccacttaaatctctgaaaatgcaacttgttctttgcatttattacataattcgctacttatggtacagaaatggatacaatacaa<br>aaatatttccttataagatacactgtgaccaatgagcttttaaatagctgtaatcagtaacatgtatttgacttttcaaaacacatttctggag<br>ggatatcagtgctttatttccccaaatatctgaatccctatgctttagtacaaaacaacttctgaagaatttagtaaccatatgtgttgatctctt<br>gtttttctaactagtctttcataagaaatgactagaatagcaacagggaaatgattgccttttaaggtttttgtttctcaatataaaattttggtga<br>accattttttattgataaatacaggtatttttactttcttaaatcacttgatttaaaattactttgattaaatatgcatataaagtcagttgtttttaactc<br>tcaatacttatcaaaaaaatttaacttgctgtacattctgtataaacctaattctattcaactaaaattattttaaacatttag |
| SEQ ID NO: 279<br>Gene: OPA1<br>NMD Exon: GRCh38/hg38: chr3 193628509 to 193628616<br>NMD Exon Sequence:<br>CTTTAGCTTGTTTCTGCGGAGGATTCCGCTCTTTCTCCATCAGTTTCATAGCCCTG<br>GAATTGTAGAAAAGCTCTGGTTTCAAGACCATTGATATCCATTTCTGTCAGG |

Example 2: Confirmation of NMD Exon Via Cycloheximide Treatment

Figure 4:
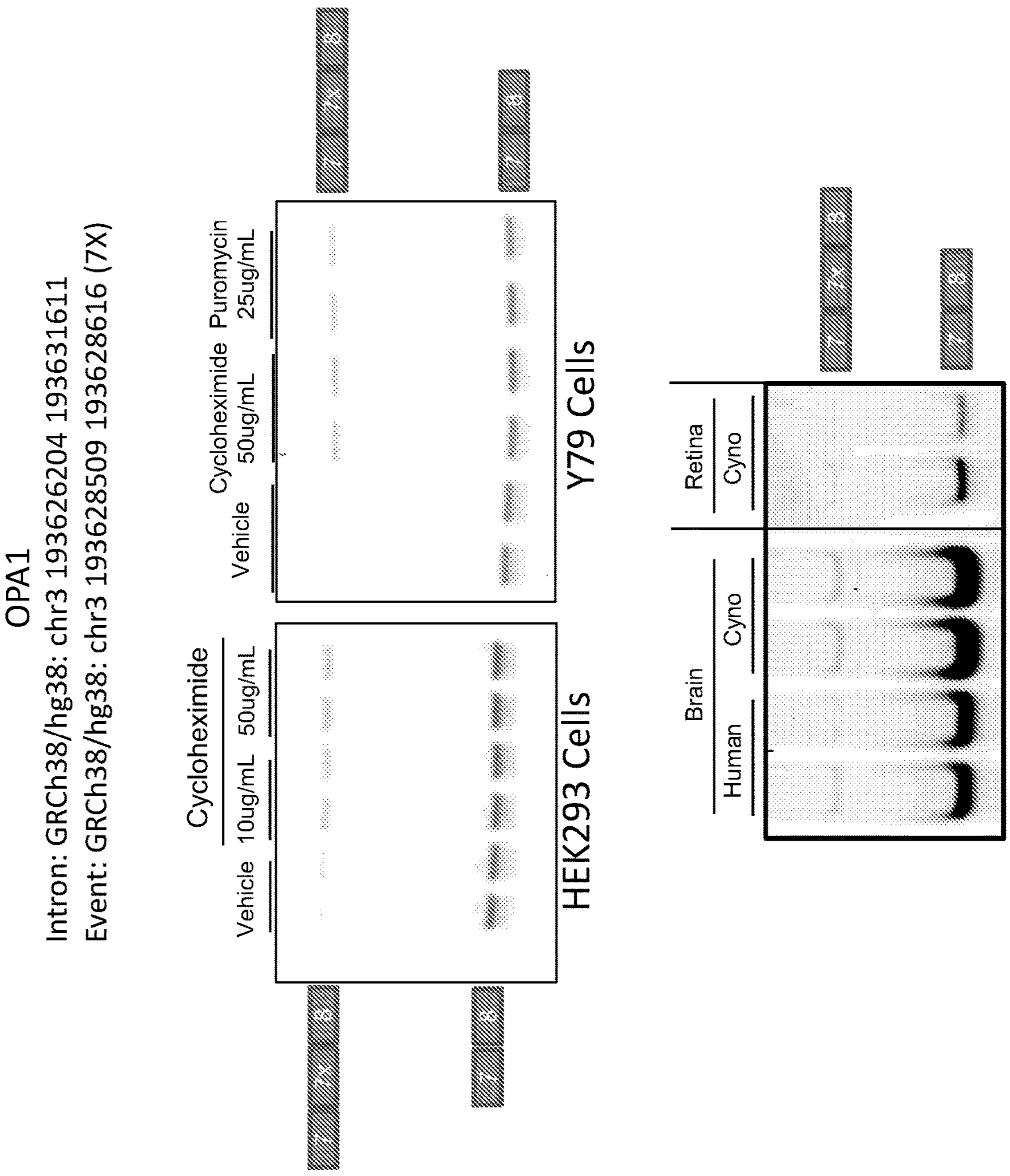
FIG. 4 depicts confirmation of NMD-inducing exon via puromycin or cycloheximide treatment in various cell lines, as well as the confirmation of NMD-inducing exon in brain and retina samples. RT-PCR analysis using total RNA from water-treated, DMSO-treated, puromycin-treated, or cycloheximide-treated cells confirmed the presence of a band corresponding to the NMD-inducing exon 7x (GRCh38/hg38: chr3 193628509 to 193628616) of OPA1 gene

RT-PCR analysis using cytoplasmic RNA from DMSO-treated or puromycin or cycloheximide-treated human cells and primers in exons was used to confirm the presence of a band corresponding to an NMD-inducing exon. The identity of the product was confirmed by sequencing. Densitometry analysis of the bands was performed to calculate percent NMD exon inclusion of total transcript. Treatment of cells with cycloheximide or puromycin to inhibit NMD can lead to an increase of the product corresponding to the NMD-inducing exon in the cytoplasmic fraction. FIG. 4 depicts confirmation of exemplary NMD exons in OPA1 gene transcripts using cycloheximide or puromycin treatment, respectively.

Example 3: NMD Exon Region ASO Walk

Figure 5:
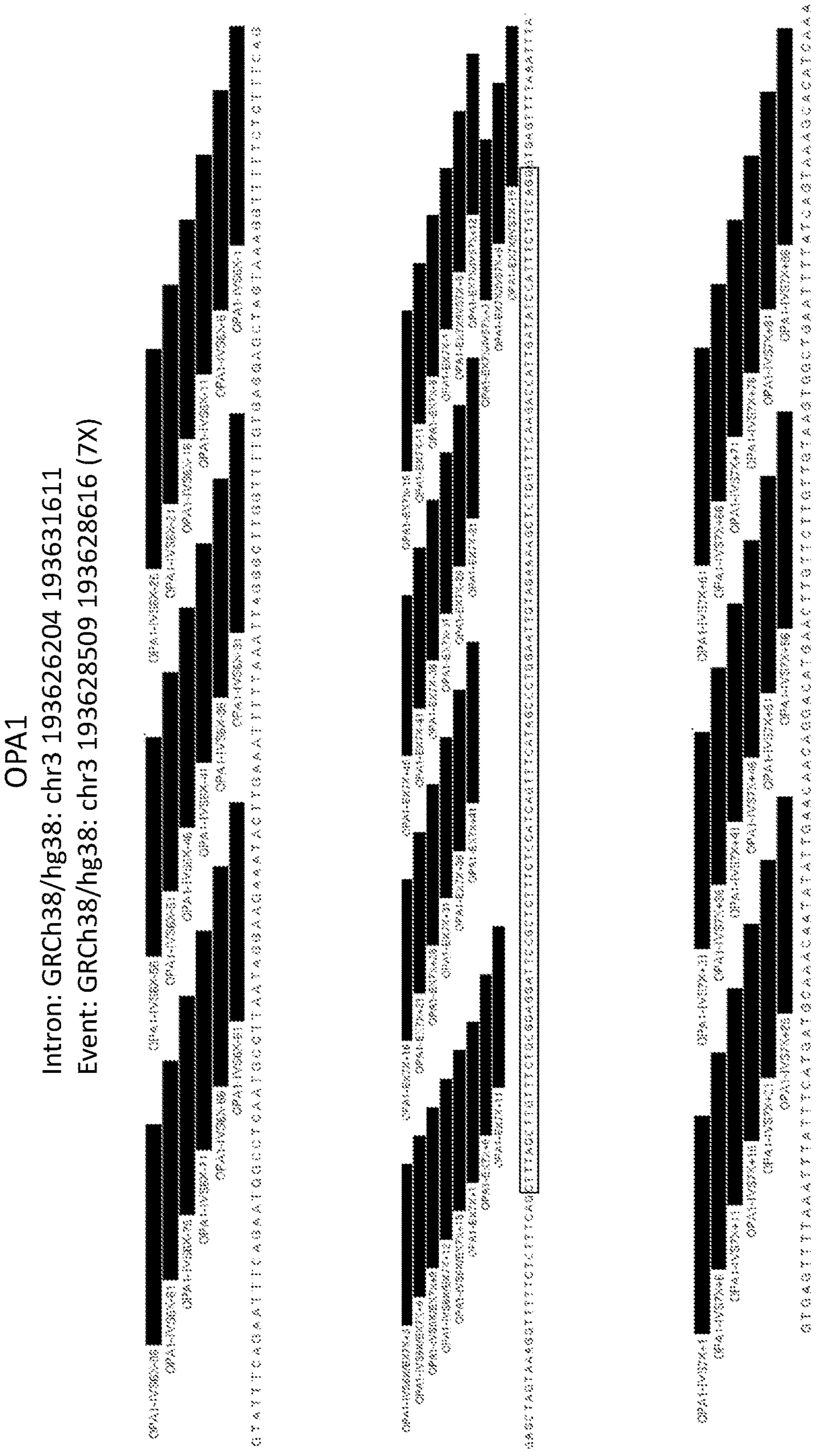
FIG. 5 depicts an exemplary ASO walk around OPA1 exon 7x (GRCh38/hg38: chr3 193628509 193628616) region. A graphic representation of an ASO walk performed for around OPA1 exon 7x (GRCh38/hg38: chr3 193628509 193628616) region targeting sequences upstream of the 3' splice site, across the 3'splice site, exon 7x, across the 5' splice site, and downstream of the 5' splice site is shown. ASOs were designed to cover these regions by shifting 5 nucleotides at a time or 3 nucleotides across the splice site regions.

An ASO walk was performed for NMD exon region targeting sequences immediately upstream of the 3' splice site, across the 3'splice site, the NMD exon, across the 5' splice site, and downstream of the 5' splice site using 2'-MOE ASOs, PS backbone. ASOs were designed to cover these regions by shifting 5 nucleotides at a time. FIG. 5 depicts an ASO walk for an exemplary OPA1 NMD exon region.

Example 4: NMD Exon Region ASO Walk Evaluated by RT-PCR

Figure 6:
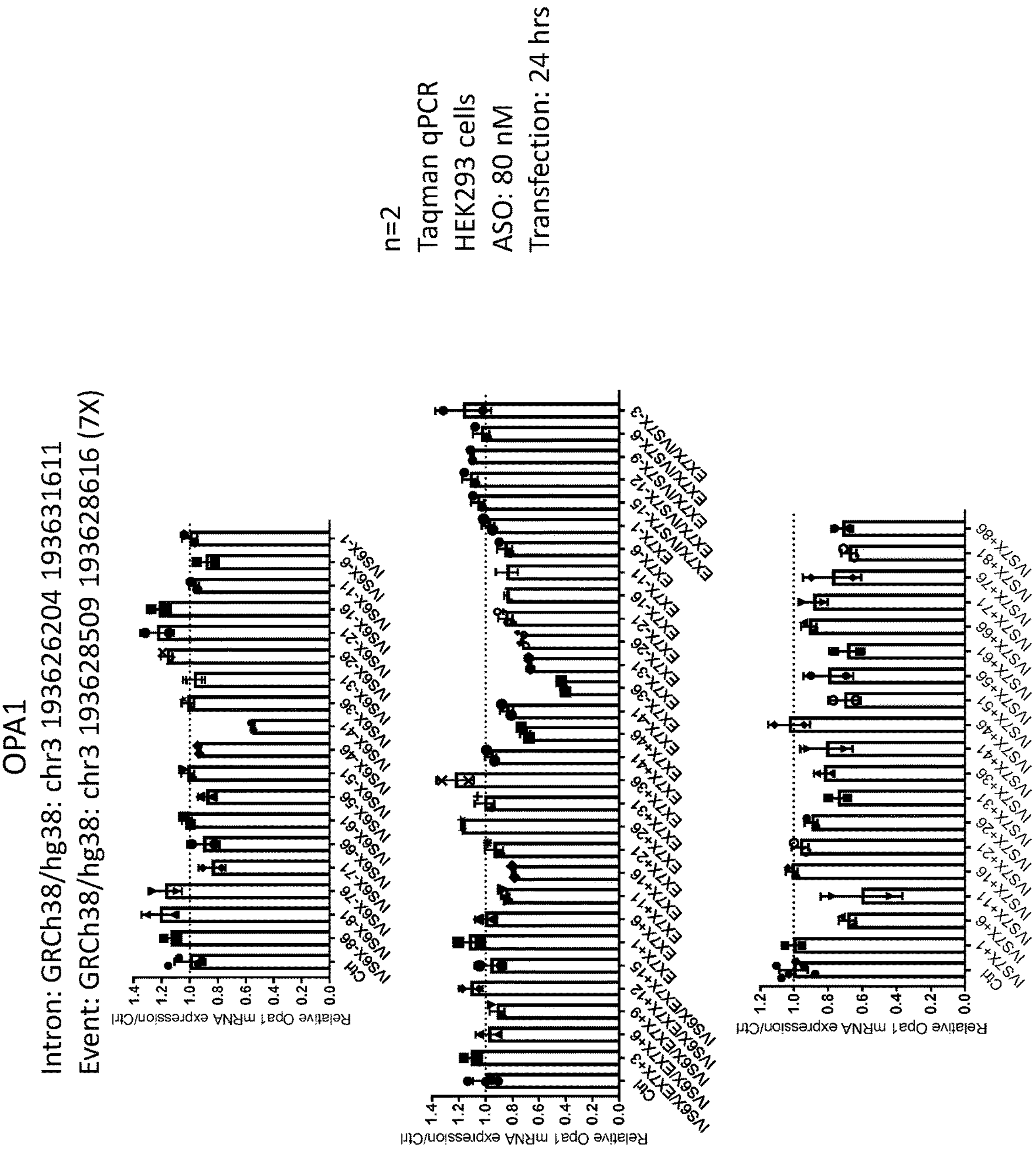
FIG. 6 depicts an OPA1 exon 7x (GRCh38/hg38: chr3 193628509 193628616) region ASO walk evaluated by Taqman RT-qPCR. Graphs of fold-change of the OPA1 productive mRNA product relative to Sham are plotted.

ASO walk sequences were evaluated by RT-PCR. HEK293 cells were transfected using Lipofectamine RNAiMax with control ASO treated (Ctrl), or with a 2'-MOE ASO targeting the OPA1 NMD exon regions as described herein. Products corresponding to OPA1 mRNA were quantified and normalized to RPL32 internal control, and fold-change relative to control was plotted. FIG. 6 depicts evaluation via TaqMan qPCR of various exemplary ASO walk along exemplary NMD exon regions. The measurement of the amount of OPA1 mRNA was carried out with HEK293 cells 24 hours after treatment with 80 nM of an exemplary ASO in the absence of cycloheximide, by Taqman qPCR using probes spanning exon 7 and exon 8.

Example 5: NMD Exon Region ASO Microwalk Evaluated by RT-qPCR

Figure 7:
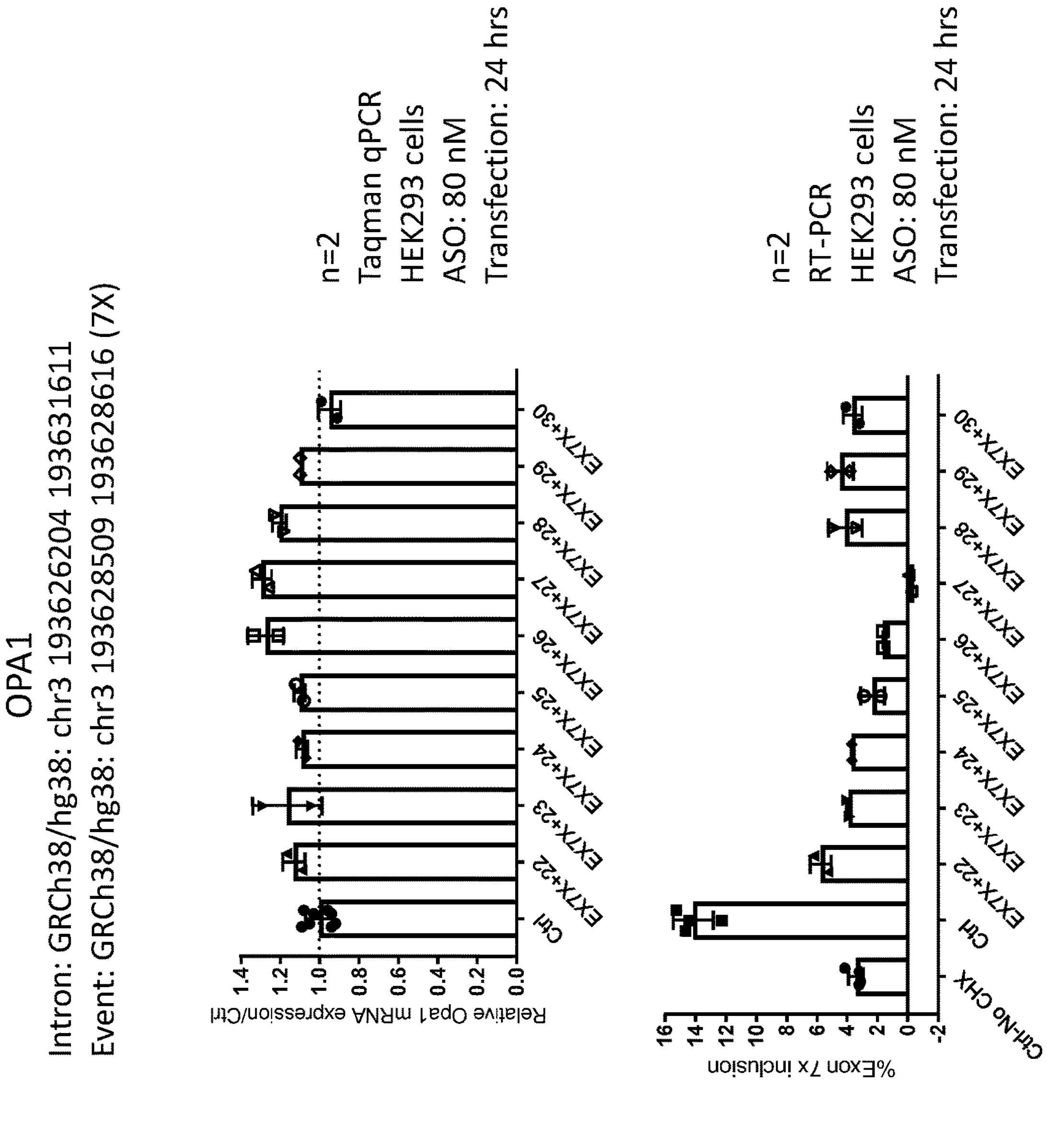
FIG. 7 depicts an OPA1 exon 7x (GRCh38/hg38: chr3 193628509 193628616) region ASO walk evaluated by Taqman RT-qPCR. Graphs of fold-change of the OPA1 productive mRNA product relative to Sham are plotted.

ASO microwalk sequences (across exon 7x) were evaluated by RT-PCR. HEK293 cells were transfected using Lipofectamine RNAiMax with control ASO treated (Ctrl), or with a 2'-MOE ASO targeting the OPA1 NMD exon regions as described herein. Products corresponding to NMD exon inclusion and full-length were quantified and percent NMD exon inclusion was plotted. FIG. 7 depicts evaluation of various exemplary ASO walk along exemplary NMD exon regions. The measurement of the amount of OPA1 mRNA was carried out with HEK293 cells 24 hours after transfection with 80 nM of an exemplary ASO in the absence of cycloheximide, by Taqman qPCR using probes spanning exon 7 and exon 8 (top panel of FIG. 7). qPCR amplification results were normalized to RPL32, and plotted as fold change relative to control. The measurement of exon 7x inclusion was carried out by quantifying exon 7x inclusion based on RT-PCR using probes spanning exon 7 and exon 8 (bottom panel of FIG. 7).

Example 6: Dose-Dependent Effect of Selected ASO in CXH-Treated Cells

PAGE can be used to show SYBR-safe-stained RT-PCR products of mock-treated (Sham, RNAiMAX alone), or treated with 2'-MOE ASOs targeting NMD exons at 30 nM, 80 nM, and 200 nM concentrations in mouse or human cells by RNAiMAX transfection. Products corresponding to NMD exon inclusion and full-length are quantified and percent NMD exon inclusion can be plotted. The full-length products can also be normalized to HPRT internal control and fold-change relative to Sham can be plotted.

Example 7: Intravitreal (IVT) Injection of Selected ASOs

PAGEs of SYBR-safe-stained RT-PCR products of mice from PBS-injected (1 μL) (−) or ASOs or Cep290 (negative control ASO; Gerard et al, *Mol. Ther. Nuc. Ac.,* 2015) 2'-MOE ASO-injected (1 μL) (+) at 10 mM concentration. Products corresponding to NMD exon inclusion and full-length (are quantified and percent NMD exon inclusion can be plotted Full-length products can be normalized to GAPDH internal control and fold-change of ASO-injected relative to PBS-injected can plotted.

Example 8: Intracerebroventricular (ICV) Injection of Selected ASOs

PAGEs of SYBR-safe-stained RT-PCR products of mice from uninjected (−, no ASO control), or 300 μg of Cep290 (negative control ASO; Gerard et al, *Mol. Ther. Nuc. Ac.,* 2015), 2'-MOE ASO-injected brains. Products corresponding to NMD exon inclusion and full-length can be quantified and percent NMD exon inclusion can be plotted. Taqman PCR can be performed using two different probes spanning NMD exon junctions and the products can be normalized to GAPDH internal control and fold-change of ASO-injected relative to Cep290-injected brains can be plotted.

Example 9: OPA1 Non-Productive Splicing Event Identification and Validation

Figure 8:
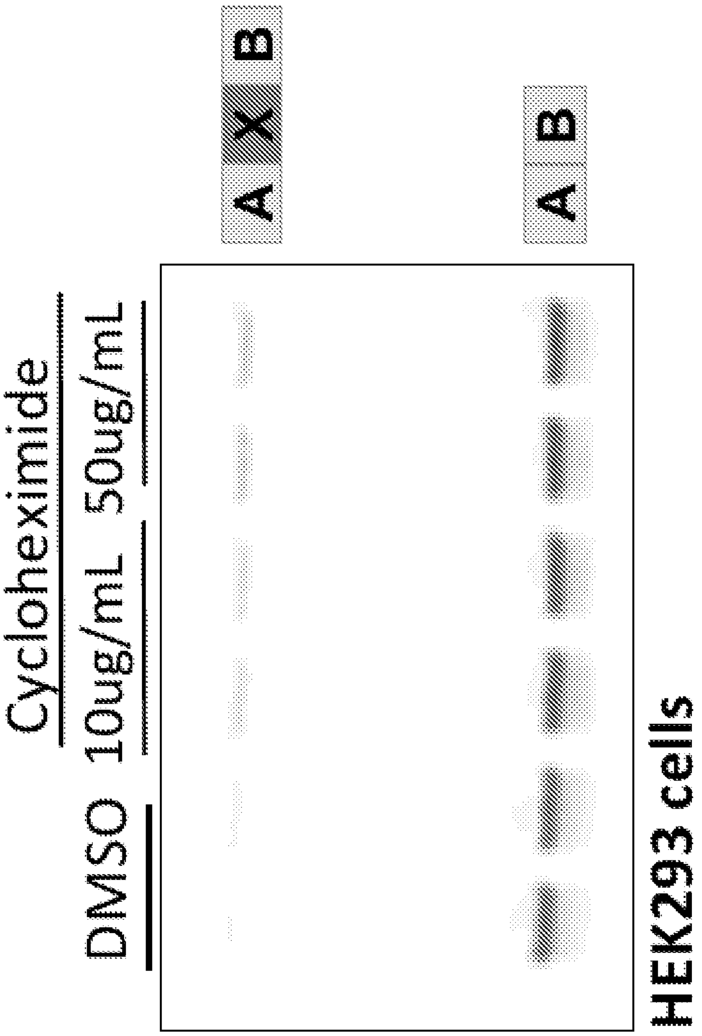
FIG. 8 illustrates expression of OPA1 transcripts containing the NMD exon in HEK293 cells treated with increasing amounts of cycloheximide.

A novel nonsense mediated decay (NMD) exon inclusion event (Exon X) was identified in the OPA1 gene which leads to the introduction of a premature termination codon (PTC) resulting in a non-productive mRNA transcript degraded by NMD, as diagramed in FIG. 1D. As NMD is a translation-dependent process, the protein synthesis inhibitor cycloheximide (CHX) was used to evaluate the true abundance of the event. FIG. 8 shows an increase in OPA1 transcripts containing the NMD exon in HEK293 cells with increasing CHX dose. Other ocular cell lines also validated for the presence of the NMD exon (ARPE-19, Y79).

Example 10: OPA1 NMD Event is Conserved in Primate Eyes

Figure 9A:
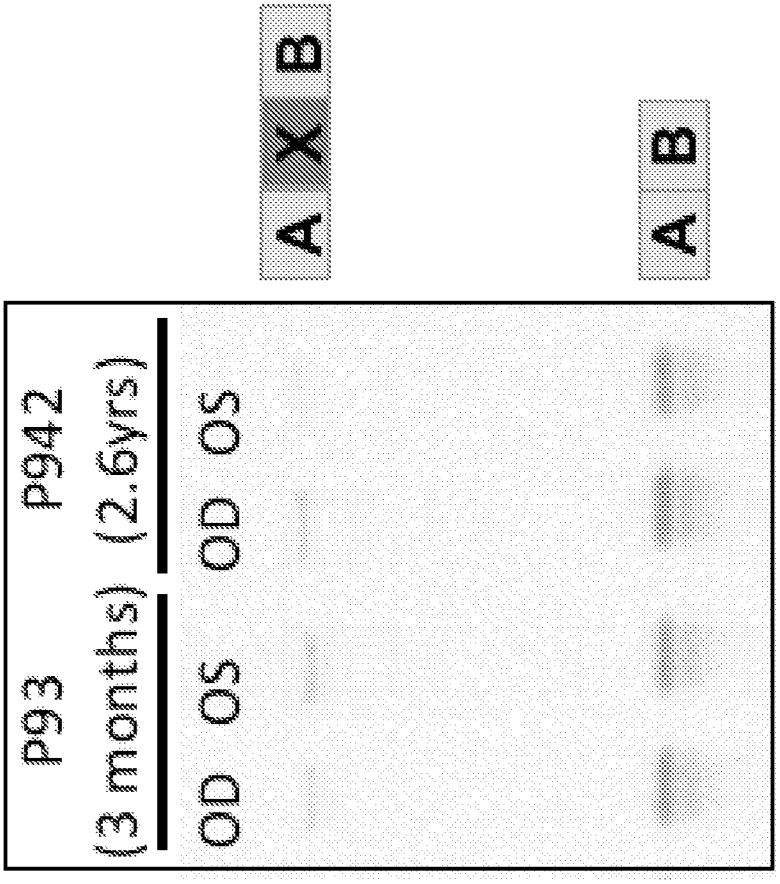
FIG. 9A illustrates RT-PCR data from the posterior segment of the eye of *Chlorocebus sabaeus* (green monkey) at postnatal data P93 (3 months) and postnatal day P942 (2.6 years).
Figure 9B:
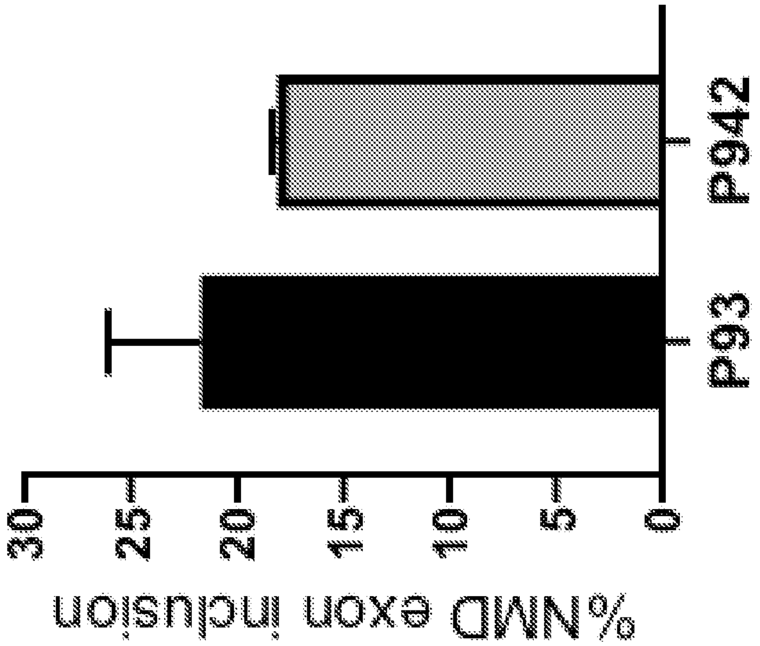
FIG. 9B illustrates quantification of the NMD exon abundance from FIG. 9A.

FIG. 9A shows reverse transcription PCR data from the posterior segment of the eye of *Chlorocebus sabaeus* (green monkey) at postnatal data P93 (3 months) and postnatal day P942 (2.6 years) for the right eye (OD) and left eye (OS). FIG. 9B shows quantification of the NMD exon abundance at 3 months and 2.6 years of age (N=1/age). Data represents average of right eye and left eye values for each animal. The abundance of the event may be higher in vivo, given that NMD is presumed active in the tissue.

Figure 10A:
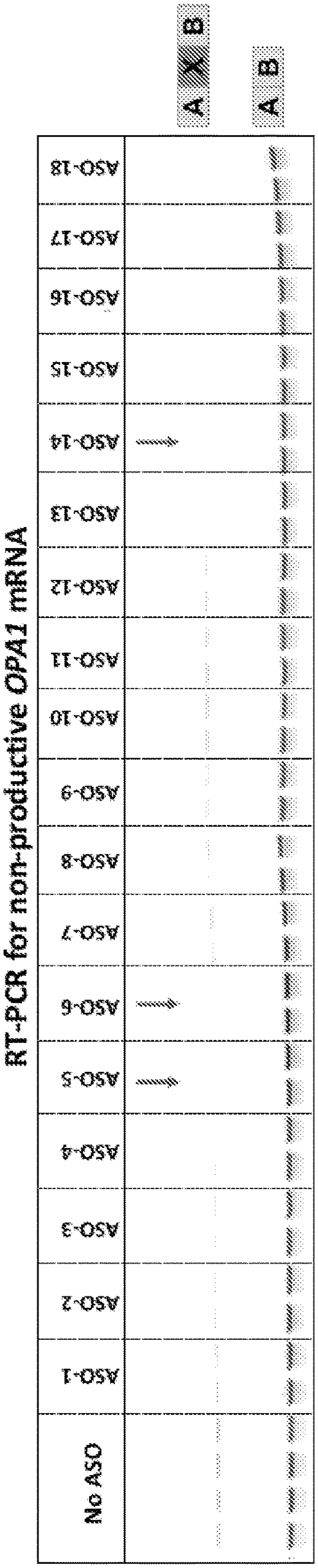
FIG. 10A illustrates RT-PCR of the productive and non-productive OPA1 mRNA after treatment of HEK293 cells with various ASOs and cycloheximide.
Figure 10B:
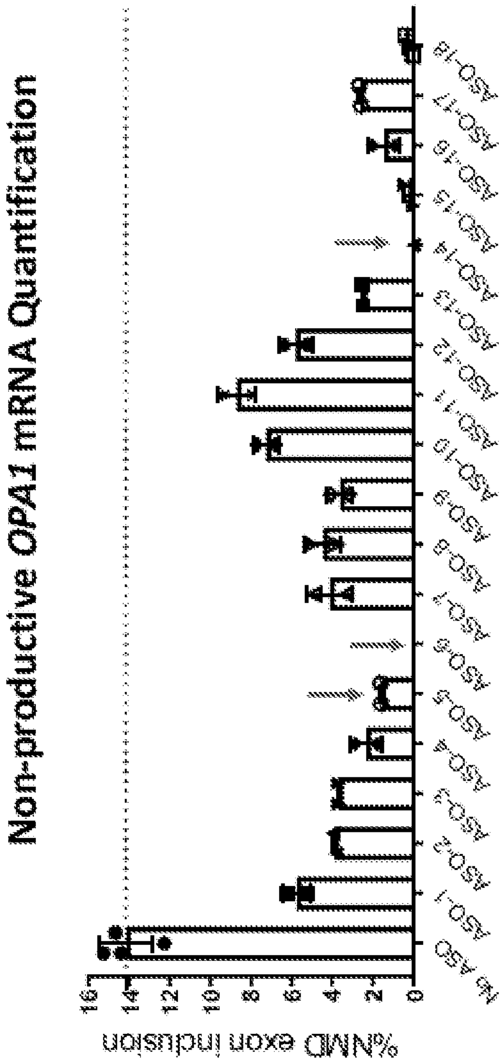
FIG. 10B illustrates quantification of the data in FIG. 10A.
Figure 11:
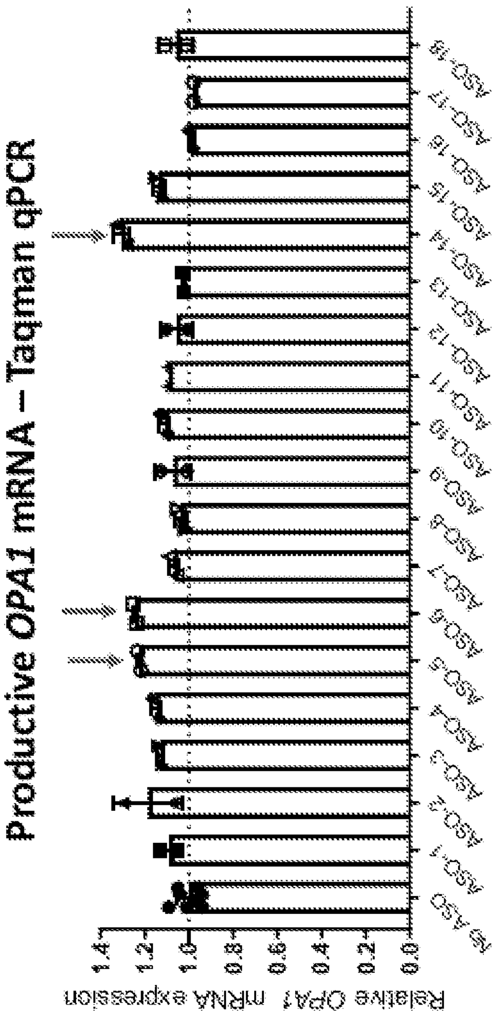
FIG. 11 illustrates expression of productive OPA1 mRNA by quantitative PCR in HEK293 cells treated with various ASOs and not treated with cycloheximide.

Example 11: OPA1 Antisense Oligonucleotides Reduce Non-Productive Splicing and Increase Productive OPA1 mRNA Levels In Vitro Exemplary antisense oligomers (ASOs) were transfected at 80 nM dose into HEK293 cells using Lipofectamine RNAiMax as a transfection agent. To assess the effect on the NMD exon, cells were treated with CHX (50 μg/ml, 3 hrs.) 21 hours after transfection. RNA was isolated for RT-PCR using probes spanning exon 7 and exon 8, as shown in FIG. 10A, and quantified in FIG. 10B. To assess levels of productive OPA1 mRNA expression, non-cycloheximide treated cells were used for Taqman qPCR using probes spanning exon 23 and exon 24, and mRNA expression of OPA1 was normalized to RPL32, as shown in FIG. 11. Arrows highlight ASOs that reduce non-productive splicing and increase OPA1 mRNA expression by at least 20%. Among these, ASO-14 produces the most increase in OPA1 mRNA (30%).

Figure 12A:
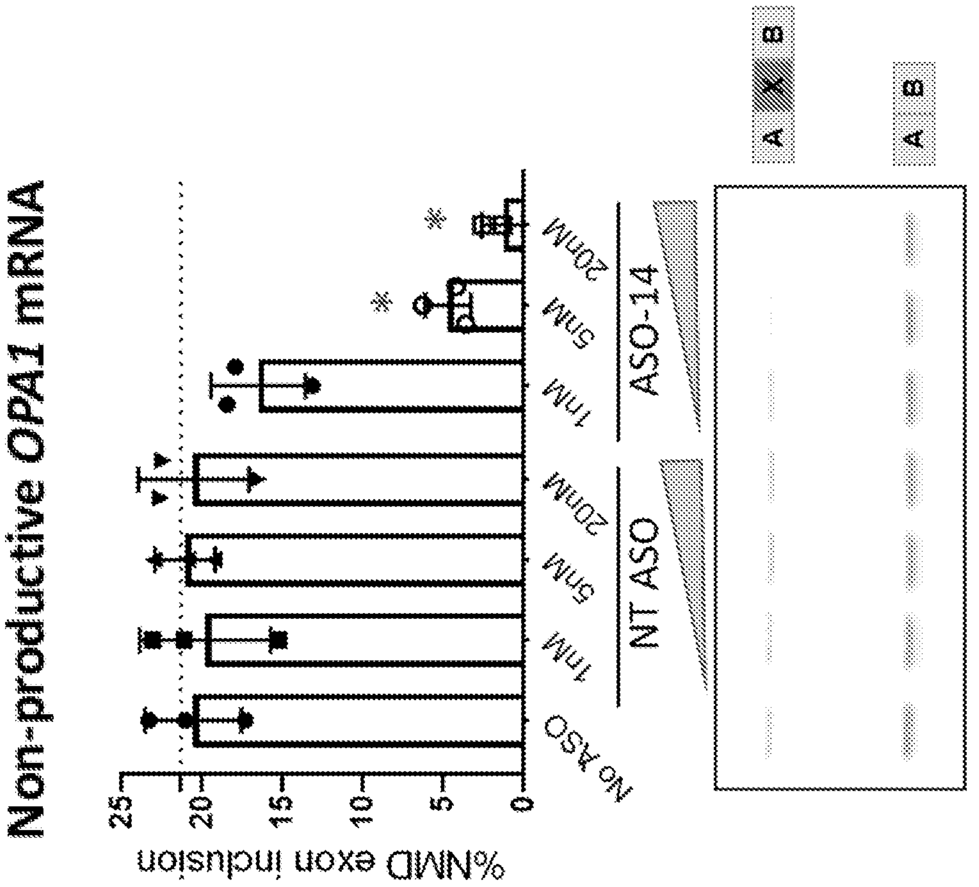
FIG. 12A illustrates RT-PCR for non-productive OPA1 mRNAs in HEK293 cells after treatment with ASO-14 and cycloheximide.
Figure 12B:
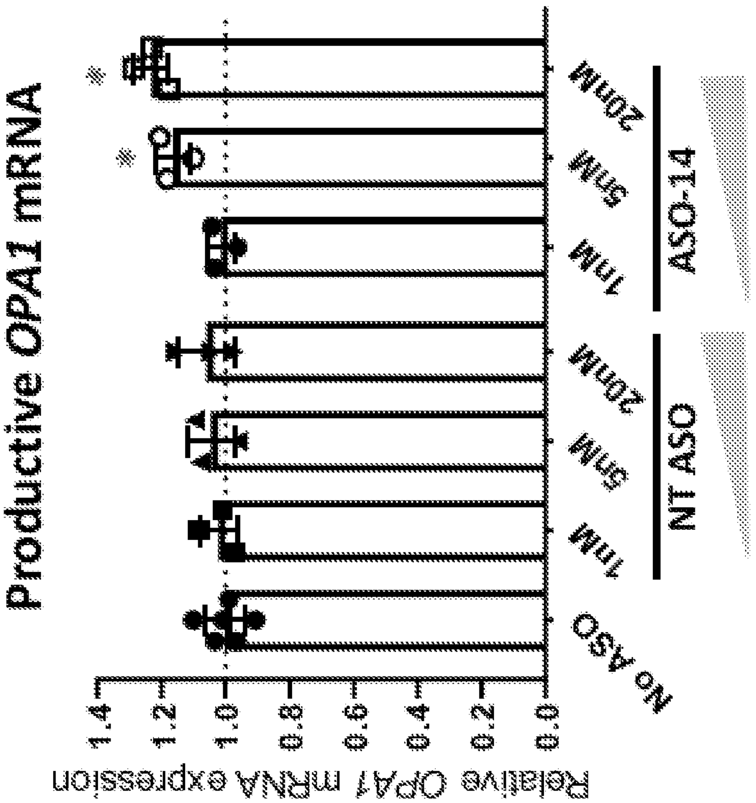
FIG. 12B illustrates quantification of productive OPA1 mRNAs in HEK293 cells after treatment with ASO-14 in the absence of cycloheximide.
Figure 12C:
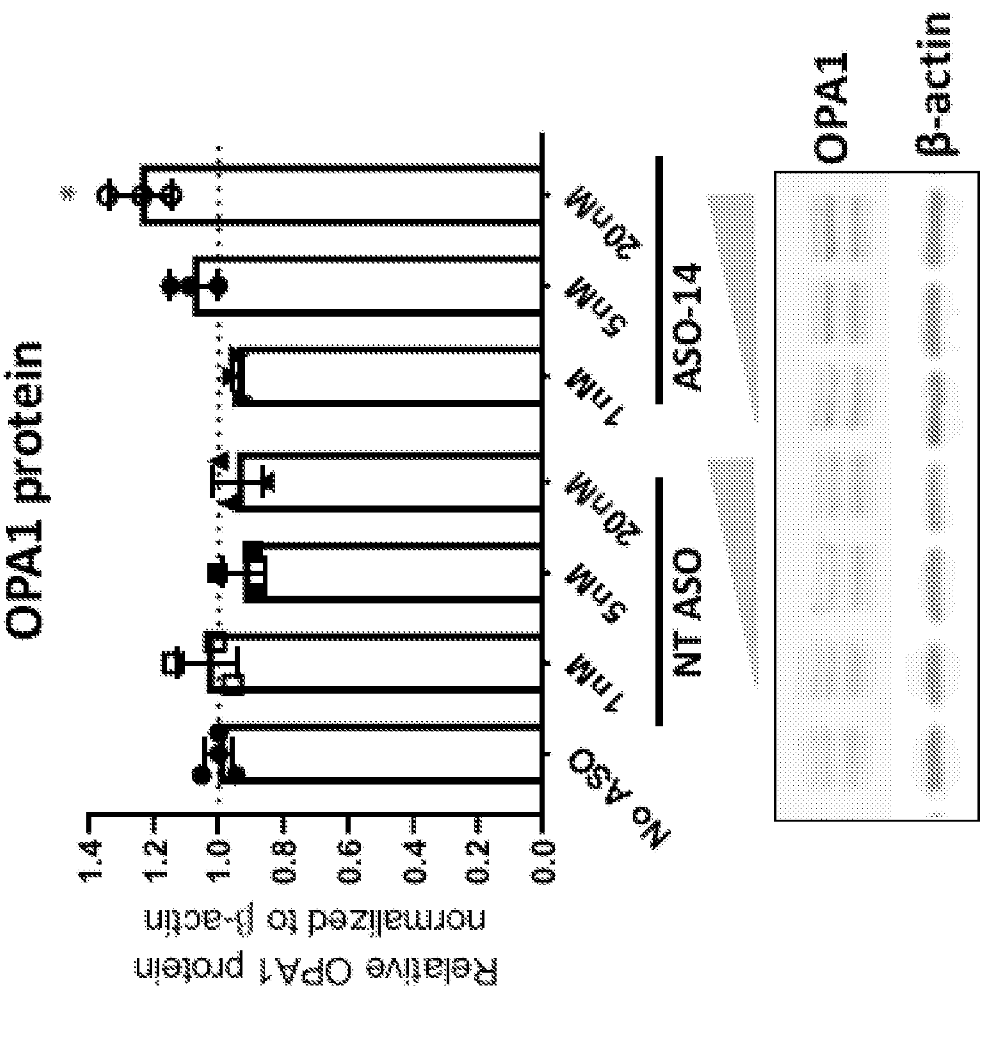
FIG. 12C illustrates protein expression of OPA1 in HEK293 cells after treatment with ASO-14 in the absence of cycloheximide.

Example 12: ASO-14 Decreases Non-Productive OPA1 mRNA and Increases OPA1 Expression in a Dose-Dependent Manner In Vitro HEK293 cells were transfected with different doses of ASO-14 or non-targeting (NT) ASO. RNA was isolated 24 hours after transfection and analyzed for impact on non-productive OPA1 mRNA (FIG. 12A) and OPA1 mRNA expression (FIG. 12B) similarly to in Example 11. For protein analysis, cells were lysed with RIPA buffer 48 hours after transfection and western blots were probed with antibodies targeting OPA1 and β-actin, as shown in FIG. 12C. Multiple bands correspond to different isoforms of OPA1. Data represent the average of three independent experiments (*$P<0.05$ by one-way ANOVA compared to "NO ASO" group). The Non-targeting ASO targets an unrelated gene.

Figure 13A:
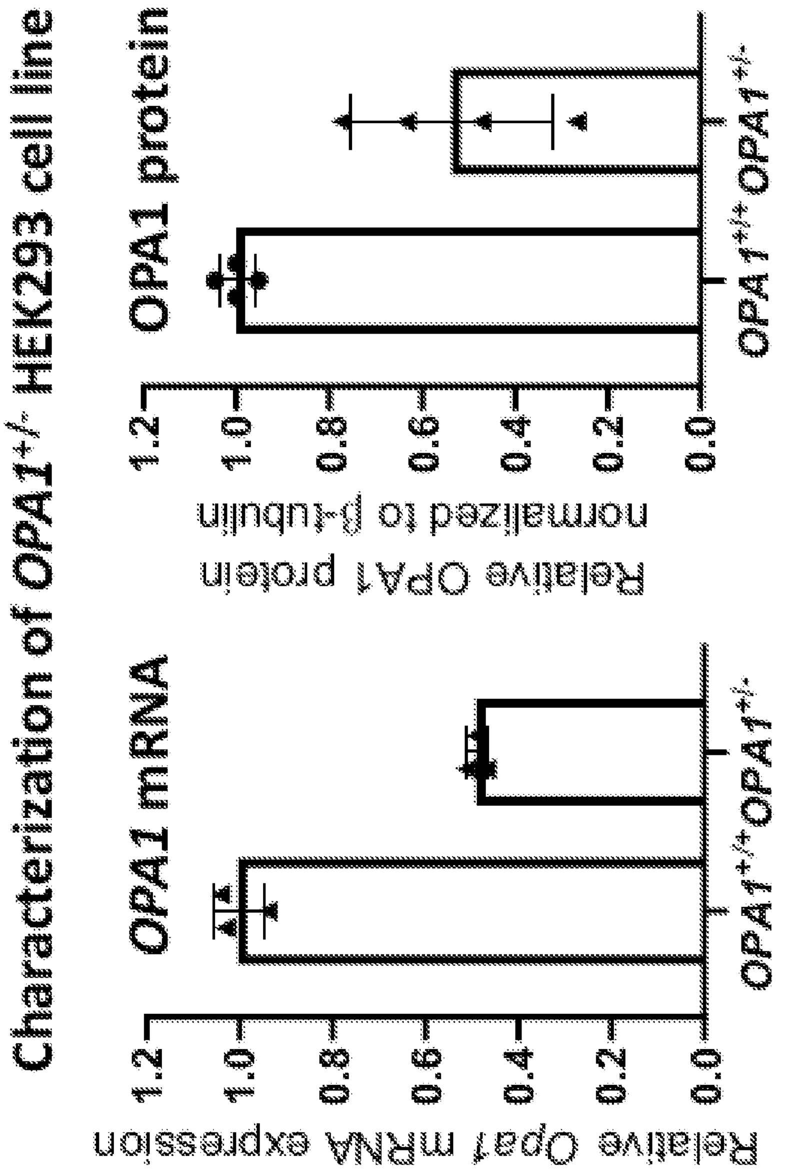
FIG. 13A illustrates mRNA and protein levels of OPA1 gene in OPA1 haploinsufficient (OPA1+/−) HEK293 cells.
Figure 13B:
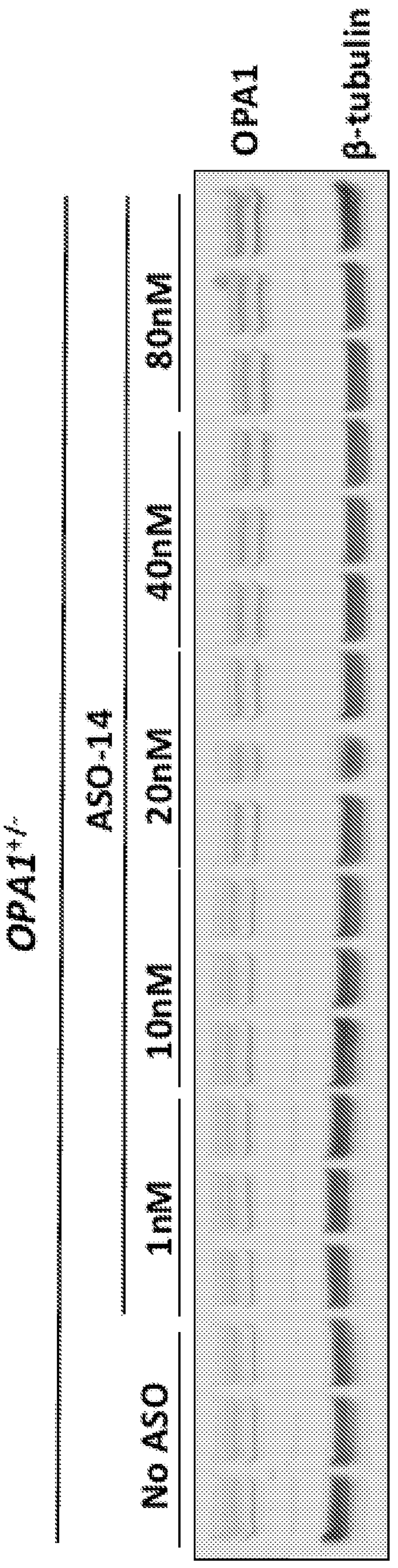
FIG. 13B illustrates OPA1 protein expression in the OPA1 haploinsufficient (OPA1+/−) HEK293 cells after treatment with ASO-14.
Figure 13C:
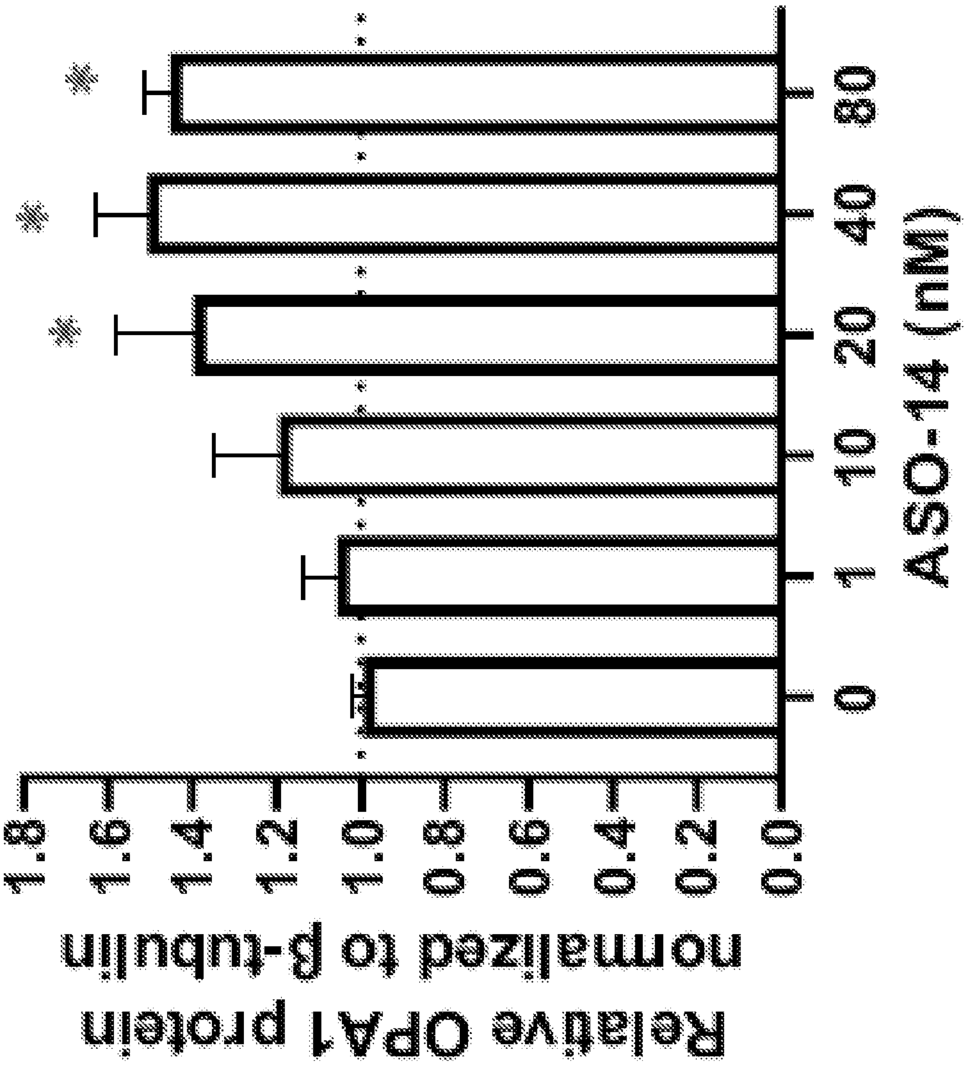
FIG. 13C illustrates quantification of OPA1 protein expression in the OPA1 haploinsufficient (OPA1+/−) HEK293 cells after treatment with ASO-14.

Example 13: ASO-14 Increases OPA1 Expression in an OPA1 Haploinsufficient (OPA1+/−) Cell Line OPA1 haploinsufficient (OPA1+/−) HEK293 cells were generated using CRISPR-Cas9 gene editing. Similar to ADOA patient cells, OPA1+/−HEK293 cells show approximately 50% mRNA and protein levels of that observed in OPA1+/+ cells (FIG. 13A). The OPA1+/−HEK293 cells were transfected with different doses of ASO-14 as indicated in FIG. 13B, and total protein was isolated 72 hours after transfection. Western blots were probed with antibodies targeting OPA1 and β-tubulin, a representative blot is shown in FIG. 13B and quantification of two independent experiments is shown in FIG. 13C (*$P<0.05$ by one-way ANOVA compared to "No ASO" group). ASO-14 increases OPA1 protein levels in OPA1+/−HEK293 cells by 50%, which translates to 75% of wild-type levels.

Figure 14A:
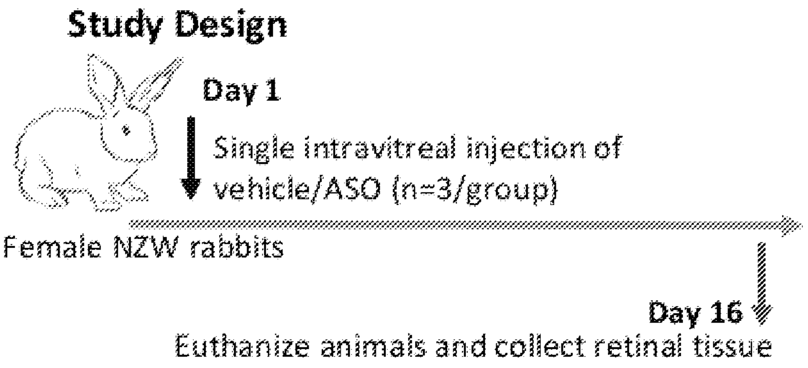
FIG. 14A illustrates study design for the in vivo rabbit experiment of Example 14.
Figure 14B:
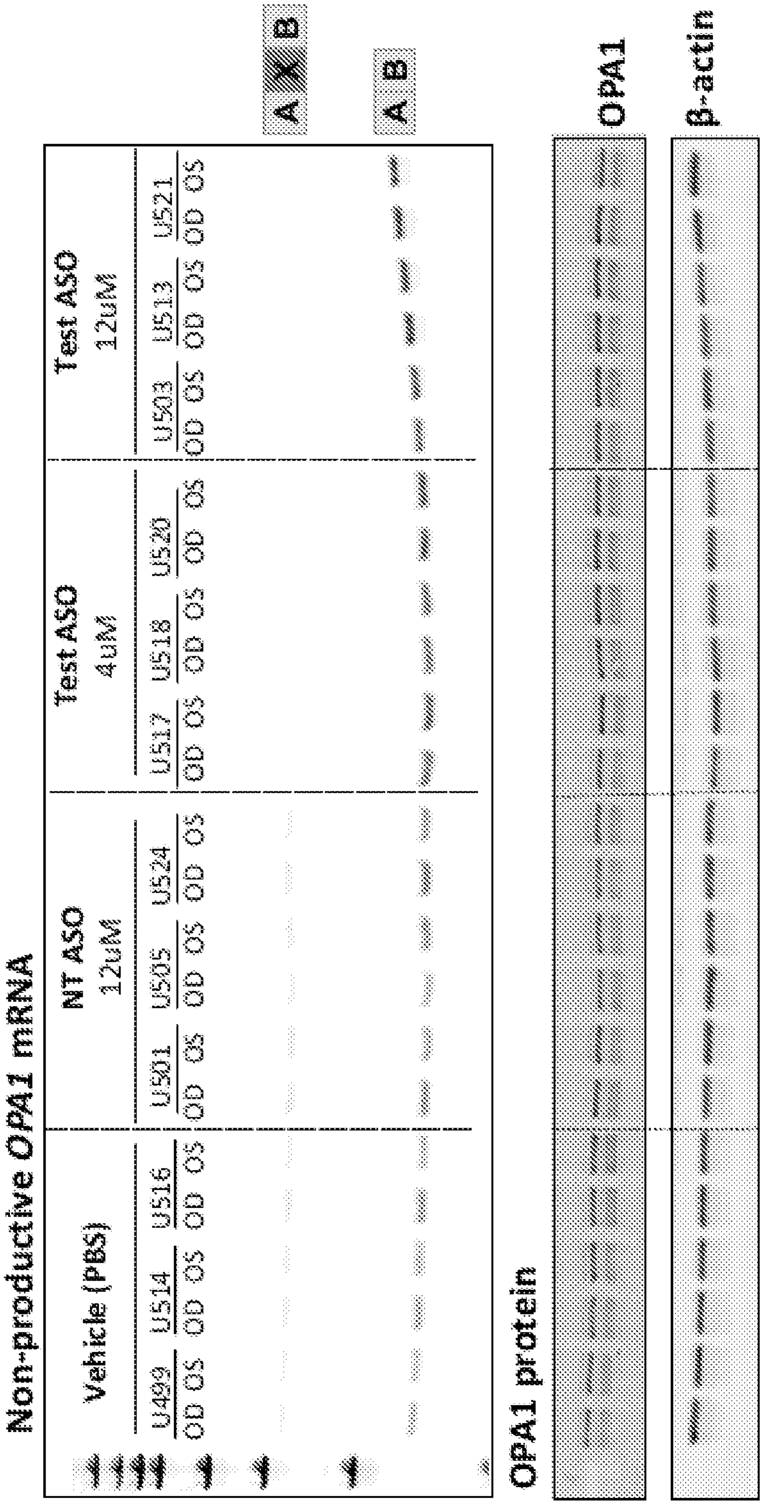
FIG. 14B illustrates levels of productive and non-productive OPA1 mRNA and protein.
Figure 14C:
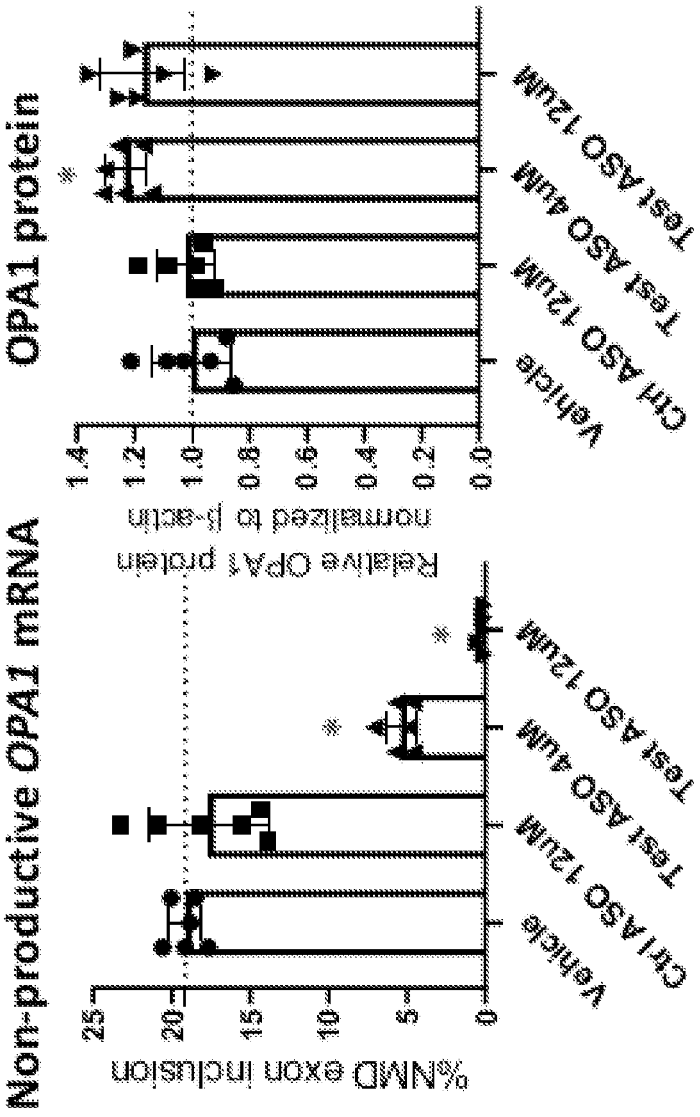
FIG. 14C illustrates quantification of the data from FIG. 14B.

Example 14: Exemplary OPA1 ASOs Decrease Non-Productive Splicing and Increase OPA1 Expression in Wild-Type Rabbit Retinae Following Intravitreal Injection Female New Zealand White (NZW) adult rabbits were injected with either vehicle, non-targeting (NT), or test, antisense oligonucleotides. Animals were euthanized after 15 days to obtain retinal tissue. FIG. 14A outlines the study design, (*Final concentration in the vitreous calculated assuming vitreal volume in the rabbit as 1.5 mL). FIG. 14B shows levels of productive and non-productive OPA1 mRNA and protein, and FIG. 14C shows quantification of this data (*$P<0.05$ by one-way ANOVA compared to Vehicle group). OD: oculus dextrus (right eye), OS: oculus sinister (left eye).

It was also found that the antisense oligonucleotides were well-tolerated in wild-type rabbit for up to 28 days after intravitreal injection.

Figure 16A:
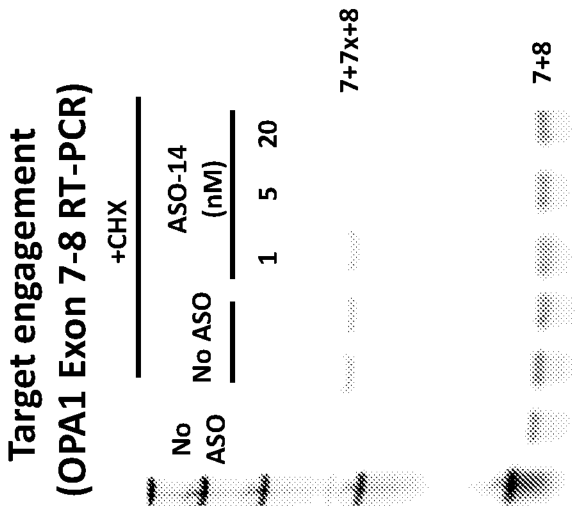
FIG. 16A illustrates RT-PCR results for OPA1 mRNAs using probes spanning exon 7 and exon 8 in HEK293 cells after treatment with ASO-14 and cycloheximide.
Figure 16B:
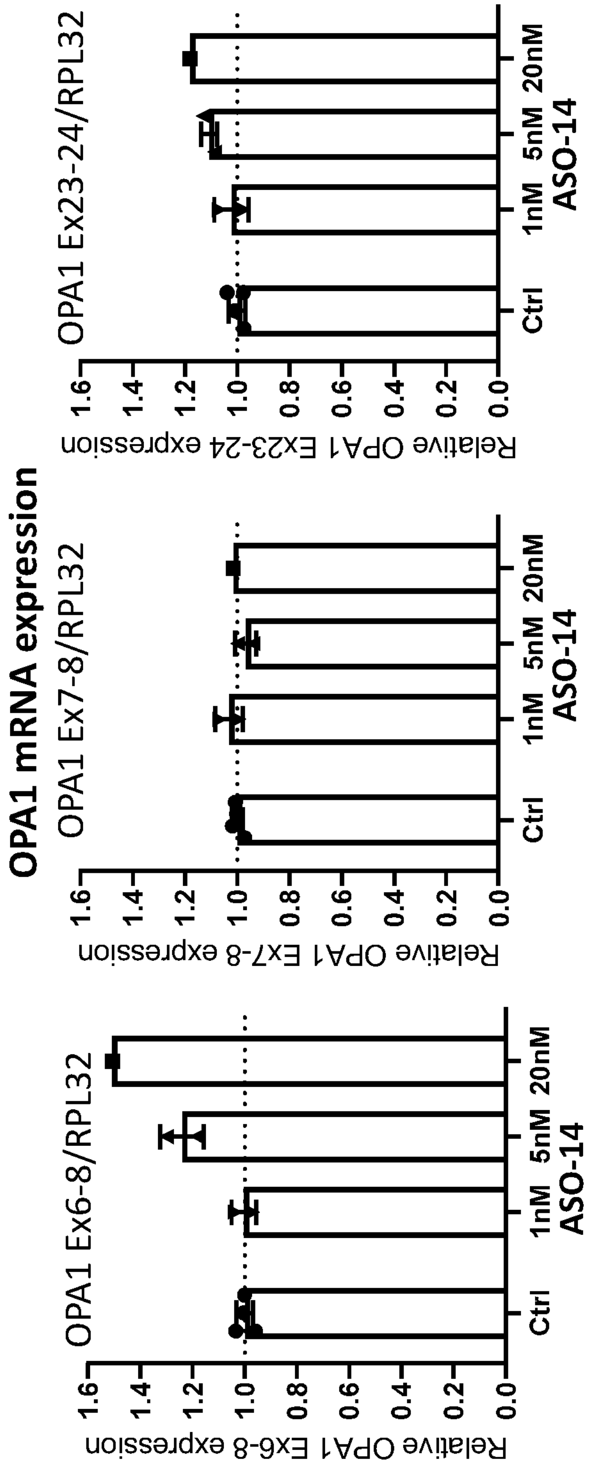
FIG. 16B illustrates quantification of OPA1 mRNAs in HEK293 cells after treatment with ASO-14 in the absence of cycloheximide based on qPCR using probes spanning exons 6 and 8, probes spanning exons 7 and 8, or probes spanning exons 23 and 24.
Figure 16C:
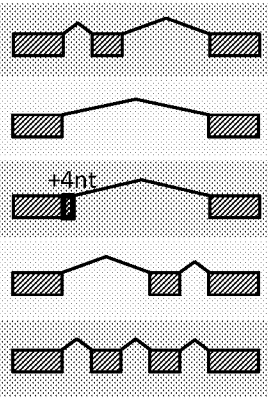
FIG. 16C illustrates sequencing data on the relative amount of various OPA1 mRNA transcripts in HEK293 cells transfected with ASO-14.

Example 15: ASO-14 Modulates Inclusion of Both Exon 7 and Exon 7x in OPA1 mRNA Transcript HEK293 cells were transfected with different doses of ASO-14 or no ASO, in the presence or absence of cycloheximide. RNA was isolated 24 hours after transfection and analyzed for impact on OPA1 mRNA splicing and OPA1 mRNA expression similarly to in Example 11. FIG. 16A shows gel image of PCR products from RT-PCR reaction using probes spanning exon 7 and 8. As shown in the figure, the dose of ASO-14 increased from 1 nM, 5 nM, to 20 nM, the amount of transcripts having exon 7x between exons 7 and 8 ("7+7x+8") gradually decreased, as compared to relatively stable amount of transcripts lacking exon 7x between exons 7 and 8 ("7+8"). FIG. 16B shows plots summarizing the relative amount of various OPA1 mRNA transcripts quantified by qPCR reactions using different pairs of probes: "Ex6-8," probes spanning exons 6 and 8; "Ex7-8," probes spanning exons 7 and 8; and "Ex23-24," probes spanning exons 23 and 24. Results were normalized to RPL32 as an internal control. FIG. 16C shows a chart summarizing the quantification of various OPA1 mRNA transcripts based on sequencing of the RNA extracts from the treated HEK293 cells in the absence of cycloheximide. As suggested by the figures, ASO-14 appeared to induce reduction in OPA1 exon 7x inclusion, increase in OPA1 Ex6-8 transcripts (transcripts having exon 6 and exon 8 in tandem, thus lacking exon 7 and exon 7x), modest decrease or no change in OPA1 Ex7-8 transcripts (transcripts having exon 7 and exon 8 in tandem, thus lacking exon 7x).

Figure 17A:
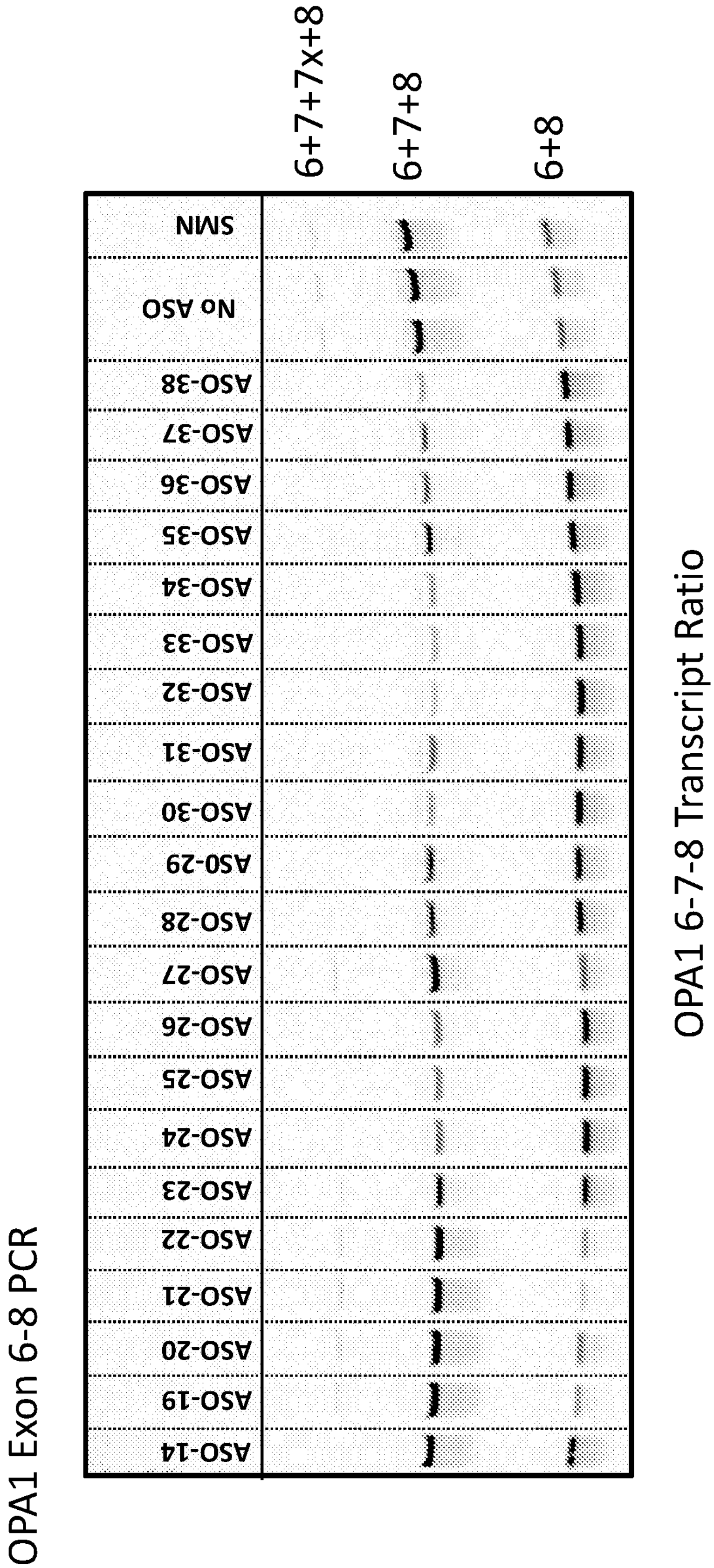
FIG. 17A illustrates RT-PCR results for OPA1 mRNAs using probes spanning exon 6 and exon 8 in HEK293 cells after treatment with various exemplary OPA1 ASOs.
Figure 17B:
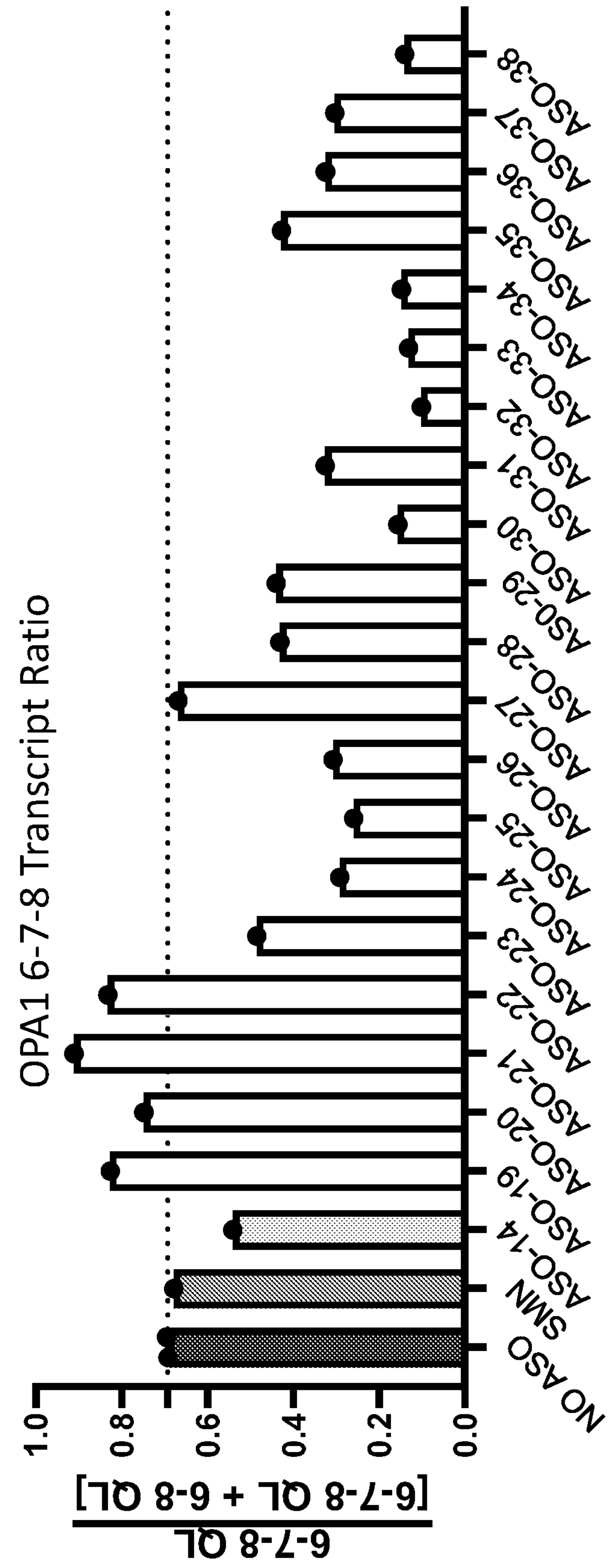
FIG. 17B illustrates relative ratio of OPA1 mRNA transcripts having exons 6, 7, and 8 in tandem ("6-7-8") over the total amount of "6-7-8" transcripts and transcripts having exons 6 and 8 in tandem ("6-8"), in HEK293 cells after treatment with various exemplary OPA1 ASOs.
Figure 17C:
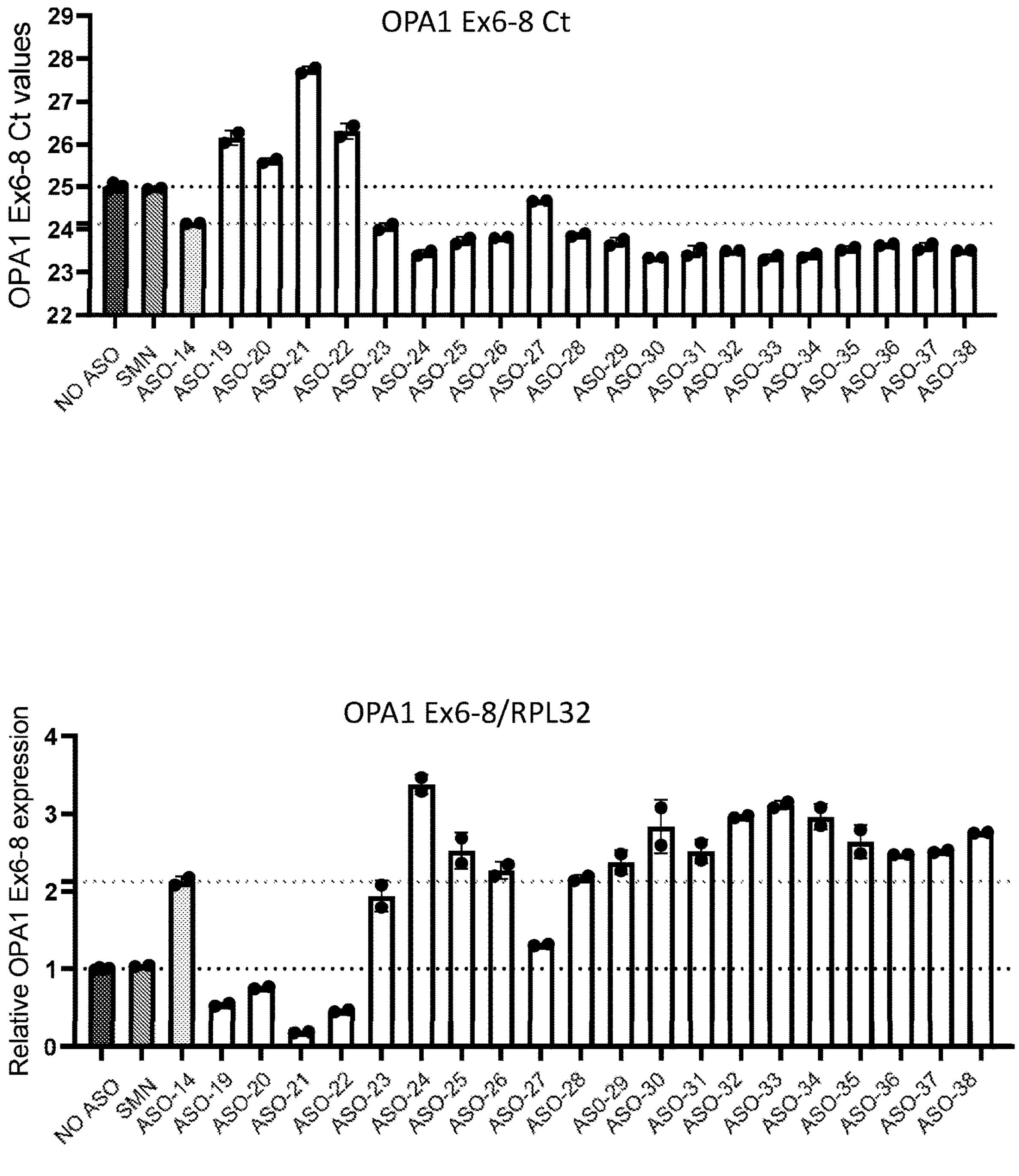
FIGS. 17C and 17D illustrate quantification of OPA1 mRNAs using probes spanning exons 6 and 8, and probes spanning exons 7 and 8, respectively, in HEK293 cells after treatment with various exemplary OPA1 ASOs.
Figure 17D:
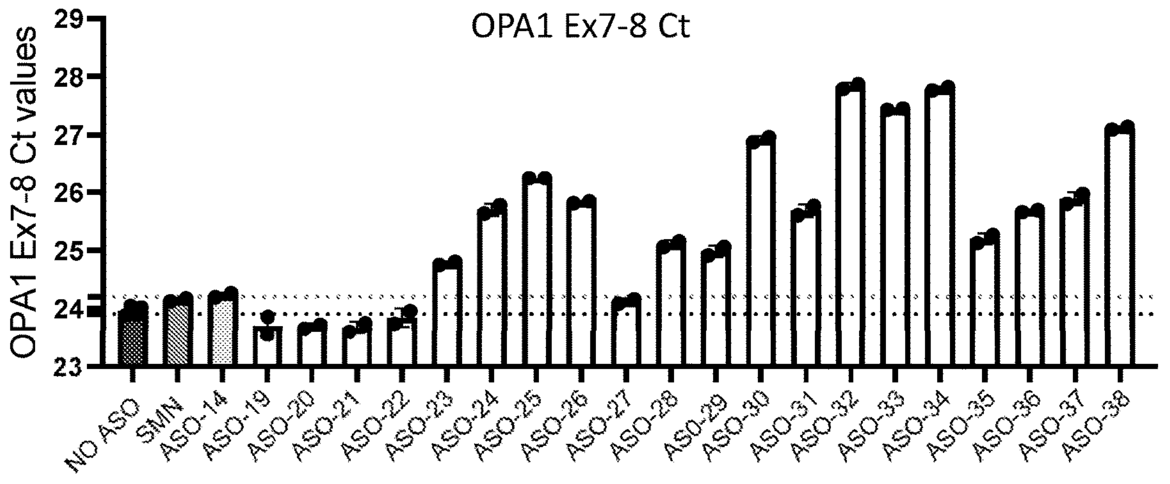
Figure 17D:
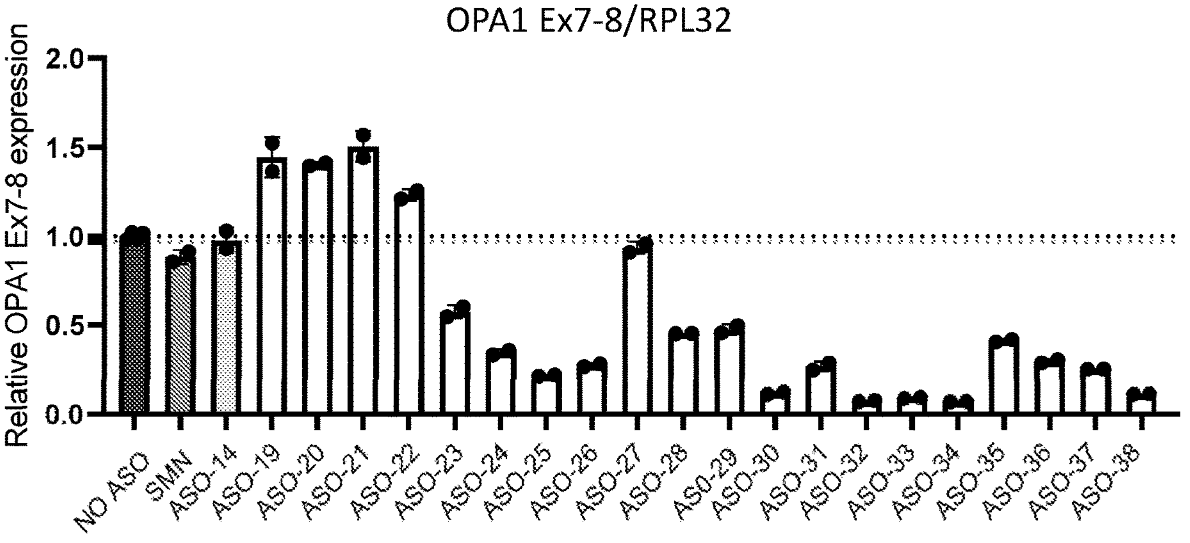

Example 16: Exemplary OPA1 Antisense Oligomers Modulate Inclusion of Exon 7, Exon 7x, or Both in OPA1 mRNA Transcript HEK293 cells were transfected with different exemplary OPA1 modified 2'MOE-PS (2' methoxyethyl and phosphorothioate) ASOs. Each well of HEK 293 cells (about 100, 000 cells/well) were treated with an exemplary ASO at 80 nM final concentration in the presence of 0.9 μL of Lipofectamine® RNAiMax in the absence of cycloheximide. The cells were harvested 24 hours after transfection and RNA was isolated and analyzed for impact on OPA1 mRNA splicing and OPA1 mRNA expression similarly to in Example 11. FIG. 17A shows gel image of PCR products from RT-PCR reaction using probes spanning exon 6 and 8, and FIG. 17B is a plot summarizing the relative ratio of the amount of transcripts having exons 6, 7, and 8 in tandem ("6-7-8") over the total amount of "6-7-8" transcripts and transcripts having exons 6 and 8 in tandem ("6-8"). As shown in the figures, certain ASOs, such as ASO-19, ASO-20, ASO-21, ASO-22, induced increase in the relative amount of "6-7-8" transcripts, suggesting an increase in the inclusion of exon 7 in mature OPA1 mRNA transcripts. Some ASOs, such as ASO-23, ASO-24, ASO-25, ASO-26, ASO-28, ASO-29, ASO-30, ASO-31, ASO-32, ASO-33, ASO-34, ASO-35, ASO-36, ASO-37, and ASO-38, in contrast, induced reduction in the relative amount of "6-7-8" transcripts, suggesting a reduction in the inclusion of exon 7 in mature OPA1 mRNA transcript. FIGS. 17C and 17D show the Ct values for the qPCR reaction (upper plots) for, and quantification of the relative amount (bottom plots) of, OPA1 transcripts having exons 6 and 8 ("Ex6-8") and OPA1 transcripts having exons 7 and 8 ("Ex7-8"), respectively. Cells treated with ASO-29, ASO20, ASO-21, and ASO-22 showed reduced amount of "Ex6-8" transcripts and increased amount of "Ex7-8" transcripts, consistent with the suggestion that these ASOs promote the inclusion of exon 7 in OPA1 mature mRNA transcripts. Cells treated with ASO-23, ASO-24, ASO-25, ASO-26, ASO-28, ASO-29, ASO-30, ASO-31, ASO-32, ASO-33, ASO-34, ASO-35, ASO-36, ASO-37, and ASO-38 showed increase in the amount of "Ex6-8" transcripts and decrease in the amount of "Ex7-8" transcripts, consistent with the suggestion that these ASOs promote the exclusion of exon 7 from OPA1 mature mRNA transcripts.

Figure 18A:
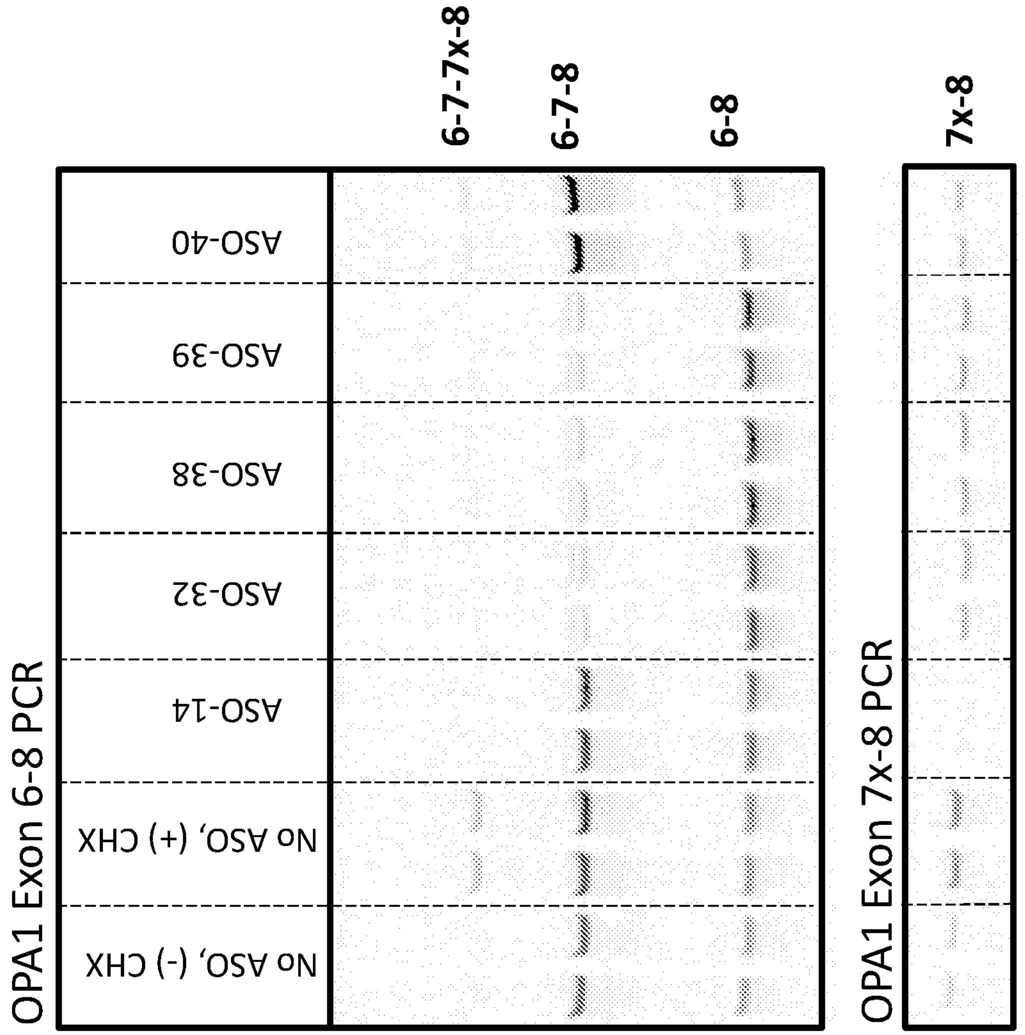
FIG. 18A illustrates RT-PCR results for OPA1 mRNAs using probes spanning exon 6 and exon 8 ("Exon 6-8 PCR"), or probes spanning exon 7x and exon 8 ("Exon 7x-8 PCR"), in HEK293 cells after treatment with various exemplary OPA1 ASOs and treatment with cycloheximide.

Example 17: Exemplary OPA1 Antisense Oligomers Modulate Inclusion of Exon 7, Exon 7x, or Both in OPA1 mRNA Transcript And Modulate Expression Level of OPA1 Protein HEK293 cells were transfected with different exemplary OPA1 modified 2'MOE-PS (2' methoxyethyl and phosphorothioate) ASOs. Each well of HEK 293 cells (about 50,000 cells/well) were treated with an exemplary ASO at 80 nM final concentration in the presence of 0.9 μL of Lipofectamine® RNAiMax. Here, the cells were harvested 72 hours after transfection to test ASO's effect on OPA1 mRNA and protein expression. The cells were treated with cycloheximide (50 μg/mL) for 3 hours prior to harvest for mRNA analysis. FIG. 18A shows gel image of PCR products from RT-PCR reaction using probes spanning exon 6 and 8. As shown in the figure, ASO-14 induced reduction in the amount of transcripts having exons 6, 7, 7x, and 8 in tandem ("6-7-7x-8"). ASO-32, ASO-38, and ASO-39 induced significant reduction in the amount of "6-7-8" transcripts, and modest reduction in the amount of "6-7-7x-8" transcripts, whereas ASO-40 induced increase in the amount of "6-7-8" transcripts. These data suggest that ASO-14 promotes exclusion of exon 7x from OPA1 mRNA transcript, ASO-32, ASO-38, and ASO-39 promote exclusion of exon 7 from OPA1 mRNA transcript, and they also promote exclusion of exon 7x from OPA1 mRNA transcript. In contrast, the data suggest that ASO-40 promotes inclusion of exon 7 in OPA1 mRNA transcript.

Figure 18B:
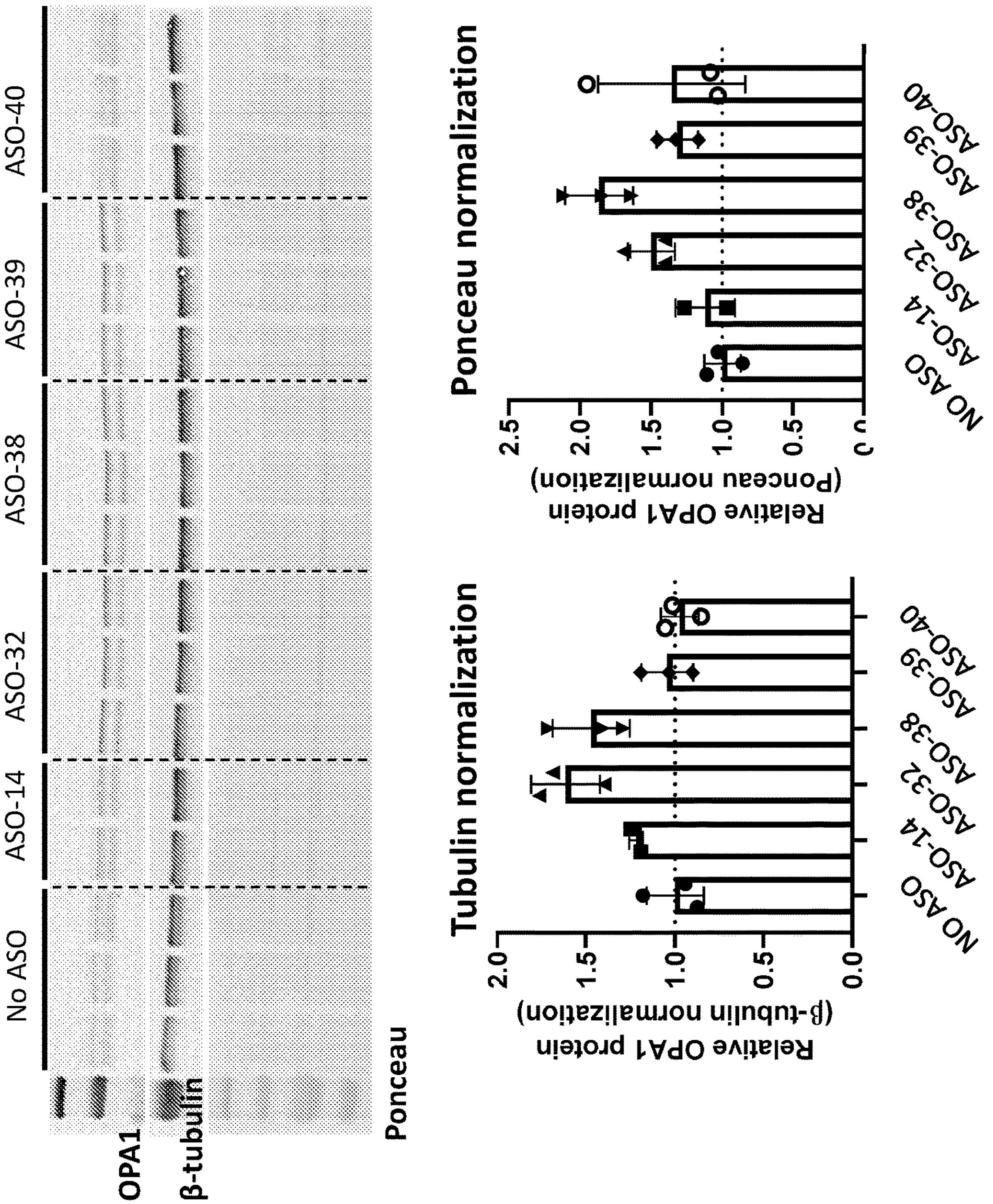
FIG. 18B illustrates expression level of OPA1 protein in HEK293 cells after treatment with various exemplary OPA1 ASOs.

FIG. 18B shows image of Western blot using antibody against OPA1 protein and antibody against β-tubulin protein in the cells after treatment with different ASOs or no ASO (control), as well as Ponceau staining image of the same blot. FIG. 18B also shows plots summarizing the amount of OPA1 protein under different treatment conditions as normalized relative to the amount of β-tubulin or Ponceau staining intensity. The data suggest that ASO-14, ASO-32, ASO-38, and ASO-39 all may induce increase in OPA1 protein expression, whereas ASO-40 may not significantly change the expression level of OPA1 protein.

Figure 18C:
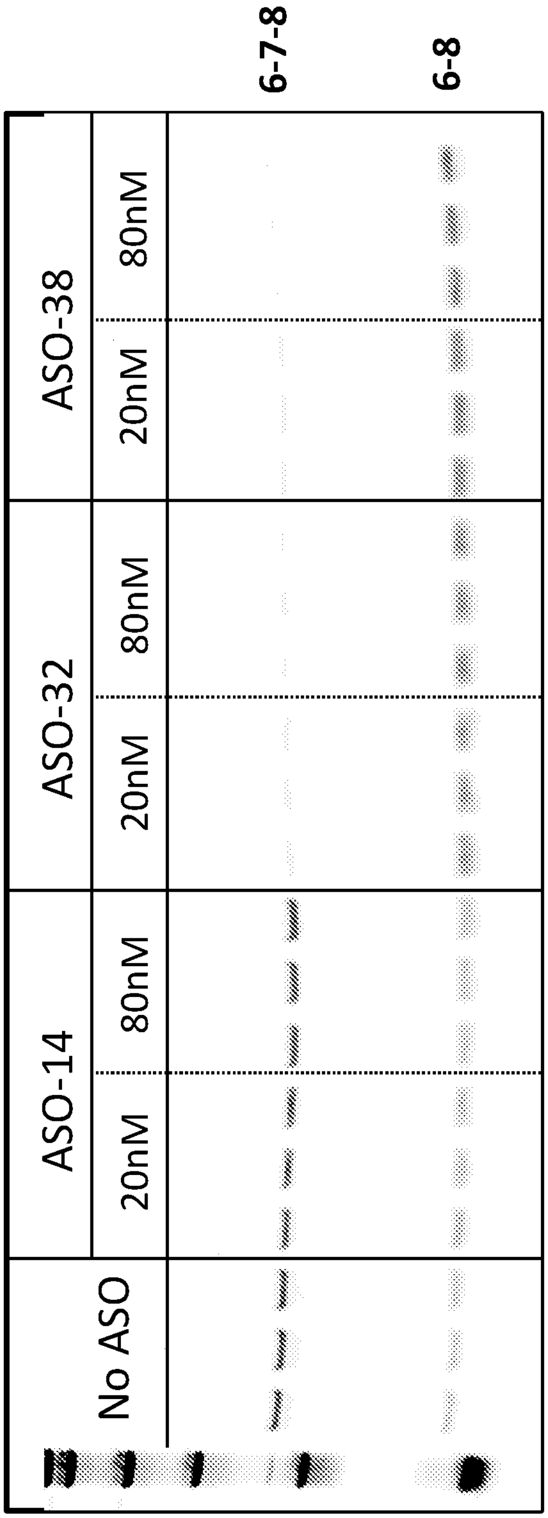
FIG. 18C illustrates dose response in OPA1 mRNAs using probes spanning exon 6 and exon 8 in HEK293 cells after treatment with various exemplary OPA1 ASOs.
Figure 18D:
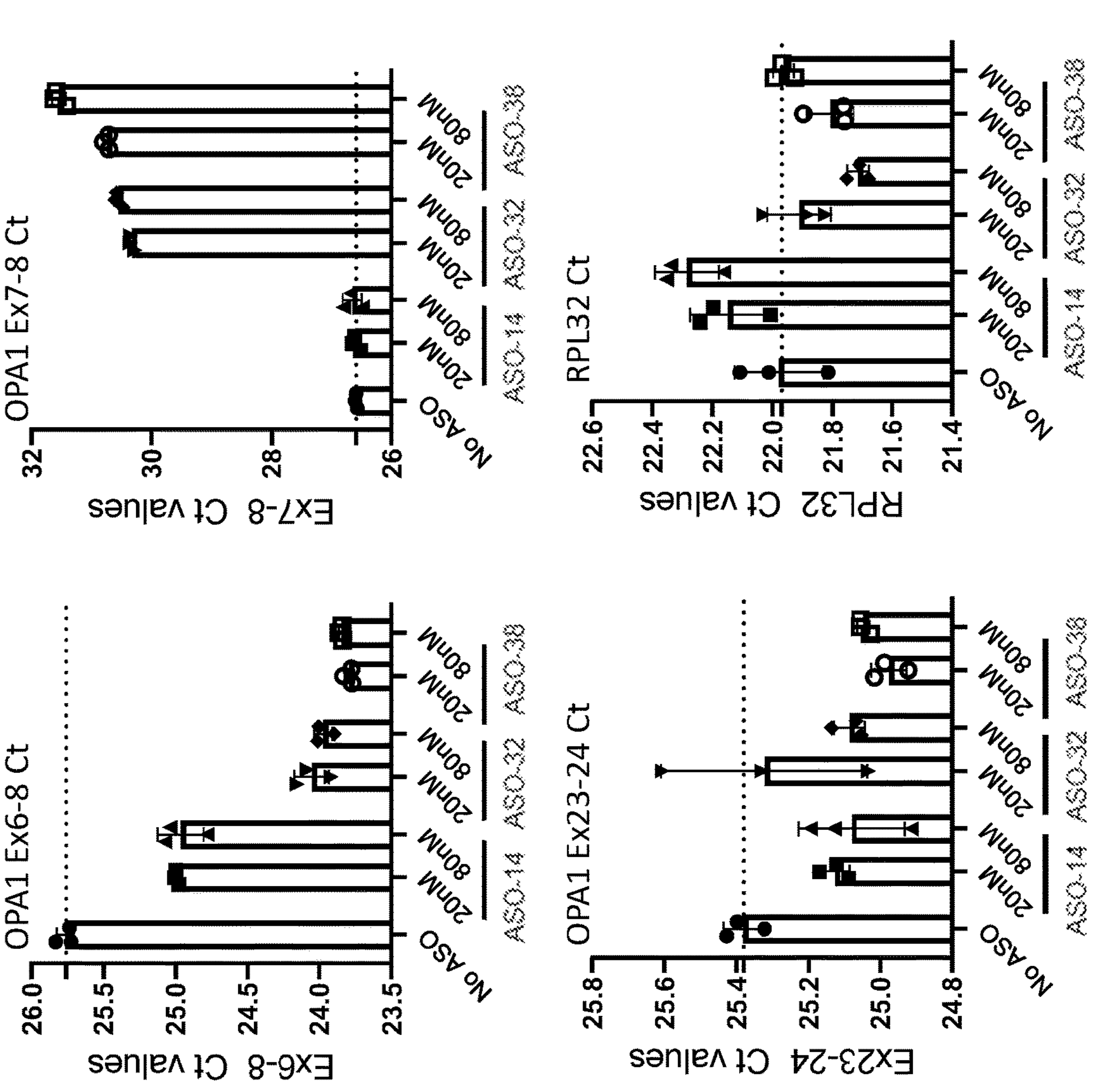
FIGS. 18D and 18E illustrate quantification of the dose response in OPA1 mRNAs using probes spanning exons 6 and 8, probes spanning exons 7 and 8, probes spanning exons 23 and 24, respectively, in HEK293 cells after treatment with various exemplary OPA1 ASOs.
Figure 18E:
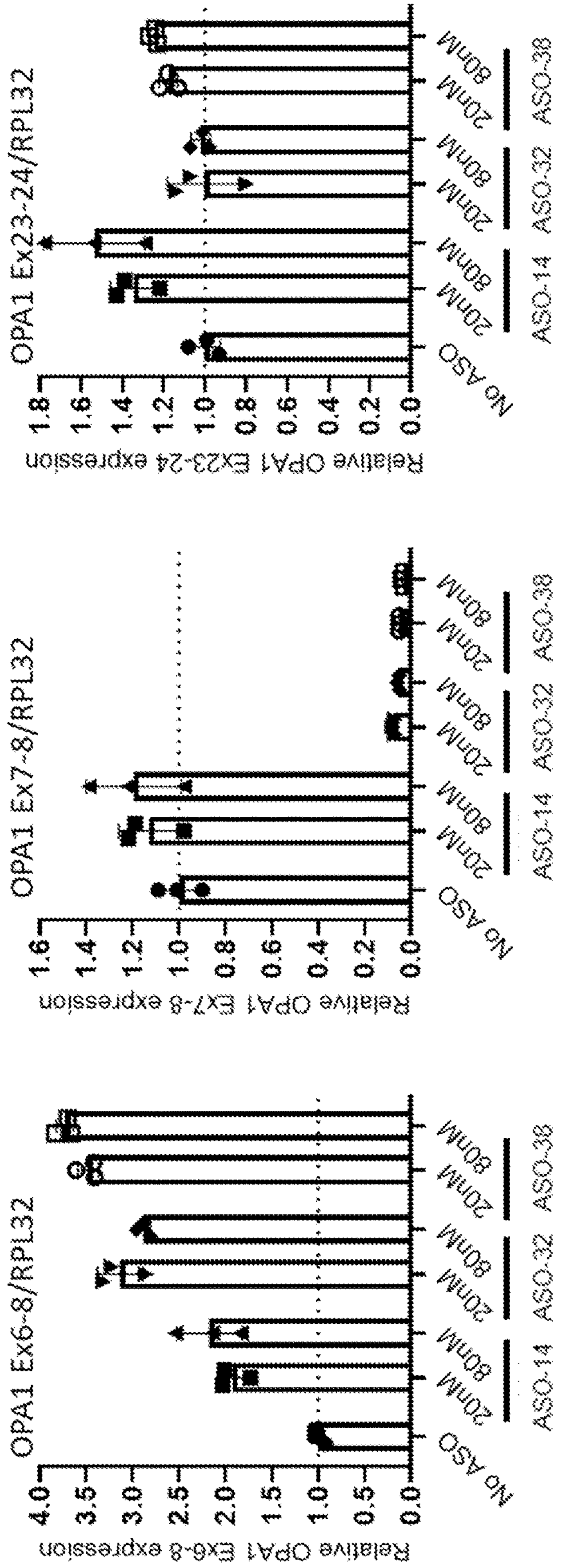
Figure 18F:
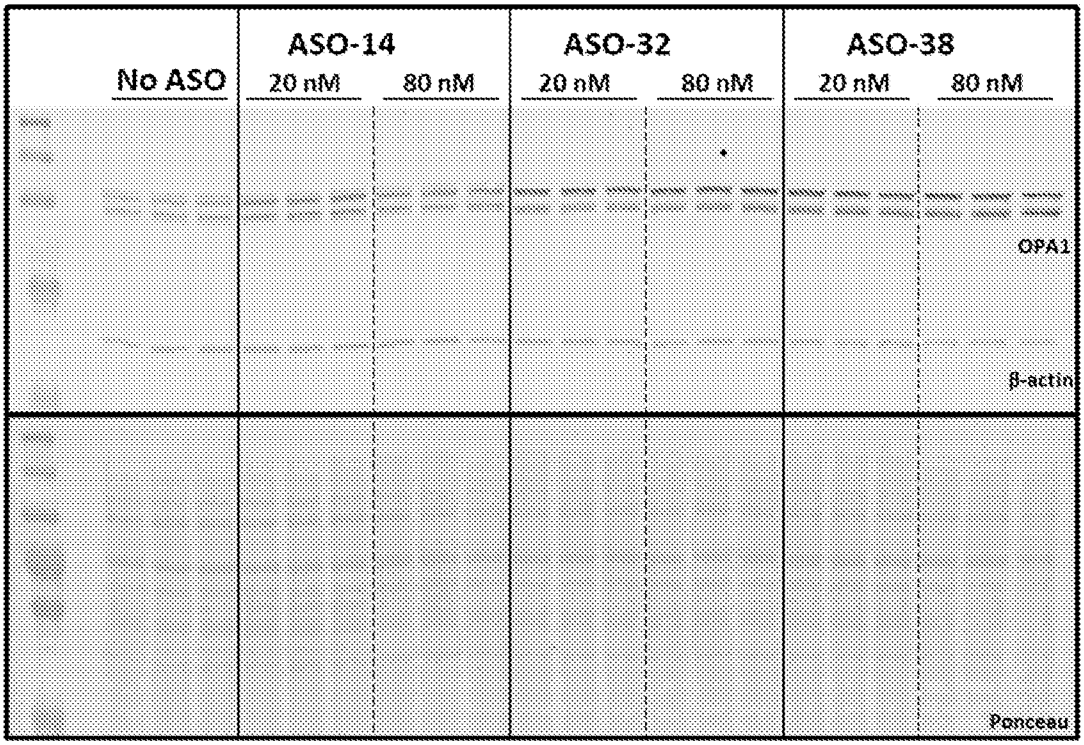
FIG. 18F illustrates dose response in expression level of OPA1 protein in HEK293 cells after treatment with various exemplary OPA1 ASOs.
Figure 18F:
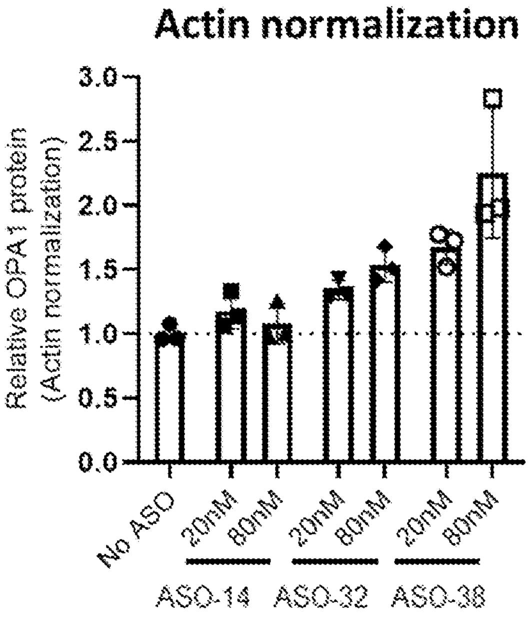
Figure 18F:
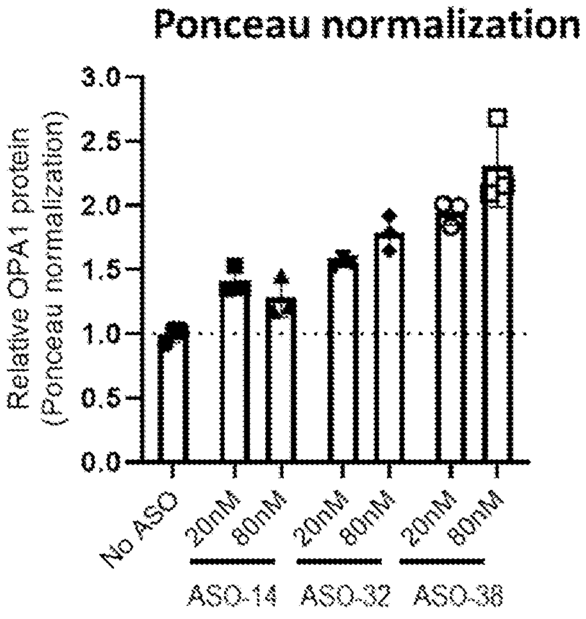

Dose response of ASO-32 and ASO-38 were also tested along with ASO-14. ASO treatment, cell harvest, and RNA isolation and analysis were conducted similarly to the experiment above in this example. Each well of HEK293 cells (about 50,000 cells/well) were treated with either 20 nM or 80 nM of ASO-14, ASO-32, ASO-38, or no ASO. FIG. 18C shows gel image of products from RT-PCR reaction using probes spanning exon 6 and 8. FIG. 18D shows quantification of qPCR Ct values for reactions under different experimental conditions using probes spanning exons and 8 ("Ex6-8"), probes spanning exons 7 and 8 ("Ex7-8"), and probes spanning exons 23 and 24 ("Ex23-24"), and FIG. 18E shows quantification of relative amount of the corresponding transcripts. The data show consistent observation that ASO-32 and ASO-38 promote exclusion of exon 7 from mature OPA1 mRNA transcripts. FIG. 18F shows the data on the OPA1 expression level after treatment of ASO-14, ASO-32, or ASO-38. Consistently, ASO-32 and ASO-38 increased OPA1 protein level.

Example 18: ASO Microwalk Evaluated by RT-qPCR

In one experiment, microwalk was conducted to test ASOs that have sequences listed in Table 7. Briefly, about 30,000 HEK293 cells per well were treated gymnotically with 20 μM one of the 20 exemplary ASOs (free uptake) listed in Table 7 for 72 hours. After the treatment, the cells were harvested for analysis. RT-PCR reactions were conducted for products corresponding to Exon 7 or Exon 7x inclusion and full-length.

Figure 19B:
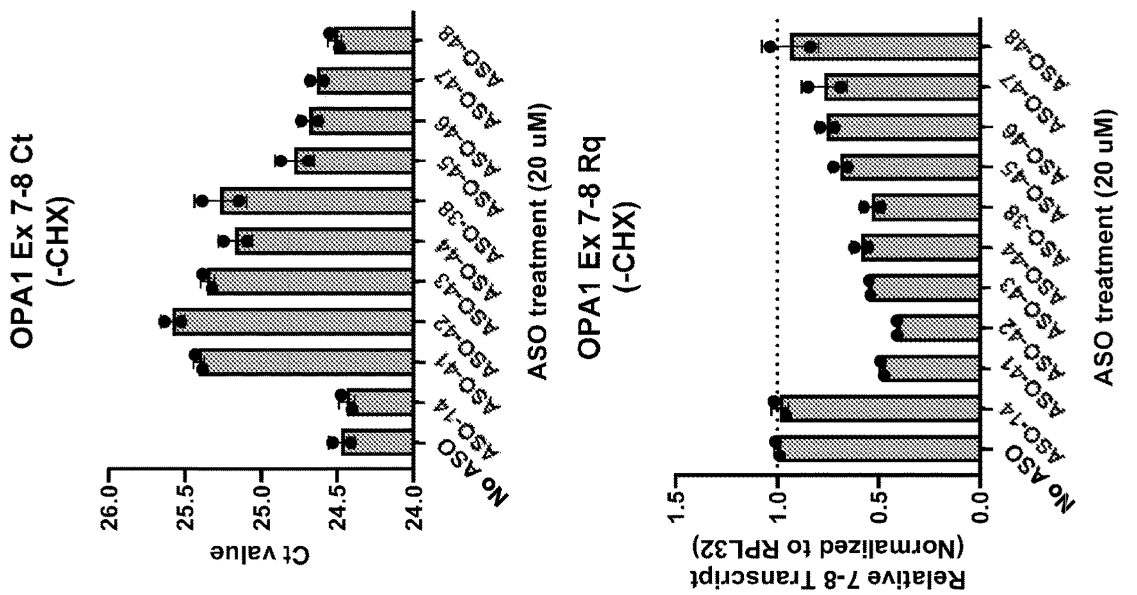
FIGS. 19A-19D illustrate RT-PCR results for OPA1 mRNAs using probes spanning exon 6 and exon 8 ("Exon 6-8"), or probes spanning exon 7x and exon 8 ("Exon 7-8"), in HEK293 cells after treatment with various exemplary OPA1 ASO 18-mers and treatment with or without cycloheximide.
Figure 19A:
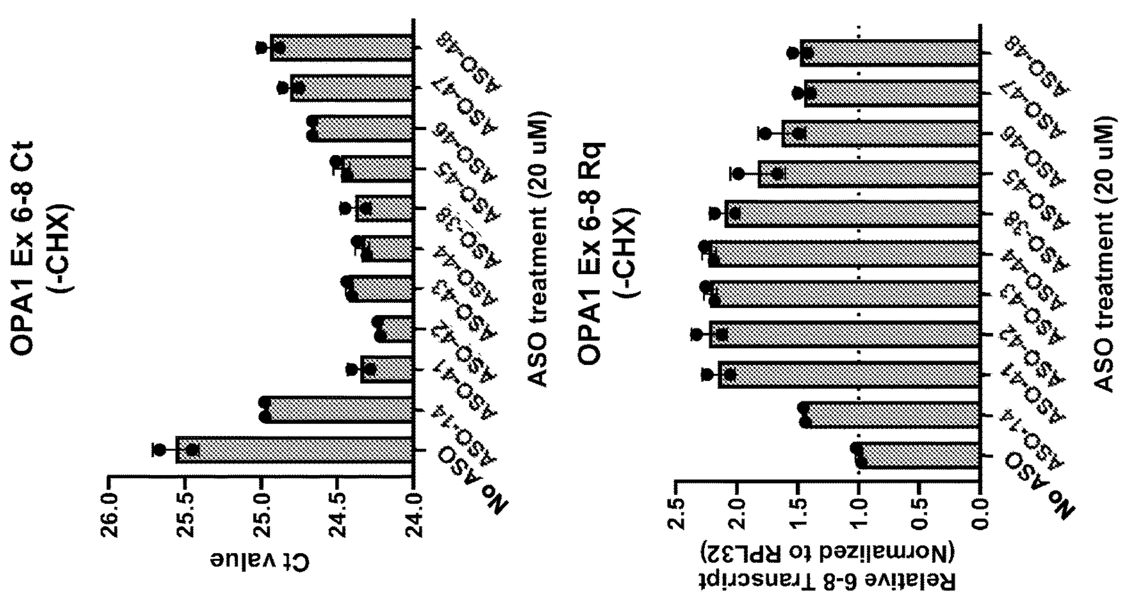
Figure 19C:
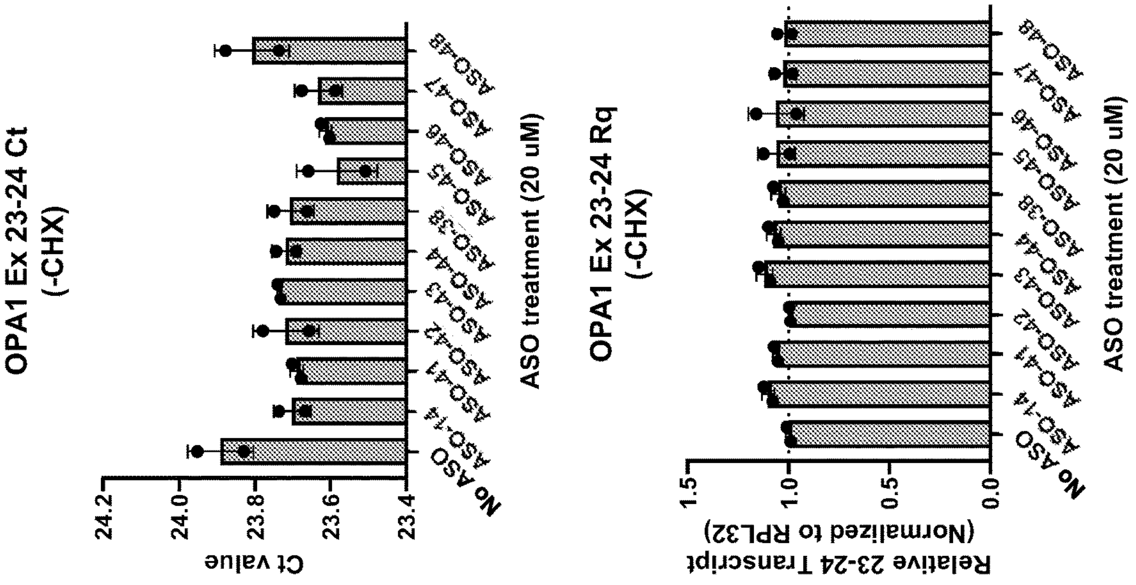
Figure 19D:
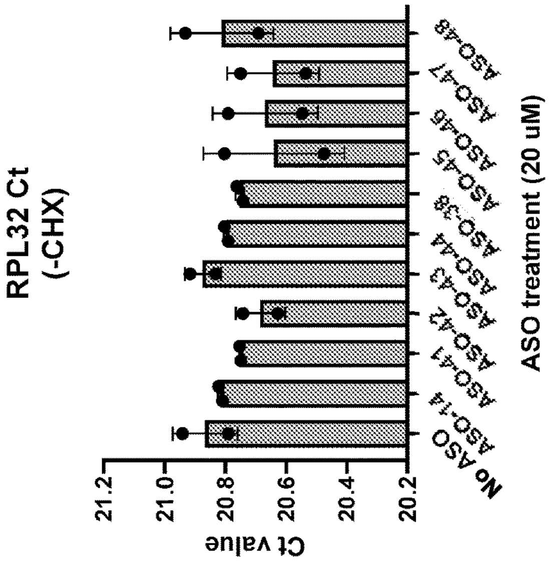
Figure 20B:
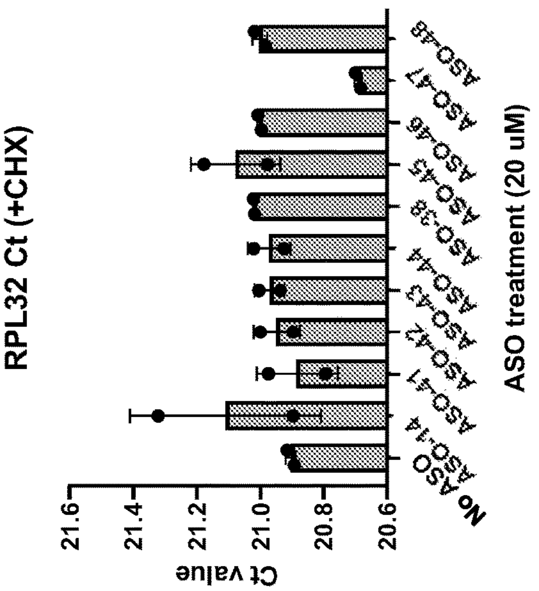
FIGS. 20A-20B illustrate RT-PCR results for OPA1 mRNAs using probes spanning exon 6 and exon 8 ("Exon 6-8"), or probes spanning exon 7x and exon 8 ("Exon 7x-8"), in HEK293 cells after treatment with various exemplary OPA1 ASO 18-mers and treatment with or without cycloheximide.
Figure 20A:
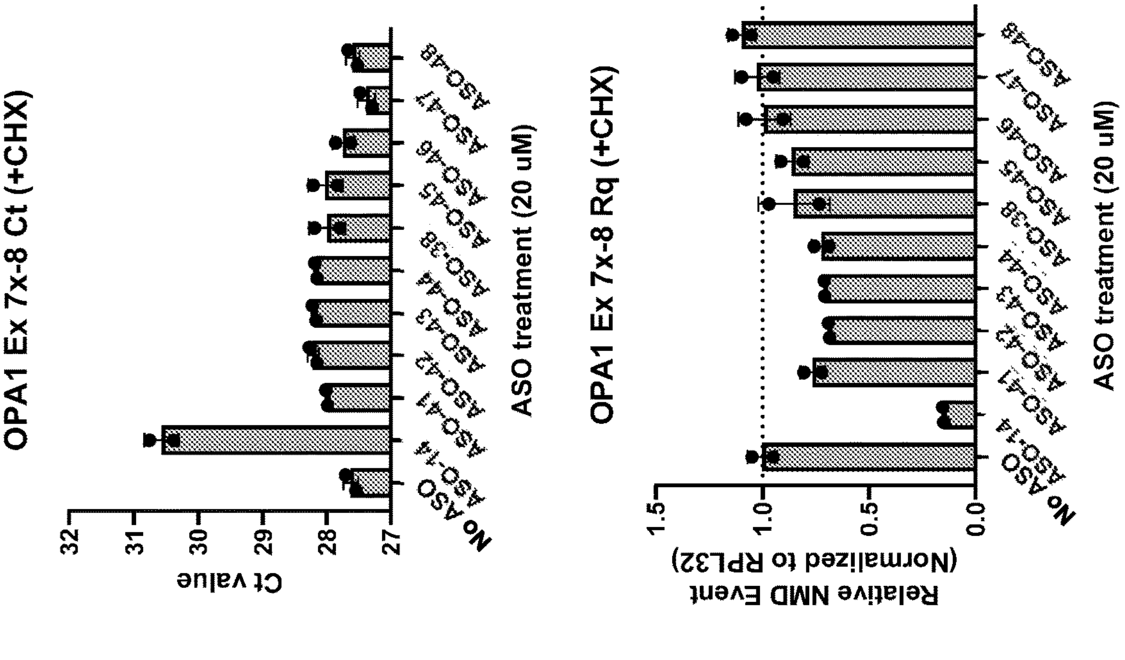

FIGS. 19A-20B demonstrate data from experiments with some of the 18-mers (named ASO-41 to ASO-48) listed in Table 7. FIGS. 19A-19B show the Ct values for the qPCR reaction (upper plots) for, and quantification of the relative amount (lower plots; normalized to Ct value of RPL32 qPCR product) of, OPA1 transcripts having exons 6 and 8 ("Ex6-8") and OPA1 transcripts having exons 7 and 8 ("Ex7-8"), respectively. FIG. 19C shows the Ct values for the qPCR reaction (upper plots) for, and quantification of the relative amount (lower plots; normalized to Ct value of RPL32 qPCR product) of, OPA1 transcripts having exons 23 and 24 ("Ex23-24"), and FIG. 19D shows the Ct values for RPL32 transcripts as a loading control. These data demonstrate that cells treated with ASO-41 to ASO-47 all showed increased amount of "Ex6-8" transcripts and decreased amount of "Ex7-8" transcripts, suggesting these ASOs promote exclusion of Exon 7 from OPA1 transcripts. No cycloheximide was applied to the cells that were subject to these analyses for Exon 7 inclusion. FIG. 20A shows the Ct values for the qPCR reaction (upper plots) for, and quantification of the relative amount (lower plots; normalized to Ct value of RPL32 qPCR product) of, OPA1 transcripts having exons 7x and 8 ("Ex7x-8"), and FIG. 20B shows the Ct values for RPL32 transcripts as a loading control. These data demonstrate that cells treated with ASO-41 to ASO-44 all showed decreased amount of "Ex7x-8" transcripts, suggesting these ASOs promote exclusion of Exon 7x from OPA1 transcripts. Cycloheximide was applied to the cells for these analyses for Exon 7x inclusion.

Figure 21B:
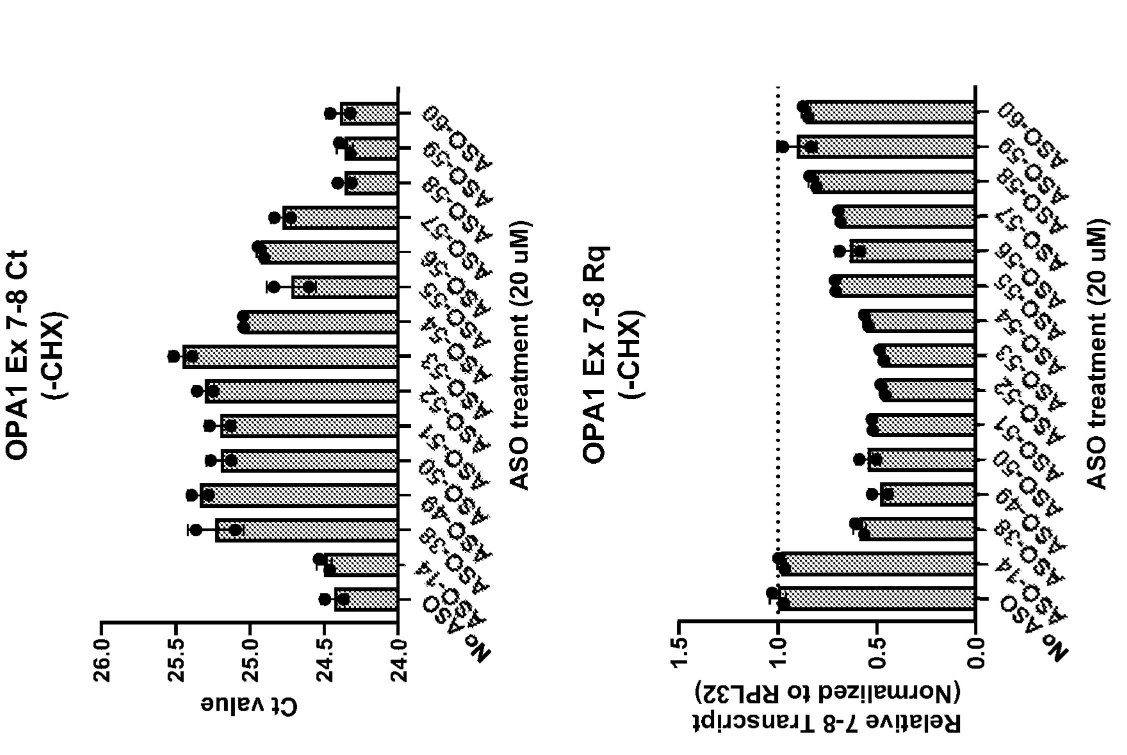
FIGS. 21A-21D illustrate RT-PCR results for OPA1 mRNAs using probes spanning exon 6 and exon 8 ("Exon 6-8"), or probes spanning exon 7x and exon 8 ("Exon 7-8"), in HEK293 cells after treatment with various exemplary OPA1 ASO 16-mers and treatment with or without cycloheximide.
Figure 21A:
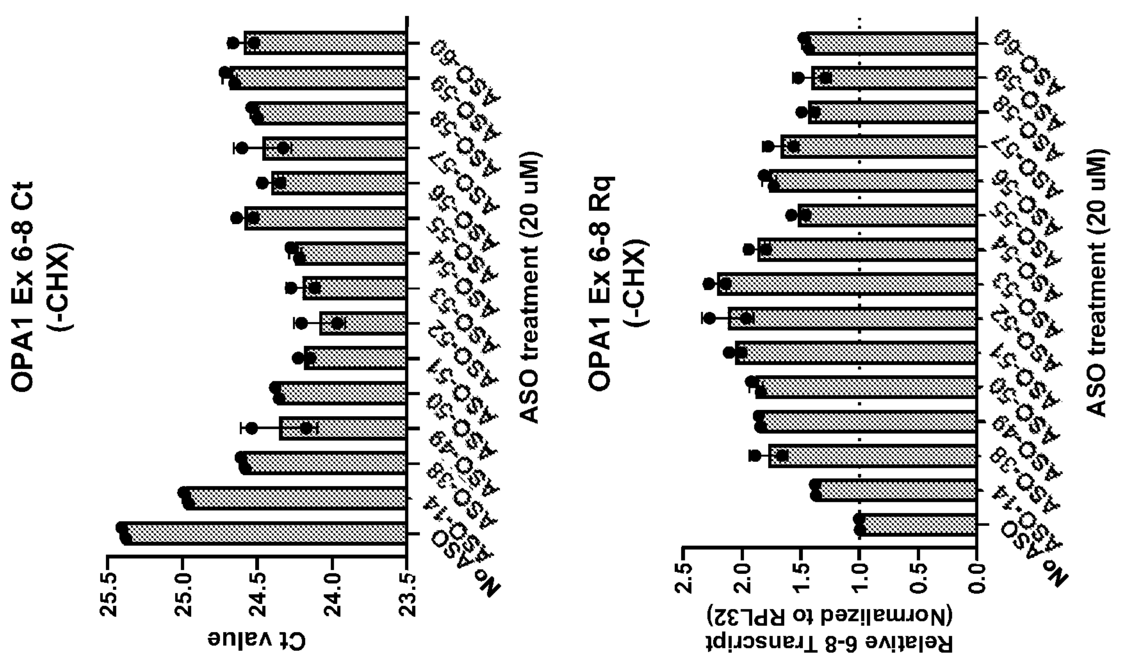
Figure 21D:
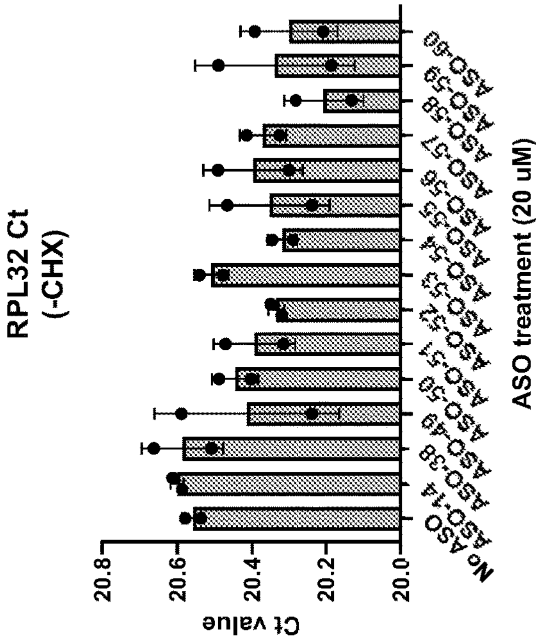
Figure 21C:
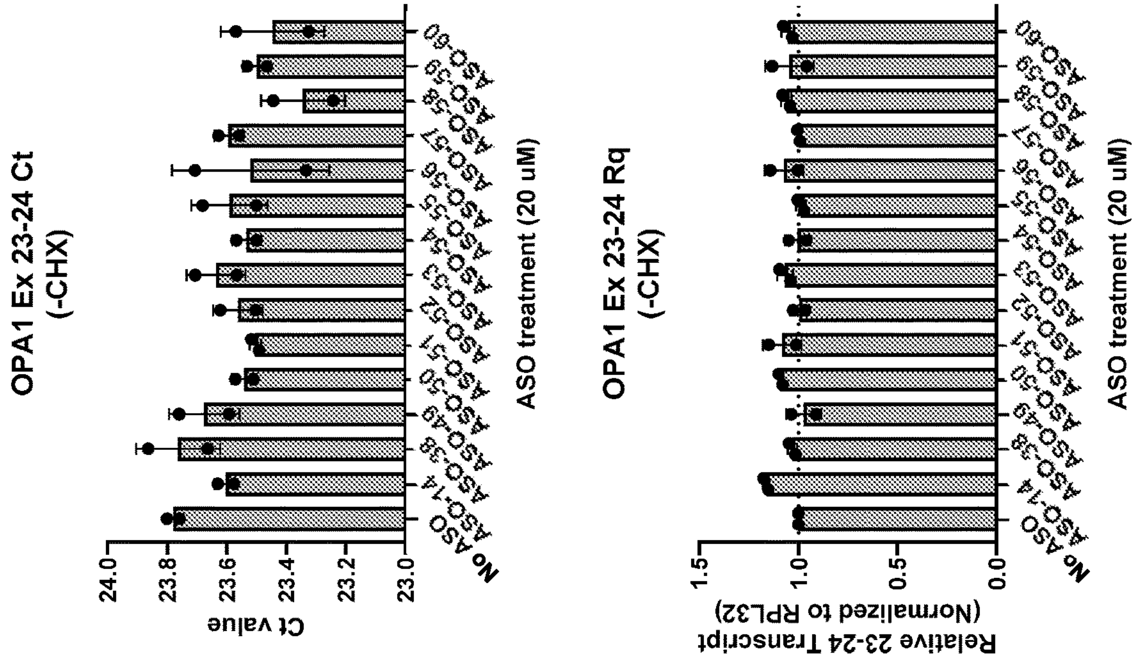
Figure 22A:
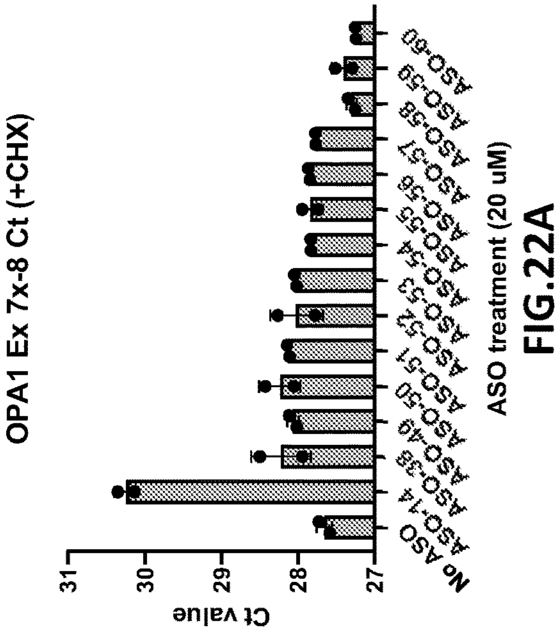
FIGS. 22A-22C illustrate RT-PCR results for OPA1 mRNAs using probes spanning exon 6 and exon 8 ("Exon 6-8"), or probes spanning exon 7x and exon 8 ("Exon 7x-8"), in HEK293 cells after treatment with various exemplary OPA1 ASO 15-mers and treatment with or without cycloheximide.
Figure 22B:
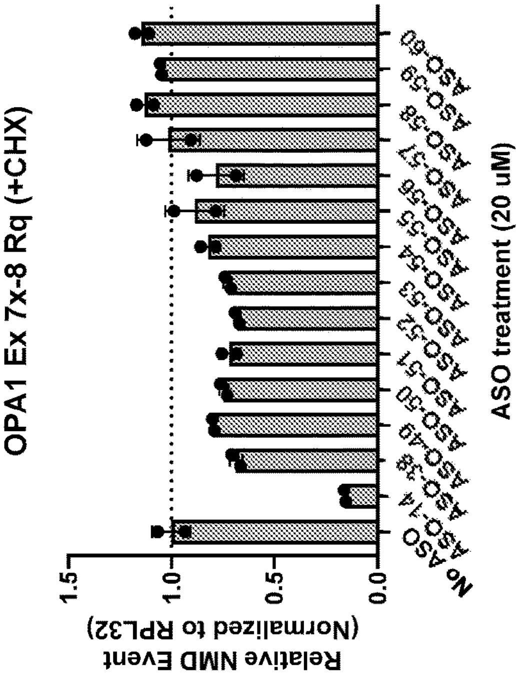
Figure 22C:
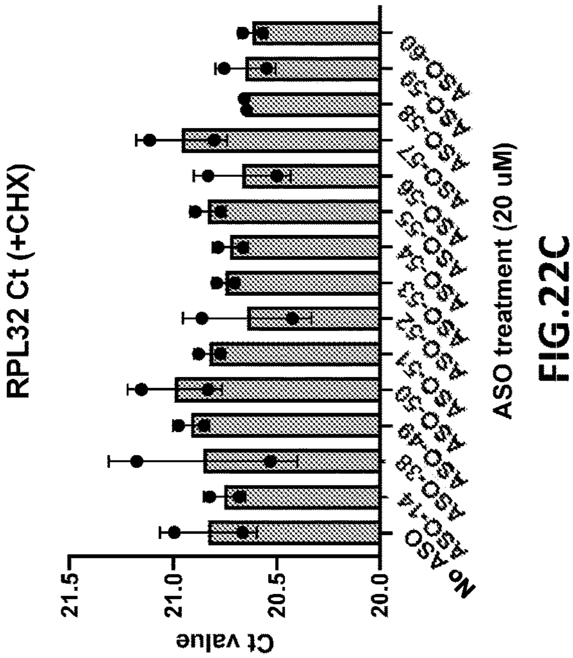

FIGS. 21A-22C demonstrate data from experiments with some of the 16-mers (named ASO-49 to ASO-60) listed in Table 7. FIGS. 21A-21B show the Ct values for the qPCR reaction (upper plots) for, and quantification of the relative amount (lower plots; normalized to Ct value of RPL32 qPCR product) of, OPA1 transcripts having exons 6 and 8 ("Ex6-8") and OPA1 transcripts having exons 7 and 8 ("Ex7-8"), respectively. FIG. 21C shows the Ct values for the qPCR reaction (upper plots) for, and quantification of the relative amount (lower plots; normalized to Ct value of RPL32 qPCR product) of, OPA1 transcripts having exons 23 and 24 ("Ex23-24"), and FIG. 21D shows the Ct values for RPL32 transcripts. These data demonstrate that cells treated with ASO-49 to ASO-60 all showed increased amount of "Ex6-8" transcripts and decreased amount of "Ex7-8" transcripts, suggesting these ASOs promote exclusion of Exon 7 from OPA1 transcripts. No cycloheximide was applied to the cells that were subject to these analyses for Exon 7 inclusion. FIG. 22A shows the Ct values for the qPCR reaction (upper plots) for, and quantification of the relative amount (lower plots; normalized to Ct value of RPL32 qPCR product) of, OPA1 transcripts having exons 7x and 8 ("Ex7x-8"), and FIG. 22C shows the Ct values for RPL32 transcripts as a loading control. These data demonstrate that cells treated with ASO-49 to ASO-56 all showed decreased amount of "Ex7x-8" transcripts, suggesting these ASOs promote exclusion of Exon 7x from OPA1 transcripts. Cycloheximide was applied to the cells for these analyses for Exon 7x inclusion.

Figure 23A:
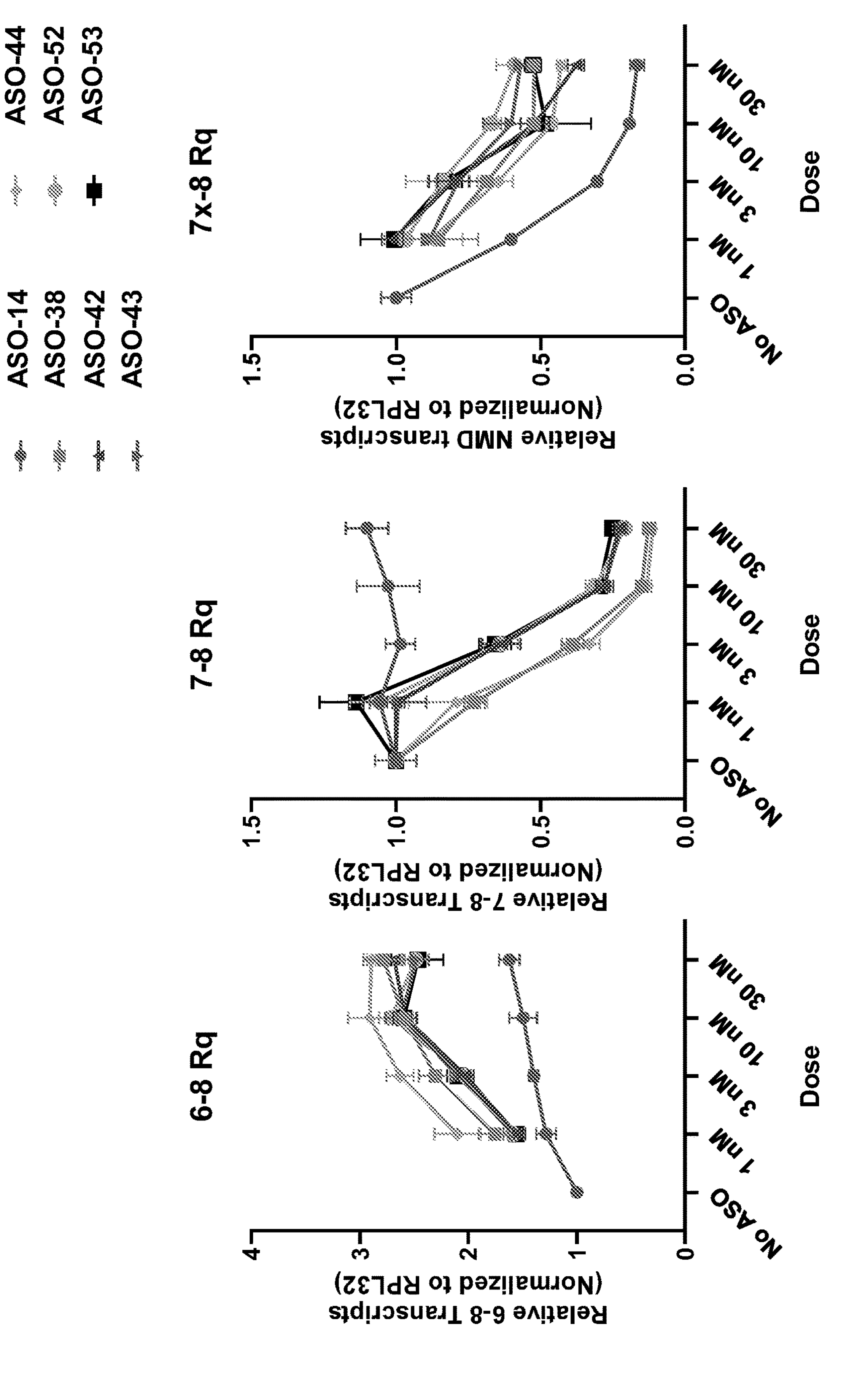
FIGS. 23A-23B illustrate dose response in OPA1 mRNAs having Exon 6 and Exon 8 ("6-8"), having Exon 7 and Exon 8 ("7-8"), or having Exon 7x and Exon 8 ("7x-8") in HEK293 cells after treatment with different concentrations of various exemplary OPA1 ASOs.
Figure 23B:
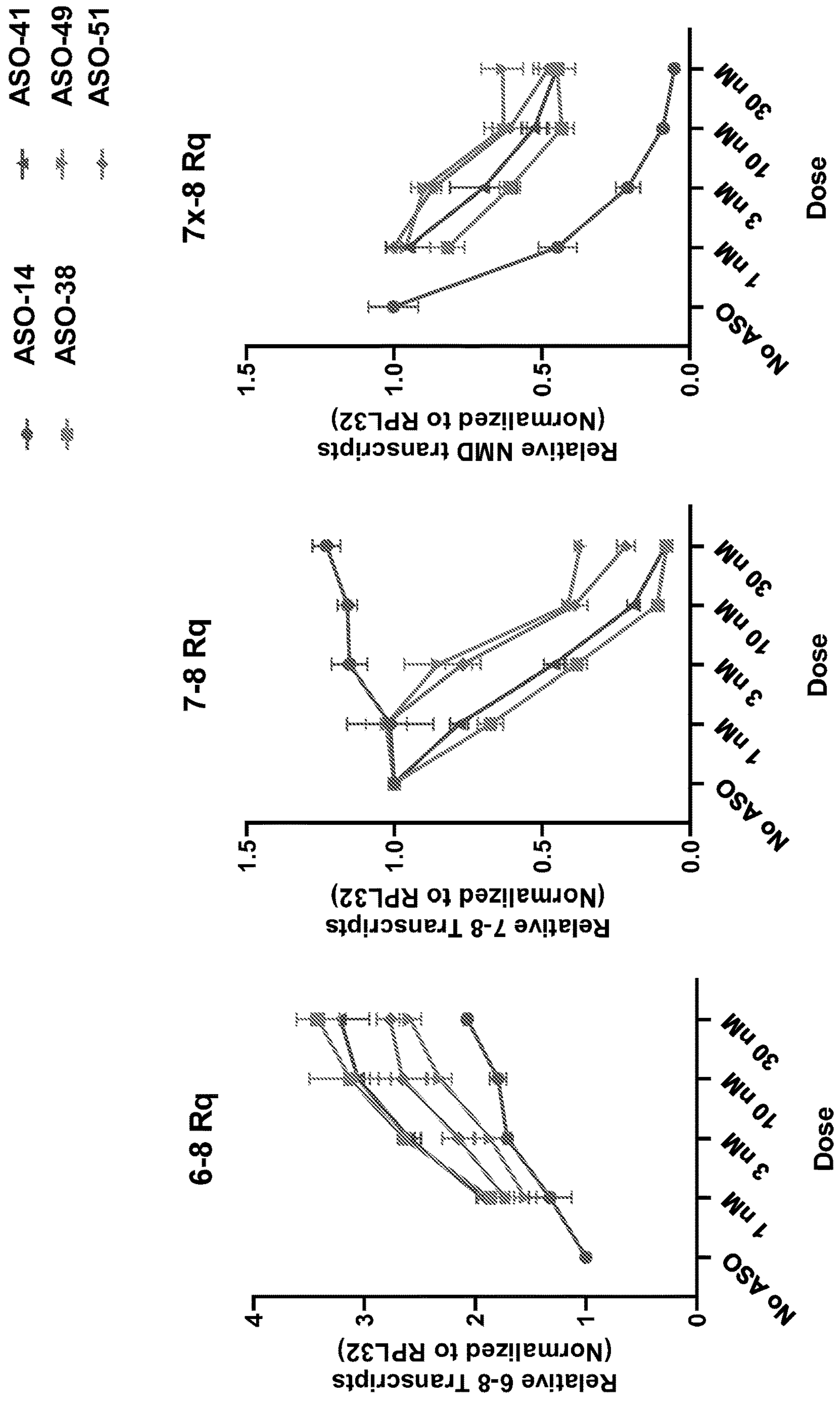

Another experiment was conducted to assess transfection dose response relationship with select ASOs among the ASOs tested above in the microwalk analyses. Briefly, 100,000 HEK293 cells per well were transfected with 1, 3, 10, or 30 nM of an exemplary ASO with 0.45 μL lipofectamine for 24 hours. Cells were later harvested for qPCR analysis as above. FIGS. 23A-23B show plots depicting the dose response curves of relative amounts of different OPA1 transcripts versus the transfection concentration of exemplary ASOs, ASO-14, 38, 41, 42, 43, 44, 49, 51, 52, and 53. The plots show that as a general trend, in cells treated with ASOs like ASO-38, 41, 42, 43, 44, 49, 51, 52, or 53, the amount of OPA1 transcripts having Exon 6 and 8 ("6-8") increased, while the amounts of OPA1 transcripts having Exon 7 and 8 ("7-8") and OPA1 transcripts having Exon 7x and 8 ("7x-8") decreased, as concentration of the exemplary ASO increased. In contrast, in cells treated with ASO-14, while "7x-8" decreased and "6-8" transcripts increased, "7-8" transcripts did not significantly change. These data suggest that ASO-38, 41, 42, 43, 44, 49, 51, 52, and 53 may all promote exclusion of both Exon 7 and Exon 7x, while ASO-14 may promote exclusion of Exon 7x

TABLE 5

Exemplary OPA1 ASO sequences

| SEQ ID NO.: | Sequence (5'-3') | Coordinates GRCh38/hg38: chr3 Oligo Start | Oligo End |
|---|---|---|---|
| 6 | AGGCCATTCTGAAATTCT | 193628406 | 193628423 |
| 7 | CATTGAGGCCATTCTGAA | 193628411 | 193628428 |
| 8 | TAAGGCATTGAGGCCATT | 193628416 | 193628433 |
| 9 | CCTATTAAGGCATTGAGG | 193628421 | 193628438 |
| 10 | TTCTTCCTATTAAGGCAT | 193628426 | 193628443 |
| 11 | AGTATTTCTTCCTATTAA | 193628431 | 193628448 |
| 12 | TTTCAAGTATTTCTTCCT | 193628436 | 193628453 |
| 13 | AAAAATTTCAAGTATTTC | 193628441 | 193628458 |
| 14 | AATTTAAAAATTTCAAGT | 193628446 | 193628463 |
| 15 | GCCCTAATTTAAAAATTT | 193628451 | 193628468 |
| 16 | ACCAAGCCCTAATTTAAA | 193628456 | 193628473 |
| 17 | ACAAAACCAAGCCCTAAT | 193628461 | 193628478 |
| 18 | TCCTCACAAAACCAAGCC | 193628466 | 193628483 |
| 19 | CTAGCTCCTCACAAAACC | 193628471 | 193628488 |
| 20 | CTTTACTAGCTCCTCACA | 193628476 | 193628493 |
| 21 | AAAACCTTTACTAGCTCC | 193628481 | 193628498 |
| 22 | AGAGAAAAACCTTTACTA | 193628486 | 193628503 |
| 23 | CTGAAAGAGAAAAACCTT | 193628491 | 193628508 |
| 24 | AAGCTGAAAGAGAAAAAC | 193628494 | 193628511 |
| 25 | CTAAAGCTGAAAGAGAAA | 193628497 | 193628514 |
| 26 | AAGCTAAAGCTGAAAGAG | 193628500 | 193628517 |
| 27 | AACAAGCTAAAGCTGAAA | 193628503 | 193628520 |
| 28 | AGAAACAAGCTAAAGCTG | 193628506 | 193628523 |
| 29 | CGCAGAAACAAGCTAAAG | 193628509 | 193628526 |
| 30 | TCCTCCGCAGAAACAAGC | 193628514 | 193628531 |
| 31 | CGGAATCCTCCGCAGAAA | 193628519 | 193628536 |
| 32 | AAGAGCGGAATCCTCCGC | 193628524 | 193628541 |
| 33 | GGAGAAAGAGCGGAATCC | 193628529 | 193628546 |
| 34 | CTGATGGAGAAAGAGCGG | 193628534 | 193628551 |
| 35 | TGAAACTGATGGAGAAAG | 193628539 | 193628556 |
| 36 | GGCTATGAAACTGATGGA | 193628544 | 193628561 |

TABLE 5-continued

Exemplary OPA1 ASO sequences

| SEQ ID NO.: | Sequence (5'-3') | Coordinates GRCh38/hg38: chr3 Oligo Start | Oligo End |
|---|---|---|---|
| 37 | TCCAGGGCTATGAAACTG | 193628549 | 193628566 |
| 38 | ACAATTCCAGGGCTATGA | 193628554 | 193628571 |
| 39 | TTTCTACAATTCCAGGGC | 193628559 | 193628576 |
| 40 | GAGCTTTTCTACAATTCC | 193628564 | 193628581 |
| 41 | AACCAGAGCTTTTCTACA | 193628569 | 193628586 |
| 42 | CTTGAAACCAGAGCTTTT | 193628574 | 193628591 |
| 43 | ATGGTCTTGAAACCAGAG | 193628579 | 193628596 |
| 44 | TATCAATGGTCTTGAAAC | 193628584 | 193628601 |
| 45 | ATGGATATCAATGGTCTT | 193628589 | 193628606 |
| 46 | CAGAAATGGATATCAATG | 193628594 | 193628611 |
| 47 | CCTGACAGAAATGGATAT | 193628599 | 193628616 |
| 48 | CACCCTGACAGAAATGGA | 193628602 | 193628619 |
| 49 | ACTCACCCTGACAGAAAT | 193628605 | 193628622 |
| 50 | AAAACTCACCCTGACAGA | 193628608 | 193628625 |
| 51 | TTTAAAACTCACCCTGAC | 193628611 | 193628628 |
| 52 | AAATTTAAAACTCACCCT | 193628614 | 193628631 |
| 53 | AATAAATTTAAAACTCAC | 193628617 | 193628634 |
| 54 | CATGAAATAAATTTAAAA | 193628622 | 193628639 |
| 55 | TGCATCATGAAATAAATT | 193628627 | 193628644 |
| 56 | TTGTTTGCATCATGAAAT | 193628632 | 193628649 |
| 57 | ATATATTGTTTGCATCAT | 193628637 | 193628654 |
| 58 | GTTCAATATATTGTTTGC | 193628642 | 193628659 |
| 59 | CTGTTGTTCAATATATTG | 193628647 | 193628664 |
| 60 | ATGTCCTGTTGTTCAATA | 193628652 | 193628669 |
| 61 | AGTTCATGTCCTGTTGTT | 193628657 | 193628674 |
| 62 | GAACAAGTTCATGTCCTG | 193628662 | 193628679 |
| 63 | AACAAGAACAAGTTCATG | 193628667 | 193628684 |
| 64 | CTTACAACAAGAACAAGT | 193628672 | 193628689 |
| 65 | AGCCACTTACAACAAGAA | 193628677 | 193628694 |
| 66 | AATTCAGCCACTTACAAC | 193628682 | 193628699 |
| 67 | GATAAAATTCAGCCACTT | 193628687 | 193628704 |
| 68 | TTACTGATAAAATTCAGC | 193628692 | 193628709 |
| 69 | GTGCTTTACTGATAAAAT | 193628697 | 193628714 |
| 70 | TTGATGTGCTTTACTGAT | 193628702 | 193628719 |
| 71 | TGGAGAAAGAGCGGAATC | 193628530 | 193628547 |
| 72 | ATGGAGAAAGAGCGGAAT | 193628531 | 193628548 |

TABLE 5-continued

Exemplary OPA1 ASO sequences

| SEQ ID NO.: | Sequence (5'-3') | Coordinates GRCh38/hg38: chr3 Oligo Start | Oligo End |
|---|---|---|---|
| 73 | GATGGAGAAAGAGCGGAA | 193628532 | 193628549 |
| 74 | TGATGGAGAAAGAGCGGA | 193628533 | 193628550 |
| 75 | ACTGATGGAGAAAGAGCG | 193628535 | 193628552 |
| 76 | AACTGATGGAGAAAGAGC | 193628536 | 193628553 |
| 77 | AAACTGATGGAGAAAGAG | 193628537 | 193628554 |
| 78 | GAAACTGATGGAGAAAGA | 193628538 | 193628555 |
| 79 | ATGAAACTGATGGAGAAA | 193628540 | 193628557 |
| 80 | TATGAAACTGATGGAGAA | 193628541 | 193628558 |
| 81 | CTATGAAACTGATGGAGA | 193628542 | 193628559 |
| 82 | GCTATGAAACTGATGGAG | 193628543 | 193628560 |
| 83 | GGGCTATGAAACTGATGG | 193628545 | 193628562 |
| 84 | AGGGCTATGAAACTGATG | 193628546 | 193628563 |
| 85 | CAGGGCTATGAAACTGAT | 193628547 | 193628564 |
| 86 | CCAGGGCTATGAAACTGA | 193628548 | 193628565 |
| 87 | CTGATGGAGAAAGAGCGGAATC | 193628530 | 193628551 |
| 88 | CTGATGGAGAAAGAGCGGAA | 193628532 | 193628551 |
| 89 | AACTGATGGAGAAAGAGCGGAA | 193628532 | 193628553 |
| 90 | AACTGATGGAGAAAGAGCGG | 193628534 | 193628553 |
| 91 | GAAACTGATGGAGAAAGAGCGG | 193628534 | 193628555 |
| 92 | GGCTATGAAACTGATGGAGAAA | 193628540 | 193628561 |
| 93 | GGCTATGAAACTGATGGAGA | 193628542 | 193628561 |
| 94 | AGGGCTATGAAACTGATGGAGA | 193628542 | 193628563 |
| 95 | AGGGCTATGAAACTGATGGA | 193628544 | 193628563 |
| 96 | CCAGGGCTATGAAACTGATGGA | 193628544 | 193628565 |
| 97 | TTCTTACCCATTTAATTA | 193655041 | 193655059 |
| 98 | TGCTTCTTACCCATTTAA | 193655044 | 193655062 |
| 99 | TAATGCTTCTTACCCATT | 193655047 | 193655065 |
| 100 | AGATAATGCTTCTTACCC | 193655050 | 193655068 |
| 101 | CAGATAATGCTTCTTACC | 193655051 | 193655069 |
| 102 | CCCTTCAGATAATGCTTC | 193655056 | 193655074 |
| 103 | CTACTCCCTTCAGATAAT | 193655061 | 193655079 |
| 104 | AGCTCCTACTCCCTTCAG | 193655066 | 193655084 |
| 105 | TTCACAGCTCCTACTCCC | 193655071 | 193655089 |
| 106 | TAAAATTCACAGCTCCTA | 193655076 | 193655094 |
| 107 | AAATCTAAAATTCACAGC | 193655081 | 193655099 |
| 108 | GAATAAAATCTAAAATTC | 193655086 | 193655104 |
| 109 | GATGGGAATAAAATCTAA | 193655091 | 193655109 |

TABLE 5-continued

Exemplary OPA1 ASO sequences

| SEQ ID NO.: | Sequence (5'-3') | Coordinates GRCh38/hg38: chr3 Oligo Start | Oligo End |
|---|---|---|---|
| 110 | GCTGTGATGGGAATAAAA | 193655096 | 193655114 |
| 111 | TAGAGGCTGTGATGGGAA | 193655101 | 193655119 |
| 112 | AAAGATAGAGGCTGTGAT | 193655106 | 193655124 |
| 113 | AAAAGAAAGATAGAGGCT | 193655111 | 193655129 |
| 114 | GACCTAAAAGAAAGATAG | 193655116 | 193655134 |
| 115 | ATAAAGACCTAAAAGAAA | 193655121 | 193655139 |
| 116 | GAGATATAAAGACCTAAA | 193655126 | 193655144 |
| 117 | GGCTGTGATGGGAATAAA | 193655097 | 193655115 |
| 118 | AGGCTGTGATGGGAATAA | 193655098 | 193655116 |
| 119 | GAGGCTGTGATGGGAATA | 193655099 | 193655117 |
| 120 | AGAGGCTGTGATGGGAAT | 193655100 | 193655118 |
| 121 | ATAGAGGCTGTGATGGGA | 193655102 | 193655120 |
| 122 | GATAGAGGCTGTGATGGG | 193655103 | 193655121 |
| 123 | AGATAGAGGCTGTGATGG | 193655104 | 193655122 |
| 124 | AAGATAGAGGCTGTGATG | 193655105 | 193655123 |
| 125 | TAGAGGCTGTGATGGGAATAAA | 193655097 | 193655119 |
| 126 | ATAGAGGCTGTGATGGGAATAA | 193655098 | 193655120 |
| 127 | GATAGAGGCTGTGATGGGAATA | 193655099 | 193655121 |
| 128 | AGATAGAGGCTGTGATGGGAAT | 193655100 | 193655122 |
| 129 | AAGATAGAGGCTGTGATGGGAA | 193655101 | 193655123 |
| 130 | GAGGCTGTGATGGGAATAAA | 193655097 | 193655117 |
| 131 | AGAGGCTGTGATGGGAATAA | 193655098 | 193655118 |
| 132 | TAGAGGCTGTGATGGGAATA | 193655099 | 193655119 |
| 133 | ATAGAGGCTGTGATGGGAAT | 193655100 | 193655120 |
| 134 | GATAGAGGCTGTGATGGGAA | 193655101 | 193655121 |
| 135 | AGATAGAGGCTGTGATGGGA | 193655102 | 193655122 |
| 136 | AAGATAGAGGCTGTGATGGG | 193655103 | 193655123 |
| 137 | CTGTGATGGGAATAAA | 193655097 | 193655113 |
| 138 | GCTGTGATGGGAATAA | 193655098 | 193655114 |
| 139 | GGCTGTGATGGGAATA | 193655099 | 193655115 |
| 140 | AGGCTGTGATGGGAAT | 193655100 | 193655116 |
| 141 | GAGGCTGTGATGGGAA | 193655101 | 193655117 |
| 142 | AGAGGCTGTGATGGGA | 193655102 | 193655118 |
| 143 | TAGAGGCTGTGATGGG | 193655103 | 193655119 |
| 144 | ATAGAGGCTGTGATGG | 193655104 | 193655120 |
| 145 | GATAGAGGCTGTGATG | 193655105 | 193655121 |

TABLE 5-continued

Exemplary OPA1 ASO sequences

| SEQ ID NO.: | Sequence (5'-3') | Coordinates GRCh38/hg38: chr3 Oligo Start | Oligo End |
|---|---|---|---|
| 146 | AGATAGAGGCTGTGAT | 193655106 | 193655122 |
| 147 | AAGATAGAGGCTGTGA | 193655107 | 193655123 |
| 148 | AGGCTGTGATGTGAATAA | 193655099 | 193655116 |
| 149 | AGAGGCTGTGATGTGAAT | 193655101 | 193655118 |
| 150 | TAGAGGCTGTGATGTGAA | 193655102 | 193655119 |
| 151 | GATAGAGGCTGTGATTGG | 193655104 | 193655121 |
| 152 | GGCTGTGATGTGAATA | 193655100 | 193655115 |
| 153 | GAGGCTGTGATGTGAA | 193655102 | 193655117 |
| 154 | TAGAGGCTGTGATTGG | 193655104 | 193655119 |
| 155 | ATGAAACTGATGGAGA | 193628542 | 193628557 |
| 156 | CTATGAAACTGATGGA | 193628544 | 193628559 |
| 157 | GGCTATGAAACTGATG | 193628546 | 193628561 |
| 158 | GAAACTGATGGAGA | 193628542 | 193628555 |
| 159 | ATGAAACTGATGGA | 193628544 | 193628557 |
| 160 | CTATGAAACTGATG | 193628546 | 193628559 |
| 161 | GGCTATGAAACTGA | 193628548 | 193628561 |
| 162 | TAGAGGCTGTGATGGGAATAAAAT | 193655096 | 193655119 |
| 163 | ATAGAGGCTGTGATGGGAATAAAA | 193655097 | 193655120 |
| 164 | ATAGAGGCTGTGATGGGAATAAAAT | 193655096 | 193655120 |
| 165 | AAAGATAGAGGCTGTGATGGGAATA | 193655100 | 193655124 |
| 166 | GGCTATGAAACTGATGGAGAA | 193628541 | 193628561 |
| 167 | GGCTATGAAACTGATGGAGAAAGA | 193628538 | 193628561 |
| 168 | AGGGCTATGAAACTGATGGAGAAAG | 193628539 | 193628563 |
| 169 | CATTTAATTAAATTATAT | 193655033 | 193655051 |
| 170 | CCATTTAATTAAATTATA | 193655034 | 193655052 |
| 171 | CCCATTTAATTAAATTAT | 193655035 | 193655053 |
| 172 | ACCCATTTAATTAAATTA | 193655036 | 193655054 |
| 173 | TACCCATTTAATTAAATT | 193655037 | 193655055 |
| 174 | TTACCCATTTAATTAAAT | 193655038 | 193655056 |
| 175 | CTTACCCATTTAATTAAA | 193655039 | 193655057 |
| 176 | TCTTACCCATTTAATTAA | 193655040 | 193655058 |
| 177 | GATAGAGGCTGTGATGG | 193655104 | 193655122 |
| 178 | GGCTGTGAAACTGATGGA | 89481662 | 89481679 |
| 179 | GGCTGTGAAACTGATGGAGA | 89481660 | 89481679 |
| 180 | GCTATGAAACTGATGG | 193628545 | 193628560 |
| 181 | TATGAAACTGATGG | 193628545 | 193628558 |
| 182 | GCTATGAAACTGAT | 193628547 | 193628560 |

TABLE 5-continued

Exemplary OPA1 ASO sequences

| SEQ ID NO.: | Sequence (5'-3') | Coordinates GRCh38/hg38: chr3 Oligo Start | Oligo End |
|---|---|---|---|
| 183 | GCTGTGAAACTGATGGAGAA | 89481659 | 89481678 |
| 184 | GGGCTGTGAAACTGATGGAG | 89481661 | 89481680 |
| 185 | TGTGAAACTGATGGAGAA | 89481659 | 89481676 |
| 186 | CTGTGAAACTGATGGAGA | 89481660 | 89481677 |
| 187 | GCTGTGAAACTGATGGAG | 89481661 | 89481678 |
| 188 | GGGCTGTGAAACTGATGG | 89481663 | 89481680 |
| 189 | TGAAACTGATGGAGAA | 89481659 | 89481674 |
| 190 | GTGAAACTGATGGAGA | 89481660 | 89481675 |
| 191 | TGTGAAACTGATGGAG | 89481661 | 89481676 |
| 192 | CTGTGAAACTGATGGA | 89481662 | 89481677 |
| 193 | GCTGTGAAACTGATGG | 89481663 | 89481678 |
| 194 | GGCTGTGAAACTGATG | 89481664 | 89481679 |
| 195 | GGGCTGTGAAACTGAT | 89481665 | 89481680 |
| 196 | CGGTCCAGGAATGAC | 193593285 | 193593303 |
| 197 | CCGGTCCAGGAATGA | 193593286 | 193593304 |
| 198 | CCCGGTCCAGGAATG | 193593287 | 193593305 |
| 199 | TCCCGGTCCAGGAAT | 193593288 | 193593306 |
| 200 | CTCCCGGTCCAGGAA | 193593289 | 193593307 |
| 201 | GCTCCCGGTCCAGGA | 193593290 | 193593308 |
| 202 | GGCTCCCGGTCCAGG | 193593291 | 193593309 |
| 203 | CGGGAGCCCCCGTGT | 193593318 | 193593336 |
| 204 | GCGGGAGCCCCCGTG | 193593319 | 193593337 |
| 205 | CGCGGGAGCCCCCGT | 193593320 | 193593338 |
| 206 | ACGCGGGAGCCCCCG | 193593321 | 193593339 |
| 207 | CACGCGGGAGCCCCC | 193593322 | 193593340 |
| 208 | CCACGCGGGAGCCCC | 193593323 | 193593341 |
| 209 | GCCACGCGGGAGCCC | 193593324 | 193593342 |
| 210 | GGCCACGCGGGAGCC | 193593325 | 193593343 |
| 211 | CGGCCACGCGGGAGC | 193593326 | 193593344 |
| 212 | ACGGCCACGCGGGAG | 193593327 | 193593345 |
| 213 | GACGGCCACGCGGGA | 193593328 | 193593346 |
| 214 | AGACGGCCACGCGGG | 193593329 | 193593347 |
| 215 | GCTAGGGAGGGATGGTTA | 193625988 | 193626006 |
| 216 | TGTAAGCTAGGGAGGGAT | 193625993 | 193626011 |
| 217 | ACAGATGTAAGCTAGGGA | 193625998 | 193626016 |
| 218 | AAGGAACAGATGTAAGCT | 193626003 | 193626021 |

TABLE 5-continued

Exemplary OPA1 ASO sequences

| SEQ ID NO.: | Sequence (5'-3') | Coordinates GRCh38/hg38: chr3 Oligo Start | Oligo End |
|---|---|---|---|
| 219 | CAACAAAGGAACAGATGT | 193626008 | 193626026 |
| 220 | GGGTGCAACAAAGGAACA | 193626013 | 193626031 |
| 221 | ACCAAGGGTGCAACAAAG | 193626018 | 193626036 |
| 222 | GTTAAACCAAGGGTGCAA | 193626023 | 193626041 |
| 223 | ATAATGTTAAACCAAGGG | 193626028 | 193626046 |
| 224 | GGAGAATAATGTTAAACC | 193626033 | 193626051 |
| 225 | GGGGAGGAGAATAATGTT | 193626038 | 193626056 |
| 226 | AAATTGGGGAGGAGAATA | 193626043 | 193626061 |
| 227 | AGAGGAAATTGGGGAGGA | 193626048 | 193626066 |
| 228 | GGAGAAGAGGAAATTGGG | 193626053 | 193626071 |
| 229 | AATGAGGAGAAGAGGAAA | 193626058 | 193626076 |
| 230 | TTCACAATGAGGAGAAGA | 193626063 | 193626081 |
| 231 | ACGAGTTCACAATGAGGA | 193626068 | 193626086 |
| 232 | CTGCCACGAGTTCACAAT | 193626073 | 193626091 |
| 233 | AGACCCTGCCACGAGTTC | 193626078 | 193626096 |
| 234 | CAAGCAGACCCTGCCACG | 193626083 | 193626101 |
| 235 | CTCACCAAGCAGACCCTG | 193626088 | 193626106 |
| 236 | GAGCTCACCAAGCAGACC | 193626091 | 193626109 |
| 237 | AGAATGAGCTCACCAAGC | 193626096 | 193626114 |
| 238 | GTAAGAGAATGAGCTCAC | 193626101 | 193626119 |
| 239 | TTGTTGTAAGAGAATGAG | 193626106 | 193626124 |
| 240 | ATTTGTTGTTGTAAGAGA | 193626111 | 193626129 |
| 241 | CTTGAATTTGTTGTTGTA | 193626116 | 193626134 |
| 242 | ATGCTCTTGAATTTGTTG | 193626121 | 193626139 |
| 243 | TCTTCATGCTCTTGAATT | 193626126 | 193626144 |
| 244 | CTTCCTCTTCATGCTCTT | 193626131 | 193626149 |
| 245 | GCGCGCTTCCTCTTCATG | 193626136 | 193626154 |
| 246 | GCTCTGCGCGCTTCCTCT | 193626141 | 193626159 |
| 247 | GGCCAGCGGCTCTGCGCG | 193626149 | 193626167 |
| 248 | ATATTGGCCAGCGGCTCT | 193626154 | 193626172 |
| 249 | GTGCTATATTGGCCAGCG | 193626159 | 193626177 |
| 250 | AGCTCGTGCTATATTGGC | 193626164 | 193626182 |
| 251 | GGCATAGCTCGTGCTATA | 193626169 | 193626187 |
| 252 | TGTTGGGCATAGCTCGTG | 193626174 | 193626192 |
| 253 | GCTTCTGTTGGGCATAGC | 193626179 | 193626197 |
| 254 | CTTGCGCTTCTGTTGGGC | 193626184 | 193626202 |
| 255 | CACCTTGCGCTTCTGTTG | 193626187 | 193626205 |

TABLE 5-continued

| Exemplary OPA1 ASO sequences | | | |
|---|---|---|---|
| SEQ | | Coordinates GRCh38/hg38: chr3 | |
| ID NO.: | Sequence (5'-3') | Oligo Start | Oligo End |
| 256 | TCCATCACCTTGCGCTTC | 193626192 | 193626210 |
| 257 | AACCATCCATCACCTTGC | 193626197 | 193626215 |
| 258 | CCTTAAACCATCCATCAC | 193626202 | 193626220 |
| 259 | AGCCCCCTTAAACCATCC | 193626207 | 193626225 |
| 260 | TCGGTAGCCCCCTTAAAC | 193626212 | 193626230 |
| 261 | ATGTATCGGTAGCCCCCT | 193626217 | 193626235 |
| 262 | TGTGAATGTATCGGTAGC | 193626222 | 193626240 |
| 263 | ATTAGTGTGAATGTATCG | 193626227 | 193626245 |
| 264 | GGCTGATTAGTGTGAATG | 193626232 | 193626250 |
| 265 | GAAATGGCTGATTAGTGT | 193626237 | 193626255 |
| 266 | TGGCAGAAATGGCTGATT | 193626242 | 193626260 |
| 267 | GATCTTGGCAGAAATGGC | 193626247 | 193626265 |
| 268 | GACATGATCTTGGCAGAA | 193626252 | 193626270 |
| 269 | GAGGTGACATGATCTTGG | 193626257 | 193626275 |
| 270 | AGATTGAGGTGACATGAT | 193626262 | 193626280 |
| 271 | TGAACAGATTGAGGTGAC | 193626267 | 193626285 |
| 272 | GTCCATGAACAGATTGAG | 193626272 | 193626290 |
| 273 | TTGGAGTCCATGAACAGA | 193626277 | 193626295 |
| 274 | TGTATTTGGAGTCCATGA | 193626282 | 193626300 |
| 275 | TTTCTTGTATTTGGAGTC | 193626287 | 193626305 |

TABLE 6

| Exemplary OPAI ASO sequences | | | | |
|---|---|---|---|---|
| SEQ | | | Coordinates: GRCh38/hg38: chr3 | |
| ID NO | Region | Sequence (5'-3') | Oligo Start | Oligo End |
| 215 | OPA1-IVS6-86 | GCTAGGGAGGGATGGTTA | 193625988 | 193626006 |
| 216 | OPA1-IVS6-81 | TGTAAGCTAGGGAGGGAT | 193625993 | 193626011 |
| 217 | OPA1-IVS6-76 | ACAGATGTAAGCTAGGGA | 193625998 | 193626016 |
| 218 | OPA1-IVS6-71 | AAGGAACAGATGTAAGCT | 193626003 | 193626021 |
| 227 | OPA1-IVS6-26 | AGAGGAAATTGGGGAGGA | 193626048 | 193626066 |
| 228 | OPA1-IVS6-21 | GGAGAAGAGGAAATTGGG | 193626053 | 193626071 |
| 229 | OPA1-IVS6-16 | AATGAGGAGAAGAGGAAA | 193626058 | 193626076 |
| 230 | OPA1-IVS6-11 | TTCACAATGAGGAGAAGA | 193626063 | 193626081 |
| 231 | OPA1-IVS6-6 | ACGAGTTCACAATGAGGA | 193626068 | 193626086 |
| 232 | OPA1-IVS6-1 | CTGCCACGAGTTCACAAT | 193626073 | 193626091 |

TABLE 6-continued

| Exemplary OPAI ASO sequences | | | | |
|---|---|---|---|---|
| SEQ | | | Coordinates: GRCh38/hg38: chr3 | |
| ID NO | Region | Sequence (5'-3') | Oligo Start | Oligo End |
| 233 | OPA1-IVS6-EX7 + 5 | AGACCCTGCCACGAGTTC | 193626078 | 193626096 |
| 234 | OPA1-IVS6-EX7 + 10 | CAAGCAGACCCTGCCACG | 193626083 | 193626101 |
| 235 | OPA1-IVS6-EX7 + 15 | CTCACCAAGCAGACCCTG | 193626088 | 193626106 |
| 236 | OPA1-EX7 + 1 | GAGCTCACCAAGCAGACC | 193626091 | 193626109 |
| 237 | OPA1-EX7 + 6 | AGAATGAGCTCACCAAGC | 193626096 | 193626114 |
| 238 | OPA1-EX7 + 11 | GTAAGAGAATGAGCTCAC | 193626101 | 193626119 |
| 239 | OPA1-EX7 + 16 | TTGTTGTAAGAGAATGAG | 193626106 | 193626124 |
| 240 | OPA1-EX7 + 21 | ATTTGTTGTTGTAAGAGA | 193626111 | 193626129 |
| 241 | OPA1-EX7 + 26 | CTTGAATTTGTTGTTGTA | 193626116 | 193626134 |
| 242 | OPA1-EX7 + 31 | ATGCTCTTGAATTTGTTG | 193626121 | 193626139 |
| 250 | OPA1-EX7 − 21 | AGCTCGTGCTATATTGGC | 193626164 | 193626182 |
| 267 | OPA1-IVS7 + 46 | GATCTTGGCAGAAATGGC | 193626247 | 193626265 |

TABLE 7

| Exemplary OPA1 ASO sequences | | | | |
|---|---|---|---|---|
| | | | Coordinates: GRCh38/hg38: chr3 | |
| SEQ ID NO | Region | Sequence (5'-3') | Oligo Start | Oligo End |
| 280 | OPA1-EX7 + 27 | TCTTGAATTTGTTGTTGT | 193626117 | 193626135 |
| 281 | OPA1-EX7 + 28 | CTCTTGAATTTGTTGTTG | 193626118 | 193626136 |
| 282 | OPA1-EX7 + 29 | GCTCTTGAATTTGTTGTT | 193626119 | 193626137 |
| 283 | OPA1-EX7 + 30 | TGCTCTTGAATTTGTTGT | 193626120 | 193626138 |
| 284 | OPA1-EX7 + 32 | CATGCTCTTGAATTTGTT | 193626122 | 193626140 |
| 285 | OPA1-EX7 + 33 | TCATGCTCTTGAATTTGT | 193626123 | 193626141 |
| 286 | OPA1-EX7 + 34 | TTCATGCTCTTGAATTTG | 193626124 | 193626142 |
| 287 | OPA1-EX7 + 35 | CTTCATGCTCTTGAATTT | 193626125 | 193626143 |
| 288 | OPA1-EX7 + 26 | TGAATTTGTTGTTGTA | 193626116 | 193626132 |
| 289 | OPA1-EX7 + 27 | TTGAATTTGTTGTTGT | 193626117 | 193626133 |
| 290 | OPA1-EX7 + 28 | CTTGAATTTGTTGTTG | 193626118 | 193626134 |
| 291 | OPA1-EX7 + 29 | TCTTGAATTTGTTGTT | 193626119 | 193626135 |
| 292 | OPA1-EX7 + 30 | CTCTTGAATTTGTTGT | 193626120 | 193626136 |
| 293 | OPA1-EX7 + 31 | GCTCTTGAATTTGTTG | 193626121 | 193626137 |
| 294 | OPA1-EX7 + 32 | TGCTCTTGAATTTGTT | 193626122 | 193626138 |
| 295 | OPA1-EX7 + 33 | ATGCTCTTGAATTTGT | 193626123 | 193626139 |
| 296 | OPA1-EX7 + 34 | CATGCTCTTGAATTTG | 193626124 | 193626140 |
| 297 | OPA1-EX7 + 35 | TCATGCTCTTGAATTT | 193626125 | 193626141 |

TABLE 7-continued

| Exemplary OPA1 ASO sequences | | | | |
|---|---|---|---|---|
| | | | Coordinates: GRCh38/hg38: chr3 | |
| SEQ ID NO | Region | Sequence (5'-3') | Oligo Start | Oligo End |
| 298 | OPA1-EX7 + 36 | TTCATGCTCTTGAATT | 193626126 | 193626142 |
| 299 | OPA1-EX7 + 37 | CTTCATGCTCTTGAAT | 193626127 | 193626143 |

Example 19: ASO-14 Mediates ATP Upregulation in OPA1 Haploinsufficient HEK293 Cell Line The ATP levels generated through mitochondrial oxidative phosphorylation and glycolytic pathway were measured in HEK293 cell lysates using a commercially available kit (Cat #ab83355, Abcam; USA) according to the manufacturer's instructions. Briefly, about $3\times10^5$ OPA1+/+ (wildtype) and OPA1+/−HEK293 cells were plated in a T-25 flask and treated with 10 UM ASO-14. For the ATP test, 96-hrs after treatment, cells were harvested, and two aliquots of cell suspension were prepared. One aliquot was processed for deproteinizing using commercially available kit (Cat #ab204708, Abcam; USA) to remove residual protein for executing ATP fluorescence assay to measure total ATP level. The second aliquot was used for BCA assay (Cat #23225, Thermo Fisher; USA) to measure total protein level. ATP level was then calculated by normalizing the measured total ATP level to the measured total protein level.

Figure 24B:
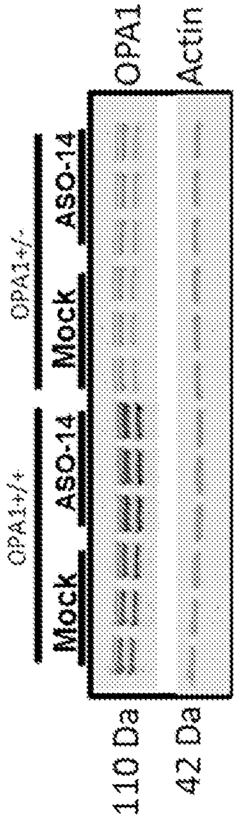
FIGS. 24B-24C demonstrate the OPA1 protein was increased by ASO-14 in OPA1+/+HEK293 cells.
Figure 24C:
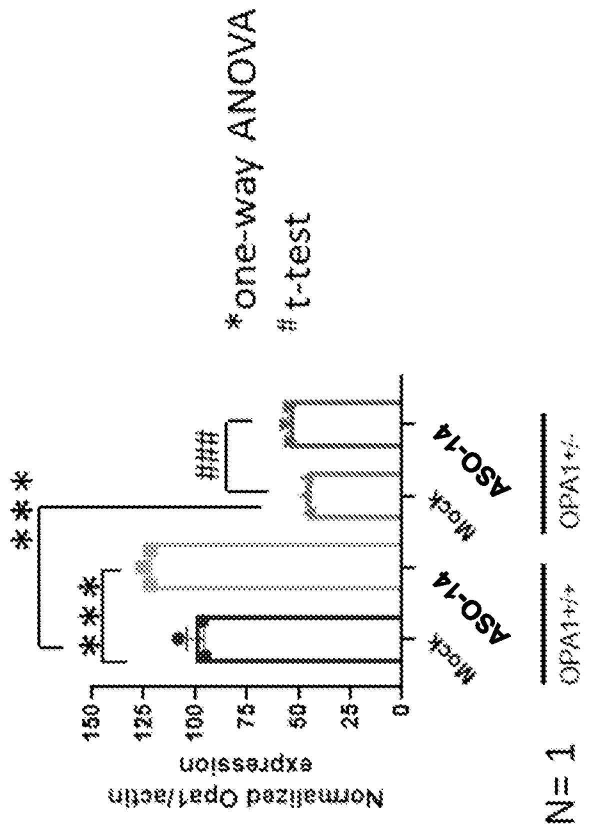
Figure 24A:
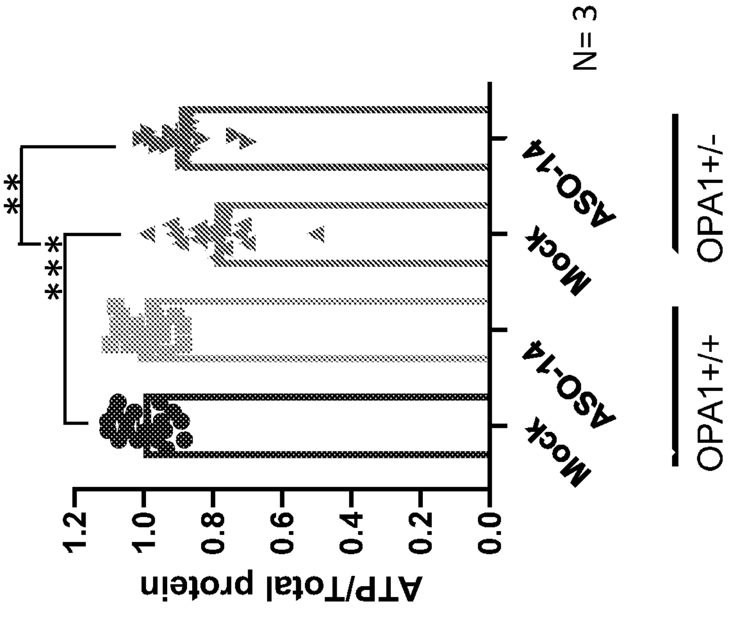
FIG. 24A is a histogram that demonstrates ATP level was reduced in mock-treated OPA1+/−HEK293 cells as compared to OPA1+/+HEK293 cells, and ASO-14 treatment of OPA1+/−HEK293 cells increased the ATP level in the cells.

FIG. 24A summarizes the ATP level measured under each condition. In the mock group, untreated OPA1+/−HEK293 cells were found to have 0.79±0.02 ATP level as compared to untreated OPA1+/+HEK293 cells. There was about 20% ATP deficit in OPA1+/−HEK293 cells. In comparison, OPA1+/−HEK293 cells treated with ASO-14 had ATP levels 0.88±0.01, significantly higher than the mock-treated OPA1+/−HEK293 cells, suggesting that treatment of ASO-14 reduced the deficit by about 50%. Data were collected from three independent experiments. (Statistics: Ordinary one-way ANOVA; *P<0.0001; P<0.0080).

FIGS. 24B-24C demonstrate the OPA1 protein under each condition. 96 hours after treatment with ASO-14 or no treatment (mock), cells were lysed with RIPA buffer and immunoblot blot was probed with antibodies targeting OPA1 and β-actin. The data show that treatment of ASO-14 upregulated about 18% OPA1 protein in OPA1+/− cells. FIG. 24B shows the immunoblot gel images. Multiple bands on the immunoblot image represent various isoforms of OPA1. FIG. 24C summarizes quantification of the immunoblot results. Untreated (mock) OPA1+/−HEK293 cells were found to have 46=0.5% OPA1 protein level as compared to untreated (mock) OPA1+/+HEK293 cells. OPA1+/+ cells treated with ASO-14 had OPA1 levels 123.2±1.3 of untreated OPA1+/+ cells. OPA1+/− cells treated with ASO-14 had OPA1 levels 54.54±0.6% of untreated OPA1+/+ cells. Statistics performed with corresponding mock. ***P<0.0001, by Ordinary one-Way ANOVA and ###P<0.0001, by Welch's t test. Data represent average of three technical replicates.

Example 20: Exemplary Antisense Oligomers Restore OPA1 Expression in Cells with OPA1 Mutations from Diagnosed Patients This example examines OPA1 mRNA and protein levels in cells with mutations in OPA1 gene from patients diagnosed with Autosomal dominant optic atrophy (ADOA), as well as effects of exemplary antisense oligomer ASO-14 on OPA1 mRNA and protein levels, and mitochondrial bioenergetics in the patient cells.

Figure 25A:
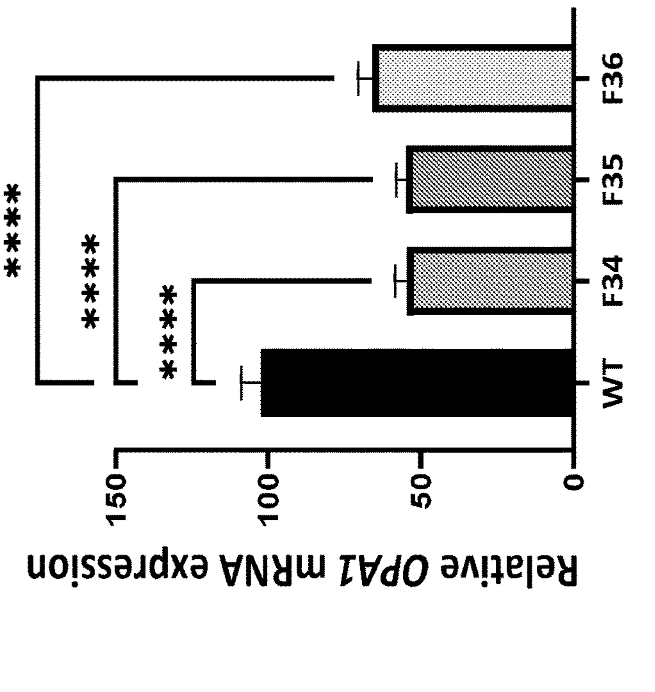
FIGS. 25A-25B show histograms that demonstrate mRNA (FIG. 25A) and protein expression (FIG. 25B) of OPA1 gene were reduced in fibroblast cells from diagnosed patients that have haploinsufficient mutation in OPA1 gene as compared to wildtype (WT) fibroblast cells.
Figure 25B:
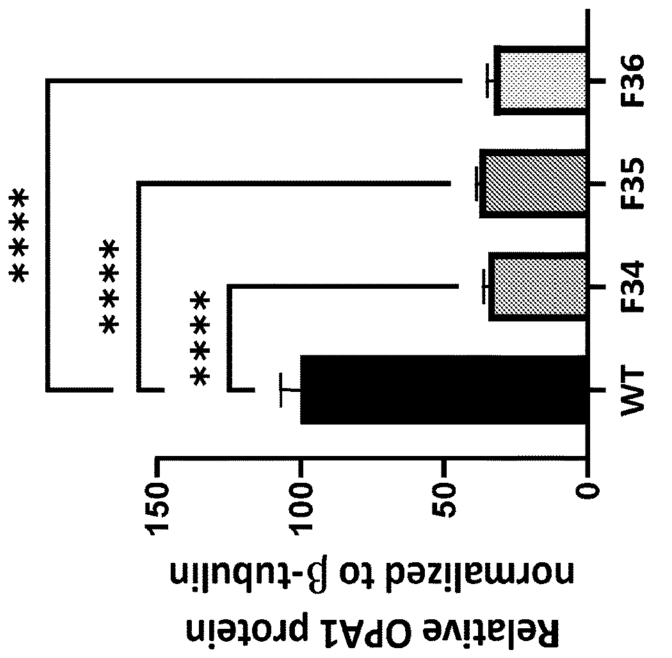
Figure 25C:
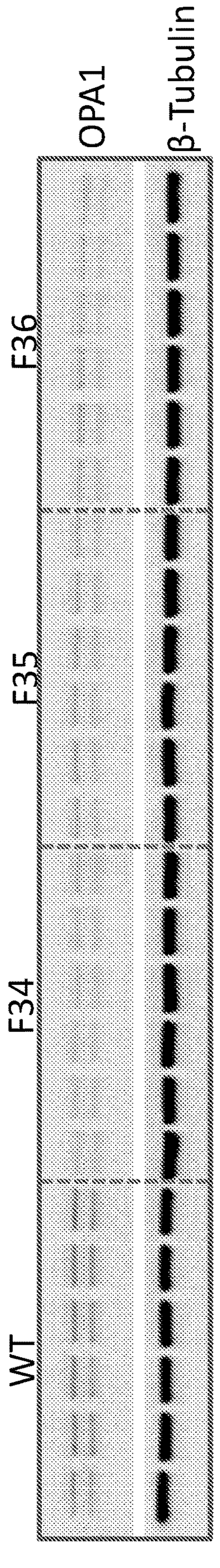
FIG. 25C shows a representative immunoblot image of OPA1 protein expression level in diseased fibroblast cells.

FIGS. 25A-25C summarize mRNA and protein expression of OPA1 gene in fibroblast cells from diagnosed patients that have haploinsufficient mutation in OPA1 gene: F34 (OPA1 canonical splice mutation at c. 1608+1delGTGAGG); F35 (OPA1 frameshift mutation at c.2873_2876del); F36 (OPA1 frameshift mutation at c.635_636delAA). mRNA expression level of OPA1 gene in patient cells is about 50% to 60% of the mRNA level in wildtype (WT) cells (FIG. 25A); OPA1 protein level in patient cells is about 30% to about 40% of the protein level in WT cells (FIG. 25B). Histograms in FIGS. 25A-25B show mean±SEM of 3 independent experiments; one-way ANOVA compared to WT group (**P<0.0001). FIG. 25**C shows a representative immunoblot image of OPA protein expression level in diseased fibroblast cells.

Figure 26B:
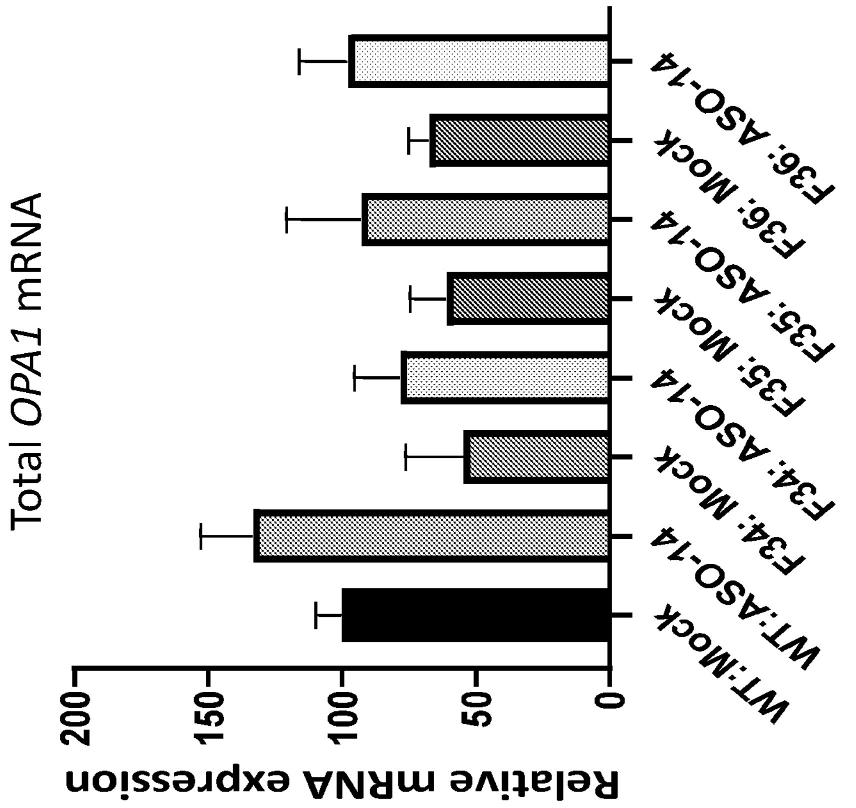
FIGS. 26A, 26B, and 26D show histograms that demonstrate exemplary antisense oligomer, ASO-14, decreased OPA1 NMD exon inclusion (FIG. 26A), increased OPA1 total mRNA level (FIG. 26B), and protein level (FIG. 26D) in wildtype (WT) fibroblast cells and fibroblast cells from diagnosed patients that have haploinsufficient mutation in OPA1 gene.
Figure 26A:
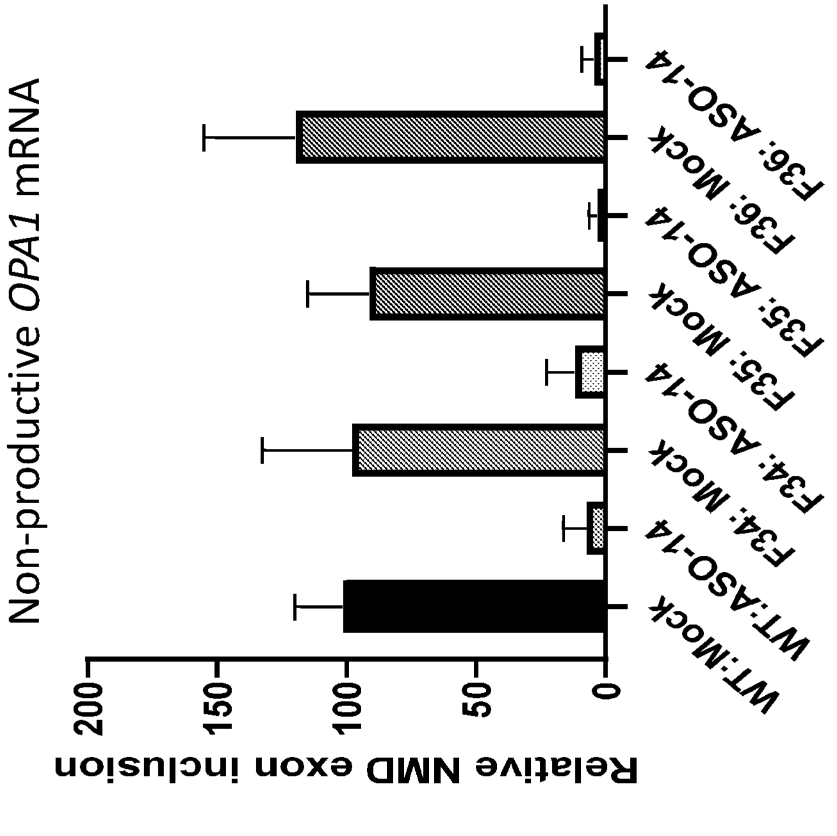
Figure 26C:
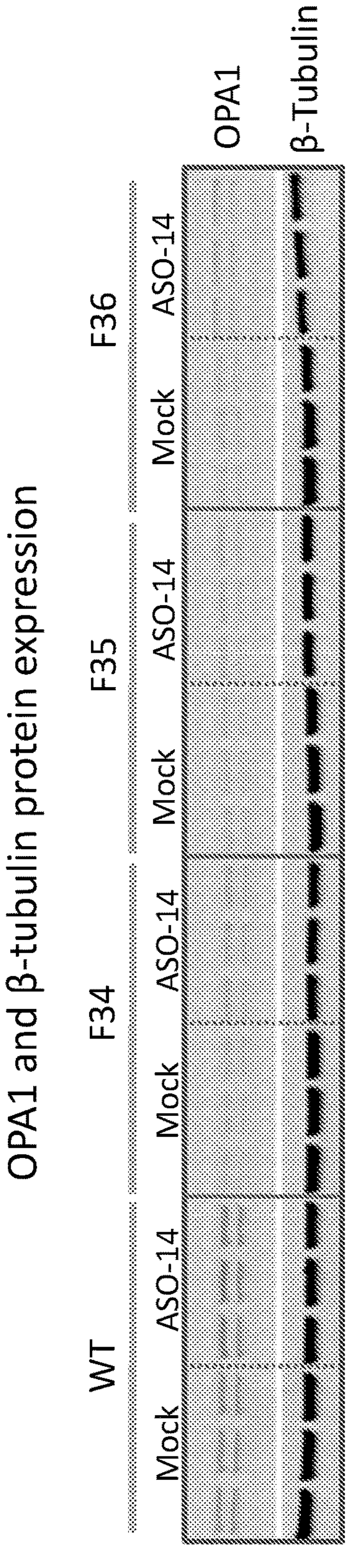
FIG. 26C shows representative immunoblot images of OPA1 protein and loading control β-Tubulin under all types of conditions.
Figure 26D:
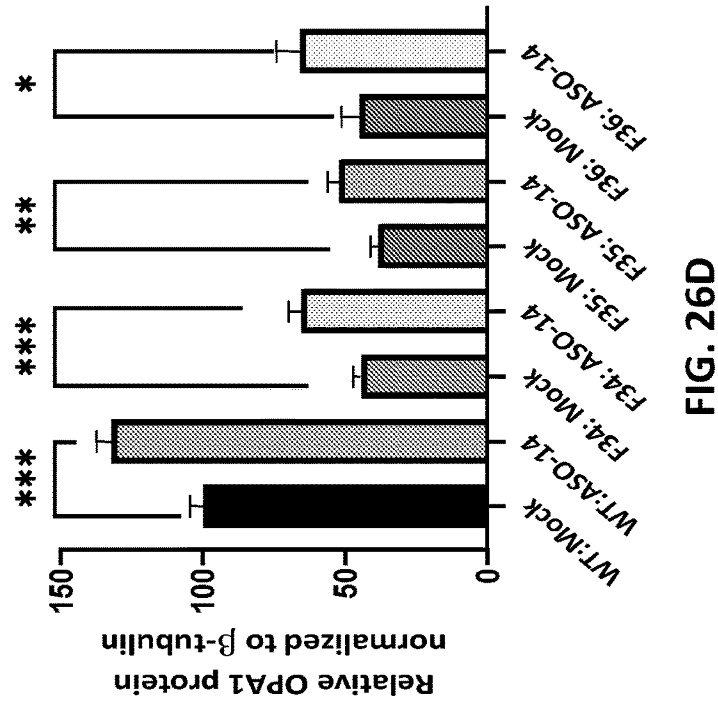

FIGS. 26A-26D demonstrate the effects of exemplary antisense oligomer, ASO-14, on OPA1 NMD exon inclusion, mRNA level, and protein level in wildtype (WT) fibroblast cells and fibroblast cells from diagnosed patients that have haploinsufficient mutation in OPA1 gene. The fibroblast cells were transfected with ASO-14 (40 nM), and RNA was isolated 24 hrs after transfection and analyzed. For non-productive OPA1 mRNA measurement, cells were treated with cycloheximide (50 μg/mL) for 3 hrs. prior to RNA isolation. Immunoblot was performed 72 hrs. post transfection with antibodies targeting OPA1 and β-tubulin. As shown in FIG. 26A, ASO-14 significantly decreased inclusion of NMD exon (exon 7x), measured by level of non-productive OPA1 mRNA, in WT cells and all diseased cells to lower than 20% level of the normalized level in WT cells. There was a trend of increase in total OPA1 mRNA level in all types of cells by the treatment of ASO-14 (FIG. 26B). Histograms in FIGS. 26A-26B show mean±SEM of 2-3 independent experiments; one-way ANOVA vs. Mock for respective cell line (*P<0.05; *P<0.001; P<0.0001). Correspondingly, OPA1 protein level was significantly increased by the treatment of ASO-14 in all types of cells (FIGS. 26C-26D). FIG. 26C shows representative immunoblot images of OPA1 protein and loading control β-Tubulin under all types of conditions; FIG. 26**D shows the statistical summary of the OPA1 protein levels, the histograms show mean±SEM of 3 independent experiments; unpaired t-test vs. Mock for respective cell line (*P<0.05, P<0.01, *<0.001).

Figure 27C:
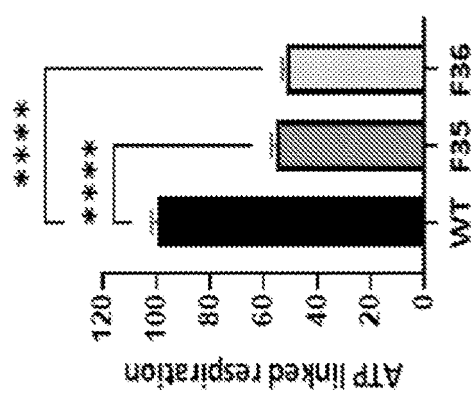
FIGS. 27A-27E demonstrate that patient fibroblast cells (cell lines F35 and F36) show deficiencies in mitochondrial bioenergetics.
Figure 27E:
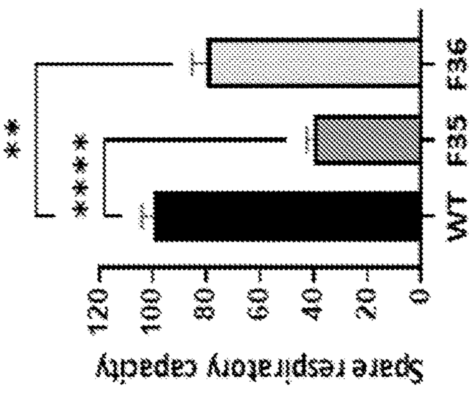
Figure 27B:
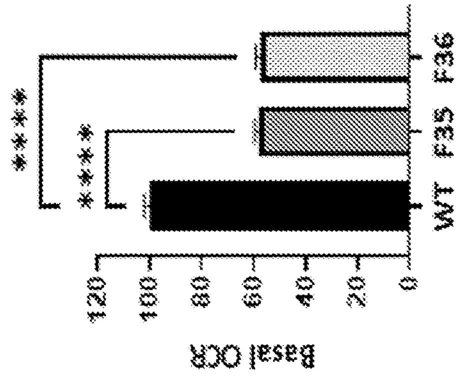
Figure 27D:
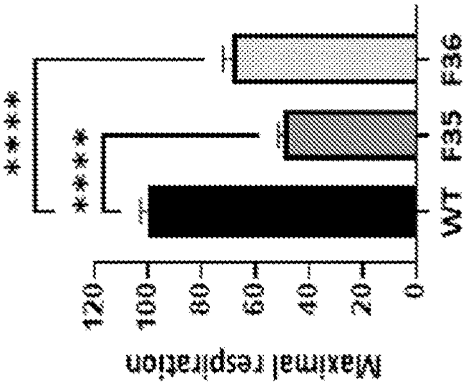
Figure 27A:
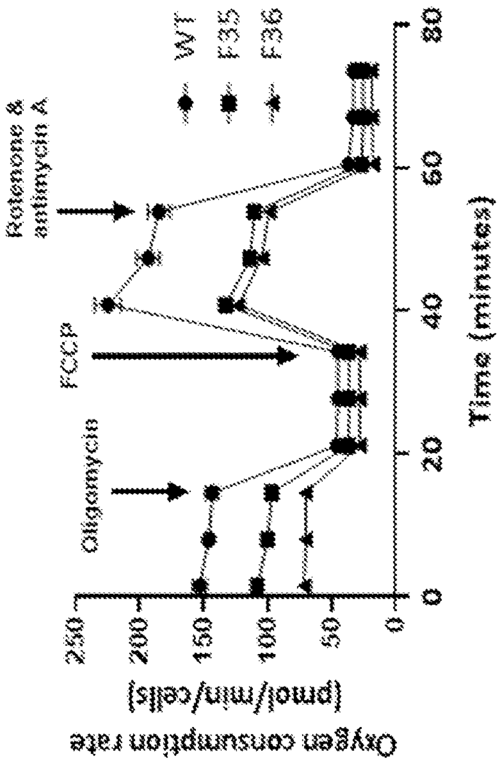

FIGS. 27A-27E demonstrate that patient fibroblast cells (cell lines F35 and F36) show deficiencies in mitochondrial bioenergetics. FIG. 27A shows representative time courses of the oxygen consumption rate of WT cells, F35 cells, and F36 cells at baseline level and when challenged sequentially with oligomycin, FCCP, rotenone and antimycin A. Patient fibroblast cells, F35 and F36 cells, were found to have reduced basal oxygen consumption rate (FIG. 27B), ATP linked respiration (FIG. 27C), maximal respiration (FIG. 27D), and spare respiratory capacity (FIG. 27E), as compared to WT fibroblast cells. Units in FIGS. 27B-27E are pmol/min/cells, data normalized to wild-type (WT). Histograms in FIGS. 27B-27E show mean±SEM of >18 individual measurements from 2 independent experiments; one-way ANOVA vs. WT (P<0.01; **P<0.0001).

Figure 28A:
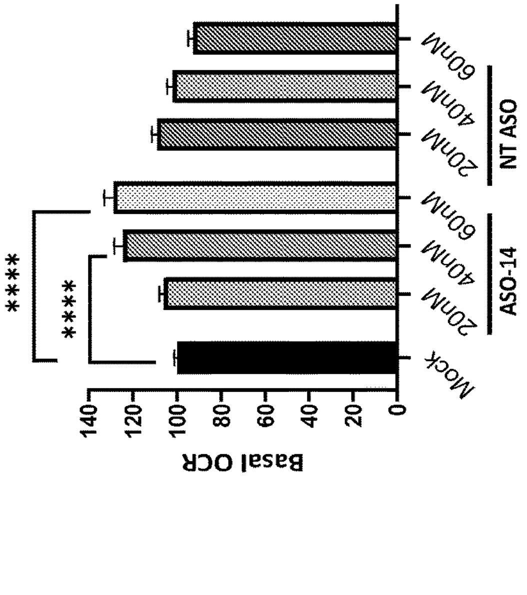
FIGS. 28A-28D show histograms demonstrating that treatment of ASO-14 at 20 nM, 40 nM, and 60 nM increased basal oxygen consumption rate (FIG. 28A), ATP linked respiration (FIG. 28B), maximal respiration (FIG. 28C), and spare respiratory capacity (FIG. 28D) of F35 patient cells in a dose-dependent manner.
Figure 28B:
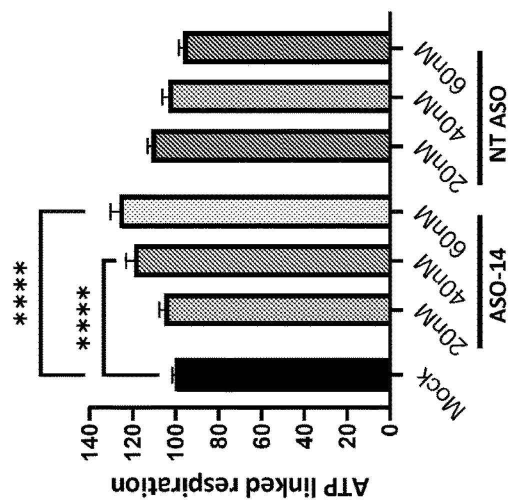
Figure 28C:
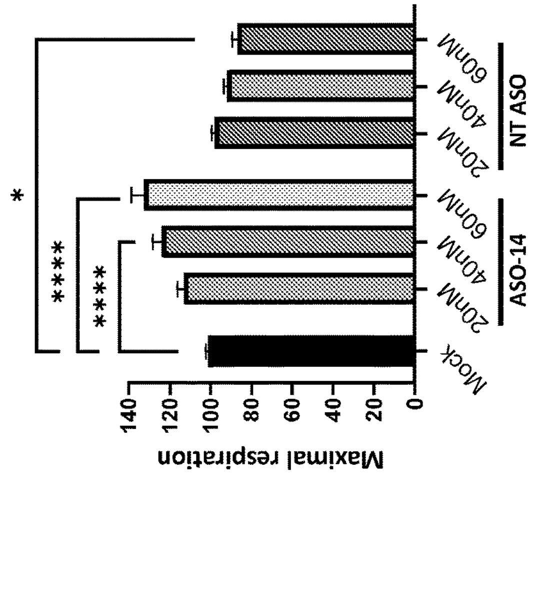
Figure 28D:
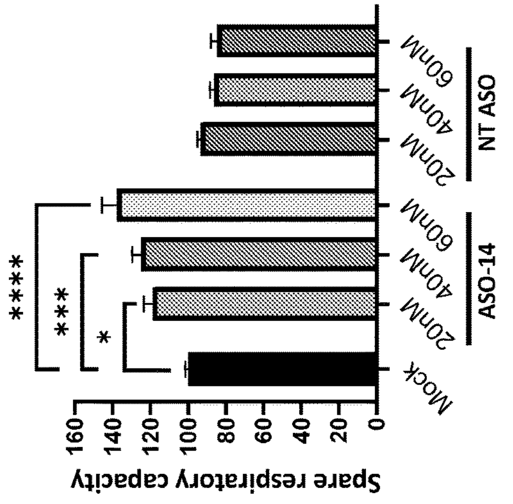
Figures 29A, 29B, 29C, 29D:
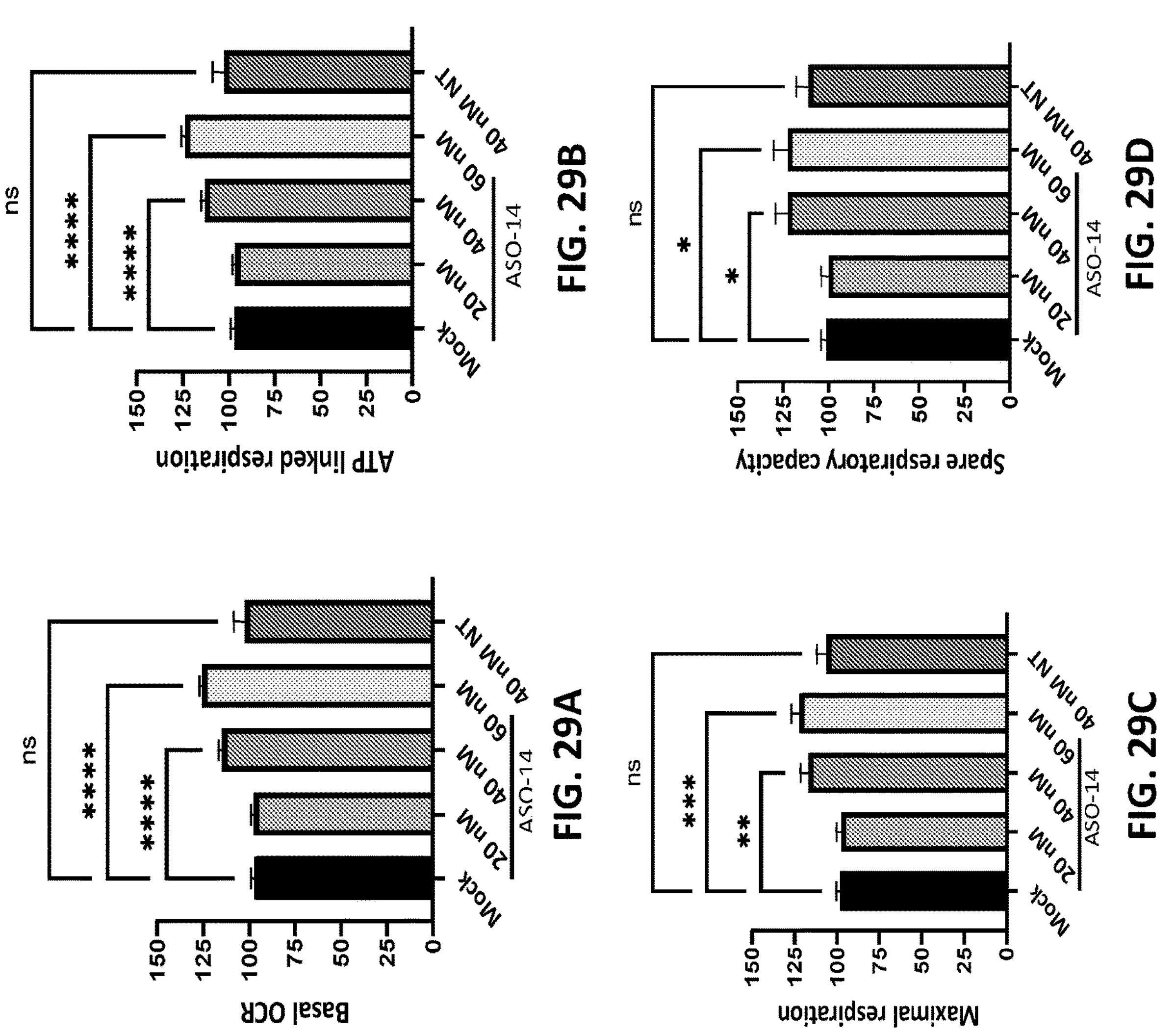
FIGS. 29A-29D show histograms demonstrating that treatment of ASO-14 at 20 nM, 40 nM, and 60 nM increased basal oxygen consumption rate (FIG. 29A), ATP linked respiration (FIG. 29B), maximal respiration (FIG. 29C), and spare respiratory capacity (FIG. 29D) of F36 patient cells in a dose-dependent manner.

FIGS. 28A-28D demonstrate that ASO-14 increased mitochondrial energetics in F35 patient cell line. As shown in the figures, treatment with 40 nM or 60 nM ASO-14 increased basal oxygen consumption rate (FIG. 28A), ATP linked respiration (FIG. 28B), maximal respiration (FIG. 28C), and spare respiratory capacity (FIG. 28D) of F35 patient cells in a dose-dependent manner. Treatment with 20 nM ASO-14 also significantly increased spare respiratory capacity (FIG. 28D). In contrast, non-targeting ASO (NT ASO, targeting an unrelated gene) did not significantly alter the parameters at any of the tested concentrations. Units in the figures are pmol/min/cells; the Oxygen Consumption Rates (OCR) are normalized to total cell count and plotted to Mock (No ASO). The histograms show mean±SEM of >20 individual measurements from at least 3 independent experiments; one-way ANOVA vs. Mock (*P<0.05; *P<0.001; **P<0.0001).

FIGS. 29A-29D demonstrate that ASO-14 increased mitochondrial energetics in F36 patient cell line. As shown in the figures, ASO-14 also increased basal oxygen consumption rate (FIG. 29A), ATP linked respiration (FIG. 29B), maximal respiration (FIG. 29C), and spare respiratory capacity (FIG. 29D) of F36 patient cells in a dose-dependent manner from 20 nM, 40 nM, to 60 nM. In contrast, non-targeting ASO did not significantly alter the parameters at 40 nM. Units in the figures are pmol/min/cells; the Oxygen Consumption Rates (OCR) are normalized to total cell count and plotted to Mock (No ASO). The histograms show mean±SEM of >20 individual measurements from 2-5 independent experiments; one-way ANOVA vs. Mock (*P<0.05; P<0.01; *P<0.001 ****P<0.0001).

The experiments in F35 and F36 cells suggest that the dose-dependent improvement in mitochondrial bioenergetics by ASO-14 is mutation-independent.

The foregoing preclinical data support the TANGO disease modifying approach in ADOA. As demonstrated by the data, the exemplary antisense oligomer, ASO-14, reduced non-productive exon inclusion, increased total OPA1 mRNA and protein expression in all three patient fibroblast cell lines; increased ASO-14 dose increased mitochondrial respiration in two fibroblast cell lines. The data further suggest that the ASO mediated increase in OPA1 protein expression is disease modifying in ADOA in a mutation-independent manner.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the present disclosure may be employed in practicing the present disclosure. It is intended that the following claims define the scope of the present disclosure and that methods and structures within the scope of these claims and their equivalents be covered thereby.

What is claimed is:

1. A method of modulating expression of an OPA1 protein in a cell having a pre-mRNA, wherein the pre-mRNA is transcribed from an OPA1 gene, and wherein the pre-mRNA comprises a coding exon, the method comprising:

contacting an agent or a vector encoding the agent to the cell, whereby the agent promotes exclusion of the coding exon from the pre-mRNA in the cell, thereby increasing a level of a processed mRNA that is processed from the pre-mRNA in the cell; and that lacks the coding exon, wherein the agent comprises an antisense oligomer, and wherein the antisense oligomer comprises a sequence with at least 80% sequence identity to one of the sequences set forth in SEQ ID NOs: 227-242, 250, 280-283, 288, and 290-292.

2. The method of claim 1, wherein the agent:

(a) binds to a targeted portion of the pre-mRNA;

(b) modulates binding of a factor involved in splicing of the coding exon; or (c) a combination of (a) and (b).

3. The method of claim 1, wherein the exclusion of the coding exon from the pre-mRNA in the cell contacted with the agent or the vector is increased by at least about 1.1-fold as compared to a corresponding cell that is not contacted with the agent or the vector.

4. The method of claim 1, wherein a level of the OPA1 protein expressed from the processed mRNA in the cell contacted with the agent or the vector is increased by at least about 1.1-fold as compared to a corresponding cell that is not contacted with the agent or the vector.

5. The method of claim 1, wherein the OPA1 protein expressed from the processed mRNA is a functional OPA1 protein.

6. The method of claim 1, wherein the antisense oligomer comprises the sequence set forth in any one of SEQ ID NOs: 227-242, 250, 280-283, 288, and 290-292.

7. The method of claim 1, wherein the method comprises contacting the agent to the cell, and wherein the antisense oligomer comprises a backbone modification, a modified sugar moiety, or a combination thereof.

8. The method of claim 1, wherein the method comprises contacting the agent to the cell, and wherein the antisense oligomer comprises a phosphorothioate linkage.

9. The method of claim 1, wherein the method comprises contacting the agent to the cell, and wherein the antisense oligomer comprises a 2'-O-methoxyethyl moiety.

10. The method of claim 1, wherein the antisense oligomer is from 16 to 50 nucleotides in length.

11. The method of claim 1, wherein the method comprises contacting the cell with the vector, and wherein the vector comprises a viral vector encoding the agent.

12. The method of claim 11, wherein the viral vector comprises an adenoviral vector, adeno-associated viral (AAV) vector, lentiviral vector, Herpes Simplex Virus (HSV) viral vector, or retroviral vector.

13. The method of claim 1, wherein the antisense oligomer comprises a sequence with at least 80% sequence identity to the sequence set forth in SEQ ID NO: 228.

14. The method of claim 1, wherein the antisense oligomer comprises a sequence with at least 80% sequence identity to the sequence set forth in SEQ ID NO: 234.

15. The method of claim 1, wherein the antisense oligomer comprises a sequence with at least 80% sequence identity to the sequence set forth in SEQ ID NO: 235.

16. The method of claim 1, wherein the antisense oligomer comprises a sequence with at least 80% sequence identity to the sequence set forth in SEQ ID NO: 236.

17. The method of claim 1, wherein the antisense oligomer comprises a sequence with at least 80% sequence identity to the sequence set forth in SEQ ID NO: 237.

18. The method of claim 1, wherein the antisense oligomer comprises a sequence with at least 80% sequence identity to the sequence set forth in SEQ ID NO: 238.

19. The method of claim 1, wherein the antisense oligomer comprises a sequence with at least 80% sequence identity to the sequence set forth in any one of SEQ ID NOs: 242, 280-283, 288, and 290-292.

20. The method of claim 1, wherein the antisense oligomer comprises the sequence set forth in any one of SEQ ID NOs: 242, 280-283, 288, and 290-292.

* * * * *

SEQUENCE LISTING

```
<160> NUMBER OF SEQ ID NOS: 607

<210> SEQ ID NO 1
<211> LENGTH: 111668
<212> TYPE: DNA
<213> ORGANISM: Homo sapiens

<400> SEQUENCE: 1

ataaacaaac attataaaat aatgtggatt taatcattaa caaacaattt caagttcttg      60

cacagtttca caaaggttaa tgtgacccaa agcttcacct ttataaagac aactctcgaa     120

tctgtattgc aagccccatc tccctgtgga actccaaagc ttgatttcta actgccacct     180

gaataaccca ttcacacttc agcaccaatc atcattccaa agccagcatt atcatcccct     240

tgtaatcagc ttttctatat ttgtgactgt tactaataat gtcaattgac tttggcttca     300

accccattat cttttgattc ctcttcctag tttcttcatt tagcttttca ttgttttaaa     360

tactccgaag tatcctttca aagaatctct cacttcttcc cattaccagg ctttggttaa     420

gggccctcac acttgacttt ctcaacagcc ccctatccag tcttcctgac cctcagtttc     480

cctctttaca aattcatcct tttctgtttc tccaggatta tcttttttga gcccacttta     540

tgacactata gtctgcctct gtgggtagta actgttgcta cccattactt ggtcctcagc     600

ttgtactacc tcacattaat gtttaccttt tatgtatgtc tgtcttccta accaaaccat     660

ggttagttga gggtgggaac tgtggtttac tctttttaaa aaaatatatc ctcaggcctg     720

gcacggtggc tgatgcctgt aatcctagca ctttggaagg ttgaggcagg cagattactt     780

gaggtcagga gtttgaaacc agcctggcca aaatggtgaa accccgtctc tactaaaata     840
```

caaaaactta gccaggcatg gtggcatgca cctgtaatcc cagctactca ggagactgag 900
gcaggagaat cacttaaacc tgggaggtgg aggttacagt gagccgagat tgtgccactg 960
cgctccagcc tgggcgacaa agtgagactc tgtctcaaaa caaacaaaca aacaaacaaa 1020
aaccaaatat atatatatgt gtgtgtgtgt gtgtatataa tttgtgtgtg tatatatatg 1080
tatttatatc ctcgactagg gttcatagga agtgactgta aatgtttgtt aataaggatt 1140
ataacatgct tttctgaggg ctggggagag tttgataatg atgatggtgc aaacatgtat 1200
gacttcagct aattattggc ttctccagga aaccacaaag agtagtgtta aggaacttgg 1260
agatctccca agaagaactt tgcaaaagct tttatgtata aatttaaata taaaacttat 1320
gaaatcaatt ttaaacattt ccatttccat taacatctct cattaccttc ctttctgaaa 1380
atttctgatt cgttggataa ttctgaaaag ggtccctttt cctgctaagg taaatattta 1440
gagttttacc tggtgaattg ctcaattccc agctgaactg gaaaatttag tttaaagtag 1500
taaaattatt tcatgacttc tggatcagaa aaatattttt aacatgtttt tacaagtaat 1560
taatacacaa gttcagagta taaaagggtt tacaataaat gtaagcctcc ctcccactca 1620
tgacccacta acttcaagtc cttccttgac tctgcccttc actagggctt atcaactcaa 1680
atattttcgt gggttaggca tgtaacataa atgagtaatg caagtatgtc tgttgtataa 1740
tgtcatatta aattgtattc atataattta ttcatataat tttacttgcc tacttgcata 1800
cttgtgttct tttgccaaaa aaaaaaaaaa aaaaagctct ttctcattgt tttggaaatg 1860
gctgaccctc tcagtccttc attttctctc acttttcata ttgtaatcat ccagcaggtt 1920
cttcctgctc actgcacaga caaaatcatt tcactgagac cagggcatcg cagtagaaaa 1980
agagtttaac tgattcaaga ccagcctatg caggagaact ggagttgtca ctcaaatcaa 2040
tcttcctgaa ggctctgagg ttagaggttt ttatggacaa tttagtgggc aaggggtagg 2100
gaatggatgc tgctgattgg ttggggatga aataatagga aaacattcct tgtgtgctga 2160
gtccacctct gggcggggcc acaggatcac ttgagtcatg agtcataagt ctcgatgggg 2220
tgagtctgaa atataccgca aaaaagcagt cttagattct atagtaatga tgttatctat 2280
aggagcaatt ggggaagtca taagatttgt gagttctggc cacattgatt cctgagcagt 2340
aagggactat agaaaccata cctacgtctt agcacagttc aggcccctct catgatcctg 2400
ttctcttggc ctttcttaca aaggtggttt ttggttcctg agcaacgagg gagttagctt 2460
taggaaggga ctattataat cctttctttc aagttaaact ataaactaca ttcctcccca 2520
aagttcattt ggcttaagtc caggaatgag caaggacagc ttggaggtca gaagcaagat 2580
ggagtcaact atgtcaggtt cctcttgtca taattttgcc aaggcagttt caatataagt 2640
agtggttgtt tttcctctta atttttacta agaaaagtag aagcacaagc ttcatgataa 2700
acagtaattg atgtgttcaa tttcagaaag atgaaggagt gtgaactacc ggagaggaca 2760
tgagtgcctg aaggataaaa ctactacttg gctcctggtt ccgagacatt ttttgtatat 2820
aagaattgaa ggttgatgtt gttaggcatc ctgatatttt tatgtgattt tttaaaatgt 2880
gaaatttgtt gatttttatt tggcaacaaa tgtagcattt ttttgcttgt ttgtttttga 2940
gacggagtct cgatctgtcg ctcaggctgg agtgcagtgg cacaatctca gctcactgca 3000
acctctgcct cctgggttca agcaattttt ctgcctcagc ctccgagtag ctggctaatt 3060
tttttatttt tagtagagac agggtttcac catattggcc aggctggtct caaactcctg 3120
acctcgtgat ctgccttcct cggcctccca aagtgctggg attacaggca taagccgcca 3180

-continued tgcccagccc aaatgtagtg ttatttttaa aacactgcat aggccaacac tgtctaaacc 3240
aaacaaaaca ggtctgtggg ctgaatttgg tccaatggtt gcagtttatt atacaacagt 3300
ttgccctttt ttcatggcaa cactatgtat ctatgggaga tcattcctta tcaggacata 3360
cagacctaaa gcataggttt tcatggctag tacggatgta atttatgtgt ctagttccta 3420
tacatggaca tttatactga ttccaatctt ttcccatttc atacagtgca gaaataaaca 3480
tcatcatgca tacatctttg catacatggg aatgattcca caggataaat gcctagaagt 3540
agaactgcaa aacaagggct tcataaaaca tatgataacc atatataaat ggtgatggtg 3600
gttagtttct cctttttta tggttaaagt cttttatccc taatttttct tttttgttgt 3660
tgttgttaaa gtctcttggt ttctcttatt ttattttcta aaataacaag gaagtaacga 3720
ttacaaagac actttttgta caaccctaca atcccaggaa gatctacagt ttgcacaggt 3780
tggtacagca aattgctctc tggacctgcc attgaaacag tcaccacaat aaataaagaa 3840
aattctaaga gtcctgcatt tgggaagttt actatcaatg gctaggtcta ctcttggtgg 3900
tattgtgagt gcatgggtcc agacttatga ttctgacaat taagggaaaa ggaattgtct 3960
ttatgctctg tgtatttgtg tatgtgtgtg gcatgggtgg ggggcgggta gtggggagga 4020
ggtgaaaggt ccctgaagta aagaggatgc acaggaccct tttattttag tccctaaaaa 4080
ttggcttcat aaccgttcac aggccacatc ccttttacgg gccctggttt ccttacaaaa 4140
cataaaaggt ttgtgttgga aggggaaagg agtatttaaa gtgatggagg agaggagctc 4200
aagatggctg agatctgggc ctgtccaaca ttgagaaatt tgggagggga gccatcaaag 4260
aagcctggga gcagcagttc cagggaaaaa ggagaatgtg atggccagag agccaaaaga 4320
aaaagtagtt gaaggagtgc tcagcactag gcatctgaac tgaatgctgt ggcaggctca 4380
ctggccacaa acaataggga gctggtggag gccttgacga ggaccatttc aacaaactgg 4440
tgggcttaaa atccggaaga aacagttgaa caaatcattt tgacgccttt tataaaccac 4500
acaagcttat tccaaacccg ttactggcct aactgattta agtccctttc ccatctgatc 4560
ctcagagatt ctaagggact tagcctatcc atgactcttc gtcctgcttc tcacctccca 4620
tgattgccct aacgatgtga aagtgctttc aaacaaagat gcccaagaaa gaaggtaggc 4680
aaatgtgcaa gcattagttt gtagtacgct attactgtat ttcaccttgc actctctagt 4740
ttccttcgtg ctccctcaat atccaactct taataaattc atggctcccg gtgagcattc 4800
atcaattctc attccacgcc tttagccctt cccgttcccg cccaactctc gctccctccc 4860
ctggccaaat ctctaacctg caaggctaat tccgaattcc aaatcggaag caagagggcg 4920
gggccccgtg agaggcgatg gattgctcca gtccgttccc gacgcactgt gcgcatgcgc 4980
tggtcctccg cggaccgttc gtgctgcccg cctagaaagg gtgaagtggt tgtttccgtg 5040
acggactgag tacgggtgcc tgtcaggctc ttgcggaagt ccatgcgcca ttgggagggc 5100
ctcggccgcg gctctgtgcc cttgctgctg agggccactt cctgggtcat tcctggaccg 5160
ggagccgggc tggggctcac acgggggctc ccgcgtggcc gtctcggcgc ctgcgtgacc 5220
tccccgccgg cgggatgtgg cgactacgtc gggccgctgt ggcctggtaa gtgcaggctc 5280
taatctggcc ccgttaattc tggggcctct tgagagtggg gctgtcttat ctctatctcc 5340
aaaaatgtgc aggtgactct caggccaggc cgacggcagt tggagaattc ccagatgttc 5400
ttgaggaccc agaatgacag gagccctggc tgggcttacg ttcggagccg gcttcaatac 5460
tggccctttt ctctggccct acccaacccg aaaattctgg acgcctctca atcttggccc 5520
gtctctattg tcctttgtc tctgcccttt acacccttgt gtcttcagtg ttctgtctgt 5580

-continued ctctggttgc ctcttttgcc ttttttctgt cctctccctg ccaggtttgg ctctgtccat 5640
gagtcacctc tctccacatt tctcctaact ctcggtgtct tctttttctt ccatttccac 5700
gccatgtgta cattgcatct tcaggtacct gggctcttct atcggggaaa ggggcgtccg 5760
tctctttccc tagcccgctg atagaagtca gaactagagc aatgacgcac acggtgtcag 5820
agacggtgat tcgagatgcc ctttcaatag cagctttttt ctgtgtttcg ggagggagac 5880
ttactttttg atgcaaggtc gtgaacgtgg caccaccttt ctaatctcaa tcattgttgc 5940
cctggggtgg tttaattcta aatagaaaat catagaaatc ttttcatttc tgtgcgttac 6000
tatatgcatt gtaatgagat taaattggat tttataggaa attttgttct agtatcatta 6060
gataccttca agcttagctc attgttgcag gcatttgata ggaagtaaga tgcatcaagc 6120
aaaattggaa aaacgtggtt ttcctgaatt aacttctaag cagttgtttt gaatttttttc 6180 cagacctttt taagtggtat agataattta tcgtgtttat aaggaatgga atgcattcgt 6240
tagtttgttt ttgttttgtt ttgagacgga gtcttgctct gtcgtccagg ctggagtgca 6300
gtagcgctat ctcggctcac tgcaacctcc gcctcccagg ttcaagcaat tctcctgtct 6360
ccgcctccgg agtagctgga attacaggca cgcgccagca cgcctagcta atttttgtat 6420
ttttagtaga gagggggttt caccattttg gccaggctgg tctcgaactc ctgacctcat 6480
gtgatccacc ctcctcgact tcccaaagtg ctgggattac aaccgtgagc caccgcgccc 6540
ggcccaattt gttttatata ggttaactgg agtccaaaat acagaactag atgagataac 6600
aatagttaac agtgttagtc agttagaatt attgcatagg tatttttaat ctcatggaat 6660
tttagtcttt gagtaagttc acagcccttg gtattaaagt aagttattta caacccttgc 6720
atttctactt ctcaatattt agtgaggaaa catatctgat tttctttaaa taaaaagaga 6780
aaagactgca gaagatagca ttctctgttg gagcaattaa gatgtataag aagaactaca 6840
aagacggagt tttaaaacaa actgatttat aagtggtatt tatttaattg gctgtcattg 6900
ggctaaatta tttctaaagt taccatggat gccattgagt catggcttaa aaatgtctcc 6960
tggtgatggc acagtttagc tacctaaaga agtagagatg tgggaagcca gaagccccaa 7020
gctctgcagt ttttcttttg ctatagttcc tttgcatgtt gtgaaagaat acagttaaat 7080
tcctgctccc taacagatga gagcataagc atttctttgg gcatacatat gtaaatacat 7140
gctcatggac atgtgaaaag atcaatacta acatttgggt gcaataaata attgtgtaaa 7200
attattttta aaagaattac atattaggaa atgatatatt gattaaaagt gatagtcaat 7260
gaacaagaga gtagatttct gggggaaacc tattttgcat catacttgat ttttagtttt 7320
gactgaatat tgaagtctat attcaaaatt cttttccttt agaactgtaa aggcattgct 7380
gcattttctt ctaatgtaat tgtttattgc tgctgagaat tcttatgaca atctgatttt 7440
ttcatcttca tgattatctt gtttttccct tcatggaatc tgttagggtc ttgactttat 7500
cctttatcct aaatttctca aggcttggac caggtgtggg tttggttttg ttttcttttg 7560
ctactcattt gacttggcac actcagtggg cctttccctt tatctttctt catttctgag 7620
acgtttttct ctcttatttt ttattatctt cctttcattt ttcctgtcct ttttctttct 7680
agacatctct taggaggata gtggtcctct tagattgata tgttatgtcc gtgatttcca 7740
aagtaagatt tgtactcgtc gtctgttaaa aggaaaagca tacatatacc ctatgtatat 7800
atgcacactt ttttattttt aaattatata tgtatctgta ctaattattt acattgtaag 7860
tcaaccctaa cataatctta aaggataaga tacaaaacat actgcatcta gaagcttcag 7920

-continued

```
tactttcttc ctgaatccca gtagatcctt ttgttcatcc cacgggatgc attccgcccc   7980
catcctccca ctccctttgg ataccacatt accacagctc tgcatcactt aactttcctc   8040
ttatgttttt caccttttt ttttttttt ttttgcattt tatgtcctgg ggaatttcct   8100
taattcattt catggtttta ctgttgattt ttttaatatt ggccatcgca acttttcttt   8160
tcttttcctt tcctttcctt tcctttcctt tccttttctt ttcttttctt ttcttttctt   8220
aattttcttt tcttttcttt tcttttctgt tcttttcttt tcttttcttt tcttttcttt   8280
cacacaggat cttggcgtgt tgtccaggct ggcctcgaac tcctgggctc aggtaatcct   8340
ctcaccttgg cctcccaaaa tgccaggatt acaggcgtgc gccactgcat ttggcggcaa   8400
cttaattttt ttatttttat ttttcctttt agaggacacc tagcactgag cattgcaact   8460
tttcatttcc atgaactttt aagaaaactc ttaaagacat gtttaattct gtacactttc   8520
tattgttctt tgattgctgt ttttgaataa caacaaggag tacgccttag cattttgatg   8580
gtatcctctt aatagtcgca ataatagtcc ccttggcgct ctgtatactc tcaagtctta   8640
aatgttttgt atgcagctgt acgttgacag ttgaatggtc tcgctccaag tggatcagca   8700
agaacataaa gaatcattta actggtacag gctgcggctt gtgaattccc tattaacacc   8760
aaagaagacg tgtgagactc cgtactgaaa ctaaagacga cttgtgagtt ccacactgag   8820
atcaaataag tctttatgat ggtgacagag agtggtgtca acgcctaaag ttttggttaa   8880
tctctctaaa ttgaggggct gaccaaaagg gggaacttaa ctgtattaga cataattttg   8940
agaaacatgg gtatgtggat ggtaatggag gaaatgggtg tagatgagat tgcctaggga   9000
gagtgagaag taggttaggt ctaagccttg atgagttccc aacatttcca agggtagttg   9060
aggatactga aaatgagtgg ccagtgagat agaggtaaag ctagagactg cccaggggag   9120
aggaattttc aacaatgagg aggtgtcaac attgtcaggt attgctgaga ggtcagataa   9180
aaccagaatt gagcaaaatg gccattggaa gcctatggtg ccctccgtaa gagctgtttc   9240
gctgaagtga tagaaacgga aatcaggctg ggcacagtgg ctcactcctg taatcccagc   9300
actttgggag gccgaggtgg gcggatcacc tgaggttagg agttcgagac cagcctggcc   9360
aacatggtga aaccctgtct ctactaaaaa tacaaaaagt agccaggtgt ggtggcaggt   9420
ccctgtaatc ccagctactc aggaggctga ggcaggagaa tcgcttgagc cccagaggcg   9480
gaggttgcag tgagcagaga tcgagccact gcactccaac ctgggtgaca gagcaagact   9540
ccgtttcaaa aaaaaaaaaa aaaaaagaaa tggaaatcag gatggtttgg cttttatttt   9600
aataaaatag ctagagcagg gaaatggggt acttttttc cccttttaa gatgagacat   9660
agccaggtgc agtggcttac acctgtaatc ccaacacttt gaaagggagg gtcgcttgag   9720
ctcaggagtt tgagaccagc ctaggcaaca tagcaagacc ttgtctctac taaaattcaa   9780
aaaaaattaa ctgggcatgc tggcacacac ctctagtccc agctatttat gaagctgagg   9840
caggaggatc acacttgagc ccagatacgt ggggctgcag tgagccctga taatgccatt   9900
gcactccacg ttgggcaaca gagcaagact tcgtctcaaa aataaataaa taccctgtct   9960
caaaaataaa aaataaatat gggaggagag atttgactta gattcctcaa agggcaggag  10020
gaaagagaat tccaaacagt gattcacctt taatgggaga aagatcgctt aattttacat  10080
gaggaagaag aggattggtg gagatacagt aggtgaacag tttttgtatg aggaagttga  10140
acatgtgtca ttctaatagc ttccattctc tgtgaagtag agggcaaggt catctactga  10200
gagttgggga ggtcaagaga gataagggga gattagaaga gctcttctag cagagagtgg  10260
aagaatgaat tgctaagaga gatgaagtag gattgttaag tagttttgag ggccctgttg  10320
```

-continued agatgtgctt ccagttgggt gtgattttct ccagtagtgc tttatttccc tgggtacagg 10380
cagagagaaa aacaataagg ctcatgtagg gtttgtattt tgttggacaa gtcaaacaga 10440
aaagtcagag gacgagggag tttagaatgt ttgcaaaaga gttattgaaa cgatgaaccg 10500
cataatctaa ggtggtaagt gggtgaatag ataaggagga tgtgaatagg taaggagaag 10560
aaagaaatat cagattattg attattgatg gcgactctct aatacagcta ttatgccatt 10620
ttaaccgatt aagaaactaa ggctttagaa aattcataat ttgccctaac tgcacagcta 10680
gtaagcagtg gaaatgtgat tggaaccaga gttcttctga ctcaatagac taaatggatg 10740
taaggatgta gttgaaagaa gggtgagcta aacgttgtgg aaccatgagc tctttctctg 10800
gttgatatcc ctctctgtaa gtgataacat gggtcacgct ggataaaacc ttgtggtgat 10860
tggtgacttt cctttgtcct tcctcctgtg cctagtctgg cgagtatctg cctttccctt 10920
tcctttctca ttgctgccac ctaactttag gctcttcccc ttacatctgg gtaactgaaa 10980
taagatcacc tttttgttcc ccttctgatt tactttgacc taacattatc tttactattt 11040
tctttaaatt aatgtttcat tagtcttatt ctactcagga actctgtagt tccccattgc 11100
ctacgaaaaa aagttaagcc tcagccttat attcagtgac tcttcaattg gatattcagt 11160
ccagttttac tcctcctatg agccttctat gccagctcct tgggtctctt gccctttcat 11220
tgtctcagct ctgcaccctt ctttctcttt tttattcttt tttttttttg tacttttttg 11280
gtttttctttt tggtttcttt ttttgtttta tttattaaac ctccatcaca cttcatccta 11340
tggagttttg aaccacagca aggtgcagta tcatcctggg gctctggagg aagtggcagg 11400
gagtccaaaa tgtcacctta gcttcttatc tggggccaca tgtatttctg catctgctgc 11460
ttcccacact cttgcccaca agtgtcgctt gtggaaataa tttgagattt actgtctggc 11520
tgaccctagt ttcaatctct tttccaccat ttgctaatca ttctaccttg ggcaaaacat 11580
agaattaaaa gaaaacttca gacaagttaa atttgatgga gtttaattga gcaaagaaaa 11640
aaaatgatcc acaaattggg cagtctccag aatcaccgca gattcagaga gactccaggg 11700
gtgcctcgtg gtcagaacaa atttatagac agaaaaggta aagtgaccta caggaatcag 11760
aattgagaca tagaaacagt gagattggtt acagctcggc gtttgcctta tttgaacgca 11820
gtttgaacac tcagcagtct atgagtggtt gaagtatggc cgctgggatt ggccaacact 11880
cagctgttat tacagatgca tactactaag ttaggttttc gattttgtct gcctatttga 11940
gctaggttac agttcgtcca caaggactca aatataaaag tacggagtcc tcttcgggcc 12000
atatttagtt cgctttaaca attccccctt ttggtcagcc cctcaattta gagagattga 12060
ccaaaacttt aggcgttgac accactctct gtcaccatca taaagactta tttggtctca 12120
gtgtggaact cacaagtcgt ctttagtttc agtatggagt ctcacacatc ttctttggtg 12180
ttaataggga attcacaagt tgcaactttg taccagctaa atgattcttt atgttcttgc 12240
tgatccagtt ggagtaagac cattcaactg tcaatgtaca gctgcataca aaacatttaa 12300
gacttgagag tatacagtgc accaagggga ctattattat gactgttaag aggacaccgt 12360
caaaatgcta aggtgtactc cttaataaaa gttcttatga aatgaactga accaaatcag 12420
ccaagttaag gttcagacaa tataagcagt tcagcagtat tggggtctga ttggtcagag 12480
tcttcagttg gagtatgata gtgattaagg atcatagttc gctgtaaagt agcttgactt 12540
aaagaggtgc tcgttttcat tgttaccttg ttaatacaag tcataataac ttgaaaacct 12600
gctagaagag atataaagat tagaaaccct tggaaaaccc aagcttgcca ttcaccactt 12660

-continued

```
aggatgcctg caaaccaact gttagttgct cctataaaca tatcgtgggt tcctttctct  12720
tgagagattt ctttattgta cttggtggca gtgtctaagg aaacagcagt atcagccacc  12780
ttttaaatta agctttttgt agtaacagaa tcaggggagg gattagtaca aaattcagtt  12840
ttgtttaaca ccaaacatag gcctccagct tgagcaaaaa gaagatctaa gactgcatga  12900
tcttccatta agtgttttcg ttgaatatgt atgttgtcat gtgcctttct gagagtagct  12960
tctacccatc tgaaaccctg ggaggtctga ttggctacca aatccaagaa ttttcccaat  13020
atacaaatta gttttaaatt ccgtacaaat ggtacttcac taccaccaag agtgagcccc  13080
caggaacccc agtggaatct ttccccggta gaaactagct tatcctcgtc tatttcgagg  13140
ctagtgctaa tttcagttat tgatcatttt ggcctccaag tataagggct atcatgagaa  13200
ttttcagggg aagcaattcg aaaggcagga gcaggccagg ccagataaca agaaccaaac  13260
caaccaagga ggcagaacag aatatgcaga ttctccacag acccaataga gaccctcagg  13320
ggttggaaaa gggggccacc tagttgtatt tgagcaggga tcattcaggt ttgttcgacc  13380
atgaatctgt agctcctgaa taacatccag tgggaaattt acttttctat ggcccctttg  13440
tagtgtgttg taagggtgta taaccacatc tagtaaaaag agaccctact ggatatacaa  13500
gcaatcactt gtactaacat aagtaattcc caaatcttga gtatgtgatg cctgcaagca  13560
caatatacgt tttgtaggca tcatttggat ttgtttttta tatttggtgt gatcgacttt  13620
atcagttgaa aaagagtgtt gtttttagtg agtgtaggaa agcaagtact agtgatgttt  13680
agagtatcaa gaatagcttt ccattcttcc cttggggttt cagggtgact cattgggaaa  13740
cgtggagggg cactggcacc cttggaatca tttcctgatt ttttggcatt agcccacaaa  13800
cccaacagtt accctggttt tgtgctagag cataagcttg agctgaagcc atccactgat  13860
tatggtccca tggattttca tgtaaggaaa aggaaaggat tagggaaaaa aataaggaaa  13920
acagaaaaac acataaggct ttcatggtgg tagagaagtc ttgatctgtg atctagggaa  13980
agctgtctgt aaccaggatg ctgtctgctt ctgggaagag atttccctgg tcagctttac  14040
cttaaagtct ccaacgggta tatagtacca ggagtctgag gggggccttt tgaattgtga  14100
gatgtggacc catggttcaa agccctgaag cttctctgca ctgtgggtgg taagaaggac  14160
ttggtatggt cccatccaac gaggttcaag agtgatcttc ttctgatgtc atttccggaa  14220
ggcccagtct ccaaattcca gaccatggag ggtttgattg tcctcagttg gtggatcttg  14280
aaatgcttcc tttacctggt ggaagtatac tttggcgtaa tacattaaag ccttgcagta  14340
tttagtcata tcagagttta agagagcagg agaagcatga gatgctatta ttagggacat  14400
gggcctccca gtgactattt cataaggggt caatttatgt tttccaacag gattgaatct  14460
gattgccatt aaaaccaaaa ggtagtacct ttggccaagg caactcaatt gattcagtta  14520
acttggacag tttcagtttt caaatgccat ttgttctttc aagctttcct gaagactgag  14580
ggtaataagg acaatggtaa tgcaactgtg tcagtaacac cttatttaac tgctttataa  14640
cttgctcagt aaaatgagtt cctctatcac tggagacttt tagagggatc ccccataaag  14700
gaaaaacatt ttctaataat ttcttagcta tggtcacagc atcagctttc ctacatggga  14760
aggcctttat ccaaccagaa aacatgcaaa ctattacaag aacatactga taccccattg  14820
agggtggtaa ctgaatgaag tccatctgta aatgttcaaa tggtccatca ggtggtggaa  14880
atatactgcc tctagttttt ctgggattat gagtttgaca agtcaaacat tgattataag  14940
ccattttagt aatgtcagaa tagtcacccc accagtattt tttcataatt tggatcactt  15000
tgtctgttcc atgatgagct gtggagagct ttcaataatg gaagcttcaa agattcagga  15060
```

```
aggaccaggc ggccgtccgg gccctttgtg agtctttgct tcacgttaaa tttacatcct  15120
tttagatacc agttttgttt ttgcaaatca gatgcgttgc actgtttatt aaataggtca  15180
tcgtaaggaa attggcttgg attaatctta tggagttcat tcagattgcg tatcttgatg  15240
gttccagcac tagctgattg agcataaaaa tctgctaaag catttcactg atatttgggt  15300
tcatttctac aagtatgagc ttcagtctta ataacagcaa tctgcatttg taacaggata  15360
gcagaaagga gctcatctgt ttggagtcca tttttgatgg ggatcccact agaggtgaga  15420
aaccttcgta gtttccatat catgccaaaa tcacgtacta ctccaaaagc atgtctacta  15480
tccgtaaata tttactgact tgtccttagc tgtgtgacat gttcaggtaa gggcagaaag  15540
ttctgcaggt tgggctgact tgacttgaag agttcgcttc tctattaact cattttgggt  15600
ggtaacagca tatcctgact gatatttttt tttctgagtt tttggcatag gacccatcaa  15660
caaaaagtgt taattcagga ttatccagtg gagtatcttg tatagcaaca cgaggggcca  15720
ctatttctga tactacactc acaccgttgt ggtcttcacc atcatcaggc agagataaca  15780
gagtagcagc attaagtaga ttacagcctt ttagatgaag ataagaagga gataggagaa  15840
gtaattcata agatgttagt ctactcactg aaaaatgctg ggtttgattg gaatttaata  15900
gactttccac agcgtgtggg acttgcaaat taagttcatt tcctaaaacc agatctgatg  15960
aagcttctac cagcttggct gctgctactg cttttaaaca attaggatat gccttagaga  16020
ctgggcctaa ttgcaggcta tagtatgcag tggtcctatg tttagcaccg tgttcctgat  16080
tattacattc atgaacaaac aaagtgaaag gtttagtgta atttggaagt cctaaagctg  16140
ggggctgttg taaggccaac ttcatttggc taaaagcctg ctcatgactg tcttcccaag  16200
gtaaaggctc tggtacagca tttttagtga gctcatacag tggtgaagct attaaggaaa  16260
aatttggaac ccaggatctg caatatcctg caagcctaag aaagcctttt gtcttttggt  16320
tgcaggtcga ggaaaacttt aaataggttt tatcctctca ggtaagaggg aaatcccttc  16380
agcagccaag tcatgtccca aatagtggac tttttctttt gaaaattgaa gttttggcca  16440
ggcatggtgg ctaacgcctg taatcccagc actttgggag gctgaggcag gcggatcacc  16500
tgaggtcggg agttcaagga cagcctgacc aacatggaga aaccctgtct ctactaaaaa  16560
tacaaaatta gccaggcgtg gtggtgcatg cctgtaatcc cagctactcg ggaggctgag  16620
gcaggagaat cgcttgaacc caggaggcag aggttgtggt gagccagtat cacaccattg  16680
cactccagcc tgggcaacaa gagtgaaact ccatctcaaa aaaaaaaaaa aagaaaaaag  16740
aaaagaaaaa attgaagttt ttccattgaa gccctgtgac ctttatatgc aagttgctgt  16800
aaaaggtaaa ctgagtcaat ttccgggcac tccttaatag gagagcataa caataagtta  16860
tctacatact gaatgagagt agaattttga ggaaactgta gtgtcattaa ctcctgatgc  16920
agtgcctggg gaaaatatga aggggcttca gtaaaccctt gtggcattac actccaggtg  16980
tattgctgat ttttccaagt aaaggcaaac aagtattgac tttctttatg gaatgctaga  17040
gaaggctgag ccaagatcta ttactgtgga caacttggaa tcagtgggta cattaggtta  17100
taaagtatta ggatttggga ctacaggaaa tcttggtatt acaattttat taattgcctg  17160
taaatctgga acaaatctcc agtctcatcc attttgtttt ttaactggta ggattggagt  17220
gttacagggg ctggtgcatg gaattatgag tccttgttta attaaatctt ctacaattgg  17280
tgagagccct taaattgctt caggttttag tggatattgt ggtaattagg caaaggttta  17340
gaatgatctg ttagtacttt tataggttct acacttttaa ttcttcctat atcagttggg  17400
```

-continued

```
aagaggccca taaacattag gtgttttcga aagatcaggg gtattacagg cttgagtttc  17460
gatcttatca atttctgcct gtagacagca taacaattct agttcaggag aatcaggaaa  17520
actcttaaga ttatttctgt ttctgaggaa aattttaggt gcccttttag ctttgaaagt  17580
aaatcttgcc ctaccaagtt tactggaaca gtatcacgta gtaaaaaact gtgtttttct  17640
gaaaggggc tcagagttaa ttggatgggt tcagatatgg gaacctctgg aacttgattt  17700
gaaacccctg tcacagaaat gaccttttta ctctaaggga tttgttggct tattaaggtg  17760
gggtttatgg tagatagagt agccctggta tccataagga ctatacacaa ctccctattt  17820
attttaacct ctgtttcccc atgttccttt aaaggtatta cggggagcaa tccactggag  17880
aatcccttag agcctccttt aagttgaata ttgtcaggag gactaaggtc tcttgggctc  17940
cctctagtgg tgaaacagtt tggcctagag ggaggtttat cagccgacaa tccctttcc  18000
agtgccctgg ttgtttgcaa tacaggcaga catcttgggg taaagaaatt cttgttctgg  18060
gacctcttga tttgattttt ttaatatata attttaaaaa tattttccaa agtgtgactt  18120
aaaaaaattt ttttttatta tactttaagt tttagggtac atgtgcacaa cgtgcaggtt  18180
tgttacatat gtatacatgt gccatgttgg tgtgctgcac ccattaactc atcatttaca  18240
ttaggtatat ctcctaatgc tatccctccc ccctccccca accccacaac aggccccagt  18300
gtgtgatgtt ccccttcctg tgtccaagtg ttctcactgt tcagttccca cctacgagtg  18360
agaacatgcg gtgtttggtt ttttgtcctt gtgatagttt gctgagaatg atggtttcca  18420
gcttcatcca tgtccctaca aaggacatta actcatcatt ttttatggct ccatagtatt  18480
ccatggtgta tatatgccac atttcttaa tccagtctat cattgttgga catttgtgtt  18540
ggttccaagt ctttgctatt gtgaatagtg ctgcaataaa catacgtgtg catgtgtctt  18600
tatagcagca tgatttataa tcctttgggt atatacccag taatgggatg gctgggtcaa  18660
acggtatttc tagttctaga tccctgagga attgccacac tgacttccac aatggttgaa  18720
ctagtttaca gtcccaccaa cagtgtaaaa gtgttcctat ttctccacat cctctccagc  18780
acctgttgtt tcctgacttt ttaatgattg ccattctaac tggtgtgagt tggtatctca  18840
ttgtggtttt gatttgcatt tctctgatgg ccagtgatga tgagcatttt ttcatgtgtc  18900
ttttggctgc ataaatgtct tcttttgaga agtgtctgtt catatccttc acccacttgt  18960
tgatggggtt gtttgttttt ctcttgtaag tttgtttgag ttctttgtag attctggata  19020
ttagcccttt gtcagatgag aagtttcaga aattttctcc cattctgtag gttgcctgtt  19080
cactctgatg gtagtttctt ttgctgtgca gaagctcttt actttaatga gatcccattt  19140
gtcaattttg gcttttgttg ccattgcttt tggtgtttta gacatgaagt ccttggccat  19200
gcctatgtcc tgaatggtat tgcctaggtt ttcttctagg atttttatgg ttttaggtct  19260
aaattaagtc tttaatctat cttgaattaa tttttgtata aggtgtaagg aagggatcca  19320
gtttcagctt tctacatatg gctagccagt tttcccagca ccatttatta aatagggaat  19380
cgtttccccg tttcttgttt ttgtcaggtt tgtcaaagat cagatagttg tagatatgcg  19440
gcgttatttc tgagggctct gttctgttcc attggcctat atctctgttt tggtaccagt  19500
accatgctgt tttggtgact gtagccttgt atagtttgaa gtcaggtagc gtgatgcctc  19560
cagctttgtt ctttggctta ggattgactt ggcaatgcag gctctttttt ggttccatat  19620
gaactttaaa gtagtttttt ccaattctgt gaagaaagtc tttggtagct tgatggggat  19680
ggcattgaat ctataaatta ccctgggcag tatggccatt ttcacgatat tgattcttcc  19740
tacccatgag catggaatgt tcttccattt gtttgtatcc tcttttattt ccttgagcag  19800
```

tggtttgtag ttctccttga agaggtcttt cacatccctt gtatgttgga ttcctaggta 19860
ttttattctc tttgaagcaa ttgtgaatga gagttcactc atgatttggc tctctgtttg 19920
tctgttattg gtatataaga atgctctctt ttgttctttg ttagtcttgc tagcggtcta 19980
tcaattttgt tgatcttttc gaaaaaccag ttactggatt cattgatttt ttgaagggtt 20040
ttttgtgtct ctatctcctt cagttctgct ctggtcttat ttatttcttg ccttctgctg 20100
gcttttgaat gtgtttgctc ttgcttctct agttctttta attgtgacgt tagggtgtca 20160
attttagatc tttcctactt tctcttgtgg gcatttagtg ctataaattt ccctctacac 20220
actgctttga atgtgtccca gagattctgg tatgttgtgt ctttgttctc attggtttca 20280
aagaacatct ttacttctgc cttcatttcg ttatgtaccc agtagtcatt caggagcagg 20340
ttgttcagtt tccatgtagt tgagcagttt tgagtgagtt tcttaatcct gagttctagt 20400
ttgattccac tgtggtctga gagacagttt gttataattt gtattctttt acattttctg 20460
aggagagctt tatttccaac tatgtggtca attttggaat aagtgcagtg tggtgctaag 20520
aagaacgtat gttctgttga tttggggtgg agagttctgt agatgtgtat taggtccgct 20580
tggtgcagag ctgagttgaa ttcctggata tccttgttaa ctttctgtct cgttggtctg 20640
tctaatgttg acagtggggt gttaaagtct cccattattg ttgtgtggga gtctgagtct 20700
ctttgtaggt cactcagggc ttgctttatg aatctgggtg ctcctgtatt ggttgcatat 20760
atatttagga tagttagctc ttcttgttga attgatccct ttaccattat gtaatggcct 20820
tctttgtctc ttttgatctt tgttggttta aagtctgttt taccagagac taggattgaa 20880
acccctgcct ttttttgttt tccatttgct tggtagatct tcctccatcc ctttattttg 20940
agcctatgtg tgactctgca cgtgagatgg gtttcctgaa tacagcacac tgatgggtct 21000
tgactcttta tccaatttgc cagtccgtgt cttttaattg gagcatttag cccatttaca 21060
tttaaggtta atattgttat gtgtgaattt gatcctgtca ttctctcaac atttgcttgt 21120
ctgtaaagga ttttatttct ccttcactta tgaagcttag tttggctgga tatgaaattc 21180
tgggttgaaa attcttttct ttaagaatgt tgaatattgg cctccactct cttctggcgt 21240
gtagagtttc tgccgagaga tcagctgttg gtctgatggg cttccctttg tgggtaacct 21300
gacctttctc tctagctgcc attaacattt tttccttcat ttcaactttg gtgaatctga 21360
caattatgtg tcttggagtt gctcttttcg aggagtatct ttgtggcatt ctctgtgttt 21420
cctgaatttg aatgttggcc tgccttgcta gattggggaa gttctcctgg ataatatcct 21480
gcagagtgtt ttccaacttg gttccattct tcccgtcact ttcaggtaca ccaatcagac 21540
gtagatttgg tcttttcaca tagtcccata tttcttggag gctttgttcg tttcttttta 21600
ttcttttttc tctaaacttc tcttcccgct tcatttcatt gatttgatct tccatcactg 21660
atacccttc ttccagttga tcgaatcggc tactgaggct tgtgcatccg tcacgtagtt 21720
ctcgtgcctt ggttttcagc tccatcaggt cctttaagga cttctctgca ttagttattc 21780
tagttagccg ttcgtcgaat ttttttcaag gtttttaact tctttgccat gggttcgaac 21840
ttcctccttt agcttggata gtttgattgt ctgaagtctt cttctctcag ctcgtcaaag 21900
tcattctctg tccagctttg ttccgttgct ggtgaggagc tgcattcctt tggaggagga 21960
gaggtgctct gatttttaga attttcagta tttttgctct gtttcttccc catctttgtg 22020
gttttgtcta cctttggtct ttgatgatgg tgatgtacag atgggttttt ggtgtggatg 22080
tcctttctgt ttgttagttt tccttctaac agtcaggacc ctcagctgca ggtctattgg 22140
agtttgctgg aggtccactc cagaccatgt ttgcctgggt atcagcagcg gaggctgcag 22200
aacaacgaat attggtgaac agcagatgtt gctgcctgat cgttcctctg gaagttttgt 22260
ctcagagggg tacccggcca tgtgaggtgt cagtctgccc ctactggggg gtgcctccca 22320
gttaggctat tcgggggtca gggacccact tgaggaggca gtctgtctgt tctcagatct 22380
caagctgtgt gctgggagaa ccactgctct cttccaagct gtcagacagg gacatttaag 22440
tctgcagagg tttctgctgc cttttgttcg gctatgccct gcctgcagag gtggagtcta 22500
cagaggaagg caggcctcct tgagctgcag tgggctccac ccagttcgag cttcccagct 22560
gctttttta cctgctcaag cctccgcaat ggcgggcacc cctcccccag cctcgctgcc 22620
accttgcagt ttgatctcag actgctgtgc tagcaatgag cgaggctcca tgggcatagg 22680
acccgctgag ccaggcgcgg gatatagtct cctggtgtgc tgtttgctaa gaccatcgga 22740
aaagcgcagt attagggtgg gagtgaccca attttccagg tgctgtctgt caccccttc 22800
cttggctagg aaagggaatt ccctgacccc ttgtgcttcc tgggtgaggc gatgcctcgc 22860
cctgctttgg ctcatgctcg gtgcgctgca cccactgtcc tgcacccact gtctgacaat 22920
ccccagtgag atgaacccag tacctcagtt ggaaatgcag aaatcacccg ttttctgcgt 22980
cgctcaagct gggagctgta gactggagct gttcctattt ggccatcttg gaaccgcccg 23040
attgtgattt aaaatgagaa cgagatggtc cctttggttc ctggtccctg taactgttgc 23100
aattgaaggg gcataagctt attagccttt tgaggttttt tttgctctag agtcttctca 23160
aaatgcttag ctaggttggg cacgatggct cacgcctgta atcccagcac tttggaaggc 23220
caaggtggga ggatcacgag gtcaggagat caagaccatc ctggctaaga tggtgaaatc 23280
ccatctctac taaaaataca cagattagct gggcatggtg gcacacgcct gtagtcgcag 23340
ctactcggga ggctgaggca agagaattgc ttgaacctgg gaggcagagg ttgcagtgag 23400
ccgagattgc gccactacac tctagcctgg gtgacagagc aagactccac ctcaaaaaaa 23460
aaaaaaaaaa aaaaaaaagt tcagctaagg ccaccaattc agtcacatct ctaacttccc 23520
attgcaactt atgtttttta gttaaactgc taagttcagg atggagtcca tttataagta 23580
aagcagttaa tgctgtttca gcccctgcag ggaatactcc ttgctgtact ttgagcccag 23640
gatgtttcac aaatatttct aagcgacttc tgtaatctga aactggttca tcttttcttt 23700
tcttttttt ttgcttacaa gattgtatga tggaccaatt ttttgtggaa aaattttagg 23760
aactgaatgt taaaaggttt tcagcgattt ttctagctat ttttggtcct tcttgtgagg 23820
agctcttaga gggcccttta aaatgtcctc ctcaggtttg tcccattctg ctgctgccat 23880
ccatttctga gcttcaccag cccccagtat catatgaata aattggtaaa ttcatgaagt 23940
cctggatcgt aagctcctat taggattcta aattcctcag taaatttttg agacttttcc 24000
cttggaccag ggaagtcctt cacaatgggg ctaagctcag ttttagacca tggagtgaaa 24060
gtagttacag caggcaggcc tggctgatat aaggtctcac tttgtaagac atctgtctaa 24120
cttcctttt tttttttt ttttttaaa tcatcttcag ggtgaaagtg taatttaaca 24180
aaaagtttag tggactcaga gtatgtaggt agagatggac aaagaaggaa cagtccgagt 24240
tagatcagtc aaagtacagt cctctttctt catgtccttg gtctgttgct taagcttttc 24300
atttggtttt tgcaaagaat cttttaagga ggcacttttt gattcactta gtcttttgga 24360
ggcctttgcg tatccatgag acaatacatc ccactgtatt tgtgggggct ttgatcccct 24420
ttttctaata tgccttgcaa acaattttat ccaaattaaa acttctccat tgtggccatt 24480
ttaattctaa gttttcttta gtgaggttaa cccattttac tgaaaatgca catgttctgg 24540

```
gcccataatt tttatacgta aaattagctg gagtccctga agatggagtc ccagactcct  24600
tggattgaga tgatcccatt attaaataag gtacttatca gaggtctgag gcctctaact  24660
gaatccaatc cagttaatta tcaaatccaa tttgatcttg gatccagtcc aggctaagta  24720
ttgcttgagt aaactcggag agctcaaaac acaagttagt ggagctcgga atctgagaga  24780
aaactcaccc atgacctcca gttacaatca agagaccagt gagagcaacg gcctcagtgg  24840
gtacctcacc aggtcacctg gtgttccagg gggttgccag agtttttctt caaatcccac  24900
ttctgacacc agatctgtta aaagaaaact tcagacaagt taaatttgat ggagtttaat  24960
taagcaagga aaataaacac tttgcaaatc aggcagcctc cagaattgaa tgcagtttga  25020
acacttagca gtctattagt gcttgaagta tggccactgg gattggccaa cactcagcta  25080
ttattacaga tgcatactac tcaggttttc cattttgtct gcctattgtg ctaggttatg  25140
gtttgtccac aagaacacaa atatagaagt atggagtcct tctcaggcca tatttagttt  25200
gctttaacaa tacttaaaaa aaaaatttgt aaaataagga tacttaacct tactcggtgt  25260
ttctgagagt taacatttat atagttatgc tgtagtgaaa acagctagcg taatgtctgg  25320
tatgtatagg aacacaagag ataccgcttt tcccatatcc ccataccatt cttcacagca  25380
ttgctcctgt cttccttgat tcctcctcct ccttctttgt tttttttttg tttgtttgtt  25440
tgtttttttt tggaggtgga gtctcactct gttgcccagg ctggagtgca gtggtgtgat  25500
ctcagcttac tgcaacctct gcctcctggg ttcaagtgat tctcctgcct cagcctcctg  25560
aatagctggg attacaggca cacaccaaca cactcagcta atttttgtat ttttagtagg  25620
gatggggttt caccatgttg gccaggctgg tcttgaactc ctgacctcag gtgattcacc  25680
cacctcagcc tcccaaagtg ctgggattac aggtgtgagc caccacaccc tgcctccttc  25740
ttaagaagtt tccagtccct tgtaattaaa ggaattaata tttttaact acttagaatc  25800
agactggccc tgattattag taagcaacta atagtaagca agcaactatg tatgcaacta  25860
tgagtgtatg ttaagatatg gttgttggta acctttcatt ctcttcagga agaagaagag  25920
ggtggagctc tacagtcaat gtgtacattt aaattctgtt ccctttcgag cttttttgct  25980
actttcattc ttctggggat ccaggtgctt gagttgggat tgattaactt ccttaatttc  26040
cacccctgtg ctgtcaggat cgggagacat agatgaaggt gttctaaact gctagaaatt  26100
ttgtttttga aagcaaaagt ttgcatgcat ttttgtttc aacttttact tacagtgaat  26160
agtagttaat aaaataagtc cctgcctttt ctctctttgg tttcaattcc tgagaccagg  26220
atcatagccc acatattaga gtggagtccc actgctttgg tttgaatcat gcctttgttt  26280
cttatgtcag tgtgactttg ggcaagttat ttaagtcttt gcaccacatt ttcctcatct  26340
gtaaaatgag gataatacta gtactttcta catgggattg ttagcaggat taaatgagat  26400
agcacatact gtaaccatgt ctggcacata gtcaatggtt agtaaatgtg aactattgtg  26460
tgacattgtg gttagtcacg tatggggctg tgtttccttt agtatattgc tcttttaatg  26520
tcatttcctt tgtactgtta ccctctctga tctttcttcc atattcattt ttctttcagt  26580
gaggtctgcc agtctttagt gaaacacagc tctggaataa aaggaagttt accactacaa  26640
aaactacatc tggtttcacg aagcatttat cattcacatc atcctacctt aaagcttcaa  26700
cgaccccaat taaggacatc ctttcagcag ttctcttctc tgacaaacct tcctttacgt  26760
aaactgaaat tctctccaat taaatatggc taccagcctc gcaggaattt ttggccagca  26820
agattagcta cgagactctt aaaacttcgc tatctcatac taggatcggc tgttgggggt  26880
```

ggctacacag ccaaaaaggt gaacttgaca ttcctcctgg ttttccaatt attatatcat 26940
gattaagttt ctatagcata aatcattttt gtgtagtgga atacaattgg atgtttaaac 27000
atttattttg tgtctctacc atggactaga ttgttttaat gatgctaata ggaagatgcc 27060
tttagaatct tagttataat tacaggaaat taaaatggcc tagtggaagg agcacagggc 27120
tgggaatagg aacacctagg tttgattttg agcttagaca tttagtagca cagatgtgaa 27180
agtcaggtgg cattctcaca caagcacttc ttggcaggtc tgggaccaga ggcaaggcgt 27240
cctgtctccc agtctgtctt ccttctaccc cacagtaata tttagggcaa aattatgaaa 27300
cctgtttgaa ataggagtat attctgaatt tttacatttt ccatatttaa cagaggagtg 27360
ttaacttgtt ttatatgctt gtttgctgag accacttaat tttgtttctt aaaagttttg 27420
aacataatac attattctta gtagattaat gtgttttaat taaataattt ttctttacat 27480
gtttatttgg catgcagagc atctgattga cacactttct tgtcttttag acttttgatc 27540
agtggaaaga tatgataccg gaccttagtg aatataaatg gattgtgcct gacattgtgt 27600
gggaaattga tgagtatatc gattttggtt tgtatcatga acattaaaat actttttttg 27660
gtcatctcga ggaaagagaa atagtttatt gagatagttt cttaacttat gaacctaata 27720
tatcacggtt ttattttaat gatataagta atagaatatc aatgaaaaaa tctgtataaa 27780
agaaataccc agtagcccat aattttacca cagctgccac taactgtttg gagcattttc 27840
ttttaattat acttactata tgtggttagt atctttttaa cttatcgatt gagacaggat 27900
cttgctctgt cactcaggct gaagtgcggt cttggaatca taactcactg cagccctgaa 27960
ctggctaaag tagtccttcc gactctgcct cccaagtagc cgggactaca tgtgtgtgcc 28020
accatgcccg actgattttt taatttcttg tagagatgaa gtctcactat gttgcccagg 28080
ctagtctcaa attccttagc tcaaacctct cacctcagcc tctcaaagca ctgagattac 28140
aagtgtgagc cactatgcct ggcttgagtt tttttctttt aatttttttc ttttcatgaa 28200
tactaccaca gaatagtatt ttagttccct ttttaaaaat tatgtaatca tggtgaatat 28260
tcactttggt attttgtctt ttgctaccta acatattttg tcagcatttc catgctgcca 28320
agtagccttt ctattaataa tatcattttc tgcattatgt aatgttgccc agagcatatt 28380
tattgtgacc cacctagcta gctccttttg attggatacc ttggttatct ctaccttttg 28440
tagccaagtt ctttaaaagt ctgttagtat ccagggtaat ttcttttctt agttggccac 28500
tgccctccct ttttcaatag gtggatgaga aaaaagtata ttggatcgct atgattgcca 28560
gtaattcatg gtgatcttta agaaatatat tttcatcaaa tttttttaaa acctttgtca 28620
gatttcttag tttaggtgta tgtggaggtg gaattaatct atacttgcac ttattcacag 28680
aatttataaa gataaaactg ttctatgttg acgaatccat ttgcaaaaaa agcacacttt 28740
caaattgttc ttctaatatt aatgaggaga gctttcaaat tgatgtattt gccagtacca 28800
cagcgtagtg gctgagagcc tgtattctgg agctggactg cctgggctgg aacccgggct 28860
cctccacttc cttgctgtgt accttagttt ctcatctgta aatggtgttg ataatagtag 28920
ctgttttgta gggttgtcat gaggattaaa caagttaata ctttagccct ttataagaat 28980
agtatctgac atattttctt agtttcatac tctatatgtt ttgatctttt ccagagaaaa 29040
ttagaaaagc ccttcctagt tcagaagacc ttgtaaagtt agcaccagac tttgacaaga 29100
ttgttgaaag ccttagctta ttgaaggact tttttacctc aggtaaggaa gaagctgttt 29160
gatctaattt aaaaatttaa gaaccatgga ggaaaaatac atggattatt tgtttattcc 29220
catttttttta aaattaaaat atttagtacc aatgaaaaac aggacatttt ttaaaaagat 29280

```
aaacacaaag ttttgttaca caatggtttt aatctttgtg tagcccagta aaatgacagt  29340
tcctaagcac ttaaacatac ttggctttta gtgaggggaa aaaatgtatc acttgttctt  29400
gacaagtaga tgagacttcc tatgtatttg cttttcataa gtggttggac caatttggtg  29460
gttttaaaac aaatttaagt atgatagacc ataatgagta gcatttatta agtttaatcc  29520
tggcatattt gcccaattat tgccctatcg taatatgaaa tctgagatct cagacatctt  29580
tgtttgctca tttctgttaa attttacatt tctatttccc cttttgctga tttttcacag  29640
gtcacaaatt ggttagtgaa gtcataggag cttctgacct acttctcttg ttaggtgtgt  29700
aaacagacat ttttgctgac cttaacatgc cttttaaatg cttctaataa actagttgca  29760
aataaaattg cagaccaaat ttataatgct gcttatgctg aattttaaaa ccccagaact  29820
atattaggca aactcattat cctttaggtg gaaataataa aataattatt ttgtgataac  29880
actaaaattc ttaaatatgt atgtgtatta taagattaaa gctattaaaa gaaaatttac  29940
ttagcaaaaa tattttcttg aaatagatct aattgttttt gataattgaa atgaaaagta  30000
attttagttt gtctcatctg ccctgtcatg gttgacattt aaatttgttt tccggccggg  30060
cgcggtggct catgcctgta atcccagcat tttgggaggc caaggcaggc ggatcatgag  30120
gtcaggagat cgagaccatc ctggctaaca cggtgaaacc ccatctctac taaaaataca  30180
aaaaatttgc cgggcgtggt ggcacacgcc tgtagtccta gctactcggg aggctgaggc  30240
aggagaattg cttgaaccca ggaggcggag gttgcagtga gccaagatcg cgccactgca  30300
ctccagcctg ggcgacagag ggagactctg ccccccaccc ccaaaaaaaa aaagaaaaga  30360
aaaaaaaatt gttttcctgc tatacatggt ctgtaatgcc agtggtatgt ggctgaactg  30420
taagtactct catgtaaaat aatccttacc aaagattgtc ttattttttt attgtaattt  30480
tcagttatat atttttaatt gttaggttaa acatatgctg cgattgctat agttagtttt  30540
tttttattt tctgcacagg ttatcagtca tgttccttaa aataagaata aaggcgattt  30600
gattctttga atctgagttg ctctaaaaat ccattcacct tttcattgac tcgatgtaat  30660
ttgaaattca gcttaggctg ttgacatcac tggagaatgt aaagggttgc atatttatct  30720
ttaaggttct ccggaagaaa cggcgtttag agcaacagat cgtggatctg aaagtgacaa  30780
gcattttaga aaggtaagtg taaaagagaa ttgttcatgt aggtagtctt gaaagatttt  30840
ttaaagtttt tacttctttg gaagatttta aaatgataac atctgagaag caaatacaaa  30900
aacatccaag tagagatatc gttactaatc ttagtgcaaa gtacaaggta ttacgtggca  30960
gttctggaaa tataattgag aagcccattt ctttcacata tgtccagtga agcattagtt  31020
tcgagggttg tccccaagaa agagttgtgt tgttaagtgt gtggggggag aaaggctcgt  31080
ttagacaagg caagcggact tcttttcttt ccctaggacc tctcatactg taatatactc  31140
atgcgcattg tgaatttcca aggagtcaaa gcatacagtg ttttcccaaa ttatttatca  31200
acagaaccct tttgctcatg gaacgtcgta tagggactag atttcacttt ggggaaacta  31260
gaaagggaat aggaattggg ttattaggaa ataaatcaat tccctgatat tgatagttaa  31320
caaagttatg tatggggtta tttatggtat gttattttca acacatattc attaacaaaa  31380
tccatatgaa agttatagga gaattgctga ggtagaataa catactttgt ttgtatttat  31440
aatactcata tatttacctg acgttttctg agtcttcact tttttcattc ttttggaatt  31500
ggtaaaataa ctgattcctt gaaagttttt ttctaaataa tacctagata atagatttat  31560
agaaaaaata ttgtatgaat gttttaacat tcatgtaata tggaacatgt aatttttata  31620
```

-continued ctggaggtta ttatagtttt aatacatcaa agaaataatg tttattttgg aagcagaaag 31680
aagaaataat ttctatgaat aggttttcat ctctttcctt gttcttcaac tttgaacttt 31740
ttatattcca aattttaatt atatttcaaa agattttttt cttttgcctt ttaattttat 31800
cttttggaga aaaatgtatg tcaaaatgta tgtacgtgta tttgtctttt gatttgatct 31860
tttttgaccc tcttttgcat tgacattatt ttaaccaaag gacactcttg attgttcatg 31920
ctactggggg aaaaaaaaat aagtagaaat tagcctaata gttgtggctt attttgagtg 31980
aaggccttag cccttaaggc aattaaattt actgtggaga gaagagctaa tctaatgggg 32040
agaaggagcc tttgttacag gtgtggtagt gtggttcttt gagtgacaag atttctgttt 32100
gccagattgg ttaggagaag tctgtgtgtc tgctttctct cttatggcct aggatcactg 32160
tggtgaatga aaaacctgtc tcagggcctg actcagataa ttcccttaaa acccggctaa 32220
ggtcatagat gaataatcag taattgaaca gaagctctgc aatagaaaag aagccagata 32280
attattttg gaaatttaat tatatttaca gattttattt tatacagtag acatggaatt 32340
aaatttatta cattatgttc taatttactc tttgcttgtt ttgatttgct tgtttgacaa 32400
tacatgtcct tgtaaactat ttccttttaa ctttttctca atttatggtg cttattttcc 32460
ccattaaaga cttaccaatt tttttttaa ctatttgtta cacatactga atctagagtt 32520
gtaattaagc tactttcatt actggttaag tcaaattata gcaaatgcta ctataaaaat 32580
ttactatcca aaaatgtgtc tcaagcccca actgatggtt tcaaattctg ttattaataa 32640
tatgcagcat tgtgtttgca aagcttggct gttacttgtg atgcttgaga atgatgagtc 32700
actcagctaa actgagtgat tttgagactt gtgtacaaat tgatggttga atgtaagcat 32760
gcaaagagag accttagctt agcagtaccc tttttgaaat cactctgaca tcaagtttga 32820
aaatgtgggc aataatcaga ggtggtaagg tggccaggct ttagctgaat acttttttaa 32880
ctggttcagt ctgagggctg aaagccccag atttaaacag tatttagaat ttgaagcagt 32940
caagtattag tttaatggtt gtcaggtttg taacaaagtt tctggctaga cttctactag 33000
aaatgtaaaa gtgcatgtga atcagctttt taaaaaagta ataataattg aaaaacattt 33060
ctacaactag aactaaagaa aagatttgtc ctttctaata ggaaaacaca tctggagaag 33120
tgctggcaac tagcagaaca gttaggacca ttcagaatca actgaagtga aagtgacggg 33180
gagctgaggg gaacacagat agtttgactt cagtcagaca gaataaacat gatgaaccga 33240
taacctgtga ttcccagcct ggggttacta ctggagtttt aggtgtcctg gaaagttata 33300
ataccggtct tcaaaaagtc tacagaaagc atagatttcc acataatgct gcacaggcta 33360
acgaattaat caagtttctt tggtttggcc tggatttata tccattcagt ttgtggacac 33420
tactgaatta tttatgtcat gttgatcaaa agttctgata tgatttgatt aatgaaacat 33480
tgaaaaaaat agtaaaacca accattttta accttacact actatcttga ggtatgattg 33540
acatacatta aaaccacctc ttaataaatg cttcttgtta atcaaaaatt tgaaaacgta 33600
tgtccactgg aggaaaaaag acatagccct ggatgtgaac tgaatattac tgagactcgg 33660
agaccttcag aactacctga agatgaatcg aagtgctgcc tactttagag aattggacta 33720
atttaatttg ggagtcagca gattgctgta tatcagtcat catatatacc ggtgacaaga 33780
ccacttagtt cattcccttt tttagattct gtaagattat tgtgttccag tgaaattgat 33840
ttgcaaaatg agacatttta ttttctgtgc ttttgttcta tcatgtttct gattggtcat 33900
aagcatctca cagaagtaag aaatatggcg attcagaagg caacaagcac atttataatt 33960
tatagaaaat atttgaagga ctttttcatg gcccaaatca tgaaaagtag tagtattgtt 34020

-continued

```
ttaagtataa ttattaaatt ataatacatt aatgttcttt cttgcaacat attactctca  34080
ttcttttttt tttttttttt ttttgagacg gagtctcact ctgtcacccg gctggagtac  34140
agtggtacga tcttggccca ctgcaacctc tgcctcccgg gttcaagcga ttctcctgcc  34200
tcagcctccc aagtagctgg gattacaggc tcctgccacc acgcctagct aatttttgta  34260
tttttagtag agacagggtt tcaccaggtt ggccaggatg gtcttgatct cttgacctca  34320
tggtccgtcc acctctgcct cccaaagtgt tgggattaca ggcgtgagcc acccagcagt  34380
ctgattctta attttatagt ttatgttgta cctccccagc tgaagtatct cttttctttt  34440
ttcccgcgtg tttagtgttc actcatcttt atagcatagc tcaattgtca cttcatgaag  34500
ccttccataa cctttgtagc tccattaatt atattcttct gagtgtttaa aacacttgcc  34560
atatgaaaca ctatttactt tggcttacat tcttactatc taatcggcca tttctgttac  34620
taaatctttt tctcagagca cctgggatag tcttgtgtct tagtaaaatc agttgattga  34680
tttaactcgg tagagtagag gctgattaaa gtaaataaat ctggttgatg ccaacaaaat  34740
tttggtcccc tcaatttttt gctctcatta cctgcaaatt ctccctggcc ttcatatttg  34800
gcaaccattg aggagaacaa ggctgtaaaa gtagttcatg tacttgatat tctgaattgg  34860
aattaagcag agttgcttaa gtaggacttg cttttctggg atttcttatg caacaaataa  34920
tgtagtaact ggaaatccaa gttcaagaca ctggcagatt cgatgtcttt tgaggaccct  34980
tggcttcata gatgatgcct tctccctata tccttacata gcaaaagggg ccaggcagct  35040
ctggcctttt tttgtaaggc caataactcc agaaacctca tgacctcatc acctcccaaa  35100
ggccccacct ctcaatacta tcacattgtg aggctaggtt tcaacatatg aattgtggga  35160
gacaaaaatt cagaccatag tataatattt caagattact taaactcttc tctaccaaac  35220
tcattaactt ttaggttagc acagtatttt cattgatatt ttggtttctg gagttattac  35280
taattttctt gatctgatgt tataattaaa aaaaaacagg actttgtacg tgaaatgaga  35340
ctgagataag gaagctgatt cagagatgga gatttaaaaa aagagagatg agagattgag  35400
atctgcagtg tcaaactgac aatagccagg agtcaggaga tattaagaga ctatatcatc  35460
tgtgattgtt aatgattatt tattgttatt tataaatact actgtatttt atatattata  35520
tacattgttt taaaaattat ttttgtacca tttcttgaaa gaaaaatgtc taagcttggg  35580
aaaatattta ttgaaaaatg tggtttgtac atctgaggag tgtatcttgc acagtaggtg  35640
catagatttc ttcctcttcc tgttccacat ggccttagct tagaggctgt gtggccatca  35700
cttggtattt agggtaagac tggtgcacaa aatcaaagac aggtaacctt ggtataagtg  35760
tagtatcatg taaatagctt ttctatgtct aattcttgtt ttcttcctac tttttcagga  35820
ggtcaatttc agttcatttc aactatcttt acataatagt gctttagtaa caggcatgga  35880
aggaaagaga catgtcccta gagtgttttc ttgaaatcta atagatgatt ggagtattta  35940
ccatgcagtt gtgtatatac ataagcagtg aattcgagag gaatttttaa gctgtaaaaa  36000
aaagcattgt gtgccttata gacgcgagtg agaaatgtgg aatatggctg atccaaaggg  36060
aatgagttat ctcaattgat taatcacagt cagttacaga ttgaactctt tgttctactc  36120
tttgccccct tctcactatt gctcttgact agtcttaaga aagaaatgtg gaatattttc  36180
tcacggcttt gggattttat aaattagaat actagtggta tgtaaataca gcaggtacac  36240
tactgtataa accaacatag gaagccttct ttaaagggaa ttgtttgaga aatttgaaca  36300
cttggataat ttgaataaag gattgtgata aatgatcaaa tgaaagaaaa taaatcaggt  36360
```

tactcttctt tctgcttgat aaagcaataa ttttttttaa aggtaaaaat tatgagaatg 36420
atgaggatag tagttagcat tgtctttctt tgataggttt gttaatgatc ataaaactga 36480
tttatttaaa gacatgtctt tttataacta ttttatactg ttgtatctgg aaacaaatat 36540
tgaatttcat ttgtcatgtg gaagaaatca actagtttta acctttgatt tataataaat 36600
caaccacttt catttattgt ctaatactgg caatgaacac agcctaatgt atcaaaacta 36660
acagaataaa aattctccaa gttatatcca gactttaaga cactttctaa ttatataaaa 36720
taaaatattt tgggcagtca ttttttaact ctgaaactat ttaaaactcc taatttagaa 36780
tatcttaata aatacccatt ttcctctttt tatttttata acttggtaaa aattgagtcc 36840
attgttttcc cagaacgctg ttcttaaaca aatggttacc tccttcatta gaactttact 36900
ttttttagga tttctaatta agaaaacatt aggcttgtaa cattgtcaaa tcttggtggt 36960
ctttcttcca cgtttttttga ggtcgattat ctaagaggcc atcagttaat aaagctatgc 37020
aggaaatgac atcatgccac atgtgaatat cctgtattaa aaattgtatc aatatactat 37080
tttataatta tgaagtggaa tgaattttag aaatagaaaa ggtgattttt tgtgcatagg 37140
tccaaactgt gttttgtttt catttcagaa tttcataata actatattgt ctccatatct 37200
taattgtgtt tttttatagc acttttgttt agtaatttgt atatgcttgg ctgtattctc 37260
agaggctgtt tctatttaat gttgtcaaaa cagctcataa aaagtgaaaa ttcggtcaga 37320
ctagttattt gatattatat atgaaatcaa aacaacctga aacattatct tttaatttaa 37380
ataaagaacc ccaaatttta atcaaatgta tgcaaaggca catagaatat atgacttaat 37440
gtacaacctt tattaacttg atgatggaaa cctgttccta gggaccttta cttgaataaa 37500
tgaaatatca agaaaaaata ctaacttaag aataataatt taataagtaa gtaagctatt 37560
atgatcttca atcagtcctg agagaatcat ggttgagaat tagaaaattt agaccagtaa 37620
gatcaacact gttaaaaaaa aaaaaaaatc agtatttttt ctccatattt tttatatatc 37680
tggatcattt tatttagcac ttattattgc actttccttt tcacttttta aactatgctg 37740
ttttattttt ctgagacatc tgatttactg aggaggaaaa tggaaatgcg gtacagagcc 37800
caagggtatg acggctttaa atgagtttcc atttctgttt taagttaacc atccctccct 37860
agcttacatc tgttcctttg ttgcaccctt ggtttaacat tattctcctc cccaatttcc 37920
tcttctcctc attgtgaact cgtggcaggg tctgcttggt gagctcattc tcttacaaca 37980
acaaattcaa gagcatgaag aggaagcgcg cagagccgct ggccaatata gcacgagcta 38040
tgcccaacag aagcgcaagg tgatggatgg tttaaggggg ctaccgatac attcacacta 38100
atcagccatt tctgccaaga tcatgtcacc tcaatctgtt catggactcc aaatacaaga 38160
aattaatttg acaaagtgaa aatataaaag atgcatcata taaatatgta acttttctgg 38220
agtgggtagt ataggtaaag ccaaaagaaa caaattcaag cagaggaatt ttggtttctg 38280
aaaattaggt tgtctgtagg gtccctgtat ttatacttag aacaaaatta ggaatttctg 38340
tttatgtggt ccagttattg agtcacccta agtttgtagg catcttacct acctacttgc 38400
tccccaagtt tttatttcta aaatgaaaag cattgctgta gatgaccagt ttacactaaa 38460
gaataacatt tatttatttg ttttagctaa agtatatgga cagggaacat tcatattctt 38520
gtagaagaaa attattttga cttttgggca aaagcatgta gttcttatac actttgacaa 38580
actcattgcg tacatttttc acattaatca aagtcagcac aaataaattt tcaccttgga 38640
ccacggaggg tttgaacact ggaaatttga tataattctg gttgctaaag aacaagttct 38700
aataaaagct taagtgtata ccaatatgtg gctgttggtg caatcagcag gtccgtaaaa 38760
atatgatttt aatggttagg taatcccaca acggagatcc caaagttcat gtttggaaga 38820
gacttttggg tcaaagtgaa atcagtgtaa tgaatttaaa attatactct gagatcttga 38880
aatcagctaa ttatgttaca tcttattagc tcagaaaagt tttgaagtta tatacaaatg 38940
ctagtcagga aaaaagattc agtcatgtaa ttcttgtaca ttctactatt taaatcaacc 39000
aatattatag attatgattt agtgcagtaa ttctgctggc taaccttatc tcatttggtg 39060
gtggttagta cttcagagta ctcaccatag tttcatttat gttttcagca tcacttcctg 39120
gtttttctca attccatggc tgtggaatca attcatatgt atatttagct tcggtgagca 39180
aaaacatagc tagaaaaaga aaagaagtga gtttcctacc tggttaaatt aaagtcgatg 39240
tgttaagcca aggaggactt cttttgaatg gtactttaac aatccctgtt ctgtatactg 39300
tgaatatatc atttaaatag cctaataaat tggatgctta ggctgagcca cctatacttt 39360
agttttgtta tggaaagaag ggagaggagc aagtatgttc ttatatgtta cttagaaata 39420
agaatgtagc tgtagttaca cattgttctt aagttttttt cgtaagacaa cttgaaatga 39480
gtcccatagg cctgctattt aacattctaa gatatgactt aaggttaatg atgagctttt 39540
gaatctgaca attcaagaga tatccataat gaatactgat tcattttcta cattgctgaa 39600
agctaatgtt cattttaagc ctactttagt agcctttatt tgggcttaga gatgttattc 39660
ctctttctga tatttattgg gttatctgtt taacccttttt atatctccct ttcccgattt 39720
gtaaattaga gactggcaag actttttacc ctgagtagag caccaaacat ggcttgtttc 39780
tgcccacact gtagttacct tgaggggaag taaatgggac tttaaaagca atttatgctc 39840
ttttatagtg aaattatccc tcttactatc ccgaaagact gttaccttac aatatcctcc 39900
actcctttcc ccctgtagtt actatagaga tgacttttcg gttcttcact gccataatga 39960
tcaaaatcct aattcatgag atttttatca ttccaggcat gtgaggttta cttgatgcat 40020
aaaaccgcaa gtacttttttg ttgtttttta attgtttttt ctctcttatc ttcttgaaag 40080
tctaagtaga tcatcatttt tgatgtctta ttagtagcaa ctaataaatt ttccctgtat 40140
cttctcagca aaagaactca agcagagaca gaagattaga actaccattg gtagttttgc 40200
ttcctatgga tatgttcaca tacatagaaa tttttacaat gacctttttta tatatgtatt 40260
tcagaatttc agaatggcct caatgcctta ataggaagaa atacttgaaa tttttaaatt 40320
agggcttggt tttgtgagga gctagtaaag gtttttctct ttcagcttta gcttgtttct 40380
gcggaggatt ccgctctttc tccatcagtt tcatagccct ggaattgtag aaaagctctg 40440
gtttcaagac cattgatatc catttctgtc agggtgagtt ttaaatttat ttcatgatgc 40500
aaacaatata ttgaacaaca ggacatgaac ttgttcttgt tgtaagtggc tgaattttat 40560
cagtaaagca catcaaaata aaatataccc caattgctag ttaagaccta gagtgacaga 40620
ttgaaaatag cttgtgttat tctcttaaga aaatatataa aaattatcat ctcatcaatc 40680
tttaatgttt gttttataaa tctaaatgtt tttatattgt ttcctaggaa atattaggtc 40740
taatttttta ctttaccacc agctgtcttt tattttactc tttttttgag acggagtttc 40800
gctcttgttg cttaggctag agtgcagtgg cactatctca gctcactgcg acctctgcct 40860
cccgggttca agcgattctc ctgcctcagt ctcccgagta gctgggatta caggcacatg 40920
ccactacacc aggctaattt tgtatttttta gtagagacgg ggtttcttca tgttggtcag 40980
gctggtctcg aactcccgac ctcaggtgat ccgcctgcct cggcctccca gagtgctggg 41040
attacaggca tgagccaccg cacctggcca gctgtctttt aatataacat tatgattaat 41100

-continued

```
tgtgatgttc cattaaacta agcggagagg aaacatgctg gtaaaccatg tgtgagttat  41160
tcattgtacc agaaaggcaa atgatacatt ttatcctaaa attcaaattt ataaacatct  41220
taacacttgt gatcattaaa tactactaat ctagcatata aattatattt gtaggcgggg  41280
cacggtggct cacgcctgta atcccagcac tttgggaggc tgaggtgggc agatcacgag  41340
gtcaggagat cgagaccatc ctggctaaca tggtgaaacc ccatctctac taaaaataca  41400
aaaaaaatta gctgggtgtg ctggcgggca cctgtagtcc cagctacttg ggaggctgag  41460
gcaggagaat ggcgtgaccc caggaggcag agcttccagc ctgggcgact ccgtctcaaa  41520
aaaaaagaaa aaagaaatta tatttgtaat attctactaa ccttatatca ttttaacttt  41580
ttatataact tttttatttt accaaattaa gttaaccttt tatagccctt ggcttatact  41640
aaacatccta actttttgt ttaattgtat tagtttttaa gttattgccc cagatgtcaa  41700
gtaatgttgg attttctata ataatttagg atatattgca tgaagtcagt tagtatttac  41760
atttaaaact aaaacaattt atactaatac agtttataca tttcatacta atttagctac  41820
agttggataa atatttaatg gaacaaagta aatcaaagta ccttttcaaa tgaattggaa  41880
attaaatcca cataacaatt ttttatgacc acactattac agtgtgatgg catgccaaat  41940
gatcataatg tggaattatg tatttcttca ttggctttca agattctgtt ctttagtttg  42000
tgggctcctc tccaacttgc ttgtctcctc acagtttagg cgactgttta taattcttgt  42060
ccatcctgca taaacacaca cagtcaaaat gaaaaaaagc ttctatcagc agatctgtgc  42120
ttgctgtaca gaaatgggaa aacaattgaa gtttgcatta tctttttct aattaccaga  42180
tcgtttttgg agctatttag gcatacgctt ttaaggaaaa aagaaaaaaa gagtgtacct  42240
tttgtttcta acaaaggttg ttatctatat tattgaaata aaaaattggg gatagttatg  42300
acaaagtatt tagaaatagg aattaaaatc ttaaaataac ttttcatagc atggacaaga  42360
cttattaatg tctacctcaa taagcaaatc atttaaaaat ttttcatgta tatttgctgc  42420
catgatgtgt tgtgattgct taaataacca atgaatgaag atcaacaagg atttaaatga  42480
agaagaatat ggatttaact attttctcct gtgaaataag ttcatattta caagttttga  42540
ttttcagaaa ttagacaatt atttttaaag gctgggatga caacttctgc ctcttaccaa  42600
gaagtcaaag cacagttatg tgaattcatc ataaatcaca tcatttttat tatattttgt  42660
atttataatt gtattgtgac tactttaaaa cctgttataa aataaaattg tttttaata  42720
ttttatttta gaattattag cattaataac aatttgaagt agtttacaca atacctgtga  42780
gttttatttt tgttttatat tgaaattaat tttagttgct ttacttggct tcattgctat  42840
ggatgcattc tctgtgttac gagttagcag atctttcctt ggaactgaat ttaaaagcaa  42900
gcatttggct ccacttaaat ctctgaaaat gcaacttgtt ctttgcattt attacataat  42960
tcgctactta tggtacagaa atggatacaa tacaaaaata tttccttata agatacactg  43020
tgaccaatga gctttttaaa tagctgtaat cagtaacatg tatttgactt ttcaaaacac  43080
atttctggag ggatatcagt gctttatttc cccaaatatc tgaatcccta tgctttagta  43140
caaaacaact tctgaagaat ttagtaacca tatgtgttga tctcttgttt ttctaactag  43200
tctttcataa gaaatgacta gaatagcaac agggaaatga ttgcctttta aggtttttgt  43260
ttctcaatat aaaattttgg tgaaccattt ttattgataa atacaggtat ttttactttc  43320
ttaaatcact tgatttaaaa ttactttgat taaatatgca tataaagtca gttgttttta  43380
actctcaata cttatcaaaa aaatttaact tgctgtacat tctgtataaa cctaattcta  43440
ttcaactaaa attattttaa acatttaggt gtcagacaaa gagaaaattg accaacttca  43500
```

```
ggaagaactt ctgcacactc aggtaatcat gatgactaag aaaaactagg gacttttaaa  43560
aattatattc gaatgtaact ttggtgatat ggacatttat tttttcaaca gagcaaaatt  43620
tggaaggtgt aatgatagaa ccttattatt atcgatagat gcaaaagcta attgagaaat  43680
aaggaataaa gacagaacta gataagtatg gagttaactc atttatatgt aaaaacctat  43740
tttgagtgaa tcttatgccc aaaagggaga aagtggcttg tccttatata aacttatgct  43800
tgcattttta cattgataag ctaatacagt taaagaaatt cgagttgagt ctaccacatc  43860
gttctagtgg gctctcagga acctttactt tgcttcgcaa gtctgaaagc agtcagacaa  43920
tgcttatcta aagctctttc tggcactact tagaaaagct attttcttat agttggtgat  43980
aaaattatta ctttaaggac ctattttgtg caatgtaatg agtgggtaac attctagtac  44040
aaaattaccc tatcacagcc aggcacggtg gctcacgcct gtaatcccaa cactttggga  44100
ggccgaagtg ggcggatcac aaggtcagga gatcgagacc atcctggcta acacagtgaa  44160
accccttctc tactaaaaat acaaaaaatt agctgggcgt ggtggcaggc gcctgtagtc  44220
ccagctactc aggaggctga ggcaggagaa tggtgtgaac ccaggaggcg gagcttgcag  44280
tgagcccaga tggcgccact gcactccagc ctgggcgaca gagcaagact ccatctcaaa  44340
aagaaaaaaa agttacccta ttactcaatc atcagttttt ctatataggt gacactgaca  44400
tgcattaatt aacttatttt ttaaagttca aagagttact atcagctggg catggtgggt  44460
catgcctgta atcccagcac tttgagaggc tgaggcagga ggatcgcttg agcccaggag  44520
tttgagacca gcttgggcaa cccggagaaa ccccgtatct ataaaaattt ttttaaaaat  44580
tagccaggtg tggtggttgt gcctgtagtc ccagcaactg ggaggctaag gcgggaggat  44640
cacttgagcc ccaggaggtc aaggctactg taagccatga ttgctccctg gccaatagag  44700
caagaccctg tctggaagaa aacaaaaaag aataagaaaa agagttaatc ttggatctct  44760
tttttgtgaa aaagtgaaac gactacaagt tgaatatctc ttatctgagg tgcttggggc  44820
cagcgtgttt tggatttcag atttttgaat tagggataat cagtcagtag tatgttttga  44880
gtcacaggtt tctttggtat ctatttattg agtctcaaac ctcactatac gctagactca  44940
cctgtgctct gagtggcact atatctatgt ttttaagggt tcctagccag gtgattccaa  45000
tctgcaacca ggggtaagag tcattggtca caaagcatag cctctggagc acattagaaa  45060
tgcacattct tgaccccatc ccataccttc tgaagaatca gaaactctgg gatgaaactc  45120
agcaatctgt ttttaaatgc cctcaagata attctgatgc attctaaagt ttgagaatta  45180
ttgttctaga gctttgagag acagctcaat agcacatctc ttcaggatgg ctacaaattg  45240
gcatctgtac caaaatgttt ccatccccag aaaatgtaga ccccaaaatt gattttgtgt  45300
ttacaaagaa atgagccagt ggaaattcta ccctcttata tgccttgata caaacccttc  45360
aatttgtgca attgtaattg tcagtcacta ggcactgata gactgtatta tggagaattc  45420
actgggttat ctatatcaat gatgtccaat agaaatatac aagccacctg tgtaattttt  45480
aatttttaca ttaaaaaggg gtaaaaagaa acgtggaatt agttttaata atatatttaa  45540
cccagtctat cccagatagt atcatttcaa catgtgatca gtataaaaaa tatgaatgag  45600
gtattttaca cttacagcac aacctcactt caggccagcc acatttcagg tgcttgataa  45660
ctacatgtgg ctagtagctg ccgtgttaaa caacacagat ctaatcctta gatactacca  45720
gaattttgtt aaatatacta ttactagata taaatgagtg agtttatgta aaaatatgtt  45780
tatagtagag tctagccagt agttctgcct gtctcatact atgtaggtgt tcaattatgt  45840
```

-continued

```
atgcgttctt ttaatttggc ttgagttgga cttgctgtaa ggatagaacc atgatttcct  45900
gttaattact ttgttcttga aagattccaa taagctaaaa aaattgtaag gaatattttt  45960
tattataaaa ggcatattat aagttggaca taaacattct gctggttgta agaatgggtt  46020
atttttaata gttttctctg tgttgttaat gtttagagaa gaaataaaag ctgggaagac  46080
aaattagaaa ggatcaaatt tatttgagac ggaaaatgtg tagacaagca actacttaca  46140
aaaaaaaaac ctgtttagac atattagtct tctttaaaaa tctgttttta tatgattctt  46200
tttgattttg gtgttttgtt ttgttttttt gtcaagtagt tgcttggcta cacattttcc  46260
ttctcaatta aatttggtcc tttctgattt gtcttcccag cttttttttgt cttcgccagg  46320
ctggagtgca gtggtgcaat cttggctcgc tgcaacctcc gcctcccggg ttcaagcgat  46380
tctcctgcct cagcctccct agtagctggg actacaggtg cccgccacga cgcctggcta  46440
atttttagta gagacagggt ttcaccatgt tggccagaat gctctcgatc tcttggcatc  46500
gtgatccgtc tgcctcggcc tcccaaagtg ctgggattac aggtgtgagc ctctgcgccc  46560
agcctatatc attttttgaa atagtaatat attatctctg gacatggaaa cataacaaaa  46620
catagaagag tttgagcctc tgacagccct ctattcaaaa ccctgctcct ctactaagtg  46680
accttggtca ggctctcaga tattcctcgc tctttattcc tagtctgtgt aattcctgct  46740
ttatggggtt tttgtgaagg ctaagggagt taatgcgttt gcaccactta ctaaggagtc  46800
tgtcacataa tgcatgcttg ggtactgcta gctattattt tatagcatct taattaaaat  46860
ctaaaataat gtgaagaaag ggaagaattt gaatttttgt taagtggccc tgtaatgtga  46920
agacttaaaa ttttgatata ataggaaata ctcccttcta gaatgtattt aagaactact  46980
tctttaaatt cttacgtttt cactatttca aaataatttt ttcaatgtga gtagcaagga  47040
attttccaag tgaaattctt aattatgata gaaaattaca atgatttcca ctgtttgtaa  47100
gagataatag tcattgttta ttttattcct aatgttttcg tagatgcttt taaaatgtaa  47160
tacattttaa ataggagata tgacttcaag attttggaag attttaattt agacttaata  47220
ctatttgata acccatcttt tgcttatata gttacactta ttattttatt gcagttgaag  47280
tatcagagaa tcttggaacg attagaaaag gagaacaaag aattgagaaa attagtattg  47340
cagaaagatg acaaaggcat tcatcataga aagcttaagg tattctaagt ttgtcttgtt  47400
tattctcaaa attttaccgc ttaacgttgt gtgttcatca gtaccagttt ctaaggagct  47460
gtaaagtatt ctgtcatcct tttctttcta acctaatgtg cttggaggat ggaggatctc  47520
ttcctatatt aagacatttt ataagttgta gtctccaaat acttgtttta tactatgccc  47580
ataaaatctt tacactttta agagttattt cgtgtgaatc agtttatttt tctgaaatat  47640
ctagtttatc tctaggctta acttttacat aaaattttat ataaaatcag aattgttaat  47700
tgatggacat gtaagtgact tatcatcatt gctttacttg tatgccagtg aatgattaga  47760
ccactttctt cagtttttaa aaaattaaca cttttcttct aaggagagct ttcttaggca  47820
tttcaaagaa ctttcgaaaa agtgtgtgct ggtattgtta ctatcagcac attggtgaac  47880
ttatttacca ataaatcaag tcttactatt ccccacccaa ctaaaccaca tgtgctaaat  47940
tgaattgaaa caattattta acttaaatct catataagta agcagagttt atatgtagca  48000
aaactgcagt aaatcatggc atgtacattc tgtagtcaag gtccaaagat aatacagttc  48060
tagcttaaca aacatgcatt agtagctttg actataaatc atgactgcat aaaacagata  48120
acatgactat ttacaagtgg cacttagaac tgagaaaagt catttccaag tgctaatata  48180
tgtagagttt acctcagaaa cagtattttc tctcataaaa tgcagtggca attaacattt  48240
```

```
tttgtttatt tttaggctgg tgggttggca attgcttgcc atttaatttt ttctagggat  48300
taagaaatga aaggaccctt aagccatcat tttgctcctg ccttagcatt aaaacttatc  48360
cataattatt aaatgcttga tggtacccct ttttttcagg cctgtgtatt tttttgttca  48420
ttcattcatc aaatttacat gaagcttgtt acacgcaatg caaggcacca cattcatttc  48480
tgattctaca gcaagaaacg atacaggata tttgcccttg ctacactcat atttcagcct  48540
gcccagttgt cagtggatac ttaaccaccc ttactggttt aacagtcttc ctggtttatc  48600
ctttattcag atgcttgctt gcacgtgctc tctgtcctct ctctttctct ctcatgcatg  48660
cctcaaactt agcaaagaat aatttcattg tcagttggtt acctgaccac cttttttttg  48720
ccttttggt gttaatggtc ttttcttgca ttcagtatta gctcatcagt attaagtaat  48780
aatttccatc ttatttaatt agaatgttag gaaatcctga attaatttac tttattaaat  48840
cattgtatct aaataaactg aatgagaaat ggacttttaa tctgtaccgt tttagttttt  48900
acgatgaaga tgtatttatg taatttgaga aaacagtaca atgattatgg aaaaacaatt  48960
tgaatttatc actttttct cttgacacat ctgttatatt tttttcttta cttttactgt  49020
tttatattat aactttttaa aatttttaca gaaatctttg attgacatgt attctgaagt  49080
tcttgatgtt ctctctgatt atgatgccag ttataatacg caagatcatc tgccacgggt  49140
atgtgaaaaa ttgatagtga acttgccaat tagcaaaaaa agaagcagct tagcttccta  49200
aaaattatgt gtatatatgt acacatacac atatatacat actagatgta ggcatttata  49260
tttttatgt aatcttacat gttccaagta atgtcttaag caatattatt tgactatttt  49320
agttcattat aaatattaat aaatataagt acattatatt tatgagttac tgtatgtgtt  49380
ataaaggaag atatttggct ttatatgtct taatattagt aatatttaaa tactgaacag  49440
tggattaaat tagccatatg cgtgaaattt aagctaatag aattgaaaat gtgtttgtaa  49500
acagtaaact agctatggaa aagatttatg gaaagttaat aacctggttt tagaaatact  49560
ggtttaaatt agcacaagtt tttaaaataa aaattaggct ataaacagtg gatccagtta  49620
tagttttgct gttcctattt tcaatgtgca cacatgcatc aatcaccatt tttttacgga  49680
ttttaaaata ttttttcacc tgtagaaatt ttaaaagact aaaaaactca gagcagcatt  49740
acaaataggt tttaatttta atttggtatc agaaaaatat gaataagtgt tctttgtttt  49800
gtgggaaggt tgttgtggtt ggagatcaga gtgctggaaa gactagtgtg ttggaaatga  49860
ttgcccaagc tcgaatattc ccaagaggat ctggggagat gatgacacgt tctccagtta  49920
aggtaagaac ataggccgtc tcagtgaggt tccttaggag agtaactgct tcagtgagac  49980
ctgttcattg tgttgaaatg aggactttta accaaagaaa gacttgatac atagtgtttg  50040
gaatgatccc tagtgtggaa atcagtagaa ggcacagcca ggaggccagt gtggcaggag  50100
ctgagtgagg ggagagtggt aggagaggat gacagagacc cagttgggag gcctttggat  50160
tttattctga ataagataag agagaagtta agagaatgag aatattggaa gtggagtcaa  50220
tgaatataga taattttcta gttttattgt gacaaaagag cagagaaatg aagcagtagc  50280
aattgaatat tgttgaatta agggaaggtt tttaaccctt ttcctgttta gaaaaaaagt  50340
gcagctcaac accagtgctc atttaatttt acgtaaacac actctctgaa gctgaagcaa  50400
atctgactaa ttttcaatgt gaaaataaaa tataaaaact gttcttagag ttatttctaa  50460
acagtactaa catcagaatc gtcccaatca tcagaatgtc tgttttttaa aagtcagatt  50520
tatcaaatca atcttcggcc aacaactttt tgagaatgat gtaaacatca cacataggaa  50580
```

-continued

```
ttccgcattt tctaggattt gacattttca gctattgaaa attactatat tttgtaaatg  50640
gacgtaccgc tactaaaaac agaatgcttg aaatagaatg tcttttgttt ccaaagtcag  50700
tacactagag ctatgtgaaa ataatcataa aagtgaagat attttatggc agagttatgt  50760
tggggcaaat gctgcagctg caagcggtgc tggcaaatat tgtcggagca agtgggaaaa  50820
ggattaaaga tgtttatatg ctgattataa tgatctaata aaggggggaa atgatgcaag  50880
agagagggaa aattgcaaga gcaaagttac tgaggtgaag gagattgtga cttggtgtac  50940
tagtccatat ctgggagcac tgacaatttc tccagggtca caggaagaag gtatggggct  51000
gcagagtctt tcattgaaca gatatttacg gaatgcttaa tatgtaccag tagcattcta  51060
ggcaatatgt tggtaaacag caacaacaaa gaagaacctt gccttaatgg agggtatgtt  51120
ctagtagagg gagacagata atagataata aatataatac ataattgtat agtaggttag  51180
aaggcaatag tgttgtacaa caagaaaaag cagaaccagg caaggagaat gagggtgcca  51240
gagtattcat agattgcatt gataaggtgg catttgaacc aagatttgca gaaagtgagg  51300
gagtagtcct gaggatatcc tgtgttcagc aaggagaata gctgatgcaa agcctctgag  51360
gtggttgtgt ggctgtcatg ttcaaggaac aacaaagagg cctgtgtggt caggtcgggg  51420
tgaagagcta gccatggtcg gggcaaatga tgacattaga ggaataatga agagcgggga  51480
ggaacagatc aataaggcct tataggccat tgtacagact tccgttttaa gtaaaatgga  51540
aagccagtgc aggatttcga gcaaagtaac aaaagtgcct tttaaaaggc tgctcttttg  51600
aaaatagttg tagccaagat gtagaaccag ggagtctagg ctactggagt atccaggtga  51660
tacttgggct agggaagtag cagtgaaact ggtaagaaat ggatagatta taaatgtgtt  51720
ttgaaagtag aattaacagg atttcttgac aggtttgata tggagagggg agagaagaaa  51780
agcaatgggg agagagagag agagtgtcaa tcatcaatga tgcctccagg gtctttagcc  51840
tgaacaaatt gaaggatgta gtttgcatgg aagtctgtca gtggatcagg tttgggggaa  51900
gaagatcagg agttcagttt tggacttgct gagtggtgat aacaagcagt tgggtataca  51960
agtttagaca gaggtgtggg ccagagacat acatttagga gtcatgatca actatctaaa  52020
agtagtattt aaagtcatga tcttactgga gaagatcttc aagggagtga gtagagatag  52080
agaaaacaca gaagcaagca gtatattctg ggcactctga acattaagat gttgagggaa  52140
gagaaaataa caaaggaatg tgtgaaggcc caaccagtat agtaagaggg aaagcagagc  52200
aggacagtgt gcgcaaagtc aggtaaacaa aaagaaaaca tggaggagga gggagtgctc  52260
agtgaggtca catgctgctg atccatcaag gaaggtgaac atagaaacca gtcgttgagt  52320
tcaccagtgg aggcaagaaa ggggaacgtg tggaagtttc cttctgattg cttccgctta  52380
ctcagtgaaa tactaagcca gatgatcagc tgttaattag aaaggagaag agattaaaga  52440
ctgaggcagg aagaaaaagt gaagtctgtt aacagatcgt ggtgactcta ggagtgaatc  52500
agtggagaaa gtcaagtgat attaggatta ctgaggtgga ctgaagtccc tttaagttct  52560
gtggacataa attttaaatg aatcattatg attgtgtttt gtttttttca tgtttagctg  52620
gtgggggggta ggtgtagaat aattggaaga ttgaaattac caagaattat ggcaagaata  52680
gtgggagaaa gacagtgagg ctgatgctga aatcttcaag aaatgaaatc tgtttacaag  52740
tgcaacaggg tatgggcagc ctagtgtgat tcatctagat tgcacttttg tgggtctagc  52800
tatggattga atcgtgttat gtgttactag ttctgtgtgt ggtactgtgt gactgtacca  52860
gactttacat atccatttta ctaccgatgg gaatttgggg tacatctaac ctagagaaaa  52920
aaacaaaatg aacctcagac tacacctcat atcctgttca ataatcagtt gtaaaaacat  52980
```

-continued

```
gggagagaaa cctacctttt acattgttac tagcatccta attgtagaag ctgtggatga  53040
tacttcaaga agaaattaat tttgttttgg caggcagggt gtggacaggt ttccttgaaa  53100
cagatgaggc tggtctcttt ccggtttgtc attagtccct tagtgtttac tagagcttct  53160
ccttgaccaa ccctgaattc cagtttttttg tttccctaga gcagtgaaag tgccaaaacc  53220
ccagcttagc attttaacct ccttagcagc ttctttctgc ttggtttcct aaaatgtgaa  53280
tgccgtgaaa ggaaattgtg cgcaggatgt agggttttgt tttgttttgg aggtttattt  53340
ctgcagttca tttttctttg ggattgtggc accttaagac gtgactactt aataactcgg  53400
aattccaatc ttgtctactc aacccagtga aactgctaca cattttaagt ttttctcttg  53460
ggcctttgcc ctgtgctaca aatcagcaaa tcctctgatg gaaaatagct aaacagcttt  53520
ccaacagctg tttattgttt ttaaatttag cctgtttagc taatctcagt agaaggaatt  53580
gtatttttaa agtaaaataa ctatagagaa gctagaaagg tgtcaattag gcatttagaa  53640
gttcttgtga aaccactgac tgttaatata cattgctata acatttcttg gctgggtgca  53700
gtggctcatg cctgtaatcc cagcactttg ggaggctgag gagggcggat cacctgaggt  53760
caagagttca agaccagcct ggccaacatg gcgaaaccct gtctctacta aaagtacaaa  53820
aaacttgcca ggtgtggtgg cgggcatctg taatcccagc tactcgggag gctgaggcag  53880
gagaatcacc tgaaaccgcg aagtggaggt tgcagtgagc cgagatcatg ccactgcact  53940
tcagcctggg cgacagaatg agactcggtc tcaaaacaaa caaaaaaaca aacaaaacaa  54000
aatttcttac ccaaatatca ctccttgagt gaagcctgtc gtagctccct tatcatcagt  54060
tccattctct tctgtggcac cctaggtttt gtcactctct tctattatgt ctgtgtatat  54120
ttctcccagc atgtgatgag gtctaaaact gggacagtca gctctgtgtt tccccaccta  54180
caacacctga cacatagttc actctctata gaggttgaat gaatgaattg tcctttacct  54240
aaattcatct ttgaggttaa atgcaaggtt tccttttagt gtttcaagtt ttagagagat  54300
gattttgggc ttagtgctgt gtatagcatt gactggggaa agaaagaggc agcagcattt  54360
taggtcataa gcgatataaa ggaaccagca ttcttgttgg gaaatcacaa catatatgac  54420
atatatacaa acaatacaaa tacaaaatta ttgtcttgtc agaactacca tgttgacagc  54480
ttcagggggt gccccagcag tagtgtgaag ggactcttgg atttgtgcaa tgcagtagcc  54540
ctgtctagac cacatacggg ctgtgggaat taatattact tataaataca tcattacctc  54600
tcagttttct gttactatca ggtgactctg agtgaaggtc ctcaccatgt ggccctattt  54660
aaagatagtt ctcgggagtt tgatcttacc aaagaagaag atgtaagtaa aattcatcta  54720
aggttgatat gtgtaatttt ataacctgga tgagcttata aaagacagtt aaagaatatt  54780
tgtgaattaa gattttctta gattttctta ggattttgtg ttttccatta gcttgcagca  54840
ttaagacatg aaatagaact tcgaatgagg aaaaatgtga aagaaggctg taccgttagc  54900
cctgaggtaa gggttgcaat tcatttcagt gacgttttat ggaaattaaa tgtttatgat  54960
ttcaaataaa tcaaaatcta ggtattgatg tttagattgc tgctatctag atatgtagag  55020
cttttaaaaa aaaatccaaa taatatatca ttttgtgggt aattttccag aataattact  55080
tttaggatca gagaaagaat accatttttg tgagcgtctt atctgaatgg atgagatata  55140
gaatttttag aatacatttc accaaaaaaa attcttgaca aattcccccc aaactttagc  55200
attgttttat ttttattttt cctgagtaga ccatatcctt aaatgtaaaa ggccctggac  55260
tacagaggat ggtgcttgtt gacttaccag gtgtgattaa tgtaagtata tacaaaacat  55320
```

-continued

```
gtattttatt ttattcttat tgtgtgaagc atttataatg acatttaaaa ccttttttctt  55380
taagactgtg acatcaggca tggctcctga cacaaaggaa actattttca gtatcagcaa  55440
agcttacatg cagaatccta atgccatcat actgtgtatt caaggtaaat catatcaaaa  55500
gattttaatg tactgatatg ttttcttctt tagcaatcca agctttgcat taaatagttt  55560
gtgttatgta aacatacaag ataaatgcat ttttgccttc tcttcgtatt cattttatta  55620
gtaaattaaa ttgaagttga aattattttg ataagtttta cataagcatc attgaaattt  55680
ttatcggcta ggatttcttt ttagtaaata acgtaaatgt attaaaatct ttcttgctat  55740
aatgtagaca caggggtata atttgtactg agttttaaaa gtctacttta catcttaaaa  55800
ttccacagtg tcattttttt attttttttca gatggatctg tggatgctga acgcagtatt  55860
gttacagact tggtcagtca aatggaccct catggaagga gaaccatatt cgttttgacc  55920
aaagtagacc tggcagagaa aaatgtagcc agtccaagca gggtgaggtc aaattctttg  55980
ttgcgagaat agattctttg taaaagctcc agctgtgata gggatttgtt atttaaaaaa  56040
acaacaacaa caacaaaaaa acaccttaca actaagattt attacaatga aaggataaag  56100
caaaatcaca aaaggaaatg gtacatggta tgaagtctga aggaaaccag gctcacgttt  56160
ttccactagt tcattcccag tagactctac tgggcacatt taattcctcc agcaacaagc  56220
tgcttgttag agactcagct cctaaggttt tcatcggagg ttagtcattt cggcaccctc  56280
atgtaccaaa attatttcat actcccaaaa ggaaagcata tgttataatt aaaccacatt  56340
acttcagtag tgagccactg ttatataagg aaaggtttat atcagtgtag ggaactgttt  56400
accagttaag ttttcagata ccagccaaag acaggcaggc ctttttaagg acagtagtct  56460
caggcctgct gtgttaaccc ttttctaggt agccaccata acctctgttc tgctttcttt  56520
ttaagggtaa ggcctgccgt ggcattaatg gttctgatat ggagaagggg agaagtgagg  56580
tagaaacaaa tttctgtggc ctcctcccca tctttcttca ttcctttcat ttctttcaac  56640
tctaggatag tgagtttata tttcttctga gatgcaactg aagcttattt cagtcctttt  56700
tgtataaaag attcagcatt agcttaggtg taacttgtct taaaggaggg attctcatcc  56760
cattattaat ctgaatgggc ttcagggggt agaaactcta acatatgtga aaggtctcta  56820
tgcaaatatg catttttctg ggtacatagt cttttttttt ttttagtcac atttagaaat  56880
ggatttttga tcctaaaaga gttgagaagc agtggatcca aatattaaag aagaaggtgg  56940
gaggggagga aggagtaaaa gaagacaatc cagcttggtt agaatttaga tatttgaaga  57000
aagtatggaa aaataataat agctaccatt tattgagtgc ttcatgcctg gcactgtatc  57060
atattgtccc ataatctcac caaccttttt gaaaaaatta agttgtttac ttaaggtcgc  57120
ataactacta ggcagcagag caggaattca aactaaggtc tgtctgactt taaagaacta  57180
cacatcattc cgggttttcg atacgtgtgt tttaataata cattttcaat gtagtaaaat  57240
taaatgtatt tttttcaaat agcaatggaa aaacatttta aatgcttttg tgcagattta  57300
tttaactata tacatgtata gcattatttt gctttctaaa ttgtatatta cgcttttaaa  57360
acttatgtaa actatatctc acattaattt ttcccacttt taaaaataga ttcagcagat  57420
aattgaagga aagctcttcc caatgaaagc tttaggttat tttgctgttg taacaggaaa  57480
aggtatgcaa agatggatta taataactta tttttagttt ctgttgtttt caaataataa  57540
agagtaattt tcttgatgaa aatttgacca tcattcttcc ccagggaaca gctctgaaag  57600
cattgaagct ataagagaat atgaagaaga gttttttcag aattcaaagc tcctaaagta  57660
ggtatcttgt taaaacattt aaacatttta cagtaagaga gtagcttaaa ttgaactgtt  57720
```

ttcacttaaa acatcaggtt ttataactat tagtttaaca tcggatttct agaatttttc 57780
ccaaatagtg aactgtatct aataaacaag tccttagcta ctttttggca gaattgagag 57840
cagtttatca catggtacaa tacatactgg catgcttcct tggacgtggg cactgaaaga 57900
caacatagat atctgcctct tactttattt tacttataaa gtggttttag aaaatcgacg 57960
ctttcacttt taaacgtgta catatttctc ttacagtatt ggggaagatt ggagtggggt 58020
tgtcgaagaa gtatccctag atatatattg acaggagata agataagcaa aaagagctaa 58080
aggccagttg tattactgta tactaaaact ttatatgttg agtttctgga aatagaaaag 58140
tatgtttgtt cctaggttag tacggtaagt caagatagtt cttgcaaacc ataatcttac 58200
gtgctttggg gagtgcactg acaacatata gaactgtgct gtctaatatg gtatcactag 58260
ttttgtgtag ttattaaaat ttaaattagt tggaattaaa ttaatttctg gaagatggct 58320
ttcttcatgt tctttttaaa ggcatggtgg ctcacacctg taatcccagt actttgagag 58380
gccaaggcag gcggatcact tgaggccagg agtttgagac cagcctgtcc aacatggtga 58440
aaccccatct ctactaaaag tacaaaaaaa attagctggg catggcgatg ggcagctgta 58500
accccagcta ctcaggaggc tgaggcggga gaatcgcttg aaccccgagg gggtgggggg 58560
cggaagttgt agtgacccaa tatcacgcca ctgcactcca gcccggacga cagtgcaaga 58620
ttccaattca aaaaaataat aaaataaaat ataacattaa atttaaatta gttaaaattc 58680
aacaaaattc aaaatacagt tcctcagtta cactagccac acatttccag ggctcaataa 58740
cccagtgtgc cagtagctac cgtattggaa tgttttcctc ctcacataaa tttttattga 58800
acagcactgg tatgaaaggt aagagtggct gttagcaagc acattcgcag acttggtggt 58860
agtattgttg tcctttttgt cattttaata tactttagct cttgttattt ttttttaata 58920
ggacaagcat gctaaaggca caccaagtga ctacaagaaa tttaagcctt gcagtatcag 58980
actgcttttg gaaaatggta cgagagtctg ttgaacaaca ggctgatagt ttcaaaggta 59040
agttggattt tttaaagaag caagcaaatt aagacatttt attagctggc aatctttggc 59100
atccatacga ttctgtactt ctttccttta acagttgctt ggtagttcat ttacaattag 59160
acagtatctg gaaaatagaa gaatacaaac cttcagttgt tatacaagaa caagattttt 59220
cctttcagag gaaacatctc tagaaacaca tttgcagagt tcaaacagat gagaacattt 59280
gctagtgctt ggaagtacac aataaactat agagaattct agattcaccc tgttgaggat 59340
gaaggagcag atgtgttggg aagcagagcc ctctgaactt cctttacttg gcaccatttc 59400
ctgaatccca cactttcctg ctcagtgtct tttatcggaa gagaatatat ttgctttctc 59460
ttttcccata tgtaaatcct acctgatcct acctatttat gccagttagt ccctctgcaa 59520
tcttgtatta ctttcatttc cattttacag aagaggaaac agaagacagt tacttaccca 59580
aataacttat cctattaccc agtgtcacac aacatgggta ataggcccag gatttggctg 59640
ttggtggtac aactgcagag tccattctct cagcagctct atggtactaa actacttcag 59700
ctgtgtgcta atggatttaa catggagaaa ctagaatcag ggagaatagt tttgaaagct 59760
attgcaaaaa tgaaattctg agacgttgag atcccagagt actaaggggt cataggcgca 59820
ctctcagaaa ttcagttaat acagaggata tgtattttaa ccactttaac cactacatct 59880
ggaaagaagg agggtcatca aacttgaact tttccttctt cctcagcaac acgttttaac 59940
cttgaaactg aatggaagaa taactatcct cgcctgcggg aacttgaccg ggtaatattt 60000
ggatactcgt gtattttgta tatatcttaa tttaatgttg tttgctaact aaatttatgt 60060

```
tgagagaaaa atctgataag ctaaagtact ttggttttga ctataactac taatttgtaa  60120
gaatacatct ctaggagcag ttatctcttt cagtaattta aattatttat tatataacat  60180
taaaaatgga ttataagatg tcaaaacaag tgttgaaagt gttttctgag aaggtaatga  60240
atgtgcttta aaggttttgt agaattcgtg tattcctgta atttagtggg aattaaacat  60300
tgtttttcct tgattttaaa atccccatta gttaataaaa cacagcatta atatatagtt  60360
actgatgtac taaattaata tgtattgatg ctttcacata acgtgaacaa gtgttatgtg  60420
aaaaactgca ttcaaacttg agaaggtaga tatttatgtc agtttctttg tccttatctg  60480
cataatggca ttcctaaaaa aaaacactag aagtgcattt ttgctagtca tgtataatta  60540
aacccaaatt cagcctagtc aaaaacctcc ctttggttat ctctgaaaat catgacaggg  60600
taaatttact gtcttatgga aatcttactt acttgtattt atattgccta gaatgaacta  60660
tttgaaaaag ctaaaaatga aatccttgat gaagttatca gtctgagcca ggttacacca  60720
aaacattggt aagtatttga tattaatctc ttttctgaaa gactttactg tacaggttat  60780
aatgaaatgc taaaacttag attgataaag cagtgattta ttgttgcctt ggctcatagg  60840
caaaaacgta atagtatatt tttttggcaa tatctaacta cttttgtagt ctaaccagtt  60900
gaatttcttc atgttctttt taaatcttga ttctctttgc cttttcttta tcttatacct  60960
aataaatacg taatcatgat ttctgtaaaa tcctttgggc agaagttttg tcaaattata  61020
ctttaggtaa atatcaacct gtcaaaattg atttataaag ggagttggta tatattttca  61080
ggttctccat tctgagtaag aacagttagt gctttctgta acatgtggtt aatatgttgt  61140
atacaaatca cattttgaac ttaatgctat taatacttga aatttttaaa aatagcaagt  61200
aaatgcacct ttttgaaaaa tatgttaatc ttttctaagg caaactgtta ccttcagttt  61260
atattttatg taagtttggc cattcctaaa ttcagtggaa tgagacacgg taaaacaagc  61320
tatgtataaa tagccttgac atttttgtag tcacatgtta attaacaaat tcctcatgca  61380
gaaattatct ttctaatgaa gactgtggta tttttaagaa tttatttttg gagcagagct  61440
atcctcactg ccattcattg taaatatttt ctgtacctag tctattcact cagttaaagg  61500
ttatcaaaag tgagcctaga tagtagtatc tggtctgttt gaattcagca tcactagttt  61560
cctcatttca gtgccctttc ttcctcagtg gtgaaacctc ttctatcttc aagtagtcca  61620
catttgcctg tttttaatct ccgttcctta tccaaaaaaa gagatctaat tgtatctatt  61680
cttgttgatt aatcaaacat tgttatgaca caacttatgt ttgtttattt gtatcttagc  61740
ccagttccat ggctttgtgt cagtcagctt tcaagttaca aagagatata taggtttaca  61800
gattgagtat aatactagtt gccttgctag attgtatgag ggcatttaat gtatataaaa  61860
gtgatatgta aactgtaaca actaataatg ctgtttatgg ggagaaaatg tggtccttct  61920
ataaattaat ttttggtatc atcaaatgga aaggttagtt ttgtttggac agagcaaccc  61980
tgaaatcaaa gtatttcttc actaaagtga gccttgaaga taaatgtaat ttatttaata  62040
caaaggtaac tgaagagaat tgtgagggga cagtgaacgc ataccaccag attgcccatt  62100
gaaaaggcaa cggtcagatc tgggacatct ggctgctaga gatttacttg tgtaagctgc  62160
cggatcatat atgattctct gtgttttcag actgtagagg ctgaaaaaat gttatgttaa  62220
cgcaaatata aatcagagta gcaggtccaa gccttagctg ttcataccac attgaattca  62280
agtacattac accccaaata ttttccacat attttattat tttgacatag ttgatgttgt  62340
cttgaagttt ttattggtat ctttttgctg aataatccta tgtgatattt taggacactg  62400
cctaaaatgt ttacaattat ttaagtcata agactgtttg atctatattt ggttatctgg  62460
```

aaagtgttaa aagcatttta tgtcataaca tgacagtttg ttatttcctt tagacattcc 62520
actgtccttc agttaagttt taggaaggtt attaggggta tagatttgac atataataca 62580
ttatagtagg aaatactcac tcagcatttt tacgctgtgc ctggttttca agagtgaatc 62640
actgacattc agaaggagat attgatatat cattaacatc atgtgaccag caatgtagac 62700
atatcttttc tagaaggata gctggctagc ttcacagaaa tacatttttt ctaaaaatgc 62760
tactatggta catttttaga aattctcgga cttcagaaat caaagatttg caatatcata 62820
atttgaaatt taaaacatga ataagtgtta aggcagaggc aggaatatgg taagggccac 62880
gagatgagaa caagaaaggc gacacaggta gctgtgtcct gtggctttaa cataaatggg 62940
ggcaagaggc aggagataaa acagtagatg taagcaaaat attgggttta ttaaccatat 63000
tcagaagctt agtgtgtatt ccataagcag taggggagg gtggtcactg aagaggatta 63060
ggtcaggttt gcattttaga aaggtctttg tagtaggcaa aatggaatac aggcggagaa 63120
aactgtaagc aaggaggcag ttggcttttg caataattta ggcaagatgt gatcatggct 63180
taaacttgga tagtgagtgg tagtacaggt agagaagaga cacttgtgag atacttgaga 63240
ggttacctaa aagatagaat tgacaggatt tagtgattgt gtagataatg aagagtctat 63300
taaataatga gtatgtttat attcagtaat tacattgcta ggaatatatg caaatgatat 63360
atttgacaaa gatgaacaca caagaccttt caccttgatt ttttaaataa atgtgaagaa 63420
atggaaagca atttatgtgt cccatttgga attatatagt atttggttta tatagagcag 63480
attactgctc tatggataga agtagccttt gaaaagtata ggatgttgac atggaaaact 63540
aaatacaata tacttttaga tttaaaaaag ggatttataa aacagtatgt ataattatga 63600
accacttgtg taaatacaca caaatagtta cgtagacata attttttaa taataaaacc 63660
ataaatagtg gttatcttat aaaagaggaa ctatggggta cttcttacat tttctgtatt 63720
ggttgaaatt attatatgga gtataatagt cctctacttt aaaataaaaa aaaatccatt 63780
ttaaaaagaa tttaattaaa gtggaatgta ggtaaagttt ctgtagataa agaaggcaat 63840
aaaactatta cctttattat attttgctaa ttatattttg tgtattagta gaagttatcc 63900
ctggttgatg gcaaaacctg gaatagagaa gtcacctata ataacacaga atatagtcca 63960
ggcacggtgg ctcatgcctg taatcccagc actttgggag gcccctatgg tcggatcact 64020
taagctcagg aattcaagac caacctgggc aacatggtga aaccctgtc tctaataaat 64080
atacaaaaat tagccaggca tggtggtgca cgcttgtaat cccatctact tgggtggctg 64140
aagtgggaga atcgcttgaa cccaggaagc ggaggttgct gtgagccgag actgtgccac 64200
tgcacttcag cctgggtgac agagtgagac cctgtctgaa aacaaacaaa caaaaaaaaa 64260
aaaccataga atataggctg ggaaaattgt tagatgatag cagcaagcaa taaggtagca 64320
gatgacataa ctagatgaag tggcttcaca gtgtaatggt ttttatatga acattgagaa 64380
ctgatggttc agaagagaga ctggggtgag gaggacttaa cttctacttt ctaactctga 64440
aggccattta actgctgaat agcttcatct cagcagaatt tgaggacaga ggacaatcac 64500
tttccttaag gaaaggtttg gaggtaagaa tagggaaaga gaatgagagt gtaaaatggt 64560
ttgtcatgga accgggtatt acaggagcac aacagaaatt gttgggatgg aggggagcag 64620
tgggagtctg agacagagga cagcagcttg gcgatgaaag gcaggagagg ctgggcaagg 64680
agaagtgata acagctgcat ctgtggatgt caaagcagca acctcccttg agaaagttgc 64740
ctttagcttc tcgggatttg gtaatcagga ttttaaaaag ggtgtcaggg atatggattc 64800

-continued

```
ctggcccaca gactccaggg aaaaataaca gactatgtct cttctgaagc aggatgagaa  64860
aaaagccctg gaggtcagag gctggatcct ggtcttcagt tcaactttca gtaatcttct  64920
tgagattgtg tataaagtgg tatctgaaga ggaggccctg acaggctgct tttcttcatc  64980
ttgctcctta aattctccca ctctctgtca ttaactcagt gactaaattg tctttgtcct  65040
tttgggcccc agtcatatat cctcctcaga ctctgatttc tttactggtt gtaactggaa  65100
agtgacctga aagttagcag tgggaaacca ggatctgtgt tgattgattc agtagactta  65160
attttacaca aaatgtttag taaatagtct tggagggtag gagatgttga ctctcctcac  65220
cagagaagtt cagctgggct tttggacagc aggatatttc tgctaccctg agatttgtgg  65280
ctatatccta aagggttgag attattctta agaaggatcc cctgataagc agagtttttt  65340
ttttatattg tagtattcta agtttattac ccaaataaat atttccttga gatttcaaat  65400
tgaaatagtt gtattttttt attagtgacc catgttcttt taagatgtct ttcaaggcag  65460
aattttcaac atgattatgc atcttttaca ttgttacctt aatcatgaat tattgaaaaa  65520
ttttatctac agcattctat aacatctctg tgctgtgatc tgataagttg tcatatttat  65580
accaagaaat tttcagtctc agactctccc gtaagcacat gaagtatatg ttaatactag  65640
gcagataagt gtgcatgaaa agatgctcag aattattagt cattagagaa atacaacgta  65700
aaaccacaat gaccactata aacttactaa aatggctaca attttaaatg acagactata  65760
ccaagtgttg gcaaggatgt agaggatcta gaactctcat tctctgctag tggaaatgta  65820
aactgaggca aacatttcaa aaaaaaatta aacatgtaat taccatatga tccaaacatt  65880
ccactcttag gtatttacct aagaggaatg aaagcatgtg ttcataagaa agacttgtac  65940
gtgaattctc atagcagctt tatttgtagt agccaaaagc tggaaacagc ctaagggtct  66000
atcaacacaa gaatggataa acacattcat gcaacataat actacacaga aataaaaaga  66060
agtgaaatat tgctagatgc ggtgtctcac acttgtaatc ccaacacttt gggaggccaa  66120
ggcaagagga ttgcttgagc ccaggagttc aagaccagcc tcagcaacat agtgagaccc  66180
catctctaca aaattttaaa aaattagcca ggcataatgg cgtccacctg tagtcccacc  66240
tactcgggag gataaggtgg gaggatggct tgagcccagg aggttgaggc tccagtgagc  66300
catgaatgtg ccactgtact ccatccagcc tgggcaacta agcaagaccc tgtctcaaaa  66360
aaaaaaaaag tgaaatatta atacatacaa cagcatgatg aacctcaaaa taattatgct  66420
ggagtggaag aacaaagaca aaaaaagagt atatgccaca tgattgcatt tatataaatt  66480
tctagaaaat acaaagtaat cacagtgaca gaaagcagtt ccagtggtta caactttttga  66540
ggatgatgga tgcgttcatt atcttgactg gtgcgattta caggtatata cacatgtgaa  66600
aacttatcaa aattttaaat atgtacagtt tattataagt taatgatact tcagtcaagc  66660
tgtttttaaa aacaatatta tatttagatt tggtgctttt gatacttttt tatttcaggg  66720
aggaaatcct tcaacaatct ttgtgggaaa gagtatcaac tcatgtgatt gaaaacatct  66780
accttccagc tgcgcagacc atgaattcag gaacttttaa caccacagtg gatatcaagc  66840
ttaaacagtg gactgataaa caacttccta ataaagcagt agaggttagg atataattta  66900
attaaatggg taagaagcat tatctgaagg gagtaggagc tgtgaatttt agattttatt  66960
cccatcacag cctctatctt tcttttaggt ctttatatct catttattct ttattcctca  67020
tctctgtttt gggactaacc ttaatgttgc taccagttac tacggttata aaaatttact  67080
aattggtatg atgttggcct gagggtattg gtacttcttc caaagacaat atttaacaag  67140
caaattttgc ttgaatatga aatatttgct tgagtatttg cttgaatgtg aaatattttg  67200
```

aacattttct gtggattctg tggattatag agattccata aagaaaatac ttaatagatg 67260
aagcatttca tctgagctca gttatactta aattatcatt ttcttaggat cctgacagaa 67320
gattaaacta ggaattatta aaaaacaaaa caaaacaaaa caaaaaacta ccttaaagaa 67380
tctatttctg ctaccatgta tcttggcttt atcacttaat agctgtgtga tcctttgcct 67440
agttgcttaa ctttcctatg tgttttttca tctataaaat ggtgacaata atgttgccta 67500
cctcacagca ttgttataag gattaagtaa gtaattatat gtaaaatact tagacaatgc 67560
ccagcccatg gtaactgctc agggaatgga cctgctgtta ttatggtcct catcatctga 67620
attgatccat catgtacatc accccataaa cagcgattgt tcaagctaag agtcagtgtg 67680
tcctgtgctt gtgtgtgagg ttgctcacaa aattgaagtc aatgttaaaa gtaattttgt 67740
ttttcatacc tatcttaaag gcagtgtcag tttctaatta ttcggatgtg atttcacccc 67800
tttcctatct tgctccagtg ttaacttcct tatctctgtt ctcaatttct tcaagcccct 67860
ttctaagaac tccagcagcc tccctgccta agttgcacgt tgctgagccc tggcagttct 67920
tgacacattt accccctgaag aagttagaga gctgctgcta ccccttcagt agctctcatt 67980
actggcacta acattttttc tgcgccctgt cccatgatag gatattttca catcctaagg 68040
ttcaagcagt ggaagtggtt atgaaagcat caatttttct ttccactgct gctttctgtc 68100
cctcagcact aggtgtcatg gaaagaatgt agatctggtg agaaggtcag gaaacatgga 68160
tcttaatact caccccacca ctcactccgt atttttggac agtcactttc ttttttaaaa 68220
tgagagaggg ctaaaatcca gcattaaaaa gcccacatag ttataagtag attttgttct 68280
tcattatttt tgacactgtg ctcttccttt caccgttcag atcattagga gttagctata 68340
atacaaagct gaatactctt cggctatgtt ttaaagtgtt ggtgcattgc ttcatatctt 68400
tgcttaaaga caaagctatg aagatgactg aatcattaag acatttaaaa ccttttgcag 68460
tgtgaaagaa gcagtcagac tcatgtctta gaggttgaaa taaataaatg aactaacttg 68520
ggtggcaggc ttagaataca taccttatct tgaagagaca gccctgttca gctacagtag 68580
gtggtgtcat gtaggaatat gggtatatcc ttctcagtta gtccaagaga agccgtaaat 68640
gcagactttt atatgaaatc tctcaatttt taaatattag catgcaattt taaaaatgag 68700
aaccgctata catgtctagg aaaacatacc aggaagccat atctgtcccc agcaacccgt 68760
gtgagacctc tacatcatgg tttatatttg cctttttgtt aatgtagttt cacatatatt 68820
ttctgataag ctgatttatt tatcacatct gtttggcttg agctcgtgtt atttttcatg 68880
ttaaccattg aagtatgtag taataaatatg gcttttttttc tttcaaataa ttataggttg 68940
cttgggagac cctacaagaa gaattttccc gctttatgac agaaccgaaa gggaaagagc 69000
atgatgacat atttgataaa cttaaagagg ctgttaagga agaaagtatt aaacgacaca 69060
agtggaatga ctttgcggag gacagcttgg tatgttgttt gtatactggg gtatcagcct 69120
catattttta tataacttct caaattgata ctttttcata ggagacttta tatgactaaa 69180
ttacattctg aattaaaaat aatgaagtaa agaaacagat ttatgatctg taatctgccc 69240
tttaatattt ccctgccctt ctaaaatcac ctgttgctgt ttctttcttg gctatcattt 69300
cagaaaaaag taaaactttg cagtaaacag actctgataa acttctacaa attgtcatct 69360
gttagccatt ttatgggcct gtctgtagat aggtgcttct aattttaccc tctgtgataa 69420
tgaaaggaac tacatgcgtt ggttttcagt ggattataaa atgttagacg cctaaaatca 69480
taacaccagc taccatgtat tgaatgctta ctatgtgcca ggaactctgc taggtatttt 69540

-continued gcaagcatta tttgatttaa ttcttaacca ctcctgttat tgtcattgac agagctggga 69600
ttcaagcccc tctctaatgg caaagcctgg ttcctgacac cacctgataa atcttttgtt 69660
atgtagactg ctctcactac caaaatcaaa tctgttaagt gcctgctgtg ctcagagagt 69720
tactagaggt gttgttgaat tacaggattg agcgattttc tgggaaaatg cagagctggt 69780
tgtaattata attttgtttt aaagaagtgt ttgtctttat ggccgggcgt ggtggctcac 69840
acctgtaatc ccagcacttt gggaggccga ggtgggtgga tcacctgagg tccggagttt 69900
gagaccagcc tgaccaacgt ggataaaccc cgtctctact aaaaatacaa aattaaccag 69960
gcatggtggt gcatgcctgt aatcccagct actcgggagg ctgaggcagg agaattgctt 70020
gaacccagga aggggaggtt gcggttagcc gagatcgtgc cattgcactc cagccaaggc 70080
aacaagagca aaactccgtt ttcaaaaaaa aaaaaaaaaa agaaagaaaa ccatatttat 70140
tcttgttaaa tgccttatta agactggctt actgagaaaa cagcttcatt tttattcatc 70200
caaaaattat aaaatttgga agccaatttt caactgtaat aaataacttt tatgatttta 70260
tagacctttt aaatgtctac cttattactt ttttcgttgc tgttaacact gggaataatg 70320
gttaataatt tttttctcct catttttgaa aaggctaaca tgtaggtcac atggcaaaaa 70380
gcgatgaaca tgatctgaat tattaaaccc tgaattttag gtttctagat gttgcatttc 70440
atgtagttaa atttgtaata ttttgtataa tgtaaatgtg taatattacc cacgcacccc 70500
atatggttag cttgtttaat ttgggccagg agagaatctc cactctttat tttttagata 70560
gcaagctaac aaataagcag gcaagtaaaa gaagcttatg catttttata ggaaggatat 70620
atttttatgc tggtttatat acatggttat ttttccatat ttactaagct gtcaatttga 70680
ataaaactac taaaatgatg agatgtaaaa caagttggct ttttctcttc ttgttatttt 70740
cagagggtta ttcaacacaa tgctttggaa gaccgatcca tatctgataa acagcaatgg 70800
gatgcagcta tttattttat ggaagaggct ctgcaggctc gtctcaagga tagtaagtgg 70860
agacacggct tattgagttc tgagttcaca gtggtgaagg agtcatccaa ctttagtgaa 70920
catttgtaga aatagattga acatttcaaa gtctttgtca ttaatactat agtcgaatat 70980
tatttgtgga atttttttag tcaactgctt tgtaactact aaaaccaatg aataaaatgg 71040
acacatgatg cttatatgca tttatattct ataaagctat aatgcagaat attttagtgt 71100
gttcgctact gtacttatag gaattttata agcaattata cttttaggta tcttaaacac 71160
atatataatt aaactcttac acatgtgcca tatcagtcat gtgggttttt tcctttattt 71220
caactgcctt catattgata tagcactttg aaatagttaa gaaagcaaga ccattattag 71280
ttataatttg tgtgtgtgta agtgataaaa ttcttgatta attaattttt ttttctagct 71340
gaaaatgcaa ttgaaaacat ggtgggtcca gactggaaaa agaggtggtt atactggaag 71400
aatcggaccc aagaacaggt agaaataaac aagtctctag tcttatgatg atataatttt 71460
gttcatttta attcaggcat taaaatataa cctttttgtg gctctagacc agtctcagga 71520
atattaaatg ttttatatca tactttctaa aatataatga atctttagaa taaagaataa 71580
actacataag aaagtttttt ttaagtgaag tagccatgtt gttaaaagac aagagatgaa 71640
acatgcccct tttgtggttg attacattgt tcatttcaat tccctgtttg aggtaaaaag 71700
gaagattaaa gttatgaaca ggccaggcac ggtgtctcat tcctgtaatc acaacccttt 71760
gggaggccaa gtcagaggaa tcgcttgagt taaggagttc gagaccagcc tgggcaacat 71820
agcaagacct cctctttact aaaagtcaaa aaaaattagc caggtgtggt ggcgcatacc 71880
tgttatccca gctactagtg aggctgaggt gggaaggatt gcttgagcct gggagatcga 71940
agctgcaggg aaaataactt gtgaatagaa aaaaatagta aggttttcag aggatgtaca 72000
atgaatatga ttggcgggaa aagatacaat ttttcttgcc ttatttttatt atcttatcta 72060
tatctaccat taaagtccct acccctcacc tccacccctg ttcattcctt tccgattctt 72120
atagcttctt ttcctatcta gcattcagtc ttataccact gtctcattcc ttgttcattc 72180
cttaaatgaa agaatctaaa tagaatatag aatctaacta cataaattaa tgaaataatg 72240
aagatgaaaa agatttagca tccaatccat tttcttttct tgtttgcttt gttccttgaa 72300
ttcatttaga gaaaggagat caagtaatgg aaaaatagag gagacaaagg gaataaaaat 72360
tgaccaaatg agatgtccct atttctttat tttatatttt cattttcatt ttaaatacag 72420
ttaattgtat aatctatatc ctattttttt cctagtttcc cacatttctt gtttcataag 72480
ttctctatca gatgtgagtc tcaactttcc tcaaaataat gaagagacag tcttcttttt 72540
ctctgtgttt ctttactatt tttttttttg gtaatgactt ttgtgaaaaa tgagccatta 72600
agagactgaa gcaaagctga ggaagcagac agttagtgat tgggtcatgc atgtgttcag 72660
ggtgcgttgg ttatctctgc tctacagatg ggccgagaga aggaggtctg tcagaagaga 72720
atttctagag atccatccaa ggtttctgac tttgatagag gaagatgcat tgattagaaa 72780
gagctgctgt aagggagata aactgcaaaa gaaaaatggt atctggcctt caagacttag 72840
tgatattagg cctaaagtct ctagaacagt tggtggcaga acttgcctca gcaactgact 72900
ggtggtaaat gtgctttggc caaacactct ctgaaagaag tgattcctgc tcgtaagtta 72960
tttttgtcag gaacttaaac ccatagggga atcccttcaa gagaaagaaa ggaatttgct 73020
ttaaagtcag tgcaaagggt ctgtaagcct agaagaggaa tctggaaacc ctttacagaa 73080
gagccttctc cccacaggat ttcagggcag catgtgtgag acccaggctg actgtagaac 73140
agaggccata atttggaata tagaagggag gggcatctga atcacccggg gaggtgttta 73200
tatatagtgt tttgtttttt cttcaaaagc tagcctcatg tcagactcat tgagtcaagc 73260
tctccttctc tatcctttct atccctccca ctcccagttg aagacaagtg ttttcaacct 73320
catacctgga ggttacagtg agacatggat tctagaagag gttgagaata tccctaggtc 73380
tcacatcgta agttcactta gctgaatgac aggatttggc aggaaaagaa acttaaagat 73440
gagaaatcca ttctctgaaa agtattttgt gcttttgtgt ttcttttgtt ttctaggaaa 73500
attcatccct ttgaaacatt ctcgccttgt ttaagccaaa ctaatggaaa ttttggtcag 73560
gatagatcca agagtagttc tctcttctaa tggccaagtg tggtgacagt caaatgatgg 73620
gtagaaaggg ggaagtaaaa catgaggcag gatgagcttg ggaacaccat taccagcgat 73680
ttcctttcca tctcagactg aatagtacat gtttaagcaa acagtgaact ttctctttat 73740
caaatgctct tttttctgaa gtattagttt tcagagagta ttaattagta gttccattta 73800
caagttaatt gtttgcattt atgtgttaat cttgtctact cagatttcat agctgtgata 73860
gagtttgggg caaaaaaaaa cactcagttt cgtagctgtg gtagattttc tattctagta 73920
atttatttag ggtaatgatt gaatttaaag ctagtttctt ctatcatata caattttgag 73980
tggaggtttg aaaaatgaca agattaattt aacacagtat aagaatcttg ttatcaaaca 74040
taactagtgt aggtaagttt tcctcctttg gtaaagagat tatgaataat tacagataag 74100
agactggaag tgaatttaag aaggacagat acctcacagg agcagtctga agtaccattt 74160
tttatgaaaa agctttttaa aaatcaagct atgcatttta tatttattgg aaaagaaaca 74220
tgtcaacaag tttaagtcct tacagtaatc tcgttcttaa gtatagttct tagatatgaa 74280

```
gcattttaga acatcagctc ttcctatgca ttcagggtgc tttttcctag attcaaatta  74340
taccctacgg tcaagaaaga aagaaaatac atggtaagat tcctggtgct gtaacttcca  74400
caggaaaaaa catttcagca aaagtaaata cataacaagt agggctaatc cctgggtttt  74460
ctaccctctc ataaggcaaa ttcttctgtg ttcataggcc atttaccata ttcataagcc  74520
ggggtgctgt gttctttctt gtgtttcttt cttgtttgtt gtgattaagc ttgtgttatc  74580
ttttatgcaa tagtaatgta tttattaaaa ttgagactgt ttttcaagca ccaaattatg  74640
aaccatctaa acacagtcct tttttaaaca ttttaaagtg tgttcacaat gaaaccaaga  74700
atgaattgga gaagatgttg aaatgtaatg aggagcaccc agcttatctt gcaagtgatg  74760
aaataaccac agtccggaag aaccttgaat cccgaggagt agaagtagat ccaagcttgg  74820
taataaatac tgctgagaag caggaatctg cttccttaat atttgtttct tgcagtaaat  74880
gttactacat gtgttagtta gatatttaag tgcttaattt gacttttgtc acgtgtacat  74940
ttgctgacag taaaagctta gtcattttga ttgcgtgaag agaaggaatt ttattctcag  75000
tattgctttt ttaagagtaa tgctttaatt tgtaaatgga gaaatttact ttggcaagtt  75060
caatggtcaa cagtcagttc atgcaaaatg ggatgaaacc gacctagacc tttgccccac  75120
gtcacgctgt ttcagattgc aaaatagaat ttctgtttaa aaatggcata tatatgtgtt  75180
tttgtgtgtg gtttacagtc aaatgtaact caattagatg tgagtggatt cagaaaaaat  75240
aaaaatgttg tttttattaa attggatatg accattgagt tctttctcca ttgtcctctt  75300
ttgttaatgt gagaataaaa atagtctaca ctttaggcta ctttttgctt accttcatga  75360
tgcttttttt gaggatgaat tttaaaaaat actttcgggc ccacgttttt taaaaactac  75420
attctctact gcttagttaa gatgtaagga attcaaaagc tccttataat attagcttaa  75480
gtgaacacaa ttagaaaaat aagtctagtg gggaaagcaa tcattaacaa atttcaaagc  75540
cacacaaact cttttaaaga ttatgtgcta tttatgtttc tgtacttgag ggatgagtat  75600
acttatttta aattccacca caggtcagaa caagtaaaaa aataaaaata aaattggtaa  75660
aactcaaagc agttatatac atctagcatt atttatatat tgaaaatgag atgaaagcta  75720
atgattacat gagctgtttg agttgaatgt ggatttaggt tttattcttg ttggtcccag  75780
ctctcgttaa caataagtta tattcagttt gacactttta aacgttatgt ggcacgttgg  75840
tgaatacagt aggagggatt ttctcttcag agtggtatag aagagatgtt acgtgatttt  75900
ttttttaaac tttttgctca tgtcttaggc aatgaattga ctgtatgtct taattagttt  75960
ctaagaccaa gaaaacctca ggttttttaa gtgacagttt gttcagtgca ctttgcaaag  76020
ctataaaata agtagcaaag taccacgaga agaatattgc atggactaga tatcaggaca  76080
tgtgaattct agtgtatttc cattatatta gctaataata tgtcctttaa taattgatac  76140
cacttttctg acctcactta cctcatctgt caaaaggggt tgatgttttt ctagttaaca  76200
ttattattgt tttgctcaaa aaaggacaga gggtattaaa gaatattgga cactcagagt  76260
atctagtaat aaagtggtag ggatcatatt ggtatggtag cagtaaaatt tttataaacag  76320
aaaggaaatg ttgagttgct agacatgatc tgagaccatc ttaagttcta actctgtttt  76380
tagataaggc tttcaacctc tttctgcatt ggtttcctca cctctaacta ggggaaggta  76440
atacctaccc tgtctactcc acaagatgat tatttgatta tagtaacagc atttgtttaa  76500
atcattgcta atttttaagt acataaactg gtaatgggtc agagtagtag taaatctaat  76560
ctttgcctta aaaaaagtaa gtgaataaaa aaatttgaat aactatgtaa agaataacct  76620
tgcttttgct tttaattaac ttttttggta aatataattt ttgtacaact tctcagtgtg  76680
```

gttgatcaac atgaagaata tacagtaact ctgggctttc ttttttctca ttttagatta 76740
aggatacttg gcatcaagtt tatagaagac atttttttaaa aacagctcta aaccattgta 76800
acctttgtcg aagaggtttt tattactacc aaaggcattt tgtagattct gaggtaaggt 76860
ttccaaaaac aaagagaagt atttttaagc aacagttgtc aaaatatgct taaaagtaaa 76920
ctttagctta agcattaatt ttaagtcctt tgatcatctg gggaaaaaaa gtatgtgtaa 76980
tttataaaga ataatctaac tcttatattt tcaaagatat ttgccacttt gttcgtgata 77040
cgtgcatatt atccccaatg cttataagaa tatgtgaata taaatagtaa aaaaaagtgt 77100
gaatataaat agtaaaaaaa ataaataaat aacaggaaat agtcccttat tccctgacct 77160
gtaagaattt tagttaacat ttttatgtat ttcttttcaa ctttttctgt acatagggag 77220
agagacagag agggaaagag aaagtgtgtg tgtatctgtg tgtgtaacat aaccatccat 77280
ttgcataatg gaaatcatcc tgcaaaacag tttttatcat gctttttttca ggtgtcataa 77340
ttatttcttc atatcactaa atcttgtttt aaataatcat aaagttcttg tattaaaatg 77400
attcataatt taaagtaacc cctaggtggc agcagtctga tatattttca gcattttctt 77460
acaagcaaaa atgcttttaa atatcctttt gataaagctc agttaatcaa caatcttatt 77520
taattgagac ttctaacatg ctgttctttt gttttcagta gatgaacata aatttatatt 77580
taaatgcacc taattaaaag tggcaagttt tttttgcata attttaattg tagagtgaac 77640
ttctttctat agaaacttct gtagaaagaa gaaacttctg tagaaactgc cttctgtaga 77700
ataagcttct ttttaaatac atcactttat tttcacacag ctgaatttta aaaatggctt 77760
gagtacagac tcaaagaaaa gaggttaacc taaggacgta tttaagataa acatggttag 77820
ctgaaactaa atataaatgg agggtatatg ctgtgaattt caacttacat acaatgtaat 77880
gtaatttgct actactcaag cttatttact ttgtcattag aattgaaaca aagctatcta 77940
ggtgtcagac agatataagc caaattatgc agaatttcat ggctccgtac agaaaggatt 78000
ctgtagctta tatctacagt atatgcatta ggtaaatctg agtacttttt aagcttagga 78060
catatctact ggttctagta gttgtatgtg tttacgatga tagttttcat tttaactttg 78120
catctggtaa tcttagttac ttaatatttc agttggaatg caatgatgtg gtcttgtttt 78180
ggcgtataca gcgcatgctt gctatcaccg caaatacttt aaggcaacaa cttacaaata 78240
ctgaaggtaa gccacatagg gactgcagtc ttattttgac attaaaaaat aatagtggta 78300
atatccatat ttaatagaag gatgccaaaa tacttcccaa aagtagattt attagaaaaa 78360
ctggccaggt gtggtagctc atgcctgtaa tctcagcatg ttgagaggcc gaggcaggaa 78420
aaccgcttga ggcctgtagt ttgagaccag cctgggcaac attgtgagac tctatctcta 78480
caaacaataa aataaattag ccgggcatgg tggcacacat ctgtagttct agctacttgg 78540
gaggctgaga tgggaggatc acttgagccc taggattttg aggctacaat gagctatgat 78600
catactactg cactctagcc taggtgacag agtaagacct tgtctcttta aaaaaaaaag 78660
acaaaaatta ttatttgctt ttaaaataaa tcataattgg aaaagatggg tgataaaaca 78720
taccaggagt ttattttcat tgcatgaaac tctgttggga atggactcct aggtatcact 78780
tagtttttttg ggaaatctgc acttccatta aagtgtatag cttaagaata tgacattctc 78840
tgagactata taggtttcat gctgataaaa ctactgtata acagagattt tctatgacta 78900
tgaaaagtat tagcaatagt tctaacatga taaaaaattt actctccata tatataggtt 78960
aattttatca tctttattca tttataaaaa cgatgctcct caggtttttt aactttcttt 79020

-continued

```
aaacagttag gcgattagag aaaaatgtta aagaggtatt ggaagatttt gctgaagatg  79080
gtgagaagaa gattaaattg cttactggta aacgcgttca actggcggaa gacctcagtg  79140
agtagttctt actgccctct accttactac ctttccacct ttcccatttc catttgtttg  79200
ttgatccatt taatctcaaa cttacagaaa agttacaagg aactgggctg agcacggtgg  79260
ctcacgcttg taatcccagc actttgggag gccaagatgg gtggaaaaca aggtcagaag  79320
atcaagacca tcctggctaa cacagtgaaa ccccgtctct actaaaaata caaaaaactt  79380
agccaggtgt ggtggtgggt gcctatagtc ccagctactt gggaggctga ggcaggagaa  79440
tggtgtgaac ccgggaggcg gagcttgcgg tgagccaaga tcctgccact gcactccagc  79500
ctgagcgaca gggcgagatt ctgtctcaaa aaaaaaaaaa aaaaaaaagt tacaaggaat  79560
tttttcttc tctgaagtat ttgagagtaa gttgctgacc ttaagtccta tcacttccaa  79620
gtaggttcat gtatagttct tagaaacaga ttttctcata gcaaccgaac attgataaat  79680
tacaatatct aattctcaga cccctttcaa gtttcacccg ttgtcccagt attatccctc  79740
catataacaa gatgttccag gctcaatacc tgacccagct tcctttttt gaagaatggt  79800
gtttagaaat ggagacctag aaattatata tgctgttatt ggaatatcac tgttccctgg  79860
tttctcagtg gaaagagcta ggaactaagt gttgtgaatg tttgtgtgtg tgcaggtgaa  79920
tatacacaca ctgacatctg tattcctaaa tcatgtgtat atttatttat taaaaactgt  79980
gagttgatgc tgatacttcc cattttaatc cagcattaca aggtttgttc tagtgttctc  80040
cctttcgata tttgtcactt gctttcctga tagaaaacgg gcttctagta tccttaatat  80100
attttcatat tttggtcagt cctcctatac gtaacccaac ttgaatgaag atatgtcctt  80160
ttccattgca gaaatgttct ttttccccag ctcggactca acactacaca ccaggccacc  80220
acatggcgcc gcacccagca ttgacacttc ttttaccttg tctgggctct gacatccgtg  80280
ccaggttgct cttcgtcatg gagtcccttt tactgagctc tgctctgacg ctttgtgcca  80340
ggtgcctctc catctcatcc ttcccacccg ctagcctctg cccgacccca gacagattcc  80400
ttcctcacct gaagccagac catgcctttg tggagatacc ctctttaccc tgcctgtgct  80460
tcgccagcct gcaccaggcc accctcctgc acagatactc tcctcagtac tggaccaggc  80520
taccaacagc cccatgtgaa cccattgtaa cccaggtcag gcattaacac ctgcagtagg  80580
ctaccatggc ttccccttcc cacccccccta gcttggccct actaataatc actttgtcac  80640
tgtttggggt tgatatttgg ttgtttcttg taggttccta gctttaagat aggattgcat  80700
actaaaattt acttagatct ttgagaactc aaggaaatca gtgaaacatt attgttatta  80760
aataaaaata aaatacctgt agttggtacc tctgtttgag cctgccttgt tacaagtttc  80820
actgacttca gcttcgtgta acaaagtatc tttttctttc aacgtgtact taaatttcct  80880
gtcttattag ttttctgata tctaaaagga aaaaaagcag atatcgttaa taaattagaa  80940
agaagttctg caaatttaaa agtgccttct aagctgagtt gtaggattac agtacaatcc  81000
atagggttat cctgaagaag ccaggcaggg ctcttctgtg ttacaccctg tgcctgcgca  81060
gcatgctcac cccttgccat cagcgcttgc ggccccattc tctccctcta gtaataatct  81120
aagttctgca ttgctttctc ctttcctttt ctttcttcct ttaaatattc ttctttcgag  81180
acatatctca ttttaacttt tattttcatt ttctgtcact tttggttttt ctcatgccac  81240
cttggcaatg tagttaagtt tgtgctaacg tagaagatta gtgctcaaat ctgaattgcc  81300
atttactact agctgtgtca tcttcggcag ggaatctccc agagccttag cttctttatt  81360
tgtaaaatga ctattatagt ggttatttct caggattgtt agaattactt ccgcaaacat  81420
```

```
ttgcaagtcc ctggttcata atttcatgct aaattagtac cgttacagga agtggtatat  81480
cattgtcaca gtgtatacaa atatatttct tttatatccc tcgtgatata attatcaaga  81540
cagtgaaaca attcaatgaa ttttaccagc ataacacatt tttaagtgat tggaaaatca  81600
taagtatctt ttcttatgtt tttagtagag gctttgcaac cccattactc tccgctccca  81660
atttgattat ttaaaggaag tggattacta actcagatat gtacactgtc aagccaagtt  81720
ctatgttcta ctgctggttt tcctgagaaa gcagtcatat aactcccttg aaatgattta  81780
ctacttttgt acatataaaa ttataatggt gttaatgtac caaataatgt ccttggaagc  81840
aagggttttg ccagtaactc agctgcatca gtcaccctca aggagatgag ccatgacttt  81900
gttcattagt tggaaaagag tctggagagt gccttttcgt tactgtttat ctttggtctg  81960
acacttggga atagggtcat ggatacttca gccagaaaac tttccaaatt taagttatta  82020
atgtattata aggatcaaag tttctagtat agcctgttca attagaacat agtgtgttgg  82080
ttgattggat ttggagaaag ggaggcaatc aaatttttac tacagtttca gcctgttaca  82140
gaatattgta tagagtgtta aaatgttgat gcattcatat ttttgccagt tttaagcttg  82200
tacgatttta aatcatttcc ttaccttgga gacttccccc ccaccttttt tttttttttt  82260
gagatggagt ctcgctgtgt cgcccaggct agagtgcagt ggcacgatct cggctcactg  82320
caaggtggtt ctcccacctc tgcctcccga gtagctgggg ctacaggcgc ccgccaccat  82380
gcctggctta ttttttgtat ttttagtaga gacggggttt ccccatgtta gccaggatgg  82440
tctcgatctc ctgacctcat gatccgcccg cctcggcctc ccaaagtgct ggaattatag  82500
gcatgagcca ccatgcccag ccctgactgc cctttaagat gagtacataa gtagtagtag  82560
tacatttttc tttcacatcc tggagaagat atactgtgtt cactattgaa atgaaaccat  82620
aaagctagag ttaggaagat tgaagaaatg aaaaaggagc tcacatgatt ttgtctcagg  82680
agaggctctt ccaggattct ttggagatat ggtagattcc atagctggag cagggaaagg  82740
acaggatgag cctgtgggtg tagaaaggaa gggagtgctt gaaagatgat gaggagatgt  82800
cagcaggtca cagaaaccct ctgaaggagg ctccaactgg ccaggctggg gacaatttgg  82860
gccccaaaat aatgacagta acaaattgta actcattgaa tgaaatagga atccatacat  82920
tggtaattat ataaataagg gaataaaacc atgatgcaaa aagggatgtt tatgtcatca  82980
cgcaaaatat gttcacagaa aatatgtact aattaaaaga gggaaaagag taactttaca  83040
gtggatgaag cctggcaatc atcactttaa gcaagtggtc agagttaata ttatcagtaa  83100
tggtcaaatc aaaaccatat gcaagaagac tctaaaatgc aagaagactc ctgaagtact  83160
tcttaccaaa gatgtagaac ttaaattcag tcataacaat acatgagaca aacccaagtt  83220
agagcacagt ctgcaaaata actggcctgt aatcttcaaa tgcatcaaga tcatgaaaga  83280
caaggaaaga gtgaagagct gctccagttg gaagagactt aaaactaaat gcaatgtatg  83340
atcctagatt ggatcttttt gctctaagga cattaatggg ccagttagtg atatttgaag  83400
gggatccgag ggttccattg tagtaatata tcagtgttaa tttttaaatt tttattaggt  83460
tgggattatt ttggaaaata ccattattca tagcgaatac aaagtagaat atttggggat  83520
gataatgcat gattacaaca aatgtttcag gagaaatatg atctttgtag tggtcttgca  83580
acttttctgt aagtctgaaa ttgtttatgc ataaaaggtt aaaaaaaggt taaattttgt  83640
ttttataact aataatggat tagggtcatg tgaaagtact ttagaggaaa tgagactttt  83700
gagaacatca tccctgaaga cgttgaaaca ctgagttacc tcatggataa tttaatagga  83760
```

tatgcagctg atttttctac cttaatttct tgtttgcagt atctacccat acttagaatt 83820
gtctggtgtt aaaatatgcc cactgggact ttcatgaaat tcttttgatt ttctagaaaa 83880
ttcagtttca aaggattttt taaatagata ttttaagttt ggtgtcaact tagataaaat 83940
ctgtttggag tcccagtgta agttttagta atgtgtccaa tctgtttatt gaaatagtat 84000
aactttagaa tactttcttt ggagagatga agattggtat gttatagttc aattcaaagt 84060
tgttctttct attatgatct attttataat tcataaaatc tatcttatga ttgtcatcat 84120
aagtgcaatt tgtttttttgc cccattctac ctcagaaact aagtatctgg gcatcaataa 84180
caattggtag tagtgtttgc tgctaagcca agtttcacca gtacagtgtg gaattatttt 84240
attgtttttt ctgtgaacat tgtatctgct gttactaggt tattgtgagg tattgggcct 84300
tcatagaaat tgcctggaac ccttgttcac taaagcctgt tacacttttt attctctgtg 84360
cgtgtaatca gagacttatt gatactgaca cattcaaggg gcattattga tcatttagat 84420
tgctctaaga cctaaggagt cttggccgga tgcggtgcct cacgcctgta atcccagcac 84480
tatgggaggc cgaggcgggt ggatcacctg aggtcaggag ttcgagatca gcctggccaa 84540
catggtgaaa ccccgtctct actaaaaatg cgaaaattag ctgggcatgg tggcaggcgc 84600
ctgtaattcc agctactcgg gaggctgaga caggagaatc gcctgaaccc gggaggcaga 84660
ggttgcagtg agccaagact gtgccattgc attccagcct gggtaacaga gcgagactcc 84720
atctcaaaaa aaaaaaaaaa acgaaaaaca aaaacctaag gagtcttttc tccttatttt 84780
acaataaatt ccttttgatt ttgtgtaaaa acttgaaact gtttatgaat gtaaaataac 84840
atttgaatac ttttcttgtg ccagatatta ggttaaatgc tttatgtgaa ttttcatttg 84900
attctcacaa cttttgagtt aggtagttat ttttctcatt ttacagatga aatggagggt 84960
taggaactcg taggtagtag atgctgaagc tgagatttgg gcctgggtct tttcactact 85020
gtgccagaat catttgggag ggagtaaaaa ctcaagcctt tggaaaatat gatgacataa 85080
aattgtcctt tatattgaga agcttccata gttaccagtg tccttcacag ggttgatcgg 85140
aaagacatac atgttagtga tgatgataat gatgaagata atcattatta ccacaggtac 85200
ttcctataat ataagcatct ttcaaattgt atgagaactt tcatagaaca tctgagtaaa 85260
tgaacagtac agtgtgcatg aaaccactaa gcaaaccaag ggaagttaat tttctttata 85320
tgaattgtaa acatgtctct agatatcctt tatcagattc caccatgcgt aagtagtgtc 85380
taagttgccc catatttaga gtttttcaat gaggttgtgt tcctacttag aatcctaaag 85440
ttcagctata acagatatat taataaaatc tgtggaatct ttaattgagc ataatggtgg 85500
ctgttatttt aacttgaggc tttttgttga gctggattgg aagtgcaact tattagaaat 85560
tacagtgtat ttattcctat ttcttgttct ttatgtgaga gaagatatac tttagtagac 85620
tgaatacttc agagctgtat ctcatttacc aataaaatgt gaaaacagtg gtaaattcct 85680
tcacttgggc taccattgta caggcctatt ttaatggtat agtttgatat ccttaatgtt 85740
aaaagcaata tagcttaaag aggctggtaa attagaattt tccaatatcc tcagcttttt 85800
ttcctctcac agttaatttg ctctgctgac tccctacgcg aggtggcaac agctggccct 85860
tttactggag cttgtgggga ttagagagtc gggctcgcag cagcgtgctc ggcctcttgc 85920
ctctgttgac tgttctttat tgtttgatgc ctgagcatct cccagacagc gagcaattgt 85980
ttctggaaac ttaaagtttg tttctcttgg gagtagacaa tgcttttggg gcttgtcttt 86040
gtgtttcttc actttcccag tctcctctta tccttcatcc tgtgctttct cttgataatt 86100
agaaaggagc aaagatacca ccttttttatt taggtctgca tgagattcta aaacttagaa 86160

```
gtataggcta tagatgaaag tttctttttt cagtaagcca cctcagtaac aaatcatgtt  86220
ttaaatgaaa actttgttct tcataatatc atttagtgag agaaaacaaa tgcatgagtg  86280
catttttgaa attatggtac taaaagggag cagcagcaag gtgacctaat actgccattt  86340
taaaagctag gattagaaat gtatcataac tgcttaaatc taaaaagatt ctttcactga  86400
atccaaaata tagttctaat ttataggata gttataagaa atctctatgc catgtggaaa  86460
catgaataaa aagtagtcag aacatagcta aatagaaccc tgaggtaggc agaatgattt  86520
tattcttcac atttagaaaa gaaaacatca aggtaccctg gaacttaatt tctacagtga  86580
cttcacattc cgacacttct cccatacctg ccataccctt gagtgttgtt acggatgaga  86640
atatcgtctg tgaagtagta tgagatggaa attttcctag aaagattatt gtactcggaa  86700
tttggaactg aaaagtgtag aaaggggaag tgatgtgttt aaaactgttt gcggaggtgg  86760
ggctctgcca tgtgtatttt gacaaagcta cacaggtgat tcttgccatc cccgattacc  86820
gtgtacccgc ctgcccctga gctggcactc caaagagttc tttcagtgca tagcaagaca  86880
atttttcatg ctattaattg ggataaaatt gacatacatt catttgtaga gtctgagaca  86940
caacgtcact ttggaaaatt tggtgagcaa tttgaactgc atctgcactg gtgtgttctt  87000
tttgtttctg tagacttaac caaagaaaat gaactttaaa gggactttaa aggcatctgc  87060
actggtgtgt tctttttgtt tctgtagact taaccaaaga aaatgaattt taaaggaaga  87120
gagggtgata ccaagttgta gaattctagg tatgtaggtt cagaggagat tttttttttt  87180
taagaaaaaa aaaaaaaaaa aaaaaaacac ccaatcaaga agaatagagc agggtgtccc  87240
gaagagaacg tgtgagctcg aagcatcccg gcagcatctt tcatatctca gtactgttgc  87300
tctgtttctt gggctcacaa caccatttcc tctctcctgg cttttaacac atctcgaggc  87360
aacctttcc ctttcttttt atgcacttct ctcactgcgt ctcttctata tcatcatcac  87420
ttcaacctaa cccagtattt ttatcccacc tgcttattta ccttccttca gtgactaaaa  87480
accttactca gatactgcca gtgttgttta attgagcaga atagaggctt ctcactatag  87540
gcaactgtaa atcaatgaaa ataaccattt aaagaagaaa aacattttca tgtctatcac  87600
ggtcgatccc ttctgccaaa gtgatttggt tcattcataa attccccata cctcgtgtgt  87660
tacatattgt actgtacaca tttactgaat gttcgattgt gatcttgtaa tacagactgt  87720
tcattagccc ccttctcttg acttaaaaag ttggggggaa ctaactcttt tcatcccaag  87780
gaaactttct tctactctgt cttgccagaa agttactgct catttctctt gtagagcagc  87840
ttgcctgtgt ggcattcact cctgttctgc ccactcccctt cctaatatcg tgcagtctgg  87900
ctttcatcta tatcaaaacc acttattgat agatcaccaa tgatttccta atgccagtct  87960
acccagttca ccaggaaact ttaataactt tttatgttta ttaggaattt ttaagttcat  88020
tggaatacat tcaagtactt tttggaatga ttatatgatg tagaaatgtg tatgtttgag  88080
agacagaaaa attgattttt ttttcctctt cactacagaa taaataatgt atttgtttta  88140
tggtagcaat acttgaactc tttaaggcat cttttcatgg taaatctggc aattttaaaa  88200
atctgggctt tgtaaaataa tttttttat agtaaggcag ttaacacatt aaagcaacta  88260
ggaaagatag tgaagaatta tttttacctt gagtctgtat agatgaagta ggctctgctt  88320
tgtgttggaa cagaacaaac aaacaaaaaa acctgagttg atacaaagat aaagtaatcc  88380
tcaaggaaag tcctctctgt tagagaagtg gttatttaca cacagaattc cacatgacaa  88440
cgcctgagtg gtgtggtttc caggttattg atgagaaaat cgagactcaa aatgggtctt  88500
```

ttagaatgaa gtacattttt catggcctaa gtctgtcttt aaaagtcacc gttgtggccg 88560
ggtgtggtgg ctcacgcctg taatcccagc actttaggag gccaaggtgg gcggatcaca 88620
aggtcaggag atccagacca tcctggctaa cacagtgaaa ccccgtctct actaaaaata 88680
caaaaaattt agccaggcgt ggtggcgggc gcctgtagtc ccagctgctg gggaggctga 88740
ggcaggagaa tggcgtgaac ctgggaggcg gagcttgcgg tgagccgaga tcgcgccact 88800
gcactccagc ctgggtgaca gagcaagact cgtctcaaaa aaaaaaaaaa aaaaaaaaaa 88860
agtcactgtt gaagaatatc aataaattag tacaagcgta aaagaacatt ttcttttcta 88920
taatattata catgctgctg gtaatcaaca ctttactagc aagtatattc ttttgcttta 88980
aactcaagtt ttaactgatt aagaataaag acaagaatgt tctctacaat aatgtatgga 89040
ttgaatttgc catttatcat tttaatgtag gttttactta tatactattg tgaaaatact 89100
cttaatgtat tcaaaaggcc agtgcacaat ttttttttct tttacttctt tttttttttt 89160
tttttctttt agaaagagtg tcacttgctg cccaggctag agtgcagtgg tgtgatcatg 89220
gctcactgca gccttgaact cctgggctca agtgatctaa tacctttaaa gttgggaata 89280
aactttatct taagcgtttt tatttttaaa ttatgttttt gcatatttga tagaaaaagt 89340
agaatgtagt aattgaaaac ctaatcacaa aacaattcat tggactctgc aacagtatat 89400
aaaaaataaa attaaacgag ataggaaatc ttaagggatt ggtggattga tgcacatgaa 89460
actggtaacc tctgttaagt acagttctcc aggtagttgg agaaattagt taaatgtgaa 89520
gagaatttta attttgcact attttgtaca tttctaaact gtgtctccca cagcccttct 89580
cccccagtga gcacgattca gaattacttt gaaatgttgt agtcttaatt atcctattca 89640
tggaaatgac gaagctaata cacgatgtgc tctatcttaa aagtaacaga tattttccca 89700
agtaacctac tgctggttgt gatgctgagg gacatttcat gggactgcat ggtcgttgct 89760
catcgtgata ccatcctcag tggttggggg attcacagtg aattctcata tcctgtaact 89820
atgcatcatg gatctatcat ctgaaaataa atcaaaatct ttgttgaact cacagtttcc 89880
acacttgtat cacccattta agattgtttc attgttacct cctgtgtaca gaatatttca 89940
tttcaatttc tcttagaaca gctcattcat ctattctcta gtttcaatat tctgagcagt 90000
agaagtttgc tgttttgatt aacttcagtt agatctcttt tctgggccaa gaattaaagc 90060
cattttatct ttagtctctc cttttgttgg cactgcttca tagactgtgt catatataca 90120
gatctgtctt tagactgatc tttaccaaag tacactactg gaatttgagg gttttttttt 90180
ttaacatcct tttcattatg agagagctag tgtatatgca ttgtgggaaa ttagaaacta 90240
tagatggcaa aattttaaaa aataattgcc accacccaga gattgcactg tagtttaaga 90300
cacttttgaa tgtggtccta gggacataat ttctggaaca catttttcgt gaagaggtct 90360
caggttggct tcttataccc acagctcgtt gtcattgccc ctagttttaa tttcccatcg 90420
ctcagtgggc tagatttttt ttcattttct tcatataaac ttatttcaga aatgttcatt 90480
aagaggaata agcagcatta gtaaaaatga aacctatggt acccattact ttatatagtt 90540
caagtattct ggaagccata ttgtagcata gcatgtactg aaaatcactc tcctttgaac 90600
agtaatccca tacctgtatt tgggacctgg ccttcctttg tgtgcttgtg tattcattat 90660
atccccttc tctcttcaaa gatgctcaag tcattctcat cttaaaacta atgggttgaa 90720
ccttccatgc agtctagtag ctactgtgaa ctctaatctc tattacaaag gttagctctt 90780
tgagtctcac ttctactgaa gttgtttttt tttcccaaga ttactgaaaa tttaagagaa 90840
aataatggcc caggcatgca ttcaggacta gaaaatactt ccatgtacag aaaaccaaac 90900

```
accacatgtt ctcactcata agtgggaatt gaacattgag aacacatgga cacagggagg  90960
ggaacagcat acgccagggc ctgttggggc gtggggggcg aggggaggga acttagagga  91020
cttaagtgca gcagaccacc atggcacacg tatacctgtg tagcctgcac attctgcaca  91080
tagagcccgc ttttgttttt gtttttgttt ttaagaagaa ataacgggga aaaaaaaggt  91140
ttcaaaactc ataaagaaag agaaagagag ggagggaggg agggaagaaa atgcttccat  91200
gtaactgcat catttggtac tttggagtcc atatcctact tgaaactcta ggatctggcc  91260
ctcacattta tgtagtgctt tattttacag tttacaaaac ttctgcttgt ccatgtgtgt  91320
ctgtaaagtc atatgaggca ttatgcccat tgttcagata gagaaattaa cgttcattga  91380
cataaatggt taagcccatt atgtaaatat ttatggcaaa gctggggcta atcatatgtg  91440
ttacagatag gacttttttt aaagaattgt ttaggtattc tgttcatcat tagtctctgg  91500
gtttgtgttt gtggtaacca tagacaacca agttcatata atttggcttc ttttttatgt  91560
gatttttgat acgtgttaag gatctataac aatgaatttg cctcctaaag aggtacataa  91620
tgttttcatt cctccaaaaa gataattcta ggtttataaa tctatgtatg ctcagtgcca  91680
gttgaatttt gtgattgttc aatagaaaag aaattgtgac ttaaaggtga ttttccagtt  91740
taatggaata aatgaaatta gtttagaagt tattttttatt tttctgagcc tgattctcac  91800
tcagttgtga taaacagcac ctctgtaaga taaactcggt gataaaccga gaacttctga  91860
aatcagccta acatgaatac ctgttcttct tgtgctaagt ttcataatgc tttatcctaa  91920
tacaccattt ttttaagaaa tggaacttgt atttcatttt tgctttcatc tcacctaatt  91980
cataatttta ttaaaaccta cgatttttaa tttcttttt tatgaatttt tagtttggtg  92040
tataaatcag aattacattc tctgatcttt tacttttaaa attacagtga tgaactgact  92100
gtttaagaat cattctcatg attcattcgt ctgttatgcc tcctttttaa agcttcagca  92160
ctgaaggtct tttgacaaac caatatttat aacagtttga cagcaggatg aggaacagcg  92220
tttgtctttg taacagcttg aagaaagacc ctttccagga cccagtcatg cagttacaat  92280
cttgacctct ttcttatgct gggaacatgc atacagcagc acctcccatg tgtttttcttg  92340
tcccattgac tgtccattca cttcccatct gttttgcagt cttaaaggaa cagaaggggc  92400
cttcttataa atctgtcttt gcaggtgata aatgatgcct acctctttaa gagctgcctg  92460
ggtggttttc cttttcttag aacatttctg ctttcctcct aactaaatca gggaaaaata  92520
caattttagg aataagagaa aaagaagaaa agatgaattt ttaaagcatt taattgacta  92580
agaatatttt actgatcttt tttaatcttc ccaattaatt gcctaaatca tattttttaa  92640
aatgtattat cgatatttag atttttgtca gggagtaaaa tgaatgtatt cattttgaaa  92700
taatgtaact ctttttgag aaaacaaagc catgtatcat taatgagtta acatataaaa  92760
taacttttta agttttttgt gataatttaa gtgtggagca tcttatgtat tggatacaaa  92820
agtaaaatat ttcagagtaa atcattgtaa tcttatggta aaatctattc atttttttaca  92880
tttaaaaaga tgatcataaa tcccataaac atttatgctt ttacttctgt tgctgaaaat  92940
aagtattgta ggaatagata ttgatatcat tgggttttct aagaattcag cagaaataaa  93000
aataatttac tttttctccc atgcagaaat tatttatgca aggttttatg taacaaatat  93060
tgtccctcta tggccctgca gaatattctt aaattactga tttaaaaact attaccagta  93120
taaaatgacc acttttagaa tattgtggtg tattatgtga atcagctggc taataatata  93180
tcttctgtgg actagcttgt tagtttgttt attaattccc tggcatattc caaaaggaat  93240
```

-continued ttgaggcagc ttacatatat cctacgcaaa agataaaact acttaagtga aaaatttggg 93300
ttgaaagaaa aggaaaatcc aggcaagtga aataaagtaa actttcagat aaaattggtg 93360
cccctcaaag tgcatgctca agggttctac gtacaggcag acctcattgt attgcatgtc 93420
actttattgc acttcacagt tattgcattt ttaacaatag aagttttgtg gcaaccctgc 93480
attgaacaag cctgttggca ctattttccc aacagccatg tgctcacctc atgtcactgt 93540
cacattttgg taattcttgc aatatttcaa atttttccat tattattctg tctgtcatgg 93600
tgatctttga tgtttgtatt gtagctattt tgggtaccac taactgtgcc catattagtc 93660
agtgacctta atcagtaaac gtgtgtattc tggctgttcc accaactaga cattccctgt 93720
ctctctcctc ctcttcaggc ctccctattc cataggacac aacaatattg aaatttggcc 93780
agctaataac cctacaatgg cctctacatg ttcaagtgaa agaaagagtg ccatatttca 93840
ctttaaatca acaactagaa atgattaagc ttagtaaagg aggtttgttg aaagccaaaa 93900
tgggctatta gccaaattgt gaatgcaaaa gaaaagttct tgaaggaaat taaaagtgtt 93960
attccagtga acacacgaat gataaagcag aacagcctta ttgcctgaga cgcaggaagt 94020
ttcactggtc tggatagaag atcaaaccag ccataacatt cccttaagct aaaacctaat 94080
ccagagcaag ttcctaactc tattcaattc tccgaaagct gagaggtgag gaagctgcag 94140
aataaaattt gaagctagca aagtttggtt cataaggttt aagaggaaaa aagccattct 94200
gcaacatgaa agtgcaaggt gctgatgtag cagctgcagc aagttatcaa gaatatctaa 94260
ctaagataat tgatgaaggt gattatacta aacaacagat tcttgatgca gatgaagtag 94320
ctgtctattg gaagacgatg ccatctagta atttaatagc tagagagaag tcaatgccca 94380
gcttcgaggc ttcgaaagag aggctatccc ctcattttgg gtgccaatgc agcaggtgcc 94440
tttaagttga agccaaccta aagaatttac cattctgaaa atcctagggc ccttaaggat 94500
tatgctaagt ctatcctgct tgttttctaa aagtggaaca aaaagcctgg atgacagcac 94560
atctgtttac agcatggttt actgaatatt ataactctcg agacctgctc agaaaagttt 94620
tctttcaaaa tattactgct cattgacaat gcatctggtc aagcaagagt tctgagggag 94680
atgtacaagg agatttatgt tgtttttgtg cctgctagca caacatccat tctgcagccc 94740
atggatcaag gaatactttc aaccttgaag tcttattatt ttaaaaatac gtgtcttaag 94800
gccctagctg ccatagatag tgattcctct gatggattta ggagaaaaaa aaaggaaaag 94860
cttctggaaa ggactcacca ttttagatgc tgttaagacc attcaggatt catgggagga 94920
ggtcagaatg tcaccattaa cagtttggaa gaagttgatt ccaaccctca tggatgactt 94980
tgaagagttt gggacttaag aggaggaagt aactgcagat atggtagaga cagcaataga 95040
actagaatta gttctgttgt aatatgataa aacttgaaca gatgaaacat tgctttttat 95100
ggacaagcaa agaaagtggt ttcttttttc tttttttttt ttttggcagt ctcagtttga 95160
agaaagtggt ttcttgagat ggaatctgtt cctggtgaag atgctgtgaa cattgttgaa 95220
atggcagtaa aggatttaga atattacata aacttagtag ataaagcagc tgcagggttt 95280
gagaagatag tgtcccaatt tttaaagaag aaaaatttga gtaaatttgg gtaaaattta 95340
cccaaaatta cctattgtgg gtaaaatgct atcagacagc atcacatcct actgtgaaat 95400
ctttcatgaa aggaagaatc aatcagtgca gcaaactaca attgttgtct tattttaaga 95460
aattgccata gccaccgtaa cctgcaacag ccaccaccct gatcagtcag cagccatcaa 95520
cgtcagggcc agaccctcca ccagcaaaaa gattatgact tgctgaaggc tcaggtgatc 95580
cttagcattt gttagcaata aagtactttt aaataagtta tgtacattgt ctttttagac 95640
ataatgctat tacacactta atatattaca gtatactgta aacgtaactt aaacgcaccg 95700
gaaaaccaaa aaaccttatg tgactcactt tattgtgata tacgctttat tgtggcagtc 95760
tagaaccaaa cttgcatatc tcccaagtat gctgggactt tgctagaggt aagctgcaaa 95820
tttagccctc agtttcctgg tggctggcag ttacaaaatg gaaagcagag gtcattccat 95880
cattcatggt ggccatcaga caacaacaca gcagttgctt aggagaagca tgggtcttct 95940
tcgtacgcac aactgagaga aatttccctt aaagtggaca ctgagttaga tgatacaatg 96000
aatctaatgg ctacacataa tcatgaaaat catggggccc tttattgtaa tgtttctcat 96060
gcgggctaac atgcgtagtt ctagggaaaa tatgatgctg tccaaacata cagctatttg 96120
gtttggctta tctaaagata aaatacatag tatccagaga aatagatgaa ctgtatgtcc 96180
tccatacagt ctcccataaa tattatttct ttttgcagct gatcctttta gtaaatatca 96240
ggtagccaga agttcaagat tttacactca ttgacattga caagcacctg gaatggtact 96300
accttttttt tttttttttt tttttgagac agagtcttgc tctgtcaccc aggctggagt 96360
gcagtggcat gatcttggct cactacaacc tccgcctcct ggattcaagt gattctcctg 96420
cctcagcctc ccaggtagct gggattacag gcgcccgcca ctacgcccgg ctaatttttg 96480
tatttttagt agagatgggt tttcgccatg ttggccaggg tgatcttgaa ctcctgacct 96540
catgtgatcc acccgcctcg gcctcccaaa gtgctgggat tacaggcgtg agccactgcg 96600
cccagccaag tactattttt attagttaag tcagagccat aatcattata actgagctga 96660
aattagaatt gccatccact taagaaagtt gagtggtcta acaagtataa aagcctaaat 96720
ataaggctaa ttcatgttca tactgaagcc ttttggggaa taggccttaa aatatgtaga 96780
aagtatttga agcggtttta attgtactag ccaaaaggag cctagtagaa atgcttgtgt 96840
tataagagtt tattttttaa aaagctgaat ttatctgacc aggcgcggtg gttcacgcct 96900
gtaatcccag cactttggga ggccaaggca ggtggatcac gaggtcagga gtttgagacc 96960
agcctagcca atatggtgaa accccatcac tactaaaaat acaaaaaaat tggccaggca 97020
tggtgatgcc tgcctgtagt cccagctact ccggaggctg aggcagaaga atcatttgaa 97080
accgggaggc ggaggttgca gtgagccgag attgcgccac tgcactccag cctggacgac 97140
agagcgagac tccatctcaa aaaaaaaaaa agctgaattt atcaacaaat tgctgtggag 97200
ttttttatat attcagcagg catcagttgt aatttacctc acagactttc ttaaggttgc 97260
tttctttcta aattatactt tatgggggtc acaaaatagc aatttttaaa taatcacctt 97320
taatgattaa gtattgttta agtcagatca ctcaactatg aatgcatgaa tattcatgga 97380
catctattac atagcaagca gtgctatgct gggccgagtg attttaaatg acagactttt 97440
tggtaagtag agaatttacc caagcagtcc ttgctgttct ccacattaat gctcagaaaa 97500
aatacattat aaaaatgatc tttccaaaat gaattatgaa gccccatgag aatgatatgg 97560
caatttgtgg ttacatattt tactagagga ttaatatcca ataaataaaa agatactaag 97620
gaataaacaa aaaaaattta aaagatgaag tatataatga attagaacaa tacattttaa 97680
tcataagttt taaattagtg tggactttga attctcctgg acagattcct tcattttata 97740
gataaagcta ggactgtgac ttatccagtt atgaggttaa cggcgaatac aacattgtca 97800
tatattttaa atgacacaca ttacaacatg ttctctgctt tataaaaatc atatcaaata 97860
attgccccat agattattaa aggtgttaga ctagggattc ttaaaaaaaa ttttcatcaa 97920
atgtttcttt cattattaat cccatgaagt ccatgttaca gaagattttg tctacaacag 97980

-continued

```
tgcagttaca ttcttctcgt tagaaataca accaccagtt agagttccta atcagtataa  98040
ggaagtagtt gttaggagag gggatgggtt tcttgtccaa atgaagtttt ccatttgagt  98100
ttttgaagta gtgaaactaa cccagcgttt acaggcccca gaaatctggg aacctcagct  98160
ttcaaagtac tgtaccagtc tttaacagtt ttcctggacg tgtgaattga tgcctccttc  98220
tgtaacatgc aggagtgttc tgtctgtctt cattgagtgt taaaaaataa tcatgcctat  98280
ttcaaggaaa aaatctacag aactaagatg cagaagataa gtgctagatt taatcatatt  98340
ccttcatcta tctgtttggt tcaacctttc atcaactaaa agatgcacct tttttcttgt  98400
gctaactcta agattttagc tacagttttg agaatcttga gtgtagtctc ttgtttacct  98460
tttttccttt ttttgtttcc cccacaccct agattcattt aaatactgaa cttctaaagg  98520
gcaagtatat agtgtagttt aataaaaagc aaaccttttc atgaacaata tatattacat  98580
aataagaagc gttcctttac ttttcagtac tctagtgaat agctttctac agtagaatct  98640
cacttagagg gtgtcttaaa gcttaacacc aagtgctcag gcagcatgtt atacaacagt  98700
tccattaagg tacatttgga tctttggatg tgtggtttgc ttaaagtaca ctgcattagt  98760
aagttggcag cttgctttct ttaaaaacat caaaagtttt aaaaggttta tttcagggca  98820
tgtgttagtg ttttgtgtgt ggttctttgt tcctgttcta aactgttatt aaccactgaa  98880
gtgaaccttc tcccgggttt ggccttttgg tattcacagt gtattcaaaa cctaattaca  98940
gattagtcta tatttgagac ttttagagca agtatcagaa gacccaaaaa gaaaatgaga  99000
gtagcagtat catttcatgt agagataaag agacccaaaa catgaatggg tgtcaagtca  99060
gctgaagaaa agaaaaaaga gaaggaactt cattcactga gacggtttat gagttgggga  99120
ttatgggaat attcatgact caatcaagaa gcacagtgaa ttgatgtttg aaatagctca  99180
tcttttaagt aaacattgga taaatggaaa gtagactcag tattcactac acgtagaaat  99240
agctatttct gtatagcaga aatagcagtt tgttaatccc ttcctgagtt ggtttaattt  99300
accaagtaaa tcacaaattt tattctttat ttgtgaatat ttaattcaaa tatttaatgg  99360
aaatatgagt ttgctttata attagtcatg ctgatccata cacgtatttc tgagagaaag  99420
caatttctaa tggtgaaata gttacaataa tatttttgaa atttgaaagc accgtgatac  99480
tgaagcatta atctgaagga tcggaaagta gggagttttt gttgccaaca tttaacttca  99540
ttgtttatgg ataacttggt tttctgggca gccagatggc acagttagta tacagacatt  99600
cttggaaact tgtatcaaaa tttaaaatga atgaatttat gagaaataat tctgcttatt  99660
atttgtaatg tagctttctt gaaaagcaag aaatcggaat gtagtttcta aagctgcaag  99720
tgaatatgta tacatagcca gctctttcag ccttgataat aaggtgcaac cattaagatg  99780
aagggatttt tttttcccac ttgtgttttt gggcccgagt atcctgatct gtgttgcttg  99840
tctggttcag gtgtgagcca ccagctttct ttgactttca ttatctatgt gtatcttgcc  99900
tcctgttccc aggcttgctc tagctcttct gatcctgtct tcctccctct tgatcactag  99960
tgtagtattc atgaagccag ctaagttagt ttttcccttt gaaaaccaca gcccttatct 100020
tctgtgccat attttgggca acttcgttta tcattgattg accgtacgca gtgatcaggc 100080
cttgttctag acactgaaga ctctgagcat ttttgggccc attttgtact cctgtattgt 100140
tctccagggg cttctccaag tgtgcgtcaa tttagtcttc tcaagagggc atcattttca 100200
tcagaatatg atagcatatt atggagtgtc cggtcatcct taggcataga ctacttagga 100260
ggtgtaactg ttttgttccc tgatttttac tgaaatgggt cttttctttt tttttttttt 100320
tttttttttt tttttttttt tttttttttt tttgagacag agtctcgcta tgtcaccagg 100380
```

ctggagtgca gtggcatgat ctcagctcac tgcaacctcc gcctcccgat tctccctgaa 100440
atgcgtctta ttttaagtca aaggtaatac ttaaaaaaga ccaaagagac ttaaaataac 100500
agcatttgct tcgtcactat gagctttgtt attatgagtt aacatacagt agcagactgg 100560
gtgtagtagc tcacgccctg taattccagc agtttgtgaa gccgagtggg gaggattgct 100620
tgaggccaag acttcgagac cagcctgggc aacatagtga gacccccatc ttgacaaaaa 100680
aaattgtttt aaattagcca ggtgtggtgc tgcatgcctg tggtcccagc tacttggaag 100740
gctaaggtag gagaatcgct tgagcctggg aggtcgaggc tgtagtgagc cgtgtttgca 100800
tcactgcact cctgggtgac agtgcaagac tctgcgtcag acaaacaaac atcgtagcag 100860
atgtgtttct taatcagaga agtgtagaca aggctaactc caggctttaa tgtcctcata 100920
tttagcaatg atacctgcaa ggttgtatga gaaccaaatg aaacgccaaa tttggaaata 100980
catagtagat acatcatagc agagtaagcc aggaatgctt ctcaaaggta ggatatcatc 101040
tgtgtcctca tatcacttta tgaagtacat tgtgaaagtg aaagaacaaa gaaataaatg 101100
ttttttagtt aatgtttaaa ggatacattt atcataattg ctcttttaac actcacctcc 101160
agtctcccct ccgttcacac ctcctacccc cattacttcc tggtaactta gttaagtgtc 101220
ctttgtcatt cctgaggttt caaggcatgg tagtactgtg tcctgatatt ctaatcgtaa 101280
atatttaagg gaaattcggc attttttcat tttgtggttt tcatattaaa gtacattaaa 101340
tagtcttttt gcttttattt aggaaaaaaa ctgcttacct gttaatttta gaaaaatctg 101400
attttcattt agaccttaca gggtgagaca cctgcatcag ggtggctctt ggtatctttc 101460
aattcaattg gatcttctct gaatagtctc ttgtagggag tgaggctgct gtaccacctc 101520
cctgcagtag tccatccagc ttaagatggg ggtcaccagt aggccaaaag aatgggtaga 101580
cctggccatg cactgcccta ttgtactcaa atcgtgtatc aaatggagtt ggatttcttc 101640
tcttcataca gtacagcatt tccaagtaga aatatttctc aatgaaatgt ggagagaagc 101700
acccgtttga gattcccgtg tgttgtgtga tttaagttag atggtttttt aagaccacat 101760
tcatttccag cattctaggt aacaatttag aaaatgtctt tctcctaacc tccccacttt 101820
ttaaaaatcc tccaactgat gaactgatgt gaaactttct tacattcact gaaaaaaaaa 101880
aaaaataggt taagctgttt ctaagcaact agatgaatta atttttaaac taagaatgtg 101940
gccttatttt gggaaaacaa gaatatttac ttgtttgtct gctgtttaaa aaatggaagt 102000
cagcctacca aaaaattgag actcaacttc taggagatgg gttaggattt tttttttaa 102060
gtttctctag tttaatttta tatataaggg gttaatgcta ccttcataat aactattatc 102120
atattttctc aatacatagc ttgattaaaa caactggact cccccccac cccaccccac 102180
acacacacag attttatatc agtctgaatc taatgcctag aataagaagt gcttcagcca 102240
ggcatagtgg cactcacctg tagtctcagc tactcaggag gctgaggcag caggatcaat 102300
tgagcccagg agtctgagtc tagcctgggc aacatagtga gacctagaag ttttaaatta 102360
ctggaaaaat aatatgaaaa gaataaatta ctggaaaaag aatatgaaaa tgttacgttc 102420
tttatatcca accgtggtag gctttttga gttcctgcaa tgctaataag aattcataaa 102480
aaggacaatt cttcattttc ttgggtactc atcactaata gctgcctcgc tggtaaaaag 102540
gaatacatgt atcttcaatt gcagattatt tacttttaaa tataaaagat ataaatgtca 102600
aatattaaat gcatcttaca tggttttcct acatagtgaa agtagaatgc ttgccagttt 102660
tgcctctagg tcactcactt tgaaccagcc aacccacctt aattgatcat ttccactaat 102720

-continued atgttaaatt accttaaaag aacaaaaata tttatcatgc ttactataac ctgtgtttta 102780
aaataggagg ccaggcacag tggctcacac ctgtaatccc aggactttgg gaggccaagg 102840
caggaggatc acttgagccc aggtgttcag gaccagcctg ggcaacaaag tgagatccta 102900
tctccacaaa aaaattaaaa ataaaaactt agccaggcgt ggtggcacgt gcctgtggtc 102960
ttagctacgt gggaggccaa ggcgggagga tcacctgagc tcaggaggtt gaggctgcag 103020
taagccctgc caacaccact gcacgccaac ctgggcgaca gagtaggacc cccatctcag 103080
aatataaaat aaagtaggag gtgcatgtga agtagtatag atcatgactt ttccaatttt 103140
aagaggggat tggcatgtac tatgagcagt tcacatttgt ggaggaaatc tacatttcag 103200
agagtatata tttcatttgg aagtctataa acatgaaaac ctaaaataaa taatgtaaat 103260
ctacctctag tggctctggt atttttaaac ttatttatag ctggcaaagt actttttttgt 103320
atgtattttt atagcaccat tgcacttctc atgtttgttg caagcatctc ccacagcttc 103380
ctttgtcttt taattttatg acatataaat aaaagtatac atttcaatat ggccatattg 103440
attgatcttt tcctttgtaa ctcttactac tttatattta aaaagtcatt tcccagtcta 103500
aggccacctc tattttcttt tagtttttta aaatggtttc attgttttat atttgcctat 103560
gatccagaca ttagtaactg tgggttctta attgggcttc agagaatctg agaattcctt 103620
aaaattctct acataattgt acatgtactt aatacatgct tttttccatg ttaagagtcc 103680
agagtttttg ttagatcctc aaaggggtca gtcagtctct cctcccactt ccaaaaaatg 103740
tctgagacct actactataa tccatctgga ctttatttgg gtaaaaggtg gtatggtgag 103800
actcatattt ttctttttcc cgcaaatagt taagtatacc aaccatttag taaataatta 103860
cctcctgatt tgtgatacct ttgaaaaata aatgttttttc tttattttta tctccacaga 103920
gaaagttaga gaaattcaag aaaaacttga tgctttcatt gaagctcttc atcaggagaa 103980
ataaattaag tgagtaaaaa ttctctaact gtattggtgc tgactaaata caaaattaca 104040
cttttcttaa tagtttatca ttctgcttca tttacatcct gcttgtcact tatgctgtaa 104100
tttcaatggc atgaatctct gaaactagct tccgaatttc atttgtataa cgttgctttg 104160
aataacttga ttgccttctg gctgaattaa gaatatcctc tagaactcat tttgaataga 104220
acaaaggtga acacagagct aagatattgt ataatatgca ggtgactcat tttctaggtg 104280
taaagaattg agctgtagtt gacattactt tattcttctt gcctatagtc tatcaataat 104340
gatgtgtatg ttaaatattt aacttagaaa gttttctgtt tgacttaatt aaaattttaa 104400
taattgttct taatccttat ctcttttgtt taaaaacatt tagataagtg tttttcctac 104460
ttaatttata tagccttaga atttagtact ccttgaattt actttcttgt ctgattctgc 104520
tttctggcat tagaggcatg ttcctaataa aatacatatt taaggacttt tccttagtag 104580
cataatcaat taattgttgc tgaagaattt taatcagtaa gtcacttgct tgagaggaga 104640
cctcgctctg ccacccaggc tggagtgcag tagtgcaatc actgttcact gcagcctcaa 104700
cctcctgggc tcaagcagtc ctcccacatc agcctctcaa ggaactgggg ccacaggctc 104760
atgccaccat gcccagctaa tttctttaat tttttgtaga gatggggttt caccccgttg 104820
tccaggctgg catttgcttt tataaaagaa gttgaggaaa gaaaaatact gtagttaagt 104880
cattatcact tcaaatattt tgtcactttt gtctgtgacc cttaccctac agacagcctg 104940
cagcaggctc agaactagaa ggagtagaaa tgtaaaaggt tccctccctg gctacgctcg 105000
gttcaggtca gttcagaaaa ggctcttaaa ccaaactacc tactttcctg tcaggaaaat 105060
gtatttgaga aagcagggtg gaaagggaag tacaacttcc atggtacatc attcggaaca 105120
gtgtgccagc aaaggaggag agaaacaaga cctagaaaac ttgaaaataa agctttgtaa 105180
ctttatttca tttgtttctt tagtaagtta agacaggcca gtgcggtggc tcactcctgt 105240
aatcccagca cttagggaga ccaaggcggg cggatcactt gaggtcagga gttggagacc 105300
agcctgacca acatggtgaa accccgtctc taataaaaat acaaaaattg cccaggtgtg 105360
ctggcacatg cctgtaatcc cagctactcg ggagcctgag tcaggagaat cacttgaacc 105420
tggaaggtag tggttgcagt aagcagaaat cgtgccactg cactccagcc tgggcgacag 105480
agcgagactc ttgtctcaaa aaaaaagtga agacagatat atggaaatat acaaaaatac 105540
ataatcatct ttaacacaag ctaaacataa tttttgtgtt ttataagtgt ccgtgttcat 105600
aaatgttttc tatgtctttt gtgtatgaat attttatttt aaaaccatta agtgttacaa 105660
tatcacccta atcatggtgg ttaccgtgaa tacttactat tagaaataaa catctgtagc 105720
gcctccttga tctccccttt agcaccagag cttacatcat agttctattt actgacctgt 105780
gtgtgctttg cggggaaaaa ttgatgaaag ccccggaagc cccgttaaaa agacaagctg 105840
tatttctgtt tttttaacaa aatgaggaag ctgaaagcca gccagtgttt tacataatgg 105900
tgtctctccc ctcagctgat cagtgtgaca tccagagttg ctgttgctgc tacctgtcta 105960
gtctctaaga cccttttcaa cccttgtgac ttaagactct gtgaactttt acaaagtatc 106020
ttgtgatctg gacagatgat ctgttttgta ccctgcagat gcatttaaaa gaataaatct 106080
ggcagaatgg taaccttgct tcattctgac cattttatca aagttaccaa ggaccctaag 106140
gaatactttc tcaagtatag ttttaacaca taggattcct aattaattgt tattctaata 106200
tttgctgaag gtgtttatat gctatacagt catacacaga ttcttcttca attaatttta 106260
gtatatgctt ttaacttatg tttgataaaa aaattatgcc aatattgtta ggtcggtgat 106320
agactatata agtttagtaa aactagcaaa ggtaagcggt taggcttcaa cattgttgtg 106380
atcatgcagt catcaacttt gtttagaaat tttgcattta tctcccctga cctcagtttg 106440
ttaaatgggt ttatttttac agaatcgtac tcataatcag ctctgcatac atctgaagaa 106500
caaaaacatc aacgtctttt gtccagcctc tttttcttct gctgttccac ctttctaaac 106560
atacaataaa gtcatgggat aaaaataatc gatgtatgtt acgggcgctt taaccatcag 106620
ctgcctctcg aatggaagaa cagtggtaat ggattaacat cctattttgt tgtactaaag 106680
tgacaaatcg gaataatata attggtatgg ccattaggtt cagtccttga agataagaaa 106740
cttgttctct gtttgttgtc ttatttgtgg tggcactcgt ttaatggatt aactgaggtt 106800
gctcaatgtt cagtttcttt tccagaaata caatgctagg tgttttgaaa taaaacttat 106860
atagcaattg tttaaagtta tcaattgtat ataaaatcac agtagcctgc taaatcattg 106920
tatgtgtctg tagtattcta ttcccagaaa ctatttgacc atgataattc agtttatatt 106980
caccacatga aagaaaaatg ggtaacagaa gaacccttaa aacaggttaa tttggattgt 107040
aacgttcagt gaaagaaatt tcaacccttc atagccagcg aagaaatttg ccttggaagc 107100
caagtcagta ccagcttacc tatttgattc agttgctgtt ttctcactct ctatatccat 107160
ttgaaattga tttattttag atgttgtata cttacgttag gctttctgtt aatagtggtt 107220
tttctcctgt tgacagagcc accggattat gacacaggat gaggaagatt aaggataatc 107280
aattgactaa tttcatttag aatattatca aacatttcaa ctaggtatca gaaaaaggct 107340
ttctttcata agactatttt aaatagaaat tatttcaaca attaaagtaa tgttgaccat 107400
ccccctctca gctgaataaa gaaaaattta gttcaattta ttgcaattta attacaatac 107460

-continued

```
taccttcaca acattttcat gtgttttaaa taaatatttt ttaattggct aaaggacatt 107520
caagcaaaga aatgctttct ttacttaaaa tgtctatctc atttgctgcc ttttcactaa 107580
gcctttactt tgttaataaa agtgtccatt gtgtgatgtt tttgatttta cagtttgcta 107640
aatcttattt tcttggagtt gctttttggt aacagcccca ttgctactcc ccattttatt 107700
gttttacatc aatgcatgct tcgttgtgat ccctcaagat gtaacacttg gtatgctcgg 107760
ttgaggatat gaaaaaatac ttccgaaacc aggaattcaa tgtatgtttg ttttatactg 107820
tttgataaga aaagtaggtc cagccttaag cagcacagat gcgctggtag atgcatagtc 107880
aggaactttt tttatttctt ttaggtctag ggacaggagt gaatagaaag ggaggagagc 107940
tctattatgt tctatacaca gattaggaga tgaccttact gggtacaccc ctctaaccag 108000
tgcttacagg ttaatgcatg ttaatgaata tttttgcagt tgtaaagcat aacaattaca 108060
actacacatc tatttctaaa gaataaaaca ggaccatatt tatttacttc tgtcaactat 108120
agaaagaaag accttcagct gtatttccac agatttctcc caaggaaaag gctaatatta 108180
gtcactactg ttatcacatc cctttgtata agttttaaaa agagatggag ggagatcttc 108240
atttctttga ggagatcagt attgtaacgt atgtgaatag atgataacaa ttaatattac 108300
taaaagtccc acatgagagt cctgacgccc tctccatgcc ccacagtaat gtggcttctt 108360
tcatgggttt tttttcttc tttttagctg atctcatcct aagcatgctt tatttttcct 108420
tgaaagctag gtatttatca actgcagatg ttattgaaag aaaataaaat tcagtctcaa 108480
gagtaaaccc tgtgtcttgt gtctgtagtt caaaagtcag aaatgattct aatttaaaca 108540
aaaagatact aaatatacag aagttaaatt cgaactagcc acagaatcat ttgtttttat 108600
gtcagaattt gcaaagagtg gagtggacaa agctctgtat ggaagactga acaactgtaa 108660
atagatgata tccaaactta atttggctag gacttcaatt ttaaaaatca gtgtacctag 108720
gcagtgcaca gcacgaaata agtggccctt gcagcttccc cgtttaaccc actgtgctat 108780
agttgcgggt ggaacagtca acctttctag tagtttatga tattgccctc tttgtattcc 108840
cattttctac agtttttttcc gcagacttct ttctgcaaat tattcagcct ccaaatgcaa 108900
atgaatgata taaaaataag tagggaacat ggcagagagt ggtgcttccc agcctcacaa 108960
tgtgggaatt tgacatagga tgagagtcag agtataggtt taaaagataa aatctttagt 109020
taataatttt gtatttattt attctagatg tatgtatctg aggaaagaaa tctggtattt 109080
ttgctttcca ataaagggga tcaaagtaat ggtttttctc tcagttctct aagctggtct 109140
atgttatagc tctagcagta tggaaatgtg ctttaaaata tgcttacctt ttgaatgatc 109200
atggctatat gttgttgaga tatttgaaac ttaccttgtt ttcacttgtg cactgtgaat 109260
gaactttgta ttattttttt aaaaccttca cattacgtgt agatattatt gcaacttata 109320
ttttgcctga gcttgatcaa aggtcatttg tgtagatgag taattaaaaa atatttaaat 109380
cacattataa ttctattatt ggagagcatc ttttaaattt ttttctgttt taacgaggga 109440
aagagaaacc tgtataccta gggtcattat ttgaccccat agtataacca gattcatggt 109500
ctaacaagct ctcagtgtgg cttttctctg aatgcttgaa tttcacatgc cttgcatttc 109560
acagttgtac tccatggtca accggtgctt tttttcacat cgtggtactt gtcaaaacat 109620
tttgttattt tccttggtaa aatatataaa aaaggttttc taatttcact ttgctgccaa 109680
ggctgtcatt ttcattaatg ctgccaacat gttcatatga ggcttactaa gaagttataa 109740
ctaagcttta gaactggaag agactttaat ttcatctacc atctgattat aaactcctgt 109800
tactcacttt gttattcctc cagaactttg ctcataaatg atacctacta attgtcgatc 109860
```

attggatatg tcaagttagg tagcgtatag gtgtgccttc ttaattcctt cagaagatgc 109920
agaggcaaga acatgtttca atcgtgttag cattggtttt ctttatcagt gctaacagac 109980
tcagtgtgag gccccatact ttattttaaa ctaggttttc atccttgtgt aattcaagtt 110040
cagaatcttc gtgtatcaaa acgtttgaag aatttagtta ctgaagattt aatagagcaa 110100
ttaatttttt tagcatgtct gattgaagaa ttaatatatt tatcaaattg aaatagctac 110160
catgtgccta tagataatac agatgtattt aattatgaag tacgtcttaa aataaccaca 110220
tacccgattt gtgataacta aaacaatcat gtcctgcaca tattagaccc agttaataag 110280
tgtagaaaac ttaagtgttc aaacaaatac tacaaaaatt gttaaaggtt caaaaccagg 110340
agacagtatc aggaaggctt aaatatgggt gatctctagc tggaagaaga cagcttctaa 110400
aactaagggt aggaaaaacc tatatcataa ggcatttgtt taaatttata tcctaaaatg 110460
acagaattga gcttgaaaat tgagagtatg tatgtgattc ctctccaaga cttctcgtga 110520
gttacgtaca tattctgcag aagccgcgtt aaggtgcatt tgtggccaag tcactgacaa 110580
ggaggtaaat actacttata aatgctgtta aatgaaaatc tttttttttt tttttttttt 110640
tttttgagtt ggagtcttgc tctgtcgccc aggctggagt gcagtggcgc gatctcagct 110700
cactgcaagc tccacctccc gggttcaggc cattctcctg cctcagcctc ccgagtagct 110760
gggactacag gcacctgcca ccatgcctgg ctaatttttt gtatttttag tagagatggg 110820
gtttccccat gttagccagg atggtctcaa tctcctgacc tcgtgatcca cccgcctcgg 110880
cctcccaaag tgctgggatc acaggcgtga ttgttactct ttgtgataaa aaattcttgt 110940
tcctgctgtt agtactttta attcattaac ccaggtgtaa actgttcctt tccaagtatt 111000
tgggaaattc agagatctgt ttttgaaaaa actaggccag aggcacccct gaagatctag 111060
tcacagtgca gtgatactgc cagcagcccc ccacagagat atgtcttacg gctgtattaa 111120
gaatataagt tacactcttt aatgttcaga acagaatact cattctgctg cttactcttg 111180
tagttattaa atcacagagc aacaatacgg aagttagaat tttatccatt tgtcagaaaa 111240
tatgctcatg gtttatgtga cctaatactt tccaaaagct cttgagacct ctgatatttg 111300
tgagagaata tgtagggaat aggttaacct cctttttttg ctttggtaaa cttcatctga 111360
gattaggcca aatcatcaga aagcaatact gcctgggctg ctacttacct acctctttga 111420
tattacgtcc ttggcttcac aggcaagacc ttatgacaca tctatttgaa gaaaatacac 111480
agtctctttt gcagaagtct aacctaatga catgtcttga ttatcactga aattcattaa 111540
ggattactag atagtaccag cggtttcccc tccagacaca tgtatgtact gctctccttg 111600
tgacaatgag aactcaagac tttaccattt tctttgcttc agctgccagg aaatgctgaa 111660
attaattt 111668

<210> SEQ ID NO 2
<211> LENGTH: 5409
<212> TYPE: DNA
<213> ORGANISM: Homo sapiens

<400> SEQUENCE: 2
gtgatggatg gtttaagggg gctaccgata cattcacact aatcagccat ttctgccaag 60
atcatgtcac ctcaatctgt tcatggactc caaatacaag aaattaattt gacaaagtga 120
aaatataaaa gatgcatcat ataaatatgt aacttttctg gagtgggtag tataggtaaa 180
gccaaaagaa acaaattcaa gcagaggaat tttggtttct gaaaattagg ttgtctgtag 240

```
ggtccctgta tttatactta gaacaaaatt aggaatttct gtttatgtgg tccagttatt    300
gagtcaccct aagtttgtag gcatcttacc tacctacttg ctccccaagt ttttatttct    360
aaaatgaaaa gcattgctgt agatgaccag tttacactaa agaataacat ttatttattt    420
gttttagcta aagtatatgg acagggaaca ttcatattct tgtagaagaa aattattttg    480
acttttgggc aaaagcatgt agttcttata cactttgaca aactcattgc gtacattttt    540
cacattaatc aaagtcagca caaataaatt ttcaccttgg accacggagg gtttgaacac    600
tggaaatttg atataattct ggttgctaaa gaacaagttc taataaaagc ttaagtgtat    660
accaatatgt ggctgttggt gcaatcagca ggtccgtaaa aatatgattt taatggttag    720
gtaatcccac aacggagatc ccaaagttca tgtttggaag agacttttgg gtcaaagtga    780
aatcagtgta atgaatttaa aattatactc tgagatcttg aaatcagcta attatgttac    840
atcttattag ctcagaaaag ttttgaagtt atatacaaat gctagtcagg aaaaaagatt    900
cagtcatgta attcttgtac attctactat ttaaatcaac caatattata gattatgatt    960
tagtgcagta attctgctgg ctaaccttat ctcatttggt ggtggttagt acttcagagt   1020
actcaccata gtttcattta tgttttcagc atcacttcct ggtttttctc aattccatgg   1080
ctgtggaatc aattcatatg tatatttagc ttcggtgagc aaaaacatag ctagaaaaag   1140
aaaagaagtg agtttcctac ctggttaaat taaagtcgat gtgttaagcc aaggaggact   1200
tcttttgaat ggtactttaa caatccctgt tctgtatact gtgaatatat catttaaata   1260
gcctaataaa ttggatgctt aggctgagcc acctatactt tagttttgtt atggaaagaa   1320
gggagaggag caagtatgtt cttatatgtt acttagaaat aagaatgtag ctgtagttac   1380
acattgttct taagtttttt tcgtaagaca acttgaaatg agtcccatag gcctgctatt   1440
taacattcta agatatgact taaggttaat gatgagcttt tgaatctgac aattcaagag   1500
atatccataa tgaatactga ttcattttct acattgctga aagctaatgt tcattttaag   1560
cctactttag tagcctttat ttgggcttag agatgttatt cctctttctg atatttattg   1620
ggttatctgt ttaacccttt tatatctccc tttcccgatt tgtaaattag agactggcaa   1680
gactttttac cctgagtaga gcaccaaaca tggcttgttt ctgcccacac tgtagttacc   1740
ttgaggggaa gtaaatggga ctttaaaagc aatttatgct cttttatagt gaaattatcc   1800
ctcttactat cccgaaagac tgttacctta caatatcctc cactcctttc cccctgtagt   1860
tactatagag atgacttttc ggttcttcac tgccataatg atcaaaatcc taattcatga   1920
gatttttatc attccaggca tgtgaggttt acttgatgca taaaaccgca agtacttttt   1980
gttgtttttt aattgttttt tctctcttat cttcttgaaa gtctaagtag atcatcattt   2040
ttgatgtctt attagtagca actaataaat tttccctgta tcttctcagc aaaagaactc   2100
aagcagagac agaagattag aactaccatt ggtagttttg cttcctatgg atatgttcac   2160
atacatagaa atttttacaa tgaccttttt atatatgtat ttcagaattt cagaatggcc   2220
tcaatgcctt aataggaaga aatacttgaa atttttaaat tagggcttgg ttttgtgagg   2280
agctagtaaa ggtttttctc tttcagcttt agcttgtttc tgcggaggat tccgctcttt   2340
ctccatcagt ttcatagccc tggaattgta gaaaagctct ggtttcaaga ccattgatat   2400
ccatttctgt cagggtgagt tttaaattta tttcatgatg caaacaatat attgaacaac   2460
aggacatgaa cttgttcttg ttgtaagtgg ctgaatttta tcagtaaagc acatcaaaat   2520
aaaatatacc ccaattgcta gttaagacct agagtgacag attgaaaata gcttgtgtta   2580
ttctcttaag aaaatatata aaaattatca tctcatcaat ctttaatgtt tgttttataa   2640
```

atctaaatgt ttttatattg tttcctagga aatattaggt ctaatttttt actttaccac 2700
cagctgtctt ttattttact cttttttga gacggagttt cgctcttgtt gcttaggcta 2760
gagtgcagtg gcactatctc agctcactgc gacctctgcc tcccgggttc aagcgattct 2820
cctgcctcag tctcccgagt agctgggatt acaggcacat gccactacac caggctaatt 2880
ttgtattttt agtagagacg gggtttcttc atgttggtca ggctggtctc gaactcccga 2940
cctcaggtga tccgcctgcc tcggcctccc agagtgctgg gattacaggc atgagccacc 3000
gcacctggcc agctgtcttt taatataaca ttatgattaa ttgtgatgtt ccattaaact 3060
aagcggagag gaaacatgct ggtaaaccat gtgtgagtta ttcattgtac cagaaaggca 3120
aatgatacat tttatcctaa aattcaaatt tataaacatc ttaacacttg tgatcattaa 3180
atactactaa tctagcatat aaattatatt tgtaggcggg gcacggtggc tcacgcctgt 3240
aatcccagca ctttgggagg ctgaggtggg cagatcacga ggtcaggaga tcgagaccat 3300
cctggctaac atggtgaaac cccatctcta ctaaaaatac aaaaaaaatt agctgggtgt 3360
gctggcgggc acctgtagtc ccagctactt gggaggctga ggcaggagaa tggcgtgacc 3420
ccaggaggca gagcttccag cctgggcgac tccgtctcaa aaaaaaagaa aaaagaaatt 3480
atatttgtaa tattctacta accttatatc attttaactt tttatataac tttttttattt 3540
taccaaatta agttaacctt ttatagccct tggcttatac taaacatcct aactttttttg 3600
tttaattgta ttagttttta agttattgcc ccagatgtca agtaatgttg gattttctat 3660
aataatttag gatatattgc atgaagtcag ttagtattta catttaaaac taaaacaatt 3720
tatactaata cagtttatac atttcatact aatttagcta cagttggata aatatttaat 3780
ggaacaaagt aaatcaaagt accttttcaa atgaattgga aattaaatcc acataacaat 3840
tttttatgac cacactatta cagtgtgatg gcatgccaaa tgatcataat gtggaattat 3900
gtatttcttc attggctttc aagattctgt tctttagttt gtgggctcct ctccaacttg 3960
cttgtctcct cacagtttag gcgactgttt ataattcttg tccatcctgc ataaacacac 4020
acagtcaaaa tgaaaaaaag cttctatcag cagatctgtg cttgctgtac agaaatggga 4080
aaacaattga agtttgcatt atcttttttc taattaccag atcgtttttg gagctattta 4140
ggcatacgct tttaaggaaa aaagaaaaaa agagtgtacc ttttgtttct aacaaaggtt 4200
gttatctata ttattgaaat aaaaaattgg ggatagttat gacaaagtat ttagaaatag 4260
gaattaaaat cttaaaataa cttttcatag catggacaag acttattaat gtctacctca 4320
ataagcaaat catttaaaaa tttttcatgt atatttgctg ccatgatgtg ttgtgattgc 4380
ttaaataacc aatgaatgaa gatcaacaag gatttaaatg aagaagaata tggatttaac 4440
tattttctcc tgtgaaataa gttcatattt acaagttttg attttcagaa attagacaat 4500
tatttttaaa ggctgggatg acaacttctg cctcttacca agaagtcaaa gcacagttat 4560
gtgaattcat cataaatcac atcattttta ttatattttg tatttataat tgtattgtga 4620
ctactttaaa acctgttata aaataaaatt gttttttaat attttatttt agaattatta 4680
gcattaataa caatttgaag tagtttacac aatacctgtg agttttattt ttgttttata 4740
ttgaaattaa ttttagttgc tttacttggc ttcattgcta tggatgcatt ctctgtgtta 4800
cgagttagca gatctttcct tggaactgaa tttaaaagca agcatttggc tccacttaaa 4860
tctctgaaaa tgcaacttgt tctttgcatt tattacataa ttcgctactt atggtacaga 4920
aatggataca atacaaaaat atttccttat aagatacact gtgaccaatg agctttttaa 4980
atagctgtaa tcagtaacat gtatttgact tttcaaaaca catttctgga gggatatcag 5040
tgctttattt ccccaaatat ctgaatccct atgctttagt acaaaacaac ttctgaagaa 5100
tttagtaacc atatgtgttg atctcttgtt tttctaacta gtctttcata agaaatgact 5160
agaatagcaa cagggaaatg attgcctttt aaggtttttg tttctcaata taaaattttg 5220
gtgaaccatt tttattgata aatacaggta tttttacttt cttaaatcac ttgatttaaa 5280
attactttga ttaaatatgc atataaagtc agttgttttt aactctcaat acttatcaaa 5340
aaaatttaac ttgctgtaca ttctgtataa acctaattct attcaactaa aattatttta 5400
aacatttag 5409

<210> SEQ ID NO 3
<211> LENGTH: 24782
<212> TYPE: DNA
<213> ORGANISM: Homo sapiens

<400> SEQUENCE: 3
gtgagtagtt cttactgccc tctaccttac tacctttcca cctttcccat ttccatttgt 60
ttgttgatcc atttaatctc aaacttacag aaaagttaca aggaactggg ctgagcacgg 120
tggctcacgc ttgtaatccc agcactttgg gaggccaaga tgggtggaaa acaaggtcag 180
aagatcaaga ccatcctggc taacacagtg aaaccccgtc tctactaaaa atacaaaaaa 240
cttagccagg tgtggtggtg ggtgcctata gtcccagcta cttgggaggc tgaggcagga 300
gaatggtgtg aacccgggag gcggagcttg cggtgagcca agatcctgcc actgcactcc 360
agcctgagcg acagggcgag attctgtctc aaaaaaaaaa aaaaaaaaaa agttacaagg 420 aattttttc ttctctgaag tatttgagag taagttgctg accttaagtc ctatcacttc 480
caagtaggtt catgtatagt tcttagaaac agattttctc atagcaaccg aacattgata 540
aattacaata tctaattctc agacccctt caagtttcac ccgttgtccc agtattatcc 600
ctccatataa caagatgttc caggctcaat acctgaccca gcttcctttt tttgaagaat 660
ggtgtttaga aatggagacc tagaaattat atatgctgtt attggaatat cactgttccc 720
tggtttctca gtggaaagag ctaggaacta agtgttgtga atgtttgtgt gtgtgcaggt 780
gaatatacac acactgacat ctgtattcct aaatcatgtg tatatttatt tattaaaaac 840
tgtgagttga tgctgatact tcccatttta atccagcatt acaaggtttg ttctagtgtt 900
ctccctttcg atatttgtca cttgctttcc tgatagaaaa cgggcttcta gtatccttaa 960
tatattttca tattttggtc agtcctccta tacgtaaccc aacttgaatg aagatatgtc 1020
cttttccatt gcagaaatgt tctttttccc cagctcggac tcaacactac acaccaggcc 1080
accacatggc gccgcaccca gcattgacac ttcttttacc ttgtctgggc tctgacatcc 1140
gtgccaggtt gctcttcgtc atggagtccc ttttactgag ctctgctctg acgctttgtg 1200
ccaggtgcct ctccatctca tccttcccac ccgctagcct ctgcccgacc ccagacagat 1260
tccttcctca cctgaagcca gaccatgcct ttgtggagat accctcttta ccctgcctgt 1320
gcttcgccag cctgcaccag gccaccctcc tgcacagata ctctcctcag tactggacca 1380
ggctaccaac agccccatgt gaacccattg taacccaggt caggcattaa cacctgcagt 1440
aggctaccat ggcttcccct tcccaccccc ctagcttggc cctactaata atcactttgt 1500
cactgtttgg ggttgatatt tggttgtttc ttgtaggttc ctagctttaa gataggattg 1560
catactaaaa tttacttaga tctttgagaa ctcaaggaaa tcagtgaaac attattgtta 1620
ttaaataaaa ataaaatacc tgtagttggt acctctgttt gagcctgcct tgttacaagt 1680

```
ttcactgact tcagcttcgt gtaacaaagt atctttttct ttcaacgtgt acttaaattt   1740
cctgtcttat tagttttctg atatctaaaa ggaaaaaaag cagatatcgt taataaatta   1800
gaaagaagtt ctgcaaattt aaaagtgcct tctaagctga gttgtaggat tacagtacaa   1860
tccatagggt tatcctgaag aagccaggca gggctcttct gtgttacacc ctgtgcctgc   1920
gcagcatgct caccccttgc catcagcgct tgcggcccca ttctctccct ctagtaataa   1980
tctaagttct gcattgcttt ctcctttcct tttctttctt cctttaaata ttcttctttc   2040
gagacatatc tcattttaac ttttattttc attttctgtc acttttggtt tttctcatgc   2100
caccttggca atgtagttaa gtttgtgcta acgtagaaga ttagtgctca aatctgaatt   2160
gccatttact actagctgtg tcatcttcgg cagggaatct cccagagcct tagcttcttt   2220
atttgtaaaa tgactattat agtggttatt tctcaggatt gttagaatta cttccgcaaa   2280
catttgcaag tccctggttc ataatttcat gctaaattag taccgttaca ggaagtggta   2340
tatcattgtc acagtgtata caaatatatt tcttttatat ccctcgtgat ataattatca   2400
agacagtgaa acaattcaat gaattttacc agcataacac atttttaagt gattggaaaa   2460
tcataagtat cttttcttat gtttttagta gaggctttgc aaccccatta ctctccgctc   2520
ccaatttgat tatttaaagg aagtggatta ctaactcaga tatgtacact gtcaagccaa   2580
gttctatgtt ctactgctgg ttttcctgag aaagcagtca tataactccc ttgaaatgat   2640
ttactacttt tgtacatata aaattataat ggtgttaatg taccaaataa tgtccttgga   2700
agcaagggtt ttgccagtaa ctcagctgca tcagtcaccc tcaaggagat gagccatgac   2760
tttgttcatt agttggaaaa gagtctggag agtgcctttt cgttactgtt tatctttggt   2820
ctgacacttg ggaatagggt catggatact tcagccagaa aactttccaa atttaagtta   2880
ttaatgtatt ataaggatca aagtttctag tatagcctgt tcaattagaa catagtgtgt   2940
tggttgattg gatttggaga aagggaggca atcaaatttt tactacagtt tcagcctgtt   3000
acagaatatt gtatagagtg ttaaaatgtt gatgcattca tatttttgcc agttttaagc   3060
ttgtacgatt ttaaatcatt tccttacctt ggagacttcc cccccacctt tttttttttt   3120
tttgagatgg agtctcgctg tgtcgcccag gctagagtgc agtggcacga tctcggctca   3180
ctgcaaggtg gttctcccac ctctgcctcc cgagtagctg ggctacaggg cgcccgccac   3240
catgcctggc ttattttttg tatttttagt agagacgggg tttccccatg ttagccagga   3300
tggtctcgat ctcctgacct catgatccgc ccgcctcggc ctcccaaagt gctggaatta   3360
taggcatgag ccaccatgcc cagccctgac tgccctttaa gatgagtaca taagtagtag   3420
tagtacattt ttctttcaca tcctggagaa gatatactgt gttcactatt gaaatgaaac   3480
cataaagcta gagttaggaa gattgaagaa atgaaaaagg agctcacatg attttgtctc   3540
aggagaggct cttccaggat tctttggaga tatggtagat tccatagctg gagcagggaa   3600
aggacaggat gagcctgtgg gtgtagaaag gaagggagtg cttgaaagat gatgaggaga   3660
tgtcagcagg tcacagaaac cctctgaagg aggctccaac tggccaggct ggggacaatt   3720
tgggccccaa aataatgaca gtaacaaatt gtaactcatt gaatgaaata ggaatccata   3780
cattggtaat tatataaata agggaataaa accatgatgc aaaaagggat gtttatgtca   3840
tcacgcaaaa tatgttcaca gaaaatatgt actaattaaa agagggaaaa gagtaacttt   3900
acagtggatg aagcctggca atcatcactt taagcaagtg gtcagagtta atattatcag   3960
taatggtcaa atcaaaacca tatgcaagaa gactctaaaa tgcaagaaga ctcctgaagt   4020
```

```
acttcttacc aaagatgtag aacttaaatt cagtcataac aatacatgag acaaacccaa   4080
gttagagcac agtctgcaaa ataactggcc tgtaatcttc aaatgcatca agatcatgaa   4140
agacaaggaa agagtgaaga gctgctccag ttggaagaga cttaaaacta aatgcaatgt   4200
atgatcctag attggatctt tttgctctaa ggacattaat gggccagtta gtgatatttg   4260
aaggggatcc gagggttcca ttgtagtaat atatcagtgt taatttttaa atttttatta   4320
ggttgggatt attttggaaa ataccattat tcatagcgaa tacaaagtag aatatttggg   4380
gatgataatg catgattaca acaaatgttt caggagaaat atgatctttg tagtggtctt   4440
gcaacttttc tgtaagtctg aaattgttta tgcataaaag gttaaaaaaa ggttaaattt   4500
tgtttttata actaataatg gattagggtc atgtgaaagt actttagagg aaatgagact   4560
tttgagaaca tcatccctga agacgttgaa acactgagtt acctcatgga taatttaata   4620
ggatatgcag ctgatttttc taccttaatt tcttgtttgc agtatctacc catacttaga   4680
attgtctggt gttaaaatat gcccactggg actttcatga aattcttttg attttctaga   4740
aaattcagtt tcaaaggatt ttttaaatag atattttaag tttggtgtca acttagataa   4800
aatctgtttg gagtcccagt gtaagtttta gtaatgtgtc caatctgttt attgaaatag   4860
tataacttta gaatactttc tttggagaga tgaagattgg tatgttatag ttcaattcaa   4920
agttgttctt tctattatga tctattttat aattcataaa atctatctta tgattgtcat   4980
cataagtgca atttgttttt tgccccattc tacctcagaa actaagtatc tgggcatcaa   5040
taacaattgg tagtagtgtt tgctgctaag ccaagtttca ccagtacagt gtggaattat   5100
tttattgttt tttctgtgaa cattgtatct gctgttacta ggttattgtg aggtattggg   5160
ccttcataga aattgcctgg aacccttgtt cactaaagcc tgttacactt tttattctct   5220
gtgcgtgtaa tcagagactt attgatactg acacattcaa ggggcattat tgatcattta   5280
gattgctcta agacctaagg agtcttggcc ggatgcggtg cctcacgcct gtaatcccag   5340
cactatggga ggccgaggcg ggtggatcac ctgaggtcag gagttcgaga tcagcctggc   5400
caacatggtg aaaccccgtc tctactaaaa atgcgaaaat tagctgggca tggtggcagg   5460
cgcctgtaat tccagctact cgggaggctg agacaggaga atcgcctgaa cccgggaggc   5520
agaggttgca gtgagccaag actgtgccat tgcattccag cctgggtaac agagcgagac   5580
tccatctcaa aaaaaaaaaa aaaacgaaaa acaaaaacct aaggagtctt ttctccttat   5640
tttacaataa attccttttg attttgtgta aaaacttgaa actgtttatg aatgtaaaat   5700
aacatttgaa tacttttctt gtgccagata ttaggttaaa tgctttatgt gaattttcat   5760
ttgattctca caacttttga gttaggtagt tatttttctc attttacaga tgaaatggag   5820
ggttaggaac tcgtaggtag tagatgctga agctgagatt tgggcctggg tcttttcact   5880
actgtgccag aatcatttgg gagggagtaa aaactcaagc ctttggaaaa tatgatgaca   5940
taaaattgtc ctttatattg agaagcttcc atagttacca gtgtccttca cagggttgat   6000
cggaaagaca tacatgttag tgatgatgat aatgatgaag ataatcatta ttaccacagg   6060
tacttcctat aatataagca tctttcaaat tgtatgagaa ctttcataga acatctgagt   6120
aaatgaacag tacagtgtgc atgaaaccac taagcaaacc aagggaagtt aattttcttt   6180
atatgaattg taaacatgtc tctagatatc ctttatcaga ttccaccatg cgtaagtagt   6240
gtctaagttg ccccatattt agagtttttc aatgaggttg tgttcctact tagaatccta   6300
aagttcagct ataacagata tattaataaa atctgtggaa tctttaattg agcataatgg   6360
tggctgttat tttaacttga ggctttttgt tgagctggat tggaagtgca acttattaga   6420
```

-continued

```
aattacagtg tatttattcc tatttcttgt tctttatgtg agagaagata tactttagta   6480
gactgaatac ttcagagctg tatctcattt accaataaaa tgtgaaaaca gtggtaaatt   6540
ccttcacttg ggctaccatt gtacaggcct attttaatgg tatagtttga tatccttaat   6600
gttaaaagca atatagctta aagaggctgg taaattagaa ttttccaata tcctcagctt   6660
tttttcctct cacagttaat ttgctctgct gactccctac gcgaggtggc aacagctggc   6720
ccttttactg gagcttgtgg ggattagaga gtcgggctcg cagcagcgtg ctcggcctct   6780
tgcctctgtt gactgttctt tattgtttga tgcctgagca tctcccagac agcgagcaat   6840
tgtttctgga aacttaaagt ttgtttctct tgggagtaga caatgctttt ggggcttgtc   6900
tttgtgtttc ttcactttcc cagtctcctc ttatccttca tcctgtgctt tctcttgata   6960
attagaaagg agcaaagata ccaccttttt atttaggtct gcatgagatt ctaaaactta   7020
gaagtatagg ctatagatga aagtttcttt tttcagtaag ccacctcagt aacaaatcat   7080
gttttaaatg aaaactttgt tcttcataat atcatttagt gagagaaaac aaatgcatga   7140
gtgcattttt gaaattatgg tactaaaagg gagcagcagc aaggtgacct aatactgcca   7200
ttttaaaagc taggattaga aatgtatcat aactgcttaa atctaaaaag attctttcac   7260
tgaatccaaa atatagttct aatttatagg atagttataa gaaatctcta tgccatgtgg   7320
aaacatgaat aaaaagtagt cagaacatag ctaaatagaa ccctgaggta ggcagaatga   7380
ttttattctt cacatttaga aaagaaaaca tcaaggtacc ctggaactta atttctacag   7440
tgacttcaca ttccgacact tctcccatac ctgccatacc cttgagtgtt gttacggatg   7500
agaatatcgt ctgtgaagta gtatgagatg gaaattttcc tagaaagatt attgtactcg   7560
gaatttggaa ctgaaaagtg tagaaagggg aagtgatgtg tttaaaactg tttgcggagg   7620
tggggctctg ccatgtgtat tttgacaaag ctacacaggt gattcttgcc atccccgatt   7680
accgtgtacc cgcctgcccc tgagctggca ctccaaagag ttctttcagt gcatagcaag   7740
acaattttc atgctattaa ttgggataaa attgacatac attcatttgt agagtctgag   7800
acacaacgtc actttggaaa atttggtgag caatttgaac tgcatctgca ctggtgtgtt   7860
ctttttgttt ctgtagactt aaccaaagaa aatgaacttt aaagggactt taaaggcatc   7920
tgcactggtg tgttcttttt gtttctgtag acttaaccaa agaaaatgaa ttttaaagga   7980
agagagggtg ataccaagtt gtagaattct aggtatgtag gttcagagga gatttttttt   8040
ttttaagaaa aaaaaaaaaa aaaaaaaaaa cacccaatca agaagaatag agcagggtgt   8100
cccgaagaga acgtgtgagc tcgaagcatc ccggcagcat ctttcatatc tcagtactgt   8160
tgctctgttt cttgggctca caacaccatt tcctctctcc tggcttttaa cacatctcga   8220
ggcaaccttt tccctttctt tttatgcact tctctcactg cgtctcttct atatcatcat   8280
cacttcaacc taacccagta tttttatccc acctgcttat ttaccttcct tcagtgacta   8340
aaaaccttac tcagatactg ccagtgttgt ttaattgagc agaatagagg cttctcacta   8400
taggcaactg taaatcaatg aaaataacca tttaaagaag aaaaacattt tcatgtctat   8460
cacggtcgat ccccttctgcc aaagtgattt ggttcattca taaattcccc atacctcgtg   8520
tgttacatat tgtactgtac acatttactg aatgttcgat tgtgatcttg taatacagac   8580
tgttcattag cccccttctc ttgacttaaa aagttggggg gaactaactc ttttcatccc   8640
aaggaaactt tcttctactc tgtcttgcca gaaagttact gctcatttct cttgtagagc   8700
agcttgcctg tgtggcattc actcctgttc tgcccactcc cttcctaata tcgtgcagtc   8760
```

-continued

```
tggctttcat ctatatcaaa accacttatt gatagatcac caatgatttc ctaatgccag   8820
tctacccagt tcaccaggaa actttaataa ctttttatgt ttattaggaa tttttaagtt   8880
cattggaata cattcaagta ctttttggaa tgattatatg atgtagaaat gtgtatgttt   8940
gagagacaga aaaattgatt tttttttcct cttcactaca gaataaataa tgtatttgtt   9000
ttatggtagc aatacttgaa ctctttaagg catcttttca tggtaaatct ggcaatttta   9060
aaaatctggg ctttgtaaaa taattttttt tatagtaagg cagttaacac attaaagcaa   9120
ctaggaaaga tagtgaagaa ttatttttac cttgagtctg tatagatgaa gtaggctctg   9180
ctttgtgttg gaacagaaca aacaaacaaa aaaacctgag ttgatacaaa gataaagtaa   9240
tcctcaagga aagtcctctc tgttagagaa gtggttattt acacacagaa ttccacatga   9300
caacgcctga gtggtgtggt ttccaggtta ttgatgagaa aatcgagact caaaatgggt   9360
cttttagaat gaagtacatt tttcatggcc taagtctgtc tttaaaagtc accgttgtgg   9420
ccgggtgtgg tggctcacgc ctgtaatccc agcactttag gaggccaagg tgggcggatc   9480
acaaggtcag gagatccaga ccatcctggc taacacagtg aaaccccgtc tctactaaaa   9540
atacaaaaaa tttagccagg cgtggtggcg ggcgcctgta gtcccagctg ctggggaggc   9600
tgaggcagga gaatggcgtg aacctgggag gcggagcttg cggtgagccg agatcgcgcc   9660
actgcactcc agcctgggtg acagagcaag actcgtctca aaaaaaaaaa aaaaaaaaaa   9720
aaaagtcact gttgaagaat atcaataaat tagtacaagc gtaaaagaac atttctttt   9780
ctataatatt atacatgctg ctggtaatca acactttact agcaagtata ttcttttgct   9840
ttaaactcaa gttttaactg attaagaata aagacaagaa tgttctctac aataatgtat   9900
ggattgaatt tgccatttat cattttaatg taggttttac ttatatacta ttgtgaaaat   9960
actcttaatg tattcaaaag gccagtgcac aatttttttt tcttttactt cttttttttt  10020
tttttttttc tttagaaaga gtgtcacttg ctgcccaggc tagagtgcag tggtgtgatc  10080
atggctcact gcagccttga actcctgggc tcaagtgatc taataccttt aaagttggga  10140
ataaacttta tcttaagcgt ttttattttt aaattatgtt tttgcatatt tgatagaaaa  10200
agtagaatgt agtaattgaa aacctaatca caaaacaatt cattggactc tgcaacagta  10260
tataaaaaat aaaattaaac gagataggaa atcttaaggg attggtggat tgatgcacat  10320
gaaactggta acctctgtta agtacagttc tccaggtagt tggagaaatt agttaaatgt  10380
gaagagaatt ttaattttgc actattttgt acatttctaa actgtgtctc ccacagccct  10440
tctcccccag tgagcacgat tcagaattac tttgaaatgt tgtagtctta attatcctat  10500
tcatggaaat gacgaagcta atacacgatg tgctctatct taaaagtaac agatattttc  10560
ccaagtaacc tactgctggt tgtgatgctg agggacattt catgggactg catggtcgtt  10620
gctcatcgtg ataccatcct cagtggttgg gggattcaca gtgaattctc atatcctgta  10680
actatgcatc atggatctat catctgaaaa taaatcaaaa tctttgttga actcacagtt  10740
tccacacttg tatcacccat ttaagattgt ttcattgtta cctcctgtgt acagaatatt  10800
tcatttcaat ttctcttaga acagctcatt catctattct ctagtttcaa tattctgagc  10860
agtagaagtt tgctgttttg attaacttca gttagatctc ttttctgggc caagaattaa  10920
agccatttta tctttagtct ctccttttgt tggcactgct tcatagactg tgtcatatat  10980
acagatctgt ctttagactg atctttacca aagtacacta ctggaatttg agggtttttt  11040
tttttaacat ccttttcatt atgagagagc tagtgtatat gcattgtggg aaattagaaa  11100
ctatagatgg caaaatttta aaaaataatt gccaccaccc agagattgca ctgtagttta  11160
```

agacactttt gaatgtggtc ctagggacat aatttctgga acacattttt cgtgaagagg 11220
tctcaggttg gcttcttata cccacagctc gttgtcattg cccctagttt taatttccca 11280
tcgctcagtg ggctagattt tttttcattt tcttcatata aacttatttc agaaatgttc 11340
attaagagga ataagcagca ttagtaaaaa tgaaacctat ggtacccatt actttatata 11400
gttcaagtat tctggaagcc atattgtagc atagcatgta ctgaaaatca ctctcctttg 11460
aacagtaatc ccatacctgt atttgggacc tggccttcct ttgtgtgctt gtgtattcat 11520
tatatcccct ttctctcttc aaagatgctc aagtcattct catcttaaaa ctaatgggtt 11580
gaaccttcca tgcagtctag tagctactgt gaactctaat ctctattaca aaggttagct 11640
ctttgagtct cacttctact gaagttgttt tttttccca agattactga aaatttaaga 11700
gaaaataatg gcccaggcat gcattcagga ctagaaaata cttccatgta cagaaaacca 11760
aacaccacat gttctcactc ataagtggga attgaacatt gagaacacat ggacacaggg 11820
aggggaacag catacgccag ggcctgttgg ggcgtggggg gcgaggggag ggaacttaga 11880
ggacttaagt gcagcagacc accatggcac acgtatacct gtgtagcctg cacattctgc 11940
acatagagcc cgcttttgtt tttgtttttg tttttaagaa gaaataacgg ggaaaaaaaa 12000
ggtttcaaaa ctcataaaga aagagaaaga gagggaggga gggagggaag aaaatgcttc 12060
catgtaactg catcatttgg tactttggag tccatatcct acttgaaact ctaggatctg 12120
gccctcacat ttatgtagtg ctttatttta cagtttacaa aacttctgct tgtccatgtg 12180
tgtctgtaaa gtcatatgag gcattatgcc cattgttcag atagagaaat taacgttcat 12240
tgacataaat ggttaagccc attatgtaaa tatttatggc aaagctgggg ctaatcatat 12300
gtgttacaga taggactttt tttaaagaat tgtttaggta ttctgttcat cattagtctc 12360
tgggtttgtg tttgtggtaa ccatagacaa ccaagttcat ataatttggc ttcttttta 12420
tgtgattttt gatacgtgtt aaggatctat aacaatgaat ttgcctccta aagaggtaca 12480
taatgttttc attcctccaa aaagataatt ctaggtttat aaatctatgt atgctcagtg 12540
ccagttgaat tttgtgattg ttcaatagaa aagaaattgt gacttaaagg tgattttcca 12600
gtttaatgga ataaatgaaa ttagtttaga agttattttt atttttctga gcctgattct 12660
cactcagttg tgataaacag cacctctgta agataaactc ggtgataaac cgagaacttc 12720
tgaaatcagc ctaacatgaa tacctgttct tcttgtgcta agtttcataa tgctttatcc 12780
taatacacca tttttttaag aaatggaact tgtatttcat ttttgctttc atctcaccta 12840
attcataatt ttattaaaac ctacgatttt taatttcttt ttttatgaat ttttagtttg 12900
gtgtataaat cagaattaca ttctctgatc ttttactttt aaaattacag tgatgaactg 12960
actgtttaag aatcattctc atgattcatt cgtctgttat gcctcctttt taaagcttca 13020
gcactgaagg tcttttgaca aaccaatatt tataacagtt tgacagcagg atgaggaaca 13080
gcgtttgtct ttgtaacagc ttgaagaaag accctttcca ggacccagtc atgcagttac 13140
aatcttgacc tctttcttat gctgggaaca tgcatacagc agcacctccc atgtgttttc 13200
ttgtcccatt gactgtccat tcacttccca tctgttttgc agtcttaaag gaacagaagg 13260
ggccttctta taaatctgtc tttgcaggtg ataaatgatg cctacctctt taagagctgc 13320
ctgggtggtt ttccttttct tagaacattt ctgctttcct cctaactaaa tcagggaaaa 13380
atacaatttt aggaataaga gaaaaagaag aaaagatgaa tttttaaagc atttaattga 13440
ctaagaatat tttactgatc ttttttaatc ttcccaatta attgcctaaa tcatattttt 13500
taaaatgtat tatcgatatt tagatttttg tcagggagta aaatgaatgt attcattttg 13560
aaataatgta actctttttt gagaaaacaa agccatgtat cattaatgag ttaacatata 13620
aaataacttt ttaagttttt tgtgataatt taagtgtgga gcatcttatg tattggatac 13680
aaaagtaaaa tatttcagag taaatcattg taatcttatg gtaaaatcta ttcatttttt 13740
acatttaaaa agatgatcat aaatcccata aacatttatg cttttacttc tgttgctgaa 13800
aataagtatt gtaggaatag atattgatat cattgggttt tctaagaatt cagcagaaat 13860
aaaaataatt tacttttttct cccatgcaga aattatttat gcaaggtttt atgtaacaaa 13920
tattgtccct ctatggccct gcagaatatt cttaaattac tgatttaaaa actattacca 13980
gtataaaatg accactttta gaatattgtg gtgtattatg tgaatcagct ggctaataat 14040
atatcttctg tggactagct tgttagtttg tttattaatt ccctggcata ttccaaaagg 14100
aatttgaggc agcttacata tatcctacgc aaaagataaa actacttaag tgaaaaattt 14160
gggttgaaag aaaaggaaaa tccaggcaag tgaaataaag taaactttca gataaaattg 14220
gtgcccctca aagtgcatgc tcaagggttc tacgtacagg cagacctcat tgtattgcat 14280
gtcactttat tgcacttcac agttattgca tttttaacaa tagaagtttt gtggcaaccc 14340
tgcattgaac aagcctgttg gcactatttt cccaacagcc atgtgctcac ctcatgtcac 14400
tgtcacattt tggtaattct tgcaatattt caaatttttc cattattatt ctgtctgtca 14460
tggtgatctt tgatgtttgt attgtagcta ttttgggtac cactaactgt gcccatatta 14520
gtcagtgacc ttaatcagta aacgtgtgta ttctggctgt tccaccaact agacattccc 14580
tgtctctctc ctcctcttca ggcctcccta ttccatagga cacaacaata ttgaaatttg 14640
gccagctaat aaccctacaa tggcctctac atgttcaagt gaaagaaaga gtgccatatt 14700
tcactttaaa tcaacaacta gaaatgatta agcttagtaa aggaggtttg ttgaaagcca 14760
aaatgggcta ttagccaaat tgtgaatgca aaagaaaagt tcttgaagga aattaaaagt 14820
gttattccag tgaacacacg aatgataaag cagaacagcc ttattgcctg agacgcagga 14880
agtttcactg gtctggatag aagatcaaac cagccataac attcccttaa gctaaaacct 14940
aatccagagc aagttcctaa ctctattcaa ttctccgaaa gctgagaggt gaggaagctg 15000
cagaataaaa tttgaagcta gcaaagtttg gttcataagg tttaagagga aaaaagccat 15060
tctgcaacat gaaagtgcaa ggtgctgatg tagcagctgc agcaagttat caagaatatc 15120
taactaagat aattgatgaa ggtgattata ctaaacaaca gattcttgat gcagatgaag 15180
tagctgtcta ttggaagacg atgccatcta gtaatttaat agctagagag aagtcaatgc 15240
ccagcttcga ggcttcgaaa gagaggctat cccctcattt tgggtgccaa tgcagcaggt 15300
gcctttaagt tgaagccaac ctaaagaatt taccattctg aaaatcctag ggcccttaag 15360
gattatgcta agtctatcct gcttgttttc taaaagtgga acaaaaagcc tggatgacag 15420
cacatctgtt tacagcatgg tttactgaat attataactc tcgagacctg ctcagaaaag 15480
ttttctttca aaatattact gctcattgac aatgcatctg gtcaagcaag agttctgagg 15540
gagatgtaca aggagattta tgttgttttt gtgcctgcta gcacaacatc cattctgcag 15600
cccatggatc aaggaatact ttcaaccttg aagtcttatt attttaaaaa tacgtgtctt 15660
aaggccctag ctgccataga tagtgattcc tctgatggat ttaggagaaa aaaaaaggaa 15720
aagcttctgg aaaggactca ccattttaga tgctgttaag accattcagg attcatggga 15780
ggaggtcaga atgtcaccat taacagtttg gaagaagttg attccaaccc tcatggatga 15840
ctttgaagag tttgggactt aagaggagga agtaactgca gatatggtag agacagcaat 15900
agaactagaa ttagttctgt tgtaatatga taaaacttga acagatgaaa cattgctttt 15960
tatggacaag caaagaaagt ggtttctttt ttcttttttt tttttttggc agtctcagtt 16020
tgaagaaagt ggtttcttga gatggaatct gttcctggtg aagatgctgt gaacattgtt 16080
gaaatggcag taaaggattt agaatattac ataaacttag tagataaagc agctgcaggg 16140
tttgagaaga tagtgtccca atttttaaag aagaaaaatt tgagtaaatt tgggtaaaat 16200
ttacccaaaa ttacctattg tgggtaaaat gctatcagac agcatcacat cctactgtga 16260
aatctttcat gaaaggaaga atcaatcagt gcagcaaact acaattgttg tcttatttta 16320
agaaattgcc atagccaccg taacctgcaa cagccaccac cctgatcagt cagcagccat 16380
caacgtcagg gccagaccct ccaccagcaa aaagattatg acttgctgaa ggctcaggtg 16440
atccttagca tttgttagca ataaagtact tttaaataag ttatgtacat tgtcttttta 16500
gacataatgc tattacacac ttaatatatt acagtatact gtaaacgtaa cttaaacgca 16560
ccggaaaacc aaaaaacctt atgtgactca ctttattgtg atatacgctt tattgtggca 16620
gtctagaacc aaacttgcat atctcccaag tatgctggga ctttgctaga ggtaagctgc 16680
aaatttagcc ctcagtttcc tggtggctgg cagttacaaa atggaaagca gaggtcattc 16740
catcattcat ggtggccatc agacaacaac acagcagttg cttaggagaa gcatgggtct 16800
tcttcgtacg cacaactgag agaaatttcc cttaaagtgg acactgagtt agatgataca 16860
atgaatctaa tggctacaca taatcatgaa aatcatgggg ccctttattg taatgtttct 16920
catgcgggct aacatgcgta gttctaggga aaatatgatg ctgtccaaac atacagctat 16980
ttggtttggc ttatctaaag ataaaataca tagtatccag agaaatagat gaactgtatg 17040
tcctccatac agtctcccat aaatattatt tctttttgca gctgatcctt ttagtaaata 17100
tcaggtagcc agaagttcaa gattttacac tcattgacat tgacaagcac ctggaatggt 17160
actacctttt tttttttttt ttttttttga gacagagtct tgctctgtca cccaggctgg 17220
agtgcagtgg catgatcttg gctcactaca acctccgcct cctggattca agtgattctc 17280
ctgcctcagc ctcccaggta gctgggatta caggcgcccg ccactacgcc cggctaattt 17340
ttgtattttt agtagagatg ggttttcgcc atgttggcca gggtgatctt gaactcctga 17400
cctcatgtga tccacccgcc tcggcctccc aaagtgctgg gattacaggc gtgagccact 17460
gcgcccagcc aagtactatt tttattagtt aagtcagagc cataatcatt ataactgagc 17520
tgaaattaga attgccatcc acttaagaaa gttgagtggt ctaacaagta taaaagccta 17580
aatataaggc taattcatgt tcatactgaa gccttttggg gaataggcct taaaatatgt 17640
agaaagtatt tgaagcggtt ttaattgtac tagccaaaag gagcctagta gaaatgcttg 17700
tgttataaga gtttattttt taaaaagctg aatttatctg accaggcgcg gtggttcacg 17760
cctgtaatcc cagcactttg ggaggccaag gcaggtggat cacgaggtca ggagtttgag 17820
accagcctag ccaatatggt gaaaccccat cactactaaa aatacaaaaa aattggccag 17880
gcatggtgat gcctgcctgt agtcccagct actccggagg ctgaggcaga agaatcattt 17940
gaaaccggga ggcggaggtt gcagtgagcc gagattgcgc cactgcactc cagcctggac 18000
gacagagcga gactccatct caaaaaaaaa aaaagctgaa tttatcaaca aattgctgtg 18060
gagtttttta tatattcagc aggcatcagt tgtaatttac ctcacagact ttcttaaggt 18120
tgctttcttt ctaaattata ctttatgggg gtcacaaaat agcaattttt aaataatcac 18180
ctttaatgat taagtattgt ttaagtcaga tcactcaact atgaatgcat gaatattcat 18240
ggacatctat tacatagcaa gcagtgctat gctgggccga gtgattttaa atgacagact 18300
ttttggtaag tagagaattt acccaagcag tccttgctgt tctccacatt aatgctcaga 18360
aaaaatacat tataaaaatg atctttccaa aatgaattat gaagccccat gagaatgata 18420
tggcaatttg tggttacata ttttactaga ggattaatat ccaataaata aaaagatact 18480
aaggaataaa caaaaaaaat ttaaaagatg aagtatataa tgaattagaa caatacattt 18540
taatcataag ttttaaatta gtgtggactt tgaattctcc tggacagatt ccttcatttt 18600
atagataaag ctaggactgt gacttatcca gttatgaggt taacggcgaa tacaacattg 18660
tcatatattt taaatgacac acattacaac atgttctctg ctttataaaa atcatatcaa 18720
ataattgccc catagattat taaaggtgtt agactaggga ttcttaaaaa aaattttcat 18780
caaatgtttc tttcattatt aatcccatga agtccatgtt acagaagatt ttgtctacaa 18840
cagtgcagtt acattcttct cgttagaaat acaaccacca gttagagttc ctaatcagta 18900
taaggaagta gttgttagga gaggggatgg gtttcttgtc caaatgaagt tttccatttg 18960
agtttttgaa gtagtgaaac taacccagcg tttacaggcc ccagaaatct gggaacctca 19020
gctttcaaag tactgtacca gtctttaaca gttttcctgg acgtgtgaat tgatgcctcc 19080
ttctgtaaca tgcaggagtg ttctgtctgt cttcattgag tgttaaaaaa taatcatgcc 19140
tatttcaagg aaaaaatcta cagaactaag atgcagaaga taagtgctag atttaatcat 19200
attccttcat ctatctgttt ggttcaacct ttcatcaact aaaagatgca cctttttttct 19260 tgtgctaact ctaagatttt agctacagtt ttgagaatct tgagtgtagt ctcttgttta 19320 cctttttcc ttttttgtt tcccccacac cctagattca tttaaatact gaacttctaa 19380
agggcaagta tatagtgtag tttaataaaa agcaaacctt ttcatgaaca atatatatta 19440
cataataaga agcgttcctt tacttttcag tactctagtg aatagctttc tacagtagaa 19500
tctcacttag agggtgtctt aaagcttaac accaagtgct caggcagcat gttatacaac 19560
agttccatta aggtacattt ggatctttgg atgtgtggtt tgcttaaagt acactgcatt 19620
agtaagttgg cagcttgctt tctttaaaaa catcaaaagt tttaaaaggt ttatttcagg 19680
gcatgtgtta gtgttttgtg tgtggttctt tgttcctgtt ctaaactgtt attaaccact 19740
gaagtgaacc ttctcccggg tttggccttt tggtattcac agtgtattca aaacctaatt 19800
acagattagt ctatatttga gacttttaga gcaagtatca gaagacccaa aaagaaaatg 19860
agagtagcag tatcatttca tgtagagata aagagaccca aaacatgaat gggtgtcaag 19920
tcagctgaag aaaagaaaaa agagaaggaa cttcattcac tgagacggtt tatgagttgg 19980
ggattatggg aatattcatg actcaatcaa gaagcacagt gaattgatgt ttgaaatagc 20040
tcatctttta agtaaacatt ggataaatgg aaagtagact cagtattcac tacacgtaga 20100
aatagctatt tctgtatagc agaaatagca gtttgttaat cccttcctga gttggtttaa 20160
tttaccaagt aaatcacaaa ttttattctt tatttgtgaa tatttaattc aaatatttaa 20220
tggaaatatg agtttgcttt ataattagtc atgctgatcc atacacgtat ttctgagaga 20280
aagcaatttc taatggtgaa atagttacaa taatattttt gaaatttgaa agcaccgtga 20340
tactgaagca ttaatctgaa ggatcggaaa gtagggagtt tttgttgcca acatttaact 20400
tcattgttta tggataactt ggttttctgg gcagccagat ggcacagtta gtatacagac 20460
attcttggaa acttgtatca aaatttaaaa tgaatgaatt tatgagaaat aattctgctt 20520
attatttgta atgtagcttt cttgaaaagc aagaaatcgg aatgtagttt ctaaagctgc 20580
aagtgaatat gtatacatag ccagctcttt cagccttgat aataaggtgc aaccattaag 20640

```
atgaagggat tttttttcc cacttgtgtt tttgggcccg agtatcctga tctgtgttgc  20700
ttgtctggtt caggtgtgag ccaccagctt tctttgactt tcattatcta tgtgtatctt  20760
gcctcctgtt cccaggcttg ctctagctct tctgatcctg tcttcctccc tcttgatcac  20820
tagtgtagta ttcatgaagc cagctaagtt agtttttccc tttgaaaacc acagcccctta 20880
tcttctgtgc catattttgg gcaacttcgt ttatcattga ttgaccgtac gcagtgatca  20940
ggccttgttc tagacactga agactctgag catttttggg cccattttgt actcctgtat  21000
tgttctccag gggcttctcc aagtgtgcgt caatttagtc ttctcaagag ggcatcattt  21060
tcatcagaat atgatagcat attatggagt gtccggtcat ccttaggcat agactactta  21120
ggaggtgtaa ctgttttgtt ccctgatttt tactgaaatg ggtcttttct tttttttttt  21180
tttttttttt tttttttttt tttttttttt ttttttgaga cagagtctcg ctatgtcacc  21240
aggctggagt gcagtggcat gatctcagct cactgcaacc tccgcctccc gattctccct  21300
gaaatgcgtc ttattttaag tcaaaggtaa tacttaaaaa agaccaaaga gacttaaaat  21360
aacagcattt gcttcgtcac tatgagcttt gttattatga gttaacatac agtagcagac  21420
tgggtgtagt agctcacgcc ctgtaattcc agcagtttgt gaagccgagt ggggaggatt  21480
gcttgaggcc aagacttcga gaccagcctg ggcaacatag tgagaccccc atcttgacaa  21540
aaaaaattgt tttaaattag ccaggtgtgg tgctgcatgc ctgtggtccc agctacttgg  21600
aaggctaagg taggagaatc gcttgagcct gggaggtcga ggctgtagtg agccgtgttt  21660
gcatcactgc actcctgggt gacagtgcaa gactctgcgt cagacaaaca aacatcgtag  21720
cagatgtgtt tcttaatcag agaagtgtag acaaggctaa ctccaggctt taatgtcctc  21780
atatttagca atgatacctg caaggttgta tgagaaccaa atgaaacgcc aaatttggaa  21840
atacatagta gatacatcat agcagagtaa gccaggaatg cttctcaaag gtaggatatc  21900
atctgtgtcc tcatatcact ttatgaagta cattgtgaaa gtgaaagaac aaagaaataa  21960
atgtttttta gttaatgttt aaaggataca tttatcataa ttgctctttt aacactcacc  22020
tccagtctcc cctccgttca cacctcctac ccccattact tcctggtaac ttagttaagt  22080
gtcctttgtc attcctgagg tttcaaggca tggtagtact gtgtcctgat attctaatcg  22140
taaatattta agggaaattc ggcatttttt cattttgtgg ttttcatatt aaagtacatt  22200
aaatagtctt tttgctttta tttaggaaaa aaactgctta cctgttaatt ttagaaaaat  22260
ctgattttca tttagacctt acagggtgag acacctgcat cagggtggct cttggtatct  22320
ttcaattcaa ttggatcttc tctgaatagt ctcttgtagg gagtgaggct gctgtaccac  22380
ctccctgcag tagtccatcc agcttaagat gggggtcacc agtaggccaa aagaatgggt  22440
agacctggcc atgcactgcc ctattgtact caaatcgtgt atcaaatgga gttggatttc  22500
ttctcttcat acagtacagc atttccaagt agaaatattt ctcaatgaaa tgtggagaga  22560
agcacccgtt tgagattccc gtgtgttgtg tgatttaagt tagatggttt tttaagacca  22620
cattcatttc cagcattcta ggtaacaatt tagaaaatgt ctttctccta acctccccac  22680
tttttaaaaa tcctccaact gatgaactga tgtgaaactt tcttacattc actgaaaaaa  22740
aaaaaaaata ggttaagctg tttctaagca actagatgaa ttaattttta aactaagaat  22800
gtggccttat tttgggaaaa caagaatatt tacttgtttg tctgctgttt aaaaaatgga  22860
agtcagccta ccaaaaaatt gagactcaac ttctaggaga tgggttagga tttttttttt  22920
taagtttctc tagtttaatt ttatatataa ggggttaatg ctaccttcat aataactatt  22980
```

atcatatttt ctcaatacat agcttgatta aaacaactgg actccccccc caccccaccc 23040
cacacacaca cagattttat atcagtctga atctaatgcc tagaataaga agtgcttcag 23100
ccaggcatag tggcactcac ctgtagtctc agctactcag gaggctgagg cagcaggatc 23160
aattgagccc aggagtctga gtctagcctg ggcaacatag tgagacctag aagttttaaa 23220
ttactggaaa aataatatga aaagaataaa ttactggaaa aagaatatga aaatgttacg 23280
ttctttatat ccaaccgtgg taggcttttt tgagttcctg caatgctaat aagaattcat 23340
aaaaaggaca attcttcatt ttcttgggta ctcatcacta atagctgcct cgctggtaaa 23400
aaggaataca tgtatcttca attgcagatt atttactttt aaatataaaa gatataaatg 23460
tcaaatatta aatgcatctt acatggtttt cctacatagt gaaagtagaa tgcttgccag 23520
ttttgcctct aggtcactca ctttgaacca gccaacccac cttaattgat catttccact 23580
aatatgttaa attaccttaa aagaacaaaa atatttatca tgcttactat aacctgtgtt 23640
ttaaaatagg aggccaggca cagtggctca cacctgtaat cccaggactt tgggaggcca 23700
aggcaggagg atcacttgag cccaggtgtt caggaccagc ctgggcaaca aagtgagatc 23760
ctatctccac aaaaaaatta aaaataaaaa cttagccagg cgtggtggca cgtgcctgtg 23820
gtcttagcta cgtgggaggc caaggcggga ggatcacctg agctcaggag gttgaggctg 23880
cagtaagccc tgccaacacc actgcacgcc aacctgggcg acagagtagg acccccatct 23940
cagaatataa aataaagtag gaggtgcatg tgaagtagta tagatcatga cttttccaat 24000
tttaagaggg gattggcatg tactatgagc agttcacatt tgtggaggaa atctacattt 24060
cagagagtat atatttcatt tggaagtcta taaacatgaa aacctaaaat aaataatgta 24120
aatctacctc tagtggctct ggtattttta aacttattta tagctggcaa agtacttttt 24180
tgtatgtatt tttatagcac cattgcactt ctcatgtttg ttgcaagcat ctcccacagc 24240
ttcctttgtc ttttaatttt atgacatata aataaaagta tacatttcaa tatggccata 24300
ttgattgatc ttttcctttg taactcttac tactttatat ttaaaaagtc atttcccagt 24360
ctaaggccac ctctatttc ttttagtttt ttaaaatggt ttcattgttt tatatttgcc 24420
tatgatccag acattagtaa ctgtgggttc ttaattgggc ttcagagaat ctgagaattc 24480
cttaaaattc tctacataat tgtacatgta cttaatacat gcttttttcc atgttaagag 24540
tccagagttt ttgttagatc ctcaaagggg tcagtcagtc tctcctccca cttccaaaaa 24600
atgtctgaga cctactacta taatccatct ggactttatt tgggtaaaag gtggtatggt 24660
gagactcata tttttctttt tcccgcaaat agttaagtat accaaccatt tagtaaataa 24720
ttacctcctg atttgtgata cctttgaaaa ataaatgttt ttctttattt ttatctccac 24780
ag 24782

<210> SEQ ID NO 4
<211> LENGTH: 5409
<212> TYPE: DNA
<213> ORGANISM: Homo sapiens

<400> SEQUENCE: 4
gtgatggatg gtttaagggg gctaccgata cattcacact aatcagccat ttctgccaag 60
atcatgtcac ctcaatctgt tcatggactc caaatacaag aaattaattt gacaaagtga 120
aaatataaaa gatgcatcat ataaatatgt aacttttctg gagtgggtag tataggtaaa 180
gccaaaagaa acaaattcaa gcagaggaat tttggtttct gaaaattagg ttgtctgtag 240
ggtccctgta tttatactta gaacaaaatt aggaatttct gtttatgtgg tccagttatt 300

-continued

```
gagtcaccct aagtttgtag gcatcttacc tacctacttg ctccccaagt ttttatttct    360
aaaatgaaaa gcattgctgt agatgaccag tttacactaa agaataacat ttatttattt    420
gttttagcta aagtatatgg acagggaaca ttcatattct tgtagaagaa aattattttg    480
acttttgggc aaaagcatgt agttcttata cactttgaca aactcattgc gtacattttt    540
cacattaatc aaagtcagca caaataaatt ttcaccttgg accacggagg gtttgaacac    600
tggaaatttg atataattct ggttgctaaa gaacaagttc taataaaagc ttaagtgtat    660
accaatatgt ggctgttggt gcaatcagca ggtccgtaaa aatatgattt taatggttag    720
gtaatcccac aacggagatc ccaaagttca tgtttggaag agacttttgg gtcaaagtga    780
aatcagtgta atgaatttaa aattatactc tgagatcttg aaatcagcta attatgttac    840
atcttattag ctcagaaaag ttttgaagtt atatacaaat gctagtcagg aaaaaagatt    900
cagtcatgta attcttgtac attctactat ttaaatcaac caatattata gattatgatt    960
tagtgcagta attctgctgg ctaaccttat ctcatttggt ggtggttagt acttcagagt   1020
actcaccata gtttcattta tgttttcagc atcacttcct ggtttttctc aattccatgg   1080
ctgtggaatc aattcatatg tatatttagc ttcggtgagc aaaaacatag ctagaaaaag   1140
aaaagaagtg agtttcctac ctggttaaat taaagtcgat gtgttaagcc aaggaggact   1200
tcttttgaat ggtactttaa caatccctgt tctgtatact gtgaatatat catttaaata   1260
gcctaataaa ttggatgctt aggctgagcc acctatactt tagttttgtt atggaaagaa   1320
gggagaggag caagtatgtt cttatatgtt acttagaaat aagaatgtag ctgtagttac   1380
acattgttct taagtttttt tcgtaagaca acttgaaatg agtcccatag gcctgctatt   1440
taacattcta agatatgact taaggttaat gatgagcttt tgaatctgac aattcaagag   1500
atatccataa tgaatactga ttcattttct acattgctga aagctaatgt tcattttaag   1560
cctactttag tagcctttat ttgggcttag agatgttatt cctctttctg atatttattg   1620
ggttatctgt ttaacccttt tatatctccc tttcccgatt tgtaaattag agactggcaa   1680
gactttttac cctgagtaga gcaccaaaca tggcttgttt ctgcccacac tgtagttacc   1740
ttgaggggaa gtaaatggga ctttaaaagc aatttatgct cttttatagt gaaattatcc   1800
ctcttactat cccgaaagac tgttacctta caatatcctc cactcctttc cccctgtagt   1860
tactatagag atgacttttc ggttcttcac tgccataatg atcaaaatcc taattcatga   1920
gatttttatc attccaggca tgtgaggttt acttgatgca taaaaccgca agtacttttt   1980
gttgtttttt aattgttttt tctctcttat cttcttgaaa gtctaagtag atcatcattt   2040
ttgatgtctt attagtagca actaataaat tttccctgta tcttctcagc aaaagaactc   2100
aagcagagac agaagattag aactaccatt ggtagtttg cttcctatgg atatgttcac   2160
atacatagaa atttttacaa tgaccttttt atatatgtat ttcagaattt cagaatggcc   2220
tcaatgcctt aataggaaga aatacttgaa atttttaaat tagggcttgg ttttgtgagg   2280
agctagtaaa ggtttttctc tttcagcttt agcttgtttc tgcggaggat tccgctcttt   2340
ctccatcagt ttcatagccc tggaattgta gaaaagctct ggtttcaaga ccattgatat   2400
ccatttctgt cagggtgagt tttaaattta tttcatgatg caaacaatat attgaacaac   2460
aggacatgaa cttgttcttg ttgtaagtgg ctgaatttta tcagtaaagc acatcaaaat   2520
aaaatatacc ccaattgcta gttaagacct agagtgacag attgaaaata gcttgtgtta   2580
ttctcttaag aaaatatata aaaattatca tctcatcaat ctttaatgtt tgttttataa   2640
```

-continued

```
atctaaatgt ttttatattg tttcctagga aatattaggt ctaatttttt actttaccac   2700
cagctgtctt ttattttact cttttttga gacggagttt cgctcttgtt gcttaggcta   2760
gagtgcagtg gcactatctc agctcactgc gacctctgcc tcccgggttc aagcgattct   2820
cctgcctcag tctcccgagt agctgggatt acaggcacat gccactacac caggctaatt   2880
ttgtattttt agtagagacg gggtttcttc atgttggtca ggctggtctc gaactcccga   2940
cctcaggtga tccgcctgcc tcggcctccc agagtgctgg gattacaggc atgagccacc   3000
gcacctggcc agctgtcttt taatataaca ttatgattaa ttgtgatgtt ccattaaact   3060
aagcggagag gaaacatgct ggtaaaccat gtgtgagtta ttcattgtac cagaaaggca   3120
aatgatacat tttatcctaa aattcaaatt tataaacatc ttaacacttg tgatcattaa   3180
atactactaa tctagcatat aaattatatt tgtaggcggg gcacggtggc tcacgcctgt   3240
aatcccagca ctttgggagg ctgaggtggg cagatcacga ggtcaggaga tcgagaccat   3300
cctggctaac atggtgaaac cccatctcta ctaaaaatac aaaaaaaatt agctgggtgt   3360
gctggcgggc acctgtagtc ccagctactt gggaggctga ggcaggagaa tggcgtgacc   3420
ccaggaggca gagcttccag cctgggcgac tccgtctcaa aaaaaaagaa aaaagaaatt   3480
atatttgtaa tattctacta accttatatc attttaactt tttatataac tttttttattt   3540
taccaaatta agttaacctt ttatagccct tggcttatac taaacatcct aactttttttg   3600
tttaattgta ttagttttta agttattgcc ccagatgtca agtaatgttg gattttctat   3660
aataatttag gatatattgc atgaagtcag ttagtattta catttaaaac taaaacaatt   3720
tatactaata cagtttatac atttcatact aatttagcta cagttggata aatatttaat   3780
ggaacaaagt aaatcaaagt accttttcaa atgaattgga aattaaatcc acataacaat   3840
tttttatgac cacactatta cagtgtgatg gcatgccaaa tgatcataat gtggaattat   3900
gtatttcttc attggctttc aagattctgt tctttagttt gtgggctcct ctccaacttg   3960
cttgtctcct cacagtttag gcgactgttt ataattcttg tccatcctgc ataaacacac   4020
acagtcaaaa tgaaaaaaag cttctatcag cagatctgtg cttgctgtac agaaatggga   4080
aaacaattga agtttgcatt atcttttttc taattaccag atcgtttttg gagctattta   4140
ggcatacgct tttaaggaaa aaagaaaaaa agagtgtacc ttttgtttct aacaaaggtt   4200
gttatctata ttattgaaat aaaaaattgg ggatagttat gacaaagtat ttagaaatag   4260
gaattaaaat cttaaaataa cttttcatag catggacaag acttattaat gtctacctca   4320
ataagcaaat catttaaaaa tttttcatgt atatttgctg ccatgatgtg ttgtgattgc   4380
ttaaataacc aatgaatgaa gatcaacaag gatttaaatg aagaagaata tggatttaac   4440
tattttctcc tgtgaaataa gttcatattt acaagttttg attttcagaa attagacaat   4500
tatttttaaa ggctgggatg acaacttctg cctcttacca agaagtcaaa gcacagttat   4560
gtgaattcat cataaatcac atcattttta ttatattttg tatttataat tgtattgtga   4620
ctactttaaa acctgttata aaataaaatt gtttttttaat attttatttt agaattatta   4680
gcattaataa caatttgaag tagtttacac aatacctgtg agttttattt ttgttttata   4740
ttgaaattaa ttttagttgc tttacttggc ttcattgcta tggatgcatt ctctgtgtta   4800
cgagttagca gatctttcct tggaactgaa tttaaaagca agcatttggc tccacttaaa   4860
tctctgaaaa tgcaacttgt tctttgcatt tattacataa ttcgctactt atggtacaga   4920
aatggataca atacaaaaat atttccttat aagatacact gtgaccaatg agctttttaa   4980
atagctgtaa tcagtaacat gtatttgact tttcaaaaca catttctgga gggatatcag   5040
```

tgctttattt ccccaaatat ctgaatccct atgctttagt acaaaacaac ttctgaagaa 5100
tttagtaacc atatgtgttg atctcttgtt tttctaacta gtctttcata agaaatgact 5160
agaatagcaa cagggaaatg attgcctttt aaggtttttg tttctcaata taaaattttg 5220
gtgaaccatt tttattgata aatacaggta tttttacttt cttaaatcac ttgatttaaa 5280
attactttga ttaaatatgc atataaagtc agttgttttt aactctcaat acttatcaaa 5340
aaaatttaac ttgctgtaca ttctgtataa acctaattct attcaactaa aattatttta 5400
aacatttag 5409

<210> SEQ ID NO 5
<211> LENGTH: 21301
<212> TYPE: DNA
<213> ORGANISM: Homo sapiens

<400> SEQUENCE: 5
gtaagtgcag gctctaatct ggccccgtta attctggggc ctcttgagag tggggctgtc 60
ttatctctat ctccaaaaat gtgcaggtga ctctcaggcc aggccgacgg cagttggaga 120
attcccagat gttcttgagg acccagaatg acaggagccc tggctgggct tacgttcgga 180
gccggcttca atactggccc ttttctctgg ccctacccaa cccgaaaatt ctggacgcct 240
ctcaatcttg gcccgtctct attgtccttt tgtctctgcc ctttacaccc ttgtgtcttc 300
agtgttctgt ctgtctctgg ttgcctcttt tgcctttttt ctgtcctctc cctgccaggt 360
ttggctctgt ccatgagtca cctctctcca catttctcct aactctcggt gtcttctttt 420
tcttccattt ccacgccatg tgtacattgc atcttcaggt acctgggctc ttctatcggg 480
gaaaggggcg tccgtctctt tccctagccc gctgatagaa gtcagaacta gagcaatgac 540
gcacacggtg tcagagacgg tgattcgaga tgccctttca atagcagctt ttttctgtgt 600
ttcgggaggg agacttactt tttgatgcaa ggtcgtgaac gtggcaccac ctttctaatc 660
tcaatcattg ttgccctggg gtggtttaat tctaaataga aaatcataga aatcttttca 720
tttctgtgcg ttactatatg cattgtaatg agattaaatt ggattttata ggaaattttg 780
ttctagtatc attagatacc ttcaagctta gctcattgtt gcaggcattt gataggaagt 840
aagatgcatc aagcaaaatt ggaaaaacgt ggttttcctg aattaacttc taagcagttg 900
ttttgaattt tttccagacc tttttaagtg gtatagataa tttatcgtgt ttataaggaa 960
tggaatgcat tcgttagttt gtttttgttt tgttttgaga cggagtcttg ctctgtcgtc 1020
caggctggag tgcagtagcg ctatctcggc tcactgcaac ctccgcctcc caggttcaag 1080
caattctcct gtctccgcct ccggagtagc tggaattaca ggcacgcgcc agcacgccta 1140
gctaattttt gtatttttag tagagagggg gtttcaccat tttggccagg ctggtctcga 1200
actcctgacc tcatgtgatc caccctcctc gacttcccaa agtgctggga ttacaaccgt 1260
gagccaccgc gcccggccca atttgtttta tataggttaa ctggagtcca aaatacagaa 1320
ctagatgaga taacaatagt taacagtgtt agtcagttag aattattgca taggtatttt 1380
taatctcatg gaattttagt ctttgagtaa gttcacagcc cttggtatta aagtaagtta 1440
tttacaaccc ttgcatttct acttctcaat atttagtgag gaaacatatc tgattttctt 1500
taaataaaaa gagaaaagac tgcagaagat agcattctct gttggagcaa ttaagatgta 1560
taagaagaac tacaaagacg gagttttaaa acaaactgat ttataagtgg tatttattta 1620
attggctgtc attgggctaa attatttcta aagttaccat ggatgccatt gagtcatggc 1680

```
ttaaaaatgt ctcctggtga tggcacagtt tagctaccta aagaagtaga gatgtgggaa   1740
gccagaagcc ccaagctctg cagtttttct tttgctatag ttcctttgca tgttgtgaaa   1800
gaatacagtt aaattcctgc tccctaacag atgagagcat aagcatttct ttgggcatac   1860
atatgtaaat acatgctcat ggacatgtga aaagatcaat actaacattt gggtgcaata   1920
aataattgtg taaaattatt tttaaaagaa ttacatatta ggaaatgata tattgattaa   1980
aagtgatagt caatgaacaa gagagtagat ttctggggga aacctatttt gcatcatact   2040
tgatttttag ttttgactga atattgaagt ctatattcaa aattcttttc ctttagaact   2100
gtaaaggcat tgctgcattt tcttctaatg taattgttta ttgctgctga gaattcttat   2160
gacaatctga tttttttcatc ttcatgatta tcttgttttt cccttcatgg aatctgttag   2220
ggtcttgact ttatccttta tcctaaattt ctcaaggctt ggaccaggtg tgggtttggt   2280
tttgttttct tttgctactc atttgacttg gcacactcag tgggcctttc cctttatctt   2340
tcttcatttc tgagacgttt ttctctctta tttttttatta tcttcctttc atttttcctg   2400
tcctttttct ttctagacat ctcttaggag gatagtggtc ctcttagatt gatatgttat   2460
gtccgtgatt tccaaagtaa gatttgtact cgtcgtctgt taaaaggaaa agcatacata   2520
taccctatgt atatatgcac actttttttat ttttaaatta tatatgtatc tgtactaatt   2580
atttacattg taagtcaacc ctaacataat cttaaaggat aagatacaaa acatactgca   2640
tctagaagct tcagtacttt cttcctgaat cccagtagat ccttttgttc atcccacggg   2700
atgcattccg cccccatcct cccactccct ttggatacca cattaccaca gctctgcatc   2760
acttaacttt cctcttatgt ttttcacctt tttttttttt tttttttgc atttatgtc   2820
ctggggaatt tccttaattc atttcatggt tttactgttg attttttaa tattggccat   2880
cgcaactttt cttttctttt cctttccttt cctttccttt cctttccttt tcttttcttt   2940
tcttttcttt tcttaatttt cttttctttt cttttctttt ctgttctttt cttttctttt   3000
cttttctttt ctttcacaca ggatcttggc gtgttgtcca ggctggcctc gaactcctgg   3060
gctcaggtaa tcctctcacc ttggcctccc aaaatgccag gattacaggc gtgcgccact   3120
gcatttggcg gcaacttaat ttttttattt ttatttttcc ttttagagga cacctagcac   3180
tgagcattgc aacttttcat ttccatgaac ttttaagaaa actcttaaag acatgtttaa   3240
ttctgtacac tttctattgt tctttgattg ctgtttttga ataacaacaa ggagtacgcc   3300
ttagcatttt gatggtatcc tcttaatagt cgcaataata gtccccttgg cgctctgtat   3360
actctcaagt cttaaatgtt ttgtatgcag ctgtacgttg acagttgaat ggtctcgctc   3420
caagtggatc agcaagaaca taaagaatca tttaactggt acaggctgcg gcttgtgaat   3480
tccctattaa caccaaagaa gacgtgtgag actccgtact gaaactaaag acgacttgtg   3540
agttccacac tgagatcaaa taagtcttta tgatggtgac agagagtggt gtcaacgcct   3600
aaagttttgg ttaatctctc taaattgagg ggctgaccaa aagggggaac ttaactgtat   3660
tagacataat tttgagaaac atgggtatgt ggatggtaat ggaggaaatg ggtgtagatg   3720
agattgccta gggagagtga gaagtaggtt aggtctaagc cttgatgagt tcccaacatt   3780
tccaagggta gttgaggata ctgaaaatga gtggccagtg agatagaggt aaagctagag   3840
actgcccagg ggagaggaat tttcaacaat gaggaggtgt caacattgtc aggtattgct   3900
gagaggtcag ataaaaccag aattgagcaa aatggccatt ggaagcctat ggtgccctcc   3960
gtaagagctg tttcgctgaa gtgatagaaa cggaaatcag gctgggcaca gtggctcact   4020
cctgtaatcc cagcactttg ggaggccgag gtgggcggat cacctgaggt taggagttcg   4080
```

```
agaccagcct ggccaacatg gtgaaaccct gtctctacta aaaatacaaa aagtagccag   4140
gtgtggtggc aggtccctgt aatcccagct actcaggagg ctgaggcagg agaatcgctt   4200
gagccccaga ggcggaggtt gcagtgagca gagatcgagc cactgcactc caacctgggt   4260
gacagagcaa gactccgttt caaaaaaaaa aaaaaaaaaa gaaatggaaa tcaggatggt   4320
ttggctttta ttttaataaa atagctagag cagggaaatg gggtactttt tttcccccttt   4380
ttaagatgag acatagccag gtgcagtggc ttacacctgt aatcccaaca ctttgaaagg   4440
gagggtcgct tgagctcagg agtttgagac cagcctaggc aacatagcaa gaccttgtct   4500
ctactaaaat tcaaaaaaaa ttaactgggc atgctggcac acacctctag tcccagctat   4560
ttatgaagct gaggcaggag gatcacactt gagcccagat acgtggggct gcagtgagcc   4620
ctgataatgc cattgcactc cacgttgggc aacagagcaa gacttcgtct caaaaataaa   4680
taaataccct gtctcaaaaa taaaaaataa atatgggagg agagatttga cttagattcc   4740
tcaaagggca ggaggaaaga gaattccaaa cagtgattca cctttaatgg gagaaagatc   4800
gcttaatttt acatgaggaa gaagaggatt ggtggagata cagtaggtga acagtttttg   4860
tatgaggaag ttgaacatgt gtcattctaa tagcttccat tctctgtgaa gtagagggca   4920
aggtcatcta ctgagagttg gggaggtcaa gagagataag gggagattag aagagctctt   4980
ctagcagaga gtggaagaat gaattgctaa gagagatgaa gtaggattgt taagtagttt   5040
tgagggccct gttgagatgt gcttccagtt gggtgtgatt ttctccagta gtgctttatt   5100
tccctgggta caggcagaga gaaaaacaat aaggctcatg tagggtttgt attttgttgg   5160
acaagtcaaa cagaaaagtc agaggacgag ggagtttaga atgtttgcaa aagagttatt   5220
gaaacgatga accgcataat ctaaggtggt aagtgggtga atagataagg aggatgtgaa   5280
taggtaagga gaagaaagaa atatcagatt attgattatt gatggcgact ctctaataca   5340
gctattatgc cattttaacc gattaagaaa ctaaggcttt agaaaattca taatttgccc   5400
taactgcaca gctagtaagc agtggaaatg tgattggaac cagagttctt ctgactcaat   5460
agactaaatg gatgtaagga tgtagttgaa agaagggtga gctaaacgtt gtggaaccat   5520
gagctctttc tctggttgat atccctctct gtaagtgata acatgggtca cgctggataa   5580
aaccttgtgg tgattggtga ctttcctttg tccttcctcc tgtgcctagt ctggcgagta   5640
tctgcctttc cctttccttt ctcattgctg ccacctaact ttaggctctt ccccttacat   5700
ctgggtaact gaaataagat caccttttg ttccccttct gatttacttt gacctaacat   5760
tatctttact attttcttta aattaatgtt tcattagtct tattctactc aggaactctg   5820
tagttcccca ttgcctacga aaaaaagtta agcctcagcc ttatattcag tgactcttca   5880
attggatatt cagtccagtt ttactcctcc tatgagcctt ctatgccagc tccttgggtc   5940
tcttgccctt tcattgtctc agctctgcac ccttctttct ctttttatt cttttttttt   6000
tttgtacttt tttggttttc tttttggttt ctttttttgt tttatttatt aaacctccat   6060
cacacttcat cctatggagt tttgaaccac agcaaggtgc agtatcatcc tggggctctg   6120
gaggaagtgg cagggagtcc aaaatgtcac cttagcttct tatctggggc cacatgtatt   6180
tctgcatctg ctgcttccca cactcttgcc cacaagtgtc gcttgtggaa ataatttgag   6240
atttactgtc tggctgaccc tagtttcaat ctcttttcca ccatttgcta atcattctac   6300
cttgggcaaa acatagaatt aaaagaaaac ttcagacaag ttaaatttga tggagtttaa   6360
ttgagcaaag aaaaaaaatg atccacaaat tgggcagtct ccagaatcac cgcagattca   6420
```

-continued gagagactcc aggggtgcct cgtggtcaga acaaatttat agacagaaaa ggtaaagtga 6480
cctacaggaa tcagaattga gacatagaaa cagtgagatt ggttacagct cggcgtttgc 6540
cttatttgaa cgcagtttga acactcagca gtctatgagt ggttgaagta tggccgctgg 6600
gattggccaa cactcagctg ttattacaga tgcatactac taagttaggt tttcgatttt 6660
gtctgcctat ttgagctagg ttacagttcg tccacaagga ctcaaatata aaagtacgga 6720
gtcctcttcg ggccatattt agttcgcttt aacaattccc ccttttggtc agcccctcaa 6780
tttagagaga ttgaccaaaa ctttaggcgt tgacaccact ctctgtcacc atcataaaga 6840
cttatttggt ctcagtgtgg aactcacaag tcgtctttag tttcagtatg gagtctcaca 6900
catcttcttt ggtgttaata gggaattcac aagttgcaac tttgtaccag ctaaatgatt 6960
ctttatgttc ttgctgatcc agttggagta agaccattca actgtcaatg tacagctgca 7020
tacaaaacat ttaagacttg agagtataca gtgcaccaag gggactatta ttatgactgt 7080
taagaggaca ccgtcaaaat gctaaggtgt actccttaat aaaagttctt atgaaatgaa 7140
ctgaaccaaa tcagccaagt taaggttcag acaatataag cagttcagca gtattggggt 7200
ctgattggtc agagtcttca gttggagtat gatagtgatt aaggatcata gttcgctgta 7260
aagtagcttg acttaaagag gtgctcgttt tcattgttac cttgttaata caagtcataa 7320
taacttgaaa acctgctaga agagatataa agattagaaa cccttggaaa acccaagctt 7380
gccattcacc acttaggatg cctgcaaacc aactgttagt tgctcctata aacatatcgt 7440
gggttccttt ctcttgagag atttctttat tgtacttggt ggcagtgtct aaggaaacag 7500
cagtatcagc cacctttaa attaagcttt ttgtagtaac agaatcaggg gagggattag 7560
tacaaaattc agttttgttt aacaccaaac ataggcctcc agcttgagca aaaagaagat 7620
ctaagactgc atgatcttcc attaagtgtt ttcgttgaat atgtatgttg tcatgtgcct 7680
ttctgagagt agcttctacc catctgaaac cctgggaggt ctgattggct accaaatcca 7740
agaattttcc caatatacaa attagtttta aattccgtac aaatggtact tcactaccac 7800
caagagtgag cccccaggaa ccccagtgga atctttcccc ggtagaaact agcttatcct 7860
cgtctatttc gaggctagtg ctaatttcag ttattgatca ttttggcctc caagtataag 7920
ggctatcatg agaattttca ggggaagcaa ttcgaaaggc aggagcaggc caggccagat 7980
aacaagaacc aaaccaacca aggaggcaga acagaatatg cagattctcc acagacccaa 8040
tagagaccct caggggttgg aaaagggggc cacctagttg tatttgagca gggatcattc 8100
aggtttgttc gaccatgaat ctgtagctcc tgaataacat ccagtgggaa atttactttt 8160
ctatggcccc tttgtagtgt gttgtaaggg tgtataacca catctagtaa aaagagaccc 8220
tactggatat acaagcaatc acttgtacta acataagtaa ttcccaaatc ttgagtatgt 8280
gatgcctgca agcacaatat acgttttgta ggcatcattt ggatttgttt tttatatttg 8340
gtgtgatcga ctttatcagt tgaaaaagag tgttgttttt agtgagtgta ggaaagcaag 8400
tactagtgat gtttagagta tcaagaatag ctttccattc ttcccttggg gtttcagggt 8460
gactcattgg gaaacgtgga ggggcactgg cacccttgga atcatttcct gatttttggg 8520
cattagccca caaacccaac agttaccctg gttttgtgct agagcataag cttgagctga 8580
agccatccac tgattatggt cccatggatt ttcatgtaag gaaaaggaaa ggattaggga 8640
aaaaaataag gaaaacagaa aaacacataa ggctttcatg gtggtagaga agtcttgatc 8700
tgtgatctag ggaaagctgt ctgtaaccag gatgctgtct gcttctggga agagatttcc 8760
ctggtcagct ttaccttaaa gtctccaacg ggtatatagt accaggagtc tgagggggcc 8820

```
cttttgaatt gtgagatgtg gacccatggt tcaaagccct gaagcttctc tgcactgtgg   8880
gtggtaagaa ggacttggta tggtcccatc caacgaggtt caagagtgat cttcttctga   8940
tgtcatttcc ggaaggccca gtctccaaat tccagaccat ggagggtttg attgtcctca   9000
gttggtggat cttgaaatgc ttcctttacc tggtggaagt atactttggc gtaatacatt   9060
aaagccttgc agtatttagt catatcagag tttaagagag caggagaagc atgagatgct   9120
attattaggg acatgggcct cccagtgact atttcataag ggtcaattt atgttttcca   9180
acaggattga atctgattgc cattaaaacc aaaaggtagt acctttggcc aaggcaactc   9240
aattgattca gttaacttgg acagtttcag ttttcaaatg ccatttgttc tttcaagctt   9300
tcctgaagac tgagggtaat aaggacaatg gtaatgcaac tgtgtcagta acaccttatt   9360
taactgcttt ataacttgct cagtaaaatg agttcctcta tcactggaga cttttagagg   9420
gatcccccat aaaggaaaaa cattttctaa taatttctta gctatggtca cagcatcagc   9480
tttcctacat gggaaggcct ttatccaacc agaaaacatg caaactatta caagaacata   9540
ctgatacccc attgagggtg gtaactgaat gaagtccatc tgtaaatgtt caaatggtcc   9600
atcaggtggt ggaaatatac tgcctctagt ttttctggga ttatgagttt gacaagtcaa   9660
acattgatta taagccattt tagtaatgtc agaatagtca ccccaccagt attttttcat   9720
aatttggatc actttgtctg ttccatgatg agctgtggag agctttcaat aatggaagct   9780
tcaaagattc aggaaggacc aggcggccgt ccgggccctt tgtgagtctt tgcttcacgt   9840
taaatttaca tccttttaga taccagtttt gtttttgcaa atcagatgcg ttgcactgtt   9900
tattaaatag gtcatcgtaa ggaaattggc ttggattaat cttatggagt tcattcagat   9960
tgcgtatctt gatggttcca gcactagctg attgagcata aaaatctgct aaagcatttc  10020
actgatattt gggttcattt ctacaagtat gagcttcagt cttaataaca gcaatctgca  10080
tttgtaacag gatagcagaa aggagctcat ctgtttggag tccatttttg atggggatcc  10140
cactagaggt gagaaacctt cgtagtttcc atatcatgcc aaaatcacgt actactccaa  10200
aagcatgtct actatccgta aatatttact gacttgtcct tagctgtgtg acatgttcag  10260
gtaagggcag aaagttctgc aggttgggct gacttgactt gaagagttcg cttctctatt  10320
aactcatttt gggtggtaac agcatatcct gactgatatt tttttttctg agtttttggc  10380
ataggaccca tcaacaaaaa gtgttaattc aggattatcc agtggagtat cttgtatagc  10440
aacacgaggg gccactattt ctgatactac actcacaccg ttgtggtctt caccatcatc  10500
aggcagagat aacagagtag cagcattaag tagattacag ccttttagat gaagataaga  10560
aggagatagg agaagtaatt cataagatgt tagtctactc actgaaaaat gctgggtttg  10620
attggaattt aatagacttt ccacagcgtg tgggacttgc aaattaagtt catttcctaa  10680
aaccagatct gatgaagctt ctaccagctt ggctgctgct actgctttta aacaattagg  10740
atatgcctta gagactgggc ctaattgcag gctatagtat gcagtggtcc tatgtttagc  10800
accgtgttcc tgattattac attcatgaac aaacaaagtg aaaggtttag tgtaatttgg  10860
aagtcctaaa gctgggggct gttgtaaggc caacttcatt tggctaaaag cctgctcatg  10920
actgtcttcc caaggtaaag gctctggtac agcattttta gtgagctcat acagtggtga  10980
agctattaag gaaaaatttg gaacccagga tctgcaatat cctgcaagcc taagaaagcc  11040
ttttgtcttt tggttgcagg tcgaggaaaa ctttaaatag gttttatcct ctcaggtaag  11100
agggaaatcc cttcagcagc caagtcatgt cccaaatagt ggactttttc ttttgaaaat  11160
```

tgaagttttg gccaggcatg gtggctaacg cctgtaatcc cagcactttg ggaggctgag 11220
gcaggcggat cacctgaggt cgggagttca aggacagcct gaccaacatg gagaaaccct 11280
gtctctacta aaaatacaaa attagccagg cgtggtggtg catgcctgta atcccagcta 11340
ctcgggaggc tgaggcagga gaatcgcttg aacccaggag gcagaggttg tggtgagcca 11400
gtatcacacc attgcactcc agcctgggca acaagagtga aactccatct caaaaaaaaa 11460
aaaaaagaaa aaagaaaaga aaaaattgaa gtttttccat tgaagccctg tgacctttat 11520
atgcaagttg ctgtaaaagg taaactgagt caatttccgg gcactcctta ataggagagc 11580
ataacaataa gttatctaca tactgaatga gagtagaatt ttgaggaaac tgtagtgtca 11640
ttaactcctg atgcagtgcc tggggaaaat atgaaggggc ttcagtaaac ccttgtggca 11700
ttacactcca ggtgtattgc tgatttttcc aagtaaaggc aaacaagtat tgactttctt 11760
tatggaatgc tagagaaggc tgagccaaga tctattactg tggacaactt ggaatcagtg 11820
ggtacattag gttataaagt attaggattt gggactacag gaaatcttgg tattacaatt 11880
ttattaattg cctgtaaatc tggaacaaat ctccagtctc atccattttg ttttttaact 11940
ggtaggattg gagtgttaca ggggctggtg catggaatta tgagtccttg tttaattaaa 12000
tcttctacaa ttggtgagag cccttaaatt gcttcaggtt ttagtggata ttgtggtaat 12060
taggcaaagg tttagaatga tctgttagta cttttatagg ttctacactt ttaattcttc 12120
ctatatcagt tgggaagagg cccataaaca ttaggtgttt tcgaaagatc aggggtatta 12180
caggcttgag tttcgatctt atcaatttct gcctgtagac agcataacaa ttctagttca 12240
ggagaatcag gaaaactctt aagattattt ctgtttctga ggaaaatttt aggtgccctt 12300
ttagctttga aagtaaatct tgccctacca agtttactgg aacagtatca cgtagtaaaa 12360
aactgtgttt ttctgaaagg gggctcagag ttaattggat gggttcagat atgggaacct 12420
ctggaacttg atttgaaacc cctgtcacag aaatgacctt tttactctaa gggatttgtt 12480
ggcttattaa ggtggggttt atggtagata gagtagccct ggtatccata aggactatac 12540
acaactccct atttatttta acctctgttt ccccatgttc ctttaaaggt attacgggga 12600
gcaatccact ggagaatccc ttagagcctc ctttaagttg aatattgtca ggaggactaa 12660
ggtctcttgg gctccctcta gtggtgaaac agtttggcct agagggaggt ttatcagccg 12720
acaatccctt ttccagtgcc ctggttgttt gcaatacagg cagacatctt ggggtaaaga 12780
aattcttgtt ctgggacctc ttgatttgat ttttttaata tataatttta aaaatatttt 12840
ccaaagtgtg acttaaaaaa attttttttt attatacttt aagttttagg gtacatgtgc 12900
acaacgtgca ggtttgttac atatgtatac atgtgccatg ttggtgtgct gcacccatta 12960
actcatcatt tacattaggt atatctccta atgctatccc tcccccctcc cccaacccca 13020
caacaggccc cagtgtgtga tgttcccctt cctgtgtcca agtgttctca ctgttcagtt 13080
cccacctacg agtgagaaca tgcggtgttt ggttttttgt ccttgtgata gtttgctgag 13140
aatgatggtt tccagcttca tccatgtccc tacaaaggac attaactcat catttttat 13200 ggctccatag tattccatgg tgtatatatg ccacattttc ttaatccagt ctatcattgt 13260
tggacatttg tgttggttcc aagtctttgc tattgtgaat agtgctgcaa taaacatacg 13320
tgtgcatgtg tctttatagc agcatgattt ataatccttt gggtatatac ccagtaatgg 13380
gatggctggg tcaaacggta tttctagttc tagatccctg aggaattgcc acactgactt 13440
ccacaatggt tgaactagtt tacagtccca ccaacagtgt aaaagtgttc ctatttctcc 13500
acatcctctc cagcacctgt tgtttcctga ctttttaatg attgccattc taactggtgt 13560
gagttggtat ctcattgtgg ttttgatttg catttctctg atggccagtg atgatgagca 13620
tttttcatg tgtcttttgg ctgcataaat gtcttctttt gagaagtgtc tgttcatatc 13680
cttcacccac ttgttgatgg ggttgtttgt ttttctcttg taagtttgtt tgagttcttt 13740
gtagattctg gatattagcc ctttgtcaga tgagaagttt cagaaatttt ctcccattct 13800
gtaggttgcc tgttcactct gatggtagtt tcttttgctg tgcagaagct ctttacttta 13860
atgagatccc atttgtcaat tttggctttt gttgccattg cttttggtgt tttagacatg 13920
aagtccttgg ccatgcctat gtcctgaatg gtattgccta ggttttcttc taggattttt 13980
atggttttag gtctaaatta agtctttaat ctatcttgaa ttaatttttg tataaggtgt 14040
aaggaaggga tccagtttca gctttctaca tatggctagc cagttttccc agcaccattt 14100
attaaatagg gaatcgtttc cccgtttctt gtttttgtca ggtttgtcaa agatcagata 14160
gttgtagata tgcggcgtta tttctgaggg ctctgttctg ttccattggc ctatatctct 14220
gttttggtac cagtaccatg ctgttttggt gactgtagcc ttgtatagtt tgaagtcagg 14280
tagcgtgatg cctccagctt tgttctttgg cttaggattg acttggcaat gcaggctctt 14340
ttttggttcc atatgaactt taaagtagtt ttttccaatt ctgtgaagaa agtctttggt 14400
agcttgatgg ggatggcatt gaatctataa attaccctgg gcagtatggc cattttcacg 14460
atattgattc ttcctaccca tgagcatgga atgttcttcc atttgtttgt atcctctttt 14520
atttccttga gcagtggttt gtagttctcc ttgaagaggt ctttcacatc ccttgtatgt 14580
tggattccta ggtattttat tctctttgaa gcaattgtga atgagagttc actcatgatt 14640
tggctctctg tttgtctgtt attggtatat aagaatgctc tcttttgttc tttgttagtc 14700
ttgctagcgg tctatcaatt ttgttgatct tttcgaaaaa ccagttactg gattcattga 14760
ttttttgaag ggttttttgt gtctctatct ccttcagttc tgctctggtc ttatttattt 14820
cttgccttct gctggctttt gaatgtgttt gctcttgctt ctctagttct tttaattgtg 14880
acgttagggt gtcaatttta gatctttcct actttctctt gtgggcattt agtgctataa 14940
atttccctct acacactgct ttgaatgtgt cccagagatt ctggtatgtt gtgtctttgt 15000
tctcattggt ttcaaagaac atctttactt ctgccttcat ttcgttatgt acccagtagt 15060
cattcaggag caggttgttc agtttccatg tagttgagca gttttgagtg agtttcttaa 15120
tcctgagttc tagtttgatt ccactgtggt ctgagagaca gtttgttata atttgtattc 15180
ttttacattt tctgaggaga gctttatttc caactatgtg gtcaattttg gaataagtgc 15240
agtgtggtgc taagaagaac gtatgttctg ttgatttggg gtggagagtt ctgtagatgt 15300
gtattaggtc cgcttggtgc agagctgagt tgaattcctg gatatccttg ttaactttct 15360
gtctcgttgg tctgtctaat gttgacagtg gggtgttaaa gtctcccatt attgttgtgt 15420
gggagtctga gtctctttgt aggtcactca gggcttgctt tatgaatctg ggtgctcctg 15480
tattggttgc atatatattt aggatagtta gctcttcttg ttgaattgat ccctttacca 15540
ttatgtaatg gccttctttg tctcttttga tctttgttgg tttaaagtct gttttaccag 15600
agactaggat tgaaacccct gcctttttttt gttttccatt tgcttggtag atcttcctcc 15660
atccctttat tttgagccta tgtgtgactc tgcacgtgag atgggtttcc tgaatacagc 15720
acactgatgg gtcttgactc tttatccaat ttgccagtcc gtgtctttta attggagcat 15780
ttagcccatt tacatttaag gttaatattg ttatgtgtga atttgatcct gtcattctct 15840
caacatttgc ttgtctgtaa aggattttat ttctccttca cttatgaagc ttagtttggc 15900

-continued

```
tggatatgaa attctgggtt gaaaattctt ttctttaaga atgttgaata ttggcctcca  15960
ctctcttctg gcgtgtagag tttctgccga gagatcagct gttggtctga tgggcttccc  16020
tttgtgggta acctgacctt tctctctagc tgccattaac atttttttcct tcatttcaac  16080
tttggtgaat ctgacaatta tgtgtcttgg agttgctctt ttcgaggagt atctttgtgg  16140
cattctctgt gtttcctgaa tttgaatgtt ggcctgcctt gctagattgg ggaagttctc  16200
ctggataata tcctgcagag tgttttccaa cttggttcca ttcttcccgt cactttcagg  16260
tacaccaatc agacgtagat ttggtctttt cacatagtcc catatttctt ggaggctttg  16320
ttcgtttctt tttattcttt tttctctaaa cttctcttcc cgcttcattt cattgatttg  16380
atcttccatc actgataccc tttcttccag ttgatcgaat cggctactga ggcttgtgca  16440
tccgtcacgt agttctcgtg ccttggtttt cagctccatc aggtccttta aggacttctc  16500
tgcattagtt attctagtta gccgttcgtc gaattttttt caaggttttt aacttctttg  16560
ccatgggttc gaacttcctc ctttagcttg gatagtttga ttgtctgaag tcttcttctc  16620
tcagctcgtc aaagtcattc tctgtccagc tttgttccgt tgctggtgag gagctgcatt  16680
cctttggagg aggagaggtg ctctgatttt tagaattttc agtatttttg ctctgtttct  16740
tccccatctt tgtggttttg tctacctttg gtctttgatg atggtgatgt acagatgggt  16800
ttttggtgtg gatgtccttt ctgtttgtta gttttccttc taacagtcag gaccctcagc  16860
tgcaggtcta ttggagtttg ctggaggtcc actccagacc atgtttgcct gggtatcagc  16920
agcggaggct gcagaacaac gaatattggt gaacagcaga tgttgctgcc tgatcgttcc  16980
tctggaagtt ttgtctcaga ggggtacccg gccatgtgag gtgtcagtct gcccctactg  17040
gggggtgcct cccagttagg ctattcgggg gtcagggacc cacttgagga ggcagtctgt  17100
ctgttctcag atctcaagct gtgtgctggg agaaccactg ctctcttcca agctgtcaga  17160
cagggacatt taagtctgca gaggtttctg ctgccttttg ttcggctatg ccctgcctgc  17220
agaggtggag tctacagagg aaggcaggcc tccttgagct gcagtgggct ccacccagtt  17280
cgagcttccc agctgctttt tttacctgct caagcctccg caatggcggg cacccctccc  17340
ccagcctcgc tgccaccttg cagtttgatc tcagactgct gtgctagcaa tgagcgaggc  17400
tccatgggca taggacccgc tgagccaggc gcgggatata gtctcctggt gtgctgtttg  17460
ctaagaccat cggaaaagcg cagtattagg gtgggagtga cccaattttc caggtgctgt  17520
ctgtcacccc tttccttggc taggaaaggg aattccctga ccccttgtgc ttcctgggtg  17580
aggcgatgcc tcgccctgct ttggctcatg ctcggtgcgc tgcacccact gtcctgcacc  17640
cactgtctga caatccccag tgagatgaac ccagtacctc agttggaaat gcagaaatca  17700
cccgttttct gcgtcgctca agctgggagc tgtagactgg agctgttcct atttggccat  17760
cttggaaccg cccgattgtg atttaaaatg agaacgagat ggtccctttg gttcctggtc  17820
cctgtaactg ttgcaattga aggggcataa gcttattagc cttttgaggt tttttttgct  17880
ctagagtctt ctcaaaatgc ttagctaggt tgggcacgat ggctcacgcc tgtaatccca  17940
gcactttgga aggccaaggt gggaggatca cgaggtcagg agatcaagac catcctggct  18000
aagatggtga aatcccatct ctactaaaaa tacacagatt agctgggcat ggtggcacac  18060
gcctgtagtc gcagctactc gggaggctga ggcaagagaa ttgcttgaac ctgggaggca  18120
gaggttgcag tgagccgaga ttgcgccact acactctagc ctgggtgaca gagcaagact  18180
ccacctcaaa aaaaaaaaaa aaaaaaaaaa aagttcagct aaggccacca attcagtcac  18240
atctctaact tcccattgca acttatgttt tttagttaaa ctgctaagtt caggatggag  18300
```

```
tccatttata agtaaagcag ttaatgctgt ttcagcccct gcagggaata ctccttgctg  18360
tactttgagc ccaggatgtt tcacaaatat ttctaagcga cttctgtaat ctgaaactgg  18420
ttcatctttt cttttctttt tttttgctt acaagattgt atgatggacc aattttttgt  18480
ggaaaaattt taggaactga atgttaaaag gttttcagcg atttttctag ctatttttgg  18540
tccttcttgt gaggagctct tagagggccc tttaaaatgt cctcctcagg tttgtcccat  18600
tctgctgctg ccatccattt ctgagcttca ccagccccca gtatcatatg aataaattgg  18660
taaattcatg aagtcctgga tcgtaagctc ctattaggat tctaaattcc tcagtaaatt  18720
tttgagactt ttcccttgga ccagggaagt ccttcacaat ggggctaagc tcagttttag  18780
accatggagt gaaagtagtt acagcaggca ggcctggctg atataaggtc tcactttgta  18840
agacatctgt ctaacttcct tttttttttt tttttttttt taaatcatct tcagggtgaa  18900
agtgtaattt aacaaaaagt ttagtggact cagagtatgt aggtagagat ggacaaagaa  18960
ggaacagtcc gagttagatc agtcaaagta cagtcctctt tcttcatgtc cttggtctgt  19020
tgcttaagct tttcatttgg tttttgcaaa gaatctttta aggaggcact ttttgattca  19080
cttagtcttt tggaggcctt tgcgtatcca tgagacaata catcccactg tatttgtggg  19140
ggctttgatc cccttttttct aatatgcctt gcaaacaatt ttatccaaat taaaacttct  19200
ccattgtggc cattttaatt ctaagttttc tttagtgagg ttaacccatt ttactgaaaa  19260
tgcacatgtt ctgggcccat aatttttata cgtaaaatta gctggagtcc ctgaagatgg  19320
agtcccagac tccttggatt gagatgatcc cattattaaa taaggtactt atcagaggtc  19380
tgaggcctct aactgaatcc aatccagtta attatcaaat ccaatttgat cttggatcca  19440
gtccaggcta agtattgctt gagtaaactc ggagagctca aaacacaagt tagtggagct  19500
cggaatctga gagaaaactc acccatgacc tccagttaca atcaagagac cagtgagagc  19560
aacggcctca gtgggtacct caccaggtca cctggtgttc caggggggttg ccagagtttt  19620
tcttcaaatc ccacttctga caccagatct gttaaaagaa aacttcagac aagttaaatt  19680
tgatggagtt taattaagca aggaaaataa acactttgca aatcaggcag cctccagaat  19740
tgaatgcagt ttgaacactt agcagtctat tagtgcttga agtatggcca ctgggattgg  19800
ccaacactca gctattatta cagatgcata ctactcaggt tttccatttt gtctgcctat  19860
tgtgctaggt tatggtttgt ccacaagaac acaaatatag aagtatggag tccttctcag  19920
gccatattta gtttgcttta acaatactta aaaaaaaaat ttgtaaaata aggatactta  19980
accttactcg gtgtttctga gagttaacat ttatatagtt atgctgtagt gaaaacagct  20040
agcgtaatgt ctggtatgta taggaacaca agagataccg cttttcccat atccccatac  20100
cattcttcac agcattgctc ctgtcttcct tgattcctcc tcctccttct ttgttttttt  20160
tttgtttgtt tgtttgtttt tttttggagg tggagtctca ctctgttgcc caggctggag  20220
tgcagtggtg tgatctcagc ttactgcaac ctctgcctcc tgggttcaag tgattctcct  20280
gcctcagcct cctgaatagc tgggattaca ggcacacacc aacacactca gctaattttt  20340
gtatttttag tagggatggg gtttcaccat gttggccagg ctggtcttga actcctgacc  20400
tcaggtgatt cacccacctc agcctcccaa agtgctggga ttacaggtgt gagccaccac  20460
accctgcctc cttcttaaga agtttccagt cccttgtaat taaaggaatt aatatttttt  20520
aactacttag aatcagactg gccctgatta ttagtaagca actaatagta agcaagcaac  20580
tatgtatgca actatgagtg tatgttaaga tatggttgtt ggtaaccttt cattctcttc  20640
```

-continued aggaagaaga agagggtgga gctctacagt caatgtgtac atttaaattc tgttcccttt 20700
cgagcttttt tgctactttc attcttctgg ggatccaggt gcttgagttg ggattgatta 20760
acttccttaa tttccacccc tgtgctgtca ggatcgggag acatagatga aggtgttcta 20820
aactgctaga aattttgttt ttgaaagcaa aagtttgcat gcatttttgt tttcaacttt 20880
tacttacagt gaatagtagt taataaaata agtccctgcc ttttctctct ttggtttcaa 20940
ttcctgagac caggatcata gcccacatat tagagtggag tcccactgct ttggtttgaa 21000
tcatgccttt gtttcttatg tcagtgtgac tttgggcaag ttatttaagt ctttgcacca 21060
cattttcctc atctgtaaaa tgaggataat actagtactt tctacatggg attgttagca 21120
ggattaaatg agatagcaca tactgtaacc atgtctggca catagtcaat ggttagtaaa 21180
tgtgaactat tgtgtgacat tgtggttagt cacgtatggg gctgtgtttc ctttagtata 21240
ttgctctttt aatgtcattt cctttgtact gttaccctct ctgatctttc ttccatattc 21300
a 21301

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 6
aggccattct gaaattct 18

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 7
cattgaggcc attctgaa 18

<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 8
taaggcattg aggccatt 18

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 9
cctattaagg cattgagg 18

<210> SEQ ID NO 10
<211> LENGTH: 18

<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
ttcttcctat taaggcat 18

<210> SEQ ID NO 11
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
agtatttctt cctattaa 18

<210> SEQ ID NO 12
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
tttcaagtat ttcttcct 18

<210> SEQ ID NO 13
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
aaaaatttca agtatttc 18

<210> SEQ ID NO 14
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
aatttaaaaa tttcaagt 18

<210> SEQ ID NO 15
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
gccctaattt aaaaattt 18

<210> SEQ ID NO 16
<211> LENGTH: 18
<212> TYPE: DNA

<213> ORGANISM: Artificial Sequence
<220> FEATURE:
<223> OTHER INFORMATION: Description of Artificial Sequence: Synthetic
    oligonucleotide

<400> SEQUENCE: 16
accaagccct aatttaaa                                                  18

<210> SEQ ID NO 17
<211> LENGTH: 18
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 17
acaaaaccaa gccctaat                                                  18

<210> SEQ ID NO 18
<211> LENGTH: 18
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 18
tcctcacaaa accaagcc                                                  18

<210> SEQ ID NO 19
<211> LENGTH: 18
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 19
ctagctcctc acaaaacc                                                  18

<210> SEQ ID NO 20
<211> LENGTH: 18
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 20
ctttactagc tcctcaca                                                  18

<210> SEQ ID NO 21
<211> LENGTH: 18
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 21
aaaaccttta ctagctcc                                                  18

<210> SEQ ID NO 22
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 22
agagaaaaac ctttacta 18

<210> SEQ ID NO 23
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 23
ctgaaagaga aaaacctt 18

<210> SEQ ID NO 24
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 24
aagctgaaag agaaaaac 18

<210> SEQ ID NO 25
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 25
ctaaagctga aagagaaa 18

<210> SEQ ID NO 26
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 26
aagctaaagc tgaaagag 18

<210> SEQ ID NO 27
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 27
aacaagctaa agctgaaa 18

<210> SEQ ID NO 28
<211> LENGTH: 18
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 28
agaaacaagc taaagctg 18

<210> SEQ ID NO 29
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
cgcagaaaca agctaaag 18

<210> SEQ ID NO 30
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
tcctccgcag aaacaagc 18

<210> SEQ ID NO 31
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
cggaatcctc cgcagaaa 18

<210> SEQ ID NO 32
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
aagagcggaa tcctccgc 18

<210> SEQ ID NO 33
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
ggagaaagag cggaatcc 18

<210> SEQ ID NO 34
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 34
ctgatggaga aagagcgg 18

<210> SEQ ID NO 35
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 35
tgaaactgat ggagaaag 18

<210> SEQ ID NO 36
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 36
ggctatgaaa ctgatgga 18

<210> SEQ ID NO 37
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 37
tccagggcta tgaaactg 18

<210> SEQ ID NO 38
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 38
acaattccag ggctatga 18

<210> SEQ ID NO 39
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 39
tttctacaat tccagggc 18

<210> SEQ ID NO 40
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 40
gagcttttct acaattcc 18

<210> SEQ ID NO 41
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 41
aaccagagct tttctaca 18

<210> SEQ ID NO 42
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 42
cttgaaacca gagctttt 18

<210> SEQ ID NO 43
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 43
atggtcttga aaccagag 18

<210> SEQ ID NO 44
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 44
tatcaatggt cttgaaac 18

<210> SEQ ID NO 45
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 45
atggatatca atggtctt 18

<210> SEQ ID NO 46
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 46
cagaaatgga tatcaatg 18

<210> SEQ ID NO 47
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 47
cctgacagaa atggatat 18

<210> SEQ ID NO 48
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 48
caccctgaca gaaatgga 18

<210> SEQ ID NO 49
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 49
actcaccctg acagaaat 18

<210> SEQ ID NO 50
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 50
aaaactcacc ctgacaga 18

<210> SEQ ID NO 51
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 51
tttaaaactc accctgac 18

<210> SEQ ID NO 52
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 52
aaatttaaaa ctcaccct 18

<210> SEQ ID NO 53
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 53
aataaattta aaactcac 18

<210> SEQ ID NO 54
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 54
catgaaataa atttaaaa 18

<210> SEQ ID NO 55
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 55
tgcatcatga aataaatt 18

<210> SEQ ID NO 56
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 56
ttgtttgcat catgaaat 18

<210> SEQ ID NO 57
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 57
atatattgtt tgcatcat 18

<210> SEQ ID NO 58
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 58

-continued gttcaatata ttgtttgc 18

<210> SEQ ID NO 59
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 59
ctgttgttca atatattg 18

<210> SEQ ID NO 60
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 60
atgtcctgtt gttcaata 18

<210> SEQ ID NO 61
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 61
agttcatgtc ctgttgtt 18

<210> SEQ ID NO 62
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 62
gaacaagttc atgtcctg 18

<210> SEQ ID NO 63
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 63
aacaagaaca agttcatg 18

<210> SEQ ID NO 64
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 64
cttacaacaa gaacaagt 18

<210> SEQ ID NO 65
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 65
agccacttac aacaagaa 18

<210> SEQ ID NO 66
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 66
aattcagcca cttacaac 18

<210> SEQ ID NO 67
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 67
gataaaattc agccactt 18

<210> SEQ ID NO 68
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 68
ttactgataa aattcagc 18

<210> SEQ ID NO 69
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 69
gtgctttact gataaaat 18

<210> SEQ ID NO 70
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 70
ttgatgtgct ttactgat 18

<210> SEQ ID NO 71
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 71
tggagaaaga gcggaatc 18

<210> SEQ ID NO 72
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 72
atggagaaag agcggaat 18

<210> SEQ ID NO 73
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 73
gatggagaaa gagcggaa 18

<210> SEQ ID NO 74
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 74
tgatggagaa agagcgga 18

<210> SEQ ID NO 75
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 75
actgatggag aaagagcg 18

<210> SEQ ID NO 76
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 76
aactgatgga gaaagagc 18

<210> SEQ ID NO 77
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 77
aaactgatgg agaaagag 18

<210> SEQ ID NO 78
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 78
gaaactgatg gagaaaga 18

<210> SEQ ID NO 79
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 79
atgaaactga tggagaaa 18

<210> SEQ ID NO 80
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 80
tatgaaactg atggagaa 18

<210> SEQ ID NO 81
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 81
ctatgaaact gatggaga 18

<210> SEQ ID NO 82
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 82
gctatgaaac tgatggag 18

<210> SEQ ID NO 83

-continued

```
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83

gggctatgaa actgatgg                                                    18


<210> SEQ ID NO 84
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84

agggctatga aactgatg                                                    18


<210> SEQ ID NO 85
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85

cagggctatg aaactgat                                                    18


<210> SEQ ID NO 86
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86

ccagggctat gaaactga                                                    18


<210> SEQ ID NO 87
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87

ctgatggaga aagagcggaa tc                                               22


<210> SEQ ID NO 88
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88

ctgatggaga aagagcggaa                                                  20


<210> SEQ ID NO 89
<211> LENGTH: 22
```

<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 89
aactgatgga gaaagagcgg aa 22

<210> SEQ ID NO 90
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 90
aactgatgga gaaagagcgg 20

<210> SEQ ID NO 91
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 91
gaaactgatg gagaaagagc gg 22

<210> SEQ ID NO 92
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 92
ggctatgaaa ctgatggaga aa 22

<210> SEQ ID NO 93
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 93
ggctatgaaa ctgatggaga 20

<210> SEQ ID NO 94
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 94
agggctatga aactgatgga ga 22

<210> SEQ ID NO 95
<211> LENGTH: 20
<212> TYPE: DNA

<213> ORGANISM: Artificial Sequence
<220> FEATURE:
<223> OTHER INFORMATION: Description of Artificial Sequence: Synthetic
oligonucleotide

<400> SEQUENCE: 95
agggctatga aactgatgga 20

<210> SEQ ID NO 96
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 96
ccagggctat gaaactgatg ga 22

<210> SEQ ID NO 97
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 97
ttcttaccca tttaatta 18

<210> SEQ ID NO 98
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 98
tgcttcttac ccatttaa 18

<210> SEQ ID NO 99
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 99
taatgcttct tacccatt 18

<210> SEQ ID NO 100
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 100
agataatgct tcttaccc 18

<210> SEQ ID NO 101
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
cagataatgc ttcttacc 18

<210> SEQ ID NO 102
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102
cccttcagat aatgcttc 18

<210> SEQ ID NO 103
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103
ctactccctt cagataat 18

<210> SEQ ID NO 104
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
agctcctact cccttcag 18

<210> SEQ ID NO 105
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
ttcacagctc ctactccc 18

<210> SEQ ID NO 106
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106
taaaattcac agctccta 18

<210> SEQ ID NO 107
<211> LENGTH: 18
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 107
aaatctaaaa ttcacagc 18

<210> SEQ ID NO 108
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108
gaataaaatc taaaattc 18

<210> SEQ ID NO 109
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109
gatgggaata aaatctaa 18

<210> SEQ ID NO 110
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 110
gctgtgatgg gaataaaa 18

<210> SEQ ID NO 111
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111
tagaggctgt gatgggaa 18

<210> SEQ ID NO 112
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112
aaagatagag gctgtgat 18

<210> SEQ ID NO 113
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 113
aaaagaaaga tagaggct 18

<210> SEQ ID NO 114
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 114
gacctaaaag aaagatag 18

<210> SEQ ID NO 115
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 115
ataaagacct aaaagaaa 18

<210> SEQ ID NO 116
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 116
gagatataaa gacctaaa 18

<210> SEQ ID NO 117
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 117
ggctgtgatg ggaataaa 18

<210> SEQ ID NO 118
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 118
aggctgtgat gggaataa 18

<210> SEQ ID NO 119
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 119
gaggctgtga tgggaata 18

<210> SEQ ID NO 120
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 120
agaggctgtg atgggaat 18

<210> SEQ ID NO 121
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 121
atagaggctg tgatggga 18

<210> SEQ ID NO 122
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 122
gatagaggct gtgatggg 18

<210> SEQ ID NO 123
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 123
agatagaggc tgtgatgg 18

<210> SEQ ID NO 124
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 124
aagatagagg ctgtgatg 18

<210> SEQ ID NO 125
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 125
tagaggctgt gatgggaata aa 22

<210> SEQ ID NO 126
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 126
atagaggctg tgatgggaat aa 22

<210> SEQ ID NO 127
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 127
gatagaggct gtgatgggaa ta 22

<210> SEQ ID NO 128
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 128
agatagaggc tgtgatggga at 22

<210> SEQ ID NO 129
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 129
aagatagagg ctgtgatggg aa 22

<210> SEQ ID NO 130
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 130
gaggctgtga tgggaataaa 20

<210> SEQ ID NO 131
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 131
agaggctgtg atgggaataa 20

<210> SEQ ID NO 132
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 132
tagaggctgt gatgggaata 20

<210> SEQ ID NO 133
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 133
atagaggctg tgatgggaat 20

<210> SEQ ID NO 134
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 134
gatagaggct gtgatgggaa 20

<210> SEQ ID NO 135
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 135
agatagaggc tgtgatggga 20

<210> SEQ ID NO 136
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 136
aagatagagg ctgtgatggg 20

<210> SEQ ID NO 137
<211> LENGTH: 16
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 137
ctgtgatggg aataaa 16

<210> SEQ ID NO 138
<211> LENGTH: 16
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 138
gctgtgatgg gaataa 16

<210> SEQ ID NO 139
<211> LENGTH: 16
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 139
ggctgtgatg ggaata 16

<210> SEQ ID NO 140
<211> LENGTH: 16
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 140
aggctgtgat gggaat 16

<210> SEQ ID NO 141
<211> LENGTH: 16
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 141
gaggctgtga tgggaa 16

<210> SEQ ID NO 142
<211> LENGTH: 16
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 142
agaggctgtg atggga 16

<210> SEQ ID NO 143
<211> LENGTH: 16
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 143
tagaggctgt gatggg 16

<210> SEQ ID NO 144
<211> LENGTH: 16
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 144
atagaggctg tgatgg 16

<210> SEQ ID NO 145
<211> LENGTH: 16
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 145
gatagaggct gtgatg 16

<210> SEQ ID NO 146
<211> LENGTH: 16
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 146
agatagaggc tgtgat 16

<210> SEQ ID NO 147
<211> LENGTH: 16
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 147
aagatagagg ctgtga 16

<210> SEQ ID NO 148
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 148
aggctgtgat gtgaataa 18

<210> SEQ ID NO 149
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 149
agaggctgtg atgtgaat 18

<210> SEQ ID NO 150
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 150
tagaggctgt gatgtgaa 18

<210> SEQ ID NO 151
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 151
gatagaggct gtgattgg 18

<210> SEQ ID NO 152
<211> LENGTH: 16
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 152
ggctgtgatg tgaata 16

<210> SEQ ID NO 153
<211> LENGTH: 16
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 153
gaggctgtga tgtgaa 16

<210> SEQ ID NO 154
<211> LENGTH: 16
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 154
tagaggctgt gattgg 16

<210> SEQ ID NO 155
<211> LENGTH: 16
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 155
atgaaactga tggaga 16

-continued

<210> SEQ ID NO 156
<211> LENGTH: 16
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 156
ctatgaaact gatgga 16

<210> SEQ ID NO 157
<211> LENGTH: 16
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 157
ggctatgaaa ctgatg 16

<210> SEQ ID NO 158
<211> LENGTH: 14
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 158
gaaactgatg gaga 14

<210> SEQ ID NO 159
<211> LENGTH: 14
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 159
atgaaactga tgga 14

<210> SEQ ID NO 160
<211> LENGTH: 14
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 160
ctatgaaact gatg 14

<210> SEQ ID NO 161
<211> LENGTH: 14
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 161
ggctatgaaa ctga 14

<210> SEQ ID NO 162

<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 162
tagaggctgt gatgggaata aaat 24

<210> SEQ ID NO 163
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 163
atagaggctg tgatgggaat aaaa 24

<210> SEQ ID NO 164
<211> LENGTH: 25
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 164
atagaggctg tgatgggaat aaaat 25

<210> SEQ ID NO 165
<211> LENGTH: 25
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 165
aaagatagag gctgtgatgg gaata 25

<210> SEQ ID NO 166
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 166
ggctatgaaa ctgatggaga a 21

<210> SEQ ID NO 167
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 167
ggctatgaaa ctgatggaga aaga 24

<210> SEQ ID NO 168
<211> LENGTH: 25

<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 168
agggctatga aactgatgga gaaag 25

<210> SEQ ID NO 169
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 169
catttaatta aattatat 18

<210> SEQ ID NO 170
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 170
ccatttaatt aaattata 18

<210> SEQ ID NO 171
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 171
cccatttaat taaattat 18

<210> SEQ ID NO 172
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 172
acccatttaa ttaaatta 18

<210> SEQ ID NO 173
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 173
tacccattta attaaatt 18

<210> SEQ ID NO 174
<211> LENGTH: 18
<212> TYPE: DNA

<213> ORGANISM: Artificial Sequence
<220> FEATURE:
<223> OTHER INFORMATION: Description of Artificial Sequence: Synthetic
      oligonucleotide

<400> SEQUENCE: 174
ttacccattt aattaaat 18

<210> SEQ ID NO 175
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 175
cttacccatt taattaaa 18

<210> SEQ ID NO 176
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 176
tcttacccat ttaattaa 18

<210> SEQ ID NO 177
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 177
gatagaggct gtgatgg 17

<210> SEQ ID NO 178
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 178
ggctgtgaaa ctgatgga 18

<210> SEQ ID NO 179
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 179
ggctgtgaaa ctgatggaga 20

<210> SEQ ID NO 180
<211> LENGTH: 16
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 180
gctatgaaac tgatgg 16

<210> SEQ ID NO 181
<211> LENGTH: 14
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 181
tatgaaactg atgg 14

<210> SEQ ID NO 182
<211> LENGTH: 14
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 182
gctatgaaac tgat 14

<210> SEQ ID NO 183
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 183
gctgtgaaac tgatggagaa 20

<210> SEQ ID NO 184
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 184
gggctgtgaa actgatggag 20

<210> SEQ ID NO 185
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 185
tgtgaaactg atggagaa 18

<210> SEQ ID NO 186
<211> LENGTH: 18
<212> TYPE: DNA
<213> ORGANISM: Artificial Sequence
<220> FEATURE:

<223> OTHER INFORMATION: Description of Artificial Sequence: Synthetic
oligonucleotide

<400> SEQUENCE: 186
ctgtgaaact gatggaga 18

<210> SEQ ID NO 187
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 187
gctgtgaaac tgatggag 18

<210> SEQ ID NO 188
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 188
gggctgtgaa actgatgg 18

<210> SEQ ID NO 189
<211> LENGTH: 16
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 189
tgaaactgat ggagaa 16

<210> SEQ ID NO 190
<211> LENGTH: 16
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 190
gtgaaactga tggaga 16

<210> SEQ ID NO 191
<211> LENGTH: 16
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 191
tgtgaaactg atggag 16

<210> SEQ ID NO 192
<211> LENGTH: 16
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 192
ctgtgaaact gatgga 16

<210> SEQ ID NO 193
<211> LENGTH: 16
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 193
gctgtgaaac tgatgg 16

<210> SEQ ID NO 194
<211> LENGTH: 16
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 194
ggctgtgaaa ctgatg 16

<210> SEQ ID NO 195
<211> LENGTH: 16
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 195
gggctgtgaa actgat 16

<210> SEQ ID NO 196
<211> LENGTH: 15
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 196
cggtccagga atgac 15

<210> SEQ ID NO 197
<211> LENGTH: 15
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 197
ccggtccagg aatga 15

<210> SEQ ID NO 198
<211> LENGTH: 15
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 198
cccggtccag gaatg 15

<210> SEQ ID NO 199
<211> LENGTH: 15
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 199
tcccggtcca ggaat 15

<210> SEQ ID NO 200
<211> LENGTH: 15
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 200
ctcccggtcc aggaa 15

<210> SEQ ID NO 201
<211> LENGTH: 15
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 201
gctcccggtc cagga 15

<210> SEQ ID NO 202
<211> LENGTH: 15
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 202
ggctcccggt ccagg 15

<210> SEQ ID NO 203
<211> LENGTH: 15
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 203
cgggagcccc cgtgt 15

<210> SEQ ID NO 204
<211> LENGTH: 15
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 204
gcgggagccc ccgtg 15

<210> SEQ ID NO 205
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 205
cgcgggagcc cccgt 15

<210> SEQ ID NO 206
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 206
acgcgggagc ccccg 15

<210> SEQ ID NO 207
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 207
cacgcgggag ccccc 15

<210> SEQ ID NO 208
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 208
ccacgcggga gcccc 15

<210> SEQ ID NO 209
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 209
gccacgcggg agccc 15

<210> SEQ ID NO 210
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 210
ggccacgcgg gagcc 15

<210> SEQ ID NO 211
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 211
cggccacgcg ggagc 15

<210> SEQ ID NO 212
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 212
acggccacgc gggag 15

<210> SEQ ID NO 213
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 213
gacggccacg cggga 15

<210> SEQ ID NO 214
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 214
agacggccac gcggg 15

<210> SEQ ID NO 215
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 215
gctagggagg gatggtta 18

<210> SEQ ID NO 216
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 216
tgtaagctag ggagggat 18

<210> SEQ ID NO 217
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 217
acagatgtaa gctaggga 18

<210> SEQ ID NO 218
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 218
aaggaacaga tgtaagct 18

<210> SEQ ID NO 219
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 219
caacaaagga acagatgt 18

<210> SEQ ID NO 220
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 220
gggtgcaaca aaggaaca 18

<210> SEQ ID NO 221
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 221
accaagggtg caacaaag 18

<210> SEQ ID NO 222
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 222
gttaaaccaa gggtgcaa 18

<210> SEQ ID NO 223
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 223
ataatgttaa accaaggg 18

<210> SEQ ID NO 224
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 224
ggagaataat gttaaacc 18

<210> SEQ ID NO 225
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 225
ggggaggaga ataatgtt 18

<210> SEQ ID NO 226
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 226
aaattgggga ggagaata 18

<210> SEQ ID NO 227
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 227
agaggaaatt ggggagga 18

<210> SEQ ID NO 228
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 228
ggagaagagg aaattggg 18

<210> SEQ ID NO 229
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 229
aatgaggaga agaggaaa 18

<210> SEQ ID NO 230
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 230
ttcacaatga ggagaaga 18

<210> SEQ ID NO 231
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 231
acgagttcac aatgagga 18

<210> SEQ ID NO 232
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 232
ctgccacgag ttcacaat 18

<210> SEQ ID NO 233
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 233
agaccctgcc acgagttc 18

<210> SEQ ID NO 234
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 234
caagcagacc ctgccacg 18

-continued

<210> SEQ ID NO 235
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 235
ctcaccaagc agaccctg 18

<210> SEQ ID NO 236
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 236
gagctcacca agcagacc 18

<210> SEQ ID NO 237
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 237
agaatgagct caccaagc 18

<210> SEQ ID NO 238
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 238
gtaagagaat gagctcac 18

<210> SEQ ID NO 239
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 239
ttgttgtaag agaatgag 18

<210> SEQ ID NO 240
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 240
atttgttgtt gtaagaga 18

<210> SEQ ID NO 241

<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 241
cttgaatttg ttgttgta 18

<210> SEQ ID NO 242
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 242
atgctcttga atttgttg 18

<210> SEQ ID NO 243
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 243
tcttcatgct cttgaatt 18

<210> SEQ ID NO 244
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 244
cttcctcttc atgctctt 18

<210> SEQ ID NO 245
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 245
gcgcgcttcc tcttcatg 18

<210> SEQ ID NO 246
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 246
gctctgcgcg cttcctct 18

<210> SEQ ID NO 247
<211> LENGTH: 18

<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 247
ggccagcggc tctgcgcg 18

<210> SEQ ID NO 248
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 248
atattggcca gcggctct 18

<210> SEQ ID NO 249
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 249
gtgctatatt ggccagcg 18

<210> SEQ ID NO 250
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 250
agctcgtgct atattggc 18

<210> SEQ ID NO 251
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 251
ggcatagctc gtgctata 18

<210> SEQ ID NO 252
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 252
tgttgggcat agctcgtg 18

<210> SEQ ID NO 253
<211> LENGTH: 18
<212> TYPE: DNA

<213> ORGANISM: Artificial Sequence
<220> FEATURE:
<223> OTHER INFORMATION: Description of Artificial Sequence: Synthetic
      oligonucleotide

<400> SEQUENCE: 253
gcttctgttg ggcatagc 18

<210> SEQ ID NO 254
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 254
cttgcgcttc tgttgggc 18

<210> SEQ ID NO 255
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 255
caccttgcgc ttctgttg 18

<210> SEQ ID NO 256
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 256
tccatcacct tgcgcttc 18

<210> SEQ ID NO 257
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 257
aaccatccat caccttgc 18

<210> SEQ ID NO 258
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 258
ccttaaacca tccatcac 18

<210> SEQ ID NO 259
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 259
agccccctta aaccatcc 18

<210> SEQ ID NO 260
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 260
tcggtagccc ccttaaac 18

<210> SEQ ID NO 261
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 261
atgtatcggt agccccct 18

<210> SEQ ID NO 262
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 262
tgtgaatgta tcggtagc 18

<210> SEQ ID NO 263
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 263
attagtgtga atgtatcg 18

<210> SEQ ID NO 264
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 264
ggctgattag tgtgaatg 18

<210> SEQ ID NO 265
<211> LENGTH: 18
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 265
gaaatggctg attagtgt 18

<210> SEQ ID NO 266
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 266
tggcagaaat ggctgatt 18

<210> SEQ ID NO 267
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 267
gatcttggca gaaatggc 18

<210> SEQ ID NO 268
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 268
gacatgatct tggcagaa 18

<210> SEQ ID NO 269
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 269
gaggtgacat gatcttgg 18

<210> SEQ ID NO 270
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 270
agattgaggt gacatgat 18

<210> SEQ ID NO 271
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 271
tgaacagatt gaggtgac 18

<210> SEQ ID NO 272
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 272
gtccatgaac agattgag 18

<210> SEQ ID NO 273
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 273
ttggagtcca tgaacaga 18

<210> SEQ ID NO 274
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 274
tgtatttgga gtccatga 18

<210> SEQ ID NO 275
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 275
tttcttgtat ttggagtc 18

<210> SEQ ID NO 276
<211> LENGTH: 7155
<212> TYPE: DNA
<213> ORGANISM: Homo sapiens

<400> SEQUENCE: 276
gtaagtgtaa aagagaattg ttcatgtagg tagtcttgaa agattttta aagtttttac 60 ttctttggaa gattttaaaa tgataacatc tgagaagcaa atacaaaaac atccaagtag 120
agatatcgtt actaatctta gtgcaaagta caaggtatta cgtggcagtt ctggaaatat 180
aattgagaag cccatttctt tcacatatgt ccagtgaagc attagtttcg agggttgtcc 240
ccaagaaaga gttgtgttgt taagtgtgtg gggggagaaa ggctcgttta gacaaggcaa 300
gcggacttct tttctttccc taggacctct catactgtaa tatactcatg cgcattgtga 360
atttccaagg agtcaaagca tacagtgttt tcccaaatta tttatcaaca gaaccctttt 420

-continued

```
gctcatggaa cgtcgtatag ggactagatt tcactttggg gaaactagaa agggaatagg    480
aattgggtta ttaggaaata aatcaattcc ctgatattga tagttaacaa agttatgtat    540
ggggttattt atggtatgtt attttcaaca catattcatt aacaaaatcc atatgaaagt    600
tataggagaa ttgctgaggt agaataacat actttgtttg tatttataat actcatatat    660
ttacctgacg ttttctgagt cttcactttt ttcattcttt tggaattggt aaaataactg    720
attccttgaa agtttttttc taaataatac ctagataata gatttataga aaaaatattg    780
tatgaatgtt ttaacattca tgtaatatgg aacatgtaat ttttatactg gaggttatta    840
tagttttaat acatcaaaga aataatgttt attttggaag cagaaagaag aaataatttc    900
tatgaatagg ttttcatctc tttccttgtt cttcaacttt gaacttttta tattccaaat    960
tttaattata tttcaaaaga ttttttttctt ttgcctttta attttatctt ttggagaaaa   1020
atgtatgtca aaatgtatgt acgtgtattt gtcttttgat ttgatctttt ttgaccctct   1080
tttgcattga cattatttta accaaaggac actcttgatt gttcatgcta ctgggggaaa   1140
aaaaaataag tagaaattag cctaatagtt gtggcttatt ttgagtgaag gccttagccc   1200
ttaaggcaat taaatttact gtggagagaa gagctaatct aatggggaga aggagccttt   1260
gttacaggtg tggtagtgtg gttctttgag tgacaagatt tctgtttgcc agattggtta   1320
ggagaagtct gtgtgtctgc tttctctctt atggcctagg atcactgtgg tgaatgaaaa   1380
acctgtctca gggcctgact cagataattc ccttaaaacc cggctaaggt catagatgaa   1440
taatcagtaa ttgaacagaa gctctgcaat agaaaagaag ccagataatt atttttggaa   1500
atttaattat atttacagat tttattttat acagtagaca tggaattaaa tttattacat   1560
tatgttctaa tttactcttt gcttgttttg atttgcttgt ttgacaatac atgtccttgt   1620
aaactatttc cttttaactt tttctcaatt tatggtgctt attttcccca ttaaagactt   1680
accaattttt tttttaacta tttgttacac atactgaatc tagagttgta attaagctac   1740
tttcattact ggttaagtca aattatagca aatgctacta taaaaattta ctatccaaaa   1800
atgtgtctca agccccaact gatggtttca aattctgtta ttaataatat gcagcattgt   1860
gtttgcaaag cttggctgtt acttgtgatg cttgagaatg atgagtcact cagctaaact   1920
gagtgatttt gagacttgtg tacaaattga tggttgaatg taagcatgca aagagagacc   1980
ttagcttagc agtacccttt ttgaaatcac tctgacatca agtttgaaaa tgtgggcaat   2040
aatcagaggt ggtaaggtgg ccaggcttta gctgaatact tttttaactg gttcagtctg   2100
agggctgaaa gccccagatt taaacagtat ttagaatttg aagcagtcaa gtattagttt   2160
aatggttgtc aggtttgtaa caaagtttct ggctagactt ctactagaaa tgtaaaagtg   2220
catgtgaatc agctttttaa aaaagtaata ataattgaaa aacatttcta caactagaac   2280
taaagaaaag atttgtcctt tctaatagga aaacacatct ggagaagtgc tggcaactag   2340
cagaacagtt aggaccattc agaatcaact gaagtgaaag tgacggggag ctgaggggaa   2400
cacagatagt ttgacttcag tcagacagaa taaacatgat gaaccgataa cctgtgattc   2460
ccagcctggg gttactactg gagttttagg tgtcctggaa agttataata ccggtcttca   2520
aaaagtctac agaaagcata gatttccaca taatgctgca caggctaacg aattaatcaa   2580
gtttctttgg tttggcctgg atttatatcc attcagtttg tggacactac tgaattattt   2640
atgtcatgtt gatcaaaagt tctgatatga tttgattaat gaaacattga aaaaaatagt   2700
aaaaccaacc atttttaacc ttacactact atcttgaggt atgattgaca tacattaaaa   2760
```

-continued

```
ccacctctta ataaatgctt cttgttaatc aaaaatttga aaacgtatgt ccactggagg   2820
aaaaaagaca tagccctgga tgtgaactga atattactga gactcggaga ccttcagaac   2880
tacctgaaga tgaatcgaag tgctgcctac tttagagaat tggactaatt taatttggga   2940
gtcagcagat tgctgtatat cagtcatcat atataccggt gacaagacca cttagttcat   3000
tcccttttt agattctgta agattattgt gttccagtga aattgatttg caaaatgaga    3060
cattttattt tctgtgcttt tgttctatca tgtttctgat tggtcataag catctcacag   3120
aagtaagaaa tatggcgatt cagaaggcaa caagcacatt tataatttat agaaaatatt   3180
tgaaggactt tttcatggcc caaatcatga aaagtagtag tattgtttta agtataatta   3240
ttaaattata atacattaat gttctttctt gcaacatatt actctcattc ttttttttt    3300
ttttttttt tgagacggag tctcactctg tcacccggct ggagtacagt ggtacgatct    3360
tggcccactg caacctctgc ctcccgggtt caagcgattc tcctgcctca gcctcccaag   3420
tagctgggat tacaggctcc tgccaccacg cctagctaat tttgtattt ttagtagaga    3480
cagggtttca ccaggttggc caggatggtc ttgatctctt gacctcatgg tccgtccacc   3540
tctgcctccc aaagtgttgg gattacaggc gtgagccacc cagcagtctg attcttaatt   3600
ttatagttta tgttgtacct ccccagctga agtatctctt ttcttttttc ccgcgtgttt   3660
agtgttcact catctttata gcatagctca attgtcactt catgaagcct tccataacct   3720
ttgtagctcc attaattata ttcttctgag tgtttaaaac acttgccata tgaaacacta   3780
tttactttgg cttacattct tactatctaa tcggccattt ctgttactaa atctttttct   3840
cagagcacct gggatagtct tgtgtcttag taaaatcagt tgattgattt aactcggtag   3900
agtagaggct gattaaagta aataaatctg gttgatgcca acaaaatttt ggtcccctca   3960
attttttgct ctcattacct gcaaattctc cctggccttc atatttggca accattgagg   4020
agaacaaggc tgtaaaagta gttcatgtac ttgatattct gaattggaat taagcagagt   4080
tgcttaagta ggacttgctt ttctgggatt tcttatgcaa caaataatgt agtaactgga   4140
aatccaagtt caagacactg gcagattcga tgtcttttga ggacccttgg cttcatagat   4200
gatgccttct ccctatatcc ttacatagca aaaggggcca ggcagctctg gcctttttt    4260
gtaaggccaa taactccaga aacctcatga cctcatcacc tcccaaaggc cccacctctc   4320
aatactatca cattgtgagg ctaggtttca acatatgaat tgtgggagac aaaaattcag   4380
accatagtat aatatttcaa gattacttaa actcttctct accaaactca ttaactttta   4440
ggttagcaca gtattttcat tgatattttg gtttctggag ttattactaa ttttcttgat   4500
ctgatgttat aattaaaaaa aaacaggact ttgtacgtga aatgagactg agataaggaa   4560
gctgattcag agatggagat ttaaaaaaag agagatgaga gattgagatc tgcagtgtca   4620
aactgacaat agccaggagt caggagatat taagagacta tatcatctgt gattgttaat   4680
gattatttat tgttatttat aaatactact gtattttata tattatatac attgttttaa   4740
aaattatttt tgtaccattt cttgaaagaa aaatgtctaa gcttgggaaa atatttattg   4800
aaaaatgtgg tttgtacatc tgaggagtgt atcttgcaca gtaggtgcat agatttcttc   4860
ctcttcctgt tccacatggc cttagcttag aggctgtgtg gccatcactt ggtatttagg   4920
gtaagactgg tgcacaaaat caaagacagg taaccttggt ataagtgtag tatcatgtaa   4980
atagcttttc tatgtctaat tcttgttttc ttcctacttt ttcaggaggt caatttcagt   5040
tcatttcaac tatctttaca taatagtgct ttagtaacag gcatggaagg aaagagacat   5100
gtccctagag tgttttcttg aaatctaata gatgattgga gtatttacca tgcagttgtg   5160
```

```
tatatacata agcagtgaat tcgagaggaa tttttaagct gtaaaaaaaa gcattgtgtg   5220
ccttatagac gcgagtgaga aatgtggaat atggctgatc caaagggaat gagttatctc   5280
aattgattaa tcacagtcag ttacagattg aactctttgt tctactcttt gcccccttct   5340
cactattgct cttgactagt cttaagaaag aaatgtggaa tattttctca cggctttggg   5400
attttataaa ttagaatact agtggtatgt aaatacagca ggtacactac tgtataaacc   5460
aacataggaa gccttcttta aagggaattg tttgagaaat ttgaacactt ggataatttg   5520
aataaaggat tgtgataaat gatcaaatga aagaaaataa atcaggttac tcttctttct   5580
gcttgataaa gcaataattt tttttaaagg taaaaattat gagaatgatg aggatagtag   5640
ttagcattgt ctttctttga taggtttgtt aatgatcata aaactgattt atttaaagac   5700
atgtcttttt ataactattt tatactgttg tatctggaaa caaatattga atttcatttg   5760
tcatgtggaa gaaatcaact agttttaacc tttgatttat aataaatcaa ccactttcat   5820
ttattgtcta atactggcaa tgaacacagc ctaatgtatc aaaactaaca gaataaaaat   5880
tctccaagtt atatccagac tttaagacac tttctaatta tataaaataa aatattttgg   5940
gcagtcattt tttaactctg aaactattta aaactcctaa tttagaatat cttaataaat   6000
acccattttc ctctttttat ttttataact tggtaaaaat tgagtccatt gttttcccag   6060
aacgctgttc ttaaacaaat ggttacctcc ttcattagaa ctttactttt tttaggattt   6120
ctaattaaga aaacattagg cttgtaacat tgtcaaatct tggtggtctt tcttccacgt   6180
tttttgaggt cgattatcta agaggccatc agttaataaa gctatgcagg aaatgacatc   6240
atgccacatg tgaatatcct gtattaaaaa ttgtatcaat atactatttt ataattatga   6300
agtggaatga attttagaaa tagaaaaggt gattttttgt gcataggtcc aaactgtgtt   6360
ttgttttcat ttcagaattt cataataact atattgtctc catatcttaa ttgtgttttt   6420
ttatagcact tttgtttagt aatttgtata tgcttggctg tattctcaga ggctgtttct   6480
atttaatgtt gtcaaaacag ctcataaaaa gtgaaaattc ggtcagacta gttatttgat   6540
attatatatg aaatcaaaac aacctgaaac attatctttt aatttaaata aagaacccca   6600
aattttaatc aaatgtatgc aaaggcacat agaatatatg acttaatgta caacctttat   6660
taacttgatg atggaaacct gttcctaggg acctttactt gaataaatga aatatcaaga   6720
aaaaatacta acttaagaat aataatttaa taagtaagta agctattatg atcttcaatc   6780
agtcctgaga gaatcatggt tgagaattag aaaatttaga ccagtaagat caacactgtt   6840
aaaaaaaaaa aaaaatcagt attttttctc catatttttt atatatctgg atcattttat   6900
ttagcactta ttattgcact ttccttttca ctttttaaac tatgctgttt tatttttctg   6960
agacatctga tttactgagg aggaaaatgg aaatgcggta cagagcccaa gggtatgacg   7020
gctttaaatg agtttccatt tctgttttaa gttaaccatc cctccctagc ttacatctgt   7080
tcctttgttg caccottggt ttaacattat tctcctcccc aatttcctct tctcctcatt   7140
gtgaactcgt ggcag                                                    7155
```

<210> SEQ ID NO 277
<211> LENGTH: 111
<212> TYPE: DNA
<213> ORGANISM: Homo sapiens

<400> SEQUENCE: 277

```
ggtctgcttg gtgagctcat tctcttacaa caacaaattc aagagcatga agaggaagcg     60
```

cgcagagccg ctggccaata tagcacgagc tatgcccaac agaagcgcaa g 111

<210> SEQ ID NO 278
<211> LENGTH: 5409
<212> TYPE: DNA
<213> ORGANISM: Homo sapiens

<400> SEQUENCE: 278
gtgatggatg gtttaagggg gctaccgata cattcacact aatcagccat ttctgccaag 60
atcatgtcac ctcaatctgt tcatggactc caaatacaag aaattaattt gacaaagtga 120
aaatataaaa gatgcatcat ataaatatgt aacttttctg gagtgggtag tataggtaaa 180
gccaaaagaa acaaattcaa gcagaggaat tttggtttct gaaaattagg ttgtctgtag 240
ggtccctgta tttatactta gaacaaaatt aggaatttct gtttatgtgg tccagttatt 300
gagtcaccct aagtttgtag gcatcttacc tacctacttg ctccccaagt tttatttct 360 aaaatgaaaa gcattgctgt agatgaccag tttacactaa agaataacat ttatttattt 420
gttttagcta aagtatatgg acagggaaca ttcatattct tgtagaagaa aattattttg 480
acttttgggc aaaagcatgt agttcttata cactttgaca aactcattgc gtacattttt 540
cacattaatc aaagtcagca caaataaatt ttcaccttgg accacggagg gtttgaacac 600
tggaaatttg atataattct ggttgctaaa gaacaagttc taataaaagc ttaagtgtat 660
accaatatgt ggctgttggt gcaatcagca ggtccgtaaa aatatgattt taatggttag 720
gtaatcccac aacggagatc ccaaagttca tgtttggaag agacttttgg gtcaaagtga 780
aatcagtgta atgaatttaa aattatactc tgagatcttg aaatcagcta attatgttac 840
atcttattag ctcagaaaag ttttgaagtt atatacaaat gctagtcagg aaaaaagatt 900
cagtcatgta attcttgtac attctactat ttaaatcaac caatattata gattatgatt 960
tagtgcagta attctgctgg ctaaccttat ctcatttggt ggtggttagt acttcagagt 1020
actcaccata gtttcattta tgttttcagc atcacttcct ggtttttctc aattccatgg 1080
ctgtggaatc aattcatatg tatatttagc ttcggtgagc aaaaacatag ctagaaaaag 1140
aaaagaagtg agtttcctac ctggttaaat taaagtcgat gtgttaagcc aaggaggact 1200
tcttttgaat ggtactttaa caatccctgt tctgtatact gtgaatatat catttaaata 1260
gcctaataaa ttggatgctt aggctgagcc acctatactt tagttttgtt atggaaagaa 1320
gggagaggag caagtatgtt cttatatgtt acttagaaat aagaatgtag ctgtagttac 1380
acattgttct taagtttttt tcgtaagaca acttgaaatg agtcccatag gcctgctatt 1440
taacattcta agatatgact taaggttaat gatgagcttt tgaatctgac aattcaagag 1500
atatccataa tgaatactga ttcattttct acattgctga aagctaatgt tcattttaag 1560
cctactttag tagcctttat ttgggcttag agatgttatt cctctttctg atatttattg 1620
ggttatctgt ttaacccttt tatatctccc tttcccgatt tgtaaattag agactggcaa 1680
gactttttac cctgagtaga gcaccaaaca tggcttgttt ctgcccacac tgtagttacc 1740
ttgaggggaa gtaaatggga ctttaaaagc aatttatgct cttttatagt gaaattatcc 1800
ctcttactat cccgaaagac tgttacctta caatatcctc cactcctttc cccctgtagt 1860
tactatagag atgacttttc ggttcttcac tgccataatg atcaaaatcc taattcatga 1920
gatttttatc attccaggca tgtgaggttt acttgatgca taaaaccgca agtacttttt 1980
gttgtttttt aattgttttt tctctcttat cttcttgaaa gtctaagtag atcatcattt 2040
ttgatgtctt attagtagca actaataaat tttccctgta tcttctcagc aaaagaactc 2100
aagcagagac agaagattag aactaccatt ggtagttttg cttcctatgg atatgttcac 2160
atacatagaa atttttacaa tgaccttttt atatatgtat ttcagaattt cagaatggcc 2220
tcaatgcctt aataggaaga aatacttgaa atttttaaat tagggcttgg ttttgtgagg 2280
agctagtaaa ggtttttctc tttcagcttt agcttgtttc tgcggaggat tccgctcttt 2340
ctccatcagt ttcatagccc tggaattgta gaaaagctct ggtttcaaga ccattgatat 2400
ccatttctgt cagggtgagt tttaaattta tttcatgatg caaacaatat attgaacaac 2460
aggacatgaa cttgttcttg ttgtaagtgg ctgaatttta tcagtaaagc acatcaaaat 2520
aaaatatacc ccaattgcta gttaagacct agagtgacag attgaaaata gcttgtgtta 2580
ttctcttaag aaaatatata aaaattatca tctcatcaat ctttaatgtt tgttttataa 2640
atctaaatgt ttttatattg tttcctagga aatattaggt ctaatttttt actttaccac 2700
cagctgtctt ttattttact ctttttttga gacggagttt cgctcttgtt gcttaggcta 2760
gagtgcagtg gcactatctc agctcactgc gacctctgcc tcccgggttc aagcgattct 2820
cctgcctcag tctcccgagt agctgggatt acaggcacat gccactacac caggctaatt 2880
ttgtattttt agtagagacg gggtttcttc atgttggtca ggctggtctc gaactcccga 2940
cctcaggtga tccgcctgcc tcggcctccc agagtgctgg gattacaggc atgagccacc 3000
gcacctggcc agctgtcttt taatataaca ttatgattaa ttgtgatgtt ccattaaact 3060
aagcggagag gaaacatgct ggtaaaccat gtgtgagtta ttcattgtac cagaaaggca 3120
aatgatacat tttatcctaa aattcaaatt tataaacatc ttaacacttg tgatcattaa 3180
atactactaa tctagcatat aaattatatt tgtaggcggg gcacggtggc tcacgcctgt 3240
aatcccagca ctttgggagg ctgaggtggg cagatcacga ggtcaggaga tcgagaccat 3300
cctggctaac atggtgaaac cccatctcta ctaaaaatac aaaaaaaatt agctgggtgt 3360
gctggcgggc acctgtagtc ccagctactt gggaggctga ggcaggagaa tggcgtgacc 3420
ccaggaggca gagcttccag cctgggcgac tccgtctcaa aaaaaaagaa aaaagaaatt 3480
atatttgtaa tattctacta accttatatc attttaactt tttatataac ttttttattt 3540
taccaaatta agttaacctt ttatagccct tggcttatac taaacatcct aactttttg 3600
tttaattgta ttagttttta agttattgcc ccagatgtca agtaatgttg gattttctat 3660
aataatttag gatatattgc atgaagtcag ttagtattta catttaaaac taaaacaatt 3720
tatactaata cagtttatac atttcatact aatttagcta cagttggata aatatttaat 3780
ggaacaaagt aaatcaaagt accttttcaa atgaattgga aattaaatcc acataacaat 3840
tttttatgac cacactatta cagtgtgatg gcatgccaaa tgatcataat gtggaattat 3900
gtatttcttc attggctttc aagattctgt tctttagttt gtgggctcct ctccaacttg 3960
cttgtctcct cacagtttag gcgactgttt ataattcttg tccatcctgc ataaacacac 4020
acagtcaaaa tgaaaaaaag cttctatcag cagatctgtg cttgctgtac agaaatggga 4080
aaacaattga agtttgcatt atcttttttc taattaccag atcgtttttg gagctattta 4140
ggcatacgct tttaaggaaa aaagaaaaaa agagtgtacc ttttgtttct aacaaaggtt 4200
gttatctata ttattgaaat aaaaaattgg ggatagttat gacaaagtat ttagaaatag 4260
gaattaaaat cttaaaataa cttttcatag catggacaag acttattaat gtctacctca 4320
ataagcaaat catttaaaaa tttttcatgt atatttgctg ccatgatgtg ttgtgattgc 4380
ttaaataacc aatgaatgaa gatcaacaag gatttaaatg aagaagaata tggatttaac 4440

-continued tattttctcc tgtgaaataa gttcatattt acaagttttg attttcagaa attagacaat 4500
tatttttaaa ggctgggatg acaacttctg cctcttacca agaagtcaaa gcacagttat 4560
gtgaattcat cataaatcac atcattttta ttatattttg tatttataat tgtattgtga 4620
ctactttaaa acctgttata aaataaaatt gtttttaat attttatttt agaattatta 4680
gcattaataa caatttgaag tagtttacac aatacctgtg agttttattt ttgttttata 4740
ttgaaattaa ttttagttgc tttacttggc ttcattgcta tggatgcatt ctctgtgtta 4800
cgagttagca gatctttcct tggaactgaa tttaaaagca agcatttggc tccacttaaa 4860
tctctgaaaa tgcaacttgt tctttgcatt tattacataa ttcgctactt atggtacaga 4920
aatggataca atacaaaaat atttccttat aagatacact gtgaccaatg agctttttaa 4980
atagctgtaa tcagtaacat gtatttgact tttcaaaaca catttctgga gggatatcag 5040
tgctttattt ccccaaatat ctgaatccct atgctttagt acaaaacaac ttctgaagaa 5100
tttagtaacc atatgtgttg atctcttgtt tttctaacta gtctttcata agaaatgact 5160
agaatagcaa cagggaaatg attgcctttt aaggttttg tttctcaata taaaattttg 5220
gtgaaccatt tttattgata aatacaggta tttttacttt cttaaatcac ttgatttaaa 5280
attactttga ttaaatatgc atataaagtc agttgtttt aactctcaat acttatcaaa 5340
aaaatttaac ttgctgtaca ttctgtataa acctaattct attcaactaa aattatttta 5400
aacatttag 5409

<210> SEQ ID NO 279
<211> LENGTH: 108
<212> TYPE: DNA
<213> ORGANISM: Homo sapiens

<400> SEQUENCE: 279
ctttagcttg tttctgcgga ggattccgct ctttctccat cagtttcata gccctggaat 60
tgtagaaaag ctctggtttc aagaccattg atatccattt ctgtcagg 108

<210> SEQ ID NO 280
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 280
tcttgaattt gttgttgt 18

<210> SEQ ID NO 281
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 281
ctcttgaatt tgttgttg 18

<210> SEQ ID NO 282
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 282
gctcttgaat ttgttgtt 18

<210> SEQ ID NO 283
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 283
tgctcttgaa tttgttgt 18

<210> SEQ ID NO 284
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 284
catgctcttg aatttgtt 18

<210> SEQ ID NO 285
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 285
tcatgctctt gaatttgt 18

<210> SEQ ID NO 286
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 286
ttcatgctct tgaatttg 18

<210> SEQ ID NO 287
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 287
cttcatgctc ttgaattt 18

<210> SEQ ID NO 288
<211> LENGTH: 16
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 288
tgaatttgtt gttgta 16

<210> SEQ ID NO 289
<211> LENGTH: 16
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 289
ttgaatttgt tgttgt 16

<210> SEQ ID NO 290
<211> LENGTH: 16
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 290
cttgaatttg ttgttg 16

<210> SEQ ID NO 291
<211> LENGTH: 16
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 291
tcttgaattt gttgtt 16

<210> SEQ ID NO 292
<211> LENGTH: 16
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 292
ctcttgaatt tgttgt 16

<210> SEQ ID NO 293
<211> LENGTH: 16
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 293
gctcttgaat ttgttg 16

<210> SEQ ID NO 294
<211> LENGTH: 16
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 294
tgctcttgaa tttgtt 16

<210> SEQ ID NO 295
<211> LENGTH: 16
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 295
atgctcttga atttgt 16

<210> SEQ ID NO 296
<211> LENGTH: 16
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 296
catgctcttg aatttg 16

<210> SEQ ID NO 297
<211> LENGTH: 16
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 297
tcatgctctt gaattt 16

<210> SEQ ID NO 298
<211> LENGTH: 16
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 298
ttcatgctct tgaatt 16

<210> SEQ ID NO 299
<211> LENGTH: 16
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 299
cttcatgctc ttgaat 16

<210> SEQ ID NO 300
<211> LENGTH: 308
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 300
atttcagaat ggcctcaatg ccttaatagg aagaaatact tgaaattttt aaattagggc 60
ttggttttgt gaggagctag taaaggtttt tctctttcag ctttagcttg tttctgcgga 120
ggattccgct ctttctccat cagtttcata gccctggaat tgtagaaaag ctctggtttc 180
aagaccattg atatccattt ctgtcagggt gagttttaaa tttatttcat gatgcaaaca 240
atatattgaa caacaggaca tgaacttgtt cttgttgtaa gtggctgaat tttatcagta 300
aagcacat 308

<210> SEQ ID NO 301
<211> LENGTH: 258
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 301
attgagcata aaaatctgct aaagcatttc actgatattt gggttcattt ctacaagtat 60
gagcttcagt cttaataaca gcaatctgca tttgtaacag gatagcagaa aggagctcat 120
ctgtttggag tccatttttg atggggatcc cactagaggt gagaaacctt cgtagtttcc 180
atatcatgcc aaaatcacgt actactccaa aagcatgtct actatccgta aatatttact 240
gacttgtcct tagctgtg 258

<210> SEQ ID NO 302
<211> LENGTH: 110
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 302
gtatttcaga atttcagaat ggcctcaatg ccttaatagg aagaaatact tgaaattttt 60
aaattagggc ttggttttgt gaggagctag taaaggtttt tctctttcag 110

<210> SEQ ID NO 303
<211> LENGTH: 151
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 303
gagctagtaa aggtttttct ctttcagctt tagcttgttt ctgcggagga ttccgctctt 60
tctccatcag tttcatagcc ctggaattgt agaaaagctc tggtttcaag accattgata 120
tccatttctg tcagggtgag ttttaaattt a 151

<210> SEQ ID NO 304
<211> LENGTH: 104
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 304
gtgagtttta aatttatttc atgatgcaaa caatatattg aacaacagga catgaacttg 60
ttcttgttgt aagtggctga attttatcag taaagcacat caaa 104

<210> SEQ ID NO 305
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 305
aggccattct gaaattct 18

<210> SEQ ID NO 306
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 306
cattgaggcc attctgaa 18

<210> SEQ ID NO 307
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 307
taaggcattg aggccatt 18

<210> SEQ ID NO 308
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 308
cctattaagg cattgagg 18

<210> SEQ ID NO 309
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 309
ttcttcctat taaggcat 18

<210> SEQ ID NO 310
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 310
agtatttctt cctattaa 18

<210> SEQ ID NO 311
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 311
tttcaagtat ttcttcct 18

<210> SEQ ID NO 312
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 312
aaaaatttca agtatttc 18

<210> SEQ ID NO 313
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 313
aatttaaaaa tttcaagt 18

<210> SEQ ID NO 314
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 314
gccctaattt aaaaattt 18

<210> SEQ ID NO 315
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 315
accaagccct aatttaaa 18

<210> SEQ ID NO 316
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 316
acaaaaccaa gccctaat 18

<210> SEQ ID NO 317
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 317
tcctcacaaa accaagcc 18

<210> SEQ ID NO 318
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 318
ctagctcctc acaaaacc 18

<210> SEQ ID NO 319
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 319
ctttactagc tcctcaca 18

<210> SEQ ID NO 320
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 320
aaaaccttta ctagctcc 18

<210> SEQ ID NO 321
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 321
agagaaaaac ctttacta 18

<210> SEQ ID NO 322
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 322
ctgaaagaga aaaacctt 18

<210> SEQ ID NO 323
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 323
aagctgaaag agaaaaac 18

<210> SEQ ID NO 324
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 324
ctaaagctga aagagaaa 18

<210> SEQ ID NO 325
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 325
aagctaaagc tgaaagag 18

<210> SEQ ID NO 326
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 326
aacaagctaa agctgaaa 18

<210> SEQ ID NO 327
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 327
agaaacaagc taaagctg 18

<210> SEQ ID NO 328
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 328
cgcagaaaca agctaaag 18

<210> SEQ ID NO 329

<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 329
tcctccgcag aaacaagc 18

<210> SEQ ID NO 330
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 330
cggaatcctc cgcagaaa 18

<210> SEQ ID NO 331
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 331
aagagcggaa tcctccgc 18

<210> SEQ ID NO 332
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 332
ggagaaagag cggaatcc 18

<210> SEQ ID NO 333
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 333
ctgatggaga aagagcgg 18

<210> SEQ ID NO 334
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 334
tgaaactgat ggagaaag 18

<210> SEQ ID NO 335
<211> LENGTH: 18

<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 335
ggctatgaaa ctgatgga 18

<210> SEQ ID NO 336
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 336
tccagggcta tgaaactg 18

<210> SEQ ID NO 337
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 337
acaattccag ggctatga 18

<210> SEQ ID NO 338
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 338
tttctacaat tccagggc 18

<210> SEQ ID NO 339
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 339
gagcttttct acaattcc 18

<210> SEQ ID NO 340
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 340
aaccagagct tttctaca 18

<210> SEQ ID NO 341
<211> LENGTH: 18
<212> TYPE: DNA

<213> ORGANISM: Artificial Sequence
<220> FEATURE:
<223> OTHER INFORMATION: Description of Artificial Sequence: Synthetic
oligonucleotide

<400> SEQUENCE: 341
cttgaaacca gagctttt 18

<210> SEQ ID NO 342
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 342
atggtcttga aaccagag 18

<210> SEQ ID NO 343
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 343
tatcaatggt cttgaaac 18

<210> SEQ ID NO 344
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 344
atggatatca atggtctt 18

<210> SEQ ID NO 345
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 345
cagaaatgga tatcaatg 18

<210> SEQ ID NO 346
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 346
cctgacagaa atggatat 18

<210> SEQ ID NO 347
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 347
caccctgaca gaaatgga 18

<210> SEQ ID NO 348
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 348
actcaccctg acagaaat 18

<210> SEQ ID NO 349
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 349
aaaactcacc ctgacaga 18

<210> SEQ ID NO 350
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 350
tttaaaactc accctgac 18

<210> SEQ ID NO 351
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 351
aaatttaaaa ctcaccct 18

<210> SEQ ID NO 352
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 352
aataaattta aaactcac 18

<210> SEQ ID NO 353
<211> LENGTH: 18
<212> TYPE: DNA
<213> ORGANISM: Artificial Sequence
<220> FEATURE:

<223> OTHER INFORMATION: Description of Artificial Sequence: Synthetic
oligonucleotide

<400> SEQUENCE: 353
catgaaataa atttaaaa 18

<210> SEQ ID NO 354
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 354
tgcatcatga aataaatt 18

<210> SEQ ID NO 355
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 355
ttgtttgcat catgaaat 18

<210> SEQ ID NO 356
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 356
atatattgtt tgcatcat 18

<210> SEQ ID NO 357
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 357
gttcaatata ttgtttgc 18

<210> SEQ ID NO 358
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 358
ctgttgttca atatattg 18

<210> SEQ ID NO 359
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 359
atgtcctgtt gttcaata 18

<210> SEQ ID NO 360
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 360
agttcatgtc ctgttgtt 18

<210> SEQ ID NO 361
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 361
gaacaagttc atgtcctg 18

<210> SEQ ID NO 362
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 362
aacaagaaca agttcatg 18

<210> SEQ ID NO 363
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 363
cttacaacaa gaacaagt 18

<210> SEQ ID NO 364
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 364
agccacttac aacaagaa 18

<210> SEQ ID NO 365
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 365
aattcagcca cttacaac 18

<210> SEQ ID NO 366
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 366
gataaaattc agccactt 18

<210> SEQ ID NO 367
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 367
ttactgataa aattcagc 18

<210> SEQ ID NO 368
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 368
gtgctttact gataaaat 18

<210> SEQ ID NO 369
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 369
ttgatgtgct ttactgat 18

<210> SEQ ID NO 370
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 370
tggagaaaga gcggaatc 18

<210> SEQ ID NO 371
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 371
atggagaaag agcggaat 18

<210> SEQ ID NO 372
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 372
gatggagaaa gagcggaa 18

<210> SEQ ID NO 373
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 373
tgatggagaa agagcgga 18

<210> SEQ ID NO 374
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 374
actgatggag aaagagcg 18

<210> SEQ ID NO 375
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 375
aactgatgga gaaagagc 18

<210> SEQ ID NO 376
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 376
aaactgatgg agaaagag 18

<210> SEQ ID NO 377
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 377
gaaactgatg gagaaaga 18

<210> SEQ ID NO 378
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 378
atgaaactga tggagaaa 18

<210> SEQ ID NO 379
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 379
tatgaaactg atggagaa 18

<210> SEQ ID NO 380
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 380
ctatgaaact gatggaga 18

<210> SEQ ID NO 381
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 381
gctatgaaac tgatggag 18

<210> SEQ ID NO 382
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 382
gggctatgaa actgatgg 18

<210> SEQ ID NO 383
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 383
agggctatga aactgatg 18

<210> SEQ ID NO 384
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 384
cagggctatg aaactgat 18

<210> SEQ ID NO 385
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 385
ccagggctat gaaactga 18

<210> SEQ ID NO 386
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 386
ctgatggaga aagagcggaa tc 22

<210> SEQ ID NO 387
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 387
ctgatggaga aagagcggaa 20

<210> SEQ ID NO 388
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 388
aactgatgga gaaagagcgg aa 22

<210> SEQ ID NO 389
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 389
aactgatgga gaaagagcgg 20

<210> SEQ ID NO 390
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 390
gaaactgatg gagaaagagc gg 22

<210> SEQ ID NO 391
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 391
ggctatgaaa ctgatggaga aa 22

<210> SEQ ID NO 392
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 392
ggctatgaaa ctgatggaga 20

<210> SEQ ID NO 393
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 393
agggctatga aactgatgga ga 22

<210> SEQ ID NO 394
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 394
agggctatga aactgatgga 20

<210> SEQ ID NO 395
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 395
ccagggctat gaaactgatg ga 22

<210> SEQ ID NO 396
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 396
ttcttaccca tttaatta 18

<210> SEQ ID NO 397
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 397
tgcttcttac ccatttaa 18

<210> SEQ ID NO 398
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 398
taatgcttct tacccatt 18

<210> SEQ ID NO 399
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 399
agataatgct tcttaccc 18

<210> SEQ ID NO 400
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 400
cagataatgc ttcttacc 18

<210> SEQ ID NO 401
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 401
cccttcagat aatgcttc 18

<210> SEQ ID NO 402
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 402
ctactccctt cagataat 18

<210> SEQ ID NO 403
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 403
agctcctact cccttcag 18

<210> SEQ ID NO 404
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 404
ttcacagctc ctactccc 18

<210> SEQ ID NO 405
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 405
taaaattcac agctccta 18

<210> SEQ ID NO 406
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 406
aaatctaaaa ttcacagc 18

<210> SEQ ID NO 407
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 407
gaataaaatc taaaattc 18

<210> SEQ ID NO 408

<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 408
gatgggaata aaatctaa 18

<210> SEQ ID NO 409
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 409
gctgtgatgg gaataaaa 18

<210> SEQ ID NO 410
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 410
tagaggctgt gatgggaa 18

<210> SEQ ID NO 411
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 411
aaagatagag gctgtgat 18

<210> SEQ ID NO 412
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 412
aaaagaaaga tagaggct 18

<210> SEQ ID NO 413
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 413
gacctaaaag aaagatag 18

<210> SEQ ID NO 414
<211> LENGTH: 18

<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 414
ataaagacct aaaagaaa 18

<210> SEQ ID NO 415
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 415
gagatataaa gacctaaa 18

<210> SEQ ID NO 416
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 416
ggctgtgatg ggaataaa 18

<210> SEQ ID NO 417
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 417
aggctgtgat gggaataa 18

<210> SEQ ID NO 418
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 418
gaggctgtga tgggaata 18

<210> SEQ ID NO 419
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 419
agaggctgtg atgggaat 18

<210> SEQ ID NO 420
<211> LENGTH: 18
<212> TYPE: DNA

<213> ORGANISM: Artificial Sequence
<220> FEATURE:
<223> OTHER INFORMATION: Description of Artificial Sequence: Synthetic
oligonucleotide

<400> SEQUENCE: 420
atagaggctg tgatggga 18

<210> SEQ ID NO 421
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 421
gatagaggct gtgatggg 18

<210> SEQ ID NO 422
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 422
agatagaggc tgtgatgg 18

<210> SEQ ID NO 423
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 423
aagatagagg ctgtgatg 18

<210> SEQ ID NO 424
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 424
tagaggctgt gatgggaata aa 22

<210> SEQ ID NO 425
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 425
atagaggctg tgatgggaat aa 22

<210> SEQ ID NO 426
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 426
gatagaggct gtgatgggaa ta 22

<210> SEQ ID NO 427
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 427
agatagaggc tgtgatggga at 22

<210> SEQ ID NO 428
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 428
aagatagagg ctgtgatggg aa 22

<210> SEQ ID NO 429
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 429
gaggctgtga tgggaataaa 20

<210> SEQ ID NO 430
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 430
agaggctgtg atgggaataa 20

<210> SEQ ID NO 431
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 431
tagaggctgt gatgggaata 20

<210> SEQ ID NO 432
<211> LENGTH: 20
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 432
atagaggctg tgatgggaat 20

<210> SEQ ID NO 433
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 433
gatagaggct gtgatgggaa 20

<210> SEQ ID NO 434
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 434
agatagaggc tgtgatggga 20

<210> SEQ ID NO 435
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 435
aagatagagg ctgtgatggg 20

<210> SEQ ID NO 436
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 436
ctgtgatggg aataaa 16

<210> SEQ ID NO 437
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 437
gctgtgatgg gaataa 16

<210> SEQ ID NO 438
<211> LENGTH: 16
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 438
ggctgtgatg ggaata 16

<210> SEQ ID NO 439
<211> LENGTH: 16
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 439
aggctgtgat gggaat 16

<210> SEQ ID NO 440
<211> LENGTH: 16
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 440
gaggctgtga tgggaa 16

<210> SEQ ID NO 441
<211> LENGTH: 16
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 441
agaggctgtg atggga 16

<210> SEQ ID NO 442
<211> LENGTH: 16
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 442
tagaggctgt gatggg 16

<210> SEQ ID NO 443
<211> LENGTH: 16
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 443
atagaggctg tgatgg 16

<210> SEQ ID NO 444
<211> LENGTH: 16
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 444
gatagaggct gtgatg 16

<210> SEQ ID NO 445
<211> LENGTH: 16
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 445
agatagaggc tgtgat 16

<210> SEQ ID NO 446
<211> LENGTH: 16
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 446
aagatagagg ctgtga 16

<210> SEQ ID NO 447
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 447
aggctgtgat gtgaataa 18

<210> SEQ ID NO 448
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 448
aggctgtgat gtgaataa 18

<210> SEQ ID NO 449
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 449
aggctgtgat gtgaataa 18

<210> SEQ ID NO 450
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 450
agaggctgtg atgtgaat 18

<210> SEQ ID NO 451
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 451
agaggctgtg atgtgaat 18

<210> SEQ ID NO 452
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 452
agaggctgtg atgtgaat 18

<210> SEQ ID NO 453
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 453
tagaggctgt gatgtgaa 18

<210> SEQ ID NO 454
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 454
tagaggctgt gatgtgaa 18

<210> SEQ ID NO 455
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 455
tagaggctgt gatgtgaa 18

<210> SEQ ID NO 456
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 456
gatagaggct gtgattgg 18

<210> SEQ ID NO 457
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 457
gatagaggct gtgattgg 18

<210> SEQ ID NO 458
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 458
gatagaggct gtgattgg 18

<210> SEQ ID NO 459
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 459
agatagaggc tgtgatgg 18

<210> SEQ ID NO 460
<211> LENGTH: 16
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 460
ggctgtgatg tgaata 16

<210> SEQ ID NO 461
<211> LENGTH: 16
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 461
ggctgtgatg tgaata 16

<210> SEQ ID NO 462
<211> LENGTH: 16
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 462
ggctgtgatg tgaata 16

<210> SEQ ID NO 463
<211> LENGTH: 16
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 463
gaggctgtga tgtgaa 16

<210> SEQ ID NO 464
<211> LENGTH: 16
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 464
gaggctgtga tgtgaa 16

<210> SEQ ID NO 465
<211> LENGTH: 16
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 465
gaggctgtga tgtgaa 16

<210> SEQ ID NO 466
<211> LENGTH: 16
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 466
tagaggctgt gattgg 16

<210> SEQ ID NO 467
<211> LENGTH: 16
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 467
tagaggctgt gattgg 16

<210> SEQ ID NO 468
<211> LENGTH: 16
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 468
tagaggctgt gattgg 16

<210> SEQ ID NO 469
<211> LENGTH: 16
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 469
atagaggctg tgatgg 16

<210> SEQ ID NO 470
<211> LENGTH: 16
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 470
gatagaggct gtgatg 16

<210> SEQ ID NO 471
<211> LENGTH: 16
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 471
agatagaggc tgtgat 16

<210> SEQ ID NO 472
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 472
ggctatgaaa ctgatggaga 20

<210> SEQ ID NO 473
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 473
ctatgaaact gatggaga 18

<210> SEQ ID NO 474
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 474
gctatgaaac tgatggag 18

<210> SEQ ID NO 475
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 475
ggctatgaaa ctgatgga 18

<210> SEQ ID NO 476
<211> LENGTH: 16
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 476
atgaaactga tggaga 16

<210> SEQ ID NO 477
<211> LENGTH: 16
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 477
atgaaactga tggaga 16

<210> SEQ ID NO 478
<211> LENGTH: 16
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 478
ctatgaaact gatgga 16

<210> SEQ ID NO 479
<211> LENGTH: 16
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 479
ctatgaaact gatgga 16

<210> SEQ ID NO 480
<211> LENGTH: 16
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 480
ggctatgaaa ctgatg 16

<210> SEQ ID NO 481
<211> LENGTH: 16
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 481
ggctatgaaa ctgatg 16

<210> SEQ ID NO 482
<211> LENGTH: 14
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 482
gaaactgatg gaga 14

<210> SEQ ID NO 483
<211> LENGTH: 14
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 483
atgaaactga tgga 14

<210> SEQ ID NO 484
<211> LENGTH: 14
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 484
ctatgaaact gatg 14

<210> SEQ ID NO 485
<211> LENGTH: 14
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 485
ggctatgaaa ctga 14

<210> SEQ ID NO 486
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 486
tagaggctgt gatgggaata aa 22

<210> SEQ ID NO 487

<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 487
tagaggctgt gatgggaata aaat 24

<210> SEQ ID NO 488
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 488
atagaggctg tgatgggaat aa 22

<210> SEQ ID NO 489
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 489
atagaggctg tgatgggaat aaaa 24

<210> SEQ ID NO 490
<211> LENGTH: 25
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 490
atagaggctg tgatgggaat aaaat 25

<210> SEQ ID NO 491
<211> LENGTH: 25
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 491
aaagatagag gctgtgatgg gaata 25

<210> SEQ ID NO 492
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 492
ggctatgaaa ctgatggaga a 21

<210> SEQ ID NO 493
<211> LENGTH: 22

<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 493
ggctatgaaa ctgatggaga aa 22

<210> SEQ ID NO 494
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 494
ggctatgaaa ctgatggaga aaga 24

<210> SEQ ID NO 495
<211> LENGTH: 25
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 495
agggctatga aactgatgga gaaag 25

<210> SEQ ID NO 496
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 496
catttaatta aattatat 18

<210> SEQ ID NO 497
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 497
ccatttaatt aaattata 18

<210> SEQ ID NO 498
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 498
cccatttaat taaattat 18

<210> SEQ ID NO 499
<211> LENGTH: 18
<212> TYPE: DNA

<213> ORGANISM: Artificial Sequence
<220> FEATURE:
<223> OTHER INFORMATION: Description of Artificial Sequence: Synthetic
      oligonucleotide

<400> SEQUENCE: 499
acccatttaa ttaaatta 18

<210> SEQ ID NO 500
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 500
tacccattta attaaatt 18

<210> SEQ ID NO 501
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 501
ttacccattt aattaaat 18

<210> SEQ ID NO 502
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 502
cttacccatt taattaaa 18

<210> SEQ ID NO 503
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 503
tcttacccat ttaattaa 18

<210> SEQ ID NO 504
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 504
gatagaggct gtgatgg 17

<210> SEQ ID NO 505
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 505
ggctgtgaaa ctgatgga 18

<210> SEQ ID NO 506
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 506
ggctgtgaaa ctgatggaga 20

<210> SEQ ID NO 507
<211> LENGTH: 16
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 507
ctatgaaact gatgga 16

<210> SEQ ID NO 508
<211> LENGTH: 16
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 508
gctatgaaac tgatgg 16

<210> SEQ ID NO 509
<211> LENGTH: 16
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 509
ggctatgaaa ctgatg 16

<210> SEQ ID NO 510
<211> LENGTH: 14
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 510
atgaaactga tgga 14

<210> SEQ ID NO 511
<211> LENGTH: 14
<212> TYPE: DNA
<213> ORGANISM: Artificial Sequence
<220> FEATURE:

<223> OTHER INFORMATION: Description of Artificial Sequence: Synthetic
oligonucleotide

<400> SEQUENCE: 511
tatgaaactg atgg 14

<210> SEQ ID NO 512
<211> LENGTH: 14
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 512
ctatgaaact gatg 14

<210> SEQ ID NO 513
<211> LENGTH: 14
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 513
gctatgaaac tgat 14

<210> SEQ ID NO 514
<211> LENGTH: 14
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 514
ggctatgaaa ctga 14

<210> SEQ ID NO 515
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 515
gctgtgaaac tgatggagaa 20

<210> SEQ ID NO 516
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 516
gggctgtgaa actgatggag 20

<210> SEQ ID NO 517
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 517
tgtgaaactg atggagaa 18

<210> SEQ ID NO 518
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 518
ctgtgaaact gatggaga 18

<210> SEQ ID NO 519
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 519
gctgtgaaac tgatggag 18

<210> SEQ ID NO 520
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 520
gggctgtgaa actgatgg 18

<210> SEQ ID NO 521
<211> LENGTH: 16
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 521
tgaaactgat ggagaa 16

<210> SEQ ID NO 522
<211> LENGTH: 16
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 522
gtgaaactga tggaga 16

<210> SEQ ID NO 523
<211> LENGTH: 16
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 523
tgtgaaactg atggag 16

<210> SEQ ID NO 524
<211> LENGTH: 16
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 524
ctgtgaaact gatgga 16

<210> SEQ ID NO 525
<211> LENGTH: 16
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 525
gctgtgaaac tgatgg 16

<210> SEQ ID NO 526
<211> LENGTH: 16
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 526
ggctgtgaaa ctgatg 16

<210> SEQ ID NO 527
<211> LENGTH: 16
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 527
gggctgtgaa actgat 16

<210> SEQ ID NO 528
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 528
cggtccagga atgac 15

<210> SEQ ID NO 529
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 529
ccggtccagg aatga 15

<210> SEQ ID NO 530
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 530
cccggtccag gaatg 15

<210> SEQ ID NO 531
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 531
tcccggtcca ggaat 15

<210> SEQ ID NO 532
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 532
ctcccggtcc aggaa 15

<210> SEQ ID NO 533
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 533
gctcccggtc cagga 15

<210> SEQ ID NO 534
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 534
ggctcccggt ccagg 15

<210> SEQ ID NO 535
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 535
cgggagcccc cgtgt 15

<210> SEQ ID NO 536
<211> LENGTH: 15
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 536
gcgggagccc ccgtg 15

<210> SEQ ID NO 537
<211> LENGTH: 15
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 537
cgcgggagcc cccgt 15

<210> SEQ ID NO 538
<211> LENGTH: 15
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 538
acgcgggagc ccccg 15

<210> SEQ ID NO 539
<211> LENGTH: 15
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 539
cacgcgggag ccccc 15

<210> SEQ ID NO 540
<211> LENGTH: 15
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 540
ccacgcggga gcccc 15

<210> SEQ ID NO 541
<211> LENGTH: 15
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 541
gccacgcggg agccc 15

<210> SEQ ID NO 542
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 542
ggccacgcgg gagcc 15

<210> SEQ ID NO 543
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 543
cggccacgcg ggagc 15

<210> SEQ ID NO 544
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 544
acggccacgc gggag 15

<210> SEQ ID NO 545
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 545
gacggccacg cggga 15

<210> SEQ ID NO 546
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 546
agacggccac gcggg 15

<210> SEQ ID NO 547
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 547
gctagggagg gatggtta 18

<210> SEQ ID NO 548
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 548
tgtaagctag ggagggat 18

<210> SEQ ID NO 549
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 549
acagatgtaa gctaggga 18

<210> SEQ ID NO 550
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 550
aaggaacaga tgtaagct 18

<210> SEQ ID NO 551
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 551
caacaaagga acagatgt 18

<210> SEQ ID NO 552
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 552
gggtgcaaca aaggaaca 18

<210> SEQ ID NO 553
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 553
accaagggtg caacaaag 18

<210> SEQ ID NO 554
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 554
gttaaaccaa gggtgcaa 18

<210> SEQ ID NO 555
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 555
ataatgttaa accaaggg 18

<210> SEQ ID NO 556
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 556
ggagaataat gttaaacc 18

<210> SEQ ID NO 557
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 557
ggggaggaga ataatgtt 18

<210> SEQ ID NO 558
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 558
aaattgggga ggagaata 18

<210> SEQ ID NO 559
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 559
agaggaaatt ggggagga 18

<210> SEQ ID NO 560
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 560
ggagaagagg aaattggg 18

<210> SEQ ID NO 561
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 561
aatgaggaga agaggaaa 18

<210> SEQ ID NO 562
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 562
ttcacaatga ggagaaga 18

<210> SEQ ID NO 563
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 563
acgagttcac aatgagga 18

<210> SEQ ID NO 564
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 564
ctgccacgag ttcacaat 18

<210> SEQ ID NO 565
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 565
agaccctgcc acgagttc 18

<210> SEQ ID NO 566

<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 566
caagcagacc ctgccacg 18

<210> SEQ ID NO 567
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 567
ctcaccaagc agaccctg 18

<210> SEQ ID NO 568
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 568
gagctcacca agcagacc 18

<210> SEQ ID NO 569
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 569
agaatgagct caccaagc 18

<210> SEQ ID NO 570
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 570
gtaagagaat gagctcac 18

<210> SEQ ID NO 571
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 571
ttgttgtaag agaatgag 18

<210> SEQ ID NO 572
<211> LENGTH: 18

<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 572
atttgttgtt gtaagaga 18

<210> SEQ ID NO 573
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 573
cttgaatttg ttgttgta 18

<210> SEQ ID NO 574
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 574
atgctcttga atttgttg 18

<210> SEQ ID NO 575
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 575
tcttcatgct cttgaatt 18

<210> SEQ ID NO 576
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 576
cttcctcttc atgctctt 18

<210> SEQ ID NO 577
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 577
gcgcgcttcc tcttcatg 18

<210> SEQ ID NO 578
<211> LENGTH: 18
<212> TYPE: DNA

<213> ORGANISM: Artificial Sequence
<220> FEATURE:
<223> OTHER INFORMATION: Description of Artificial Sequence: Synthetic
oligonucleotide

<400> SEQUENCE: 578
gctctgcgcg cttcctct 18

<210> SEQ ID NO 579
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 579
ggccagcggc tctgcgcg 18

<210> SEQ ID NO 580
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 580
atattggcca gcggctct 18

<210> SEQ ID NO 581
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 581
gtgctatatt ggccagcg 18

<210> SEQ ID NO 582
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 582
agctcgtgct atattggc 18

<210> SEQ ID NO 583
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 583
ggcatagctc gtgctata 18

<210> SEQ ID NO 584
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 584
tgttgggcat agctcgtg 18

<210> SEQ ID NO 585
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 585
gcttctgttg ggcatagc 18

<210> SEQ ID NO 586
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 586
cttgcgcttc tgttgggc 18

<210> SEQ ID NO 587
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 587
caccttgcgc ttctgttg 18

<210> SEQ ID NO 588
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 588
tccatcacct tgcgcttc 18

<210> SEQ ID NO 589
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 589
aaccatccat caccttgc 18

<210> SEQ ID NO 590
<211> LENGTH: 18
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 590
ccttaaacca tccatcac 18

<210> SEQ ID NO 591
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 591 agcccccctta aaccatcc 18

<210> SEQ ID NO 592
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 592
tcggtagccc ccttaaac 18

<210> SEQ ID NO 593
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 593
atgtatcggt agcccccct 18

<210> SEQ ID NO 594
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 594
tgtgaatgta tcggtagc 18

<210> SEQ ID NO 595
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 595
attagtgtga atgtatcg 18

<210> SEQ ID NO 596
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 596
ggctgattag tgtgaatg 18

<210> SEQ ID NO 597
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 597
gaaatggctg attagtgt 18

<210> SEQ ID NO 598
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 598
tggcagaaat ggctgatt 18

<210> SEQ ID NO 599
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 599
gatcttggca gaaatggc 18

<210> SEQ ID NO 600
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 600
gacatgatct tggcagaa 18

<210> SEQ ID NO 601
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 601
gaggtgacat gatcttgg 18

<210> SEQ ID NO 602
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 602
agattgaggt gacatgat 18

<210> SEQ ID NO 603
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 603
tgaacagatt gaggtgac 18

<210> SEQ ID NO 604
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 604
gtccatgaac agattgag 18

<210> SEQ ID NO 605
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 605
ttggagtcca tgaacaga 18

<210> SEQ ID NO 606
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 606
tgtatttgga gtccatga 18

<210> SEQ ID NO 607
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 607
tttcttgtat ttggagtc 18